United States Patent
Deaton et al.

(10) Patent No.: US 11,053,234 B2
(45) Date of Patent: Jul. 6, 2021

(54) 1,3 DI-SUBSTITUTED CYCLOBUTANE OR AZETIDINE DERIVATIVES AS HEMATOPOIETIC PROSTAGLANDIN D SYNTHASE INHIBITORS

(71) Applicant: GlaxoSmithKline Intellectual Property Development Limited, Brentford (GB)

(72) Inventors: David Norman Deaton, Collegeville, PA (US); Yu Guo, Collegeville, PA (US); Ashley Paul Hancock, Stevenage (GB); Christie Schulte, Collegeville, PA (US); Barry George Shearer, Collegeville, PA (US); Emilie Despagnet Smith, Apex, NC (US); Eugene L. Stewart, Collegeville, PA (US); Stephen Andrew Thomson, Del Mar, CA (US)

(73) Assignee: GlaxoSmithKline Intellectual Property Development Limited, Middlesex (GB)

( * ) Notice: Subject to any disclaimer, the term of this patent is extended or adjusted under 35 U.S.C. 154(b) by 0 days.

(21) Appl. No.: 16/341,113

(22) PCT Filed: Oct. 12, 2017

(86) PCT No.: PCT/IB2017/056320
§ 371 (c)(1),
(2) Date: Apr. 11, 2019

(87) PCT Pub. No.: WO2018/069863
PCT Pub. Date: Apr. 19, 2018

(65) Prior Publication Data
US 2019/0241554 A1 Aug. 8, 2019

Related U.S. Application Data

(60) Provisional application No. 62/407,634, filed on Oct. 13, 2016.

(51) Int. Cl.
| | | |
|---|---|---|
| C07D 417/14 | (2006.01) | |
| C07D 417/12 | (2006.01) | |
| C07C 235/40 | (2006.01) | |
| A61K 9/00 | (2006.01) | |
| A61K 9/48 | (2006.01) | |
| C07D 205/04 | (2006.01) | |
| C07D 401/04 | (2006.01) | |

(Continued)

(52) U.S. Cl.
CPC .......... *C07D 417/14* (2013.01); *A61K 9/0019* (2013.01); *A61K 9/48* (2013.01); *A61P 11/06* (2018.01); *A61P 21/00* (2018.01); *C07C 235/40* (2013.01); *C07D 205/04* (2013.01); *C07D 215/24* (2013.01); *C07D 239/42* (2013.01); *C07D 239/72* (2013.01); *C07D 257/06* (2013.01); *C07D 271/10* (2013.01); *C07D 277/44* (2013.01); *C07D 277/62* (2013.01); *C07D 277/64* (2013.01); *C07D 401/04* (2013.01); *C07D 403/04* (2013.01); *C07D 417/12* (2013.01); *C07D 471/04* (2013.01); *C07C 2601/02* (2017.05); *C07C 2601/04* (2017.05); *C07C 2601/14* (2017.05); *C07C 2602/08* (2017.05); *C07C 2603/94* (2017.05)

(58) Field of Classification Search
CPC .................................................. C07D 417/14
See application file for complete search history.

(56) References Cited

U.S. PATENT DOCUMENTS

| | | |
|---|---|---|
| 4,031,221 A | 6/1977 | Helsley et al. |
| 4,956,359 A | 9/1990 | Taylor et al. |

(Continued)

FOREIGN PATENT DOCUMENTS

| | | |
|---|---|---|
| EP | 194112 | 2/1986 |
| EP | 1217000 A1 | 12/2000 |

(Continued)

OTHER PUBLICATIONS

Abe, et al., *Gene*, 227:71-77 (1999).
(Continued)

*Primary Examiner* — Paul V Ward
(74) *Attorney, Agent, or Firm* — Stanek Lemon Crouse & Meeks, PA

(57) ABSTRACT

A compound of formula (I)

(I)

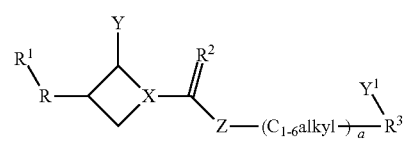

wherein R, $R^1$, $R^2$, $R^3$, Y, $Y^1$, a, X, and Z are as defined herein.

The compounds of the present invention are inhibitors of hematopoietic prostaglandin D synthase (H-PGDS) and can be useful in the treatment of Duchenne Muscular Dystrophy. Accordingly, the invention is further directed to pharmaceutical compositions comprising a compound of the invention. The invention is still further directed to methods of inhibiting H-PGDS activity and treatment of disorders associated therewith using a compound of the invention or a pharmaceutical composition comprising a compound of the invention.

12 Claims, 1 Drawing Sheet

(51) Int. Cl.

| | | |
|---|---|---|
| *C07D 239/42* | (2006.01) |
| *C07D 271/10* | (2006.01) |
| *C07D 257/06* | (2006.01) |
| *C07D 403/04* | (2006.01) |
| *C07D 277/44* | (2006.01) |
| *C07D 277/62* | (2006.01) |
| *A61P 21/00* | (2006.01) |
| *A61P 11/06* | (2006.01) |
| *C07D 215/24* | (2006.01) |
| *C07D 239/72* | (2006.01) |
| *C07D 277/64* | (2006.01) |
| *C07D 471/04* | (2006.01) |

(56) References Cited

U.S. PATENT DOCUMENTS

| | | |
|---|---|---|
| 2011/0172230 A1 | 7/2011 | Ishii et al. |
| 2011/0319413 A1 | 12/2011 | Urade et al. |
| 2012/0171614 A1 | 7/2012 | Cha et al. |
| 2015/0038483 A1 | 2/2015 | Yukimasa et al. |

FOREIGN PATENT DOCUMENTS

| | | | |
|---|---|---|---|
| EP | 2 857 404 A1 | | 4/2015 |
| WO | WO 99/37614 A1 | | 7/1999 |
| WO | WO2007/007057 | * | 1/2001 |
| WO | WO 01/07043 A1 | | 2/2001 |
| WO | WO 2005/105779 A1 | | 11/2005 |
| WO | WO 2006/077496 A1 | | 7/2006 |
| WO | WO 2007/003961 A2 | | 1/2007 |
| WO | WO 2007/007057 A1 | | 1/2007 |
| WO | WO2007/106705 | * | 9/2007 |
| WO | WO 2007/106705 A1 | | 9/2007 |
| WO | WO 2008/122787 A1 | | 10/2008 |
| WO | WO 2009/109743 A1 | | 9/2009 |
| WO | WO2011/143366 | * | 11/2011 |
| WO | WO 2011/143366 A1 | | 11/2011 |
| WO | WO 2011/143495 A1 | | 11/2011 |
| WO | WO 2012/009649 A1 | | 1/2012 |
| WO | WO 2012/035023 A1 | | 3/2012 |
| WO | WO 2012/142498 A2 | | 10/2012 |
| WO | WO 2012/160015 A1 | | 11/2012 |
| WO | WO 2013/074387 A1 | | 5/2013 |
| WO | WO 2014/127350 A1 | | 8/2014 |
| WO | WO 2014/179144 A1 | | 11/2014 |
| WO | WO 2015/179414 A1 | | 11/2015 |
| WO | WO 2016/156816 A1 | | 10/2016 |
| WO | WO2017/103851 A1 | | 6/2017 |
| WO | WO 018069863 A1 | | 4/2019 |

OTHER PUBLICATIONS

Boie, et al., *Journal of Biological Chemistry*, 270:18910-18916 (1995).
Brown, et al., *Triazole ocytocin antagonists: Identification of an aryloxyazetidine replacement for a biaryl substituent*, Bioorganic & Medicinal Chem Letters, 20(2):516-520 (2010).
Carron, et al., *ACS Med. Chem. Lett.*, 1:59-63 (2010).
Christ, et al., *J. Med. Chem.*, 53:5536-5548 (2010).
Hohwy, et al., *J. Med. Chem.*, 51:2178-2186 (2008).
Ikuko, et al., *J. Neuropath. Exp. Neur.*, 66:469-580 (2007).
Lewis, et al., *J. Immunology*, 129:1627-1631 (1982).
Jevgenija Luginina, et al., *Ring-opening of carbamate-protected aziridines and azetidines in liquid sulfur dioxide, Eur. Journal of Organic Chem*, 9:1760-1771 (2016).
Mohri, et al., *American Journal of Pathology*, 174:1735-1744 (2009).
Mohri, et al., *Journal of Neuroscience*, 26:4383-4393 (2006).
Nakagawa, et al., *Clinica Chimica Acta*, 423:10-14 (2013).
Okinaga, et al., *Acta Neuropatholigica*, 104:377-384 (2002).
Papaliodis, et al., *JPET*, 327:665-672 (2008).
Redensek, et al., *Glia*, 59:603-614 (2011).
Tanaka, et al., *American J. Physiol. Cell Physiol.*, 301:C1360-C1367 (2011).
Urade, et al., *Vitamins and Hormones*, 58:89-120 (2000).
Weber, et al., *European Journal of Medicinal Chemistry*, 45:447-454 (2010).

* cited by examiner

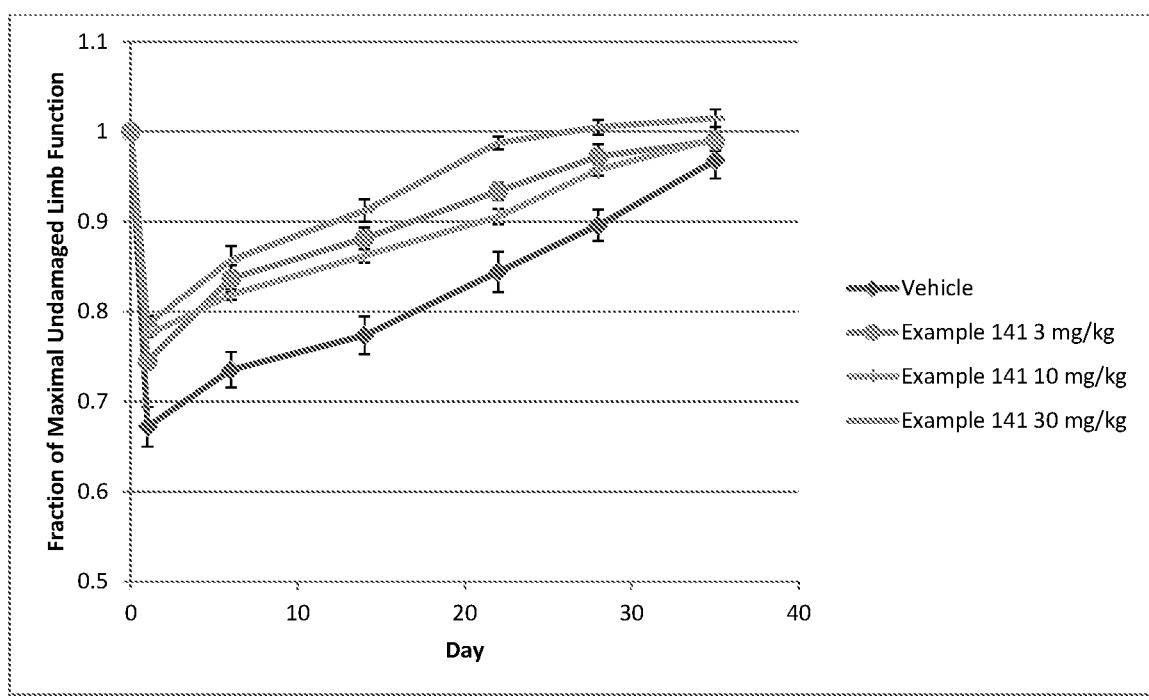

1,3 DI-SUBSTITUTED CYCLOBUTANE OR AZETIDINE DERIVATIVES AS HEMATOPOIETIC PROSTAGLANDIN D SYNTHASE INHIBITORS

This application is a 371 of International Application No. PCT/IB2017/056320, filed 12 Oct. 2017, which claims priority to U.S. 62/407,634 filed 13 Oct. 2016.

FIELD OF THE INVENTION

The present invention relates to novel compounds, to the use of the compounds as Hematopoietic Prostaglandin D Synthase (H-PGDS) inhibitors, to pharmaceutical compositions comprising the compounds and to the use of the compounds in therapy, especially in the treatment of conditions for which a H-PGDS inhibitor is indicated, such as neurodegenerative diseases and musculoskeletal diseases including Duchenne Muscular Dystrophy, where $PGD_2$ is considered to play a pathological role, for the use of a compound in the manufacture of a medicament for the treatment of conditions in which an inhibitor of H-PGDS is indicated, and a method for the treatment or prophylaxis of disorders in which inhibition of H-PGDS is indicated, in a human.

BACKGROUND OF THE INVENTION

Prostaglandin $D_2$ ($PGD_2$) is a product of arachidonic acid metabolism, and is the major prostanoid mediator synthesised by mast cells in response to stimulation via multiple mechanisms and cellular activation pathways, including allergen-mediated cross-linking of high affinity IgE receptors (Lewis et al. (1982) Prostaglandin $D_2$ generation after activation of rat and human mast cells with anti-IgE. *J. Immunol.*, 129, 1627-1631). Other cells such as dendritic cells, $T_h2$ cells, and epithelial cells also produce $PGD_2$, but at lower levels than mast cells. $PGD_2$ mediates its effects via activation of the specific G-protein coupled receptors $DP_1$ (Boie et al. (1995) Molecular cloning and characterization of the human prostanoid DP receptor. (*J. Biol. Chem.*, 270, 18910-18916)) and $DP_2$ (CRTH2) (Abe et al. (1999), Molecular cloning, chromosome mapping and characterization of the mouse CRTH2 gene, a putative member of the leukocyte chemo-attractant receptor family. (*Gene*, 227, 71-77)) and also acts via the receptor for thromboxane $A_2$ ($TXA_2$), the TP receptor, on target cells.

Prostaglandin D synthase (PGDS) is the enzyme responsible for the catalytic isomerase conversion of prostaglandin endoperoxide $PGH_2$ to $PGD_2$. $PGD_2$ is generated by the action of either H-PGDS (hematopoietic-type or H-type) or L-PGDS or (lipocalin-type or L-type) enzymes (Urade et al., (2000) Prostaglandin D synthase structure and function. *Vitamins and hormones*, 58, 89-120). H-PGDS activity is dependent on glutathione and plays an important role in the generation of $PGD_2$ by immune and inflammatory cells, including mast cells, antigen-presenting cells (e.g. dendritic cells), macrophages, and $T_h2$ cells, which are all key cells in the pathology of allergic disease. In contrast, L-type is glutathione-independent and is primarily located in the central nervous system, genital organs, and heart. These two isoforms of PGDS appear to have distinct catalytic properties, tertiary structure, and cellular and tissue distribution.

Using the inhibitor HQL-79, H-PGDS has also been implicated to play a role not only in allergic disease, but also other diseases such as Duchenne Muscular Dystrophy (Nakagawa et al. (2013) A prostaglandin $D_2$ metabolite is elevated in the urine of Duchenne muscular dystrophy patients and increases further from 8 years old, *Clinica Chimica Acta* 423, 10-14) and (Mohri et al. (2009), Inhibition of prostaglandin D synthase suppresses muscular necrosis, *Am. J. Pathol.* 174, 1735-1744) and (Okinaga et al. (2002), Induction of hematopoietic prostaglandin D synthase in hyalinated necrotic muscle fibers: its implication in grouped necrosis, *Acta Neuropathologica* 104, 377-84), spinal cord contusion injury (Redensek et al. (2011) Expression and detrimental role of hematopoietic prostaglandin D synthase in spinal cord contusion injury, *Glia* 59, 603-614), neuroinflammation (Mohri et al. (2006) Prostaglandin $D_2$-mediated microglia/astrocyte interaction enhances astrogliosis and demyelination in twitcher. *J. Neurosci.* 26, 4383-4393), and neurodegenerative disease (Ikuko et al. (2007) Hematopoietic prostaglandin D synthase and $DP_1$ receptor are selectively upregulated in microglia and astrocytes within senile plaques from human patients and in a mouse model of Alzheimer disease. *J. Neuropath. Exp. Neur.* 66, 469-480). H-PGDS has also been implicated to play a role in metabolic diseases such as diabetes and obesity, since $PGD_2$ is converted to 15-deoxy-$\Delta^{12,14}PGJ_2$, a potent ligand for PPARγ which is able to drive adipogenesis (Tanaka et al (2011) Mast cells function as an alternative modulator of adipogenesis through 15-deoxy-delta-12, 14-prostaglandin $J_2$. *Am. J. Physiol. Cell Physiol.* 301, C1360-C1367). $PGD_2$ has been implicated to play a role in niacin-induced skin flushing (Papaliodis et al (2008) Niacin-induced "flush" involves release of prostaglandin $D_2$ from mast cells and serotonin from platelets: Evidence from human cells in vitro and an animal model. *JPET* 327:665-672).

Weber et al. (2010), Identification and characterisation of new inhibitors for the human hematopoietic prostaglandin $D_2$ synthase. *Eur. J. Med. Chem.* 45, 447-454, Carron et al. (2010), Discovery of an Oral Potent Selective Inhibitor of Hematopoietic Prostaglandin D Synthase (HPGDS). *ACS Med. Chem. Lett.* 1, 59-63; Christ et al. (2010), Development and Characterization of New Inhibitors of the Human and Mouse Hematopoietic Prostaglandin $D_2$ Synthases, *J. Med. Chem.*, 53, 5536-5548; and Hohwy et al. (2008), Novel Prostaglandin D Synthase Inhibitors Generated by Fragment-Based Drug Design. *J. Med. Chem.*, 51, 2178-2186 are also of interest.

Based on this evidence, chemical inhibitors of H-PGDS which inhibit $PGD_2$ formation, simultaneously inhibit the biological actions of $PGD_2$ and its metabolites at multiple receptors and offer the potential for therapeutic benefit in the treatment of a range of diseases where $PGD_2$ is considered to play a pathological role.

International Patent Applications WO2005/094805, WO2007/007778, WO2007/041634, 2008/121670, WO2008/122787, WO2009/153720, WO2009/153721, WO2010/033977, WO2010/104024, WO2011/043359, WO2011044307, WO2011/090062, Japanese Patent Application 2007-51121 and US Patent Application 2008/0146569 disclose certain H-PGDS inhibitors and their use in the treatment of diseases associated with the activity of H-PGDS.

It is an object of the invention to provide further H-PGDS inhibitors, suitably for the treatment of Muscular Dystrophy.

SUMMARY OF THE INVENTION

The invention is directed to compounds according to Formula I:

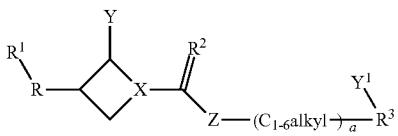

(I)

wherein R, R¹, R², R³, Y, Y¹, a, X, and Z are as defined below.

Compounds of formula (I) and their pharmaceutically acceptable salts have H-PGDS activity and are believed to be of use for the treatment or prophylaxis of certain disorders.

Accordingly, in another aspect of the invention there is provided a pharmaceutical composition comprising a compound of formula (I) according to the first aspect, or a pharmaceutically acceptable salt thereof and one or more pharmaceutically acceptable carriers or excipients.

In some embodiments, the pharmaceutical composition is for the treatment or prophylaxis of a disorder in which inhibition of H-PGDS is beneficial.

In a further aspect, the invention provides a compound of formula (I) or a pharmaceutically acceptable salt thereof according to the first aspect of the invention for use in therapy.

The invention also provides a compound of formula (I) or a pharmaceutically acceptable salt thereof, for use in the treatment of a condition for which an H-PGDS inhibitor is indicated.

This invention also relates to a method of treating Duchenne muscular dystrophy, which comprises administering to a subject in need thereof an effective amount of a H-PGDS inhibiting compound of Formula (I).

This invention also relates to a method of treating congenital myotonia, which comprises administering to a subject in need thereof an effective amount of a H-PGDS inhibiting compound of Formula (I).

This invention also relates to a method of treating muscle injury, which comprises administering to a subject in need thereof an effective amount of a H-PGDS inhibiting compound of Formula (I).

This invention also relates to a method of treating muscle lacerations, which comprises administering to a subject in need thereof an effective amount of a H-PGDS inhibiting compound of Formula (I).

This invention also relates to a method of treating chronic muscle strains, which comprises administering to a subject in need thereof an effective amount of a H-PGDS inhibiting compound of Formula (I).

This invention also relates to a method of treating Myotonic dystrophy type I, which comprises administering to a subject in need thereof an effective amount of a H-PGDS inhibiting compound of Formula (I).

This invention also relates to a method of treating myotonic dystrophy type II, which comprises administering to a subject in need thereof an effective amount of a H-PGDS inhibiting compound of Formula (I).

This invention also relates to a method of treating asthma, which comprises administering to a subject in need thereof an effective amount of a H-PGDS inhibiting compound of Formula (I).

This invention also relates to a method of treating chronic obstructive pulmonary disease, which comprises administering to a subject in need thereof an effective amount of a H-PGDS inhibiting compound of Formula (I).

This invention also relates to a method of treating rheumatoid arthritis, which comprises administering to a subject in need thereof an effective amount of a H-PGDS inhibiting compound of Formula (I).

This invention also relates to a method of treating inflammatory bowel disease, which comprises administering to a subject in need thereof an effective amount of a H-PGDS inhibiting compound of Formula (I).

This invention also relates to a method of treating osteoarthritis, which comprises administering to a subject in need thereof an effective amount of a H-PGDS inhibiting compound of Formula (I).

This invention also relates to a method of treating psoriasis, which comprises administering to a subject in need thereof an effective amount of a H-PGDS inhibiting compound of Formula (I).

This invention also relates to a method of treating a muscle degenerative disorder, which comprises administering to a subject in need thereof an effective amount of a H-PGDS inhibiting compound of Formula (I).

This invention also relates to a method of treating muscular dystrophy, which comprises administering to a subject in need thereof an effective amount of a H-PGDS inhibiting compound of Formula (I).

Also included in the present invention are methods of co-administering the presently invented H-PGDS inhibiting compounds with further active ingredients.

The invention also relates to a compound of Formula (I) or a pharmaceutically acceptable salt thereof for use in the treatment of Duchenne muscular dystrophy.

The invention also relates to a compound of Formula (I) or a pharmaceutically acceptable salt thereof for use in the treatment of congenital myotonia.

The invention also relates to a compound of Formula (I) or a pharmaceutically acceptable salt thereof for use in the treatment of muscle injury.

The invention also relates to a compound of Formula (I) or a pharmaceutically acceptable salt thereof for use in the treatment of muscle lacerations.

The invention also relates to a compound of Formula (I) or a pharmaceutically acceptable salt thereof for use in the treatment of chronic muscle strains.

The invention also relates to a compound of Formula (I) or a pharmaceutically acceptable salt thereof for use in the treatment of Myotonic dystrophy type I.

The invention also relates to a compound of Formula (I) or a pharmaceutically acceptable salt thereof for use in the treatment of myotonic dystrophy type II.

The invention also relates to a compound of Formula (I) or a pharmaceutically acceptable salt thereof for use in the treatment of asthma.

The invention also relates to a compound of Formula (I) or a pharmaceutically acceptable salt thereof for use in the treatment of chronic obstructive pulmonary disease.

The invention also relates to a compound of Formula (I) or a pharmaceutically acceptable salt thereof for use in the treatment of rheumatoid arthritis.

The invention also relates to a compound of Formula (I) or a pharmaceutically acceptable salt thereof for use in the treatment of inflammatory bowel disease.

The invention also relates to a compound of Formula (I) or a pharmaceutically acceptable salt thereof for use in the treatment of osteoarthritis.

The invention also relates to a compound of Formula (I) or a pharmaceutically acceptable salt thereof for use in the treatment of psoriasis.

The invention also relates to a compound of Formula (I) or a pharmaceutically acceptable salt thereof for use in the treatment of a muscle degenerative disorder.

The invention also relates to a compound of Formula (I) or a pharmaceutically acceptable salt thereof for use in the treatment of muscular dystrophy.

The invention provides for the use of a compound of Formula (I) or a pharmaceutically acceptable salt thereof in the manufacture of a medicament for the treatment of conditions in which an inhibitor of H-PGDS is indicated.

The invention further provides a method for the treatment or prophylaxis of disorders in which inhibition of H-PGDS is indicated, in a human, which comprises administering a human in need thereof a therapeutically effective amount of a compound of Formula (I) or a pharmaceutically acceptable salt thereof.

BRIEF DESCRIPTION OF THE FIGURE

FIG. 1 depicts the protection and acceleration of functional repair dose response curves of H-PGDS Inhibition using the compound of Example 141 following limb muscle injury in normal mice.

DETAILED DESCRIPTION OF THE INVENTION

This invention relates to novel compounds of Formula (I):

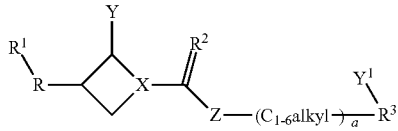

(I)

wherein:
X is selected from: carbon and nitrogen;
Y is selected from: hydrogen and $CH_3$;
$Y^1$ is absent or $CH_3$;
Z is NH or O;
a is 0 or 1;
R is selected from: O, NH, $CH_2$ and $C_1$ alkyl substituted by halogen;
$R^1$ is selected from:
  aryl,
  aryl substituted from 1 to 4 times by $R^a$,
  heteroaryl,
  heteroaryl substituted from 1 to 4 times by $R^a$,
  bicycloheteroaryl, and
  bicycloheteroaryl substituted from 1 to 4 times by $R^a$;
$R^2$ is selected from: O and S;
$R^3$ is selected from:
  aryl,
  aryl substituted from 1 to 4 times by $R^b$,
  cycloalkyl,
  cycloalkyl substituted from 1 to 4 times by $R^b$,
  heterocycle,
  heterocycle substituted from 1 to 4 times by $R^b$,
  heteroaryl,
  heteroaryl substituted from 1 to 4 times by $R^b$,
  bicycloheteroaryl, and
  bicycloheteroaryl substituted from 1 to 4 times by $R^b$;

each $R^a$ is independently selected from:
  fluoro,
  chloro,
  bromo,
  iodo,
  —OH,
  $C_{1-6}$alkyl,
  $C_{1-6}$alkyl substituted with from 1 to 5 substituents independently selected from: fluoro, chloro, bromo, iodo, $C_{1-4}$alkyloxy, —OH, $C_{1-4}$alkyl, oxo, —COOH, —$NO_2$, —$NH_2$ and —CN,
  cyano,
  —$OC_{1-6}$alkyl,
  —$OC_{1-6}$alkyl substituted with from 1 to 5 substituents independently selected from: fluoro, chloro, bromo, iodo, $C_{1-4}$alkyloxy, —OH, $C_{1-4}$alkyl, oxo, —COOH, —$NO_2$, —$NH_2$ and —CN,
  —C(O)$OC_{1-6}$alkyl, and
  —C(O)$OC_{1-6}$alkyl substituted 1 to 5 times by fluoro;
each $R^b$ is independently selected from:
  cyano,
  fluoro,
  chloro,
  bromo,
  iodo,
  $C_{1-6}$alkyl,
  $R^e$,
  —$OC_{1-6}$alkyl,
  —$OR^e$,
  oxo,
  hydroxyl,
  cycloalkyl,
  cycloalkyl substituted from 1 to 4 times by $R^f$,
  amino,
  —$NHR^x$,
    where $R^x$ is selected from aryl, heteroaryl, cycloalkyl, heterocycloalkyl, —$OC_{1-6}$alkyl, —$OC_{1-6}$alkyl substituted with from 1 to 6 substituents independently selected from:
    fluoro, oxo, and —OH, $C_{1-6}$alkyl, and $C_{1-6}$alkyl substituted with from 1 to 6 substituents independently selected from:
    fluoro, oxo, —OH, —COOH, —$NH_2$, —NHcycloalkyl, and —CN,
  heteroaryl,
  heteroaryl substituted from 1 to 4 times by $R^f$,
  heterocycle,
  heterocycle substituted from 1 to 4 times by $R^f$,
  —$SO_2$H, and
  —$SO_2C_{1-6}$alkyl;
each $R^f$ is independently selected from:
  fluoro,
  chloro,
  bromo,
  iodo,
  $C_{1-6}$alkyl,
  $R^e$,
  oxo,
  —OH,
  amino,
  —$NHR^{x1}$,
    where $R^{x1}$ is selected from aryl, heteroaryl, cycloalkyl, heterocycloalkyl, $C_{1-6}$alkyl, and $C_{1-6}$alkyl substituted with from 1 to 6 substituents independently selected from:
    fluoro, oxo, —OH, —$OC_{1-6}$alkyl, —COOH, —$NH_2$, and —CN,
  —$NR^{x2}R^{x3}$, where $R^{x2}$ and $R^{x3}$ are each independently selected from: aryl, heteroaryl, cycloalkyl, heterocycloalkyl, $C_{1-6}$alkyl, and $C_{1-6}$alkyl substituted with from 1 to 6 substituents independently selected from: fluoro, oxo, —OH, —COOH, —NH$_2$, and —CN, nitro, and cyano, and each $R^e$ is independently selected from:

$C_{1-6}$alkyl substituted with from 1 to 9 substituents independently selected from:

fluoro, chloro, bromo, iodo, $C_{1-6}$alkyl,

—O$C_{1-6}$alkyl,

—O$C_{1-6}$alkyl substituted with from 1 to 6 substituents independently selected from: fluoro, oxo, —OH, —COOH, —NH$_2$, —CN, and phenyl, oxo,

=N, hydroxyl, amino,

—NHR$^{xx}$, or =NR$^{xx}$, where R$^{xx}$ is selected from aryl, heteroaryl, cycloalkyl, heterocycloalkyl, cyano, $C_{1-6}$alkyl, and $C_{1-6}$alkyl substituted with from 1 to 6 substituents independently selected from: fluoro, oxo, —OH, —COOH, —O$C_{1-5}$alkyl, —O$C_{1-5}$alkyl substituted from 1 to 6 times by fluoro, —NR$^{xx1}$R$^{xx2}$, where R$^{xx1}$ and R$^{xx2}$ are each independently selected from: aryl, heteroaryl, cycloalkyl, heterocycloalkyl, $C_{1-6}$alkyl, and $C_{1-6}$alkyl substituted with from 1 to 6 substituents independently selected from: fluoro, oxo, —OH, —COOH, —NH$_2$, and —CN, aryl, aryl substituted from 1 to 4 times by R$^{xx3}$, where R$^{xx3}$ is selected from: fluoro, chloro, bromo, iodo, $C_{1-6}$alkyl, $C_{1-6}$alkyl substituted with from 1 to 6 substituents independently selected from: fluoro, oxo, —OH, —COOH, —NH$_2$, and —CN, —O$C_{1-5}$alkyl, and —O$C_{1-6}$alkyl substituted with from 1 to 6 substituents independently selected from: fluoro, oxo, —OH, —COOH, —NH$_2$, and —CN, cycloalkyl, cycloalkyl substituted from 1 to 4 times by R$^{xx4}$, where R$^{xx4}$ is selected from: fluoro, chloro, bromo, iodo, $C_{1-6}$alkyl, $C_{1-6}$alkyl substituted with from 1 to 6 substituents independently selected from: fluoro, oxo, —OH, —COOH, —NH$_2$, and —CN, —O$C_{1-5}$alkyl, and —O$C_{1-6}$alkyl substituted with from 1 to 6 substituents independently selected from: fluoro, oxo, —OH, —COOH, —NH$_2$, and —CN nitro, and cyano;

or a pharmaceutically acceptable salt thereof.

Suitably in the compounds of Formula (I), X is selected from: carbon and nitrogen. Suitably in the compounds of Formula (I), X is nitrogen. Suitably in the compounds of Formula (I), X is carbon.

Suitably in the compounds of Formula (I), Y is independently selected from: hydrogen and CH$_3$. Suitably in the compounds of Formula (I), Y$^1$ is absent or CH$_3$. Suitably in the compounds of Formula (I), Y hydrogen. Suitably in the compounds of Formula (I), Y$^1$ is absent.

Suitably in the compounds of Formula (I), Z is NH or O. Suitably in the compounds of Formula (I), Z is NH. Suitably in the compounds of Formula (I), Z is O.

Suitably in the compounds of Formula (I), a is 0 or 1. Suitably in the compounds of Formula (I), a is 0. Suitably in the compounds of Formula (I), a is 1.

Suitably in the compounds of Formula (I), R is selected from: O, NH, CH$_2$ and C$_1$ alkyl substituted by halogen.

Suitably in the compounds of Formula (I), R$^1$ is selected from:

phenyl, phenyl substituted from 1 to 3 times by R$^a$, benzothiazolyl, benzothiazolyl substituted from 1 to 3 times by R$^a$, quinolinyl, quinolinyl substituted from 1 to 3 times by R$^a$, thienopyridinyl, thienopyridinyl substituted from 1 to 3 times by R$^a$, benzofuranyl, benzofuranyl substituted from 1 to 3 times by R$^a$, quinazolinyl, quinazolinyl substituted from 1 to 3 times by R$^a$, benzoimidazolyl, benzoimidazolyl substituted from 1 to 3 times by R$^a$, imidazopyridinyl, imidazopyridinyl substituted from 1 to 3 times by R$^a$, benzoisothiazolyl, and benzoisothiazolyl substituted from 1 to 3 times by R$^a$;

where each R$^a$ is independently selected from:

fluoro, chloro, bromo,

—CH$_3$,

—CH$_2$CH$_3$,

—OCH$_3$,

—OCF$_3$, and

—OCHF$_2$.

Suitably in the compounds of Formula (I), R$^2$ is selected from: O and S, suitably O.

Suitably in the compounds of Formula (I), R$^3$ is selected from:

cyclohexyl, cyclohexyl substituted from 1 to 3 times by R$^b$, tetrazolyl, tetrazolyl substituted from 1 to 3 times by R$^b$, azetidinyl, azetidinyl substituted from 1 to 3 times by R$^b$, cyclobutanyl, cyclobutanyl substituted from 1 to 3 times by R$^b$, thiazolyl, thiazolyl substituted from 1 to 3 times by R$^b$, oxadiazolyl, oxadiazolyl substituted from 1 to 3 times by R$^b$, piperidinyl, piperidinyl substituted from 1 to 3 times by R$^b$, pyrimidinyl, pyrimidinyl substituted from 1 to 3 times by R$^b$, indolinyl, indolinyl substituted from 1 to 3 times by R$^b$, tetrahydroquinolinyl, tetrahydroquinolinyl substituted from 1 to 3 times by R$^b$, pyridinyl, pyridinyl substituted from 1 to 3 times by R$^b$, tetrahydropyranyl, tetrahydropyranyl substituted from 1 to 3 times by R$^b$, pyrrolidinyl,
pyrrolidinyl substituted from 1 to 3 times by $R^b$,
spiroheptanyl,
spiroheptanyl substituted from 1 to 3 times by $R^b$,
morpholinyl,
morpholinyl substituted from 1 to 3 times by $R^b$,
indolinyl,
indolinyl substituted from 1 to 3 times by $R^b$,
azaspiroheptanyl,
azaspiroheptanyl substituted from 1 to 3 times by $R^b$,
oxazolyl,
oxazolyl substituted from 1 to 3 times by $R^b$,
thiadiazolyl,
thiadiazolyl substituted from 1 to 3 times by $R^b$,
triazolyl,
triazolyl substituted from 1 to 3 times by $R^b$,
dihydroindenyl,
dihydroindenyl substituted from 1 to 3 times by $R^b$,
2-azaspiro[3.3]heptane,
2-azaspiro[3.3]heptane substituted from 1 to 3 times by $R^b$,
pyridazinyl,
pyridazinyl substituted from 1 to 3 times by $R^b$,
pyrazinyl,
pyrazinyl substituted from 1 to 3 times by $R^b$,
thiophenyl,
thiophenyl substituted from 1 to 3 times by $R^b$,
tetrahydrothiophenyl,
tetrahydrothiophenyl substituted from 1 to 3 times by $R^b$,
furanyl, and
furanyl substituted from 1 to 3 times by $R^b$;
where each $R^b$ is independently selected from:
—C(OH)(CH$_3$)$_2$,
—CH$_2$CH$_2$CH$_2$CH$_3$,
—CH$_3$,
—OH
cyano,
—OCH$_2$CH(OH)cyclopropyl,
—OCH$_2$C(CH$_3$)(OH)cyclopropyl,
—CH$_2$OH,
—NH$_2$,
—CH$_2$CHF$_2$,
—C(CH$_3$)$_3$,
—NHCH(CF$_3$)CH$_2$OH,
—CH(CH$_3$)CHF$_2$,
—NHCH(CH$_3$)CHF$_2$,
oxo,
—CH(CH$_3$)OH,
—CH(OH)cyclopropyl,
—C(CH$_3$)(CF$_3$)OH,
—C(O)OCH$_2$CH$_3$,
—C(O)cyclopropyl,
—OCH$_2$C(OH)(CH$_3$)$_2$,
—C(O)CH$_3$,
—OCH$_2$CH$_2$OCH$_3$,
—C(NHCH$_3$)Ncyano,
—NHC(O)OC(CH$_3$)$_3$,
—NHC(O)NHcyclohexyl,
NHpyrimidinyl,
—CH(CH$_3$)CF$_3$,
—C(O)OCH$_2$phenyl,
—C(O)NHtetrahydropyran,
—CH$_2$CF$_3$,
—C(O)OCH$_3$,
—C(O)OC(CH$_3$)$_3$,
—S(O)$_2$CH$_3$,
cyclopropyl,
—OCH$_3$,
—CH$_2$(chloro-methoxyphenyl),
—C(O)N(CH$_3$)$_2$,
—NHCH(CF$_3$)CH$_3$,
—NHC(CH$_3$)(OH)CHF$_2$,
—C(O)NH$_2$,
—C(O)OH,
—C(O)NH(CH$_3$),
—CH(CH$_3$)$_2$,
—CF$_3$,
—C(CH$_2$)CH$_3$,
—CH$_2$C(OH)(CH$_3$)$_2$,
—C(O)CH$_2$CH$_3$,
fluoro,
—CH$_2$C(O)CH$_2$CH$_3$,
—CH$_2$C(O)OCH$_2$CH$_3$,
thiazolyl,
thiazolyl substituted 1 or 2 times by $R^f$,
pyrimidinyl,
pyrimidinyl substituted 1 or 2 times by $R^f$,
pyridinyl,
pyridinyl substituted 1 or 2 times by $R^f$,
azetidinyl,
azetidinyl substituted 1 or 2 times by $R^f$,
oxazolyl,
oxazolyl substituted 1 or 2 times by $R^f$,
oxadiazolyl,
oxadiazolyl substituted 1 or 2 times by $R^f$,
isothiazolidinyl,
isothiazolidinyl substituted 1 or 2 times by $R^f$,
imidazolidinyl,
imidazolidinyl substituted 1 or 2 times by $R^f$,
oxooxazolidinyl,
oxooxazolidinyl substituted 1 or 2 times by $R^f$,
morpholinyl,
morpholinyl substituted 1 or 2 times by $R^f$,
tetrazolyl,
tetrazolyl substituted 1 or 2 times by $R^f$,
pyrazinyl,
pyrazinyl substituted 1 or 2 times by $R^f$,
pyridazinyl,
pyridazinyl substituted 1 or 2 times by $R^f$,
pyrazolyl,
pyrazolyl substituted 1 or 2 times by $R^f$,
thiophenyl, and
thiophenyl substituted 1 or 2 times by $R^f$; and
each $R^f$ is independently selected from:
cyano,
—C(NH)OCH$_3$,
—C(O)NH$_2$,
fluoro,
chloro,
—C(O)NH$_2$,
—C(O)NHCH$_3$,
—CH$_3$,
—C(O)OCH$_3$,
—C(O)CH$_3$,
—C(O)OCH$_2$CH$_3$,
—C(OH)(CH$_3$)$_2$,
—NHCH(CH$_3$)$_2$,
—NHCH$_2$CH$_2$OCH$_3$,
—N(CH$_3$)$_2$,
oxo,
—OCH$_3$, and
—C(O)NHCH$_2$CH$_2$OCH$_2$CH$_3$.

Included in the presently invented compounds of Formula (I) are compounds of Formula

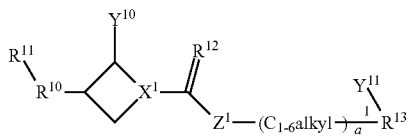

(II)

wherein:
X¹ is selected from: carbon and nitrogen;
Y¹⁰ is selected from: hydrogen and CH₃;
Y¹¹ is absent or CH₃;
Z¹ is NH or O;
a¹ is 0 or 1;
R¹⁰ is selected from: O, NH, CH₂ and C₁ alkyl substituted by halogen;
R¹¹ is selected from:
 aryl,
 aryl substituted from 1 to 3 times by $R^{a1}$,
 bicycloheteroaryl, and
 bicycloheteroaryl substituted from 1 to 3 times by $R^{a1}$;
R¹² is selected from: O and S;
R¹³ is selected from:
 aryl,
 aryl substituted from 1 to 3 times by $R^{b1}$,
 cycloalkyl,
 cycloalkyl substituted from 1 to 3 times by $R^{b1}$,
 heterocycle,
 heterocycle substituted from 1 to 3 times by $R^{b1}$,
 heteroaryl,
 heteroaryl substituted from 1 to 3 times by $R^{b1}$,
 bicycloheteroaryl, and
 bicycloheteroaryl substituted from 1 to 3 times by $R^{b1}$;
each $R^{a1}$ is independently selected from:
 fluoro,
 chloro,
 bromo,
 iodo,
 C₁₋₄alkyl,
 C₁₋₄alkyl substituted with from 1 to 4 substituents independently selected from: fluoro, chloro, bromo, iodo, C₁₋₄alkyloxy, —OH, oxo, and —COOH,
 —OC₁₋₆alkyl substituted with from 1 to 4 substituents independently selected from: fluoro, chloro, bromo, iodo, C₁₋₄alkyloxy, —OH, oxo, and —COOH, and
 —C(O)OC₁₋₃alkyl;
each $R^{b1}$ is independently selected from:
 cyano,
 fluoro,
 chloro,
 C₁₋₆alkyl,
 $R^{e1}$,
 —OC₁₋₆alkyl,
 —$OR^{e1}$,
 oxo,
 hydroxyl,
 cycloalkyl,
 cycloalkyl substituted by $R^{f1}$,
 amino,
 —$NHR^{x10}$,
  where $R^{x10}$ is selected from aryl, heteroaryl, cycloalkyl, heterocycloalkyl, —OC₁₋₆alkyl, —OC₁₋₆alkyl substituted with from 1 to 6 substituents independently selected from:
   fluoro, oxo, and —OH, C₁₋₆alkyl, and C₁₋₆alkyl substituted with from 1 to 6 substituents independently selected from:
   fluoro, oxo, —OH, —COOH, —NH₂, —NHcycloalkyl, and —CN,
 heteroaryl,
 heteroaryl substituted from 1 to 4 times by $R^{f1}$,
 heterocycle,
 heterocycle substituted from 1 to 4 times by $R^{f1}$,
 —SO₂H, and
 —SO₂C₁₋₆alkyl;
each $R^{f1}$ is independently selected from:
 fluoro,
 chloro,
 bromo,
 iodo,
 C₁₋₆alkyl,
 $R^{e1}$,
 oxo,
 —OH,
 amino,
 $NHR^{x11}$,
  where $R^{x11}$ is selected from aryl, heteroaryl, cycloalkyl, heterocycloalkyl, C₁₋₆alkyl, and C₁₋₆alkyl substituted with from 1 to 6 substituents independently selected from:
   fluoro, oxo, —OH, —OC₁₋₆alkyl, —COOH, —NH₂, and —CN,
 —$NR^{x12}R^{x13}$,
  where $R^{x12}$ and $R^{x13}$ are each independently selected from: aryl, heteroaryl, cycloalkyl, heterocycloalkyl, C₁₋₆alkyl, and C₁₋₆alkyl substituted with from 1 to 6 substituents independently selected from: fluoro, oxo, —OH, and —COOH,
 nitro, and
 cyano; and
each $R^{e1}$ is independently selected from:
 C₁₋₆alkyl substituted with from 1 to 9 substituents independently selected from:
 fluoro,
 chloro,
 C₁₋₆alkyl,
 —OC₁₋₆alkyl,
 —OC₁₋₆alkyl substituted with from 1 to 6 substituents independently selected from: fluoro, oxo, —OH, —COOH, —NH₂, and phenyl,
 oxo,
 =N,
 hydroxyl,
 amino,
 —$NHR^{xx10}$, or =$NR^{xx10}$,
  where $R^{xx10}$ is selected from aryl, heteroaryl, cycloalkyl, heterocycloalkyl, cyano, C₁₋₃alkyl, and C₁₋₃alkyl substituted with from 1 to 4 substituents independently selected from: fluoro, oxo, —OH, —COOH, —OC₁₋₅alkyl, —OC₁₋₅alkyl substituted from 1 to 4 times by fluoro,
 —$NR^{xx11}R^{xx12}$,
  where $R^{xx11}$ and $R^{xx12}$ are each independently selected from: aryl, heteroaryl, cycloalkyl, heterocycloalkyl, C₁₋₆alkyl, and C₁₋₆alkyl substituted with from 1 to 6 substituents independently selected from: fluoro, oxo, and —OH,
 aryl,
 aryl substituted from 1 to 4 times by $R^{xx13}$,
  where $R^{xx13}$ is selected from: fluoro, chloro, bromo, iodo, C₁₋₃alkyl, C₁₋₃alkyl substituted with from 1 to 6 substituents independently selected from: fluoro, oxo, —OH, —COOH, —NH$_2$, and —CN, —OC$_{1-3}$alkyl, and —OC$_{1-6}$alkyl substituted from 1 to 6 times by fluoro, cycloalkyl, and cycloalkyl substituted from 1 to 4 times by R$^{xx14}$,
  where R$^{xx14}$ is selected from: fluoro, chloro, bromo, iodo, C$_{1-3}$alkyl, C$_{1-3}$alkyl substituted with from 1 to 6 substituents independently selected from: fluoro, oxo, —OH, —COOH, —NH$_2$, and —CN, and —OC$_{1-6}$alkyl;

or a pharmaceutically acceptable salt thereof.

Suitably in the compounds of Formula (II), X$^1$ is selected from: carbon and nitrogen. Suitably in the compounds of Formula (II), X$^1$ is nitrogen. Suitably in the compounds of Formula (II), X$^1$ is carbon.

Suitably in the compounds of Formula (II), Y$^{10}$ is independently selected from: hydrogen and CH$_3$. Suitably in the compounds of Formula (II), Y$^{11}$ is absent or CH$_3$. Suitably in the compounds of Formula (II), Y$^{10}$ hydrogen. Suitably in the compounds of Formula (II), Y$^{11}$ is absent.

Suitably in the compounds of Formula (II), Z$^1$ is NH or O. Suitably in the compounds of Formula (II), Z$^1$ is NH. Suitably in the compounds of Formula (II), Z$^1$ is O.

Suitably in the compounds of Formula (II), a$^1$ is 0 or 1. Suitably in the compounds of Formula (II), a$^1$ is 0. Suitably in the compounds of Formula (II), a$^1$ is 1.

Suitably in the compounds of Formula (II), R$^{10}$ is selected from: O, NH, CH$_2$ and C$_1$alkyl substituted by halogen.

Suitably in the compounds of Formula (II), R$^{11}$ is selected from:
  phenyl,
  phenyl substituted from 1 to 3 times by R$^{a1}$,
  benzothiazolyl,
  benzothiazolyl substituted from 1 to 3 times by R$^{a1}$,
  quinolinyl,
  quinolinyl substituted from 1 to 3 times by R$^{a1}$,
  thienopyridinyl,
  thienopyridinyl substituted from 1 to 3 times by R$^{a1}$,
  benzofuranyl,
  benzofuranyl substituted from 1 to 3 times by R$^{a1}$,
  quinazolinyl,
  quinazolinyl substituted from 1 to 3 times by R$^{a1}$,
  benzoimidazolyl,
  benzoimidazolyl substituted from 1 to 3 times by R$^{a1}$,
  imidazopyridinyl,
  imidazopyridinyl substituted from 1 to 3 times by R$^{a1}$,
  benzoisothiazolyl, and
  benzoisothiazolyl substituted from 1 to 3 times by R$^{a1}$;
where each R$^{a1}$ is independently selected from:
  fluoro,
  chloro,
  bromo,
  —CH$_3$,
  —CH$_2$CH$_3$,
  —OCH$_3$,
  —OCF$_3$, and
  —OCHF$_2$.

Suitably in the compounds of Formula (II), R$^{12}$ is selected from: O and S, suitably O.

Suitably in the compounds of Formula (II), R$^{13}$ is selected from:
  cyclohexyl,
  cyclohexyl substituted from 1 to 3 times by R$^{b1}$,
  tetrazolyl,
  tetrazolyl substituted from 1 to 3 times by R$^{b1}$,
  azetidinyl,
  azetidinyl substituted from 1 to 3 times by R$^{b1}$,
  cyclobutanyl,
  cyclobutanyl substituted from 1 to 3 times by R$^{b1}$,
  thiazolyl,
  thiazolyl substituted from 1 to 3 times by R$^{b1}$,
  oxadiazolyl,
  oxadiazolyl substituted from 1 to 3 times by R$^{b1}$,
  piperidinyl,
  piperidinyl substituted from 1 to 3 times by R$^{b1}$,
  pyrimidinyl,
  pyrimidinyl substituted from 1 to 3 times by R$^{b1}$,
  indolinyl,
  indolinyl substituted from 1 to 3 times by R$^{b1}$,
  tetrahydroquinolinyl,
  tetrahydroquinolinyl substituted from 1 to 3 times by R$^{b1}$,
  pyridinyl,
  pyridinyl substituted from 1 to 3 times by R$^{b1}$,
  tetrahydropyranyl,
  tetrahydropyranyl substituted from 1 to 3 times by R$^{b1}$,
  pyrrolidinyl,
  pyrrolidinyl substituted from 1 to 3 times by R$^{b1}$,
  spiroheptanyl,
  spiroheptanyl substituted from 1 to 3 times by R$^{b1}$,
  morpholinyl,
  morpholinyl substituted from 1 to 3 times by R$^{b1}$,
  indolinyl,
  indolinyl substituted from 1 to 3 times by R$^{b1}$,
  azaspiroheptanyl,
  azaspiroheptanyl substituted from 1 to 3 times by R$^{b1}$,
  oxazolyl,
  oxazolyl substituted from 1 to 3 times by R$^{b1}$,
  thiadiazolyl,
  thiadiazolyl substituted from 1 to 3 times by R$^{b1}$,
  triazolyl,
  triazolyl substituted from 1 to 3 times by R$^{b1}$
  dihydroindenyl,
  dihydroindenyl substituted from 1 to 3 times by R$^{b1}$,
  2-azaspiro[3.3]heptane,
  2-azaspiro[3.3]heptane substituted from 1 to 3 times by R$^{b1}$,
  pyridazinyl,
  pyridazinyl substituted from 1 to 3 times by R$^{b1}$,
  pyrazinyl,
  pyrazinyl substituted from 1 to 3 times by R$^{b1}$,
  thiophenyl,
  thiophenyl substituted from 1 to 3 times by R$^{b1}$,
  tetrahydrothiophenyl,
  tetrahydrothiophenyl substituted from 1 to 3 times by R$^{b1}$,
  furanyl, and
  furanyl substituted from 1 to 3 times by R$^{b1}$;
where each R$^{b1}$ is independently selected from:
  —C(OH)(CH$_3$)$_2$,
  —CH$_2$CH$_2$CH$_2$CH$_3$,
  —CH$_3$,
  —OH
  cyano,
  —OCH$_2$CH(OH)cyclopropyl,
  —OCH$_2$C(CH$_3$)(OH)cyclopropyl,
  —CH$_2$OH,
  —NH$_2$,
  —CH$_2$CHF$_2$,
  —C(CH$_3$)$_3$,
  —NHCH(CF$_3$)CH$_2$OH,
  —CH(CH$_3$)CHF$_2$,
  —NHCH(CH$_3$)CHF$_2$, oxo,
—CH(CH₃)OH,
—CH(OH)cyclopropyl,
—C(CH₃)(CF₃)OH,
—C(O)OCH₂CH₃,
—C(O)cyclopropyl,
—OCH₂C(OH)(CH₃)₂,
—C(O)CH₃,
—OCH₂CH₂OCH₃,
—C(NHCH₃)Ncyano,
—NHC(O)OC(CH₃)₃,
—NHC(O)NHcyclohexyl,
NHpyrimidinyl,
—CH(CH₃)CF₃,
—C(O)OCH₂phenyl,
—C(O)NHtetrahydropyran,
—CH₂CF₃,
—C(O)OCH₃,
—C(O)OC(CH₃)₃,
—S(O)₂CH₃,
cyclopropyl,
—OCH₃,
—CH₂(chloro-methoxyphenyl),
—C(O)N(CH₃)₂,
—NHCH(CF₃)CH₃,
—NHC(CH₃)(OH)CHF₂,
—C(O)NH₂,
—C(O)OH,
—C(O)NH(CH₃),
—CH(CH₃)₂,
—CF₃,
—C(CH₂)CH₃,
—CH₂C(OH)(CH₃)₂,
—C(O)CH₂CH₃,
fluoro,
—CH₂C(O)CH₂CH₃,
—CH₂C(O)OCH₂CH₃,
thiazolyl,
thiazolyl substituted 1 or 2 times by $R^{f1}$,
pyrimidinyl,
pyrimidinyl substituted 1 or 2 times by $R^{f1}$,
pyridinyl,
pyridinyl substituted 1 or 2 times by $R^{f1}$,
azetidinyl,
azetidinyl substituted 1 or 2 times by $R^{f1}$,
oxazolyl,
oxazolyl substituted 1 or 2 times by $R^{f1}$,
oxadiazolyl,
oxadiazolyl substituted 1 or 2 times by $R^{f1}$,
isothiazolidinyl,
isothiazolidinyl substituted 1 or 2 times by $R^{f1}$,
imidazolidinyl,
imidazolidinyl substituted 1 or 2 times by $R^{f1}$,
oxooxazolidinyl,
oxooxazolidinyl substituted 1 or 2 times by $R^{f1}$,
morpholinyl,
morpholinyl substituted 1 or 2 times by $R^{f1}$,
tetrazolyl,
tetrazolyl substituted 1 or 2 times by $R^{f1}$,
pyrazinyl,
pyrazinyl substituted 1 or 2 times by $R^{f1}$,
pyridazinyl,
pyridazinyl substituted 1 or 2 times by $R^{f1}$,
pyrazolyl,
pyrazolyl substituted 1 or 2 times by $R^{f1}$,
thiophenyl, and
thiophenyl substituted 1 or 2 times by $R^{f1}$; and each $R^{f1}$ is independently selected from:
cyano,
—C(NH)OCH₃,
—C(O)NH₂,
fluoro,
chloro,
—C(O)NH₂,
—C(O)NHCH₃,
—CH₃,
—C(O)OCH₃,
—C(O)CH₃,
—C(O)OCH₂CH₃,
—C(OH)(CH₃)₂,
—NHCH(CH₃)₂,
—NHCH₂CH₂OCH₃,
—N(CH₃)₂,
oxo,
—OCH₃, and
—C(O)NHCH₂CH₂OCH₂CH₃.

Included in the presently invented compounds of Formula (I) are compounds of Formula (III):

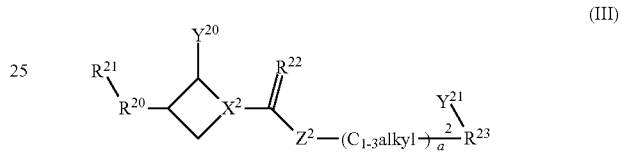

wherein:
$X^2$ is selected from: carbon and nitrogen;
$Y^{20}$ is selected from: hydrogen and CH₃;
$Y^{21}$ is absent or CH₃;
$Z^2$ is NH or O;
$a^2$ is 0 or 1;
$R^{20}$ is selected from: O, NH, CH₂ and C₁ alkyl substituted by halogen;
$R^{21}$ is selected from:
aryl,
aryl substituted from 1 to 3 times by $R^{a2}$,
bicycloheteroaryl, and
bicycloheteroaryl substituted from 1 to 3 times by $R^{a2}$;
$R^{22}$ is selected from: O and S;
$R^{23}$ is selected from:
aryl,
aryl substituted from 1 to 3 times by $R^{b2}$,
cycloalkyl,
cycloalkyl substituted from 1 to 3 times by $R^{b2}$,
heterocycle,
heterocycle substituted from 1 to 3 times by $R^{b2}$,
heteroaryl,
heteroaryl substituted from 1 to 3 times by $R^{b2}$,
bicycloheteroaryl, and
bicycloheteroaryl substituted from 1 to 3 times by $R^{b2}$;
each $R^{a2}$ is independently selected from:
fluoro,
chloro,
bromo,
iodo,
C₁₋₃alkyl,
C₁₋₃alkyl substituted 1 to 4 times by fluoro,
—OC₁₋₄alkyl, and
—OC₁₋₄alkyl substituted 1 to 4 times by fluoro;
each $R^{b2}$ is independently selected from:
cyano,
C₁₋₆alkyl,
$R^{e2}$, —OC$_{1-4}$alkyl,
—OR$^{e2}$,
oxo,
hydroxyl,
cycloalkyl,
amino,
—NHR$^{x20}$,
  where R$^{x20}$ is selected from heteroaryl, —OC$_{1-6}$alkyl,
    —OC$_{1-6}$alkyl substituted 1 to 4 times by fluoro,
    C$_{1-6}$alkyl, and C$_{1-6}$alkyl substituted with from 1 to 4
    substituents independently selected from:
    fluoro, oxo, —OH, —OC$_{1-6}$alkyl, —NH$_2$, and —NH-cycloalkyl,
heteroaryl,
heteroaryl substituted from 1 to 3 times by R$^{f2}$,
heterocycle,
heterocycle substituted from 1 to 3 times by R$^{f2}$,
—SO$_2$H, and
—SO$_2$C$_{1-6}$alkyl;
each R$^{f2}$ is independently selected from:
  fluoro,
  chloro,
  C$_{1-4}$alkyl,
  R$^{e2}$,
  oxo,
  amino,
  —NHR$^{x21}$,
    where R$^{x21}$ is selected from C$_{1-4}$alkyl, and C$_{1-4}$alkyl
      substituted by —OC$_{1-6}$alkyl,
  —NR$^{x22}$R$^{x23}$,
    where R$^{x22}$ and R$^{x23}$ are each independently selected
      from: C$_{1-4}$alkyl, and C$_{1-6}$alkyl substituted 1 to 4
      times by fluoro, and
  cyano; and
each R$^{e2}$ is independently selected from:
  C$_{1-4}$alkyl substituted with from 1 to 4 substituents independently selected from:
    fluoro,
    —OC$_{1-4}$alkyl,
    —OC$_{1-4}$alkyl substituted by phenyl,
    oxo,
    =N,
    hydroxyl,
    amino,
    —NHR$^{xx20}$, or =NR$^{xx20}$,
      where R$^{xx20}$ is selected from cyano, C$_{1-3}$alkyl, and
        C$_{1-3}$alkyl by —OC$_{1-5}$alkyl,
    —NR$^{xx21}$R$^{xx22}$,
      where R$^{xx21}$ and R$^{xx22}$ are each independently
        selected from: C$_{1-4}$alkyl,
  aryl,
  aryl substituted by —OC$_{1-3}$alkyl, and
  cycloalkyl;
or a pharmaceutically acceptable salt thereof.

Suitably in the compounds of Formula (III), X$^2$ is selected from: carbon and nitrogen. Suitably in the compounds of Formula (III), X$^2$ is nitrogen. Suitably in the compounds of Formula (III), X$^2$ is carbon.

Suitably in the compounds of Formula (III), Y$^{20}$ is independently selected from: hydrogen and CH$_3$. Suitably in the compounds of Formula (III), Y$^{21}$ is absent or CH$_3$. Suitably in the compounds of Formula (III), Y$^{20}$ hydrogen. Suitably in the compounds of Formula (III), Y$^{21}$ is absent.

Suitably in the compounds of Formula (III), Z$^2$ is NH or O. Suitably in the compounds of Formula (III), Z$^2$ is NH. Suitably in the compounds of Formula (III), Z$^2$ is O.

Suitably in the compounds of Formula (III), a$^2$ is 0 or 1. Suitably in the compounds of Formula (III), a$^2$ is 0. Suitably in the compounds of Formula (III), a$^2$ is 1.

Suitably in the compounds of Formula (III), R$^{00}$ is selected from: O, NH, CH$_2$ and C$_1$alkyl substituted by halogen.

Suitably in the compounds of Formula (III), R$^{21}$ is selected from:
  phenyl,
  phenyl substituted from 1 to 3 times by R$^{a2}$,
  benzothiazolyl,
  benzothiazolyl substituted from 1 to 3 times by R$^{a2}$,
  quinolinyl,
  quinolinyl substituted from 1 to 3 times by R$^{a2}$,
  thienopyridinyl,
  thienopyridinyl substituted from 1 to 3 times by R$^{a2}$,
  benzofuranyl,
  benzofuranyl substituted from 1 to 3 times by R$^{a2}$,
  quinazolinyl,
  quinazolinyl substituted from 1 to 3 times by R$^{a2}$,
  benzoimidazolyl,
  benzoimidazolyl substituted from 1 to 3 times by R$^{a2}$,
  imidazopyridinyl,
  imidazopyridinyl substituted from 1 to 3 times by R$^{a2}$,
  benzoisothiazolyl, and
  benzoisothiazolyl substituted from 1 to 3 times by R$^{a2}$;
where each R$^{a2}$ is independently selected from:
  fluoro,
  chloro,
  bromo,
  —CH$_3$,
  —CH$_2$CH$_3$,
  —OCH$_3$,
  —OCF$_3$, and
  —OCHF$_2$.

Suitably in the compounds of Formula (III), R$^{22}$ is selected from: O and S, suitably O.

Suitably in the compounds of Formula (III), R$^{23}$ is selected from:
  cyclohexyl,
  cyclohexyl substituted from 1 to 3 times by R$^{b2}$,
  tetrazolyl,
  tetrazolyl substituted from 1 to 3 times by R$^{b2}$,
  azetidinyl,
  azetidinyl substituted from 1 to 3 times by R$^{b2}$,
  cyclobutanyl,
  cyclobutanyl substituted from 1 to 3 times by R$^{b2}$,
  thiazolyl,
  thiazolyl substituted from 1 to 3 times by R$^{b2}$,
  oxadiazolyl,
  oxadiazolyl substituted from 1 to 3 times by R$^{b2}$,
  piperidinyl,
  piperidinyl substituted from 1 to 3 times by R$^{b2}$,
  pyrimidinyl,
  pyrimidinyl substituted from 1 to 3 times by R$^{b2}$,
  indolinyl,
  indolinyl substituted from 1 to 3 times by R$^{b2}$,
  tetrahydroquinolinyl,
  tetrahydroquinolinyl substituted from 1 to 3 times by R$^{b2}$,
  pyridinyl,
  pyridinyl substituted from 1 to 3 times by R$^{b2}$,
  tetrahydropyranyl,
  tetrahydropyranyl substituted from 1 to 3 times by R$^{b2}$,
  pyrrolidinyl,
  pyrrolidinyl substituted from 1 to 3 times by R$^{b2}$,
  spiroheptanyl,
  spiroheptanyl substituted from 1 to 3 times by R$^{b2}$, morpholinyl,
morpholinyl substituted from 1 to 3 times by $R^{b2}$,
indolinyl,
indolinyl substituted from 1 to 3 times by $R^{b2}$,
azaspiroheptanyl,
azaspiroheptanyl substituted from 1 to 3 times by $R^{b2}$,
oxazolyl,
oxazolyl substituted from 1 to 3 times by $R^{b2}$,
thiadiazolyl,
thiadiazolyl substituted from 1 to 3 times by $R^{b2}$,
triazolyl,
triazolyl substituted from 1 to 3 times by $R^{b2}$,
dihydroindenyl,
dihydroindenyl substituted from 1 to 3 times by $R^{b2}$,
2-azaspiro[3.3]heptane,
2-azaspiro[3.3]heptane substituted from 1 to 3 times by $R^{b2}$,
pyridazinyl,
pyridazinyl substituted from 1 to 3 times by $R^{b2}$,
pyrazinyl,
pyrazinyl substituted from 1 to 3 times by $R^{b2}$,
thiophenyl,
thiophenyl substituted from 1 to 3 times by $R^{b2}$,
tetrahydrothiophenyl,
tetrahydrothiophenyl substituted from 1 to 3 times by $R^{b2}$,
furanyl, and
furanyl substituted from 1 to 3 times by $R^{b2}$;
where each $R^{b2}$ is independently selected from:
—C(OH)(CH$_3$)$_2$,
—CH$_2$CH$_2$CH$_2$CH$_3$,
—CH$_3$,
—OH,
cyano,
—OCH$_2$CH(OH)cyclopropyl,
—OCH$_2$C(CH$_3$)(OH)cyclopropyl,
—CH$_2$OH,
—NH$_2$,
—CH$_2$CHF$_2$,
—C(CH$_3$)$_3$,
—NHCH(CF$_3$)CH$_2$OH,
—CH(CH$_3$)CHF$_2$,
—NHCH(CH$_3$)CHF$_2$,
oxo,
—CH(CH$_3$)OH,
—CH(OH)cyclopropyl,
—C(CH$_3$)(CF$_3$)OH,
—C(O)OCH$_2$CH$_3$,
—C(O)cyclopropyl,
—OCH$_2$C(OH)(CH$_3$)$_2$,
—C(O)CH$_3$,
—OCH$_2$CH$_2$OCH$_3$,
—C(NHCH$_3$)Ncyano,
—NHC(O)OC(CH$_3$)$_3$,
—NHC(O)NHcyclohexyl,
NHpyrimidinyl,
—CH(CH$_3$)CF$_3$,
—C(O)OCH$_2$phenyl,
—C(O)NHtetrahydropyran,
—CH$_2$CF$_3$,
—C(O)OCH$_3$,
—C(O)OC(CH$_3$)$_3$,
—S(O)$_2$CH$_3$,
cyclopropyl,
—OCH$_3$,
—CH$_2$(chloro-methoxyphenyl),
—C(O)N(CH$_3$)$_2$,
—NHCH(CF$_3$)CH$_3$,
—NHC(CH$_3$)(OH)CHF$_2$,
—C(O)NH$_2$,
—C(O)OH,
—C(O)NH(CH$_3$),
—CH(CH$_3$)$_2$,
—CF$_3$,
—C(CH$_2$)CH$_3$,
—CH$_2$C(OH)(CH$_3$)$_2$,
—C(O)CH$_2$CH$_3$,
fluoro,
—CH$_2$C(O)CH$_2$CH$_3$,
—CH$_2$C(O)OCH$_2$CH$_3$,
thiazolyl,
thiazolyl substituted 1 or 2 times by $R^{f2}$,
pyrimidinyl,
pyrimidinyl substituted 1 or 2 times by $R^{f2}$,
pyridinyl,
pyridinyl substituted 1 or 2 times by $R^{f2}$,
azetidinyl,
azetidinyl substituted 1 or 2 times by $R^{f2}$,
oxazolyl,
oxazolyl substituted 1 or 2 times by $R^{f2}$,
oxadiazolyl,
oxadiazolyl substituted 1 or 2 times by $R^{f2}$,
isothiazolidinyl,
isothiazolidinyl substituted 1 or 2 times by $R^{f2}$,
imidazolidinyl,
imidazolidinyl substituted 1 or 2 times by $R^{f2}$,
oxooxazolidinyl,
oxooxazolidinyl substituted 1 or 2 times by $R^{f2}$,
morpholinyl,
morpholinyl substituted 1 or 2 times by $R^{f2}$,
tetrazolyl,
tetrazolyl substituted 1 or 2 times by $R^{f2}$,
pyrazinyl,
pyrazinyl substituted 1 or 2 times by $R^{f2}$,
pyridazinyl,
pyridazinyl substituted 1 or 2 times by $R^{f2}$,
pyrazolyl,
pyrazolyl substituted 1 or 2 times by $R^{f2}$,
thiophenyl, and
thiophenyl substituted 1 or 2 times by $R^{f2}$; and
each $R^{f2}$ is independently selected from:
cyano,
—C(NH)OCH$_3$,
—C(O)NH$_2$,
fluoro,
chloro,
—C(O)NH$_2$,
—C(O)NHCH$_3$,
—CH$_3$,
—C(O)OCH$_3$,
—C(O)CH$_3$,
—C(O)OCH$_2$CH$_3$,
—C(OH)(CH$_3$)$_2$,
—NHCH(CH$_3$)$_2$,
—NHCH$_2$CH$_2$OCH$_3$,
—N(CH$_3$)$_2$,
oxo,
—OCH$_3$, and
—C(O)NHCH$_2$CH$_2$OCH$_2$CH$_3$.

Included in the presently invented compounds of Formula (I) are compounds of Formula (IV):

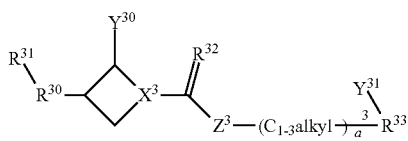
(IV)

wherein:
X³ is selected from: carbon and nitrogen;
Y³⁰ is selected from: hydrogen and CH₃;
Y³¹ is absent or CH₃;
Z³ is NH or O;
a³ is 0 or 1;
R³⁰ is selected from: O, NH, CH₂ and C₁ alkyl substituted by halogen;
R³¹ is selected from:
  phenyl,
  phenyl substituted from 1 to 3 times by R$^{a3}$,
  benzothiazolyl,
  benzothiazolyl substituted from 1 to 3 times by R$^{a3}$,
  quinolinyl,
  quinolinyl substituted from 1 to 3 times by R$^{a3}$,
  thienopyridinyl,
  thienopyridinyl substituted from 1 to 3 times by R$^{a3}$,
  benzofuranyl,
  benzofuranyl substituted from 1 to 3 times by R$^{a3}$,
  quinazolinyl,
  quinazolinyl substituted from 1 to 3 times by R$^{a3}$,
  benzoimidazolyl,
  benzoimidazolyl substituted from 1 to 3 times by R$^{a3}$,
  imidazopyridinyl,
  imidazopyridinyl substituted from 1 to 3 times by R$^{a3}$,
  benzoisothiazolyl, and
  benzoisothiazolyl substituted from 1 to 3 times by R$^{a3}$;
R³² is selected from: O and S;
R³³ is selected from:
  cyclohexyl,
  cyclohexyl substituted from 1 to 3 times by R$^{b3}$,
  tetrazolyl,
  tetrazolyl substituted from 1 to 3 times by R$^{b3}$,
  azetidinyl,
  azetidinyl substituted from 1 to 3 times by R$^{b3}$,
  cyclobutanyl,
  cyclobutanyl substituted from 1 to 3 times by R$^{b3}$,
  thiazolyl,
  thiazolyl substituted from 1 to 3 times by R$^{b3}$,
  oxadiazolyl,
  oxadiazolyl substituted from 1 to 3 times by R$^{b3}$,
  piperidinyl,
  piperidinyl substituted from 1 to 3 times by R$^{b3}$,
  pyrimidinyl,
  pyrimidinyl substituted from 1 to 3 times by R$^{b3}$,
  indolinyl,
  indolinyl substituted from 1 to 3 times by R$^{b3}$,
  tetrahydroquinolinyl,
  tetrahydroquinolinyl substituted from 1 to 3 times by R$^{b3}$,
  pyridinyl,
  pyridinyl substituted from 1 to 3 times by R$^{b3}$,
  tetrahydropyranyl,
  tetrahydropyranyl substituted from 1 to 3 times by R$^{b3}$,
  pyrrolidinyl,
  pyrrolidinyl substituted from 1 to 3 times by R$^{b3}$,
  spiroheptanyl,
  spiroheptanyl substituted from 1 to 3 times by R$^{b3}$,
  morpholinyl,
  morpholinyl substituted from 1 to 3 times by R$^{b3}$,
  indolinyl,
  indolinyl substituted from 1 to 3 times by R$^{b3}$,
  azaspiroheptanyl,
  azaspiroheptanyl substituted from 1 to 3 times by R$^{b3}$,
  oxazolyl,
  xazolyl substituted from 1 to 3 times by R$^{b3}$,
  thiadiazolyl,
  thiadiazolyl substituted from 1 to 3 times by R$^{b3}$,
  triazolyl,
  triazolyl substituted from 1 to 3 times by R$^{b3}$,
  dihydroindenyl,
  dihydroindenyl substituted from 1 to 3 times by R$^{b3}$,
  2-azaspiro[3.3]heptane,
  2-azaspiro[3.3]heptane substituted from 1 to 3 times by R$^{b3}$,
  pyridazinyl,
  pyridazinyl substituted from 1 to 3 times by R$^{b3}$,
  pyrazinyl,
  pyrazinyl substituted from 1 to 3 times by R$^{b3}$,
  thiophenyl,
  thiophenyl substituted from 1 to 3 times by R$^{b3}$,
  tetrahydrothiophenyl,
  tetrahydrothiophenyl substituted from 1 to 3 times by R$^{b3}$,
  furanyl, and
  furanyl substituted from 1 to 3 times by R$^{b3}$;
each R$^{a3}$ is independently selected from:
  fluoro,
  chloro,
  bromo,
  —CH₃,
  —CH₂CH₃,
  —OCH₃,
  —OCF₃, and
  —OCHF₂;
each R$^{b3}$ is independently selected from:
  —C(OH)(CH₃)₂,
  —CH₂CH₂CH₂CH₃,
  —CH₃,
  —OH
  cyano,
  —OCH₂CH(OH)cyclopropyl,
  —OCH₂C(CH₃)(OH)cyclopropyl,
  —CH₂OH,
  —NH₂,
  —CH₂CHF₂,
  —C(CH₃)₃,
  —NHCH(CF₃)CH₂OH,
  —CH(CH₃)CHF₂,
  —NHCH(CH₃)CHF₂,
  oxo,
  —CH(CH₃)OH,
  —CH(OH)cyclopropyl,
  —C(CH₃)(CF₃)OH,
  —C(O)OCH₂CH₃,
  —C(O)cyclopropyl,
  —OCH₂C(OH)(CH₃)₂,
  —C(O)CH₃,
  —OCH₂CH₂OCH₃,
  —C(NHCH₃)Ncyano,
  —NHC(O)OC(CH₃)₃,
  —NHC(O)NHcyclohexyl,
  NHpyrimidinyl,
  —CH(CH₃)CF₃,
  —C(O)OCH₂phenyl, —C(O)NHtetrahydropyran,
—CH$_2$CF$_3$,
—C(O)OCH$_3$,
—C(O)OC(CH$_3$)$_3$,
—S(O)$_2$CH$_3$,
cyclopropyl,
—OCH$_3$,
—CH$_2$(chloro-methoxyphenyl),
—C(O)N(CH$_3$)$_2$,
—NHCH(CF$_3$)CH$_3$,
—NHC(CH$_3$)(OH)CHF$_2$,
—C(O)NH$_2$,
—C(O)OH,
—C(O)NH(CH$_3$),
—CH(CH$_3$)$_2$,
—CF$_3$,
—C(CH$_2$)CH$_3$,
—CH$_2$C(OH)(CH$_3$)$_2$,
—C(O)CH$_2$CH$_3$,
fluoro,
—CH$_2$C(O)CH$_2$CH$_3$,
—CH$_2$C(O)OCH$_2$CH$_3$,
thiazolyl,
thiazolyl substituted 1 or 2 times by R$^{f3}$,
pyrimidinyl,
pyrimidinyl substituted 1 or 2 times by R$^{f3}$,
pyridinyl,
pyridinyl substituted 1 or 2 times by R$^{f3}$,
azetidinyl,
azetidinyl substituted 1 or 2 times by R$^{f3}$,
oxazolyl,
oxazolyl substituted 1 or 2 times by R$^{f3}$,
oxadiazolyl,
oxadiazolyl substituted 1 or 2 times by R$^{f3}$,
isothiazolidinyl,
isothiazolidinyl substituted 1 or 2 times by R$^{f3}$,
imidazolidinyl,
imidazolidinyl substituted 1 or 2 times by R$^{f3}$,
oxooxazolidinyl,
oxooxazolidinyl substituted 1 or 2 times by R$^{f3}$,
morpholinyl,
morpholinyl substituted 1 or 2 times by R$^{f3}$,
tetrazolyl,
tetrazolyl substituted 1 or 2 times by R$^{f3}$,
pyrazinyl,
pyrazinyl substituted 1 or 2 times by R$^{f3}$,
pyridazinyl,
pyridazinyl substituted 1 or 2 times by R$^{f3}$,
pyrazolyl,
pyrazolyl substituted 1 or 2 times by R$^{f3}$,
thiophenyl, and
thiophenyl substituted 1 or 2 times by R$^{f3}$; and
each R$^{f3}$ is independently selected from:
cyano,
—C(NH)OCH$_3$,
—C(O)NH$_2$,
fluoro,
chloro,
—C(O)NH$_2$,
—C(O)NHCH$_3$,
—CH$_3$,
—C(O)OCH$_3$,
—C(O)CH$_3$,
—C(O)OCH$_2$CH$_3$,
—C(OH)(CH$_3$)$_2$,
—NHCH(CH$_3$)$_2$,
—NHCH$_2$CH$_2$OCH$_3$,
—N(CH$_3$)$_2$,
oxo,
—OCH$_3$, and
—C(O)NHCH$_2$CH$_2$OCH$_2$CH$_3$;
or a pharmaceutically acceptable salt thereof.

Suitably in the compounds of Formula (IV), X$^3$ is selected from: carbon and nitrogen. Suitably in the compounds of Formula (IV), X$^3$ is nitrogen. Suitably in the compounds of Formula (IV), X$^3$ is carbon.

Suitably in the compounds of Formula (IV), Y$^{30}$ is independently selected from: hydrogen and CH$_3$. Suitably in the compounds of Formula (IV), Y$^{31}$ is absent or CH$_3$. Suitably in the compounds of Formula (IV), Y$^{30}$ hydrogen. Suitably in the compounds of Formula (IV), Y$^{31}$ is absent.

Suitably in the compounds of Formula (IV), Z$^3$ is NH or O. Suitably in the compounds of Formula (IV), Z$^3$ is NH. Suitably in the compounds of Formula (IV), Z$^3$ is O.

Suitably in the compounds of Formula (IV), a$^3$ is 0 or 1. Suitably in the compounds of Formula (IV), a$^3$ is 0. Suitably in the compounds of Formula (IV), a$^3$ is 1.

Suitably in the compounds of Formula (IV), R$^{30}$ is selected from: O, NH, CH$_2$ and C$_1$alkyl substituted by halogen.

Suitably in the compounds of Formula (IV), R$^{31}$ is selected from:
phenyl,
phenyl substituted from 1 to 3 times by R$^{a3}$,
benzothiazolyl,
benzothiazolyl substituted from 1 to 3 times by R$^{a3}$,
quinolinyl,
quinolinyl substituted from 1 to 3 times by R$^{a3}$,
thienopyridinyl,
thienopyridinyl substituted from 1 to 3 times by R$^{a3}$,
benzofuranyl,
benzofuranyl substituted from 1 to 3 times by R$^{a3}$,
quinazolinyl,
quinazolinyl substituted from 1 to 3 times by R$^{a3}$,
benzoimidazolyl,
benzoimidazolyl substituted from 1 to 3 times by R$^{a3}$,
imidazopyridinyl,
imidazopyridinyl substituted from 1 to 3 times by R$^{a3}$,
benzoisothiazolyl, and
benzoisothiazolyl substituted from 1 to 3 times by R$^{a3}$;
where each R$^{a3}$ is independently selected from:
fluoro,
chloro,
bromo,
—CH$_3$,
—CH$_2$CH$_3$,
—OCH$_3$,
—OCF$_3$, and
—OCHF$_2$.

Suitably in the compounds of Formula (IV), R$^{32}$ is selected from: O and S, suitably O.

Suitably in the compounds of Formula (IV), R$^{33}$ is selected from:
cyclohexyl,
cyclohexyl substituted from 1 to 3 times by R$^{b3}$,
tetrazolyl,
tetrazolyl substituted from 1 to 3 times by R$^{b3}$,
azetidinyl,
azetidinyl substituted from 1 to 3 times by R$^{b3}$,
cyclobutanyl,
cyclobutanyl substituted from 1 to 3 times by R$^{b3}$,
thiazolyl,
thiazolyl substituted from 1 to 3 times by R$^{b3}$, oxadiazolyl,
oxadiazolyl substituted from 1 to 3 times by $R^{b3}$,
piperidinyl,
piperidinyl substituted from 1 to 3 times by $R^{b3}$,
pyrimidinyl,
pyrimidinyl substituted from 1 to 3 times by $R^{b3}$,
indolinyl,
indolinyl substituted from 1 to 3 times by $R^{b3}$,
tetrahydroquinolinyl,
tetrahydroquinolinyl substituted from 1 to 3 times by $R^{b3}$,
pyridinyl,
pyridinyl substituted from 1 to 3 times by $R^{b3}$,
tetrahydropyranyl,
tetrahydropyranyl substituted from 1 to 3 times by $R^{b3}$,
pyrrolidinyl,
pyrrolidinyl substituted from 1 to 3 times by $R^{b3}$,
spiroheptanyl,
spiroheptanyl substituted from 1 to 3 times by $R^{b3}$,
morpholinyl,
morpholinyl substituted from 1 to 3 times by $R^{b3}$,
indolinyl,
indolinyl substituted from 1 to 3 times by $R^{b3}$,
azaspiroheptanyl,
azaspiroheptanyl substituted from 1 to 3 times by $R^{b3}$,
oxazolyl,
oxazolyl substituted from 1 to 3 times by $R^{b3}$,
thiadiazolyl,
thiadiazolyl substituted from 1 to 3 times by $R^{b3}$,
triazolyl,
triazolyl substituted from 1 to 3 times by $R^{b3}$,
dihydroindenyl,
dihydroindenyl substituted from 1 to 3 times by $R^{b3}$,
2-azaspiro[3.3]heptane,
2-azaspiro[3.3]heptane substituted from 1 to 3 times by $R^{b3}$,
pyridazinyl,
pyridazinyl substituted from 1 to 3 times by $R^{b3}$,
pyrazinyl,
pyrazinyl substituted from 1 to 3 times by $R^{b3}$,
thiophenyl,
thiophenyl substituted from 1 to 3 times by $R^{b3}$,
tetrahydrothiophenyl,
tetrahydrothiophenyl substituted from 1 to 3 times by $R^{b3}$,
furanyl, and
furanyl substituted from 1 to 3 times by $R^{b3}$;
where each $R^{b3}$ is independently selected from:
—C(OH)(CH$_3$)$_2$,
—CH$_2$CH$_2$CH$_2$CH$_3$,
—CH$_3$,
—OH
cyano,
—OCH$_2$CH(OH)cyclopropyl,
—OCH$_2$C(CH$_3$)(OH)cyclopropyl,
—CH$_2$OH,
—NH$_2$,
—CH$_2$CHF$_2$,
—C(CH$_3$)$_3$,
—NHCH(CF$_3$)CH$_2$OH,
—CH(CH$_3$)CHF$_2$,
—NHCH(CH$_3$)CHF$_2$,
oxo,
—CH(CH$_3$)OH,
—CH(OH)cyclopropyl,
—C(CH$_3$)(CF$_3$)OH,
—C(O)OCH$_2$CH$_3$,
—C(O)cyclopropyl,
—OCH$_2$C(OH)(CH$_3$)$_2$,
—C(O)CH$_3$,
—OCH$_2$CH$_2$OCH$_3$,
—C(NHCH$_3$)Ncyano,
—NHC(O)OC(CH$_3$)$_3$,
—NHC(O)NHcyclohexyl,
NHpyrimidinyl,
—CH(CH$_3$)CF$_3$,
—C(O)OCH$_2$phenyl,
—C(O)NHtetrahydropyran,
—CH$_2$CF$_3$,
—C(O)OCH$_3$,
—C(O)OC(CH$_3$)$_3$,
—S(O)$_2$CH$_3$,
cyclopropyl,
—OCH$_3$,
—CH$_2$(chloro-methoxyphenyl),
—C(O)N(CH$_3$)$_2$,
—NHCH(CF$_3$)CH$_3$,
—NHC(CH$_3$)(OH)CHF$_2$,
—C(O)NH$_2$,
—C(O)OH,
—C(O)NH(CH$_3$),
—CH(CH$_3$)$_2$,
—CF$_3$,
—C(CH$_2$)CH$_3$,
—CH$_2$C(OH)(CH$_3$)$_2$,
—C(O)CH$_2$CH$_3$,
fluoro,
—CH$_2$C(O)CH$_2$CH$_3$,
—CH$_2$C(O)OCH$_2$CH$_3$,
thiazolyl,
thiazolyl substituted 1 or 2 times by $R^{f3}$,
pyrimidinyl,
pyrimidinyl substituted 1 or 2 times by $R^{f3}$,
pyridinyl,
pyridinyl substituted 1 or 2 times by $R^{f3}$,
azetidinyl,
azetidinyl substituted 1 or 2 times by $R^{f3}$,
oxazolyl,
oxazolyl substituted 1 or 2 times by $R^{f3}$,
oxadiazolyl,
oxadiazolyl substituted 1 or 2 times by $R^{f3}$,
isothiazolidinyl,
isothiazolidinyl substituted 1 or 2 times by $R^{f3}$,
imidazolidinyl,
imidazolidinyl substituted 1 or 2 times by $R^{f3}$,
oxooxazolidinyl,
oxooxazolidinyl substituted 1 or 2 times by $R^{f3}$,
morpholinyl,
morpholinyl substituted 1 or 2 times by $R^{f3}$,
tetrazolyl,
tetrazolyl substituted 1 or 2 times by $R^{f3}$,
pyrazinyl,
pyrazinyl substituted 1 or 2 times by $R^{f3}$,
pyridazinyl,
pyridazinyl substituted 1 or 2 times by $R^{f3}$,
pyrazolyl,
pyrazolyl substituted 1 or 2 times by $R^{f3}$,
thiophenyl, and
thiophenyl substituted 1 or 2 times by $R^{f3}$; and
each $R^{f3}$ is independently selected from:
cyano,
—C(NH)OCH$_3$,
—C(O)NH$_2$,
fluoro,
chloro,
—C(O)NH$_2$,
—C(O)NHCH$_3$, —CH₃,
—C(O)OCH₃,
—C(O)CH₃,
—C(O)OCH₂CH₃,
—C(OH)(CH₃)₂,
—NHCH(CH₃)₂,
—NHCH₂CH₂OCH₃,
—N(CH₃)₂,
oxo,
—OCH₃, and
—C(O)NHCH₂CH₂OCH₂CH₃.

Included in the presently invented compounds of Formula (I) are:

3-(2-(Difluoromethoxy)-5-fluorophenoxy)-N-((trans)-4-(2-hydroxypropan-2-yl)cyclohexyl)azetidine-1-carboxamide;
(trans)-N-(1-Butyl-1H-tetrazol-5-yl)-3-(2-(difluoromethoxy)-5-fluorophenoxy)cyclobutanecarboxamide;
(trans)-3-(2-(Difluoromethoxy)-5-fluorophenoxy)-N-(1-methyl-1H-tetrazol-5-yl)cyclobutanecarboxamide;
(trans)-N-(1-(5-Cyanothiazol-2-yl)azetidin-3-yl)-3-(2-(difluoromethoxy)-5-fluorophenoxy)cyclobutanecarboxamide;
Methyl 2-(3-((trans)-3-(2-(difluoromethoxy)-5-fluorophenoxy)cyclobutanecarboxamido)azetidin-1-yl)thiazole-5-carbimidate;
2-(3-((trans)-3-(2-(Difluoromethoxy)-5-fluorophenoxy)cyclobutanecarboxamido)azetidin-1-yl)thiazole-5-carboxamide;
2-(3-((trans)-3-(2-(Difluoromethoxy)-5-fluorophenoxy)cyclobutanecarboxamido)azetidin-1-yl)pyrimidine-4-carboxamide;
(trans)-N-(1-(4-Cyanopyrimidin-2-yl)azetidin-3-yl)-3-(2-(difluoromethoxy)-5-fluorophenoxy)cyclobutanecarboxamide;
(trans)-N-(1-(2-Chloropyrimidin-4-yl)azetidin-3-yl)-3-(2-(difluoromethoxy)-5-fluorophenoxy)cyclobutanecarboxamide;
(trans)-N-(1-(4-Chloropyrimidin-2-yl)azetidin-3-yl)-3-(2-(difluoromethoxy)-5-fluorophenoxy)cyclobutanecarboxamide;
(trans)-3-(2-(Difluoromethoxy)-5-fluorophenoxy)-N-(1-(5-fluoropyrimidin-2-yl)azetidin-3-yl)cyclobutanecarboxamide;
Racemic (trans)-N-((trans)-4-(2-Cyclopropyl-2-hydroxyethoxy)cyclohexyl)-3-(2-(difluoromethoxy)-5-fluorophenoxy)cyclobutanecarboxamide;
(trans)-3-(2-(Difluoromethoxy)-5-fluorophenoxy)-N-((trans)-4-(pyrimidin-2-ylamino)cyclohexyl)cyclobutanecarboxamide;
Racemic (trans)-N-((trans)-4-(2-Cyclopropyl-2-hydroxypropoxy)cyclohexyl)-3-(2-(difluoromethoxy)-5-fluorophenoxy)cyclobutanecarboxamide;
(trans)-3-(2-(Difluoromethoxy)-5-fluorophenoxy)-N-(5-(hydroxymethyl)thiazol-2-yl)cyclobutanecarboxamide;
(trans)-(2-((trans)-3-(2-(Difluoromethoxy)-5-fluorophenoxy)cyclobutanecarboxamido)thiazol-4-yl)methyl3-(2-(difluoromethoxy)-5-fluorophenoxy)cyclobutanecarboxylate;
(trans)-(2-Aminothiazol-4-yl)methyl3-(2-(difluoromethoxy)-5-fluorophenoxy)cyclobutanecarboxylate;
(trans)-3-(2-(Difluoromethoxy)-5-fluorophenoxy)-N-(4-(hydroxymethyl)thiazol-2-yl)cyclobutanecarboxamide;
(trans)-N-(1-(2,2-Difluoroethyl)azetidin-3-yl)-3-(2-(difluoromethoxy)-5-fluorophenoxy)cyclobutanecarboxamide;
(trans)-N-(5-(tert-Butyl)-1,3,4-oxadiazol-2-yl)-3-(2-(difluoromethoxy)-5-fluorophenoxy)cyclobutanecarboxamide;
(trans)-3-(2-(Difluoromethoxy)-5-fluorophenoxy)-N-(1-(pyrimidin-2-yl)azetidin-3-yl)cyclobutanecarboxamide;
(trans)-3-(2-(Difluoromethoxy)-5-fluorophenoxy)-N-(1-(pyridin-2-yl)azetidin-3-yl)cyclobutanecarboxamide;
(trans)-N-((trans)-4-(3,3-Difluoroazetidin-1-yl)cyclohexyl)-3-(2-(difluoromethoxy)-5-fluorophenoxy)cyclobutanecarboxamide;
(trans)-3-(2-(Difluoromethoxy)-5-fluorophenoxy)-N-((trans)-4-(((S)-1,1,1-trifluoro-3-hydroxypropan-2-yl)amino)cyclohexyl)cyclobutanecarboxamide;
Racemic (trans)-3-(2-(Difluoromethoxy)-5-fluorophenoxy)-N-(1-(1,1-difluoropropan-2-yl)piperidin-4-yl)cyclobutanecarboxamide;
(trans)-3-(2-(Difluoromethoxy)-5-fluorophenoxy)-N-(pyrimidin-5-yl)cyclobutanecarboxamide;
Racemic (trans)-3-(2-(Difluoromethoxy)-5-fluorophenoxy)-N-((trans)-4-((1,1-difluoropropan-2-yl)amino)cyclohexyl)cyclobutanecarboxamide;
Racemic (trans)-3-(2-(Difluoromethoxy)-5-fluorophenoxy)-N-(2-oxoindolin-1-yl)cyclobutanecarboxamide;
Racemic (trans)-3-(2-(Difluoromethoxy)-5-fluorophenoxy)-N-(2-oxo-1,2,3,4-tetrahydroquinolin-4-yl)cyclobutanecarboxamide;
Racemic (trans)-3-(2-(Difluoromethoxy)-5-fluorophenoxy)-N-(trans)-4-(1-hydroxyethyl)cyclohexyl)cyclobutanecarboxamide;
Racemic (trans)-N-((trans)-4-(Cyclopropyl(hydroxy)methyl)cyclohexyl)-3-(2-(difluoromethoxy)-5-fluorophenoxy)cyclobutanecarboxamide;
Racemic (trans)-3-(2-(Difluoromethoxy)-5-fluorophenoxy)-N-((trans)-4-(1,1,1-trifluoro-2-hydroxypropan-2-yl)cyclohexyl)cyclobutanecarboxamide;
(trans)-3-(2-(Difluoromethoxy)-5-fluorophenoxy)-N-((trans)-4-hydroxy-4-methylcyclohexyl)cyclobutanecarboxamide;
(trans)-3-(2-(Difluoromethoxy)-5-fluorophenoxy)-N-((trans)-3-hydroxy-3-methylcyclobutyl)cyclobutanecarboxamide;
(trans)-3-(2-(Difluoromethoxy)-5-fluorophenoxy)-N-((cis)-3-hydroxy-3-methylcyclobutyl)cyclobutanecarboxamide;
(trans)-3-(2-(Difluoromethoxy)-5-fluorophenoxy)-N-(3-hydroxy-3-methylcyclobutyl)cyclobutanecarboxamide;
Ethyl 2-((trans)-3-(2-(difluoromethoxy)-5-fluorophenoxy)cyclobutanecarboxamido)thiazole-4-carboxylate;
(trans)-N-(4-(Cyclopropanecarbonyl)thiazol-2-yl)-3-(2-(difluoromethoxy)-5-fluorophenoxy)cyclobutanecarboxamide;
(trans)-3-(2-(Difluoromethoxy)-5-fluorophenoxy)-N-((trans)-4-(2-hydroxy-2-methylpropoxy)cyclohexyl)cyclobutanecarboxamide;
(trans)-3-(2-(Difluoromethoxy)-5-fluorophenoxy)-N-((trans)-4-(2-hydroxypropan-2-yl)cyclohexyl)cyclobutanecarboxamide;
(trans)-N-(4-Acetylthiazol-2-yl)-3-(2-(difluoromethoxy)-5-fluorophenoxy)cyclobutanecarboxamide;
6-(3-((trans)-3-(Benzo[d]thiazol-4-yloxy)cyclobutanecarboxamido)azetidin-1-yl)nicotinamide;
(trans)-3-(Benzo[d]thiazol-4-yloxy)-N-(1-(5-cyanopyridin-2-yl)azetidin-3-yl)cyclobutanecarboxamide;
6-(3-((trans)-3-(Benzo[d]thiazol-4-yloxy)cyclobutanecarboxamido)azetidin-1-yl)-N-methylnicotinamide;
(trans)-3-(Benzo[d]thiazol-4-yloxy)-N-(1-(5-methylpyrimidin-2-yl)azetidin-3-yl)cyclobutanecarboxamide;
Racemic 3-(Benzo[d]thiazol-4-yloxy)-N-((trans)-4-((1,1-difluoropropan-2-yl)amino)cyclohexyl)azetidine-1-carboxamide;

(trans)-3-(Benzo[d]thiazol-4-yloxy)-N-(1-(5-fluoropyrimidin-2-yl)piperidin-4-yl)cyclobutanecarboxamide;
3-(Benzo[d]thiazol-7-yloxy)-N-(1-(5-fluoropyrimidin-2-yl)piperidin-4-yl)azetidine-1-carboxamide;
3-(Benzo[d]thiazol-7-yloxy)-N-(1-(5-fluoropyridin-2-yl)azetidin-3-yl)azetidine-1-carboxamide;
(trans)-3-(Benzo[d]thiazol-4-yloxy)-N-(1-(5-fluoropyridin-2-yl)azetidin-3-yl)cyclobutanecarboxamide;
Methyl 2-(3-((trans)-3-(benzo[d]thiazol-4-yloxy)cyclobutanecarboxamido)azetidin-1-yl)oxazole-4-carboxylate;
Racemic (trans)-3-(Benzo[d]thiazol-4-yloxy)-N-((trans)-4-((1,1-difluoropropan-2-yl)amino)cyclohexyl)cyclobutanecarboxamide;
(trans)-N-(1-(4-Acetyloxazol-2-yl)azetidin-3-yl)-3-(benzo[d]thiazol-4-yloxy)cyclobutanecarboxamide;
Ethyl 2-(3-((trans)-3-(benzo[d]thiazol-4-yloxy)cyclobutanecarboxamido)azetidin-1-yl)oxazole-5-carboxylate;
(trans)-3-(Benzo[d]thiazol-4-yloxy)-N-(1-(5-(2-hydroxypropan-2-yl)oxazol-2-yl)azetidin-3-yl)cyclobutanecarboxamide;
(trans)-3-(Benzo[d]thiazol-4-yloxy)-N-(1-(2-methylpyrimidin-4-yl)azetidin-3-yl)cyclobutanecarboxamide;
Racemic (trans)-3-(Benzo[d]thiazol-4-yloxy)-N-((trans)-6-(2-hydroxypropan-2-yl)tetrahydro-2H-pyran-3-yl)cyclobutanecarboxamide;
3-(Benzo[d]thiazol-4-yloxy)-N-(1-(4-cyanopyridin-2-yl)azetidin-3-yl)azetidine-1-carboxamide;
3-(Benzo[d]thiazol-4-yloxy)-N-((trans)-4-(((S)-1,1,1-trifluoro-3-hydroxypropan-2-yl)amino)cyclohexyl)azetidine-1-carboxamide;
3-(Benzo[d]thiazol-4-yloxy)-N-(1-(pyridin-2-yl)azetidin-3-yl)azetidine-1-carboxamide;
(trans)-3-(Benzo[d]thiazol-4-yloxy)-N-(4-(2-hydroxypropan-2-yl)thiazol-2-yl)cyclobutanecarboxamide;
3-(Benzo[d]thiazol-4-yloxy)-N-(4-(2-hydroxypropan-2-yl)thiazol-2-yl)azetidine-1-carboxamide;
3-(Benzo[d]thiazol-4-yloxy)-N-((trans)-4-(3,3-difluoroazetidin-1-yl)cyclohexyl)azetidine-1-carboxamide;
(trans)-3-(Benzo[d]thiazol-4-yloxy)-N-((trans)-4-(2-methoxyethoxy)cyclohexyl)cyclobutanecarboxamide;
3-(Benzo[d]thiazol-4-yloxy)-N-((trans)-4-(2-methoxyethoxy)cyclohexyl)azetidine-1-carboxamide;
3-(Benzo[d]thiazol-4-yloxy)-N-(1-(2-chloropyrimidin-4-yl)azetidin-3-yl)azetidine-1-carboxamide;
3-(Benzo[d]thiazol-4-yloxy)-N-(1-(5-fluoropyrimidin-2-yl)azetidin-3-yl)azetidine-1-carboxamide;
N-(4-Acetylthiazol-2-yl)-3-(benzo[d]thiazol-4-yloxy)azetidine-1-carboxamide;
3-(Benzo[d]thiazol-4-yloxy)-N-(pyridin-4-yl)azetidine-1-carboxamide;
3-(Benzo[d]thiazol-4-yloxy)-N-cyclohexylazetidine-1-carboxamide;
(trans)-3-(Benzo[d]thiazol-4-yloxy)-N-(1-((E)-N'-cyano-N-methylcarbamimidoyl)azetidin-3-yl)cyclobutanecarboxamide;
tert-Butyl ((trans)-3-((trans)-3-(benzo[d]thiazol-4-yloxy)cyclobutanecarboxamido)cyclobutyl)carbamate;
(trans)-3-(Benzo[d]thiazol-4-yloxy)-N-((trans)-3-(3-cyclohexylureido)cyclobutyl)cyclobutanecarboxamide;
(trans)-N-(4-Acetylthiazol-2-yl)-3-(benzo[d]thiazol-4-yloxy)cyclobutanecarboxamide;
(trans)-3-(Benzo[d]thiazol-4-yloxy)-N-(1-(2-chloropyrimidin-4-yl)azetidin-3-yl)cyclobutanecarboxamide;
(trans)-3-(Benzo[d]thiazol-4-yloxy)-N-(1-(2-(isopropylamino)pyrimidin-4-yl)azetidin-3-yl)cyclobutanecarboxamide;
(trans)-3-(Benzo[d]thiazol-4-yloxy)-N-(1-(5-cyanothiazol-2-yl)azetidin-3-yl)cyclobutanecarboxamide;
2-(3-((trans)-3-(Benzo[d]thiazol-4-yloxy)cyclobutanecarboxamido)azetidin-1-yl)thiazole-5-carboxamide;
(trans)-3-(Benzo[d]thiazol-4-yloxy)-N-(1-(2-((2-methoxyethyl)amino)pyrimidin-4-yl)azetidin-3-yl)cyclobutanecarboxamide;
(trans)-3-(Benzo[d]thiazol-4-yloxy)-N-((trans)-3-(pyrimidin-2-ylamino)cyclobutyl)cyclobutanecarboxamide;
(trans)-3-(Benzo[d]thiazol-4-yloxy)-N-(1-(4-chloropyrimidin-2-yl)azetidin-3-yl)cyclobutanecarboxamide;
(trans)-3-(Benzo[d]thiazol-4-yloxy)-N-(1-(4-(dimethylamino)pyrimidin-2-yl)azetidin-3-yl)cyclobutanecarboxamide;
(trans)-3-(Benzo[d]thiazol-4-yloxy)-N-(1-(2-(dimethylamino)pyrimidin-4-yl)azetidin-3-yl)cyclobutanecarboxamide;
2-(3-((trans)-3-(Benzo[d]thiazol-4-yloxy)cyclobutanecarboxamido)azetidin-1-yl)pyrimidine-4-carboxamide;
(trans)-3-(Benzo[d]thiazol-4-yloxy)-N-(1-(4-cyanopyrimidin-2-yl)azetidin-3-yl)cyclobutanecarboxamide;
(trans)-3-(Benzo[d]thiazol-4-yloxy)-N-(1-(5-fluoropyrimidin-2-yl)azetidin-3-yl)cyclobutanecarboxamide;
(trans)-3-(Benzo[d]thiazol-4-yloxy)-N-(5-methyl-1,3,4-oxadiazol-2-yl)cyclobutanecarboxamide;
(trans)-3-(Benzo[d]thiazol-4-yloxy)-N-(1-(pyrimidin-2-yl)azetidin-3-yl)cyclobutanecarboxamide;
(trans)-3-(Benzo[d]thiazol-4-yloxy)-N-(1-(pyridin-2-yl)azetidin-3-yl)cyclobutanecarboxamide;
Racemic (trans)-3-(Benzo[d]thiazol-4-yloxy)-N-(1-(pyridin-2-yl)pyrrolidin-3-yl)cyclobutanecarboxamide;
Racemic (trans)-3-(Benzo[d]thiazol-4-yloxy)-N-(6-(2-hydroxypropan-2-yl)spiro[3.3]heptan-2-yl)cyclobutanecarboxamide;
Racemic (trans)-3-(Benzo[d]thiazol-4-yloxy)-N-(2-oxo-1,2,3,4-tetrahydroquinolin-4-yl)cyclobutanecarboxamide;
(trans)-3-(Benzo[d]thiazol-4-yloxy)-N-((trans)-4-(2-hydroxypropan-2-yl)cyclohexyl)cyclobutanecarboxamide;
Racemic 3-(Benzo[d]thiazol-4-yloxy)-N-(1-(1,1,1-trifluoropropan-2-yl)piperidin-4-yl)azetidine-1-carboxamide;
Racemic 3-(Benzo[d]thiazol-4-yloxy)-N-(1-(pyridin-2-yl)pyrrolidin-3-yl)azetidine-1-carboxamide;
3-(Benzo[d]thiazol-4-yloxy)-N-(1-(pyridin-2-yl)piperidin-4-yl)azetidine-1-carboxamide;
Benzyl 4-(3-(benzo[d]thiazol-4-yloxy)azetidine-1-carboxamido)piperidine-1-carboxylate;
Racemic 3-(Benzo[d]thiazol-4-yloxy)-N-(tetrahydro-2H-pyran-3-yl)azetidine-1-carboxamide;
3-(Benzo[d]thiazol-4-yloxy)-N-(1-(2,2,2-trifluoroethyl)piperidin-4-yl)azetidine-1-carboxamide;
Racemic N-(1-Acetylpiperidin-3-yl)-3-(benzo[d]thiazol-4-yloxy)azetidine-1-carboxamide;
Racemic Methyl 3-(3-(benzo[d]thiazol-4-yloxy)azetidine-1-carboxamido)piperidine-1-carboxylate;
Racemic Methyl 2-((3-(benzo[d]thiazol-4-yloxy)azetidine-1-carboxamido)methyl)morpholine-4-carboxylate;
3-(Benzo[d]thiazol-4-yloxy)-N-((trans)-4-(2-hydroxypropan-2-yl)cyclohexyl)azetidine-1-carbothioamide;
tert-Butyl 4-(3-(benzo[d]thiazol-4-yloxy)azetidine-1-carboxamido)piperidine-1-carboxylate;
3-(Benzo[d]thiazol-4-yloxy)-N-(1-(methylsulfonyl)piperidin-4-yl)azetidine-1-carboxamide;
3-(Benzo[d]thiazol-4-yloxy)-N-(4-(methylsulfonyl)cyclohexyl)azetidine-1-carboxamide;
(S)-3-(Benzo[d]thiazol-4-yloxy)-N-(2-oxopyrrolidin-3-yl)azetidine-1-carboxamide;

Racemic 3-(Benzo[d]thiazol-4-yloxy)-N-((trans)-4-(2-cyclopropyl-2-hydroxypropoxy)cyclohexyl)azetidine-1-carboxamide;
3-(Benzo[d]thiazol-4-yloxy)-N-((trans)-4-(1,1-dioxidoisothiazolidin-2-yl)cyclohexyl)azetidine-1-carboxamide;
3-(Benzo[d]thiazol-4-yloxy)-N-((trans)-4-(3-methyl-2-oxoimidazolidin-1-yl)cyclohexyl)azetidine-1-carboxamide;
3-(Benzo[d]thiazol-4-yloxy)-N-((trans)-4-(2-oxooxazolidin-3-yl)cyclohexyl)azetidine-1-carboxamide;
Racemic 3-(Benzo[d]thiazol-4-yloxy)-N-((trans)-6-(2-hydroxypropan-2-yl)tetrahydro-2H-pyran-3-yl)azetidine-1-carboxamide;
3-(Benzo[d]thiazol-4-yloxy)-N-((trans)-4-hydroxy-4-methylcyclohexyl)azetidine-1-carboxamide;
3-(Benzo[d]thiazol-4-yloxy)-N-((trans)-4-(2-hydroxy-2-methylpropoxy)cyclohexyhazetidine-1-carboxamide;
3-(Benzo[d]thiazol-4-yloxy)-N-(1-(pyrimidin-2-yl)azetidin-3-yl)azetidine-1-carboxamide;
3-(Benzo[d]thiazol-4-yloxy)-N-((trans)-4-(2-hydroxypropan-2-yl)cyclohexyl)azetidine-1-carboxamide;
(trans)-3-(Benzo[d]thiazol-4-yloxy)-N-((trans)-4-(2-hydroxypropan-2-yl)cyclohexyl)cyclobutanecarboxamide;
6-(3-((trans)-3-(6-Fluorobenzo[d]thiazol-4-yloxy)cyclobutanecarboxamido)azetidin-1-yl)nicotinamide;
2-(3-((trans)-3-((6-Fluorobenzo[d]thiazol-4-yl)oxy)cyclobutanecarboxamido)azetidin-1-yl)-5-methylpyridine 1-oxide;
(trans)-3-((6-Fluorobenzo[d]thiazol-4-yl)oxy)-N-(1-(5-methylpyrimidin-2-yl)azetidin-3-yl)cyclobutanecarboxamide;
3-((6-Fluorobenzo[d]thiazol-4-yl)oxy)-N-(1-(5-(hydroxymethyl)pyrimidin-2-yl)azetidin-3-yl)azetidine-1-carboxamide;
(trans)-3-((6-Fluorobenzo[d]thiazol-4-yl)oxy)-N-(1-(5-(hydroxymethyl)pyrimidin-2-yl)azetidin-3-yl)cyclobutanecarboxamide;
(trans)-3-((6-Fluorobenzo[d]thiazol-4-yl)oxy)-N-((trans)-4-(2-methoxyethoxy)cyclohexyl)cyclobutanecarboxamide;
Racemic (trans)-3-((6-Fluorobenzo[d]thiazol-4-yl)oxy)-N-(6-(2-hydroxypropan-2-yl)spiro[3.3]heptan-2-yl)cyclobutanecarboxamide;
(trans)-3-((6-Fluorobenzo[d]thiazol-4-yl)oxy)-N-(1-(5-fluoropyrimidin-2-yl)piperidin-4-yl)cyclobutanecarboxamide;
3-((6-Fluorobenzo[d]thiazol-4-yl)oxy)-N-(1-(5-fluoropyrimidin-2-yl)piperidin-4-yl)azetidine-1-carboxamide;
3-((6-Fluorobenzo[d]thiazol-4-yl)oxy)-N-(1-(5-fluoropyridin-2-yl)azetidin-3-yl)azetidine-1-carboxamide;
(trans)-3-((6-Fluorobenzo[d]thiazol-4-yl)oxy)-N-(1-(5-fluoropyridin-2-yl)azetidin-3-yl)cyclobutanecarboxamide;
Racemic (trans)-N-((trans)-4-((1,1-Difluoropropan-2-yl)amino)cyclohexyl)-3-((6-fluorobenzo[d]thiazol-4-yl)oxy)cyclobutanecarboxamide;
3-((6-Fluorobenzo[d]thiazol-4-yl)oxy)-N-(1-(2-methylpyrimidin-4-yl)azetidin-3-yl)azetidine-1-carboxamide;
(trans)-3-((6-Fluorobenzo[d]thiazol-4-yl)oxy)-N-(1-(2-methylpyrimidin-4-yl)azetidin-3-yl)cyclobutanecarboxamide;
Racemic 3-((6-Fluorobenzo[d]thiazol-4-yl)oxy)-N-((cis)-4-((1,1,1-trifluoro-3-hydroxypropan-2-yl)amino)cyclohexyl)azetidine-1-carboxamide;
Racemic (trans)-3-((6-Fluorobenzo[d]thiazol-4-yl)oxy)-N-((cis)-4-((1,1,1-trifluoro-3-hydroxypropan-2-yl)amino)cyclohexyl)cyclobutanecarboxamide;
Racemic (trans)-3-((6-Fluorobenzo[d]thiazol-4-yl)oxy)-N-((trans)-4-((1,1,1-trifluoro-3-hydroxypropan-2-yl) amino)cyclohexyl)cyclobutanecarboxamide;
Racemic 3-((6-Fluorobenzo[d]thiazol-4-yl)oxy)-N-((trans)-6-(2-hydroxypropan-2-yl)tetrahydro-2H-pyran-3-yl)azetidine-1-carboxamide;
3-((6-Fluorobenzo[d]thiazol-4-yl)oxy)-N-((trans)-4-(2-methoxyethoxy)cyclohexyl)azetidine-1-carboxamide;
3-((6-Fluorobenzo[d]thiazol-4-yl)oxy)-N-(1-(pyrimidin-2-yl)azetidin-3-yl)azetidine-1-carboxamide;
N-(1-(2-Chloropyrimidin-4-yl)azetidin-3-yl)-3-((6-fluorobenzo[d]thiazol-4-yl)oxy)azetidine-1-carboxamide;
(trans)-3-((6-Fluorobenzo[d]thiazol-4-yl)oxy)-N-((cis)-3-hydroxy-3-methylcyclobutyl)cyclobutanecarboxamide;
3-((6-Fluorobenzo[d]thiazol-4-yl)oxy)-N-(1-(pyridin-2-yl)azetidin-3-yl)azetidine-1-carboxamide;
(trans)-3-((6-Fluorobenzo[d]thiazol-4-yl)oxy)-N-(1-(pyrimidin-2-yl)azetidin-3-yl)cyclobutanecarboxamide;
N-(1-(4-Cyanopyridin-2-yl)azetidin-3-yl)-3-((6-fluorobenzo[d]thiazol-4-yl)oxy)azetidine-1-carboxamide;
3-((6-Fluorobenzo[d]thiazol-4-yl)oxy)-N-(1-(5-fluoropyrimidin-2-yl)azetidin-3-yl)azetidine-1-carboxamide;
(trans)-3-((6-Fluorobenzo[d]thiazol-4-yl)oxy)-N-(1-(5-fluoropyrimidin-2-yl)azetidin-3-yl)cyclobutanecarboxamide;
(trans)-3-((6-Fluorobenzo[d]thiazol-4-yl)oxy)-N-(1-(pyridin-2-yl)azetidin-3-yl)cyclobutanecarboxamide;
(trans)-3-(Benzo[d]thiazol-4-yloxy)-N-(4-cyclopropylthiazol-2-yl)cyclobutanecarboxamide;
Racemic (trans)-3-((6-Fluorobenzo[d]thiazol-4-yl)oxy)-N-((trans)-6-(2-hydroxypropan-2-yl)tetrahydro-2H-pyran-3-yl)cyclobutanecarboxamide;
(trans)-3-((6-Fluorobenzo[d]thiazol-4-yl)oxy)-N-((trans)-4-(2-hydroxypropan-2-yl)cyclohexyl)cyclobutanecarboxamide;
3-((6-Fluorobenzo[d]thiazol-4-yl)oxy)-N-((trans)-4-(2-hydroxypropan-2-yl)cyclohexyl)azetidine-1-carboxamide;
Racemic N-((trans)-4-((1,1-Difluoropropan-2-yl)amino)cyclohexyl)-3-((6-fluorobenzo[d]thiazol-4-yl)oxy)azetidine-1-carboxamide;
Racemic tert-Butyl 3-((trans)-3-(5-fluoro-2-methoxyphenoxy)cyclobutanecarboxamido)pyrrolidine-1-carboxylate;
Racemic (trans)-N-(1-(5-Cyanothiazol-2-yl)pyrrolidin-3-yl)-3-(5-fluoro-2-methoxyphenoxy)cyclobutanecarboxamide;
Racemic (trans)-N-(1-(4-Cyanopyridin-2-yl)pyrrolidin-3-yl)-3-(5-fluoro-2-methoxyphenoxy)cyclobutanecarboxamide;
(trans)-3-(5-Fluoro-2-methoxyphenoxy)-N-(indolin-1-yl)cyclobutanecarboxamide;
(trans)-N-(1-(5-Cyanothiazol-2-yl)azetidin-3-yl)-3-(5-fluoro-2-methoxyphenoxy)cyclobutanecarboxamide;
(trans)-N-(2-(4-Cyanopyridin-2-yl)-2-azaspiro[3.3]heptan-6-yl)-3-(5-fluoro-2-methoxyphenoxy)cyclobutanecarboxamide;
(trans)-N-(1-(4-Cyanopyridin-2-yl)azetidin-3-yl)-3-(5-fluoro-2-methoxyphenoxy)cyclobutanecarboxamide;
(trans)-3-(5-Fluoro-2-methoxyphenoxy)-N-((trans)-4-methoxycyclohexyl)cyclobutanecarboxamide;
(trans)-3-(5-Fluoro-2-methoxyphenoxy)-N-((trans)-4-(3-oxomorpholino)cyclohexyl)cyclobutanecarboxamide;
(trans)-3-(5-Fluoro-2-methoxyphenoxy)-N-(1-(1-methyl-1H-tetrazol-5-yl)piperidin-4-yl)cyclobutanecarboxamide;
Racemic (trans)-3-(5-Fluoro-2-methoxyphenoxy)-N-(2-oxo-1,2,3,4-tetrahydroquinolin-4-yl)cyclobutanecarboxamide;
(trans)-3-(5-Fluoro-2-methoxyphenoxy)-N-(1-(thiazol-2-yl)piperidin-4-yl)cyclobutanecarboxamide;
(trans)-N-(1-(4-Cyanopyridin-2-yl)piperidin-4-yl)-3-(5-fluoro-2-methoxyphenoxy)cyclobutanecarboxamide;

(trans)-N-(1-(3-Chloro-4-methoxybenzyl)piperidin-4-yl)-3-(5-fluoro-2-methoxyphenoxy)cyclobutanecarboxamide;
(trans)-3-(5-Fluoro-2-methoxyphenoxy)-N-(1-(pyridin-2-yl)piperidin-4-yl)cyclobutanecarboxamide;
2-((trans)-3-(5-Fluoro-2-methoxyphenoxy)cyclobutanecarboxamido)-N,N-dimethyloxazole-4-carboxamide;
(trans)-N-(6-Cyanopyridin-2-yl)-3-(5-fluoro-2-methoxyphenoxy)cyclobutanecarboxamide;
Racemic (trans)-3-(5-Fluoro-2-methoxyphenoxy)-N-(6-(2-hydroxypropan-2-yl)spiro[3.3]heptan-2-yl)cyclobutanecarboxamide;
Racemic (trans)-3-(5-Fluoro-2-methoxyphenoxy)-N-((trans)-4-((1,1,1-trifluoropropan-2-yl)amino)cyclohexyl)cyclobutanecarboxamide;
(trans)-N-((trans)-3-(5-Fluoro-2-methoxyphenoxy)cyclobutyl)-4-(2-hydroxypropan-2-yl)cyclohexanecarboxamide;
(trans)-N-(4-Acetylthiazol-2-yl)-3-(5-fluoro-2-methoxyphenoxy)cyclobutanecarboxamide;
(trans)-N-(5-Acetylthiazol-2-yl)-3-(5-fluoro-2-methoxyphenoxy)cyclobutanecarboxamide;
(trans)-3-(5-Fluoro-2-methoxyphenoxy)-N-(5-(2-hydroxypropan-2-yl)thiazol-2-yl)cyclobutanecarboxamide;
(trans)-3-(5-Fluoro-2-methoxyphenoxy)-N-(5-methyl-1,3,4-thiadiazol-2-yl)cyclobutanecarboxamide;
(trans)-N-(4-Cyclopropylthiazol-2-yl)-3-(5-fluoro-2-methoxyphenoxy)cyclobutanecarboxamide;
(trans)-3-(5-Fluoro-2-methoxyphenoxy)-N-((trans)-4-(2-hydroxypropan-2-yl)cyclohexyl)cyclobutanecarboxamide;
(trans)-3-(5-Fluoro-2-methoxyphenoxy)-N-((trans)-4-(2-hydroxy-2-methylpropoxy)cyclohexyl)cyclobutanecarboxamide;
Racemic (trans)-N-(6-(2-Hydroxypropan-2-yl)spiro[3.3]heptan-2-yl)-3-(quinolin-8-yloxy)cyclobutanecarboxamide;
Ethyl 2-((trans)-3-(quinolin-8-yloxy)cyclobutanecarboxamido)oxazole-4-carboxylate;
N,N-Dimethyl-2-((trans)-3-(quinolin-8-yloxy)cyclobutanecarboxamido)oxazole-4-carboxamide;
Racemic (trans)-3-(Quinolin-8-yloxy)-N-((trans)-4-((1,1,1-trifluoropropan-2-yl)amino)cyclohexyl)cyclobutanecarboxamide;
(trans)-N-(5-Acetyloxazol-2-yl)-3-(quinolin-8-yloxy)cyclobutanecarboxamide;
(trans)-N-(4,5-Dimethyloxazol-2-yl)-3-(quinolin-8-yloxy)cyclobutanecarboxamide;
Ethyl 5-((trans)-3-(quinolin-8-yloxy)cyclobutanecarboxamido)-4H-1,2,4-triazole-3-carboxylate;
(trans)-N-(5-Methyloxazol-2-yl)-3-(quinolin-8-yloxy)cyclobutanecarboxamide;
(trans)-N-(4-Cyclopropyloxazol-2-yl)-3-(quinolin-8-yloxy)cyclobutanecarboxamide;
(trans)-N-(5-(tert-Butyl)-1,3,4-oxadiazol-2-yl)-3-(quinolin-8-yloxy)cyclobutanecarboxamide;
Racemic (trans)-N-((trans)-4-((1,1-Difluoropropan-2-yl)amino)cyclohexyl)-3-(quinolin-8-yloxy)cyclobutanecarboxamide;
(trans)-N-(6-Methylpyridin-2-yl)-3-(quinolin-8-yloxy)cyclobutanecarboxamide;
(trans)-N-((trans)-4-Hydroxy-4-methylcyclohexyl)-3-(quinolin-8-yloxy)cyclobutanecarboxamide;
(trans)-N-(Pyridin-2-yl)-3-(quinolin-8-yloxy)cyclobutanecarboxamide;
trans-3-(8-Quinolinyloxy)-N-1,3-thiazol-2-ylcyclobutanecarboxamide;
N-((trans)-4-(2-Hydroxypropan-2-yl)cyclohexyl)-3-(quinolin-8-yloxy)azetidine-1-carboxamide;
trans-N-(4-Acetylthiazol-2-yl)-3-(quinolin-8-yloxy)cyclobutanecarboxamide;
Racemic (trans)-3-(Quinolin-8-yloxy)-N-(4-(1,1,1-trifluoro-2-hydroxypropan-2-yl)thiazol-2-yl)cyclobutanecarboxamide;
(trans)-N-(4-Cyanothiazol-2-yl)-3-(quinolin-8-yloxy)cyclobutanecarboxamide, trifluoroacetic acid salt;
2-((trans)-3-(Quinolin-8-yloxy)cyclobutanecarboxamido)thiazole-4-carboxamide, trifluoroacetic acid salt;
(trans)-N-(5-Cyanothiazol-2-yl)-3-(quinolin-8-yloxy)cyclobutanecarboxamide;
2-((trans)-3-(Quinolin-8-yloxy)cyclobutanecarboxamido)thiazole-5-carboxamide;
Ethyl 2-((trans)-3-(quinolin-8-yloxy)cyclobutanecarboxamido)thiazole-4-carboxylate;
2-((trans)-3-(Quinolin-8-yloxy)cyclobutanecarboxamido)thiazole-4-carboxylic acid;
(trans)-N-(4-(Cyclopropanecarbonyl)thiazol-2-yl)-3-(quinolin-8-yloxy)cyclobutanecarboxamide;
Racemic (trans)-N-((trans)-6-(2-Hydroxypropan-2-yl)tetrahydro-2H-pyran-3-yl)-3-(quinolin-8-yloxy)cyclobutanecarboxamide;
N-Methyl-2-((trans)-3-(quinolin-8-yloxy)cyclobutanecarboxamido)thiazole-4-carboxamide, trifluoroacetic acid salt;
N,N-Dimethyl-2-((trans)-3-(quinolin-8-yloxy)cyclobutanecarboxamido)thiazole-4-carboxamide, trifluoroacetic acid salt;
(trans)-N-(5-lsopropyl-1,3,4-thiadiazol-2-yl)-3-(quinolin-8-yloxy)cyclobutanecarboxamide;
(trans)-N-(5-Cyclopropyl-1,3,4-thiadiazol-2-yl)-3-(quinolin-8-yloxy)cyclobutanecarboxamide;
(trans)-N-(4-(2-Hydroxypropan-2-yl)thiazol-2-yl)-3-(quinolin-8-yloxy)cyclobutanecarboxamide;
(trans)-3-(Quinolin-8-yloxy)-N-(4-(trifluoromethyl)thiazol-2-yl)cyclobutanecarboxamide;
(trans)-N-(5-Acetylthiazol-2-yl)-3-(quinolin-8-yloxy)cyclobutanecarboxamide;
(trans)-N-(5-Methyl-1,3,4-thiadiazol-2-yl)-3-(quinolin-8-yloxy)cyclobutanecarboxamide;
(trans)-N-(5-(2-Hydroxypropan-2-yl)thiazol-2-yl)-3-(quinolin-8-yloxy)cyclobutanecarboxamide;
(trans)-N-(5-(Prop-1-en-2-yl)thiazol-2-yl)-3-(quinolin-8-yloxy)cyclobutanecarboxamide;
(trans)-N-(4-lsopropylthiazol-2-yl)-3-(quinolin-8-yloxy)cyclobutanecarboxamide;
(trans)-N-(4-Cyclopropylthiazol-2-yl)-3-(quinolin-8-yloxy)cyclobutanecarboxamide;
(trans)-N-(Oxazol-2-yl)-3-(quinolin-8-yloxy)cyclobutanecarboxamide;
(trans)-N-(4-(2-Hydroxy-2-methylpropyl)thiazol-2-yl)-3-(quinolin-8-yloxy)cyclobutanecarboxamide, trifluoroacetic acid salt;
(trans)-N-(5-(Hydroxymethyl)thiazol-2-yl)-3-(quinolin-8-yloxy)cyclobutanecarboxamide;
(trans)-N-(4-(tert-Butyl)thiazol-2-yl)-3-(quinolin-8-yloxy)cyclobutanecarboxamide;
Racemic (trans)-N-(2,3-Dihydro-1H-inden-1-yl)-3-(quinolin-8-yloxy)cyclobutanecarboxamide;
(trans)-N-(5-(2-Hydroxy-2-methylpropyl)thiazol-2-yl)-3-(quinolin-8-yloxy)cyclobutanecarboxamide;
(trans)-N-(3-Cyclopropyl-1H-pyrazol-5-yl)-3-(quinolin-8-yloxy)cyclobutanecarboxamide;

(trans)-N-(4-(Hydroxymethyl)thiazol-2-yl)-3-(quinolin-8-yloxy)cyclobutanecarboxamide;
(trans)-3-(Quinolin-8-yloxy)-N-(1,3,4-thiadiazol-2-yl)cyclobutanecarboxamide;
(trans)-N-(5-Methylthiazol-2-yl)-3-(quinolin-8-yloxy)cyclobutanecarboxamide;
(trans)-N-(4-Methylthiazol-2-yl)-3-(quinolin-8-yloxy)cyclobutanecarboxamide;
(trans)-N-(1-(Methylsulfonyl)piperidin-4-yl)-3-(quinolin-8-yloxy)cyclobutanecarboxamide;
(trans)-N-((trans)-4-(2-Hydroxy-2-methylpropoxy)cyclohexyl)-3-(quinolin-8-yloxy)cyclobutanecarboxamide;
(trans)-3-(Quinolin-8-ylamino)-N-(thiazol-2-yl)cyclobutanecarboxamide;
(trans)-N-((trans)-4-(2-Hydroxypropan-2-yl)cyclohexyl)-3-(quinolin-8-ylamino)cyclobutanecarboxamide;
(trans)-N-((trans)-3-(2-Hydroxypropan-2-yl)cyclobutyl)-3-(quinolin-8-yloxy)cyclobutanecarboxamide;
(trans)-3-(Quinolin-8-yloxy)-N-(1-(2,2,2-trifluoroethyl)piperidin-4-yl)cyclobutanecarboxamide;
N-((trans)-4-(2-Hydroxypropan-2-yl)cyclohexyl)-3-(quinolin-8-yloxy)cyclobutanecarboxamide;
N-((trans)-4-(2-Hydroxypropan-2-yl)cyclohexyl)-3-(thieno[3,2-b]pyridin-3-yloxy)azetidine-1-carboxamide;
(trans)-3-((5-Fluorobenzofuran-7-yl)oxy)-N-((trans)-4-(2-hydroxypropan-2-yl)cyclohexyl)cyclobutanecarboxamide;
(trans)-3-(3-Bromophenoxy)-N-((trans)-4-(2-hydroxypropan-2-yl)cyclohexyl)cyclobutanecarboxamide;
(trans)-3-(2,5-Difluorophenoxy)-N-((trans)-4-(2-hydroxypropan-2-yl)cyclohexyl)cyclobutanecarboxamide;
(trans)-3-(2-Chloro-5-fluorophenoxy)-N-((trans)-4-(2-hydroxypropan-2-yl)cyclohexyl)cyclobutanecarboxamide;
(trans)-3-((6-Fluorobenzo[d]thiazol-4-yl)oxy)-N-(1-(5-methylpyridin-2-yl)azetidin-3-yl)cyclobutanecarboxamide;
3-((6-Fluorobenzo[d]thiazol-4-yl)oxy)-N-(1-(5-methylpyridin-2-yl)azetidin-3-yl)azetidine-1-carboxamide;
(trans)-3-((6-Fluorobenzo[d]thiazol-4-yl)oxy)-N-(6-propionylspiro[3.3]heptan-2-yl)cyclobutanecarboxamide;
N-(2-Ethoxyethyl)-6-(3-((trans)-3-((6-fluorobenzo[d]thiazol-4-yl)oxy)cyclobutanecarboxamido)azetidin-1-yl)pyridazine-3-carboxamide;
(trans)-3-((6-Fluorobenzo[d]thiazol-4-yl)oxy)-N-(1-(pyrazin-2-yl)azetidin-3-yl)cyclobutanecarboxamide;
Racemic 3-((6-Fluorobenzo[d]thiazol-4-yl)oxy)-N-((trans)-4-(2-hydroxypropan-2-yl)cyclohexyl)-2-methylazetidine-1-carboxamide;
(trans)-3-((6-Fluorobenzo[d]thiazol-4-yl)oxy)-N-(3-methyl-1-(pyridazin-3-yl)azetidin-3-yl)cyclobutanecarboxamide;
(trans)-3-((6-Fluorobenzo[d]thiazol-4-yl)oxy)-N-(3-methyl-1-(pyrimidin-2-yl)azetidin-3-yl)cyclobutanecarboxamide;
(trans)-3-(Benzo[d]thiazol-4-yloxy)-N-(1-(5-methylpyridin-2-yl)azetidin-3-yl)cyclobutanecarboxamide;
Racemic 3-(Benzo[d]thiazol-4-yloxy)-N-((trans)-4-(2-hydroxypropan-2-yl)cyclohexyl)-2-methylazetidine-1-carboxamide;
(trans)-3-(Benzo[d]thiazol-4-yloxy)-N-(1-(5-methylpyridazin-3-yl)azetidin-3-yl)cyclobutanecarboxamide, trifluoroacetic acid salt;
(trans)-3-(Benzo[d]thiazol-4-yloxy)-N-(4-(methylsulfonyl)phenyl)cyclobutanecarboxamide;
(trans)-3-(Benzo[d]thiazol-4-yloxy)-N-(4-morpholinophenyl)cyclobutanecarboxamide;
3-(Benzo[d]thiazol-4-yloxy)-N-(1-(5-methylpyridin-2-yl)azetidin-3-yl)azetidine-1-carboxamide;
(trans)-3-(Benzo[d]thiazol-4-yloxy)-N-(1-(pyridazin-3-yl)azetidin-3-yl)cyclobutanecarboxamide;
(trans)-3-(Benzo[d]thiazol-4-yloxy)-N-(1-(pyrazin-2-yl)azetidin-3-yl)cyclobutanecarboxamide;
(trans)-3-(Benzo[d]thiazol-4-yloxy)-N-(2-fluoro-4-(methylsulfonyl)phenyl)cyclobutanecarboxamide;
(trans)-3-(Benzo[d]thiazol-4-yloxy)-N-(3-morpholinophenyl)cyclobutanecarboxamide;
(trans)-3-(Benzo[d]thiazol-4-yloxy)-N-(1-methyl-1H-pyrazol-5-yl)cyclobutanecarboxamide;
(trans)-3-(Benzo[d]thiazol-4-yloxy)-N-(thiophen-2-ylmethyl)cyclobutanecarboxamide;
3-(Benzo[d]thiazol-4-yloxy)-N-(3-methyl-1-(pyrimidin-2-yl)azetidin-3-yl)azetidine-1-carboxamide;
(trans)-3-(Benzo[d]thiazol-4-yloxy)-N-(thiophen-3-ylmethyl)cyclobutanecarboxamide;
(trans)-3-(Benzo[d]thiazol-4-yloxy)-N-cyclohexylcyclobutanecarboxamide;
Racemic (trans)-3-(Benzo[d]thiazol-4-yloxy)-N-(1,1-dioxidotetrahydrothiophen-3-yl)cyclobutanecarboxamide;
(trans)-3-(Benzo[d]thiazol-4-yloxy)-N-((5-methylfuran-2-yl)methyl)cyclobutanecarboxamide;
Racemic 3-(Fluoro(quinolin-8-yl)methyl)-N-((trans)-4-(2-hydroxypropan-2-yl)cyclohexyl)azetidine-1-carboxamide;
(trans)-3-(2;5-Dichlorophenoxy)-N-((trans)-4-(2-hydroxypropan-2-yl)cyclohexyl)cyclobutanecarboxamide;
N-((trans-4-(2-Hydroxypropan-2-yl)cyclohexyl)-3-(2-(trifluoromethoxy)phenoxy)azetidine-1-carboxamide;
(trans)-N-((trans)-4-(2-Hydroxypropan-2-yl)cyclohexyl)-3-(2-(trifluoromethoxy)phenoxy)cyclobutanecarboxamide;
3-(Benzofuran-7-yloxy)-N-((trans)-4-(2-hydroxypropan-2-yl)cyclohexyl)azetidine-1-carboxamide;
(trans)-3-(Benzofuran-7-yloxy)-N-(5-cyanothiazol-2-yl)cyclobutanecarboxamide;
Ethyl 2-(2-((trans)-3-(benzofuran-7-yloxy)cyclobutanecarboxamido)thiazol-4-yl)acetate;
Ethyl 2-(5-((trans)-3-(benzofuran-7-yloxy)cyclobutanecarboxamido)-1,3,4-thiadiazol-2-yl)acetate;
(trans)-N-(5-Acetylthiazol-2-yl)-3-(benzofuran-7-yloxy)cyclobutanecarboxamide;
(trans)-3-(Benzofuran-7-yloxy)-N-(5-(2-hydroxypropan-2-yl)thiazol-2-yl)cyclobutanecarboxamide;
(trans)-3-(Benzofuran-7-yloxy)-N-(5-methyl-1,3,4-thiadiazol-2-yl)cyclobutanecarboxamide;
(trans)-3-(Benzofuran-7-yloxy)-N-((trans)-4-(2-hydroxypropan-2-yl)cyclohexyl)cyclobutanecarboxamide;
(trans)-3-((2;3-Dihydrobenzofuran-7-yl)oxy)-N-((trans)-4-(2-hydroxypropan-2-yl)cyclohexyl)cyclobutanecarboxamide;
(trans)-3-((3-Bromobenzofuran-7-yl)oxy)-N-((trans)-4-(2-hydroxypropan-2-yl)cyclohexyl)cyclobutanecarboxamide;
(trans)-N-((trans)-4-(2-Hydroxypropan-2-yl)cyclohexyl)-3-((3-methylbenzofuran-7-yl)oxy)cyclobutanecarboxamide;
(trans)-N-(4-Acetylthiazol-2-yl)-3-((3-bromobenzofuran-7-yl)oxy)cyclobutanecarboxamide;
(trans)-N-(4-Acetylthiazol-2-yl)-3-(5-chloro-2-(difluoromethoxy)phenoxy)cyclobutanecarboxamide;
(trans)-3-(5-Chloro-2-(difluoromethoxy)phenoxy)-N-((trans)-4-(2-hydroxypropan-2-yl)cyclohexyl)cyclobutanecarboxamide;
(trans)-N-(4-Acetylthiazol-2-yl)-3-(5-chloro-2-methoxyphenoxy)cyclobutanecarboxamide;

(trans)-3-(5-Chloro-2-methoxyphenoxy)-N-((trans)-4-(2-hydroxypropan-2-yl)cyclohexyl)cyclobutanecarboxamide;
(trans)-N-(4-Acetylthiazol-2-yl)-3-(4-fluoro-2-methoxyphenoxy)cyclobutanecarboxamide;
(trans)-3-(4-Fluoro-2-meth oxyphe noxy)-N-((trans)-4-(2-hydroxypropan-2-yl)cyclohexyl)cyclobutanecarboxamide;
(trans)-3-(2-(Difluoromethoxy)phenoxy)-N-((trans)-4-(2-hydroxypropan-2-yl)cyclohexyl)cyclobutanecarboxamide;
(trans)-N-(4-Acetylthiazol-2-yl)-3-(4-fluoro-2-methoxyphenoxy)cyclobutanecarboxamide;
(trans)-3-((3-Fluoroquinolin-8-yl)oxy)-N-((trans)-4-(2-hydroxypropan-2-yl)cyclohexyl)cyclobutanecarboxamide;
(trans)-3-((3-Fluoroquinolin-8-yl)oxy)-N-(thiazol-2-yl)cyclobutanecarboxamide;
(trans)-3-(2-Chlorophenoxy)-N-((trans)-4-(2-hydroxypropan-2-yl)cyclohexyl)cyclobutanecarboxamide;
(trans)-3-(3,5-Difluorophenoxy)-N-((trans)-4-(2-hydroxypropan-2-yl)cyclohexyl)cyclobutanecarboxamide;
(trans)-N-((trans)-4-(2-hydroxypropan-2-yl)cyclohexyl)-3-(2-methoxyphenoxy)cyclobutanecarboxamide;
(trans)-3-(3-Ethylphenoxy)-N-((trans)-4-(2-hydroxypropan-2-yl)cyclohexyl)cyclobutanecarboxamide;
Racemic (trans)-3-(3-Chlorophenoxy)-N-(2,3-dihydro-1H-inden-1-yl)cyclobutanecarboxamide;
(trans)-3-(3-Chlorophenoxy)-N-(thiazol-2-yl)cyclobutanecarboxamide;
(trans)-3-(3-Chlorophenoxy)-N-((trans)-4-(2-hydroxypropan-2-yl)cyclohexyl)cyclobutanecarboxamide;
(trans)-3-(3-Fluorophenoxy)-N-((trans)-4-(2-hydroxypropan-2-yl)cyclohexyl)cyclobutanecarboxamide;
(trans)-3-(3-Chloro-5-fluorophenoxy)-N-((trans)-4-(2-hydroxypropan-2-yl)cyclohexyl)cyclobutanecarboxamide;
(trans)-3-((5-Fluoroquinolin-8-yl)oxy)-N-(thiazol-2-yl)cyclobutanecarboxamide, trifluoroacetic acid salt;
(trans)-3-((5-Fluoroquinolin-8-yl)oxy)-N-((trans)-4-(2-hydroxypropan-2-yl)cyclohexyl)cyclobutanecarboxamide;
(trans)-3-((6-Fluoroquinolin-8-yl)oxy)-N-((trans)-3-(2-hydroxypropan-2-yl)cyclobutyl)cyclobutanecarboxamide;
(trans)-3-((6-Fluoroquinolin-8-yl)oxy)-N-(thiazol-2-yl)cyclobutanecarboxamide;
(trans)-3-((6-Fluoroquinolin-8-yl)oxy)-N-((trans)-4-(2-hydroxypropan-2-yl)cyclohexyl)cyclobutanecarboxamide;
(trans)-N-((trans)-4-(2-Hydroxypropan-2-yl)cyclohexyl)-3-(quinazolin-8-yloxy)cyclobutanecarboxamide;
(trans)-3-((1H-Benzo[d]imidazol-4-yl)oxy)-N-(thiazol-2-yl)cyclobutanecarboxamide, di-trifluoroacetic acid salt;
(trans)-N-((trans)-4-(2-Hydroxypropan-2-yl)cyclohexyl)-3-(imidazo[1,2-a]pyridin-8-yloxy)cyclobutanecarboxamide;
3-(Benzo[d]isothiazol-4-yloxy)-N-((trans)-4-(2-hydroxypropan-2-yl)cyclohexyl)azetidine-1-carboxamide;
N-((trans)-4-(2-Hydroxypropan-2-yl)cyclohexyl)-3-((2-methylbenzo[d]thiazol-4-yl)oxy)azetidine-1-carboxamide;
(trans)-3-(Benzo[d]thiazol-4-yloxy)-N-(1H-pyrazol-5-yl)cyclobutanecarboxamide;
(trans)-3-(Benzo[d]thiazol-4-yloxy)-N-(3-cyclopropyl-1H-pyrazol-5-yl)cyclobutanecarboxamide;
(trans)-3-((6-Fluorobenzo[d]thiazol-4-yl)oxy)-N-(1-(2-hydroxy-2-methylpropanoyl)piperidin-4-yl)cyclobutanecarboxamide;
(2S,3S)-3-(Benzo[d]thiazol-4-yloxy)-N-((trans)-4-(2-hydroxypropan-2-yl)cyclohexyl)-2-methylazetidine-1-carboxamide;
(2R,3R)-3-(Benzo[d]thiazol-4-yloxy)-N-((trans)-4-(2-hydroxypropan-2-yl)cyclohexyl)-2-methylazetidine-1-carboxamide;
3-(Benzo[d]thiazol-4-yloxy)-N-(4-(methylsulfonyl)phenyl)azetidine-1-carboxamide;
(trans)-3-(Benzo[d]thiazol-4-yloxy)-N-(6-methylpyrimidin-4-yl)cyclobutanecarboxamide;
3-(Benzo[d]thiazol-4-yloxy)-N-(2-fluoro-4-(methylsulfonyl)phenyl)azetidine-1-carboxamide;
3-(Benzo[d]thiazol-4-yloxy)-N-(3-morpholinophenyl)azetidine-1-carboxamide;
3-(Benzo[d]thiazol-4-yloxy)-N-(4-morpholinophenyl)azetidine-1-carboxamide;
3-(Benzo[d]thiazol-4-yloxy)-N-(5-(methylsulfonyl)pyridin-2-yl)azetidine-1-carboxamide;
3-(Benzo[d]thiazol-4-yloxy)-N-(2-cyclopropylpyrimidin-4-yl)azetidine-1-carboxamide;
N-(2-Cyclopropylpyrimidin-4-yl)-3-((6-fluorobenzo[d]thiazol-4-yl)oxy)azetidine-1-carboxamide;
3-(Benzo[d]thiazol-4-yloxy)-N-(3-cyclopropyl-1-methyl-1H-pyrazol-5-yl)azetidine-1-carboxamide;
(trans)-3-(Benzo[d]thiazol-4-yloxy)-N-(3-(pyrimidin-2-ylamino)bicyclo[1.1.1]pentan-1-yl)cyclobutane-1-carboxamide;
3-(Benzo[d]thiazol-4-yloxy)-N-(3-(2-hydroxpropan-2-yl)bicyclo[1.1.1]pentan-1-yl)azetidine-1-carboxamide;
3-(Benzo[d]thiazol-4-yloxy)-N-(4-(2-hydroxypropan-2-yl)cuban-1-yl)azetidine-1-carboxamide;
(trans)-3-(Benzo[d]thiazol-4-yloxy)-N-(3-(2-hydroxpropan-2-yl)bicyclo[1.1.1]pentan-1-yl)cyclobutane-1-carboxamide;
Ethyl (3-((trans)-3-(benzo[d]thiazol-4-yloxy)cyclobutane-1-carboxamido)bicyclo[1.1.1]pentan-1-yl)carbamate;
(trans)-3-(Benzo[d]thiazol-4-yloxy)-N-(4-(2-hydroxpropan-2-yl)cuban-1-yl)cyclobutane-1-carboxamide;
3-(Benzo[d]thiazol-4-yloxy)-N-(5-methyl-1,3,4-thiadiazol-2-yl)azetidine-1-carboxamide;
3-(Benzo[d]thiazol-4-yloxy)-N-(1-methyl-1H-pyrazol-3-yl)azetidine-1-carboxamide;
3-(Benzo[d]thiazol-4-yloxy)-N-(5-methoxpyridin-3-yl)azetidine-1-carboxamide;
3-(Benzo[d]thiazol-4-yloxy)-N-(1-methyl-1H-pyrazol-4-yl)azetidine-1-carboxamide;
3-(Benzo[d]thiazol-4-yloxy)-N-(1-ethyl-1H-tetrazol-5-yl)azetidine-1-carboxamide;
Methyl 4-((trans)-3-(benzo[d]thiazol-4-yloxy)cyclobutane-1-carboxamido)bicyclo[2.2.2]octane-1-carboxylate;
Methyl 4-(3-(benzo[d]thiazol-4-yloxy)azetidine-1-carboxamido)bicyclo[2.2.2]octane-1-carboxylate;
3-(Benzo[d]thiazol-4-yloxy)-N-(5-isopropyl-1,3,4-oxadiazol-2-yl)azetidine-1-carboxamide;
3-(Benzo[d]thiazol-4-yloxy)-N-(4-cyano-3-methyl-1H-pyrazol-5-yl)azetidine-1-carboxamide;
4-((1-(((trans)-4-(2-Hydroxypropan-2-yl)cyclohexyl)carbamoyl)azetidin-3-yl)oxy)benzo[d]thiazole-6-carboxamide;
(trans)-3-(Benzo[d]thiazol-4-yloxy)-N-(5-methyl-1,3,4-thiadiazol-2-yl)cyclobutane-1-carboxamide;
3-(Benzo[d]thiazol-4-yloxy)-N-(5-(tert-butyl)-1,3,4-thiadiazol-2-yl)azetidine-1-carboxamide;
3-(Benzo[d]thiazol-4-yloxy)-N-(5-cyclopropyl-1,3,4-thiadiazol-2-yl)azetidine-1-carboxamide;
3-(Benzo[d]thiazol-4-yloxy)-N-(5-isopropyl-1,3,4-thiadiazol-2-yl)azetidine-1-carboxamide;

(trans)-N-(5-(Ethoxymethyl)-1H-1,2,4-triazol-3-yl)-3-((6-fluorobenzo[d]thiazol-4-yl)oxy)cyclobutanecarboxamide;

3-(Benzo[d]thiazol-4-yloxy)-N-(5-methyl-1,2,4-thiadiazol-3-yl)azetidine-1-carboxamide;

3-(Benzo[d]thiazol-4-yloxy)-N-(3-isopropyl-1,2,4-thiadiazol-5-yl)azetidine-1-carboxamide;

3-(Benzo[d]thiazol-4-yloxy)-N-(3-cyclopropyl-1,2,4-thiadiazol-5-yl)azetidine-1-carboxamide; and 3-(Benzo[d]thiazol-4-yloxy)-N-(3-(tert-butyl)-1,2,4-thiadiazol-5-yl)azetidine-1-carboxamide;

and pharmaceutically acceptable salts thereof.

The skilled artisan will appreciate that salts, including pharmaceutically acceptable salts, of the compounds according to Formula (I) may be prepared. Indeed, in certain embodiments of the invention, salts including pharmaceutically-acceptable salts of the compounds according to Formula (I) may be preferred over the respective free or unsalted compound. Accordingly, the invention is further directed to salts, including pharmaceutically-acceptable salts, of the compounds according to Formula (I).

The salts, including pharmaceutically acceptable salts, of the compounds of the invention are readily prepared by those of skill in the art.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

The compounds according to Formula (I) may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may be present in a substituent such as an alkyl group. Where the stereochemistry of a chiral center present in a compound of Formula (I), or in any chemical structure illustrated herein, if not specified the structure is intended to encompass all individual stereoisomers and all mixtures thereof. Thus, compounds according to Formula (I) containing one or more chiral centers may be used as racemic mixtures, enantiomerically enriched mixtures, or as enantiomerically pure individual stereoisomers.

The compounds according to Formula (I) may also contain double bonds or other centers of geometric asymmetry. Where the stereochemistry of a center of geometric asymmetry present in Formula (I), or in any chemical structure illustrated herein, is not specified, the structure is intended to encompass the trans (E) geometric isomer, the cis (Z) geometric isomer, and all mixtures thereof. Likewise, all tautomeric forms are also included in Formula (I) whether such tautomers exist in equilibrium or predominately in one form.

The compounds of Formula (I) or salts, including pharmaceutically acceptable salts, thereof may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Accordingly, the compounds of Formula (I) and pharmaceutically acceptable salts thereof may exist in solvated and unsolvated forms.

The skilled artisan will further appreciate that certain compounds of Formula (I) or salts, including pharmaceutically acceptable salts thereof that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Accordingly, the compounds of Formula (I) and pharmaceutically acceptable salts thereof may exist in a single crystalline form or in different polymorphic forms.

As used herein, when referring to Formula (I) it will be appreciated that any one of Formulas (II) through (IV) are also referenced unless the context dictates otherwise.

Definitions

It will be appreciated that the following definitions apply to each of the aforementioned formulae and to all instances of these terms, unless the context dictates otherwise.

"Alkyl" refers to a hydrocarbon chain having the specified number of "carbon atoms". For example, $C_1$-$C_6$ alkyl refers to an alkyl group having from 1 to 6 carbon atoms. Alkyl groups may be saturated, unsaturated, straight or branched. Representative branched alkyl groups have one, two, or three branches. Alkyl includes but is not limited to: methyl, ethyl, ethylene, ethynyl, propyl (n-propyl and isopropyl), butene, butyl (n-butyl, isobutyl, and t-butyl), pentyl and hexyl.

"Alkoxy" refers to an —O-alkyl group wherein "alkyl" is as defined herein. For example, $C_1$-$C_4$alkoxy refers to an alkoxy group having from 1 to 4 carbon atoms. Representative branched alkoxy groups have one, two, or three branches. Examples of such groups include methoxy, ethoxy, propoxy, and butoxy.

"Aryl" refers to an aromatic hydrocarbon ring system. Aryl groups are monocyclic, bicyclic, and tricyclic ring systems having a total of five to fourteen ring member atoms, wherein at least one ring system is aromatic and wherein each ring in the system contains 3 to 7 member atoms, such as but no limited to: phenyl, dihydroindene, naphthalene, tetrahydronaphthalene and biphenyl. Suitably aryl is phenyl.

"Cycloalkyl", unless otherwise defined, refers to a saturated or unsaturated non aromatic hydrocarbon ring system having from three to eight carbon atoms. Cycloalkyl groups are monocyclic or bicyclic ring systems. For example, $C_3$-$C_8$ cycloalkyl refers to a cycloalkyl group having from 3 to 8 member atoms. Examples of cycloalkyl as used herein include: cyclopropyl, cyclobutyl, cyclopentyl, cyclohexyl, cyclobutenyl, cyclopentenyl, cyclohexenyl, cycloheptyl and spiro heptane. Suitably Cycloalkyl includes: bicyclo[1.1.1] pentyl, cubanyl, bicyclo 2.2 2 octanyl, cyclohexyl, spiro heptanyl, cyclobutanyl, and cyclopropyl. Suitably Cycloalkyl includes: cyclohexyl, spiro heptanyl, cyclobutanyl, and cyclopropyl.

Suitably "Cycloalkyl", refers to a saturated or unsaturated non aromatic hydrocarbon ring system having from three to seven carbon atoms. Cycloalkyl groups are monocyclic or bicyclic ring systems. For example, $C_3$-$C_7$ cycloalkyl refers to a cycloalkyl group having from 3 to 7 member atoms. Examples of cycloalkyl as used herein include: cyclopropyl, cyclobutyl, cyclopentyl, cyclohexyl, cyclobutenyl, cyclopentenyl, cyclohexenyl, cycloheptyl and spiro heptanyl.

"Halogen" refers to the halogen radicals fluoro, chloro, bromo, and iodo.

"Heteroaryl" refers to a monocyclic aromatic 4 to 8 member ring containing from 1 to 7 carbon atoms and containing from 1 to 4 heteroatoms, provided that when the number of carbon atoms is 3, the aromatic ring contains at least two heteroatoms. Heteroaryl groups containing more than one heteroatom may contain different heteroatoms. Heteroaryl includes: pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl, tetrahydroquinolinyl. Suitably, "heteroaryl" includes: pyrazolyl, thiazolyl, and tetrahydroquinolinyl.

"Bicycloheteroaryl" refers to two fused rings, at least one of which is aromatic, containing from 1 to 6 heteroatoms as member atoms. Bicycloheteroaryl groups containing more than one heteroatom may contain different heteroatoms. Bicycloheteroaryl rings have from 6 to 11 member atoms. Bicycloheteroaryl includes: 1H-pyrrolo[3,2-c]pyridine, 1H-pyrazolo[4,3-c]pyridine, 1H-pyrazolo[3,4-d]pyrimidine, 1H-pyrrolo[2,3-d]pyrimidine, 7H-pyrrolo[2,3-d]pyrimidine, thieno[3,2-c]pyridine, thieno[2,3-d]pyrimidine, furo[2,3-c] pyridine, furo[2,3-d]pyrimidine, indolyl, isoindolyl, indolizinyl, indazolyl, purinyl, quinolinyl, isoquinolinyl, quinoxalinyl, quinazolinyl, pteridinyl, cinnolinyl, azabenzimidazolyl, tetrahydrobenzimidazolyl, benzoxadiazolyl, imidazothiazolyl, benzimidazolyl, benopyranyl, benzoxazolyl, benzofuranyl, isobenzofuranyl, benzothiazolyl, benzothienyl, imidazo[4.5-c]pyridine, imidazo[4.5-b]pyridine, furopyridinyl and napthyridinyl.

"Heterocycle" and "Heterocycloalkyl" refers to a saturated or unsaturated non-aromatic monocyclic ring system containing 4 to 8 member atoms, of which 1 to 7 are carbon atoms and from 1 to 4 are heteroatoms. Heterocycloalkyl groups containing more than one heteroatom may contain different heteroatoms. Heterocycle and heterocycloalkyl includes: pyrrolidinyl, tetrahydrofuranyl, dihydrofuranyl, pyranyl, tetrahydropyranyl, dihydropyranyl, tetrahydrothienyl, pyrazolidinyl, oxazolidinyl, oxetanyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, and azetidinyl. Suitably, "Heterocycle" and "Heterocycloalkyl" includes: pyrrolidinyl, tetrahydropyranyl, oxazolidinyl, piperidinyl, and azetidinyl.

"Heteroatom" refers to a nitrogen, sulfur or oxygen atom.

ABBREVIATIONS

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac (acetyl);
$Ac_2O$ (acetic anhydride);
ACN (acetonitrile);
AIBN (azobis(isobutyronitrile));
BINAP (2,2'-bis(diphenylphosphino)-1,1'-binaphthyl);
BMS (borane—dimethyl sulphide complex);
Bn (benzyl);
Boc (tert-Butoxycarbonyl);
$Boc_2O$ (di-tert-butyl dicarbonate);
BOP (Benzotriazole-1-yl-oxy-tris-(dimethylamino)-phosphonium hexafluorophosphate);
CAN (cerric ammonium nitrate);
Cbz (benzyloxycarbonyl);
CSI (chlorosulfonyl isocyanate);
CsF (cesium fluoride);
DABCO (1,4-Diazabicyclo[2.2.2]octane);
DAST (Diethylamino)sulfur trifluoride);
DBU (1,8-Diazabicyclo[5.4.0]undec-7-ene);
DCC (Dicyclohexyl Carbodiimide);
DCE (1,2-dichloroethane);
DCM (dichloromethane);
DDQ (2,3-Dichloro-5,6-dicyano-1,4-benzoquinone);
ATP (adenosine triphosphate);
Bis-pinacolatodiboron (4,4,4',4',5,5,5',5'-Octamethyl-2,2'-bi-1,3,2-dioxaborolane);
BSA (bovine serum albumin);
C18 (refers to 18-carbon alkyl groups on silicon in HPLC stationary phase);

CH₃CN (acetonitrile);
Cy (cyclohexyl);
DCM (dichloromethane);
DIEA (Hunig's base, N,N-Diisopropylethylamine, N-ethyl-N-(1-methylethyl)-2-propanamine);
Dioxane (1,4-dioxane);
DMAP (4-dimethylaminopyridine);
DME (1,2-dimethoxyethane);
DMEDA (N,N'-dimethylethylenediamine);
DMF (N,N-dimethylformamide);
DMSO (dimethylsulfoxide);
DPPA (diphenyl phosphoryl azide);
EDC (N-(3-dimethylaminopropyl)-N'ethylcarbodiimide);
EDTA (ethylenediaminetetraacetic acid);
EtOAc (ethyl acetate);
EtOH (ethanol);
Et₂O (diethyl ether);
HEPES (4-(2-hydroxyethyl)-1-piperazine ethane sulfonic acid);
HATU (O-(7-Azabenzotriazol-1-yl)-N,N,N',N'-tetramethyluronium hexafluorophosphate);
HOAt (1-hydroxy-7-azabenzotriazole);
HOBt (1-hydroxybenzotriazole);
HOAc (acetic acid);
HPLC (high pressure liquid chromatography);
HMDS (hexamethyldisilazide);
IPA (isopropyl alcohol);
Indoline (2,3-dihydro-1H-indole);
KHMDS (potassium hexamethyldisilazide);
LAH (lithium aluminum hydride);
LDA (lithium diisopropylamide);
LHMDS (lithium hexamethyldisilazide)
MeOH (methanol);
MTBE (methyl tert-butyl ether);
mCPBA (m-chloroperoxybenzoic acid);
NaHMDS (sodium hexamethyldisilazide);
NBS (N-bromosuccinimide);
PE (petroleum ether);
Pd₂(dba)₃ (Tris(dibenzylideneacetone)dipalladium(0));
Pd(dppf)Cl₂·DCM Complex([1,1'-Bis(diphenylphosphino) ferrocene]dichloropalladium(II)·dichloromethane complex);
PyBOP (benzotriazol-1-yl-oxytripyrrolidinophosphonium hexafluorophosphate);
PyBrOP (bromotripyrrolidinophosphonium hexafluorophosphate);
RP-HPLC (reverse phase high pressure liquid chromatography);
RT (room temperature);
Sat. (saturated)
SFC (supercritical fluid chromatography);
SGC (silica gel chromatography);
SM (starting material);
TLC (thin layer chromatography);
TEA (triethylamine);
TEMPO (2,2,6,6-Tetramethylpiperidine 1-oxyl, free radical);
TFA (trifluoroacetic acid); and
THF (tetrahydrofuran).

All references to ether are to diethyl ether and brine refers to a saturated aqueous solution of NaCl.

COMPOUND PREPARATION

The compounds according to Formula (I) are prepared using conventional organic synthetic methods. A suitable synthetic route is depicted below in the following general reaction schemes. All of the starting materials are commercially available or are readily prepared from commercially available starting materials by those of skill in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Organic Synthesis* (4th ed.), John Wiley & Sons, NY (2006). In some instances, a substituent may be specifically selected to be reactive under the reaction conditions used. Under these circumstances, the reaction conditions convert the selected substituent into another substituent that is either useful as an intermediate compound or is a desired substituent in a target compound.

As used in the Schemes, "r" groups represent corresponding positional groups on any of Formulas I to IV.

In one method of preparation, the cyclobutane carboxamides may be prepared from phenols shown in Scheme 1. First, coupling of suitable phenols with appropriate (cis)-methyl 3-hydroxycyclobutanecarboxylates via Mitsunobu conditions or direct alkylation with (trans)-methyl 3-((methylsulfonyl)oxy)cyclobutanecarboxylates provides the substituted cyclobutane carboxylic esters. Subsequent ester hydrolysis and coupling of the resulting acids with suitable amines yield the desired cyclobutane carboxamides.

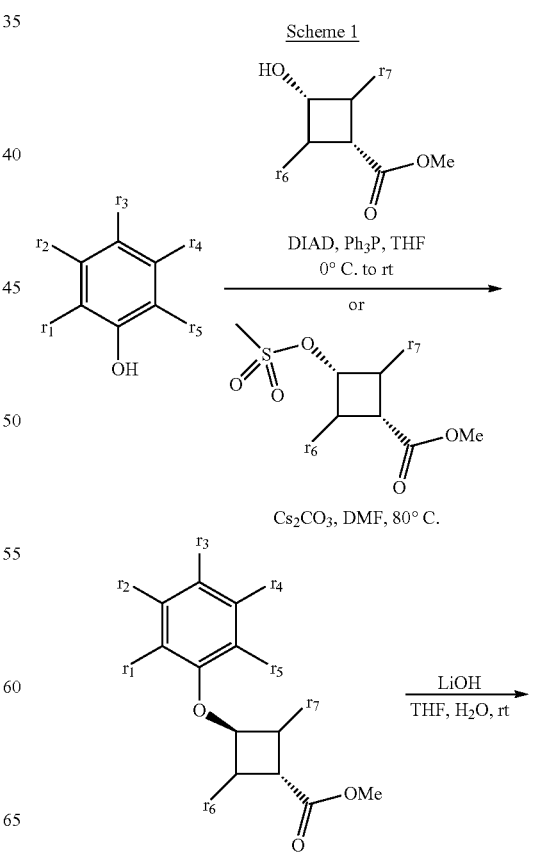

Scheme 1

-continued

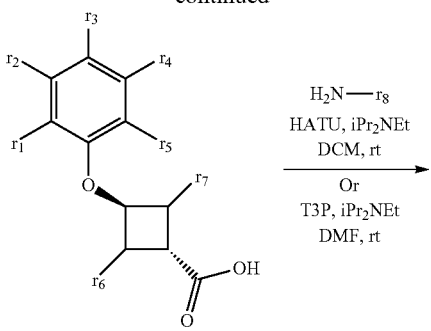

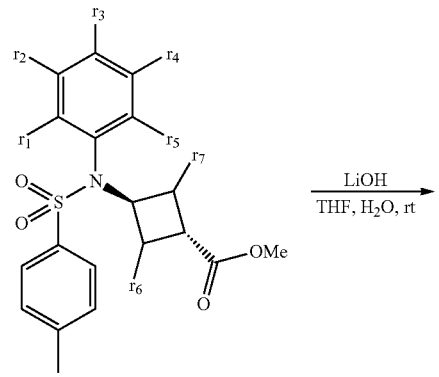

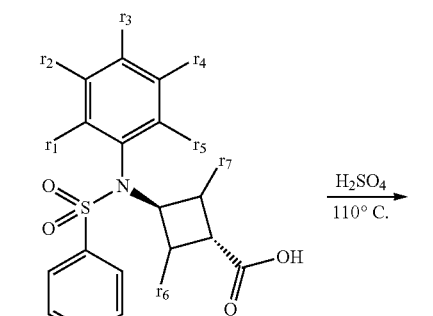

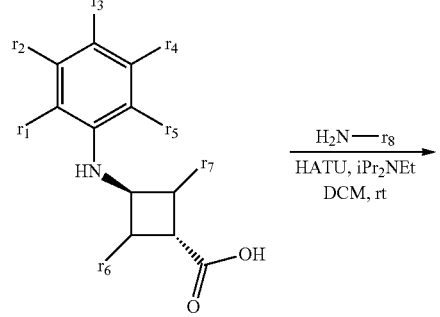

In another method of preparation, the cyclobutane carboxamides may be prepared from anilines as shown in Scheme 2. Sulfonylation of suitable anilines with p-toluenesulfonyl chloride followed by coupling of the sulfonamide with appropriate (cis)-methyl 3-hydroxycyclobutanecarboxylates via Mitsunobu conditions provides the substituted cyclobutane carboxylic esters. Subsequent ester hydrolysis followed by acidic cleavage of the sulfonyl group provides the substituted cyclobutane carboxylic acids. Coupling of the carboxylic acids with suitable amines yield the desired cyclobutane carboxamides.

Scheme 2

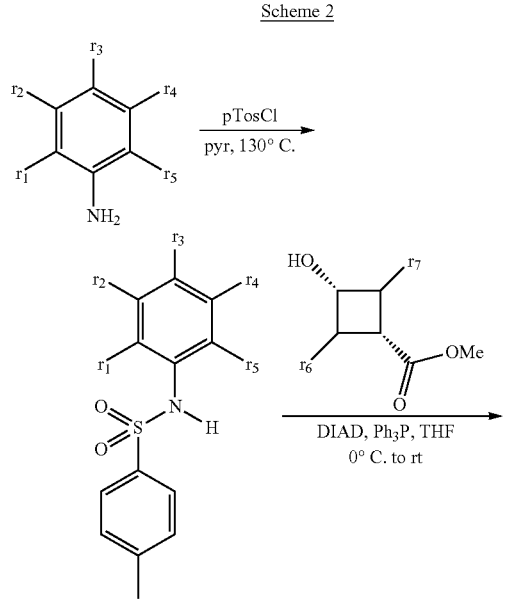

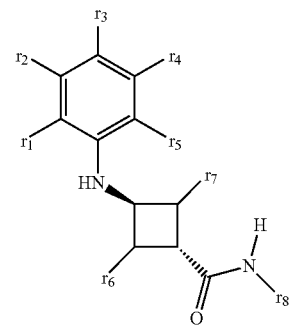

In another method of preparation, the azetidine ureas may be prepared from phenols as shown in Scheme 3. Alkylation of suitable phenols with appropriate tert-butyl 3-((methylsulfonyl)oxy)azetidine-1-carboxylates followed by acidic removal of the N-Boc protecting group provides the substituted azetidines. Coupling of the azetidine with p-nitrophenylcarbamates derived from suitable amines yield the desired azetidine ureas. Alternatively, coupling of the azetidine with suitable amines and triphosgene yield the desired azetidine ureas.

Scheme 3

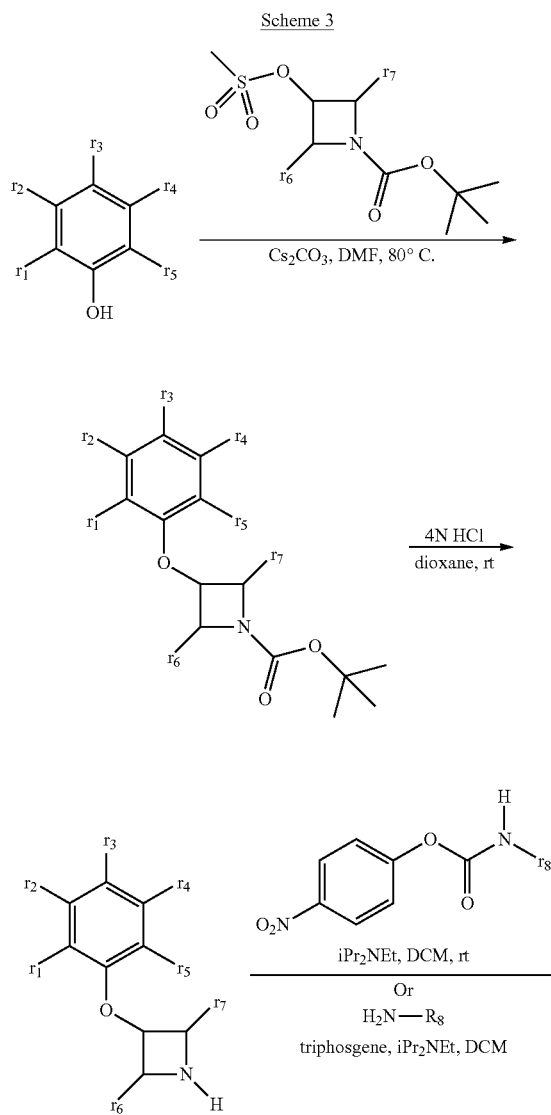

Scheme 4

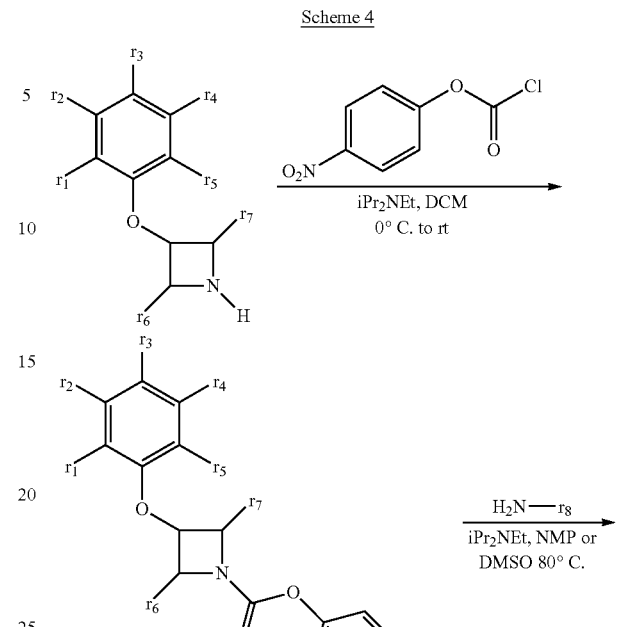

In an alternative method of preparation, the azetidine ureas may be derived from the substituted azetidine intermediate depicted in Scheme 3 as shown in Scheme 4. Acylation of a suitable azetidine with 4-nitrophenyl chloroformate provides the azetidine carbamates which upon heating with suitable amines yields the desired azetidine ureas.

In an alternative method of preparation, the azetidine ureas may be derived as shown in Scheme 5. Aromatic substitution of an aromatic ring containing a suitable leaving group with the alkoxides of appropriate tert-butyl 3-hydroxyazetidine-1-carboxylates followed by acidic removal of the N-Boc protecting group provides the substituted azetidines depicted in Scheme 3 and Scheme 4. Further elaboration to the desired azetidine ureas can be achieved using the methods described in Scheme 3 and Scheme 4.

Scheme 5

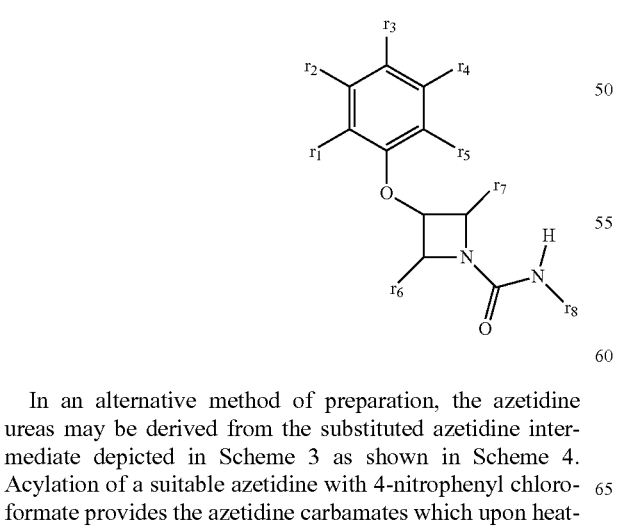

-continued

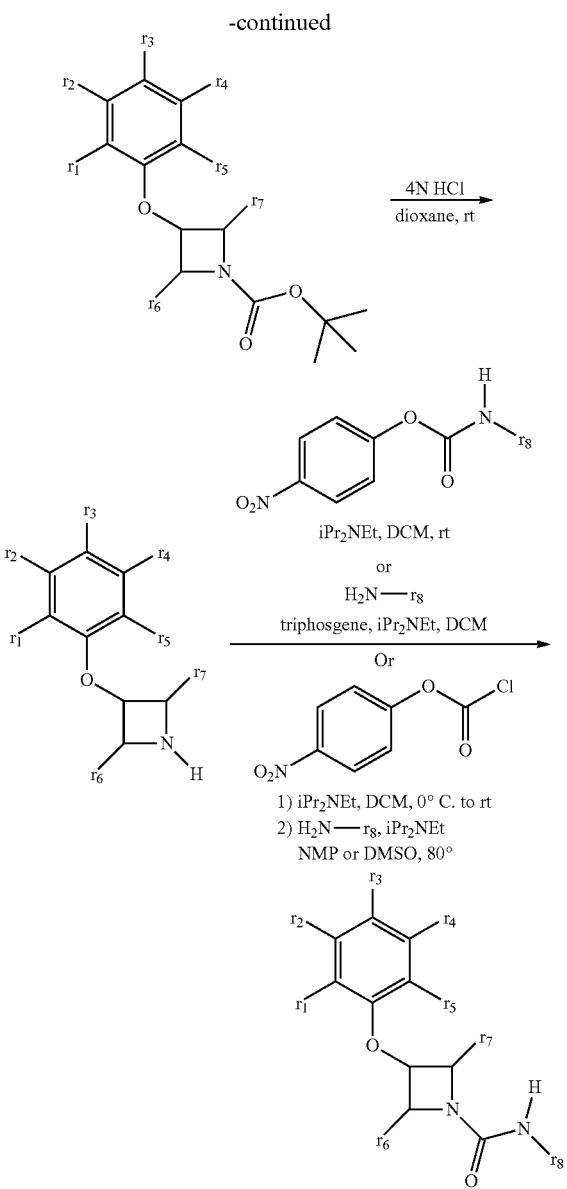

Without further elaboration, it is believed that one skilled in the art can, using the preceding description, utilize the present invention to its fullest extent.

METHODS OF USE

The inventors have shown that inhibitors of Hematopoietic Prostaglandin D Synthase (HPGDS) reduce muscle damage and preserve muscle function when administered prior to muscle damage in an in vivo assay for muscle function. Furthermore, the inventors have shown that when an HPGDS inhibitor is administered after muscle damage in the same assay, recovery of muscle function is enhanced. These results support a role for the use of HPGDS inhibitors in the treatment of muscle degenerative disorders and muscle injury.

In one aspect, the invention provides a method of treating a muscle degenerative disorder comprising administering to a human an HPGDS inhibitor of Formula (I) or a pharmaceutically acceptable salt thereof.

In particular embodiments, the muscle degenerative disorder is muscular dystrophy, myotonic dystrophy, polymyositis, or dermatomyositis.

For example, the compounds of Formula (I) or a pharmaceutically acceptable salt thereof may be used to treat a muscular dystrophy disorder selected from Duchenne MD, Becker MD, Congenital MD (Fukuyama), Emery Dreifuss MD, Limb girdle MD, and Fascioscapulohumeral MD.

The the compounds of Formula (I) or a pharmaceutically acceptable salt thereof may also be used to treat myotonic dystrophy type I (DM1 or Steinert's), myotonic dystrophy type II (DM2 or proximal myotonic myopathy), or congenital myotonia.

In some embodiments, the muscle injury is a surgery-related muscle injury, a traumatic muscle injury, a work-related skeletal muscle injury, or an overtraining-related muscle injury.

Non-limiting examples of surgery-related muscle injuries include muscle damage due to knee replacement, anterior cruciate ligament (ACL) repair, plastic surgery, hip replacement surgery, joint replacement surgery, tendon repair surgery, surgical repair of rotator cuff disease and injury, and amputation.

In one embodiment, the muscle injury is a surgery-related muscle injury and the treatment method provides for administration of at least one dose of an HPGDS inhibitor of Formula (I) or a pharmaceutically acceptable salt thereof prior to the surgery (for example, within one day before the surgery) followed by periodic administration of a dose of the HPGDS inhibitor during the recovery period.

In another embodiment, the muscle injury is a surgery-related muscle injury and the treatment method provides for administration of at least one high dose of an HPGDS inhibitor of Formula (I) or a pharmaceutically acceptable salt thereof within one day to one week following the surgery.

In yet another embodiment, the muscle injury is a surgery-related muscle injury and the treatment method provides for administration of at least one high dose of an HPGDS inhibitor of Formula (I) or a pharmaceutically acceptable salt thereof within one day to one week following the surgery, followed by periodic administration of a dose of the HPGDS inhibitor during the recovery period.

Non-limiting examples of traumatic muscle injuries include battlefield muscle injuries, auto accident-related muscle injuries, and sports-related muscle injuries. Traumatic injury to the muscle can include lacerations, blunt force contusions, shrapnel wounds, muscle pulls or tears, burns, acute strains, chronic strains, weight or force stress injuries, repetitive stress injuries, avulsion muscle injury, and compartment syndrome.

In one embodiment, the muscle injury is a traumatic muscle injury and the treatment method provides for administration of at least one dose of an HPGDS inhibitor of Formula (I) or a pharmaceutically acceptable salt thereof, immediately after the traumatic injury (for example, within one day of the injury) followed by periodic administration of a dose of the HPGDS inhibitor during the recovery period.

Non-limiting examples of work-related muscle injuries include injuries caused by highly repetitive motions, forceful motions, awkward postures, prolonged and forceful mechanical coupling between the body and an object, and vibration.

Overtraining-related muscle injuries include unrepaired or under-repaired muscle damage coincident with a lack of recovery or lack of an increase of physical work capacity.

In an additional embodiment, the muscle injury is exercise or sports-induced muscle damage resulting including exercise-induced delayed onset muscle soreness (DOMS).

In some embodiments, the invention encompasses a therapeutic combination in which the HPGDS inhibitor of Formula (I) or a pharmaceutically acceptable salt thereof is administered in a subject in combination with the implantation of a biologic scaffold (e.g. a scaffold comprising extracellular matrix) that promotes muscle regeneration. Such scaffolds are known in the art. See, for example, Turner and Badylack (2012) *Cell Tissue Res.* 347(3):759-74 and U.S. Pat. No. 6,576,265. Scaffolds comprising non-cross-linked extracellular matrix material are preferred.

In another aspect, the invention provides a method of treating tendon damage where the method comprises administering a compound of Formula (I) or a pharmaceutically acceptable salt thereof to a subject in need thereof. In a particular embodiment, the invention includes a method of enhancing the formation of a stable tendon-bone interface. In a related embodiment, the invention provides a method of increasing the stress to failure of tendons, for example surgically-repaired tendons. In an additional embodiment, the invention provides a method of reducing fibrosis at the repair site for surgically-repaired tendons. In a particular embodiment, the invention provides a method of treating tendon damage associated with rotator cuff injury, or tendon damage associated with surgical repair of rotator cuff injury.

In another aspect, the invention provides a method of treating a disease state selected from: allergic diseases and other inflammatory conditions such as asthma, aspirin-exacerbated respiratory disease (AERD), cough, chronic obstructive pulmonary disease (including chronic bronchitis and emphysema), bronchoconstriction, allergic rhinitis (seasonal or perennial), vasomotor rhinitis, rhinoconjuctivitis, allergic conjunctivitis, food allergy, hypersensitivity lung diseases, eosinophilic syndromes including eosinophilic asthma, eosinophilic pneumonitis, eosinophilic oesophagitis, eosinophilic granuloma, delayed-type hypersensitivity disorders, atherosclerosis, rheumatoid arthritis, pancreatitis, gastritis, inflammatory bowel disease, osteoarthritis, psoriasis, sarcoidosis, pulmonary fibrosis, respiratory distress syndrome, bronchiolitis, sinusitis, cystic fibrosis, actinic keratosis, skin dysplasia, chronic urticaria, eczema and all types of dermatitis including atopic dermatitis or contact dermatitis in a subject in need thereof comprising administering to the subject a therapeutically effective amount of a compound of Formula (I) or a pharmaceutically acceptable salt thereof.

By the term "treating" and derivatives thereof as used herein, in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, the term "effective amount" and derivatives thereof means that amount of a drug or pharmaceutical agent that will elicit the biological or medical response of a tissue, system, animal or human that is being sought, for instance, by a researcher or clinician. Furthermore, the term "therapeutically effective amount" and derivatives thereof means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The subject to be treated in the methods of the invention is typically a mammal in need of such treatment, preferably a human in need of such treatment.

COMPOSITIONS

The pharmaceutically active compounds within the scope of this invention are useful as inhibitors of HPGDS in mammals, particularly humans, in need thereof.

The present invention therefore provides a method of treating neurodegenerative diseases, musculoskeletal diseases and other conditions requiring HPGDS inhibition, which comprises administering an effective amount of a compound of Formula (I) or a pharmaceutically acceptable salt thereof. The compounds of Formula (I) also provide for a method of treating the above indicated disease states because of their demonstrated ability to act as HPGDS inhibitors. The drug may be administered to a patient in need thereof by any conventional route of administration, including, but not limited to, intravenous, intramuscular, oral, topical, subcutaneous, intradermal, intraocular and parenteral. Suitably, a HPGDS inhibitor may be delivered directly to the brain by intrathecal or intraventricular route, or implanted at an appropriate anatomical location within a device or pump that continuously releases the HPGDS inhibitor drug.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical compositions are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-500 mg/kg of active compound, preferably 0.001-100 mg/kg. When treating a human patient in need of a HPGDS inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages, is preferred. Parenteral administration, at high dosages, however, also can be used when safe and convenient for the patient.

Optimal dosages to be administered may be readily determined by those skilled in the art, and will vary with the particular HPGDS inhibitor in use, the strength of the preparation, the mode of administration, and the advancement of the disease condition. Additional factors depending on the particular patient being treated will result in a need to adjust dosages, including patient age, weight, diet, and time of administration.

When administered to prevent organ damage in the transportation of organs for transplantation, a compound of Formula (I) is added to the solution housing the organ during transportation, suitably in a buffered solution.

The method of this invention of inducing HPGDS inhibitory activity in mammals, including humans, comprises administering to a subject in need of such activity an effective HPGDS inhibiting amount of a pharmaceutically active compound of the present invention.

The invention also provides for the use of a compound of Formula (I) or a pharmaceutically acceptable salt thereof in the manufacture of a medicament for use as a HPGDS inhibitor.

The invention also provides for the use of a compound of Formula (I) or a pharmaceutically acceptable salt thereof in the manufacture of a medicament for use in therapy.

The invention also provides for the use of a compound of Formula (I) or a pharmaceutically acceptable salt thereof in the manufacture of a medicament for use in treating musculoskeletal diseases such as Duchenne Muscular Dystrophy, spinal cord contusion injury, neuroinflammatory diseases such as Multiple Sclerosis or neurodegenerative diseases such as Alzheimer's disease or amyotrophic lateral sclerosis (ALS).

The invention also provides for a pharmaceutical composition for use as a HPGDS inhibitor which comprises a compound of Formula (I) or a pharmaceutically acceptable salt thereof and a pharmaceutically acceptable carrier.

The invention also provides for a pharmaceutical composition for use in the treatment of cancer which comprises a compound of Formula (I) or a pharmaceutically acceptable salt thereof and a pharmaceutically acceptable carrier.

In addition, the pharmaceutically active compounds of the present invention can be co-administered with further active ingredients, such as other compounds known to treat cancer, or compounds known to have utility when used in combination with a HPGDS inhibitor.

By the term "co-administration" as used herein is meant either simultaneous administration or any manner of separate sequential administration of a HPGDS inhibiting compound, as described herein, and a further active agent or agents, known to be useful in the treatment of conditions in which a H-PGDS inhibitor is indicated. The term further active agent or agents, as used herein, includes any compound or therapeutic agent known to or that demonstrates advantageous properties when administered to a patient in need of H-PGDS inhibition. Preferably, if the administration is not simultaneous, the compounds are administered in a close time proximity to each other. Furthermore, it does not matter if the compounds are administered in the same dosage form, e.g. one compound may be administered by injection and another compound may be administered orally.

The invention also relates to the use of a compound of Formula (I) or a pharmaceutically acceptable salt thereof in the preparation of a medicament for the treatment of neurodegenerative diseases, musculoskeletal diseases and diseases associated with H-PGDS inhibition.

The invention also provides a pharmaceutical composition comprising from 0.5 to 1,000 mg of a compound of Formula (I) or pharmaceutically acceptable salt thereof and from 0.5 to 1,000 mg of a pharmaceutically acceptable excipient.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Mass Directed Auto-Preparative HPLC (MDAP)

Mass Directed Auto-Preparative HPLC is undertaken under the conditions given below. Detection is by absorption over the wavelength range 210 nm to 350 nm and mass spectra are recorded on a mass spectrometer using alternate-scan positive and negative mode electrospray ionization.

Method A

Method A is conducted on a Waters SunFire C18 column (typically 150 mm×30 mm i.d. with 5 micron particle size) at ambient temperature. The solvents employed are:

A=0.1% v/v solution of formic acid in water

B=0.1% v/v solution of formic acid in acetonitrile.

Method B

Method B is conducted on a Waters XBridge C18 column (typically 100 mm×30 mm i.d. with 5 micron particle size) at ambient temperature. The solvents employed are:

A=10 mM aqueous ammonium bicarbonate adjusted to pH 10 with ammonia solution.

B=acetonitrile.

Method C

Method C is conducted on a Waters SunFire C18 column (typically 150 mm×30 mm i.d. with 5 micron particle size) at ambient temperature. The solvents employed are:

A=0.1% v/v solution of trifluoroacetic acid in water

B=0.1% v/v solution of trifluoroacetic acid in acetonitrile.

EXAMPLES

The following Examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

INTERMEDIATES

Intermediate 1: tert-Butyl 3-((methylsulfonyl)oxy)azetidine-1-carboxylate

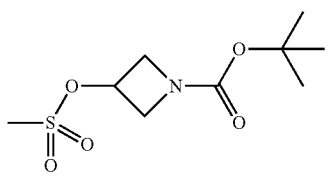 [SMILES: CC(C)(C)OC(=O)N1CC(OS(C)(=O)=O)C1]

To a stirred, cooled (0° C.) solution of tert-butyl 3-hydroxyazetidine-1-carboxylate (500 mg, 2.89 mmol in DCM (5 mL) was added triethylamine (0.90 mL, 6.46 mmol) followed by methanesulfonyl chloride (0.25 mL, 3.21 mmol). The mixture was allowed to warm to room temperature and stirred overnight. The mixture was poured into saturated brine and extracted twice with EtOAc. The combined organic layers were dried over $Na_2SO_4$ and filtered. Solvent was removed under reduced pressure. The remaining material was purified on silica gel eluting with a 0%-50% EtOAc-hexanes gradient. The appropriate fractions (identified by TLC, silica gel, 50% EtOAc/hexanes, $KMnO_4$ stain) were combined, evaporated under reduced pressure and placed in vacuo to give the title compound (699 mg, 96%) as a colorless oil that slowly solidified. $^1$H NMR (400 MHz, $CD_3SOCD_3$) δ 1.39 (s, 9H), 3.25 (s, 3H), 3.88-3.94 (m, 2H), 4.19-4.36 (m, 2H), 5.22-5.28 (m, 1H); LC-MS (LC-ES) M+H-tert-Bu=196.

Intermediate 2: 3-(2-(Difluoromethoxy)-5-fluorophenoxy)azetidine hydrochloride

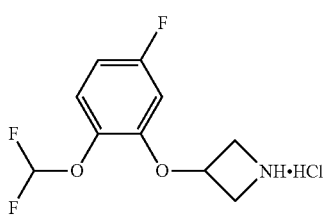

A. 2-(Benzyloxy)-4-fluorobenzaldehyde

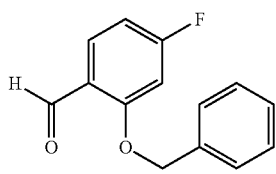 [SMILES: O=Cc1ccc(F)cc1OCc1ccccc1]

To a stirred solution of 4-fluoro-2-hydroxybenzaldehyde (5.00 g, 35.7 mmol) in DMF (50 mL) was added potassium carbonate (5.92 g, 42.8 mmol) and benzyl bromide (4.79 mL, 42.8 mmol). After 3 h, the reaction mixture was quenched with water and extracted with ethyl acetate (3×). The organic layers were dried over $Na_2SO_4$, evaporated and dried under vacuum. The residue was purified on silica gel eluting with a 0%-40% EtOAc in hexanes gradient. The appropriate fractions were combined, evaporated under reduced pressure and placed in vacuo to give the title compound (7.3 g, 89%). $^1$H NMR (400 MHz, $CD_3SOCD_3$) δ 5.28 (s, 2H), 6.78-7.01 (m, 1H), 7.23-7.26 (m, 1H), 7.29-7.39 (m, 3H), 7.45-7.54 (m, 2H), 7.69-7.75 (m, 1H), 10.29 (s, 1H); LC-MS (LC-ES) M+H=231.

B. 2-(Benzyloxy)-4-fluorophenol

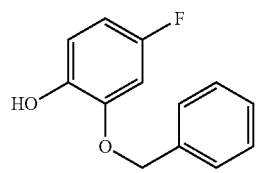 [SMILES: Oc1ccc(F)cc1OCc1ccccc1]

3-Chlorobenzoperoxoic acid (14.0 g, 81.0 mmol) was added to a solution of 2-(benzyloxy)-4-fluorobenzaldehyde (Intermediate 2A) (7.50 g, 32.6 mmol) in DCM (100 mL) and stirred at 40° C. overnight, cooled and washed with saturated $NaHCO_3$ (3×) and brine. The organic layer was dried over $Na_2SO_4$ and evaporated. The residue was dissolved in THF (100 mL) and water (50 mL), and lithium hydroxide (2.34 g, 98.0 mmol) was added. The reaction mixture was stirred at room temperature for 1 h. Citric acid was added until pH neutral, and the aqueous phase was extracted with ethyl acetate (3×). The combined organic layers were washed with brine, dried over $Na_2SO_4$ and evaporated. The residue was purified on silica gel eluting with a 0%-40% EtOAc in hexanes gradient. The appropriate fractions were combined, evaporated under reduced pressure and placed in vacuo to give the title compound (5.5 g, 78%). $^1$H NMR (400 MHz, $CD_3SOCD_3$) δ 5.11 (s, 2H), 6.53-6.59 (m, 1H), 6.74-6.78 (m, 1H), 6.87-6.91 (m, 1H), 7.31-7.36 (m, 1H), 7.39-7.42 (m, 2H), 7.45-7.49 (m, 2H), 8.95 (s, 1H); LC-MS (LC-ES) M−H=217.

C. 2-(Benzyloxy)-1-(difluoromethoxy)-4-fluorobenzene

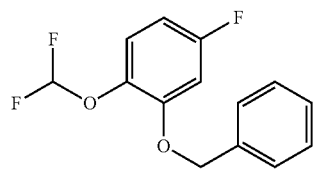 [SMILES: Fc1ccc(OC(F)F)c(OCc2ccccc2)c1]

To a stirred, cooled (−78° C.) solution of 2-(benzyloxy)-4-fluorophenol (Intermediate 2B) (175 mg, 0.802 mmol) and potassium hydroxide (900 mg, 16.0 mmol) in acetonitrile (5 mL) and water (5 mL) was added diethyl (bromodifluoromethyl)phosphonate (0.30 mL, 1.69 mmol). The cooling bath was removed and the mixture was allowed to warm to room temperature. After stirring for the weekend, the mixture was extracted twice with $Et_2O$. The combined organic layers were washed with brine, dried over $Na_2SO_4$, filtered and concentrated under reduced pressure. The residue was purified on silica gel eluting with a 0%-25% EtOAc in hexanes gradient. The appropriate fractions were combined, evapo-

D. 2-(Difluoromethoxy)-5-fluorophenol

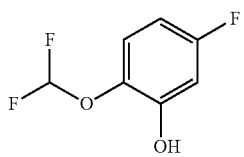

To a stirred solution of 2-(benzyloxy)-1-(difluoromethoxy)-4-fluorobenzene (Intermediate 2C) (90 mg, 0.336 mmol) in methanol (3 mL) under a nitrogen atmosphere was added 10% Pd/C (9 mg, 0.085 mmol). The reaction vessel was evacuated under reduced pressure and purged with hydrogen three times. The mixture was placed under a nitrogen atmosphere, fitted with a hydrogen filled balloon and stirred overnight under a hydrogen atmosphere. The mixture was filtered through a pad of Celite®, washing with DCM and EtOH. The filtrate was evaporated to dryness to give the crude title compound (30 mg, 50%), which was used without further purification. $^1$H NMR (400 MHz, CD$_3$SOCD$_3$) δ 6.59-6.65 (m, 1H), 6.75 (dd, J=10, 4 Hz, 1H), 6.97 (s, 1H), 7.13 (dd, J=8, 4 Hz, 1H); LC-MS (LC-ES)

E. tert-Butyl 3-(2-(difluoromethoxy)-5-fluorophenoxy)azetidine-1-carboxylate

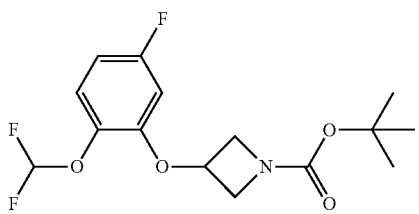 [SMILES: CC(C)(C)OC(=O)N1CC(Oc2cc(F)ccc2OC(F)F)C1]

To a stirred solution of tert-butyl 3-((methylsulfonyl)oxy)azetidine-1-carboxylate (Intermediate 1) (40 mg, 0.16 mmol) and 2-(difluoromethoxy)-5-fluorophenol (Intermediate 2D) (26 mg, 0.15 mmol) in DMF (2 mL) was added cesium carbonate (55 mg, 0.17 mmol). The mixture was heated to 80° C. overnight, and LC/MS showed starting material remained. Heating was continued overnight, and the mixture was poured into water and extracted twice with EtOAc. The combined organic layers were washed with brine, dried over Na$_2$SO$_4$, filtered and concentrated. The remaining material was purified on silica gel eluting with a 0%-25% EtOAc-hexanes gradient. The appropriate fractions were combined, evaporated under reduced pressure and placed in vacuo to give the title compound (27 mg, 55%) as a colorless oil. $^1$H NMR (400 MHz, CD$_3$SOCD$_3$) δ 1.36 (s, 9H), 3.76-3.82 (m, 2H), 4.26-4.32 (m, 2H), 4.99-5.05 (m, 1H), 6.79-6.87 (m, 2H), 7.04 (s, 1H), 7.21-7.26 (m, 1H); LC-MS (LC-ES) M+H-Boc=234.

F. 3-(2-(Difluoromethoxy)-5-fluorophenoxy)azetidine hydrochloride

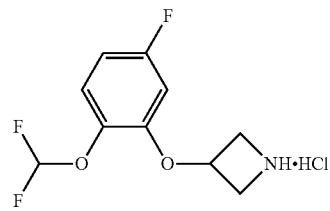

4 N Hydrochloric acid (1 mL, 4.00 mmol) in dioxane was added to tert-butyl 3-(2-(difluoromethoxy)-5-fluorophenoxy)azetidine-1-carboxylate (Intermediate 2E) (26 mg, 0.078 mmol). The mixture was stirred for 4 h and then concentrated under reduced pressure. The remaining material was diluted with DCM and concentrated under reduced pressure. This process was repeated twice to give the title compound (21 mg). LC-MS (LC-ES) peak at T=0.38 min; M+H=234.

Intermediate 3: 4-Nitrophenyl ((trans)-4-(2-hydroxypropan-2-yl)cyclohexyl)carbamate

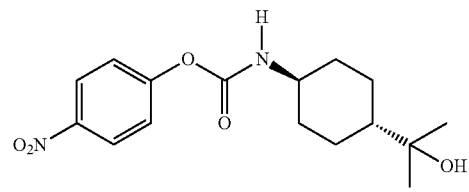 [SMILES: CC(C)(O)[C@H]1CC[C@H](NC(=O)Oc2ccc([N+](=O)[O-])cc2)CC1]

To a stirred, cooled (0° C.) solution of 4-nitrophenyl chloroformate (230 mg, 1.14 mmol) in DCM (4 mL) was added 2-((trans)-4-aminocyclohexyl)propan-2-ol (150 mg, 0.954 mmol) followed by N,N-diisopropylethylamine (0.20 mL, 1.2 mmol). The mixture was warmed to room temperature, stirred overnight and concentrated. The remaining material was purified on silica gel eluting with a 0%-60% EtOAc-hexanes gradient. The appropriate fractions were combined, evaporated under reduced pressure and placed in vacuo to give the title compound (97 mg, 31%) as a white solid. $^1$H NMR (400 MHz, CD$_3$SOCD$_3$) δ 1.01 (s, 6H), 1.03-1.27 (m, 5H), 1.87 (dd, J=48, 16 Hz, 4H), 3.22-3.43 (m, 1H), 4.04 (s, 1H), 7.39 (d, J=8 Hz, 2H), 7.97 (d, J=8 Hz, 1H), 8.25 (d, J=8 Hz, 2H); LC-MS (LC-ES) M+H=323.

Intermediate 4: (trans)-3-(2-(Difluoromethoxy)-5-fluorophenoxy)cyclobutanecarboxylic acid

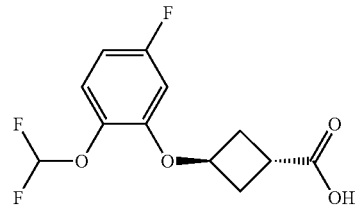 [SMILES: O=C(O)[C@H]1C[C@H](Oc2cc(F)ccc2OC(F)F)C1]

A. (trans)-Methyl 3-(2-(difluoromethoxy)-5-fluorophenoxy)cyclobutanecarboxylate

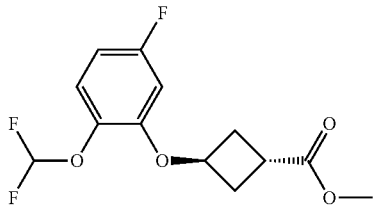 [SMILES: COC(=O)[C@H]1C[C@H](Oc2cc(F)ccc2OC(F)F)C1]

Triphenylphosphine-PS (3.27 g, 12.5 mmol) was added to a solution of 2-(difluoromethoxy)-5-fluorophenol (Intermediate 2D) (1.85 g, 10.4 mmol) in tetrahydrofuran (10 mL). The reaction mixture was cooled to 0° C., and (cis)-methyl 3-hydroxycyclobutanecarboxylate (1.33 mL, 12.5 mmol) was added, followed by DIAD (2.4 mL, 13 mmol). The reaction mixture was then warmed to room temperature, stirred for 12 h, filtered, and concentrated. The remaining material was purified on silica gel eluting with a 0%-70% EtOAc-hexanes gradient. The appropriate fractions were combined, evaporated under reduced pressure and placed in vacuo to give the title compound (1.79 g, 58%). $^1$H NMR (400 MHz, CD$_3$SOCD$_3$) δ 2.27-2.45 (m, 2H), 2.57-2.79 (m, 2H), 3.13-3.27 (m, 1H), 3.32 (s, 3H), 4.90 (dd, J=7, 6 Hz, 1H), 6.66-6.95 (m, 2H), 7.03 (s, 1H), 7.11-7.34 (m, 1H); LC-MS (LC-ES) peak at T=0.86 min.

B. (trans)-3-(2-(Difluoromethoxy)-5-fluorophenoxy)cyclobutanecarboxylic acid

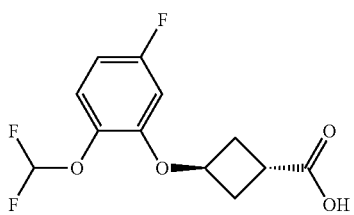 [SMILES: O=C(O)[C@H]1C[C@H](Oc2cc(F)ccc2OC(F)F)C1]

To a solution of (trans)-methyl 3-(2-(difluoromethoxy)-5-fluorophenoxy)cyclobutanecarboxylate (Intermediate 4A) (1.75 g, 6.02 mmol) in THF (30 mL) was added a solution of LiOH (0.432 g, 18.1 mmol) in water (15 mL). The reaction mixture was stirred at room temperature for 1 h. Citric acid was added until pH=4 and the reaction was extracted with ethyl acetate (3×). The combined organic layers were washed with brine, dried over Na$_2$SO$_4$ and evaporated to give the title compound (1.74 g, quantitative yield). $^1$H NMR (400 MHz, CD$_3$SOCD$_3$) δ 2.35 (ddd, J=13, 10, 6 Hz, 2H), 2.61-2.76 (m, 2H), 3.10 (dd, J=6, 5 Hz, 1H), 4.89 (dd, J=6, 5 Hz, 1H), 6.64-6.94 (m, 2H), 7.02 (s, 1H), 7.11-7.38 (m, 1H), 12.33 (br s, 1H); LC-MS (LC-ES) M−H=275.

Intermediate 5: 2-(3-Aminoazetidin-1-yl)thiazole-5-carbonitrile dihydrochloride, Methyl 2-(3-aminoazetidin-1-yl)thiazole-5-carbimidate dihydrochloride, and 2-(3-Aminoazetidin-1-yl)thiazole-5-carboxamide dihydrochloride

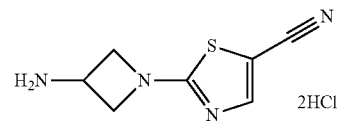

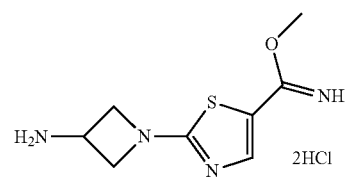

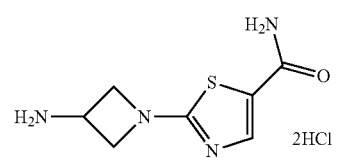

A. tert-Butyl (1-(5-cyanothiazol-2-yl)azetidin-3-yl)carbamate

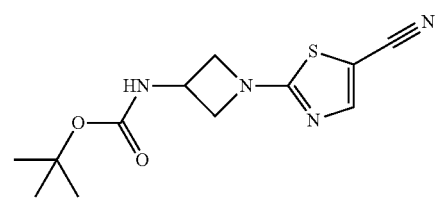 [SMILES: CC(C)(C)OC(=O)NC1CN(c2ncc(C#N)s2)C1]

To tert-butyl azetidin-3-ylcarbamate hydrochloride (300 mg, 1.44 mmol) in acetonitrile (10 mL), 2-chlorothiazole-5-carbonitrile (208 mg, 1.44 mmol) was added, followed by N,N-diisopropylethylamine (0.75 mL, 4.3 mmol). The mixture was heated in a microwave at 110° C. for 5 h, then allowed to sit at room temperature for two days as crystals appeared. This solid product was collected by filtration, the filtrate was concentrated in vacuo and the residue purified on silica gel eluting with a 10%-60% EtOAc-hexanes gradient. The appropriate fractions were combined, evaporated under reduced pressure, combined with the previously harvested crystal solid and placed in vacuo to give the title compound as a white solid (90 mg, 22%). $^1$H NMR (400 MHz, CDCl$_3$) δ 1.45 (s, 9H), 4.03-4.07 (m, 2H), 4.41-4.49 (m, 2H), 4.71 (br s, 1H), 5.05 (br s, 1H), 7.67 (s, 1H); LC-MS (LC-ES) M+H-Boc=181.

B. 2-(3-Aminoazetidin-1-yl)thiazole-5-carbonitrile dihydrochloride, Methyl 2-(3-aminoazetidin-1-yl)thiazole-5-carbimidate dihydrochloride, and 2-(3-Aminoazetidin-1-yl)thiazole-5-carboxamide dihydrochloride

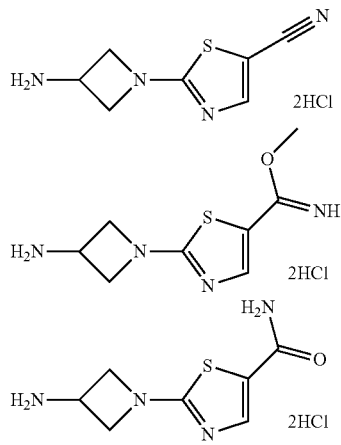

To tert-butyl (1-(5-cyanothiazol-2-yl)azetidin-3-yl)carbamate (Intermediate 5A) (370 mg, 1.32 mmol) in DCM (5 mL), HCl (10 mL, 40.0 mmol) (4 M in dioxane) was added. The mixture was stirred at room temperature for 1 h and the solvent was removed to give a mixture of the crude title compounds as a tan solid which was used without further purification.

2-(3-Aminoazetidin-1-yl)thiazole-5-carbonitrile dihydrochloride

LC-MS (LC-ES) peak at T=0.41 min; M+H=181.

Methyl 2-(3-aminoazetidin-1-yl)thiazole-5-carbimidate dihydrochloride

LC-MS (LC-ES) peak at T=0.40 min; M+H=213.

2-(3-Aminoazetidin-1-yl)thiazole-5-carboxamide dihydrochloride

LC-MS (LC-ES) peak at T=0.29 min; M+H=199.

Intermediate 6: 2-(3-Aminoazetidin-1-yl)pyrimidine-4-carboxamide dihydrochloride and 2-(3-Aminoazetidin-1-yl)pyrimidine-4-carbonitrile dihydrochloride

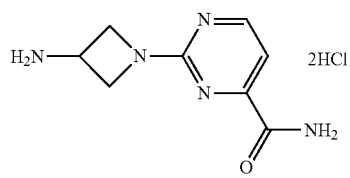

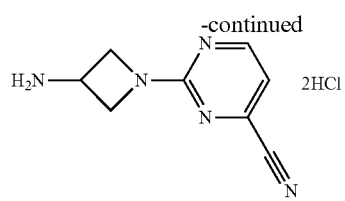

A. tert-Butyl (1-(4-cyanopyrimidin-2-yl)azetidin-3-yl)carbamate

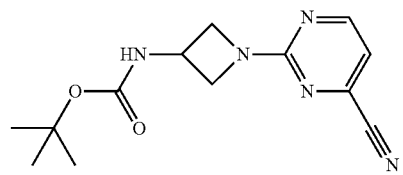 [SMILES: CC(C)(C)OC(=O)NC1CN(c2nccc(C#N)n2)C1]

To tert-butyl azetidin-3-ylcarbamate hydrochloride (300 mg, 1.44 mmol) in acetonitrile (10 mL), 2-chloropyrimidine-4-carbonitrile (241 mg, 1.73 mmol) was added, followed by N,N-diisopropylethylamine (0.75 mL, 4.3 mmol). The mixture was heated in a microwave at 90° C. for 3 h, the solvent was concentrated in vacuo and the residue purified on silica gel eluting with a 10%-60% EtOAc-hexanes gradient. The appropriate fractions were combined, evaporated under reduced pressure and placed in vacuo to give the title compound as a white solid (423 mg, quantitative yield). $^1$H NMR (400 MHz, CDCl$_3$) δ 1.46 (s, 9H), 3.91-3.99 (m, 2H), 4.40-4.48 (m, 2H), 4.63 (br s, 1H), 5.03 (br s, 1H), 6.81 (d, J=5 Hz, 1H), 8.45 (d, J=5 Hz, 1H); LC-MS (LC-ES) M+H-Boc=176.

B. 2-(3-Aminoazetidin-1-yl)pyrimidine-4-carboxamide dihydrochloride and 2-(3-Aminoazetidin-1-yl)pyrimidine-4-carbonitrile dihydrochloride

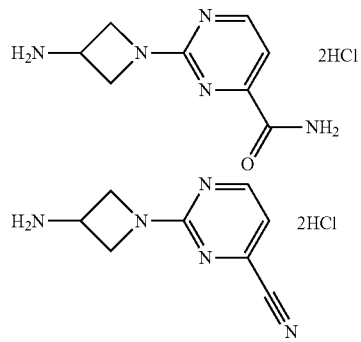

To tert-butyl (1-(4-cyanopyrimidin-2-yl)azetidin-3-yl)carbamate (Intermediate 6A) (68 mg, 0.25 mmol) in DCM (5 mL), HCl (10 mL, 40 mmol) (4 M in dioxane) was added. The mixture was stirred at room temperature for 1 h and the solvent was removed to give a mixture of the title compounds as a tan solid which was used without further purification.

2-(3-Aminoazetidin-1-yl)pyrimidine-4-carboxamide dihydrochloride

LC-MS (LC-ES) M+H=194.

2-(3-Aminoazetidin-1-yl)pyrimidine-4-carbonitrile dihydrochloride

LC-MS (LC-ES) M+H=176.

Intermediate 7: 1-(2-Chloropyrimidin-4-yl)azetidin-3-amine dihydrochloride

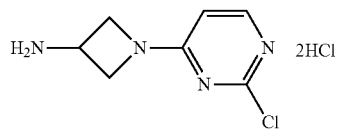

A. tert-Butyl (1-(2-chloropyrimidin-4-yl)azetidin-3-yl)carbamate

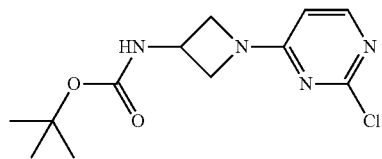 [SMILES: CC(C)(C)OC(=O)NC1CN(c2ccnc(Cl)n2)C1]

To tert-butyl azetidin-3-ylcarbamate hydrochloride (500 mg, 2.40 mmol) in methanol (10 mL), MP-carbonate (3.1 mmol/g) was added. The mixture was stirred for 1 h, filtered and washed with MeOH. To this mixture, 2,4-dichloropyrimidine (428 mg, 2.88 mmol) was added followed by N,N-diisopropylethylamine (0.42 mL, 2.4 mmol). The mixture was stirred at room temperature for 2 h, the solvent was concentrated in vacuo and the residue purified on silica gel eluting with a 10%-60% EtOAc-hexanes gradient. The appropriate fractions were combined, evaporated under reduced pressure and placed in vacuo to give the title compound (412 mg, 60%). $^1$H NMR (400 MHz, CDCl$_3$) δ 1.45 (s, 9H), 3.88-4.00 (m, 2H), 4.33-4.47 (m, 2H), 4.55-4.73 (m, 1H), 4.92-5.10 (m, 1H), 6.07 (d, J=6 Hz, 1H), 8.02 (d, J=6 Hz, 1H); LC-MS (LC-ES) M+H=285, 287 (Cl pattern).

B. 1-(2-Chloropyrimidin-4-yl)azetidin-3-amine dihydrochloride

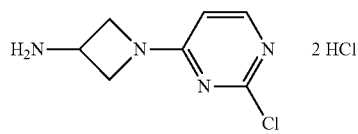 [SMILES: NC1CN(c2ccnc(Cl)n2)C1]

To tert-butyl (1-(2-chloropyrimidin-4-yl)azetidin-3-yl) carbamate (Intermediate 7A) (410 mg, 1.44 mmol) in DCM (3 mL), HCl (6 mL, 24 mmol) (4 M in dioxane) was added. The mixture was stirred at room temperature for 1 h and the solvent was removed in vacuo to give the title compound as a white solid (374 mg, quantitative yield). $^1$H NMR (400 MHz, CD$_3$OD) δ 4.35-4.45 (m, 3H), 4.68-4.74 (m, 2H), 6.75 (d, J=7 Hz, 1H), 8.18 (d, J=7 Hz, 1H); LC-MS (LC-ES) M+H=185, 187 (Cl pattern).

Intermediate 8: 1-(4-Chloropyrimidin-2-yl)azetidin-3-amine hydrochloride

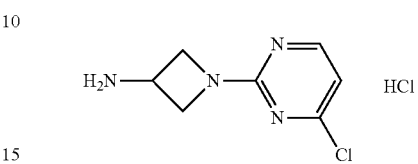

A. tert-Butyl (1-(4-chloropyrimidin-2-yl)azetidin-3-yl)carbamate

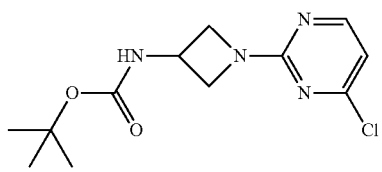 [SMILES: CC(C)(C)OC(=O)NC1CN(c2nccc(Cl)n2)C1]

To tert-butyl azetidin-3-ylcarbamate hydrochloride (500 mg, 2.40 mmol) in methanol (10 mL) was added MP-carbonate (3.1 mmol/g). The mixture was stirred for 1 h, filtered and washed with MeOH. To this mixture, 2,4-dichloropyrimidine (428 mg, 2.88 mmol) was added followed by N,N-diisopropylethylamine (0.42 mL, 2.4 mmol). The mixture was stirred at room temperature for 2 h, the solvent was concentrated in vacuo and the residue purified on silica gel eluting with a 10%-60% EtOAc-hexanes gradient. The appropriate fractions were combined, evaporated under reduced pressure and placed in vacuo to give the title compound (68 mg, 10%). $^1$H NMR (400 MHz, CDCl$_3$) δ 1.46 (s, 9H), 3.90-3.96 (m, 2H), 4.42-4.47 (m, 2H), 4.56-4.66 (m, 1H), 4.92-5.01 (m, 1H), 6.57 (d, J=5 Hz, 1H), 8.16 (d, J=5 Hz, 1H); LC-MS (LC-ES) M+H=285, 287 (Cl pattern).

B. 1-(4-Chloropyrimidin-2-yl)azetidin-3-amine hydrochloride

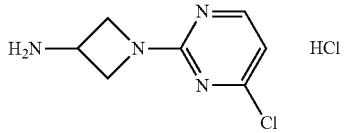 [SMILES: NC1CN(c2nccc(Cl)n2)C1 ; Cl]

To tert-butyl (1-(4-chloropyrimidin-2-yl)azetidin-3-yl) carbamate (Intermediate 8A) (68 mg, 0.24 mmol) in DCM (1.5 mL) was added 4 M HCl in dioxane (3 mL, 12 mmol). The mixture was stirred at room temperature for 1 h and the solvent was removed in vacuo to give the title compound as a white solid (60 mg, quantitative yield). $^1$H NMR (400 MHz, CD$_3$OD) δ 4.21-4.29 (m, 3H), 4.54-4.62 (m, 2H), 6.92 (d, J=6 Hz, 1H), 8.31 (d, J=6 Hz, 1H); LC-MS (LC-ES) M+H=185, 187 (Cl pattern).

Intermediate 9: 1-(5-Fluoropyrimidin-2-yl)azetidin-3-amine dihydrobromide

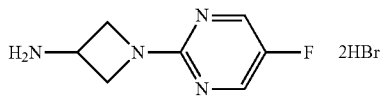

A. Benzyl (1-(5-fluoropyrimidin-2-yl)azetidin-3-yl)carbamate

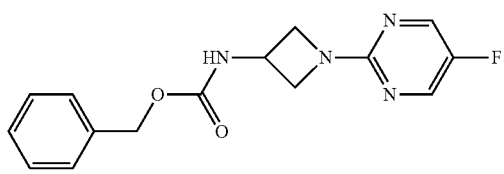 [SMILES: O=C(NC1CN(c2ncc(F)cn2)C1)OCc1ccccc1]

To a microwave reaction vial with benzyl azetidin-3-ylcarbamate hydrochloride (500 mg, 2.0 mmol) in acetonitrile (8 mL) was added 2-chloro-5-fluoropyrimidine (546 mg, 4.1 mmol) and N,N-diisopropylethylamine (1.1 mL, 6.2 mmol). The mixture was heated with a heating gun to form a solution and heated in a microwave at 155° C. for 5 h. The solvent was concentrated in vacuo and the residue purified on silica gel eluting with a 0%-60% EtOAc/EtOH (3:1) in hexanes gradient. The appropriate fractions were combined, evaporated under reduced pressure and placed in vacuo to give the title compound (560 mg, 90%). $^1$H NMR (400 MHz, CDCl$_3$) δ 3.81-3.85 (m, 2H), 4.31-4.36 (m, 2H), 4.55-4.62 (m, 1H), 5.03 (s, 2H), 5.09-5.17 (m, 1H), 7.19-7.32 (m, 5H), 8.11 (s, 2H); LC-MS (LC-ES) M+H=303.

B. 1-(5-Fluoropyrimidin-2-yl)azetidin-3-amine dihydrobromide

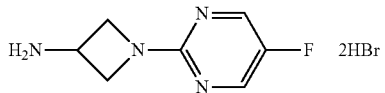

To benzyl (1-(pyrimidin-2-yl)azetidin-3-yl)carbamate (Intermediate 9A) (110 mg, 0.39 mmol) was added 33% HBr in AcOH (0.06 mL, 0.39 mmol). The mixture was stirred at room temperature for 1.5 h and the solvent was removed in vacuo to give the title compound as a tan solid (112 mg, 93%). $^1$H NMR (400 MHz, CD$_3$OD) δ 4.21-4.21 (m, 2H), 4.21-4.26 (m, 1H), 4.49-4.55 (m, 2H), 8.45 (s, 2H); LC-MS (LC-ES) M+H=169.

Alternatively 1-(5-Fluoropyrimidin-2-yl)azetidin-3-amine can be prepared as the dihydrochloride

Intermediate 9: 1-(5-Fluoropyrimidin-2-yl)azetidin-3-amine dihydrochloride

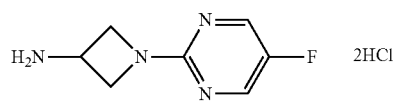

C. tert-Butyl (1-(5-fluoropyrimidin-2-yl)azetidin-3-yl)carbamate

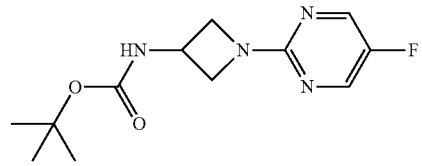 [SMILES: CC(C)(C)OC(=O)NC1CN(c2ncc(F)cn2)C1]

To a microwave reaction vial with tert-butyl azetidin-3-ylcarbamate hydrochloride (732 mg, 3.51 mmol) in acetonitrile (2 mL) was added 2-chloro-5-fluoropyrimidine (465 mg, 3.51 mmol) and N,N-diisopropylethylamine (1.23 mL, 7.02 mmol). The mixture was heated in a microwave (125° C.) for 2.5 h, cooled and some precipitated product collected by filtration. The filtrate was concentrated in vacuo and the residue purified on silica gel eluting with a 10%-50% EtOAc/EtOH (3:1) in hexanes gradient. The appropriate fractions were combined, evaporated under reduced pressure and placed in vacuo to give the title compound (620 mg, 65%) as a white solid. $^1$H NMR (400 MHz, CD$_3$OD) δ 1.47 (s, 9H), 3.89-3.98 (m, 2H), 4.32-4.39 (m, 2H), 4.43-4.53 (m, 1H), 8.31 (s, 2H); LC-MS (LC-ES) M+H=269.

D. 1-(5-Fluoropyrimidin-2-yl)azetidin-3-amine dihydrochloride

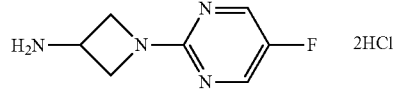 [SMILES: NC1CN(c2ncc(F)cn2)C1]

To tert-butyl (1-(5-fluoropyrimidin-2-yl)azetidin-3-yl)carbamate (Intermediate 9C) (620 mg, 2.31 mmol) in MeOH (3 mL) (with a small portion of DCM to facilitate solubility) was added 4 N HCl in dioxane (6 mL, 24 mmol). The mixture was stirred at room temperature for 3 h, and the solvent was removed in vacuo to give the title compound as a white solid (652 mg, quantitative). $^1$H NMR (400 MHz, CD$_3$OD) δ 4.11-4.20 (m, 2H), 4.20-4.26 (m, 1H), 4.50 (dd, J=10, 7 Hz, 2H), 8.47 (s, 2H); LC-MS (LC-ES) M+H=169.

Intermediate 10: Racemic 2-(((trans)-4-Aminocyclohexyl)oxy)-1-cyclopropylethanol

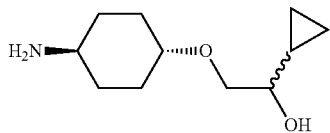 [SMILES: N[C@H]1CC[C@H](OCC(O)C2CC2)CC1]

A. trans-4-(Dibenzylamino)cyclohexanol

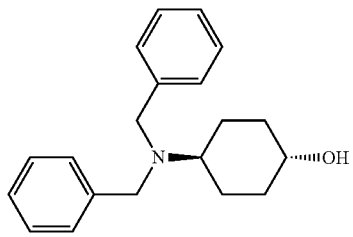 [SMILES: O[C@H]1CC[C@H](N(Cc2ccccc2)Cc2ccccc2)CC1]

Benzyl bromide (60 g, 351 mmol) was added to (trans)-4-aminocyclohexanol hydrochloride (20 g, 174 mmol) and sodium bicarbonate (40 g, 476 mmol) in EtOH (400 mL) at room temperature. The reaction was then heated to reflux for 36 h, filtered and concentrated to give a solid. To this was added hexanes and stirred overnight, filtered and air dried to afford the title compound (33.2 g, 65% yield). $^1$H NMR (CDCl$_3$) δ 1.14-1.28 (m, 2H), 1.30 (d, J=5 Hz, 1H), 1.38-1.52 (m, 2H), 1.91 (d, J=12 Hz, 2H), 2.00 (br s, 1H), 2.53 (tt, J=12, 3 Hz, 1H), 3.50-3.59 (m, 1H), 3.62 (s, 4H), 7.18-7.25 (m, 2H), 7.27-7.32 (m, 4H), 7.33-7.38 (m, 4H).

B. tert-Butyl 2-((trans-4-(dibenzylamino)cyclohexyl)oxy)acetate

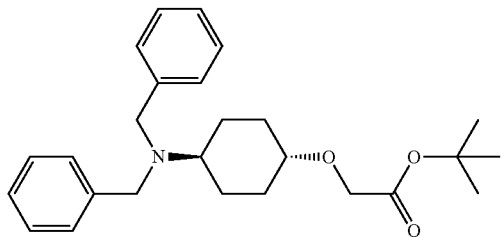 [SMILES: CC(C)(C)OC(=O)CO[C@H]1CC[C@H](N(Cc2ccccc2)Cc2ccccc2)CC1]

trans-4-(Dibenzylamino)cyclohexanol (Intermediate 10A) (1.0 g, 3.4 mmol) and tert-butyl 2-bromoacetate (1.0 mL, 6.8 mmol) were stirred in DMF (5 mL) at 55° C. A 60% dispersion of NaH in mineral oil (0.27 g, 6.8 mmol) was added portion wise over 1 h. Additional tert-butyl 2-bromoacetate (1.00 mL, 6.8 mmol) and NaH (0.27 g, 6.8 mmol) were added portion wise over 1 h. The reaction was allowed to stir at 55° C. overnight, followed by careful quenching with water. The reaction was diluted with 1.0 N aqueous NaOH and extracted with EtOAc. The organic layer was washed with water (2×), followed by brine. The combined aqueous fractions were extracted with EtOAc and the combined organics were dried over sodium sulfate, filtered, and concentrated under reduced pressure. The residue was purified by silica gel chromatography eluting with a gradient from 2-15% (3:1 ratio of EtOAc:EtOH in hexanes). The appropriate fractions were concentrated under reduced pressure to afford the title compound as a colorless oil (497 mg, 1.21 mmol). $^1$H NMR (CDCl$_3$) δ 1.43-1.46 (m, 4H), 1.47 (s, 9H), 1.92 (d, J=12 Hz, 2H), 2.07-2.14 (m, 2H), 2.48-2.58 (m, 1H), 3.24-3.30 (m, 1H), 3.61 (s, 4H), 3.96 (s, 2H), 7.17-7.24 (m, 2H), 7.26-7.32 (m, 4H), 7.34-7.38 (m, 4H); LC-MS (LC-ES) M+H=410.

C. 2-((trans-4-(Dibenzylamino)cyclohexyl)oxy)acetic acid hydrochloride

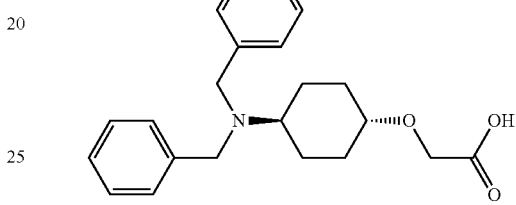

tert-Butyl 2-((trans-4-(dibenzylamino)cyclohexyl)oxy) acetate (Intermediate 10B) (2.0 g, 4.9 mmol) was stirred in DCM (5.0 mL), and TFA (3 mL) was added. The reaction was stirred at room temperature for 1 h before concentrating under reduced pressure. The residue was taken up in 1,4-dioxane (5 mL), and 4.0 M HCl in dioxane (2 mL) was added and then stirred at 0° C. Diethyl ether (20 mL) was added and the resulting precipitate was stirred at the same temperature for ~10 min before collecting by vacuum filtration. The solid was washed with diethyl ether providing the title compound as a white solid (2.03 g, 5.21 mmol). LC-MS (LC-ES) M+H=354.

D. 2-((trans-4-(Dibenzylamino)cyclohexyl)oxy)-N-methoxy-N-methylacetamide

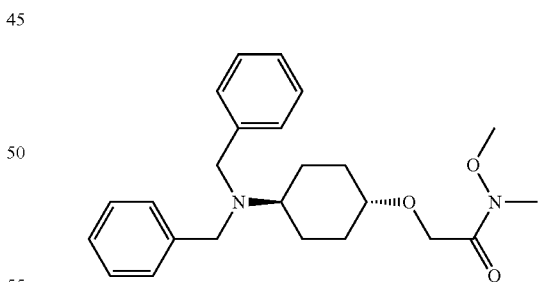

2-((trans-4-(Dibenzylamino)cyclohexyl)oxy)acetic acid hydrochloride (Intermediate 10C) (2.0 g, 5.1 mmol) was dissolved in DMF (50 mL) followed by the addition of N,N-diisopropylethylamine (3 mL, 17.2 mmol) and HATU (2.34 g, 6.16 mmol). The reaction was stirred at room temperature for ca. 5 min, and N,O-dimethylhydroxylamine hydrochloride (0.751 g, 7.69 mmol) was added. The reaction was allowed to stir at room temperature overnight, diluted with EtOAc and washed with saturated aqueous sodium bicarbonate. The organics were separated and washed with brine, dried over sodium sulfate, filtered, and concentrated under reduced pressure. The residue was purified by silica gel chromatography eluting with a gradient from 50-90% EtOAc/heptanes. The appropriate fractions were concentrated under reduced pressure and solidified under high vacuum to afford the title compound as a yellow solid (1.74 g, 4.38 mmol). $^1$H NMR (CDCl$_3$) δ 1.17-1.30 (m, 2H), 1.34-1.46 (m, 2H), 1.92 (d, J=12 Hz, 2H), 2.14 (d, J=11 Hz, 2H), 2.49-2.60 (m, 1H), 3.18 (s, 3H), 3.27-3.37 (m, 1H), 3.61 (s, 4H), 3.68 (s, 3H), 4.27 (s, 2H), 7.18-7.40 (m, 10H); LC-MS (LC-ES) M+H=398.

E. 1-Cyclopropyl-2-(((trans)-4-(dibenzylamino)cyclohexyl)oxy)ethanone

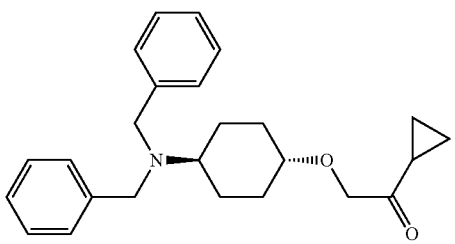 [SMILES: O=C(CO[C@H]1CC[C@H](N(Cc2ccccc2)Cc2ccccc2)CC1)C1CC1]

To 2-(((trans)-4-(dibenzylamino)cyclohexyl)oxy)-N-methoxy-N-methylacetamide (Intermediate 10D) (4.6 g, 12 mmol) in THF (15 mL) at 0° C. was added a 1.0 M solution of cyclopropylmagnesium bromide in 2-methylTHF (13 mL, 13 mmol). After 10 minutes, the reaction was warmed to room temperature. After 1 h, additional cyclopropylmagnesium bromide solution (2 mL, 2.0 mmol) was added. After another hour, the reaction was quenched with saturated aqueous NH$_4$Cl (5 mL) and partitioned between water and ethyl acetate. The organic layer was washed with saturated aqueous sodium bicarbonate, followed by brine. The combined aqueous washes were back extracted with ethyl acetate and the combined organics were dried over sodium sulfate, filtered and concentrated under reduced pressure. The residue was purified by silica gel chromatography eluting with a gradient from 30-70% ethyl acetate in heptanes. The appropriate fractions were concentrated under reduced pressure to afford the title compound as an oil that turned to a pale yellow solid (3.62 g, 83%). $^1$H NMR (CDCl$_3$) δ 0.92 (td, J=8, 4 Hz, 2H), 1.08 (quin, J=4 Hz, 2H), 1.18-1.32 (m, 2H), 1.34-1.47 (m, 2H), 1.94 (d, J=12 Hz, 2H), 2.11 (d, J=12 Hz, 2H), 2.15-2.23 (m, 1H), 2.55 (tt, J=12, 3 Hz, 1H), 3.20-3.30 (m, 1H), 3.61 (s, 4H), 4.17 (s, 2H), 7.22 (d, J=7 Hz, 2H), 7.27-7.32 (m, 4H), 7.33-7.40 (m, 4H); LC-MS (LC-ES) M+H=378.

F. Racemic 1-Cyclopropyl-2-(((trans)-4-(dibenzylamino)cyclohexyl)oxy)ethanol

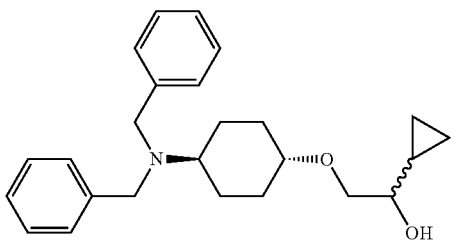 [SMILES: OC(CO[C@H]1CC[C@H](N(Cc2ccccc2)Cc2ccccc2)CC1)C1CC1]

To 1-cyclopropyl-2-(((trans)-4-(dibenzylamino)cyclohexyl)oxy)ethanone (Intermediate 10E) (1.0 g, 2.7 mmol) in THF (5 mL) at 0° C. was added a 1.0 M solution of LAH in diethyl ether (2.7 mL, 2.7 mmol). After 30 min, the reaction was warmed to room temperature for 2 hours, quenched with water (0.3 mL), 20% aqueous KOH (0.3 mL), then water (0.5 mL); and partitioned between water and ethyl acetate. The organic layer was washed with brine, dried over sodium sulfate, filtered and concentrated under reduced pressure. The residue was purified by silica gel chromatography eluting with a gradient from 30-70% ethyl acetate in heptanes. The appropriate fractions were concentrated under reduced pressure to afford the title compound as a colorless oil (886 mg, 88% yield). $^1$H NMR (400 MHz, CDCl$_3$) δ 0.21 (dq, J=9, 5 Hz, 1H), 0.37 (dq, J=9, 5 Hz, 1H), 0.43-0.62 (m, 2H), 0.75-0.87 (m, 1H), 1.09-1.23 (m, 2H), 1.35-1.48 (m, 2H), 1.93 (d, J=12 Hz, 2H), 2.04-2.14 (m, 2H), 2.38 (d, J=3 Hz, 1H), 2.54 (tt, J=12, 3 Hz, 1H), 3.02 (tt, J=8, 3 Hz, 1H), 3.18-3.29 (m, 1H), 3.38 (t, J=9 Hz, 1H), 3.59 (d, J=3 Hz, 1H), 3.62 (s, 4H), 7.17-7.24 (m, 2H), 7.29 (t, J=8 Hz, 4H), 7.34-7.40 (m, 4H); LC-MS (LC-ES) M+H=380.

G. Racemic 2-(((trans)-4-Aminocyclohexyl)oxy)-1-cyclopropylethanol

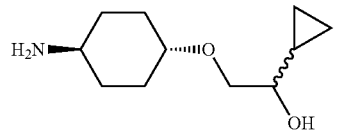

1-Cyclopropyl-2-(((trans)-4-(dibenzylamino)cyclohexyl)oxy)ethanol (Intermediate 10F) (0.886 g, 2.33 mmol) and 20 wt % Pearlman's catalyst (0.164 g, 0.233 mmol) were stirred in ethanol (20 mL) and purged with hydrogen via balloon (3×) before stirring at room temperature overnight under a hydrogen atmosphere. The reaction was purged with nitrogen, filtered through a pad of Celite® and rinsed with ethyl acetate. The filtrate was concentrated under reduced pressure to give the title compound as a colorless oil (478 mg, quantitative yield). $^1$H NMR (400 MHz, CD$_3$OD) δ 0.22 (dq, J=9, 5 Hz, 1H), 0.38 (dq, J=9, 5 Hz, 1H), 0.44-0.61 (m, 2H), 0.79-0.92 (m, 1H), 1.06-1.19 (m, 2H), 1.24-1.40 (m, 2H), 1.90 (d, J=13 Hz, 2H), 2.00-2.11 (m, 2H), 2.73 (tt, J=11, 4 Hz, 1H), 3.04 (td, J=8, 3 Hz, 1H), 3.24-3.34 (m, 1H), 3.43 (d, J=9 Hz, 1H), 3.63 (dd, J=9, 3 Hz, 1H); LC-MS (LC-ES) M+H=200.

Intermediate 11: (trans)-N1-(Pyrimidin-2-yl)cyclohexane-1,4-diamine dihydrobromide

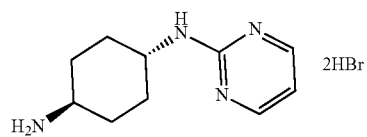 [SMILES: N[C@H]1CC[C@H](Nc2ncccn2)CC1]

A. Benzyl ((trans)-4-(pyrimidin-2-ylamino)cyclohexyl)carbamate

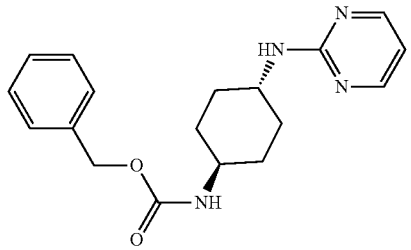 [SMILES: O=C(N[C@H]1CC[C@H](Nc2ncccn2)CC1)OCc1ccccc1]

To a microwave reaction vial with benzyl ((trans)-4-aminocyclohexyl)carbamate (600 mg, 2.4 mmol) in acetonitrile (8 mL) was added 2-chloropyrimidine (360 mg, 3.1 mmol) and N,N-diisopropylethylamine (0.63 mL, 3.6 mmol). The mixture was heated in a microwave (155° C.) for 6 h, the solvent was concentrated in vacuo and the residue purified on silica gel eluting with a 15%-80% (EtOAc/EtOH 3/1)-hexanes gradient. The appropriate fractions were combined, evaporated under reduced pressure and placed in vacuo to give the title compound as a white solid. $^1$H NMR (400 MHz, CDCl$_3$) δ 1.06-1.37 (m, 4H), 1.96-2.18 (m, 4H), 3.42-3.51 (m, 1H), 3.66-3.76 (m, 1H), 4.54-4.61 (m, 1H), 5.02 (s, 2H), 5.26-5.34 (m, 1H), 6.46 (t, J=5 Hz, 1H), 7.22-7.33 (m, 5H), 8.20 (d, J=5 Hz, 2H); LC-MS (LC-ES) M+H=327.

B. (trans)-N1-(Pyrimidin-2-yl)cyclohexane-1,4-diamine dihydrobromide

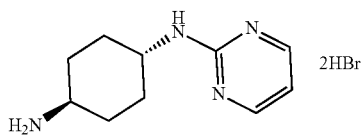 [SMILES: N[C@H]1CC[C@H](Nc2ncccn2)CC1]

To benzyl ((trans)-4-(pyrimidin-2-ylamino)cyclohexyl) carbamate (Intermediate 11A) (200 mg, 0.61 mmol) was added 33% HBr in AcOH (4 mL, 24 mmol). The mixture was stirred at room temperature for 3 h and the solvent was removed in vacuo to give the title compound as a tan solid (287 mg, quantitative yield). $^1$H NMR (400 MHz, CD$_3$OD) δ 1.53-1.65 (m, 4H), 2.04-2.30 (m, 4H), 3.13-3.27 (m, 1H), 3.87-4.06 (m, 1H), 6.82-7.18 (m, 1H), 8.31-8.94 (m, 2H); LC-MS (LC-ES) M+H=193.

Intermediate 12: Racemic 1-(((trans)-4-Aminocyclohexyl)oxy)-2-cyclopropylpropan-2-ol

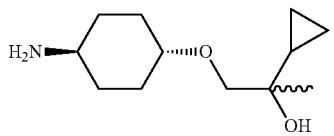

A. Racemic 2-Cyclopropyl-1-(((trans)-4-(dibenzylamino)cyclohexyl)oxy)propan-2-ol

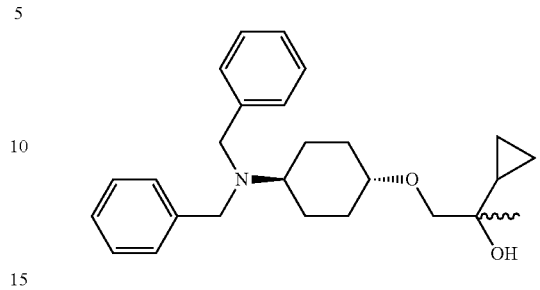

To 1-cyclopropyl-2-(((trans)-4-(dibenzylamino)cyclohexyl)oxy)ethanone (Intermediate 10E) (1.0 g, 2.7 mmol) in THF (8 mL) at 0° C. was added a 3.0 M solution of methylmagnesium chloride in diethyl ether (1 mL, 3.0 mmol). After 10 minutes, the mixture was warmed to room temperature for 2 h, quenched with saturated aqueous NH$_4$Cl (5 mL) and partitioned between water and ethyl acetate. The organic layer was washed with saturated aqueous sodium bicarbonate, followed by brine. The combined aqueous washes were back extracted with ethyl acetate, and the combined organics were dried over sodium sulfate, filtered and concentrated under reduced pressure. The residue was purified by silica gel chromatography eluting with a gradient from 10-40% ethyl acetate in heptanes. The appropriate fractions were concentrated under reduced pressure to afford the title compound as an oil that turned to a pale yellow solid (0.95 g, 91%). $^1$H NMR (CDCl$_3$) δ 0.31-0.36 (m, 3H), 0.41-0.46 (m, 1H), 0.82-0.93 (m, 1H), 1.07 (s, 3H), 1.09-1.23 (m, 2H), 1.34-1.49 (m, 2H), 1.92 (d, J=12 Hz, 2H), 2.07 (d, J=12 Hz, 2H), 2.54 (tt, J=12, 3 Hz, 1H), 3.20 (tt, J=11, 4 Hz, 1H), 3.30-3.37 (m, 2H), 3.62 (s, 4H), 7.19-7.24 (m, 2H), 7.29 (t, J=7 Hz, 4H), 7.34-7.39 (m, 4H); LC-MS (LC-ES) M+H=394.

B. Racemic 1-(((trans)-4-Aminocyclohexyl)oxy)-2-cyclopropylpropan-2-ol

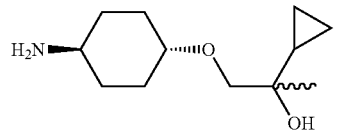

2-Cyclopropyl-1-(((trans)-4-(dibenzylamino)cyclohexyl) oxy)propan-2-ol (Intermediate 12A) (0.945 g, 2.40 mmol) and 20 wt % Pearlman's catalyst (0.169 g, 0.240 mmol) were stirred in ethanol (20 mL) and purged with hydrogen via balloon (3×) before stirring at room temperature overnight under a hydrogen atmosphere. The reaction was filtered through a pad of Celite® and rinsed with ethyl acetate. The filtrate was concentrated under reduced pressure to give the title compound as a yellow oil (470 mg, 92%). $^1$H NMR (400 MHz, CDCl$_3$) δ 0.26-0.39 (m, 3H), 0.42-0.49 (m, 1H), 0.82-0.92 (m, 1H), 1.08-1.20 (m, 5H), 1.25-1.39 (m, 2H), 1.89 (d, J=11 Hz, 2H), 2.02 (d, J=11 Hz, 2H), 2.73 (tt, J=11, 4 Hz, 1H), 3.21-3.31 (m, 1H), 3.33-3.41 (m, 2H); LC-MS (LC-ES) M+H=214.

Intermediate 13: (trans)-N-(Azetidin-3-yl)-3-(2-(difluoromethoxy)-5-fluorophenoxy)cyclobutanecarboxamide, trifluoroacetic acid salt

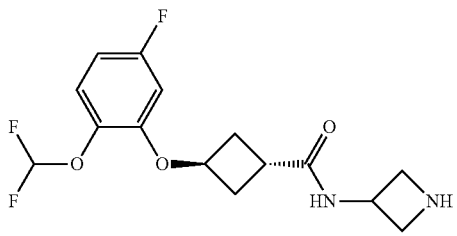

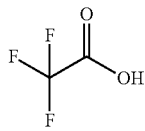

A. tert-Butyl 3-((trans)-3-(2-(difluoromethoxy)-5-fluorophenoxy)cyclobutanecarboxamido)azetidine-1-carboxylate

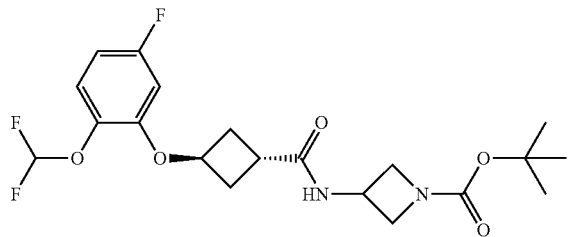 [SMILES: CC(C)(C)OC(=O)N1CC(NC(=O)[C@H]2C[C@H](Oc3cc(F)ccc3OC(F)F)C2)C1]

To a DMF (8 mL) solution of (trans)-3-(2-(difluoromethoxy)-5-fluorophenoxy)cyclobutanecarboxylic acid (Intermediate 4) (50 mg, 0.18 mmol) was added HATU (578 mg, 1.5 mmol)) and N,N-diisopropylethylamine (0.44 mL, 2.5 mmol). After 5 minutes, tert-butyl 3-aminoazetidine-1-carboxylate (262 mg, 1.5 mmol) was added, and the mixture was stirred for 2 h, diluted with water and extracted with EtOAc. The organic extracts were washed with water and brine, dried over MgSO₄, filtered and concentrated. The residue was purified on silica gel eluting with a 20%-60% EtOAc/EtOH (3:1) in hexanes gradient. The appropriate fractions were combined, evaporated under reduced pressure and placed in vacuo to give the title compound as a white foam (434 mg, 80%). ¹H NMR (400 MHz, CDCl₃) δ 1.44 (s, 9H), 2.35-2.53 (m, 2H), 2.65-2.81 (m, 2H), 2.93-3.11 (m, 1H), 3.73 (dd, J=10, 5 Hz, 2H), 4.21-4.35 (m, 2H), 4.58-4.73 (m, 1H), 4.94 (s, 1H), 5.92-6.04 (m, 1H), 6.47 (s, 1H), 6.48-6.55 (m, 1H), 6.59-6.64 (m, 1H), 7.12 (dd, J=9, 6 Hz, 1H); LC-MS (LC-ES) M+H=431.

B. (trans)-N-(Azetidin-3-yl)-3-(2-(difluoromethoxy)-5-fluorophenoxy)cyclobutanecarboxamide, trifluoroacetic acid salt

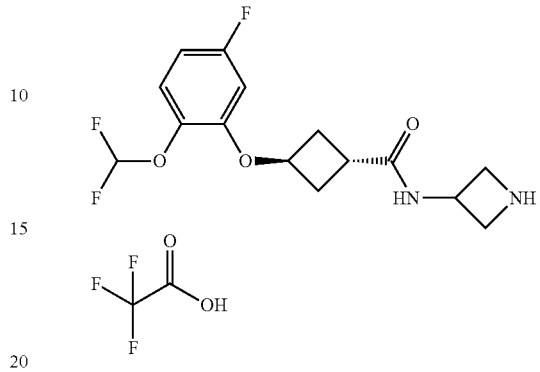

To a dichloromethane (2 mL) solution of tert-butyl 3-((trans)-3-(2-(difluoromethoxy)-5-fluorophenoxy)cyclobutanecarboxamido)azetidine-1-carboxylate (Intermediate 13A) (430 mg, 1.0 mmol) was added HCl (4 M in dioxane) (4 mL, 16 mmol). The mixture was stirred at room temperature for 1 h, and the solvent was removed in vacuo to give a sticky oil which was triturated with ether to yield a white solid. This material was loaded onto a semi-prep HPLC (TFA as modifier) to afford the title compound. ¹H NMR (400 MHz, CD₃OD) δ 2.39-2.50 (m, 2H), 2.66-2.75 (m, 2H), 3.10-3.22 (m, 1H), 4.11-4.22 (m, 2H), 4.24-4.37 (m, 2H), 4.56-4.74 (m, 1H), 4.89-4.96 (m, 1H), 6.64-6.72 (m, 3H), 7.10-7.20 (m, 1H); LC-MS (LC-ES) M+H=331.

Intermediate 14: trans-4-(3,3-Difluoroazetidin-1-yl)cyclohexanamine

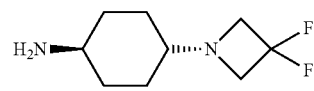

A. Benzyl (trans-4-(3,3-difluoroazetidin-1-yl)cyclohexyl)carbamate

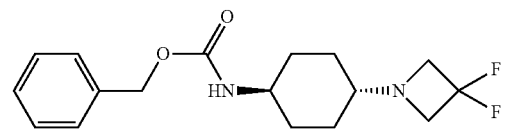

3,3-Difluoroazetidine hydrochloride (0.593 g, 4.58 mmol) was added to benzyl (4-oxocyclohexyl)carbamate (1.03 g, 4.17 mmol) in 1,2-dichloroethane (21 mL) at room temperature and stirred for 5 minutes, followed by acetic acid (0.013 g, 0.21 mmol) and 4 Å molecular sieves (4.0 g). After 2 h, sodium triacetoxyborohydride (0.883 g, 4.17 mmol) was added, and the reaction mixture was stirred for 16 h. The reaction mixture was filtered through Celite®, saturated sodium bicarbonate added, extracted with DCM, dried over magnesium sulfate, filtered, and concentrated. The residue was purified by silica gel chromatography, eluting with EtOAc:hexanes (2:3) to give the title compound (0.590 g, 42% yield). ¹H NMR (400 MHz, CD₃SOCD₃) δ 0.97 (q, J=13 Hz, 2H), 1.14 (dq, J=13, 3 Hz, 2H), 1.68 (br d, J=12 Hz, 2H), 1.76 (br d, J=12 Hz, 2H), 2.03 (t, J=10 Hz, 1H), 3.16-3.30 (m, 1H), 3.96 (t, J=12 Hz, 4H), 4.98 (s, 2H), 7.18 (d, J=8 Hz, 1H), 7.26-7.38 (m, 5H); LC-MS (LC-ES) M+H=325.

B. trans-4-(3,3-Difluoroazetidin-1-yl)cyclohexanamine

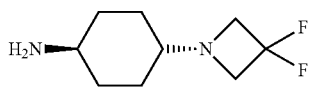

Palladium on carbon (0.019 g, 0.18 mmol) was added to benzyl (trans-4-(3,3-difluoroazetidin-1-yl)cyclohexyl)carbamate (Intermediate 14A) (0.590 g, 1.82 mmol) in MeOH (9 mL) at 25° C. under nitrogen atmosphere. The reaction vessel was fitted with a hydrogen balloon, and the vessel was repeatedly evacuated and purged with hydrogen, then stirred for 3 h under a hydrogen atmosphere. The vessel was repeatedly evacuated and purged with nitrogen, filtered through Celite® and concentrated to give the title compound (0.340 g, 93% yield). ¹H NMR (400 MHz, CD₃SOCD₃) δ 0.88-1.02 (m, 4H), 1.54 (br s, 2H), 1.68-1.74 (m, 4H), 1.96-2.06 (m, 1H), 2.40-2.52 (m, 1H), 3.48 (t, J=12 Hz, 4H); LC-MS (LC-ES) M+H=191.

Intermediate 15: (S)-2-((trans-4-Aminocyclohexyl)amino)-3,3,3-trifluoropropan-1-ol

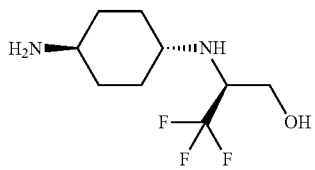

A. (S)-Benzyl (3-(trifluoromethyl)-1-oxa-4-azaspiro[4.5]decan-8-yl)carbamate

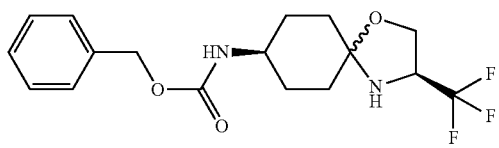

(S)-2-Amino-3,3,3-trifluoropropan-1-ol hydrochloride (0.676 g, 4.08 mmol) was added to benzyl (4-oxocyclohexyl)carbamate (1.01 g, 4.08 mmol) in benzene (41 mL) at room temperature and the reaction was heated with a Dean-Stark trap for 16 h. The reaction mixture was cooled, saturated sodium bicarbonate added, extracted with diethyl ether, dried over magnesium sulfate, filtered, and concentrated to give the title compound (1.52 g, 99% yield). ¹H NMR (400 MHz, CD₃SOCD₃) δ 1.32-1.80 (m, 8H), 3.62-4.04 (m, 4H), 4.98 & 4.99 (s, 2H), 7.20 & 7.24 (d, J=8 Hz, 1H), 7.26-7.40 (m, 5H); LC-MS (LC-ES) M+H=359.

B. Benzyl (trans-4-(((S)-1,1,1-trifluoro-3-hydroxypropan-2-yl)amino)cyclohexyl)carbamate

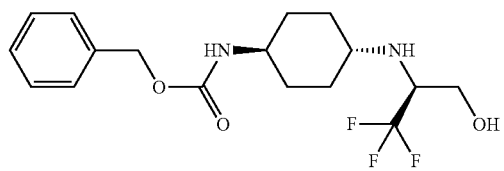 [SMILES: O=C(N[C@H]1CC[C@H](N[C@@H](CO)C(F)(F)F)CC1)OCc1ccccc1]

Sodium triacetoxyborohydride (0.899 g, 4.24 mmol) was added to benzyl ((3S)-3-(trifluoromethyl)-1-oxa-4-azaspiro[4.5]decan-8-yl)carbamate (Intermediate 15A) (1.52 g, 4.24 mmol) in 1,2-dichloroethane (21 mL) at room temperature, followed by acetic acid (0.013 g, 0.21 mmol). After 4 h, the reaction mixture was diluted with saturated sodium bicarbonate, extracted with DCM, dried over magnesium sulfate, filtered, and concentrated. The residue was purified by silica gel chromatography, eluting with EtOAc:hexanes (1:1) to give the title compound (0.771 g, 48% yield). ¹H NMR (400 MHz, CD₃SOCD₃) δ 1.02 (q, J=13 Hz, 2H), 1.14 (q, J=13 Hz, 2H), 1.72-1.92 (m, 5H), 2.36-2.48 (m, 1H), 3.14-3.28 (m, 2H), 3.40-3.50 (m, 1H), 3.54-3.64 (m, 1H), 4.96 (t, J=6 Hz, 1H), 4.98 (s, 2H), 7.15 (d, J=8 Hz, 1H), 7.26-7.38 (m, 5H); LC-MS (LC-ES) M+H=361.

C. (S)-2-((trans-4-Aminocyclohexyl)amino)-3,3,3-trifluoropropan-1-ol

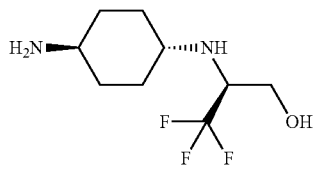 [SMILES: N[C@H]1CC[C@H](N[C@@H](CO)C(F)(F)F)CC1]

Palladium on carbon (0.023 g, 0.21 mmol) was added to benzyl (trans-4-(((S)-1,1,1-trifluoro-3-hydroxypropan-2-yl)amino)cyclohexyl)carbamate (Intermediate 15B) (0.771 g, 2.14 mmol) in MeOH (7 mL) at 25° C. under a nitrogen atmosphere. The reaction vessel was fitted with a hydrogen balloon and the vessel was repeatedly evacuated and purged with hydrogen, then stirred for 16 h under a hydrogen atmosphere. The vessel was repeatedly evacuated and purged with nitrogen, filtered through Celite®, and concentrated to give the title compound (0.504 g, 99% yield). ¹H NMR (400 MHz, CD₃SOCD₃) δ 0.92-1.06 (m, 4H), 1.46-1.88 (m, 7H), 2.36-2.50 (m, 2H), 3.16-3.28 (m, 1H), 3.40-3.50 (m, 1H), 3.54-3.64 (m, 1H), 4.97 (br s, 1H); LC-MS (LC-ES) M+H=227.

Intermediate 16: Racemic 1-(1,1-Difluoropropan-2-yl)piperidin-4-amine

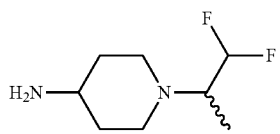

A. Racemic Benzyl (1-(1,1-difluoropropan-2-yl)piperidin-4-yl)carbamate

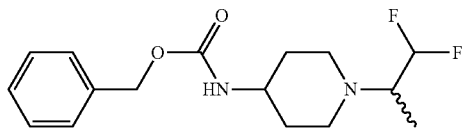

1,1-Difluoropropan-2-one (0.608 g, 6.47 mmol) was added to benzyl piperidin-4-ylcarbamate (1.01 g, 4.31 mmol) in 1,2-dichloroethane (22 mL). After 5 min, acetic acid (0.013 g, 0.21 mmol) and 4 Å molecular sieves (4.0 g) were added. After 2 h, sodium triacetoxyborohydride (0.914 g, 4.31 mmol) was added, and the reaction mixture was stirred for 20 h. The reaction mixture was filtered through Celite®, saturated sodium bicarbonate added, extracted with DCM, dried over magnesium sulfate, filtered, and concentrated. The residue was purified by silica gel chromatography, eluting with EtOAc:hexanes (1:2 to 2:3) to give the title compound (0.868 g, 61% yield). $^1$H NMR (400 MHz, CD$_3$SOCD$_3$) δ 0.95-1.10 (m, 3H), 1.28-1.39 (m, 2H), 1.67-1.72 (m, 2H), 2.27-2.40 (m, 2H), 2.49-2.52 (m, 1H), 2.71-2.80 (m, 2H), 2.82-2.98 (m, 1H), 3.19-3.31 (m, 1H), 4.99 (s, 2H), 5.99 (dt, J=8, 56 Hz, 1H), 7.25-7.38 (m, 5H); LC-MS (LC-ES) M+H=313.

B. Racemic 1-(1,1-difluoropropan-2-yl)piperidin-4-amine

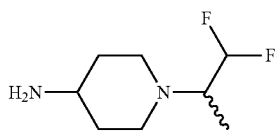

Palladium on carbon (0.030 g, 0.28 mmol) was added to benzyl (1-(1,1-difluoropropan-2-yl)piperidin-4-yl)carbamate (Intermediate 16A) (0.868 g, 2.78 mmol) in MeOH (14 mL) at 25° C. under nitrogen atmosphere. The reaction vessel was fitted with a hydrogen balloon, and the vessel was repeatedly evacuated and purged with hydrogen, then stirred for 2 h under a hydrogen atmosphere. The vessel was repeatedly evacuated and purged with nitrogen, filtered through Celite® and concentrated to give the title compound (0.452 g, 87% yield). $^1$H NMR (400 MHz, CD$_3$SOCD$_3$) δ 0.93-1.00 (m, 3H), 1.10-1.21 (m, 2H), 1.60-1.64 (m, 2H), 2.02 (br s, 2H), 2.24-2.34 (m, 2H), 2.45-2.49 (m, 1H), 2.68-2.78 (m, 2H), 2.83-2.95 (m, 1H), 5.99 (dt, J=8, 56 Hz, 1H); LC-MS (LC-ES) M+H=179.

Intermediate 17: Racemic trans-N1-(1,1-Difluoropropan-2-yl)cyclohexane-1,4-diamine

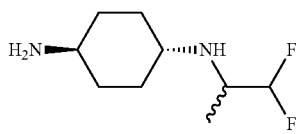

A. Racemic Benzyl (trans-4-((1,1-difluoropropan-2-yl)amino)cyclohexyl)carbamate

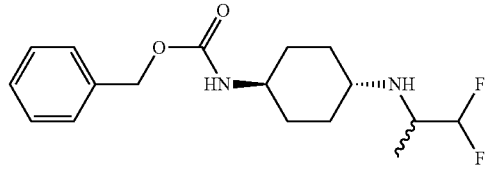 [SMILES: CC(N[C@H]1CC[C@H](NC(=O)OCc2ccccc2)CC1)C(F)F]

1,1-Difluoropropan-2-one (3.13 g, 33.3 mmol) was added to benzyl (trans-4-aminocyclohexyl)carbamate (7.52 g, 30.3 mmol) in 1,2-dichloroethane (151 mL). After 5 min, added acetic acid (0.091 g, 1.5 mmol) and 4 Å molecular sieves (20.0 g), and the reaction was stirred for 2 h at room temperature. Sodium triacetoxyborohydride (6.42 g, 30.3 mmol) was added, and the reaction mixture was stirred for 20 h. The reaction mixture was filtered through Celite®, saturated sodium bicarbonate added, extracted with DCM, dried over magnesium sulfate, filtered, and concentrated. The residue was purified by silica gel chromatography, eluting with EtOAc:hexanes (1:1) to give the title compound (8.41 g, 81% yield). $^1$H NMR (400 MHz, CD$_3$SOCD$_3$) δ 0.99 (d, J=7 Hz, 3H), 0.94-1.06 (m, 2H), 1.08-1.22 (m, 2H), 1.45 (br s, 1H), 1.70-1.88 (m, 4H), 2.36-2.48 (m, 1H), 2.86-3.00 (m, 1H), 3.14-3.28 (m, 1H), 4.97 (s, 2H), 5.74 (dt, J=56, 4 Hz, 1H), 7.16 (d, J=8 Hz, 1H), 7.26-7.38 (m, 5H); LC-MS (LC-ES) M+H=327.

B. Racemic trans-N1-(1,1-Difluoropropan-2-yl)cyclohexane-1,4-diamine

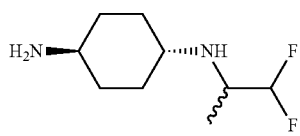

Palladium on carbon (0.137 g, 1.29 mmol) was added to benzyl (trans-4-((1,1-difluoropropan-2-yl)amino)cyclohexyl)carbamate (Intermediate 17A) (8.41 g, 25.8 mmol) in MeOH (51.5 mL) at 25° C. under nitrogen atmosphere. The reaction vessel was fitted with a hydrogen balloon and the vessel was repeatedly evacuated and purged with hydrogen, then stirred for 6 h under a hydrogen atmosphere. The vessel was repeatedly evacuated and purged with nitrogen, filtered through Celite®, and concentrated to give the title compound (5.05 g, 97% yield). $^1$H NMR (400 MHz, CD$_3$SOCD$_3$) δ 0.90-1.04 (m, 4H), 0.99 (d, J=7 Hz, 3H), 1.30-1.60 (m, 3H), 1.62-1.84 (m, 4H), 2.34-2.48 (m, 2H), 2.86-3.00 (m, 1H), 5.73 (dt, J=56, 4 Hz, 1H); LC-MS (LC-ES) M+H=193.

Intermediate 18: Racemic (R,S)-1-((trans)-4-Aminocyclohexyl)ethanol hydrochloride

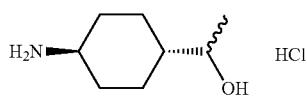

A. trans-Methyl 4-((tertbutoxycarbonyl)amino)cyclohexanecarboxylate

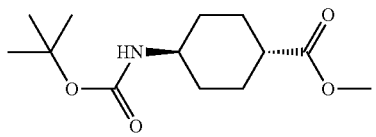 [SMILES: COC(=O)[C@H]1CC[C@H](NC(=O)OC(C)(C)C)CC1]

To (trans)-4-(methoxycarbonyl)cyclohexanecarboxylic acid (2.5 mg, 13 mmol) in tert-butanol (25 mL) was added diphenyl phosphorazidate (3.88 g, 14 mmol) and triethylamine (1.97 mL, 14 mmol). The mixture was heated at 60° C. for 1 h and then at reflux overnight. After cooling to room temperature, the mixture was quenched into ice water and extracted with EtOAc. The combined organics were washed with sat. NaHCO$_3$ and brine, dried over Na$_2$SO$_4$, filtered, and concentrated. The residue was dissolved in MeOH (6 mL) and to this was added water (18 mL). After stirring for ca. 1 h on ice, the resulting solid was collected by filtration, and washed with 3:1 water:MeOH, and hexanes to give the title compound as a white solid (2.32 g, 67% yield). $^1$H NMR (400 MHz, CD$_3$SOCD$_3$) δ 1.05-1.20 (m, 2H), 1.25-1.44 (m, 11H), 1.72-1.91 (m, 4H), 2.17 (tt, J=12, 3 Hz, 1H), 3.06-3.21 (m, 1H), 3.56 (s, 3H), 6.72 (d, J=8 Hz, 1H).

B. tert-Butyl ((trans)-4-(hydroxymethyl)cyclohexyl)carbamate

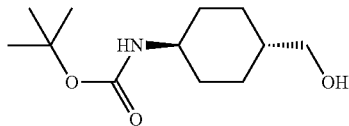 [SMILES: CC(C)(C)OC(=O)N[C@H]1CC[C@H](CO)CC1]

To a solution of (trans)-methyl 4-((tert-butoxycarbonyl)amino)cyclohexanecarboxylate (Intermediate 18A) (1.5 g, 5.8 mmol) in EtOH (24 mL) and THF (2.7 mL), cooled on ice, was added calcium chloride (1.29 g, 11.7 mmol) portion wise to give a milky suspension. NaBH$_4$ (882 mg, 23.3 mmol) was then added portion wise over ca. 25 min and the reaction was stirred on ice for 1 h. The bath was removed and the mixture was allowed to stir at room temperature overnight. The reaction was cooled to 10° C. and to this was added 5% aqueous K$_2$CO$_3$ (5.4 mL) dropwise, to give a pH of ca. 11. A white precipitate formed and was isolated by filtration. The solid was stirred with EtOAc (50 mL) and water (14 mL). The layers were separated and the organic layer was washed with 0.5 M aqueous HCl (5 mL), water and brine, dried over MgSO$_4$, filtered, and concentrated to give the title compound (474 mg) as a white solid. The initial filtrate was concentrated, then dilute with saturated aqueous NH$_4$Cl and extracted with EtOAc (3×). Combined organics were washed with brine and dried over Na$_2$SO$_4$, filtered, and concentrated to give the title compound (724 mg) as a white solid. Total isolated product was 1.19 g (89% yield). $^1$H NMR (400 MHz, CD$_3$SOCD$_3$) δ 0.78-0.93 (m, 2H), 1.01-1.15 (m, 2H), 1.35 (s, 9H), 1.64-1.80 (m, 4H), 3.10 (d, J=8 Hz, 1H), 3.16 (t, J=6 Hz, 2H), 4.33 (t, J=5 Hz, 1H), 6.64 (d, J=8 Hz, 1H).

C. tert-Butyl ((trans)-4-formylcyclohexyl)carbamate

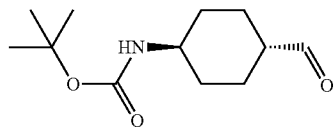 [SMILES: CC(C)(C)OC(=O)N[C@H]1CC[C@H](C=O)CC1]

To a solution of tert-butyl ((trans)-4-(hydroxymethyl)cyclohexyl)carbamate (Intermediate 18B) (375 mg, 1.64 mmol) in DCM (9 mL) and DMSO (2.8 mL), cooled on ice, was added N,N-diisopropylethylamine (1.14 mL, 6.54 mmol), followed by pyridine sulfur trioxide (1041 mg, 6.54 mmol) dissolved in DMSO (2.8 mL). The bath was removed and the reaction stirred at room temperature for 15 min. The mixture was partitioned between Et$_2$O and 1 N aqueous HCl. The organic phase was washed with 1 N HCl, water, and brine, dried over MgSO$_4$, filtered, and concentrated to give the title compound as a white solid (343 mg, 92% yield), which was used without purification. $^1$H NMR (400 MHz, CD$_3$SOCD$_3$) δ 1.10-1.23 (m, 4H), 1.35 (s, 9H), 1.73-1.93 (m, 4H), 2.07-2.19 (m, 1H), 3.05-3.20 (m, 1H), 6.74 (d, J=7 Hz, 1H), 9.53 (s, 1H).

D. Racemic tert-Butyl ((trans)-4-((R,S)-1-hydroxyethyl)cyclohexyl)carbamate

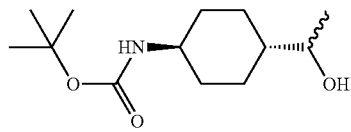 [SMILES: CC(O)[C@H]1CC[C@H](NC(=O)OC(C)(C)C)CC1]

To a solution of tert-butyl ((trans)-4-formylcyclohexyl)carbamate (Intermediate 18C) (70 mg, 0.31 mmol) in THF (4 mL), cooled to −78° C., was added methylmagnesium iodide (0.23 mL, 0.68 mmol, 3 M in THF) dropwise over ca. 2 min, and the reaction was stirred at −78° C. for 30 min. The reaction was poured into saturated NH$_4$Cl and extracted with TBME. The combined organics were washed with brine, dried over Na$_2$SO$_4$, filtered, and concentrated. The residue was purified by silica gel chromatography (0-80% EtOAc-hexanes gradient) to afford the title compound as a glass (15 mg, 20% yield).

A second reaction was run with the following procedure.

To a solution of tert-butyl ((trans)-4-formylcyclohexyl)carbamate (Intermediate 18C) (100 mg, 0.44 mmol) in THF (4 mL), cooled to −78° C., was added methylmagnesium bromide (0.18 mL, 0.55 mmol, 3 M in THF) dropwise over ca. 2-3 minutes, and the reaction was stirred at −78° C. for 30 min. The reaction was poured into saturated NH$_4$Cl and extracted with TBME. The combined organics were washed with brine, dried over Na$_2$SO$_4$, filtered, and concentrated. The residue was purified by silica gel chromatography (0-80% EtOAc-hexanes gradient) to afford the title compound as a white foam (27 mg, 25% yield). This product and the above were combined to be used in the next step. $^1$H NMR (400 MHz, 400 MHz, CD$_3$SOCD$_3$) δ 0.87-1.10 (m, 7H), 1.35 (s, 9H), 1.57 (d, J=10 Hz, 1H), 1.67-1.85 (m, 4H), 3.08 (d, J=7 Hz, 1H), 3.25-3.46 (m, 2H), 6.62 (d, J=8 Hz, 1H).

E. Racemic (R,S)-1-((trans)-4-Aminocyclohexyl)ethanol hydrochloride

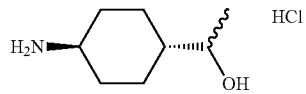

To tert-butyl ((trans)-4-((R,S)-1-hydroxyethyl)cyclohexyl)carbamate (Intermediate 18D) (40 mg, 0.16 mmol) was added 4 N HCl in dioxane (5 mL). The mixture was stirred at room temperature for 3.5 h and concentrated to give the title compound as a glass (33 mg, 112% yield). $^1$H NMR (400 MHz, CD$_3$SOCD$_3$) δ 0.99 (d, J=6 Hz, 3H), 1.06 (d, J=7 Hz, 2H), 1.20-1.29 (m, 2H), 1.63 (d, J=12 Hz, 1H), 1.84 (d, J=13 Hz, 1H), 1.93 (d, J=12 Hz, 2H), 2.85 (d, J=5 Hz, 1H), 3.46 (dd, J=12, 4 Hz, 1H), 3.62-3.74 (m, 1H).

Intermediate 19: Racemic ((trans)-4-Aminocyclohexyl)(cyclopropyl)methanol

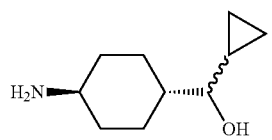 [SMILES: N[C@H]1CC[C@H](C(O)C2CC2)CC1]

A. (trans)-Methyl 4-(dibenzylamino)cyclohexanecarboxylate

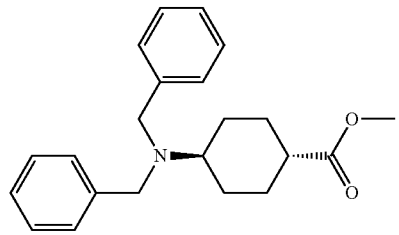 [SMILES: COC(=O)[C@H]1CC[C@H](N(Cc2ccccc2)Cc2ccccc2)CC1]

To a mixture of (trans)-methyl 4-aminocyclohexanecarboxylate hydrochloride (1.7 g, 8.78 mmol), acetonitrile (30 mL), and K$_2$CO$_3$ (4.85 g, 35.1 mmol) was added benzyl bromide (3.75 g, 22.0 mmol). The reaction was heated at 80° C. overnight, cooled to room temperature, filtered, and concentrated. The residue was purified by silica gel chromatography eluting with 0-20% EtOAc-hexanes gradient to afford the title compound as a white solid (1.55 g, 52% yield). $^1$H NMR (CDCl$_3$) δ 1.28-1.43 (m, 4H), 1.54 (s, 3H), 1.92-2.04 (m, 4H), 2.13-2.21 (m, 1H), 2.47-2.55 (m, 1H), 3.60-3.62 (m, 4H), 7.16-7.36 (m, 10H).

B. (trans)-4-(Dibenzylamino)cyclohexanecarboxylic acid

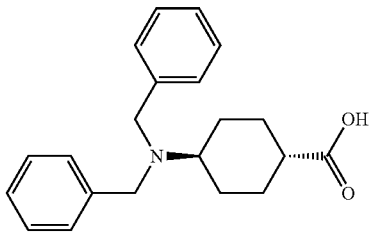 [SMILES: O=C(O)[C@H]1CC[C@H](N(Cc2ccccc2)Cc2ccccc2)CC1]

To a mixture of (trans)-methyl 4-(dibenzylamino)cyclohexanecarboxylate (Intermediate 19A) (1 g, 2.96 mmol) in THF (10 mL), methanol (5 mL) and water (5 mL), LiOH (0.213 g, 8.89 mmol) was added. After 15 hours, the mixture was concentrated under reduced pressure. The residue was taken up in water and acidified with 6.0 N aqueous HCl until a white precipitate formed. The precipitate was collected by filtration and dried under vacuum to give the title compound (791 mg, 83% yield). This procedure was repeated on multiple occasions. Representative $^1$H NMR (400 MHz, CD$_3$SOCD$_3$) δ 1.07-1.24 (m, 2H), 1.31-1.49 (m, 2H), 1.85 (d, J=11 Hz, 2H), 1.93 (d, J=12 Hz, 2H), 2.05-2.19 (m, 1H), 2.30-2.45 (m, 1H), 3.58 (s, 4H), 7.14-7.24 (m, 2H), 7.24-7.42 (m, 8H), 11.98 (br s, 1H); LC-MS (LC-ES) M+H=324.

C. (trans)-4-(Dibenzylamino)-N-methoxy-N-methyl-cyclohexanecarboxamide

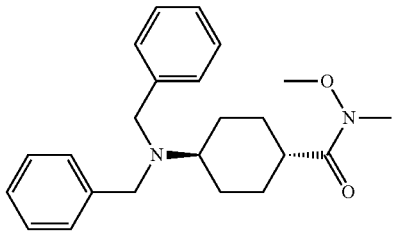 [SMILES: CON(C)C(=O)[C@H]1CC[C@H](N(Cc2ccccc2)Cc2ccccc2)CC1]

(trans)-4-(Dibenzylamino)cyclohexanecarboxylic acid (Intermediate 19B) (0.79 g, 2.4 mmol) was dissolved in DMF (20 mL) followed by the addition of N,N-diisopropylethylamine (1.3 mL, 7.3 mmol) and HATU (1.11 g, 2.93 mmol). The reaction was stirred at room temperature for ca. 10 min, and N,O-dimethylhydroxylamine hydrochloride (0.286 g, 2.93 mmol) was added. After 15 h, the reaction was diluted with EtOAc and washed with saturated aqueous sodium bicarbonate. The organics were separated and washed with brine, dried over sodium sulfate, filtered, and concentrated under reduced pressure. The residue was purified by silica gel chromatography eluting with a 30-70% EtOAc/heptanes gradient. The appropriate fractions were concentrated under reduced pressure and solidified under high vacuum to afford the title compound as a white solid (728 mg, 81%). $^1$H NMR (CDCl$_3$) δ 1.39-1.57 (m, 4H), 1.84-1.92 (m, 2H), 2.01 (d, J=9 Hz, 2H), 2.57-2.69 (m, 2H), 3.18 (s, 3H), 3.67 (s, 4H), 3.70 (s, 3H), 7.20-7.26 (m, 2H), 7.31 (t, J=7 Hz, 4H), 7.36-7.43 (m, 4H); LC-MS (LC-ES) M+H=367.

D. Cyclopropyl((trans)-4-(dibenzylamino)cyclohexyl)methanone

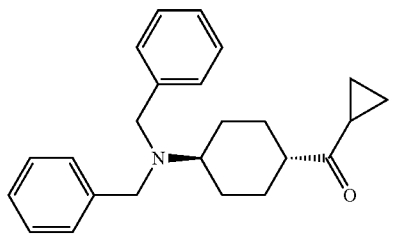 [SMILES: O=C(C1CC1)[C@H]1CC[C@H](N(Cc2ccccc2)Cc2ccccc2)CC1]

To (trans)-4-(dibenzylamino)-N-methoxy-N-methylcyclohexanecarboxamide (Intermediate 19C) (0.275 g, 0.75 mmol) in THF (1.5 mL) at 0° C. was added a 1.0 M solution of cyclopropylmagnesium bromide in 2-methylTHF (0.75 mL, 0.75 mmol). After 10 minutes, the mixture was warmed to room temperature and stirred for 2 h. Additional cyclopropylmagnesium bromide solution (0.75 mL, 0.75 mmol) was added and the mixture was stirred for 1 h, then quenched with saturated aqueous $NH_4Cl$ (5 mL) and partitioned between water and ethyl acetate. The organic layer was washed with saturated aqueous sodium bicarbonate, followed by brine. The combined aqueous washes were back extracted with ethyl acetate and the combined organics were dried over sodium sulfate, filtered and concentrated under reduced pressure to afford the title compound as a yellow oil (268 mg, quantitative). $^1H$ NMR (CDCl$_3$) δ 0.82 (dq, J=7, 4 Hz, 2H), 0.93-0.99 (m, 2H), 1.25-1.37 (m, 2H), 1.38-1.50 (m, 2H), 1.89-1.96 (m, 1H), 2.01 (d, J=11 Hz, 4H), 2.42 (t, J=12 Hz, 1H), 2.53 (t, J=12 Hz, 1H), 3.64 (s, 4H), 7.17-7.24 (m, 2H), 7.27-7.33 (m, 4H), 7.34-7.40 (m, 4H); LC-MS (LC-ES) M+H=348.

E. Racemic Cyclopropyl((trans)-4-(dibenzylamino)cyclohexyl)methanol

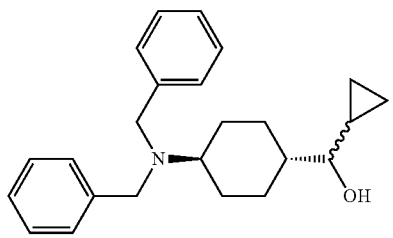 [SMILES: OC(C1CC1)[C@H]1CC[C@H](N(Cc2ccccc2)Cc2ccccc2)CC1]

To cyclopropyl((trans)-4-(dibenzylamino)cyclohexyl)methanone (Intermediate 19D) (0.260 g, 0.75 mmol) in THF (1.5 mL) at 0° C. was added a 1.0 M solution of lithium aluminum hydride in diethyl ether (0.85 mL, 0.85 mmol). After 20 min, the mixture was warmed to room temperature for 1 hour; quenched with water (0.15 mL), 10% aqueous NaOH (0.15 mL), then water (0.3 mL); and partitioned between water and ethyl acetate. After 10 min, sodium sulfate was added, solids were filtered and the filtrate concentrated under reduced pressure. The residue was purified by silica gel chromatography eluting with a 10-50% ethyl acetate in heptanes gradient. The appropriate fractions were concentrated under reduced pressure to afford the title compound (145 mg, 55% yield). $^1H$ NMR (400 MHz, CDCl$_3$) δ 0.20 (d, J=2 Hz, 2H), 0.41-0.49 (m, 1H), 0.50-0.58 (m, 1H), 0.82-0.94 (m, 1H), 0.97-1.14 (m, 2H), 1.34-1.53 (m, 4H), 1.88-2.02 (m, 4H), 2.46-2.57 (m, 2H), 3.65 (s, 4H), 7.21 (q, J=7 Hz, 2H), 7.29 (t, J=7 Hz, 4H), 7.39 (d, J=7 Hz, 4H).

F. Racemic ((trans)-4-Aminocyclohexyl)(cyclopropyl)methanol

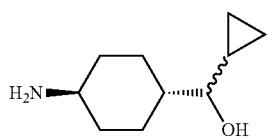 [SMILES: N[C@H]1CC[C@H](C(O)C2CC2)CC1]

Cyclopropyl((trans)-4-(dibenzylamino)cyclohexyl)methanol (Intermediate 19E) (0.145 g, 0.42 mmol) and 20 wt % Pearlman's catalyst (0.029 g, 0.04 mmol) were stirred in ethanol (4 mL) and purged with hydrogen via balloon (3×) before stirring under a hydrogen atmosphere at room temperature overnight. The reaction was filtered through a pad of Celite® and rinsed with ethyl acetate. The filtrate was concentrated under reduced pressure to give the title compound as an oil (68 mg, 97%). LC-MS (LC-ES) M+H=170.

Intermediate 20: Racemic 2-((trans)-4-Aminocyclohexyl)-1,1,1-trifluoropropan-2-ol

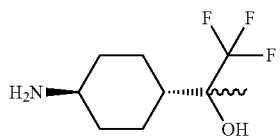

A. 1-((trans)-4-(Dibenzylamino)cyclohexyl)ethanone

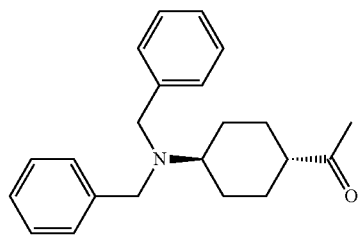 [SMILES: CC(=O)[C@H]1CC[C@H](N(Cc2ccccc2)Cc2ccccc2)CC1]

To (trans)-4-(dibenzylamino)-N-methoxy-N-methylcyclohexanecarboxamide (Intermediate 19C) (0.395 g, 1.08 mmol) in THF (2.5 mL) at 0° C. was added a 3.0 M solution of methylmagnesium bromide in diethyl ether (0.36 mL, 1.1 mmol). After 10 minutes, the mixture was warmed to room temperature, stirred for 2 h, quenched with saturated aqueous $NH_4Cl$ and stirred 10 min. The mixture was partitioned between water and ethyl acetate. The organic layer was washed with saturated aqueous sodium bicarbonate, followed by brine. The combined aqueous washes were back extracted with ethyl acetate and the combined organics were dried over sodium sulfate, filtered and concentrated under

B. Racemic 2-((trans)-4-(Dibenzylamino)cyclohexyl)-1,1,1-trifluoropropan-2-ol

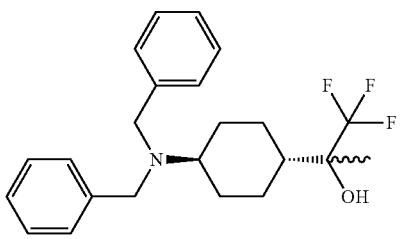 [SMILES: CC(O)([C@H]1CC[C@H](N(Cc2ccccc2)Cc2ccccc2)CC1)C(F)(F)F]

To 1-((trans)-4-(dibenzylamino)cyclohexyl)ethanone (Intermediate 20A) (0.34 g, 1.1 mmol) and cesium fluoride (0.16 g, 1.1 mmol) in THF (2.25 mL) at 0° C. was slowly added trimethyl(trifluoromethyl)silane (0.39 mL, 2.6 mmol). After 1 hour, a 1.0 M solution of TBAF in THF (1.27 mL, 1.27 mmol) was added. The mixture was stirred for 1 hour, diluted with ethyl acetate and washed with water, followed by brine. The organics were dried over sodium sulfate, filtered and concentrated under reduced pressure to an orange oil that was purified by silica gel chromatography eluting with 3% ethyl acetate in heptanes. Fractions recovered were concentrated under reduced pressure to the title compound as a white solid (271 mg, 66%). $^1$H NMR (CDCl$_3$) δ 0.90-1.09 (m, 2H) 1.11-1.66 (m, 6H), 1.81-2.02 (m, 4H), 2.39-2.50 (m, 1H), 3.53-3.68 (m, 4H), 7.15-7.44 (m, 10H); LC-MS (LC-ES) M+H=392.

C. Racemic 2-((trans)-4-Aminocyclohexyl)-1,1,1-trifluoropropan-2-ol

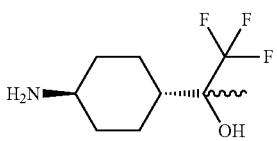

2-((trans)-4-(Dibenzylamino)cyclohexyl)-1,1,1-trifluoropropan-2-ol (Intermediate 20B) (0.27 g, 0.69 mmol) and 20 wt % palladium hydroxide on carbon (0.097 g, 0.14 mmol) were stirred in ethanol (6 mL) and purged with hydrogen via balloon (3×) before stirring under a hydrogen atmosphere at room temperature overnight. The reaction was filtered through a pad of Celite® and rinsed with ethanol. The filtrate was concentrated under reduced pressure to give the title compound as an oil (136 mg, 93%). $^1$H NMR (CD$_3$OD) δ 1.02-1.28 (m, 7H), 1.51-1.61 (m, 1H), 1.79-2.00 (m, 4H), 2.51-2.62 (m, 1H); LC-MS (LC-ES) M+H=212.

Intermediate 21: 3-Amino-1-methylcyclobutanol hydrochloride

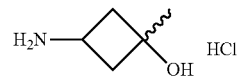

A. Methylenecyclobutanecarboxylic acid

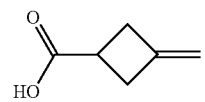

Potassium hydroxide (12.29 g, 219 mmol) was added to 3-methylenecyclobutanecarbonitrile (5.10 g, 54.8 mmol) in EtOH (27 mL) and water (27 mL) at room temperature, and the reaction mixture was heated at reflux for 16 h. After cooling, the EtOH was removed under vacuum, ice was added, and the reaction mixture was acidified to pH=1 with concentrated hydrochloric acid. The reaction mixture was extracted with EtOAc, dried over magnesium sulfate, filtered, and concentrated to give the title compound (6.37 g, 99% yield). $^1$H NMR (400 MHz, CD$_3$SOCD$_3$) δ 2.82 (dt, J=8, 2 Hz, 4H), 3.04 (p, J=8 Hz, 1H), 4.76 (p, J=2 Hz, 2H), 12.20 (br s, 1H); LC-MS (LC-ES) M−H=111.

B. tert-Butyl (3-methylenecyclobutyl)carbamate

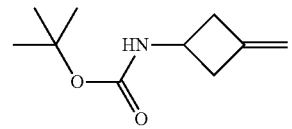

Triethylamine (11.9 mL, 85 mmol) was added to 3-methylenecyclobutanecarboxylic acid (Intermediate 21A) (6.37 g, 56.8 mmol) in tert-butanol (57 mL) at room temperature, followed by diphenyl phosphoryl azide (14.7 mL, 68.2 mmol). The reaction mixture was heated at 85° C. under nitrogen for 17 h, quenched with water and concentrated. The residue was taken up in diethyl ether, washed with 10% citric acid followed by saturated sodium bicarbonate, the organic layer dried over magnesium sulfate, filtered, and concentrated. The residue was purified by silica gel chromatography, eluting with EtOAc:hexanes (1:9) to give the title compound (6.08 g, 56% yield). $^1$H NMR (400 MHz, CD$_3$SOCD$_3$) δ 1.36 (s, 9H), 2.54-2.64 (m, 2H), 2.76-2.86 (m, 2H), 3.92 (h, J=8 Hz, 1H), 4.76 (p, J=2 Hz, 2H), 7.23 (d, J=7 Hz, 1H).

C. tert-Butyl 1-oxaspiro[2.3]hexan-5-ylcarbamate

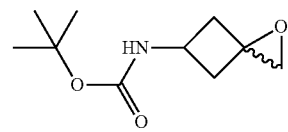

3-Chloroperbenzoic acid (6.30 g, 36.5 mmol) was added to tert-butyl (3-methylenecyclobutyl)carbamate (Intermediate 21B) (6.08 g, 33.2 mmol) in DCM (111 mL) at 0° C. After 4 h, the reaction mixture was washed with 10% sodium sulfite followed by saturated sodium bicarbonate and brine, dried over magnesium sulfate, filtered, and concentrated. The residue was purified by silica gel chromatography, eluting with EtOAc:hexanes (1:4 to 2:3) to give a 1:1 mixture of tert-butyl 1-oxaspiro[2.3]hexan-5-ylcarbamate (5.34 g, 77% yield) and recovered starting material (0.98 g, 16% yield). $^1$H NMR (400 MHz, CD$_3$SOCD$_3$) δ 1.37 & 1.37 (s, 9H), 2.30-2.40 (m, 2H), 2.44-2.54 (m, 2H), 2.62 (s, 1H), 2.66 (s, 1H), 3.83 (h, J=8 Hz, 0.5H), 3.94-4.06 (m, 0.5H), 7.24 (d, J=7 Hz, 0.5H), 7.34 (d, J=6 Hz, 0.5H).

D. tert-Butyl (3-hydroxy-3-methylcyclobutyl)carbamate

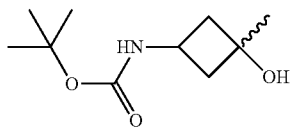

Lithium triethylborohydride (34.8 mL, 34.8 mmol) in THF (1.0 M) was added to tert-butyl 1-oxaspiro[2.3]hexan-5-ylcarbamate (Intermediate 21C) (5.34 g, 26.8 mmol) in THF (89 mL) at 0° C. under nitrogen. After 3 h, reaction mixture was quenched with water, solid potassium carbonate was added, then extracted with diethyl ether, dried over magnesium sulfate, filtered, and concentrated. The residue was purified by silica gel chromatography, eluting with EtOAc:hexanes (2:3 to 1:1) to give the title compound (5.36 g, 94% yield). $^1$H NMR (400 MHz, CD$_3$SOCD$_3$) δ 1.17 (s, 1.5H), 1.19 (s, 1.5H), 1.35 (s, 9H), 1.78-1.92 (m, 2H), 2.08-2.18 (m, 2H), 3.46 (h, J=8 Hz, 0.5H), 3.99 (h, J=8 Hz, 0.5H), 4.70 (br s, 0.5H), 4.83 (br s, 0.5H), 7.00 (d, J=6 Hz, 1H); LC-MS (ES-MS) M+H=202.

E. 3-Amino-1-methylcyclobutanol hydrochloride

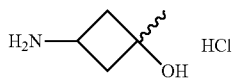

4.0 M Hydrochloric acid in dioxane (33.3 mL, 133 mmol) was added to tert-butyl (3-hydroxy-3-methylcyclobutyl)carbamate (Intermediate 21D) (5.36 g, 26.6 mmol) in MeOH (33 mL) at room temperature. After 16 h, the reaction mixture was concentrated to give the title compound (3.83 g, 99% yield). $^1$H NMR (400 MHz, CD$_3$SOCD$_3$) δ 1.22 (s, 1.5H), 1.25 (s, 1.5H), 2.04-2.14 (m, 2H), 2.14-2.26 (m, 2H), 3.15 (s, 0.5H), 3.20-3.32 (m, 0.5H), 3.56 (s, 0.5H), 3.66-3.78 (m, 0.5H), 8.09 (br s, 3H); LC-MS (LC-ES) M+H=102.

Intermediate 22: 2-((trans)-3-(2-(Difluoromethoxy)-5-fluorophenoxy)cyclobutanecarboxamido)-N-methoxy-N-methylthiazole-4-carboxamide

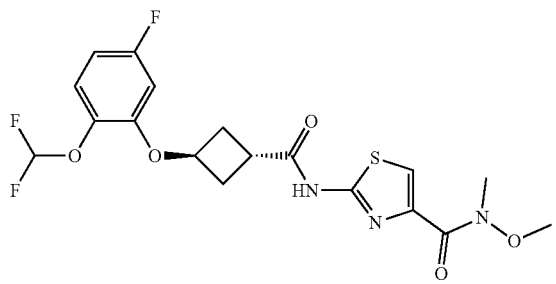 [SMILES: CON(C)C(=O)c1csc(NC(=O)[C@H]2C[C@H](Oc3cc(F)ccc3OC(F)F)C2)n1]

A. 2-((trans)-3-(2-(Difluoromethoxy)-5-fluorophenoxy)cyclobutanecarboxamido)thiazole-4-carboxylic acid

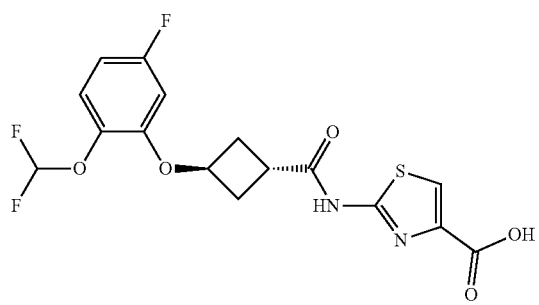 [SMILES: O=C(O)c1csc(NC(=O)[C@H]2C[C@H](Oc3cc(F)ccc3OC(F)F)C2)n1]

To a solution of ethyl 2-((trans)-3-(2-(difluoromethoxy)-5-fluorophenoxy)cyclobutanecarboxamido)thiazole-4-carboxylate (Example 31) (60 mg, 0.14 mmol) in THF (5 mL) was added LiOH (13 mg, 0.56 mmol) in water (2.5 mL). After 1 hour, the mixture was adjusted to pH=4 with aqueous citric acid. The mixture was extracted with EtOAc (3×), and the combined organic layers were washed with brine, dried over Na$_2$SO$_4$ and concentrated under reduced pressure to give the title compound (119 mg, quantitative). $^1$H NMR (400 MHz, CD$_3$SOCD$_3$) δ 2.30-2.40 (m, 2H), 2.61-2.71 (m, 2H), 3.05-3.12 (m, 1H), 4.82-4.93 (m, 1H), 6.73-6.80 (m, 2H), 7.02 (t, J=76 Hz, 1H), 7.19-7.22 (m, 1H), 7.99 (s, 1H); LC-MS (LC-ES) M+H=403.

B. 2-((trans)-3-(2-(Difluoromethoxy)-5-fluorophenoxy)cyclobutanecarboxamido)-N-methoxy-N-methylthiazole-4-carboxamide

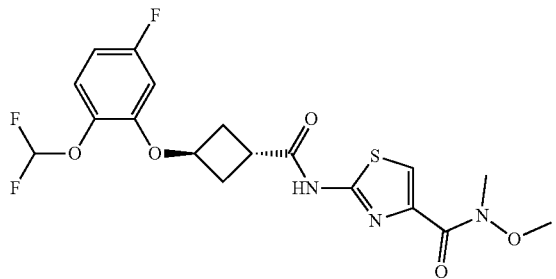 [SMILES: CON(C)C(=O)c1csc(NC(=O)[C@H]2C[C@H](Oc3cc(F)ccc3OC(F)F)C2)n1]

2-((trans)-3-(2-(Difluoromethoxy)-5-fluorophenoxy)cyclobutanecarboxamido)thiazole-4-carboxylic acid (Intermediate 22A) (55 mg, 0.14 mmol) was dissolved in DMF (4 mL) followed by the addition of N,N-diisopropylethylamine (0.14 mL, 0.82 mmol) and HATU (62 mg, 0.16 mmol). The reaction was stirred at room temperature for ca. 5 min, and N,O-dimethylhydroxylamine hydrochloride (16 mg, 0.16 mmol) was added. After 3 h, the reaction was quenched with water, extracted with EtOAc (3×), and the combined organic extracts dried over sodium sulfate, filtered, and concentrated under reduced pressure. The residue was purified on silica gel eluting with a 0%-100% EtOAc-EtOH (3:1) in hexanes gradient. The appropriate fractions were combined, evaporated under reduced pressure and placed in vacuo to give the title compound (16 mg, 26%). $^1$H NMR (400 MHz, CD$_3$SOCD$_3$) δ 2.36-2.42 (m, 2H), 2.49 (s, 3H), 2.72-2.80 (m, 2H), 3.28 (s, 3H), 3.37-3.44 (m, 1H), 4.90-5.07 (m, 1H), 6.76-6.82 (m, 1H), 6.85-6.89 (m, 1H), 7.05 (t, J=76 Hz, 1H), 7.20-7.25 (m, 1H), 7.76 (s, 1H); LC-MS (LC-ES) M+H=446.

Intermediate 23: 1-(((trans)-4-Aminocyclohexyl)oxy)-2-methylpropan-2-ol

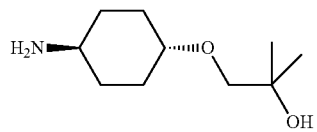

A. 1-((trans-4-(Dibenzylamino)cyclohexyl)oxy)-2-methylpropan-2-ol

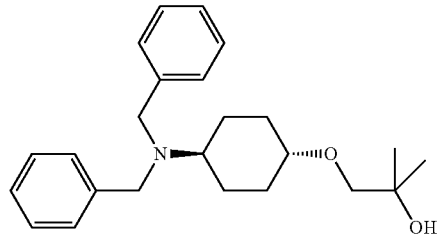 [SMILES: CC(C)(O)CO[C@H]1CC[C@H](N(Cc2ccccc2)Cc2ccccc2)CC1]

tert-Butyl 2-((trans-4-(dibenzylamino)cyclohexyl)oxy)acetate (Intermediate 10B) (0.40 g, 0.98 mmol) was stirred in THF (2.5 mL) under nitrogen at 0° C., then a 3.0 M solution of methylmagnesium bromide (0.80 mL, 2.4 mmol) in diethyl ether was added. The reaction was stirred at room temperature for 3 h then quenched with saturated aqueous NH$_4$Cl (3 mL) and stirred at room temperature overnight. The reaction was diluted with EtOAc, washed with saturated aqueous sodium bicarbonate, water (2×), and brine. The organics were dried over sodium sulfate, filtered, and concentrated under reduced pressure. The residue was purified by silica gel chromatography eluting with a gradient from 5-15% ((3:1 EtOAc:EtOH) in hexanes), providing a colorless oil that solidified over time to afford the title compound (0.168 g, 47%). $^1$H NMR (CDCl$_3$) δ 1.09-1.22 (m, 8H), 1.33-1.47 (m, 2H), 1.88-1.97 (m, 2H), 2.04-2.11 (m, 2H), 2.53 (tt, J=12, 3 Hz, 1H), 3.19 (tt, J=11, 4 Hz, 1H), 3.24 (s, 2H), 3.61 (s, 4H), 7.18-7.24 (m, 2H), 7.26-7.33 (m, 4H), 7.34-7.39 (m, 4H); LC-MS (LC-ES) M−H=368.

B. 1-(((trans)-4-Aminocyclohexyl)oxy)-2-methylpropan-2-ol

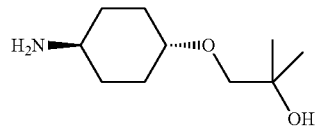

A mixture of 1-((trans-4-(dibenzylamino)cyclohexyl)oxy)-2-methylpropan-2-ol (Intermediate 23A) (620 mg, 1.69 mmol) and palladium hydroxide on carbon (300 mg, 2.14 mmol) in EtOH (5 mL) was hydrogenated at 55 psi (Fisher-Porter apparatus) for 2 h. The reaction mixture was filtered through a plug of Celite®. The catalyst was washed with MeOH and DCM. The filtrate was concentrated to dryness and dried under high vacuum to give the title compound as a grey solid (306 mg). $^1$H NMR (CDCl$_3$) δ 1.07-1.35 (m, 4H), 1.17 (s, 6H), 1.92 (m, 2H), 2.02 (m, 2H), 2.45 (br s, 3H), 2.78 (m, 1H), 3.25 (m, 3H).

Intermediate 24: 6-(3-Aminoazetidin-1-yl)nicotinamide dihydrochloride

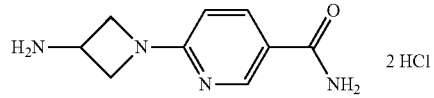

A. tert-Butyl (1-(5-carbamoylpyridin-2-yl)azetidin-3-yl)carbamate

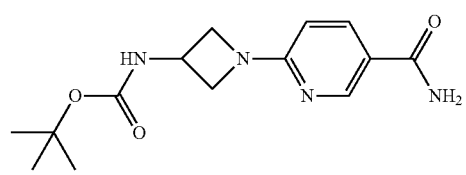 [SMILES: CC(C)(C)OC(=O)NC1CN(c2ccc(C(N)=O)cn2)C1]

To tert-butyl azetidin-3-ylcarbamate (220 mg, 1.23 mmol) in acetonitrile (2 mL) with a small amount of NMP to facilitate solubility, 6-chloronicotinamide (200 mg, 1.28 mmol) was added, followed by N,N-diisopropylethylamine (0.22 mL, 1.3 mmol). The mixture was heated in a microwave at 130° C. for 2 h, cooled, and the resulting precipitate was collected by filtration to give the title compound (140 mg, 38%). $^1$H NMR (400 MHz, CD$_3$OD) δ 1.47 (s, 9H), 3.88-3.95 (m, 2H), 4.38 (t, J=8 Hz, 2H), 4.50-4.59 (m, 1H), 6.43 (d, J=9 Hz, 1H), 8.00 (dd, J=9, 2 Hz, 1H), 8.59 (d, J=2 Hz, 1H); LC-MS (LC-ES) M+H=293.

B. 6-(3-Aminoazetidin-1-yl)nicotinamide dihydrochloride

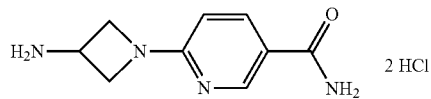

To tert-butyl (1-(5-carbamoylpyridin-2-yl)azetidin-3-yl)carbamate (Intermediate 24A) (140 mg, 0.48 mmol) in methanol (3 mL), 4 M HCl in dioxane (2 mL, 8 mmol) was added. The mixture was stirred at room temperature for 2 h and the solvent was removed in vacuo to give a solid, which was triturated with EtOAc to give the title compound (124 mg, 98%). $^1$H NMR (400 MHz, CD$_3$OD) δ 4.39-4.48 (m, 1H), 4.49-4.57 (m, 2H), 4.73-4.85 (m, 2H), 7.06 (d, J=9 Hz, 1H), 8.44 (dd, J=9, 2 Hz, 1H), 8.52 (d, J=2 Hz, 1H); LC-MS (LC-ES) M+H=192.

Intermediate 25: (trans)-3-(Benzo[d]thiazol-4-yloxy)cyclobutanecarboxylic acid

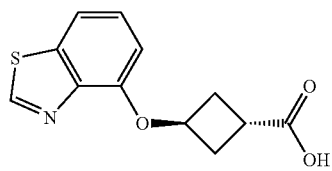 [SMILES: O=C(O)[C@H]1C[C@H](Oc2cccc3scnc23)C1]

A. (trans)-Methyl 3-(benzo[d]thiazol-4-yloxy)cyclobutanecarboxylate

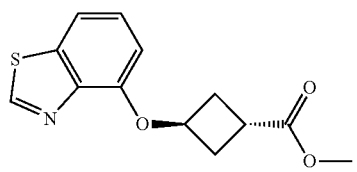 [SMILES: COC(=O)[C@H]1C[C@H](Oc2cccc3scnc23)C1]

Triphenylphosphine (9.72 g, 37.0 mmol) was added to a solution of benzo[d]thiazol-4-ol (4.00 g, 26.5 mmol) in tetrahydrofuran (80 mL). The reaction mixture was cooled to 0° C., and (cis)-methyl 3-hydroxycyclobutanecarboxylate (4.13 g, 31.7 mmol) was added, followed by the dropwise addition of DIAD (7.20 mL, 37.0 mmol). The reaction mixture was then warmed to room temperature, stirred over the weekend, and concentrated. The remaining material was purified on silica gel eluting with a 15%-60% EtOAc-hexanes gradient. The appropriate fractions were combined, evaporated under reduced pressure and placed in vacuo to give the title compound (6.72 g, 90%) which contained about 1.1 equivalent of reduced DIAD contaminant. $^1$H NMR (400 MHz, CD$_3$SOCD$_3$) δ 2.51-2.67 (m, 2H), 2.75 (td, J=7, 4 Hz, 2H), 3.10-3.19 (m, 1H), 3.67 (s, 3H), 5.03-5.10 (m, 1H), 6.68 (d, J=8 Hz, 1H), 7.26 (t, J=8 Hz, 1H), 7.45 (d, J=8 Hz, 1H), 8.84 (s, 1H); LC-MS (LC-ES) M+H=264.

B. (trans)-3-(Benzo[d]thiazol-4-yloxy)cyclobutanecarboxylic acid

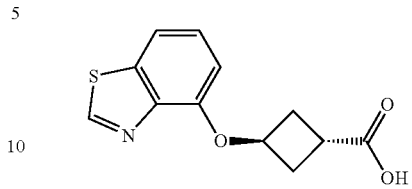

To a solution of (trans)-methyl 3-(benzo[d]thiazol-4-yloxy)cyclobutanecarboxylate (Intermediate 25A) (400 mg, 1.5 mmol) in THF (20 mL) and water (7 mL) was added LiOH (91 mg, 3.8 mmol). The reaction mixture was stirred at room temperature for 2 h. A portion of the solvents were removed in vacuo, and the remainder was partitioned between EtOAc and water. The aqueous layer was separated and adjusted to pH=4 with the addition of aqueous citric acid. The resulting white precipitate was collected by filtration, washed with water and air dried to give the title compound (140 mg, 37%). $^1$H NMR (400 MHz, CD$_3$SOCD$_3$) δ 2.17-2.34 (m, 2H), 2.44-2.57 (m, 2H), 3.11-3.22 (m, 1H), 4.72-4.89 (m, 1H), 6.88 (d, J=8 Hz, 1H), 7.38-7.44 (m, 1H), 7.71 (d, J=8 Hz, 1H), 9.27 (s, 1H); LC-MS (LC-ES) M+H=250.

C. (trans)-3-(Benzo[d]thiazol-4-yloxy)cyclobutanecarboxylic acid, lithium salt

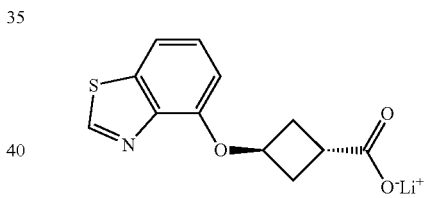

To a solution of (trans)-methyl 3-(benzo[d]thiazol-4-yloxy)cyclobutanecarboxylate (Intermediate 25A) (3.48 g, 13.2 mmol) in THF (40 mL) and water (15 mL) was added lithium hydroxide (0.790 g, 33.0 mmol). After 2 h, the solvents were removed in vacuo and the resulting solid was triturated with ether affording the title compound (5.7 g, quantitative) as a white solid. $^1$H NMR (400 MHz, CD$_3$SOCD$_3$) δ 2.20 (dd, J=7, 3 Hz, 2H), 2.61 (dt, J=6, 3 Hz, 2H), 2.65-2.74 (m, 1H), 4.96-5.09 (m, 1H), 6.80 (d, J=8 Hz, 1H), 7.37 (t, J=8 Hz, 1H), 7.65 (d, J=8 Hz, 1H), 9.23 (s, 1H); LC-MS (LC-ES) M+H-Li=250.

Intermediate 26: 6-(3-Aminoazetidin-1-yl)-N-methylnicotinamide dihydrochloride

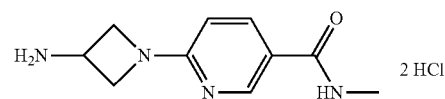

A. tert-Butyl (1-(5-(methylcarbamoyl)pyridin-2-yl)azetidin-3-yl)carbamate

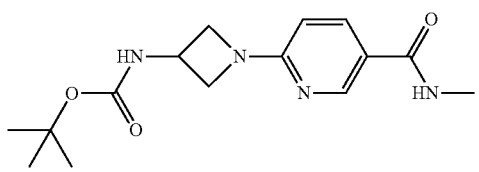 [SMILES: CNC(=O)c1ccc(N2CC(NC(=O)OC(C)(C)C)C2)nc1]

To tert-butyl azetidin-3-ylcarbamate (202 mg, 1.07 mmol) in acetonitrile (2 mL) with a small amount of NMP to facilitate solubility, 6-chloro-N-methylnicotinamide (200 mg, 1.17 mmol) was added, followed by N,N-diisopropylethylamine (0.41 mL, 2.3 mmol). The mixture was heated in a microwave at 130° C. for 2 h, cooled, and the resulting precipitate was collected by filtration to give the title compound (124 mg, 35%). $^1$H NMR (400 MHz, CD$_3$OD) δ 1.47 (s, 9H), 2.88 (s, 3H), 3.92 (dd, J=8, 4 Hz, 2H), 4.36 (t, J=8 Hz, 2H), 4.48-4.55 (m, 1H), 6.43 (d, J=9 Hz, 1H), 8.00 (dd, J=9, 2 Hz, 1H), 8.52 (d, J=2 Hz, 1H); LC-MS (LC-ES) M+H=307.

B. 6-(3-Aminoazetidin-1-yl)-N-methylnicotinamide dihydrochloride

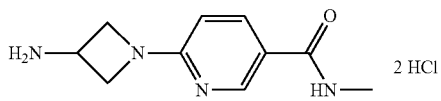

To tert-butyl (1-(5-carbamoylpyridin-2-yl)azetidin-3-yl)carbamate (Intermediate 26A) (160 mg, 0.52 mmol) in DCM (1.5 mL) was added 4 M HCl in dioxane (3 mL, 12 mmol). The mixture was stirred at room temperature for 2 h and the solvent was removed in vacuo to give the title compound as a brownish solid (142 mg, 97%). $^1$H NMR (400 MHz, CD$_3$OD) δ 2.86 (s, 3H), 4.41-4.47 (m, 1H), 4.48-4.58 (m, 2H), 4.73-4.85 (m, 2H), 7.00-7.10 (m, 1H), 8.43-8.45 (m, 1H), 8.52 (d, J=2 Hz, 1H); LC-MS (LC-ES) M+H=207.

Intermediate 27:
1-(5-Methylpyrimidin-2-yl)azetidin-3-amine dihydrochloride

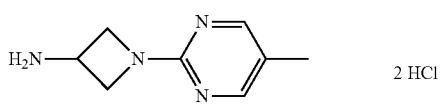

A. tert-Butyl (1-(5-methylpyrimidin-2-yl)azetidin-3-yl)carbamate

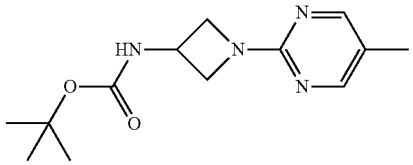 [SMILES: Cc1cnc(N2CC(NC(=O)OC(C)(C)C)C2)nc1]

To tert-butyl azetidin-3-ylcarbamate (649 mg, 3.11 mmol) in acetonitrile (10 mL) was added 2-chloro-5-methylpyrimidine (400 mg, 3.11 mmol) followed by N,N-diisopropylethylamine (2.72 mL, 15.6 mmol). The mixture was heated in a microwave at 130° C. for 3 h. The solvent was removed, and the residue was purified on silica gel eluting with a 30%-100% EtOAc in hexanes gradient. The appropriate fractions were combined, evaporated under reduced pressure and placed in vacuo to give the title compound as a white solid (373 mg, 45%). $^1$H NMR (400 MHz, CD$_3$OD) δ 1.47 (s, 9H), 2.17 (s, 3H), 3.92 (dd, J=8, 6 Hz, 2H), 4.34 (t, J=8 Hz, 2H), 4.43-4.58 (m, 1H), 8.21 (s, 2H); LC-MS (LC-ES) M+H=265.

B. 1-(5-Methylpyrimidin-2-yl)azetidin-3-amine dihydrochloride

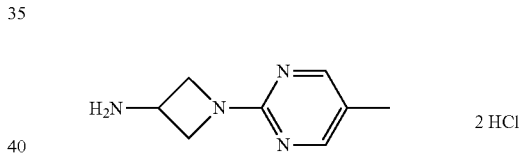

To tert-butyl (1-(5-methylpyrimidin-2-yl)azetidin-3-yl)carbamate (Intermediate 27A) (170 mg, 0.64 mmol) in DCM (6 mL) was added 4 M HCl in dioxane (6 mL, 24 mmol). The mixture was stirred at room temperature overnight and the solvent was removed in vacuo to give the title compound as a pale yellow solid (164 mg, quantitative). $^1$H NMR (400 MHz, CD$_3$OD) δ 2.31 (s, 3H), 4.43 (m, 3H), 4.71 (m, 2H), 8.55 (m, 2H); LC-MS (LC-ES) M+H=165.

Intermediate 28:
4-(Azetidin-3-yloxy)benzo[d]thiazole hydrochloride

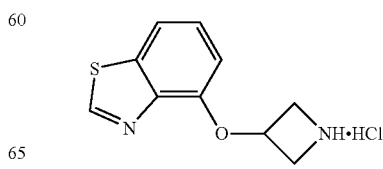

A. tert-Butyl 3-(benzo[d]thiazol-4-yloxy)azetidine-1-carboxylate

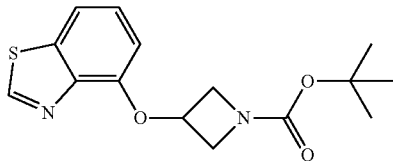

To a stirred solution of tert-butyl 3-((methylsulfonyl)oxy)azetidine-1-carboxylate (Intermediate 1) (1.47 g, 5.85 mmol) and benzo[d]thiazol-4-ol (0.884 g, 5.85 mmol) in DMF (40 mL) was added cesium carbonate (2.10 g, 6.43 mmol). The mixture was heated to 80° C. overnight, poured into water and extracted twice with EtOAc. The combined organic layers were washed with brine, dried over MgSO$_4$, filtered and concentrated. The remaining material was purified on silica gel eluting with a 5%-70% EtOAc-hexanes gradient. The appropriate fractions were combined, evaporated under reduced pressure and placed in vacuo to give the title compound (1.35 g, 75%) as a white solid. $^1$H NMR (400 MHz, CDCl$_3$) δ 1.44 (s, 9H), 4.21 (dd, J=10, 4 Hz, 2H), 4.32-4.42 (m, 2H), 5.14-5.19 (m, 1H), 6.64 (d, J=8 Hz, 1H), 7.35 (t, J=8 Hz, 1H), 7.54-7.64 (m, 1H), 8.94 (s, 1H); LC-MS (LC-ES) M+H=307.

B. 4-(Azetidin-3-yloxy)benzo[d]thiazole hydrochloride

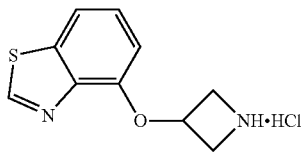

To tert-butyl 3-(benzo[d]thiazol-4-yloxy)azetidine-1-carboxylate (Intermediate 28A) (1.35 g, 4.41 mmol) in methanol (3 mL) was added 4 M HCL in dioxane (10 mL, 40 mmol). The mixture was stirred at room temperature for 2 h and the solvent was removed in vacuo to give the title compound as a white solid (1.23 g, 100%). $^1$H NMR (400 MHz, CD$_3$OD) δ 4.32 (dd, J=12, 5 Hz, 2H), 4.65 (dd, J=12, 6 Hz, 2H), 5.42-5.50 (m, 1H), 6.98 (d, J=8 Hz, 1H), 7.49 (t, J=8 Hz, 1H), 7.79 (d, J=8 Hz, 1H), 9.42 (s, 1H); LC-MS (LC-ES) M+H=207.

Alternatively, intermediate 28A can be converted to the trifluoroacetic acid salt

C. 4-(Azetidin-3-yloxy)benzo[d]thiazole hydrochloride trifluoroacetic acid salt

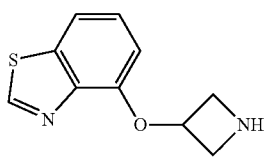

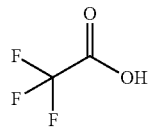

To tert-butyl 3-(benzo[d]thiazol-4-yloxy)azetidine-1-carboxylate (Intermediate 28A) (4.00 g, 12.4 mmol) in DCM (100 mL) at 0° C., TFA (16.0 mL, 208 mmol) was added. After 4 h, the solvent was removed in vacuo, and the residue triturated with diethyl ether (3×100 mL) to give the title compound as an off-white solid (3.70 g, 97%). $^1$H NMR (400 MHz, CD$_3$SOCD$_3$) δ 4.10-4.19 (m, 2H), 4.48-4.59 (m, 2H), 5.32-5.40 (m, 1H), 6.89-6.96 (m, 1H), 7.39-7.45 (m, 1H), 7.79-7.86 (m, 1H), 9.10 (br s, 2H), 9.35 (s, 1H); LC-MS (LC-ES) M+H=207.

Intermediate 29: 1-(5-Fluoropyrimidin-2-yl)piperidin-4-amine dihydrochloride

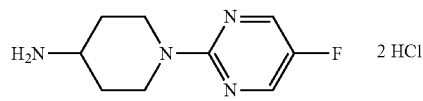

A. tert-Butyl (1-(5-fluoropyrimidin-2-yl)piperidin-4-yl)carbamate

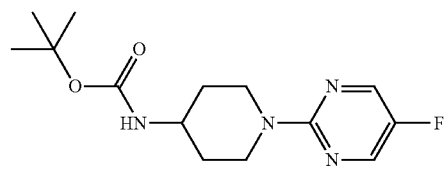 [SMILES: CC(C)(C)OC(=O)NC1CCN(c2ncc(F)cn2)CC1]

To tert-butyl piperidin-4-ylcarbamate (1.10 g, 5.50 mmol) in acetonitrile (12 mL), 2-chloro-5-fluoropyrimidine (0.66 g, 5.0 mmol) was added. The mixture was heated in a microwave at 125° C. for 3 h. The reaction was cooled, and the resulting precipitate was collected by filtration to give the title compound. The filtrate was concentrated, and the residue was purified on silica gel eluting with a 10%-60% EtOAc in hexanes gradient. The appropriate fractions were combined, evaporated under reduced pressure and placed in vacuo to give additional title compound as a white solid (1.26 g, 85%, total yield). $^1$H NMR (400 MHz, CDCl$_3$) δ 1.27-1.42 (m, 2H), 1.46 (s, 9H), 2.02 (d, J=12 Hz, 2H), 3.06 (t, J=12 Hz, 2H), 3.63-3.80 (m, 1H), 4.40-4.49 (m, 1H), 4.55 (d, J=14 Hz, 2H), 8.19 (s, 2H); LC-MS (LC-ES) M+H=297.

B. 1-(5-Fluoropyrimidin-2-yl)piperidin-4-amine dihydrochloride

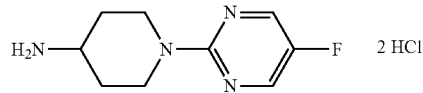

To tert-butyl (1-(5-fluoropyrimidin-2-yl)piperidin-4-yl)carbamate (Intermediate 29A) (1.26 g, 4.25 mmol) in DCM (10 mL) was added 4 M HCl in dioxane (10 mL, 40 mmol). The mixture was stirred at room temperature for 3 h and the solvent was removed in vacuo to give the title compound as a pale yellow solid (1.11 g, 97%). $^1$H NMR (400 MHz, CD$_3$OD) δ 1.57-1.74 (m, 2H), 2.09-2.23 (m, 2H), 3.09-3.23 (m, 2H), 3.45-3.55 (m, 1H), 4.70-4.82 (m, 2H), 8.45-8.54 (m, 2H); LC-MS (LC-ES) M+H=197.

Intermediate 30: 4-Nitrophenyl (1-(5-fluoropyrimidin-2-yl)piperidin-4-yl)carbamate

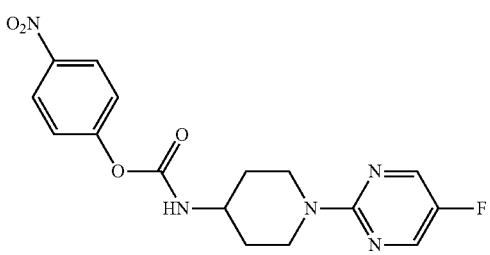 [SMILES: O=C(NC1CCN(c2ncc(F)cn2)CC1)Oc1ccc([N+](=O)[O-])cc1]

To 4-nitrophenyl chloroformate (214 mg, 1.06 mmol) in DCM (4 mL) at 0° C. was slowly added 1-(5-fluoropyrimidin-2-yl)piperidin-4-amine dihydrochloride (Intermediate 29) (220 mg, 0.82 mmol) in DCM (12 mL) and N,N-diisopropylethylamine (0.29 mL, 1.6 mmol). After one hour, the reaction was allowed to slowly warm to room temperature and stirred overnight. The solvent was removed in vacuo to afford the title compound (290 mg, 98%) which was used without further purification. LC-MS (LC-ES) M+H=362.

Intermediate 31: 4-Nitrophenyl (1-(5-fluoropyridin-2-yl)azetidin-3-yl)carbamate

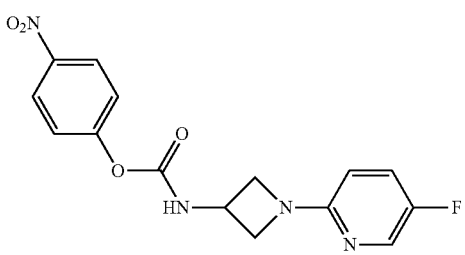 [SMILES: O=C(NC1CN(c2ccc(F)cn2)C1)Oc1ccc([N+](=O)[O-])cc1]

A. Benzyl (1-(5-fluoropyridin-2-yl)azetidin-3-yl)carbamate

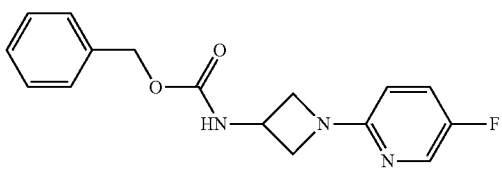 [SMILES: O=C(NC1CN(c2ccc(F)cn2)C1)OCc1ccccc1]

In a reaction vial, allylpalladium chloride dimer (33 mg, 0.091 mmol), 2-(di(adamantan-1-yl)phosphino)-N,N-dimethylaniline (77 mg, 0.18 mmol) and toluene (20 mL) were stirred for 10 min. The mixture was first clear and then turned cloudy. Sodium tert-butoxide (877 mg, 9.12 mmol) was added, then 2-chloro-5-fluoropyridine (600 mg, 4.56 mmol) and benzyl azetidin-3-ylcarbamate (1.13 g, 5.47 mmol). The vial was sealed and heated to 110° C. overnight. The mixture was cooled, filtered through Celite® and washed with EtOAc. The filtrate was concentrated in vacuo and the residue was purified on silica gel eluting with 10 to 65% EtOAc/hexanes to afford the title compound (230 mg, 17% yield) as a white solid. $^1$H NMR (400 MHz, CD$_3$OD) δ 3.83 (t, J=7 Hz, 2H), 4.27 (t, J=7 Hz, 2H), 4.57 (br s, 1H), 5.11 (s, 2H), 6.45 (d, J=8 Hz, 1H), 7.23-7.44 (m, 6H), 7.92 (br s, 1H); LC-MS (LC-ES) M+H=302.

B. 1-(5-Fluoropyridin-2-yl)azetidin-3-amine

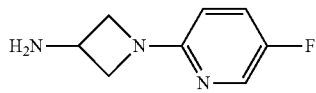 [SMILES: NC1CN(c2ccc(F)cn2)C1]

Benzyl (1-(5-fluoropyridin-2-yl)azetidin-3-yl)carbamate (Intermediate 31A) (0.230 g, 0.76 mmol) and 20 wt % Pearlman's catalyst (54 mg, 0.08 mmol) were stirred in 1:1 methanol: EtOAc (40 mL) and purged with hydrogen via balloon (3×) before stirring under a hydrogen atmosphere at room temperature overnight. The reaction was filtered through a pad of Celite® and rinsed with ethyl acetate. The filtrate was concentrated under reduced pressure to give the title compound as a yellow solid (130 mg, quantitative). $^1$H NMR (400 MHz, CD$_3$OD) δ 3.72-3.89 (m, 2H), 3.94-4.06 (m, 1H), 4.27 (t, J=8 Hz, 2H), 6.48 (d, J=8 Hz, 1H), 7.43 (t, J=8 Hz, 1H), 7.95 (s, 1H); LC-MS (LC-ES) M+H=168.

C. 4-Nitrophenyl (1-(5-fluoropyridin-2-yl)azetidin-3-yl)carbamate

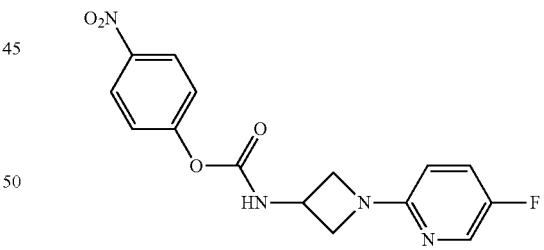

To 4-nitrophenyl chloroformate (152 mg, 0.754 mmol) in acetonitrile (3 mL) at 0° C. was slowly added 1-(5-fluoropyridin-2-yl)azetidin-3-amine (Intermediate 31B) (220 mg, 0.82 mmol) in DCM (12 mL). After one hour, sodium bicarbonate (97 mg, 1.2 mmol) was added, and the reaction was allowed to slowly warm to room temperature and stirred overnight. The solvent was removed in vacuo, the residue dissolved in EtOAc and washed with water and brine, dried over MgSO$_4$, filtered and concentrated. The residue was purified on silica gel eluting with 10 to 60% EtOAc/hexanes to afford the title compound (39 mg, 20% yield) as a pale yellow solid. $^1$H NMR (400 MHz, CDCl$_3$) δ 3.84-4.02 (m, 2H), 4.42 (t, J=8 Hz, 2H), 4.75 (d, J=6 Hz, 1H), 5.67 (d, J=6

Hz, 1H), 6.34 (d, J=6 Hz, 1H), 7.21-7.31 (m, 1H), 7.35 (d, J=9 Hz, 2H), 8.06 (br s, 1H), 8.28 (d, J=9 Hz, 1H); LC-MS (LC-ES) M+H=333.

Intermediate 32: (trans)-N-(Azetidin-3-yl)-3-(benzo [d]thiazol-4-yloxy)cyclobutanecarboxamide hydrochloride

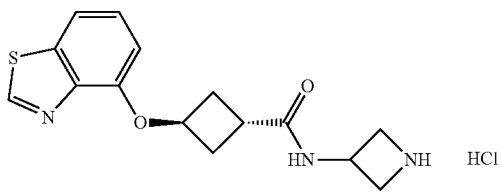 [SMILES: O=C(NC1CNC1)[C@H]1C[C@H](Oc2cccc3scnc23)C1 ; Cl]

A. tert-Butyl 3-((trans)-3-(benzo[d]thiazol-4-yloxy) cyclobutanecarboxamido)azetidine-1-carboxylate

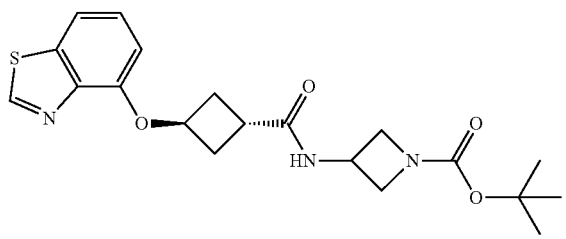 [SMILES: CC(C)(C)OC(=O)N1CC(NC(=O)[C@H]2C[C@H](Oc3cccc4scnc34)C2)C1]

To a DMF (4 mL) solution of (trans)-3-(benzo[d]thiazol-4-yloxy)cyclobutanecarboxylic acid (Intermediate 25) (400 mg, 1.61 mmol), tert-butyl 3-aminoazetidine-1-carboxylate (276 mg, 1.61 mmol) and N,N-diisopropylethylamine (0.56 mL, 0.32 mmol) was added, dropwise, a 50% solution of T3P in ethyl acetate (2.04 g, 3.21 mmol). The reaction was stirred 30 min, quenched with water and extracted with EtOAc. The organic extracts were washed with water and brine, dried over MgSO$_4$, filtered and concentrated. The residue was purified on silica gel eluting with 0 to 20% MeOH/DCM to afford the title compound (635 mg, 98% yield) as a foam. $^1$H NMR (400 MHz, CD$_3$OD) δ 1.44 (s, 9H), 2.49-2.64 (m, 2H), 2.69-2.82 (m, 2H), 3.11-3.29 (m, 1H), 3.82 (dd, J=8, 6 Hz, 2H), 4.23 (t, J=8 Hz, 2H), 4.57 (t, J=6 Hz, 1H), 5.16 (t, J=6 Hz, 1H), 6.89 (d, J=8 Hz, 1H), 7.42 (t, J=8 Hz, 1H), 7.62 (d, J=8 Hz, 1H), 9.16 (s, 1H); LC-MS (LC-ES) M+H=404.

B. (trans)-N-(Azetidin-3-yl)-3-(benzo[d]thiazol-4-yloxy)cyclobutanecarboxamide hydrochloride

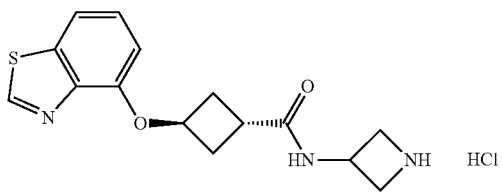 [SMILES: O=C(NC1CNC1)[C@H]1C[C@H](Oc2cccc3scnc23)C1 ; Cl]

To tert-butyl 3-((trans)-3-(benzo[d]thiazol-4-yloxy)cyclobutanecarboxamido)azetidine-1-carboxylate (Intermediate 32A) (630 mg, 1.56 mmol) in DCM (2.5 mL) and methanol (2.5 mL), 4 M HCl in dioxane (5 mL, 20 mmol) was added. The mixture was stirred at room temperature for 3 h and the solvent was removed in vacuo to give the title compound as a hygroscopic foam (596 mg, quantitative). $^1$H NMR (400 MHz, CD$_3$OD) δ 2.47-2.70 (m, 2H), 2.74-2.87 (m, 2H), 3.64-3.69 (m, 1H), 3.74-3.82 (m, 1H), 4.17-4.28 (m, 2H), 4.29-4.38 (m, 2H), 5.12-5.31 (m, 1H), 7.06-7.15 (m, 1H), 7.57-7.65 (m, 1H), 7.76-7.83 (m, 1H), 9.98 (br s, 1H); LC-MS (LC-ES) M+H=304.

Intermediate 33: 1-(2-Methylpyrimidin-4-yl)azetidin-3-amine

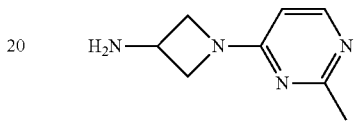

A. Benzyl (1-(2-methylpyrimidin-4-yl)azetidin-3-yl)carbamate

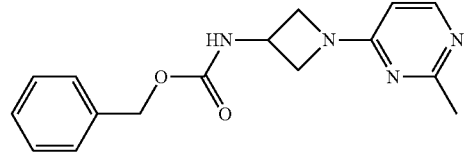 [SMILES: Cc1nccc(N2CC(NC(=O)OCc3ccccc3)C2)n1]

To benzyl azetidin-3-ylcarbamate (810 mg, 3.9 mmol) in acetonitrile (15 mL), 4-chloro-2-methylpyrimidine (420 mg, 3.3 mmol) and N,N-diisopropylethylamine (1.1 mL, 6.5 mmol) were added. The mixture was heated in a microwave at 120° C. for 1.5 h. The reaction was concentrated, and the residue was purified on silica gel eluting with a 5%-20% MeOH in DCM gradient. The appropriate fractions were combined, evaporated under reduced pressure and placed in vacuo to give the title compound as a white solid (1.38 g, quantitative). $^1$H NMR (400 MHz, CD$_3$OD) δ 2.48 (s, 3H), 3.97-4.13 (m, 2H), 4.45 (t, J=8 Hz, 2H), 4.56-4.66 (m, 1H), 5.12 (s, 2H), 6.32 (d, J=6 Hz, 1H), 7.23-7.48 (m, 5H), 8.03 (d, J=6 Hz, 1H); LC-MS (LC-ES) M+H=299.

B. 1-(2-Methylpyrimidin-4-yl)azetidin-3-amine

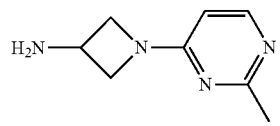

Benzyl (1-(2-methylpyrimidin-4-yl)azetidin-3-yl)carbamate (Intermediate 33A) (1.2 g, 4.0 mmol) was dissolved in EtOH (30 mL) and EtOAc (30 mL), and 10 wt % palladium on carbon (0.43 g, 0.40 mmol) was added under nitrogen and purged with hydrogen via balloon (3×) before stirring at room temperature overnight under a hydrogen atmosphere. The reaction was filtered through a pad of Celite® and rinsed with EtOAc and methanol. The filtrate was concentrated under reduced pressure to give the title compound as a white solid (505 mg, 76%). ¹H NMR (CD₃OD) δ 2.49 (s, 3H), 4.11 (dd, J=11, 4 Hz, 2H), 4.19-4.31 (m, 1H), 4.49 (dd, J=10, 8 Hz, 2H), 6.38 (d, J=6 Hz, 1H), 8.10 (d, J=6 Hz, 1H); LC-MS (LC-ES) M+H=165.

Intermediate 34: Racemic 2-((trans)-5-Aminotetrahydro-2H-pyran-2-yl)propan-2-ol

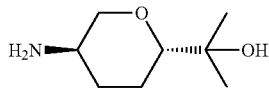

A. Racemic N-Benzyl-6-(((tertbutyldiphenylsilyl)oxy)methyl)tetrahydro-2H-pyran-3-amine

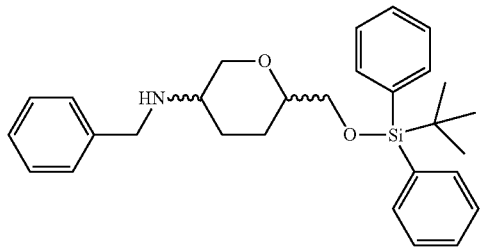 [SMILES: CC(C)(C)[Si](OCC1CCC(NCc2ccccc2)CO1)(c1ccccc1)c1ccccc1]

Benzylamine (3.17 mL, 32.6 mmol) was added to a solution of 6-(((tert-butyldiphenylsilyl)oxy)methyl)dihydro-2H-pyran-3(4H)-one (4 g, 10.9 mmol) (see; Bioorganic and Medicinal Chemistry 14 (2006), 3953) in MeOH (30 mL). After 1 h, the mixture was cooled to −78° C. and LiBH₄ (5.97 mL, 11.9 mmol) was added. After 1 h, allowed to warm to ROOM TEMPERATURE slowly overnight. The mixture was partitioned between EtOAc and saturated NaHCO₃ and the aqueous layer was extracted with EtOAc (2×). The combined organics were washed with brine, dried over Na₂SO₄, and concentrated. The residue was purified by silica gel chromatography eluting with a 0%-40% EtOAc/EtOH (3:1) in hexanes gradient to afford the title compound as a yellow oil (3.49 g, 70% yield) (mixture of cis and trans isomers). LC-MS (ES-MS) M+H=460.

B. Racemic 6-(((tert-Butyldiphenylsilyl)oxy)methyl)tetrahydro-2H-pyran-3-amine

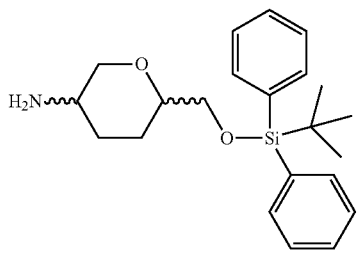 [SMILES: CC(C)(C)[Si](OCC1CCC(N)CO1)(c1ccccc1)c1ccccc1]

A Fisher-Porter bottle was flushed with N₂ and charged with N-benzyl-6-(((tert-butyldiphenylsilyl)oxy)methyl)tetrahydro-2H-pyran-3-amine (Intermediate 34A) (3.9 g, 8.5 mmol) and EtOH (80 mL). Under a N₂ atmosphere, Pearlman's catalyst (1.49 g, 2.12 mmol) was added, and the vessel was evacuated and flushed with N₂ and stirred under 50 psi H2 over 4 days. The vessel was evacuated and flushed with N₂ and filtered through a pad of Celite®, washing with MeOH. The filtrate was concentrated to give the title compound as a clear thick oil (2.98 g, 94%). LC-MS (ES-MS) M+H=370.

C. Racemic tert-Butyl (6-(((tertbutyldiphenylsilyl)oxy)methyl)tetrahydro-2H-pyran-3-yl)carbamate

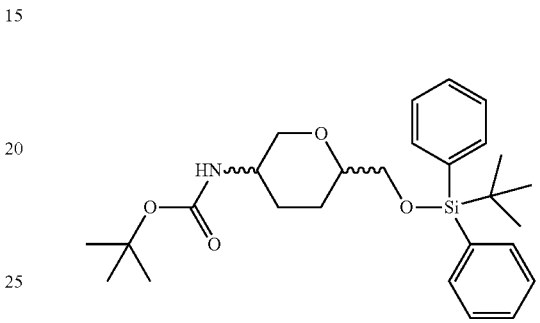

To a solution of 6-(((tert-butyldiphenylsilyl)oxy)methyl)tetrahydro-2H-pyran-3-amine (Intermediate 34B) (2.98 g, 8.06 mmol) and Et₃N (1.69 mL, 12.1 mmol) in DCM (100 mL) at 0° C. was added Boc₂O (2.15 mL, 9.27 mmol). The mixture was stirred at 0° C. for 1 h then at room temperature overnight. The reaction was diluted with DCM and washed with water and brine. The aqueous phases were back extracted with DCM, and the combined organics were dried over Na₂SO₄, filtered, and concentrated to give a thick oil. The residue was purified by silica gel chromatography eluting with a 0%-20% EtOAc-hexanes gradient to afford the title compound as a thick oil (2.4 g, 70% yield). LC-MS (ES-MS) M+H=470.

D. Racemic tert-Butyl (6-(hydroxymethyl)tetrahydro-2H-pyran-3-yl)carbamate

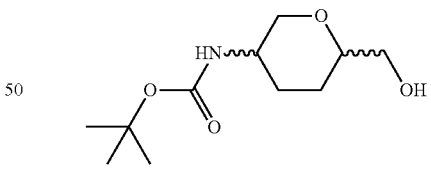

To a solution of tert-butyl (6-(((tert-butyldiphenylsilyl)oxy)methyl)tetrahydro-2H-pyran-3-yl)carbamate (Intermediate 34C) (2.4 g, 5.1 mmol) in THF (60 mL) at 0° C., was added TBAF (10.2 mL, 10.2 mmol, 1 M in THF). The reaction was stirred at room temperature for 2 h, concentrated to ca. half volume under reduced pressure, and 15 mL of saturated NaHCO₃ was added. The mixture was extracted with EtOAc (2×). The combined organics were dried over Na₂SO₄, filtered, and concentrated to give an oil. The residue was purified by silica gel chromatography (0-20% EtOAc-hexanes gradient) to afford the title compound as a white solid (1.12 g, 94% yield). This material was used directly in the next step.

E. Racemic 5-((tert-Butoxycarbonyl)amino)tetrahydro-2H-pyran-2-carboxylic acid

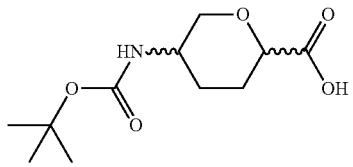 [SMILES: CC(C)(C)OC(=O)NC1CCC(C(=O)O)OC1]

To a 0° C. solution of tert-butyl (6-(hydroxymethyl)tetrahydro-2H-pyran-3-yl)carbamate (Intermediate 34D) (1.10 g, 4.76 mmol) in DCM (10 mL), acetonitrile (10 mL), and water (15 mL), was added sodium periodate (4.07 g, 19.0 mmol) and ruthenium(III) chloride (99 mg, 0.48 mmol). The mixture was vigorously stirred for 3 h, then diluted with EtOAc (50 mL) and filtered to remove solids. To the filtrate was added 10 mL of MeOH, and the mixture was filtered to remove solids. To the filtrate was added 20 mL of 10% aqueous NaHSO$_3$ solution which resulted in decolorization. The pH was adjusted to ca. 2 with addition of 20% aqueous NaHSO$_4$ and the layers were separated. The aqueous layer was extracted with EtOAc (3×) and the combined organics were dried over MgSO$_4$ and concentrated to give the title compound as a yellow foam (1.21 g, quantitative yield), which was used without further purification. LC-MS (ES-MS) M−H=244.

F. Racemic Methyl 5-((tert-butoxycarbonyl)amino)tetrahydro-2H-pyran-2-carboxylate

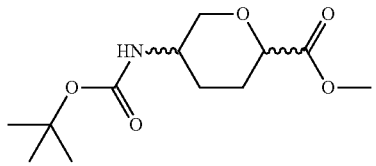 [SMILES: COC(=O)C1CCC(NC(=O)OC(C)(C)C)CO1]

A solution of diazomethane (900 mg, 21.4 mmol) in DCM (generated from N-methyl-N-nitrosourea (2.5 g) added to 30% aqueous NaOH (50 mL) and DCM (40 mL) on ice) was added slowly to a 0° C. solution of 5-((tert-butoxycarbonyl)amino)tetrahydro-2H-pyran-2-carboxylic acid (Intermediate 34E) (1.05 g, 4.28 mmol) in DCM (50 mL), and the reaction was stirred at 0° C. for 30 minutes. The bath was removed and the mixture flushed well with N$_2$ to remove excess diazomethane. To this was added CH$_3$CO$_2$H (2 drops) with stirring (to quench any remaining diazomethane), and the solution was washed with saturated NaHCO$_3$. The mixture was dried over Na$_2$SO$_4$, filtered, and concentrated. The residue was purified by silica gel chromatography (0-40% EtOAc-hexanes gradient) to afford the title compound as a white waxy solid (882 mg, 79% yield). $^1$H NMR (400 MHz, CDCl$_3$) δ 1.42 (s, 9H), 1.71-1.82 (m, 1H), 2.00-2.17 (m, 2H), 3.13 (br s, 1H), 3.66 (dd, J=12, 2 Hz, 1H), 3.76 (s, 3H), 3.86-4.04 (m, 1H), 4.17 (dd, J=11, 3 Hz, 1H), 4.35 (br s, 1H).

G. Racemic Methyl 5-aminotetrahydro-2H-pyran-2-carboxylate hydrochloride

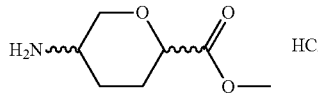

To methyl 5-((tert-butoxycarbonyl)amino)tetrahydro-2H-pyran-2-carboxylate (Intermediate 34F) (880 mg, 3.39 mmol) was added 1,4-dioxane (25 mL), followed by 4 M HCl in dioxane (8.48 mL, 33.9 mmol). The mixture was stirred at ROOM TEMPERATURE overnight. The reaction was concentrated to give the title compound as a white solid (670 mg, 101% yield). LC-MS (ES-MS) M+H=160.

H. Racemic (trans)-Methyl 5-(dibenzylamino)tetrahydro-2H-pyran-2-carboxylate

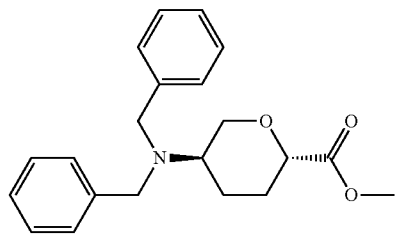 [SMILES: COC(=O)[C@@H]1CC[C@@H](N(Cc2ccccc2)Cc2ccccc2)CO1]

To a solution of methyl 5-aminotetrahydro-2H-pyran-2-carboxylate hydrochloride (Intermediate 34G) (670 mg, 3.42 mmol) in acetonitrile (25 mL), was added potassium carbonate (1.89 g, 13.7 mmol) and benzyl bromide (0.92 mL, 7.7 mmol), and the mixture was heated at 80° C. overnight. After cooling to room temperature, the mixture was filtered and concentrated. The residue was purified by silica gel chromatography (0-40% EtOAc-hexanes gradient) to afford the title compound as a clear oil (881 mg, 76% yield), which was assigned as the trans isomer by NMR. $^1$H NMR (400 MHz, CDCl$_3$) δ 1.54-1.75 (m, 2H), 2.05-2.17 (m, 2H), 2.83 (tt, J=11, 4 Hz, 1H), 3.42 (t, J=11 Hz, 1H), 3.58-3.74 (m, 7H), 3.86 (dd, J=12, 2 Hz, 1H), 4.09-4.17 (m, 1H), 7.11-7.48 (m, 10H); LC-MS (ES-MS) M+H=340.

I. Racemic 2-((trans)-5-(Dibenzylamino)tetrahydro-2H-pyran-2-yl)propan-2-ol

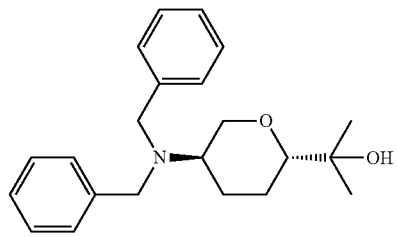 [SMILES: CC(C)(O)[C@@H]1CC[C@@H](N(Cc2ccccc2)Cc2ccccc2)CO1]

To a solution of (trans)-methyl 5-(dibenzylamino)tetrahydro-2H-pyran-2-carboxylate (Intermediate 34H) (535 mg, 1.58 mmol) in THF (18 mL) at 0° C. was added methylmagnesium bromide (4.20 mL, 12.6 mmol, 3 M in THF) dropwise. The mixture was allowed to warm to room temperature overnight. The mixture was then cooled to 0° C. and quenched by the slow addition of 1 M NH$_4$Cl (25 mL). The mixture was extracted with EtOAc (2×), and the combined organics were dried over Na$_2$SO$_4$, filtered, and concentrated. The residue was purified by silica gel chromatography (0-45%, EtOAc-hexanes gradient) to afford the title compound as a clear oil (268 mg, 50% yield). $^1$H NMR (400 MHz, CDCl$_3$) δ 1.07 (s, 3H), 1.13 (s, 3H), 1.22-1.38 (m, 1H), 1.58 (dd, J=12, 4 Hz, 1H), 1.71 (d, J=13 Hz, 1H), 2.03-2.12 (m, 1H), 2.39 (s, 1H), 2.72 (tt, J=11, 4 Hz, 1H), 2.99 (dd, J=11, 2 Hz, 1H), 3.40 (t, J=11 Hz, 1H), 3.58-3.73 (m, 4H), 3.99-4.09 (m, 1H), 7.06-7.50 (m, 10H); LC-MS (ES-MS) M+H=340.

J. Racemic 2-((trans)-5-Aminotetrahydro-2H-pyran-2-yl)propan-2-ol

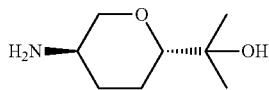

To 2-((trans)-5-(dibenzylamino)tetrahydro-2H-pyran-2-yl)propan-2-ol (Intermediate 34I) (770 mg, 2.01 mmol) and EtOH (15 mL) under a N$_2$ atmosphere was added 20% palladium hydroxide (141 mg, 0.201 mmol), and the vessel was evacuated and flushed with N$_2$ and then stirred under 40 psi H$_2$ for 24 h. The vessel was evacuated and flushed with N$_2$ and the mixture filtered through a pad of Celite® and rinsed with EtOH and EtOAc. The filtrate was concentrated to give the title compound as a clear oil (310 mg, 97% yield). $^1$H NMR (400 MHz, CD$_3$OD) δ 1.16 (s, 3H), 1.18 (s, 3H), 1.26-1.38 (m, 1H), 1.39-1.52 (m, 1H), 1.75-1.84 (m, 1H), 2.09 (dt, J=12, 3 Hz, 1H), 2.69-2.76 (m, 1H), 3.01-3.13 (m, 2H), 3.95-4.04 (m, 1H); LC-MS (ES-MS) M+H=160.

Intermediate 35: 2-(3-Aminoazetidin-1-yl)isonicotinonitrile

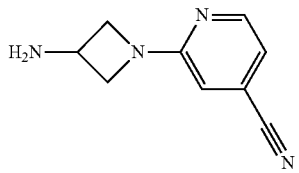 [SMILES: N#Cc1ccnc(N2CC(N)C2)c1]

A. Benzyl (1-(4-cyanopyridin-2-yl)azetidin-3-yl)carbamate

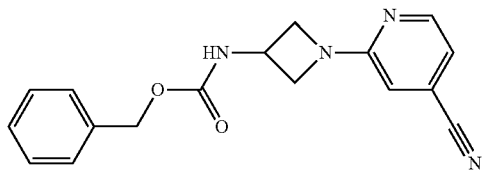 [SMILES: N#Cc1ccnc(N2CC(NC(=O)OCc3ccccc3)C2)c1]

To benzyl azetidin-3-ylcarbamate hydrochloride (400 mg, 1.65 mmol) in acetonitrile (10 mL), 2-chloroisonicotinonitrile (274 mg, 1.98 mmol) and N,N-diisopropylethylamine (0.72 mL, 4.1 mmol) were added. The mixture was heated in a microwave at 135° C. for 2.5 h. The reaction was concentrated, and the residue was purified on silica gel eluting with a 20%-90% EtOAc in hexanes gradient. The appropriate fractions were combined, evaporated under reduced pressure and placed in vacuo to give the title compound as a white solid (185 mg, 34%). $^1$H NMR (400 MHz, CD$_3$OD) δ 3.91 (dd, J=8, 6 Hz, 2H), 4.34 (t, J=8 Hz, 2H), 4.56-4.64 (m, 1H), 5.09 (s, 2H), 6.72 (s, 1H), 6.84 (d, J=5 Hz, 1H), 7.17-7.45 (m, 5H), 8.17 (d, J=5 Hz, 1H); LC-MS (LC-ES) M+H=309.

B. 2-(3-Aminoazetidin-1-yl)isonicotinonitrile

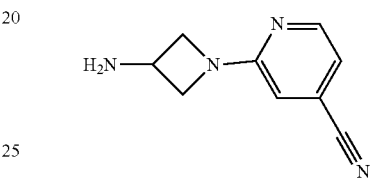

Benzyl (1-(4-cyanopyridin-2-yl)azetidin-3-yl)carbamate (Intermediate 35A) (185 mg, 0.60 mmol) was dissolved in MeOH (5 mL) and EtOAc (5 mL), and 10 wt % palladium on carbon (128 mg, 0.12 mmol) was added under nitrogen. The reaction was purged with hydrogen via balloon (3×) before stirring under a hydrogen atmosphere at room temperature overnight. The reaction was filtered through a pad of Celite® and rinsed with methanol. The filtrate was concentrated and the residue was purified on silica gel eluting with a 20%-90% EtOAc in hexanes gradient. The appropriate fractions were combined, evaporated under reduced pressure and placed in vacuo to give the title compound as a white solid (55 mg, 53%). $^1$H NMR (CDCl$_3$) δ 3.61-3.78 (m, 2H), 3.92-4.08 (m, 1H), 4.20-4.41 (m, 2H), 6.44 (s, 1H), 6.72 (d, J=5 Hz, 1H), 8.22 (d, J=5 Hz, 1H); LC-MS (LC-ES) M+H=175.

Intermediate 36: 4-Nitrophenyl ((trans)-6-(2-hydroxypropan-2-yl)tetrahydro-2H-pyran-3-yl)carbamate

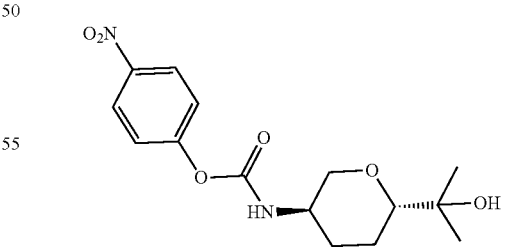

To 4-nitrophenyl chloroformate (122 mg, 0.604 mmol) in acetonitrile (2 mL) at 0° C. was slowly added 2-((trans)-5-aminotetrahydro-2H-pyran-2-yl)propan-2-ol (Intermediate 34) (74 mg, 0.47 mmol) in acetonitrile (2 mL). After 30 min, sodium bicarbonate (78 mg, 0.93 mmol) was added, and the mixture was allowed to warm to room temperature. After 1 h, the solvent was removed in vacuo, and the residue was purified on silica gel, eluting with a 0%-60% EtOAc in hexanes gradient to give the title compound as a white solid (78 mg, 52%). $^1$H NMR (400 MHz, CDCl$_3$) δ 1.19 (s, 3H), 1.23 (s, 3H), 1.38-1.66 (m, 2H), 1.81 (d, J=12 Hz, 1H), 2.27 (d, J=12 Hz, 1H), 2.42 (br s, 1H), 3.03-3.26 (m, 2H), 3.64-3.87 (m, 1H), 4.26 (dd, J=11, 3 Hz, 1H), 4.89 (d, J=8 Hz, 1H), 7.34 (d, J=9 Hz, 2H), 8.27 (d, J=9 Hz, 2H); LC-MS (LC-ES) M+H=325.

Intermediate 37: 1-(Pyridin-2-yl)azetidin-3-amine dihydrochloride

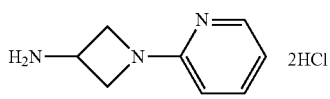

A. tert-Butyl (1-(pyridin-2-yl)azetidin-3-yl)carbamate

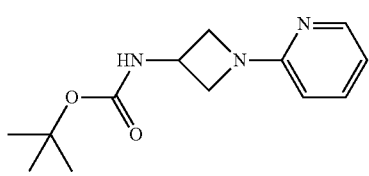 [SMILES: CC(C)(C)OC(=O)NC1CN(c2ccccn2)C1]

To tert-butyl azetidin-3-ylcarbamate hydrochloride (500 mg, 2.40 mmol) in DMF (3 mL) was added N,N-diisopropylethylamine (0.84 mL, 4.8 mmol) followed by 2-fluoropyridine (233 mg, 2.40 mmol). The mixture was heated at 85° C. for overnight, cooled, diluted with EtOAc, washed with water, and the aqueous extracted with EtOAc. The combined organic layers were washed with water (2×) and brine, dried over MgSO$_4$, filtered and concentrated. The residue was purified on silica gel eluting with a 20%-70% EtOAc in hexanes gradient. The appropriate fractions were combined, evaporated under reduced pressure and placed in vacuo to give the title compound as a white solid (90 mg, 15%). $^1$H NMR (400 MHz, CDCl$_3$) δ 1.49 (s, 9H), 3.82 (dd, J=8, 5 Hz, 2H), 4.38 (t, J=8 Hz, 2H), 4.66 (s br, 1H), 6.33 (d, J=8 Hz, 1H), 6.61-6.70 (m, 1H), 7.42-7.53 (m, 1H), 8.18 (d, J=4 Hz, 1H); LC-MS (LC-ES) M+H=250.

B. 1-(Pyridin-2-yl)azetidin-3-amine dihydrochloride

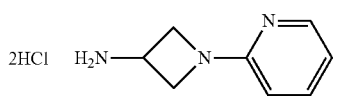

To tert-butyl (1-(pyridin-2-yl)azetidin-3-yl)carbamate (Intermediate 37A) (90 mg, 0.36 mmol) in DCM (1 mL), 4 M HCl in dioxane (2 mL, 8 mmol) was added. The mixture was stirred at room temperature for 2 h and the solvent was removed in vacuo to give the title compound as a white solid (84 mg, quantitative). $^1$H NMR (400 MHz, CD$_3$OD) δ 4.38-4.50 (m, 3H), 4.69-4.78 (m, 2H), 7.01 (d, J=9 Hz, 1H), 7.03-7.09 (m, 1H), 8.00 (d, J=6 Hz, 1H), 8.05-8.12 (m, 1H); LC-MS (LC-ES) M+H=150.

Intermediate 38: 2-(2-Aminothiazol-4-yl)propan-2-ol trifluoroacetic acid salt

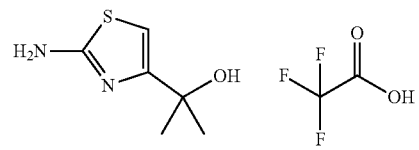

A. tert-Butyl (4-(2-hydroxypropan-2-yl)thiazol-2-yl) carbamate

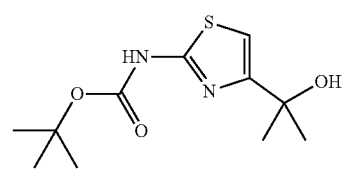 [SMILES: CC(C)(C)OC(=O)Nc1nc(C(C)(C)O)cs1]

To a solution of methyl 2-((tert-butoxycarbonyl)amino) thiazole-4-carboxylate (0.50 g, 1.9 mmol) in THF (13 mL) at 0° C. was added methylmagnesium bromide (2.58 mL, 7.7 mmol, 3 M in THF) dropwise. The mixture was allowed to warm to room temperature and stirred 36 h. The mixture was quenched with water, extracted with EtOAc (2×), and the combined organics were dried over MgSO$_4$, filtered, and concentrated. The residue was purified by silica gel chromatography (30-75% EtOAc-hexanes gradient) to afford the title compound as a white solid (360 mg, 72% yield). $^1$H NMR (400 MHz, CD$_3$OD) δ 1.50 (s, 6H), 1.54 (s, 9H), 6.78 (s, 1H); LC-MS (ES-MS) M+H=259.

B. 2-(2-Aminothiazol-4-yl)propan-2-ol trifluoroacetic acid salt

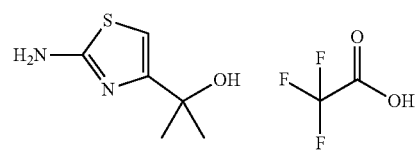

To a stirred solution of tert-butyl (4-(2-hydroxypropan-2-yl)thiazol-2-yl)carbamate (Intermediate 38A) (700 mg, 2.71 mmol) in MeOH (2.5 mL) was added trifluoroacetic acid (2.5 mL, 32.4 mmol). The resulting mixture was stirred at room temperature for 1 h. Removing the solvent in vacuo afforded the title compound (720 mg, 98%). $^1$H NMR (400 MHz, CD$_3$OD) δ 1.53 (s, 6H), 3.98 (s, 1H), 6.60 (s, 1H); LC-MS (LC-ES) M+H—H$_2$O=141.

Intermediate 39: (trans)-4-(2-Methoxyethoxy)cyclohexanamine

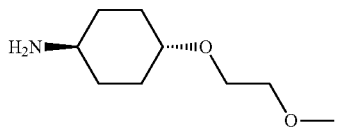

A. trans-4-(Dibenzylamino)cyclohexanol

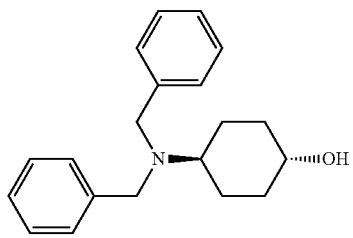 [SMILES: O[C@H]1CC[C@H](N(Cc2ccccc2)Cc2ccccc2)CC1]

Benzyl bromide (60 g, 350 mmol) was added to (trans)-4-aminocyclohexanol hydrochloride (20 g, 174 mmol) and sodium bicarbonate (40 g, 476 mmol) in EtOH (400 mL) at room temperature. The reaction was heated to reflux for 36 h, filtered and concentrated to give a solid. The solid was taken up in hexanes. The reaction was stirred overnight, filtered and air dried to afford the title compound (33.2 g, 65%). $^1$H NMR (CDCl$_3$) δ 1.14-1.28 (m, 2H), 1.30 (d, J=5 Hz, 1H), 1.38-1.52 (m, 2H), 1.91 (d, J=12 Hz, 2H), 2.00 (br s, 1H), 2.53 (tt, J=12, 3 Hz, 1H), 3.50-3.59 (m, 1H), 3.62 (s, 4H), 7.18-7.25 (m, 2H), 7.27-7.32 (m, 4H), 7.33-7.38 (m, 4H).

B. (trans)-N,N-Dibenzyl-4-(2-methoxyethoxy)cyclohexanamine hydrochloride

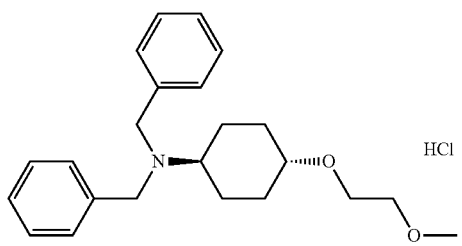 [SMILES: COCCO[C@H]1CC[C@H](N(Cc2ccccc2)Cc2ccccc2)CC1 ; Cl]

A saturated solution of KOH (175 g) and water (100 g) was prepared and allowed to cool to ambient temperature. A 250 mL three neck round bottom flask equipped with overhead stirrer was charged with (trans)-4-(dibenzylamino)cyclohexanol (Intermediate 39A) (10 g, 33.9 mmol), 1,4-dioxane (10 mL) and 1-bromo-2-methoxyethane (10 g, 71.9 mmol). To the stirred solution was added Aliquot 336 (1 g, ca. 2.25 mmol) followed by a portion of the saturated KOH solution (70 mL). The reaction mixture was stirred at ca. 42° C. internal temp under N$_2$ atmosphere for 4 h and 40 min at which point HPLC showed 77% conversion. Additional solid KOH (5 g) and 1-bromo-2-methoxyethane (10 g) were added, and stirring was continued overnight. The reaction mixture was cooled to ambient temp, and TBME (100 mL), water (50 mL) and brine (50 mL) were added. The aqueous phase was extracted with TBME (75 mL) and the combined TBME layers were washed with brine, dried over MgSO$_4$, filtered and the TBME filtrate was stirred at room temperature, and 4 N HCl in dioxane (10 mL) was added dropwise with rapid stirring. The slurry was stirred at room temperature for 20 min and the solids were collected by filtration washing with TBME to give the title compound as an off-white solid (13.1 g, 94%). $^1$H NMR (400 MHz, CD$_3$SOCD$_3$) δ 0.89-1.02 (m, 2H), 1.63-1.75 (m, 2H), 2.07 (d, J=11 Hz, 2H), 2.27 (d, J=11 Hz, 2H), 2.48-2.53 (m, 1H), 2.96-3.06 (m, 1H), 3.22 (s, 3H), 3.35-3.41 (m, 2H), 3.47-3.51 (m, 2H), 4.12 (dd, J=13, 5 Hz, 2H), 4.43 (dd, J=13, 5 Hz, 2H), 7.37-7.44 (m, 6H), 7.61-7.68 (m, 4H), 10.97 (br s, 1H).

C. (trans)-4-(2-Methoxyethoxy)cyclohexanamine

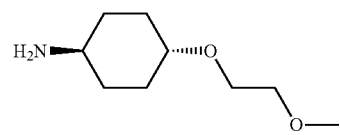

(trans)-N,N-Dibenzyl-4-(2-methoxyethoxy)cyclohexanamine hydrochloride (Intermediate 39B) (19.7 g, 50.5 mmol) in water (150 mL) was stirred until near solution was achieved. TBME (150 mL) was added, then 1 N NaOH (50 mL) was added slowly over 5 minutes (internal temp stayed steady at ambient without external cooling). The layers were separated, and the aqueous phase was extracted with TBME (30 mL). The combined TBME layers were washed with brine, dried over MgSO$_4$, filtered and concentrated chasing with EtOH. The resulting light amber oil was dissolved in EtOH (150 mL), and purged with N$_2$. Pd(OH)$_2$ on activated charcoal (1.6 g, 10-20% Pd; ~50% water as stabilizer) was added, and the stirred mixture was evacuated and purged with N$_2$ and then with Hz, and stirred under H$_2$ atmosphere at room temperature, monitoring uptake with a Buchi Pressflow apparatus. After 3 h of rapid stirring, the reaction appeared to be slowing down, so the reaction vessel was evacuated and purged with N$_2$, and charged with an additional amount of Pd(OH)$_2$ (1.62 g), and hydrogenolysis was continued for an additional 80 min. The vessel was evacuated and purged with N$_2$, and the reaction mixture was filtered through a millipore filter pad containing Celite®. The filtrate was concentrated to afford the title compound as a nearly colorless oil (7.6 g, 87%). $^1$H NMR (400 MHz, CD$_3$SOCD$_3$) δ 0.94-1.18 (m, 4H), 1.68-1.76 (m, 2H), 1.85-1.93 (m, 2H), 2.46-2.55 (m, 1H), 3.11-3.20 (m, 1H), 3.23 (s, 3H), 3.37-3.42 (m, 2H), 3.47-3.51 (m, 2H).

Intermediate 40: (trans)-N-((trans)-3-Aminocyclobutyl)-3-(benzo[d]thiazol-4-yloxy)cyclobutanecarboxamide hydrochloride

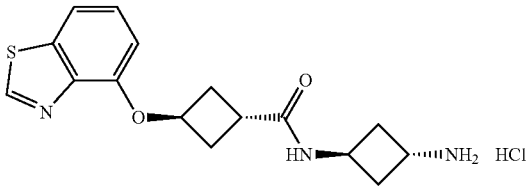 [SMILES: N[C@H]1C[C@H](NC(=O)[C@H]2C[C@H](Oc3cccc4scnc34)C2)C1 ; Cl]

To tert-butyl ((trans)-3-((trans)-3-(benzo[d]thiazol-4-yloxy)cyclobutanecarboxamido)cyclobutyl)carbamate (Example 66) (185 mg, 0.44 mmol) in DCM (2 mL) was added 4 N HCl in dioxane (4 mL, 16 mmol). The mixture was stirred at room temperature for 30 min, and the solvent was removed in vacuo to give the title compound as a white solid (194 mg, quantitative). $^1$H NMR (400 MHz, CD$_3$OD) δ 2.41-2.59 (m, 6H), 2.72-2.83 (m, 2H), 3.14-3.27 (m, 1H), 3.79-4.00 (m, 1H), 4.40-4.64 (m, 1H), 5.15-5.24 (m, 1H), 7.00-7.04 (m, 1H), 7.53-7.59 (m, 1H), 7.72-7.77 (m, 1H), 9.70 (s, 1H); LC-MS (LC-ES) M+H=318.

Intermediate 41: 1-(Pyridin-2-yl)azetidin-3-amine

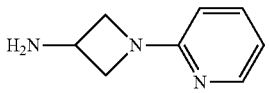 [SMILES: NC1CN(c2ccccn2)C1]

A. Benzyl (1-(pyridin-2-yl)azetidin-3-yl)carbamate

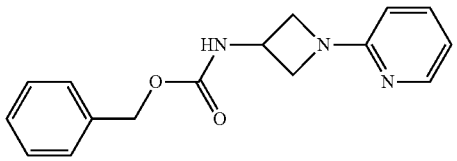 [SMILES: O=C(NC1CN(c2ccccn2)C1)OCc1ccccc1]

To a reaction vial with benzyl azetidin-3-ylcarbamate hydrochloride (800 mg, 3.30 mmol) in DMF (3 mL) was added 2-fluoropyrimidine (320 mg, 3.30 mmol) and N,N-diisopropylethylamine (1.15 mL, 6.59 mmol). The mixture was heated at 85° C. overnight, cooled, diluted with EtOAc and washed (2×) with water. The aqueous layers were extracted with EtOAc, the combined organic layers washed with water (3×) and brine, dried over MgSO$_4$, filtered and concentrated. The residue was purified on silica gel eluting with a 20%-70% EtOAc-hexanes gradient. The appropriate fractions were combined, evaporated under reduced pressure and placed in vacuo to give the title compound (160 mg, 17%) as a white solid. $^1$H NMR (400 MHz, CDCl$_3$) δ 3.81-3.89 (m, 2H), 4.31-4.41 (m, 2H), 4.69 (br s, 1H), 5.13 (s, 2H), 5.24 (br s, 1H), 6.31 (d, J=8 Hz, 1H), 6.59-6.70 (m, 1H), 7.30-7.42 (m, 5H), 7.44-7.55 (m, 1H), 8.15 (d, J=4 Hz, 1H); LC-MS (LC-ES) M+H=284.

B. 1-(Pyridin-2-yl)azetidin-3-amine

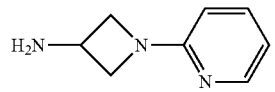 [SMILES: NC1CN(c2ccccn2)C1]

Palladium on carbon (135 mg, 0.13 mmol) was added to benzyl (1-(pyridin-2-yl)azetidin-3-yl)carbamate (Intermediate 41A) (0.180 g, 0.64 mmol) in EtOH (10 mL) at 25° C. under a nitrogen atmosphere. The reaction vessel was fitted with a hydrogen balloon, and the vessel was repeatedly evacuated and purged with hydrogen, then stirred overnight under a hydrogen atmosphere. The vessel was repeatedly evacuated and purged with nitrogen, filtered through Celite®, and concentrated to give the title compound (89 mg, 94% yield). $^1$H NMR (400 MHz, CDCl$_3$) δ 3.59-3.74 (m, 2H), 3.90-4.06 (m, 1H), 4.16-4.40 (m, 2H), 6.24-6.32 (m, 1H), 6.55-6.64 (m, 1H), 7.41-7.49 (m, 1H), 8.15 (d, J=4 Hz, 1H); LC-MS (LC-ES) M+H=150.

Intermediate 42: Racemic (trans)-3-(Benzo[d]thiazol-4-yloxy)-N-(pyrrolidin-3-yl)cyclobutanecarboxamide hydrochloride

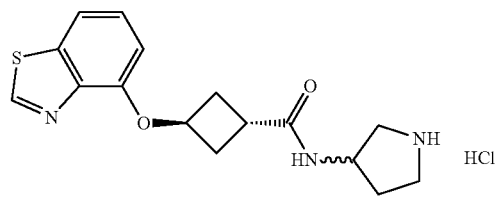 [SMILES: O=C(NC1CCNC1)[C@H]1C[C@H](Oc2cccc3scnc23)C1 ; Cl]

A. Racemic 3-((trans)-3-(Benzo[d]thiazol-4-yloxy)cyclobutanecarboxamido)pyrrolidine-1-carboxylate

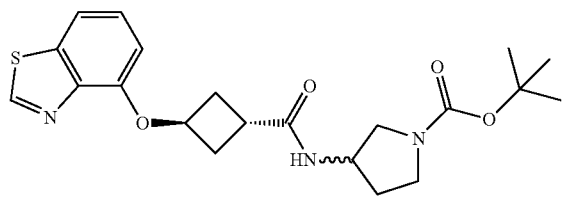 [SMILES: CC(C)(C)OC(=O)N1CCC(NC(=O)[C@H]2C[C@H](Oc3cccc4scnc34)C2)C1]

(trans)-3-(Benzo[d]thiazol-4-yloxy)cyclobutanecarboxylic acid (Intermediate 25) (350 mg, 0.80 mmol), was dissolved in DMF (8 mL) followed by the addition of N,N-diisopropylethylamine (0.44 mL, 2.5 mmol) and HATU (578 mg, 1.52 mmol). The reaction was stirred at room temperature for ca. 5 min, and tert-butyl 3-aminoazetidine-1-carboxylate (262 mg, 1.52 mmol) was added. After 2 h, the reaction was quenched with water and MeOH, and loaded onto a semi-prep HPLC (NH$_4$OH as modifier) to afford the title compound as a tan solid (71 mg, 21% yield). LC-MS (LC-ES) peak at T=0.84 min; M+H=418.

B. Racemic (trans)-3-(Benzo[d]thiazol-4-yloxy)-N-(pyrrolidin-3-yl)cyclobutanecarboxamide hydrochloride

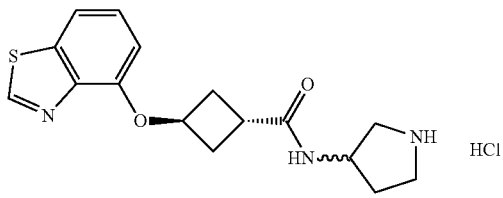 [SMILES: O=C(NC1CCNC1)[C@H]1C[C@H](Oc2cccc3scnc23)C1 ; Cl]

To 3-((trans)-3-(benzo[d]thiazol-4-yloxy)cyclobutanecarboxamido)pyrrolidine-1-carboxylate (Intermediate 42A) (76 mg, 0.18 mmol) in DCM (1 mL) was added 4 N HCl in dioxane (2 mL, 8 mmol). The mixture was stirred at room temperature for 2 h, and the solvent was removed in vacuo to give the title compound as a pale yellow solid (70 mg, quantitative). $^1$H NMR (400 MHz, CD$_3$OD) δ 2.31-2.42 (m, 1H), 2.55-2.70 (m, 1H), 2.74-2.89 (m, 2H), 3.04-3.11 (m, 2H), 3.45-3.59 (m, 2H), 3.59-3.71 (m, 1H), 3.73-3.88 (m, 2H), 3.90-3.97 (m, 1H), 4.74 (br s, 1H), 5.47 (t, J=6 Hz, 1H), 7.33 (d, J=8 Hz, 1H), 7.80-7.88 (m, 1H), 8.04 (d, J=8 Hz, 1H), 10.16 (br s, 1H); LC-MS (LC-ES) M+H=318.

Intermediate 43: Racemic 2-(6-Aminospiro[3.3]heptan-2-yl)propan-2-ol

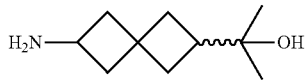

A. Methyl 3-methylenecyclobutanecarboxylate

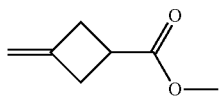

To a DMF (350 mL) mixture of 3-methylenecyclobutanecarboxylic acid (11.6 g, 103 mmol) and cesium carbonate (70.8 g, 217 mmol) was added iodomethane (17.6 g, 124 mmol). After stirring overnight, the reaction was partitioned between Et$_2$O and water, the organic layer separated and the aqueous layer extracted with Et$_2$O (3×). The combined organic layers were washed with water, dried over MgSO$_4$, filtered and concentrated to give the title compound (10.9 g, 84%) as a yellow oil. $^1$H NMR (400 MHz, CDCl$_3$) δ 2.85-2.92 (m, 2H), 2.92-3.04 (m, 2H), 3.09-3.17 (m, 1H), 3.70 (s, 3H), 4.77-4.82 (m, 2H).

B. Methyl 6-oxospiro[3.3]heptane-2-carboxylate

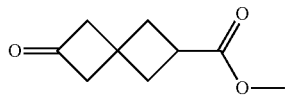

To a methyl acetate (45 mL) solution of methyl 3-methylenecyclobutanecarboxylate (Intermediate 43A) was added copper powder (2.77 g, 43.6 mmol) and zinc powder (5.70 g, 87 mmol). To this mixture was added a methyl acetate (45 mL) solution of 2,2,2-trichloroacetyl chloride (4.86 mL, 43.6 mmol) and phosphorus oxychloride (0.37 mL, 4.0 mmol) dropwise over 2 h. After 3 h, the reaction was cooled to 0° C., and additional zinc powder (5.70 g, 87 mmol) was added, followed by acetic acid (22.7 mL, 400 mmol) dropwise at a rate keeping the temperature below 7° C. The reaction was allowed to slowly warm to room temperature and after stirring overnight was filtered through Celite®, rinsing with EtOAc. The filtrate was carefully washed (warning: gas evolution) with saturated aqueous NaHCO$_3$ (2×200 mL), and the aqueous layers extracted with 1:1 EtOAc:Et$_2$O (2×100 mL). The combined organic layers were dried over MgSO$_4$, filtered and concentrated, and the residue purified on silica gel eluting with a 0%-50% EtOAc-hexanes gradient. The appropriate fractions were combined, evaporated under reduced pressure and placed in vacuo to give the title compound (4.10 g, 61%) as a yellow oil. $^1$H NMR (400 MHz, CDCl$_3$) δ 2.38-2.48 (m, 2H), 2.50-2.61 (m, 2H), 3.00-3.09 (m, 2H), 3.09-3.22 (m, 3H), 3.68 (s, 3H).

C. Racemic Methyl 6-(dibenzylamino)spiro[3.3]heptane-2-carboxylate

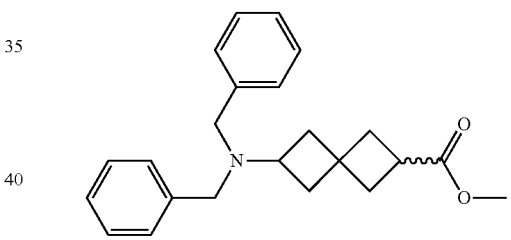

To a THF (200 mL) solution of methyl 6-oxospiro[3.3]heptane-2-carboxylate (Intermediate 43B) (3.89 g, 23.1 mmol) was added dibenzylamine (4.67 mL, 24.29 mmol). After 10 min, the reaction was cooled to 0° C., and sodium triacetoxyborohydride (7.35 g, 34.7 mmol) was added as a solid, portionwise, over 10 minutes followed by 4-5 drops of glacial acetic acid. The reaction was allowed to warm to room temperature. After 4 h, the reaction mixture was diluted with water (20 mL), extracted with Et$_2$O (200 mL) and washed with saturated sodium bicarbonate (100 mL). The aqueous layer was extracted with Et$_2$O (1×100 mL) and the organic layers were combined, dried over MgSO$_4$, filtered and concentrated, and the residue was purified on silica gel eluting with a 0%-50% EtOAc-hexanes gradient. The appropriate fractions were combined, evaporated under reduced pressure and placed in vacuo to give the title compound (5.00 g, 62%) as a white solid. $^1$H NMR (400 MHz, CDCl$_3$) δ 1.74-1.92 (m, 2H), 1.97-2.34 (m, 6H), 2.90-3.09 (m, 2H), 3.35-3.51 (m, 4H), 3.64 (s, 3H), 7.09-7.44 (m, 10H); LC-MS (LC-ES) M+H=350.

D. Racemic 2-(6-(Dibenzylamino)spiro[3.3]heptan-2-yl)propan-2-ol

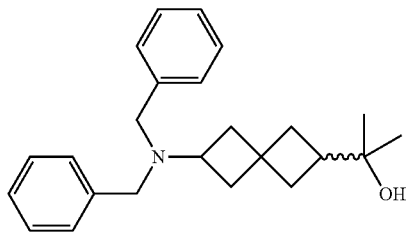 [SMILES: CC(C)(O)C1CC2(CC(N(Cc3ccccc3)Cc3ccccc3)C2)C1]

To methyl 6-(dibenzylamino)spiro[3.3]heptane-2-carboxylate (Intermediate 43C) (5.00 g, 14.3 mmol) in Et$_2$O (200 mL) at 0° C. was added a 3.0 M solution of methylmagnesium chloride in diethyl ether (15.7 mL, 47.2 mmol). After 30 minutes, the mixture was warmed to room temperature for 70 min, cooled to 0° C., quenched with 3 N HCl and partitioned between saturated aqueous NaHCO$_3$ (150 mL) and Et$_2$O (100 mL). The aqueous layer was separated and extracted with ethyl acetate 100 mL). The organic layers were combined, dried over MgSO$_4$, filtered and concentrated, and the residue was purified on silica gel eluting with a 0%-100% EtOAc-hexanes gradient. The appropriate fractions were combined, evaporated under reduced pressure and placed in vacuo to give the title compound (4.65 g, 93%) as a white solid. $^1$H NMR (CDCl$_3$) δ 1.06 (s, 6H), 1.66-1.97 (m, 7H), 2.05-2.31 (m, 2H), 2.91-3.06 (m, 1H), 3.45 (s, 4H), 7.09-7.41 (m, 10H); LC-MS (LC-ES) M+H=350.

E. Racemic 2-(6-Aminospiro[3.3]heptan-2-yl)propan-2-ol

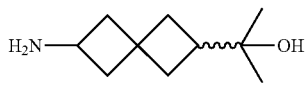

To 2-(6-(dibenzylamino)spiro[3.3]heptan-2-yl)propan-2-ol (Intermediate 43D) (4.10 g, 11.7 mmol) and EtOH (100 mL) under an N$_2$ atmosphere was added 20% palladium hydroxide (329 mg, 2.35 mmol), and the vessel was evacuated and flushed with N$_2$ and then stirred under 35 psi H2 overnight. The vessel was evacuated and flushed with N$_2$ and the mixture filtered through a pad of Celite® and rinsed with MeOH. The filtrate was concentrated to give the title compound as a white solid (2.18 g, quantitative). $^1$H NMR (400 MHz, CDCl$_3$) δ 1.07 (d, J=1 Hz, 6H), 1.39 (s, 3H), 1.52-1.61 (m, 1H), 1.63-1.69 (m, 1H), 1.74-1.97 (m, 4H), 2.11-2.27 (m, 2H), 2.35-2.48 (m, 1H), 3.30 (quin, J=8 Hz, 1H).

Intermediate 44: Racemic 4-Nitrophenyl (1-(1,1,1-trifluoropropan-2-yl)piperidin-4-yl)carbamate

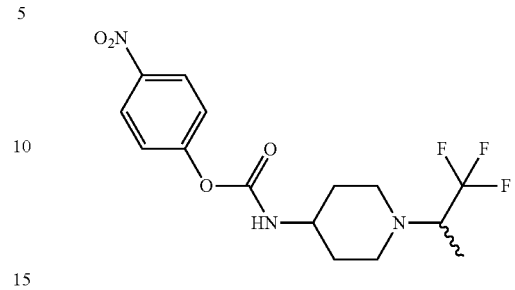

A. Racemic tert-Butyl (1-(1,1,1-trifluoropropan-2-yl)piperidin-4-yl)carbamate

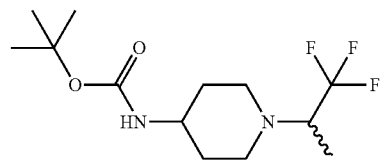 [SMILES: CC(N1CCC(NC(=O)OC(C)(C)C)CC1)C(F)(F)F]

1,1,1-Trifluoropropan-2-yl trifluoromethanesulfonate (0.472 g, 1.92 mmol) was suspended in 1,4-dioxane (3.0 ml), then tert-butyl piperidin-4-ylcarbamate (0.30 g, 1.5 mmol) and N,N-diisopropylethylamine (0.55 ml, 3.2 mmol) were added. The reaction was heated to 90° C. for 24 hours, cooled, diluted with EtOAc and washed with saturated aqueous sodium bicarbonate and brine. The organic layer was dried over sodium sulfate, filtered and concentrated. The residue was purified on silica gel eluting with 20 to 50% EtOAc in heptanes to afford the title compound (243 mg, 55% yield). $^1$H NMR (400 MHz, CD$_3$OD) δ 1.23 (d, J=7 Hz, 3H), 1.36-1.52 (m, 11H), 1.83 (t, J=8 Hz, 2H), 2.50 (t, J=11 Hz, 1H), 2.61 (t, J=11 Hz, 1H), 2.92 (t, J=11 Hz, 2H), 3.26-3.36 (m, 2H); LC-MS (LC-ES) M+H=297.

B. Racemic 1-(1,1,1-Trifluoropropan-2-yl)piperidin-4-amine dihydrochloride

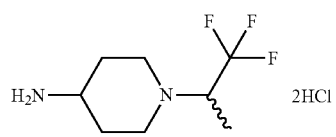

To tert-butyl (1-(1,1,1-trifluoropropan-2-yl)piperidin-4-yl)carbamate (Intermediate 44A) (240 mg, 0.81 mmol) in 1,4-dioxane (1 mL) was added 4 N HCl in dioxane (1 mL, 4 mmol). The mixture was stirred at room temperature for 3 h, and the solvent was removed in vacuo to give the title compound as a white solid (235 mg, quantitative). $^1$H NMR (400 MHz, CD$_3$SOCD$_3$) δ 1.22 (d, J=7 Hz, 3H), 1.29-1.42 (m, 2H), 1.51-1.67 (m, 2H), 1.87-1.96 (m, 2H), 2.94-3.10 (m, 2H) 3.34-3.49 (m, 1H), 3.57-3.75 (m, 1H); LC-MS (LC-ES) M+H=197.

C. Racemic 4-Nitrophenyl (1-(1,1,1-trifluoropropan-2-yl)piperidin-4-yl)carbamate

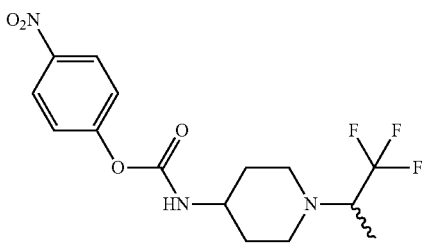 [SMILES: CC(N1CCC(NC(=O)Oc2ccc([N+](=O)[O-])cc2)CC1)C(F)(F)F]

To 4-nitrophenyl chloroformate (115 mg, 0.571 mmol) in DCM (1 mL) at 0° C. was slowly added 1-(1,1,1-trifluoropropan-2-yl)piperidin-4-amine dihydrochloride (Intermediate 44B) (100 mg, 0.372 mmol) and N,N-diisopropylethylamine (0.20 mL, 1.1 mmol) in DCM (2 mL). The reaction was allowed to slowly warm to room temperature overnight. The solvent was removed in vacuo, and the residue was purified on silica gel eluting with 5 to 50% EtOAc/Hex to afford the title compound (23 mg, 17% yield). $^1$H NMR (400 MHz, CD$_3$SOCD$_3$) δ 1.16 (d, J=7 Hz, 3H), 1.38-1.52 (m, 2H), 1.77-1.86 (m, 2H), 2.39-2.50 (m, 2H), 2.88 (t, J=13 Hz, 2H), 3.29-3.39 (m, 1H), 3.40-3.52 (m, 1H), 7.41 (d, J=9 Hz, 2H), 8.23-8.31 (m, 2H); LC-MS (LC-ES) M+H=362.

Intermediate 45: Benzyl 4-(((4-nitrophenoxy)carbonyl)amino)piperidine-1-carboxylate

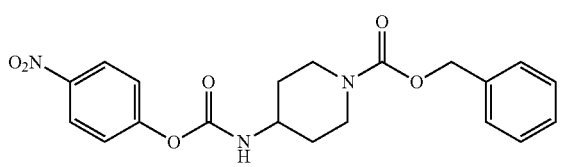 [SMILES: O=C(NC1CCN(C(=O)OCc2ccccc2)CC1)Oc1ccc([N+](=O)[O-])cc1]

To 4-nitrophenyl chloroformate (260 mg, 1.29 mmol) in DCM (2 mL) at 0° C. was slowly added benzyl 4-aminopiperidine-1-carboxylate (200 mg, 0.854 mmol) and N,N-diisopropylethylamine (0.15 mL, 0.86 mmol) in DCM (4 mL). The reaction was allowed to slowly warm to room temperature. After 5 h, the solvent was removed in vacuo, and the residue was purified on silica gel eluting with a 0% to 50% EtOAc in hexanes gradient to afford the title compound (307 mg, 90% yield) as a white solid. $^1$H NMR (400 MHz, CD$_3$SOCD$_3$) δ 1.33-1.46 (m, 2H) 1.82-1.92 (m, 2H) 2.99 (br s, 2H) 3.62 (br s, 1H) 3.91-4.01 (m, 2H) 5.09 (s, 2H) 7.28-7.47 (m, 6H) 8.12 (d, J=8 Hz, 1H) 8.24-8.31 (m, 2H); LC-MS (LC-ES) M+H=400.

Intermediate 46: 4-Nitrophenyl (1-(2,2,2-trifluoroethyl)piperidin-4-yl)carbamate

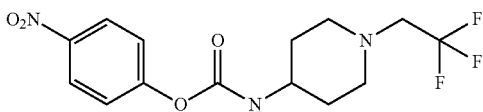

A. tert-Butyl (1-(2,2,2-trifluoroethyl)piperidin-4-yl)carbamate

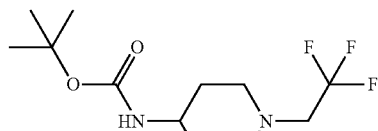

N,N-Diisopropylethylamine (0.64 mL, 3.7 mmol) was added to tert-butyl piperidin-4-ylcarbamate (368 mg, 1.84 mmol) in 1,4-dioxane (3.0 mL) at room temperature, followed by 2,2,2-trifluoroethyl trifluoromethanesulfonate (512 mg, 2.20 mmol), and the reaction was stirred at 75° C. for 7 days. The mixture was concentrated, and the residue was purified by silica gel chromatography, eluting with EtOAc:hexanes (1:4) to give the title compound (501 g, 92% yield). $^1$H NMR (400 MHz, CD$_3$SOCD$_3$) δ 1.36 (s, 9H), 1.37 (dq, J=12, 4 Hz, 2H), 1.64 (br d, J=11 Hz, 2H), 2.30 (dt, J=11, 2 Hz, 2H), 2.83 (br d, J=12 Hz, 2H), 3.09 (q, J=10 Hz, 2H), 3.12-3.26 (m, 1H), 6.76 (d, J=8 Hz, 1H); LC-MS (LC-ES) M+H=283.

B. 1-(2,2,2-Trifluoroethyl)piperidin-4-amine dihydrochloride

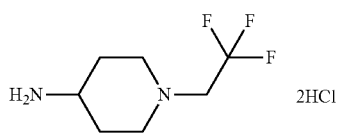 [SMILES: NC1CCN(CC(F)(F)F)CC1]

4.0 M Hydrochloric acid (4.44 mL, 17.8 mmol) in dioxane was added to tert-butyl (1-(2,2,2-trifluoroethyl)piperidin-4-yl)carbamate (Intermediate 46A) (0.501 g, 1.78 mmol) in MeOH (4.4 mL) at room temperature, and the reaction mixture was stirred for 17 h. The reaction mixture was concentrated to give the title compound (0.460 g, 97% yield). $^1$H NMR (400 MHz, CD$_3$SOCD$_3$) δ 1.56 (br q, J=11 Hz, 2H), 1.85 (br d, J=11 Hz, 2H), 2.38-2.56 (m, 2H), 2.90-3.08 (m, 3H), 3.28 (br s, 2H), 4.95 (br s, 1H), 8.00 (br s, 3H); LC-MS (LC-ES) M+H=183.

C. 4-Nitrophenyl (1-(2,2,2-trifluoroethyl)piperidin-4-yl)carbamate

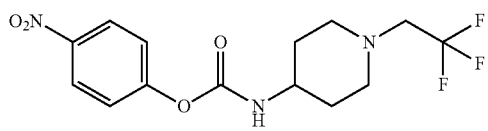 [SMILES: O=C(NC1CCN(CC(F)(F)F)CC1)Oc1ccc([N+](=O)[O-])cc1]

To 4-nitrophenyl chloroformate (240 mg, 1.19 mmol) in DCM (2 mL) at 0° C. was slowly added 1-(2,2,2-trifluoroethyl)piperidin-4-amine dihydrochloride (Intermediate 46B) (200 mg, 0.78 mmol) and N,N-diisopropylethylamine (0.42 mL, 2.4 mmol) in DCM (4 mL). The reaction was allowed to slowly warm to room temperature overnight. The resulting mixture contained solid material which was collected by vacuum filtration and dried to afford the title compound (87 mg, 32%) as a white solid. The filtrate was evaporated in vacuo, and the residue was purified on silica gel eluting with a 5% to 50% EtOAc in hexanes gradient to afford additional title compound (115 mg, 42% yield) as a white solid. ¹H NMR (400 MHz, CD₃SOCD₃) δ 1.44-1.63 (m, 2H), 1.81 (d, J=14 Hz, 2H), 2.42 (t, J=11 Hz, 2H), 2.91 (d, J=12 Hz, 2H), 3.08-3.22 (m, 2H), 3.33-3.43 (m 1H), 7.41 (d, J=9 Hz, 2H), 7.99-8.13 (m, 1H), 8.27 (d, J=9 Hz, 2H); LC-MS (LC-ES), M+H=348.

Intermediate 47: 4-Nitrophenyl 3-(benzo[d]thiazol-4-yloxy)azetidine-1-carboxylate

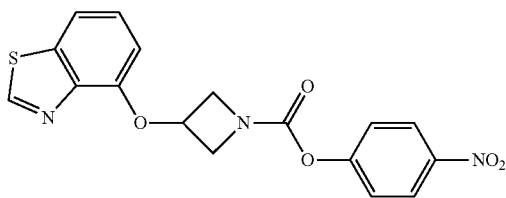 [SMILES: O=C(Oc1ccc([N+](=O)[O-])cc1)N1CC(Oc2cccc3scnc23)C1]

To 4-nitrophenyl chloroformate (390 mg, 1.94 mmol) in DCM (5 mL) at 0° C. was slowly added 4-(azetidin-3-yloxy)benzo[d]thiazole hydrochloride (Intermediate 28) (300 mg, 1.24 mmol) and N,N-diisopropylethylamine (0.50 mL, 2.9 mmol) in DCM (10 mL). The reaction was allowed to slowly warm to room temperature overnight. The solvent was removed in vacuo, and the residue was purified on silica gel eluting with a 0%-50% EtOAc in hexanes gradient to afford the title compound (331 mg, 72% yield) as a white solid. ¹H NMR (400 MHz, CD₃SOCD₃) δ 4.07-4.18 (m, 1H), 4.29-4.36 (m, 1H), 4.52-4.61 (m, 1H), 4.70-4.79 (m, 1H), 5.32-5.40 (m, 1H), 6.91 (d, J=12 Hz, 1H), 7.42 (t, J=8 Hz, 1H), 7.48 (d, J=12 Hz, 2H), 7.78 (d, J=12 Hz, 1H), 8.29 (d, J=12 Hz, 2H), 9.32 (s, 1H); LC-MS (LC-ES), M+H=372.

Intermediate 48: Racemic 1-(3-Aminopiperidin-1-yl)ethanone hydrochloride

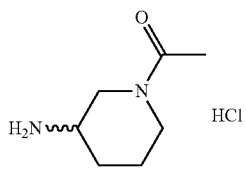

A. Racemic tert-Butyl (1-acetylpiperidin-3-yl)carbamate

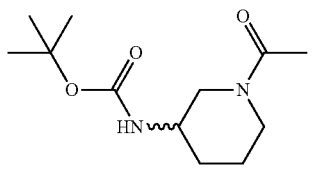

To a solution of 3-((tert-butoxycarbonyl)amino)piperidine (400 mg, 2.0 mmol) in DCM (10 mL) was added triethyl-amine (0.50 mL, 3.6 mmol) followed by acetyl chloride (0.20 mL, 2.8 mmol). After stirring overnight, the reaction was concentrated, diluted with EtOAc and washed with 0.5 N aqueous HCl, water and brine. The organic layer was dried over sodium sulfate, filtered and concentrated to afford the title compound as a yellow solid (330 mg, 68% yield). NMR showed a mixture of rotamers. ¹H NMR (400 MHz, CD₃SOCD₃) δ 1.20-1.34 (m, 2H), 1.38 (s, 4.5H), 1.40 (s, 4.5H), 1.62-1.71 (m, 1H), 1.73-1.82 (m, 1H), 1.94 (s, 1.5H), 1.97 (s, 1.5H), 2.87-2.96 (m, 1H), 3.01-3.08 (m, 1H), 3.52-3.63 (m, 1H), 3.67-3.74 (m, 1H), 4.13-4.17 (m, 0.5H), 4.17-4.22 (m, 0.5H), 6.84 (d, J=12 Hz, 0.5H), 6.96 (m, J=12 Hz, 0.5H).

B. Racemic 1-(3-Aminopiperidin-1-yl)ethanone hydrochloride

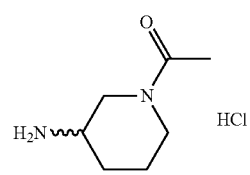

To tert-butyl (1-acetylpiperidin-3-yl)carbamate (Intermediate 48A) (170 mg, 0.70 mmol) in methanol (0.5 mL) was added 4 N HCl in dioxane (1 mL, 4 mmol). The mixture was stirred at room temperature for 1.5 h, and the solvent was removed in vacuo. The resulting residue was triturated with Et₂O to give the title compound as a beige solid (115 mg, 92%). NMR showed a mixture of rotamers. ¹H NMR (400 MHz, CD₃SOCD₃) δ 1.35-1.64 (m, 2H), 1.70-1.77 (m, 1H), 1.91-1.99 (m, 1H), 2.01 (s, 3H), 2.93-3.28 (m, 3H), 3.67-3.83 (m, 1H), 4.10-4.13 (m, 0.5H), 4.14-4.17 (m, 0.5H), 8.06 (br s, 1H), 8.17 (br s, 1H).

Intermediate 49: Racemic Methyl 3-aminopiperidine-1-carboxylate hydrochloride

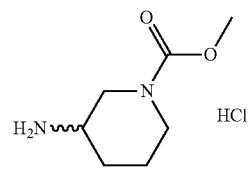

A. Racemic Methyl 3-((tert-butoxycarbonyl)amino)piperidine-1-carboxylate

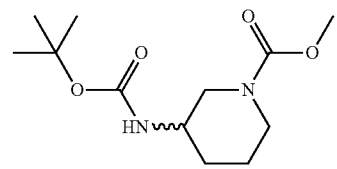 [SMILES: COC(=O)N1CCCC(NC(=O)OC(C)(C)C)C1]

To a solution of 3-((tert-butoxycarbonyl)amino)piperidine (400 mg, 2.0 mmol) in DCM (10 mL) was added triethylamine (0.50 mL, 3.6 mmol) followed by methyl chloroformate (0.20 mL, 2.6 mmol). After stirring overnight, the reaction was concentrated, diluted with EtOAc and washed with 0.5 N HCl water and brine. The organic layer was dried over sodium sulfate, filtered and concentrated to afford the title compound as a white solid (502 mg, 97% yield). $^1$H NMR (400 MHz, CD$_3$SOCD$_3$) δ 1.27-1.35 (m, 2H), 1.38 (s, 9H), 1.62-1.69 (m, 1H), 1.72-1.80 (m, 1H), 2.74-2.83 (m, 1H), 3.20-3.28 (m, 1H), 3.52-3.58 (m, 1H), 3.58 (s, 3H), 3.66-3.74 (m, 1H), 3.76-3.89 (m, 1H), 6.85-6.91 (m, 1H).

B. Methyl 3-aminopiperidine-1-carboxylate hydrochloride

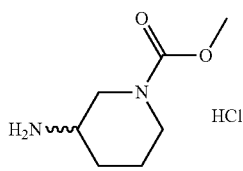

To methyl 3-((tert-butoxycarbonyl)amino)piperidine-1-carboxylate (Intermediate 49A) (100 mg, 0.39 mmol) in methanol (0.5 mL) was added 4 N HCl in dioxane (1 mL, 4 mmol). The mixture was stirred at room temperature for 1.5 h, and the solvent was removed in vacuo. The resulting residue was triturated with Et$_2$O to give the title compound as a white solid (81 mg, quantitative). $^1$H NMR (400 MHz, CD$_3$SOCD$_3$) δ 1.36-1.59 (m, 2H), 1.64-1.74 (m, 1H), 1.89-1.96 (m, 1H), 2.95-3.19 (m, 3H), 3.56-3.65 (m, 4H), 3.87-3.96 (m, 1H), 8.07 (br s, 2H).

Intermediate 50: Racemic 3-(Benzo[d]thiazol-4-yloxy)-N-(morpholin-2-ylmethyl)azetidine-1-carboxamide

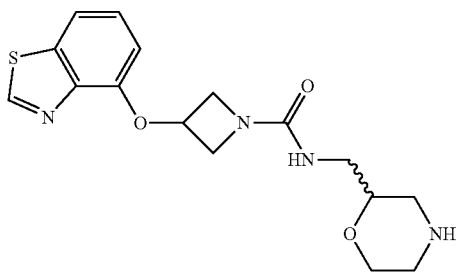 [SMILES: O=C(NCC1CNCCO1)N1CC(Oc2cccc3scnc23)C1]

A. Racemic tert-Butyl 2-((3-(benzo[d]thiazol-4-yloxy)azetidine-1-carboxamido)methyl)morpholine-4-carboxylate

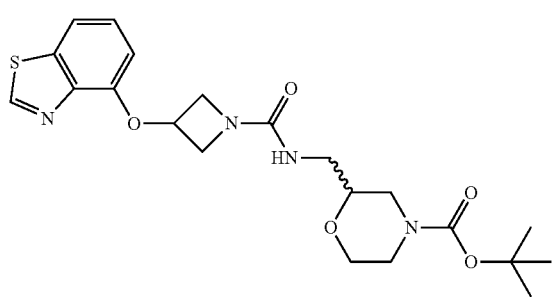 [SMILES: CC(C)(C)OC(=O)N1CCOC(CNC(=O)N2CC(Oc3cccc4scnc34)C2)C1]

To tert-butyl 2-(aminomethyl)morpholine-4-carboxylate (370 mg, 1.71 mmol) in NMP (4 mL) was added 4-nitrophenyl 3-(benzo[d]thiazol-4-yloxy)azetidine-1-carboxylate (Intermediate 47) (250 mg, 0.67 mmol). The reaction was heated to 80° C. overnight, poured into saturated aqueous NaHCO$_3$ and extracted with EtOAc (2×). The combined organic layers were washed with brine, dried over Na$_2$SO$_4$, filtered, concentrated and the residue purified on silica gel, eluting with a 0%-75% EtOAc-EtOH (3:1) in hexanes gradient to afford the title compound as a viscous yellow oil (330 mg, quantitative). $^1$H NMR (400 MHz, CD$_3$SOCD$_3$) δ 1.38 (s, 9H), 2.69 (s, 2H), 2.78-2.90 (m, 1H), 2.99-3.12 (m, 1H), 3.28-3.35 (m, 2H), 3.64-3.71 (m, 1H), 3.78-3.89 (m, 4H), 4.29-4.35 (m, 2H), 5.21-5.26 (m, 1H), 6.61 (t, J=12 Hz, 1H), 6.85 (d, J=8 Hz, 1H), 7.40 (t, J=8 Hz, 1H), 7.76 (d, J=8 Hz, 1H), 9.29 (s, 1H); LC-MS (LC-ES), M+H=449.

B. Racemic 3-(Benzo[d]thiazol-4-yloxy)-N-(morpholin-2-ylmethyl)azetidine-1-carboxamide

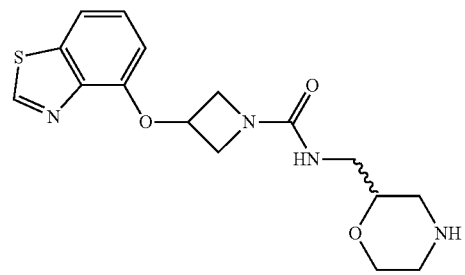 [SMILES: O=C(NCC1CNCCO1)N1CC(Oc2cccc3scnc23)C1]

To methyl tert-butyl 2-((3-(benzo[d]thiazol-4-yloxy)azetidine-1-carboxamido)methyl)morpholine-4-carboxylate (Intermediate 50A) (328 mg, 0.73 mmol) in DCM (4 mL) was added trifluoroacetic acid (1 mL, 13 mmol). The mixture was stirred at room temperature for 1.5 h and carefully neutralized with saturated aqueous NaHCO$_3$. The layers were separated, and the aqueous layer was extracted with DCM. The combined organic layers were washed with brine, dried over Na$_2$SO$_4$, filtered and concentrated to give the title compound as a yellow wax (48 mg, 19%). $^1$H NMR (400 MHz, CD$_3$SOCD$_3$) δ 2.70 (s, 2H), 2.94-2.99 (m, 2H), 3.27-3.40 (m, 2H), 3.66-3.72 (m, 1H), 3.81-3.88 (m, 3H), 4.12-4.22 (m, 1H), 4.27-4.34 (m, 2H), 5.19-5.25 (m, 1H), 6.46-6.54 (m, 1H), 6.86 (d, J=8 Hz, 1H), 7.40 (t, J=8 Hz, 1H), 7.76 (d, J=8 Hz, 1H), 9.29 (s, 1H); LC-MS (LC-ES), M+H=349.

Intermediate 51: 2-((trans)-4-Isothiocyanatocyclohexyl)propan-2-ol

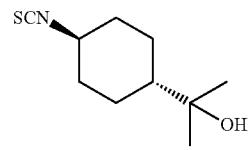

To a stirred solution of 1,1'-thiocarbonyldiimidazole (125 mg, 0.701 mmol) in DCM (3 mL) was added a solution of 2-((trans)-4-aminocyclohexyl)propan-2-ol (75 mg, 0.48 mmol) in DCM (2 mL) dropwise. After 2 h, N,N-diisopropylethylamine (0.13 mL, 0.72 mmol) was added to the mixture. After stirring overnight, the mixture was poured into water and extracted twice with EtOAc. The combined organic layers were washed with brine, dried over $Na_2SO_4$ and filtered. Solvent was removed under reduced pressure. The remaining material was purified on silica gel eluting with a 0%-50% EtOAc-hexanes gradient. The appropriate fractions were combined, evaporated under reduced pressure and placed in vacuo to give the title compound (53 mg, 56%) as a yellow oil. $^1$H NMR (400 MHz, $CD_3SOCD_3$) δ 1.00 (s, 6H), 1.00-1.08 (m, 2H), 1.12-1.20 (m, 1H), 1.36-1.48 (m, 2H), 1.74-1.82 (m, 2H), 2.08-2.13 (m, 2H), 3.64-3.73 (m, 1H), 4.08 (s, 1H); LC-MS (LC-ES), M+H—$H_2O$=182.

Intermediate 52: tert-Butyl 4-(((4-nitrophenoxy)carbonyl)amino)piperidine-1-carboxylate

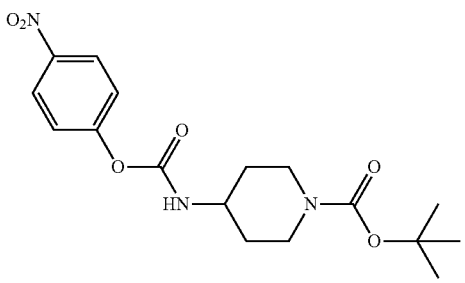 [SMILES: CC(C)(C)OC(=O)N1CCC(NC(=O)Oc2ccc([N+](=O)[O-])cc2)CC1]

To 4-nitrophenyl chloroformate (755 mg, 3.74 mmol) in DCM (5 mL) at 0° C. was slowly added tert-butyl 4-aminopiperidine-1-carboxylate (500 mg, 2.50 mmol) and N,N-diisopropylethylamine (0.50 mL, 2.9 mmol) in DCM (10 mL). The reaction was allowed to slowly warm to room temperature. After stirring overnight, the solvent was removed in vacuo, and the residue was purified on silica gel eluting with 0% to 50% EtOAc in hexanes gradient to afford the title compound as a white solid (720 mg, 79% yield). $^1$H NMR (400 MHz, $CD_3SOCD_3$) δ 1.28-1.34 (m, 2H), 1.38 (s, 9H), 1.76-1.82 (m, 2H), 2.77-2.90 (m, 2H), 3.49-3.58 (m, 1H), 3.81-3.88 (m, 2H), 7.39 (d, J=8 Hz, 2H), 8.08 (d, J=8 Hz, 1H), 8.22 (d, J=8 Hz, 2H); LC-MS (LC-ES) M+H-t-Bu=310.

Intermediate 53: 3-(Benzo[d]thiazol-4-yloxy)-N-(piperidin-4-yl)azetidine-1-carboxamide

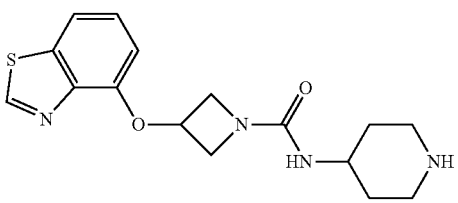 [SMILES: O=C(NC1CCNCC1)N1CC(Oc2cccc3scnc23)C1]

To tert-butyl 4-(3-(benzo[d]thiazol-4-yloxy)azetidine-1-carboxamido)piperidine-1-carboxylate (Example 96) (193 mg, 0.446 mmol) in DCM (3 mL) was added trifluoroacetic acid (0.5 mL, 6.5 mmol). The mixture was stirred at room temperature for 1.5 h and carefully neutralized with saturated aqueous $NaHCO_3$ and basified with aqueous 1 N NaOH. The layers were separated, and the aqueous layer was extracted with DCM. The combined organic layers were washed with brine, dried over $Na_2SO_4$, filtered and concentrated to give the title compound as a yellow solid (11 mg, 7%). The aqueous layer was concentrated and the resulting solid was suspended in DCM over the weekend, filtered, and the filtrate concentrated to give additional material as the title compound, a yellow solid (88 mg, 59%). $^1$H NMR (400 MHz, $CD_3SOCD_3$) δ 1.31-1.45 (m, 2H), 1.65-1.79 (m, 2H), 2.64-2.72 (m, 2H), 3.29-3.35 (m, 2H), 3.48-3.57 (m, 1H), 3.80-3.87 (m, 2H), 4.27-4.34 (m, 2H), 5.19-5.24 (m, 1H), 6.38 (d, J=8 Hz, 1H), 6.84 (d, J=8 Hz, 1H), 7.40 (t, J=8 Hz, 1H), 7.76 (d, J=8 Hz, 1H), 9.29 (s, 1H); LC-MS (LC-ES), M+H=333.

Intermediate 54: 2-(trans-4-Aminocyclohexyl)isothiazolidine 1,1-dioxide

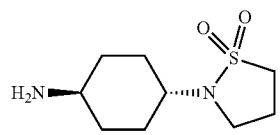 [SMILES: N[C@H]1CC[C@H](N2CCCS2(=O)=O)CC1]

A. Benzyl (trans-4-(3-chloropropylsulfonamido)cyclohexyl)carbamate

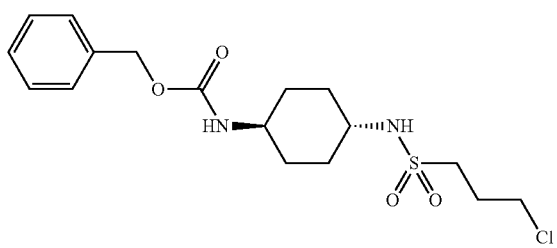 [SMILES: O=C(N[C@H]1CC[C@H](NS(=O)(=O)CCCCl)CC1)OCc1ccccc1]

Benzyl (trans-4-aminocyclohexyl)carbamate (1.01 g, 4.07 mmol) was dissolved in DMF (8 mL) and N,N-diisopropylethylamine (1.04 g, 8.02 mmol) was added. 3-Chloropropane-1-sulfonyl chloride (0.786 g, 4.44 mmol) was added slowly, and the resulting mixture was stirred at room temperature for 3 hours. Water (50 mL) was added, and the precipitated solid was collected by filtration, washed with water and dried to afford the title compound (1.42 g, 90% yield) as a white solid. $^1$H NMR (400 MHz, $CDCl_3$) δ 1.14-1.30 (m, 2H), 1.30-1.45 (m, 2H), 1.99-2.14 (m, 4H), 2.20-2.33 (m, 2H), 3.12-3.21 (m, 2H), 3.21-3.33 (m, 1H), 3.41-3.53 (m, 1H), 3.67 (t, J=6 Hz, 2H), 4.22 (d, J=8 Hz, 1H), 4.60 (d, J=7 Hz, 1H), 5.07 (s, 2H), 7.27-7.41 (m, 5H).

B. Benzyl (trans-4-(1,1-dioxidoisothiazolidin-2-yl)cyclohexyl)carbamate

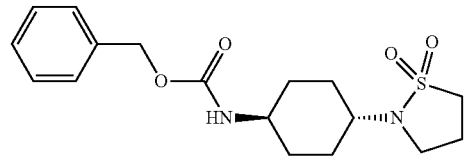 [SMILES: O=C(N[C@H]1CC[C@H](N2CCCS2(=O)=O)CC1)OCc1ccccc1]

Benzyl (trans-4-(3-chloropropylsulfonamido)cyclohexyl) carbamate (Intermediate 54A) (1.42 g, 3.65 mmol) was dissolved in THF (36 mL) and sodium hydride (60% dispersion in mineral oil) (0.325 g, 8.14 mmol) was added (gas evolution!). The solution was heated to 60° C. for 5 h. The mixture was cooled to room temperature and water (50 mL) and saturated aqueous ammonium chloride (25 mL) were added. The two layers were separated and the aqueous layer was extracted with ethyl acetate (3×20 mL). The combined organics were dried over magnesium sulfate, filtered and concentrated. The residue was purified by silica gel chromatography, eluting with a 40%-80% ethyl acetate/heptane gradient, to give the title compound as a white solid (779 mg, 61%). $^1$H NMR (400 MHz, CDCl$_3$) δ 1.20-1.33 (m, 2H), 1.50-1.67 (m, 2H), 1.92-2.03 (m, 2H), 2.09 (d, J=12 Hz, 2H), 2.27-2.39 (m, 2H), 3.12 (t, J=8 Hz, 2H), 3.26 (t, J=7 Hz, 2H), 3.36-3.55 (m, 2H), 4.62 (d, J=7 Hz, 1H), 5.08 (s, 2H), 7.28-7.41 (m, 5H).

C. 2-(trans-4-Aminocyclohexyl)isothiazolidine 1,1-dioxide

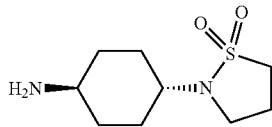 [SMILES: N[C@H]1CC[C@H](N2CCCS2(=O)=O)CC1]

Palladium on carbon (233 mg, 2.21 mmol) was added to benzyl (trans-4-(1,1-dioxidoisothiazolidin-2-yl)cyclohexyl) carbamate (Intermediate 54B) (0.779 g, 2.21 mmol) under a nitrogen atmosphere with enough methanol to wet the catalyst. The reaction vessel was fitted with a hydrogen balloon, and the vessel was repeatedly evacuated and purged with hydrogen, then stirred for 2 h under a hydrogen atmosphere. The vessel was repeatedly evacuated and purged with nitrogen, filtered through Celite®, and concentrated to give the title compound (497 mg, quantitative) as a white solid. $^1$H NMR (400 MHz, CD$_3$SOCD$_3$) δ 1.03-1.19 (m, 2H), 1.40-1.58 (m, 2H), 1.67-1.87 (m, 4H), 2.13-2.24 (m, 2H), 3.06-3.26 (m, 8H).

Intermediate 55: 1-(trans-4-Aminocyclohexyl)-3-methylimidazolidin-2-one

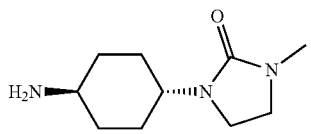

A. Benzyl (trans-4-(3-(2-hydroxyethyl)-3-methylureido)cyclohexyl)carbamate

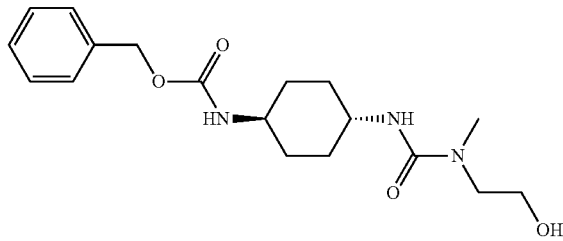 [SMILES: CN(CCO)C(=O)N[C@H]1CC[C@H](NC(=O)OCc2ccccc2)CC1]

To trans-4-(((benzyloxy)carbonyl)amino)cyclohexanecarboxylic acid (2.43 g, 8.76 mmol) suspended in toluene (20 mL) was added N,N-diisopropylethylamine (2.30 g, 17.8 mmol) followed by diphenyl phosphoryl azide (2.68 g, 9.74 mmol). The mixture was heated to 100° C. for 60 minutes, and 2-(methylamino)ethanol (795 mg, 10.6 mmol) was added. After 75 minutes, the mixture was cooled to room temperature, washed with water (100 mL) and brine (20 mL) and extracted with ethyl acetate (3×20 mL). The combined organics were dried over magnesium sulfate and concentrated. The residue was purified by silica gel chromatography, eluting with 10% isopropanol in ethyl acetate, to give the title compound as a white solid (1.86 g, 61%). $^1$H NMR (400 MHz, CD$_3$SOCD$_3$) δ 1.14-1.30 (m, 5H), 1.69-1.86 (m, 5H), 2.79 (s, 3H), 3.15-3.26 (m, 3H), 3.40-3.50 (m, 2H), 4.72 (t, J=5 Hz, 1H), 4.99 (s, 2H), 5.88 (d, J=7 Hz, 1H), 7.17 (d, J=8 Hz, 1H), 7.26-7.41 (m, 4H).

B. Benzyl (trans-4-(3-methyl-2-oxoimidazolidin-1-yl)cyclohexyl)carbamate

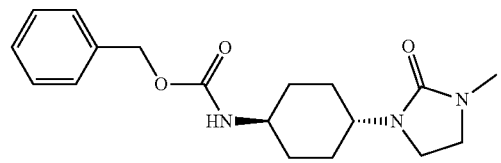 [SMILES: CN1CCN([C@H]2CC[C@H](NC(=O)OCc3ccccc3)CC2)C1=O]

Benzyl (trans-4-(3-(2-hydroxyethyl)-3-methylureido)cyclohexyl)carbamate (Intermediate 55A) (1.86 g, 5.32 mmol) was dissolved in THF (20 mL) and cooled to 0° C. Potassium tert-butoxide (1.49 g, 13.3 mmol) was added followed by p-toluenesulfonyl chloride (1.23 g, 6.44 mmol). The mixture was allowed to slowly warm to room temperature and stir overnight. Water (100 mL) and brine (20 mL) were added, and the mixture was extracted with ethyl acetate (4×20 mL). The combined organics were dried over magnesium sulfate and concentrated. The residue was purified by silica gel chromatography, eluting with ethyl acetate, to give the title compound as a white solid (1.19 g, 67%). $^1$H NMR (400 MHz, CDCl$_3$) δ 1.28 (qd, J=13, 3 Hz, 2H), 1.42-1.57 (m, 2H), 1.75 (d, J=12 Hz, 2H), 2.00-2.12 (m, 2H), 2.76 (s, 3H), 3.21-3.28 (m, 4H), 3.38-3.52 (m, 1H), 3.65-3.79 (m, 1H), 4.70 (d, J=7 Hz, 1H), 5.08 (s, 2H), 7.28-7.40 (m, 5H).

C. 1-(trans-4-Aminocyclohexyl)-3-methylimidazolidin-2-one

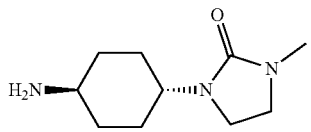

Palladium on carbon (130 mg, 0.22 mmol) was added to benzyl (trans-4-(3-methyl-2-oxoimidazolidin-1-yl)cyclohexyl)carbamate (Intermediate 55B) (402 mg, 1.21 mmol) under a nitrogen atmosphere with enough methanol to wet the catalyst. The reaction vessel was fitted with a hydrogen balloon, and the vessel was repeatedly evacuated and purged with hydrogen, then stirred for 2 h under a hydrogen atmosphere. The vessel was repeatedly evacuated and purged with nitrogen, filtered through Celite®, and concentrated to give the title compound (244 mg, quantitative) as a colorless film. $^1$H NMR (400 MHz, CD$_3$SOCD$_3$) δ 1.06-1.21 (m, 2H), 1.35-1.49 (m, 2H), 1.49-1.58 (m, 2H), 1.81 (d, J=12 Hz, 2H), 2.53-2.57 (m, 1H), 2.61 (s, 3H), 3.18 (s, 4H), 3.40-3.45 (m, 1H).

Intermediate 56: 3-(trans-4-Aminocyclohexyl)oxazolidin-2-one

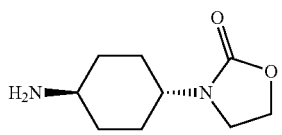 [SMILES: N[C@H]1CC[C@H](N2CCOC2=O)CC1]

A. Benzyl (2-((tert-butyldimethylsilyl)oxy)ethyl) trans-cyclohexane-1,4-diyldicarbamate

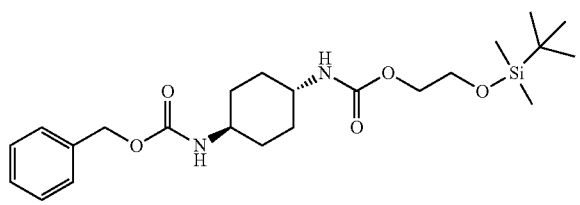 [SMILES: CC(C)(C)[Si](C)(C)OCCOC(=O)N[C@H]1CC[C@H](NC(=O)OCc2ccccc2)CC1]

To 2-((tert-butyldimethylsilyl)oxy)ethanol (1.08 g, 6.11 mmol) in DCM (12 mL) N,N-diisopropylethylamine (1.55 g, 12.0 mmol) was added, followed by triphosgene (602 mg, 2.03 mmol). After 60 minutes, the mixture was concentrated, and the residue was added slowly to a suspension of benzyl (trans-4-aminocyclohexyl)carbamate (1.02 g, 4.10 mmol) in DMF (8 mL). After stirring overnight, the mixture was poured into water (100 mL) and the precipitated solid was collected by filtration, washed with water and dried. The material was purified by silica gel chromatography, eluting with a 20%-40% ethyl acetate/heptane gradient, to give the title compound as a white solid (680 mg, 37%). $^1$H NMR (400 MHz, CD$_3$SOCD$_3$) δ 0.02 (s, 6H), 0.83 (s, 9H), 1.18 (t, J=9 Hz, 4H), 1.68-1.83 (m, 4H), 3.11-3.24 (m, 2H), 3.64-3.75 (m, 2H), 3.94 (t, J=5 Hz, 2H), 4.97 (s, 2H), 7.04 (d, J=8 Hz, 1H), 7.16 (d, J=8 Hz, 1H), 7.24-7.39 (m, 5H).

B. Benzyl (2-hydroxyethyl) trans-cyclohexane-1,4-diyldicarbamate

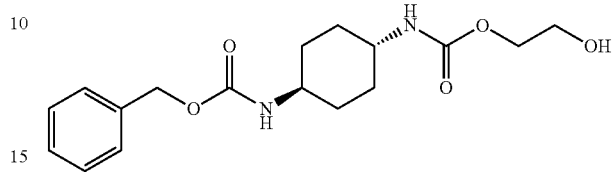

To benzyl (2-((tert-butyldimethylsilyl)oxy)ethyl) trans-cyclohexane-1,4-diyldicarbamate (Intermediate 56A) (900 mg, 2.00 mmol) in THF (4 mL), 1.0 M TBAF in THF (4.0 mL, 4.0 mmol) was added. After 2 hours, water (100 mL) was added, and the mixture was extracted with ethyl acetate (3×20 mL). The combined organics were dried over magnesium sulfate and concentrated. The residue was purified by silica gel chromatography, eluting with a 50%-90% ethyl acetate/heptane gradient, to give the title compound as a white solid (507 mg, 76%). $^1$H NMR (400 MHz, CD$_3$SOCD$_3$) δ 1.10-1.29 (m, 4H), 1.69-1.88 (m, 4H), 3.19 (br s, 2H), 3.47-3.55 (m, 2H), 3.92 (t, J=5 Hz, 2H), 4.68 (t, J=5 Hz, 1H), 4.99 (s, 2H), 7.05 (d, J=8 Hz, 1H), 7.18 (d, J=8 Hz, 1H), 7.25-7.41 (m, 5H).

C. Benzyl (trans-4-(2-oxooxazolidin-3-yl)cyclohexyl)carbamate

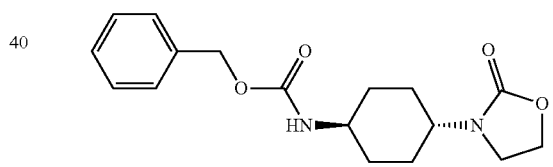

Benzyl (2-hydroxyethyl) trans-cyclohexane-1,4-diyldicarbamate (Intermediate 56B) (507 mg, 1.51 mmol) was dissolved in THF (9 mL) and cooled to 0° C. Potassium tert-butoxide (423 mg, 3.77 mmol) was added, followed by p-toluenesulfonyl chloride (345 mg, 1.81 mmol). The mixture was allowed to slowly warm to room temperature and stir 3 days. Water (50 mL) was added, and the mixture was extracted with ethyl acetate (3×15 mL). The combined organics were dried over magnesium sulfate and concentrated. The residue was purified by silica gel chromatography, eluting with a 50%-90% ethyl acetate/heptane gradient, to give the title compound as a white solid (346 mg, 72%). $^1$H NMR (400 MHz, CDCl$_3$) δ 1.27 (qd, J=13, 3 Hz, 2H), 1.45-1.60 (m, 2H), 1.60-1.72 (m, 2H), 1.87 (d, J=12 Hz, 2H), 3.20-3.31 (m, 1H), 3.36-3.42 (m, 1H), 3.47 (t, J=8 Hz, 2H), 4.23 (t, J=8 Hz, 2H), 5.00 (s, 2H), 7.22 (d, J=8 Hz, 1H), 7.27-7.44 (m, 5H).

D. 3-(trans-4-Aminocyclohexyl)oxazolidin-2-one

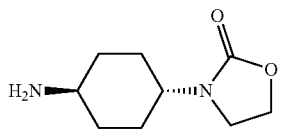 [SMILES: N[C@H]1CC[C@H](N2CCOC2=O)CC1]

Palladium on carbon (123 mg, 0.12 mmol) was added to benzyl (trans-4-(2-oxooxazolidin-3-yl)cyclohexyl)carbamate (Intermediate 56C) (346 mg, 1.09 mmol) under a nitrogen atmosphere with enough methanol to wet the catalyst. The reaction vessel was fitted with a hydrogen balloon, and the vessel was repeatedly evacuated and purged with hydrogen, then stirred overnight under a hydrogen atmosphere. The vessel was repeatedly evacuated and purged with nitrogen, filtered through Celite®, and concentrated to give the title compound (197 mg, 99%) as a colorless gel. $^1$H NMR (400 MHz, CD$_3$SOCD$_3$) δ 1.03-1.19 (m, 2H), 1.38-1.55 (m, 2H), 1.62 (d, J=11 Hz, 2H), 1.81 (d, J=12 Hz, 2H), 2.52-2.63 (m, 1H), 3.34-3.42 (m, 1H), 3.42-3.52 (m, 2H), 4.16-4.31 (m, 2H).

Intermediate 57:
trans-4-Amino-1-methylcyclohexanol

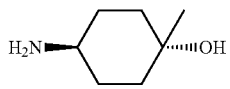

A. Benzyl (trans-4-hydroxy-4-methylcyclohexyl)carbamate

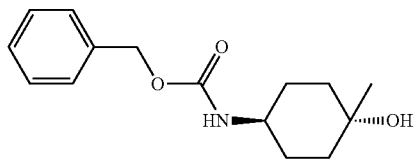 [SMILES: C[C@]1(O)CC[C@H](NC(=O)OCc2ccccc2)CC1]

Cerium(III) chloride heptahydrate (3.12 g, 8.39 mmol) was dried at 140° C. under high vacuum for 60 minutes, and then was cooled to room temperature, while remaining under vacuum overnight. The solid was placed under a nitrogen atmosphere and THF (16 mL) was added. The slurry was stirred for 90 minutes, and then cooled to −78° C. A 1.6 M solution of methyllithium in diethyl ether (5.10 mL, 8.16 mmol) was added. After 60 minutes, benzyl (4-oxocyclohexyl)carbamate (1.00 g, 4.05 mmol) in THF (5 mL) was added. After 2 hours, the mixture was poured into saturated aqueous ammonium chloride (50 mL) and water (50 mL). The resulting mixture was extracted with ethyl acetate (3×20 mL), and the combined organics were dried over magnesium sulfate and concentrated. The residue was purified by silica gel chromatography, eluting with a 40%-70% ethyl acetate-heptane gradient, to give the title compound as a white solid (524 mg, 49%). $^1$H NMR (400 MHz, CDCl$_3$) δ 1.20-1.31 (m, 4H), 1.33-1.46 (m, 2H), 1.46-1.69 (m, 4H), 1.88-2.02 (m, 2H), 3.57-3.72 (m, 1H), 4.70 (br s, 1H), 5.09 (br s, 2H), 7.28-7.43 (m, 5H).

B. trans-4-Amino-1-methylcyclohexanol

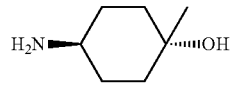

Palladium on carbon (217 mg, 0.20 mmol) was added to benzyl (trans-4-hydroxy-4-methylcyclohexyl)carbamate (Intermediate 57A) (524 mg, 1.99 mmol) under a nitrogen atmosphere with enough methanol to wet the catalyst. The reaction vessel was fitted with a hydrogen balloon, and the vessel was repeatedly evacuated and purged with hydrogen, then stirred for 1 h under a hydrogen atmosphere. The vessel was repeatedly evacuated and purged with nitrogen, filtered through Celite®, and concentrated to give the title compound (257 mg, quantitative) as a white solid. $^1$H NMR (400 MHz, CD$_3$SOCD$_3$) δ 1.08 (s, 3H), 1.09-1.19 (m, 2H), 1.26-1.38 (m, 2H), 1.45-1.56 (m, 2H), 1.59-1.72 (m, 2H), 2.59-2.66 (m, 1H).

Intermediate 58: 1-(Pyrimidin-2-yl)azetidin-3-amine dihydrochloride

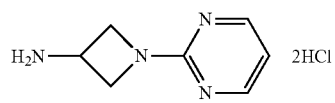 [SMILES: NC1CN(c2ncccn2)C1]

A. tert-Butyl (1-(pyrimidin-2-yl)azetidin-3-yl)carbamate

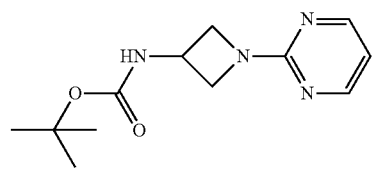 [SMILES: CC(C)(C)OC(=O)NC1CN(c2ncccn2)C1]

To a microwave reaction vial with tert-butyl azetidin-3-ylcarbamate hydrochloride (209 mg, 1.00 mmol) in NMP (2 mL) was added 2-chloropyrimidine (115 mg, 1.00 mmol) and N,N-diisopropylethylamine (0.35 mL, 2.0 mmol). The mixture was heated in a microwave (130° C.) for 2.5 h, cooled, diluted with water and MeOH, and loaded onto a semi-prep HPLC (NH$_4$OH as modifier) to afford the title compound as a pale yellow solid (147 mg, 59% yield). $^1$H NMR (400 MHz, CD$_3$OD) δ 1.45 (s, 9H), 3.93 (dd, J=9, 5 Hz, 2H), 4.36 (t, J=8 Hz, 2H), 4.42-4.57 (m, 1H), 6.67 (t, J=5 Hz, 1H), 8.31 (d, J=5 Hz, 2H); LC-MS (LC-ES) M+H=251.

B. 1-(Pyrimidin-2-yl)azetidin-3-amine dihydrochloride

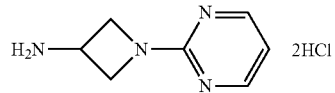 [SMILES: NC1CN(c2ncccn2)C1]

To tert-butyl (1-(pyrimidin-2-yl)azetidin-3-yl)carbamate (Intermediate 58A) (145 mg, 0.51 mmol) in MeOH (2 mL) was added 4 N HCl in dioxane (4 mL, 16 mmol). The mixture was stirred at room temperature for 2 h, and the solvent was removed in vacuo to give the title compound as a pale yellow solid (160 mg, quantitative). $^1$H NMR (400 MHz, CD$_3$OD) δ 4.32-4.40 (m, 1H), 4.40-4.46 (m, 2H), 4.72 (dd, J=11, 8 Hz, 2H), 7.07 (t, J=5 Hz, 1H), 8.65 (d, J=5 Hz, 2H); LC-MS (LC-ES) M+H=151.

Intermediate 59: (trans)-3-(6-Fluorobenzo[d]thiazol-4-yloxy)cyclobutanecarboxylic acid

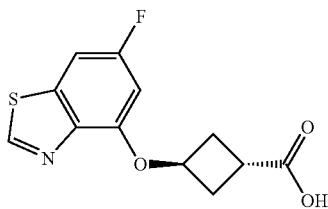 [SMILES: O=C(O)[C@H]1C[C@H](Oc2cc(F)cc3scnc23)C1]

A. (cis)-Methyl 3-((methylsulfonyl)oxy)cyclobutanecarboxylate

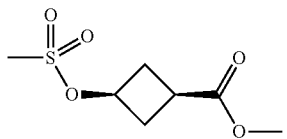

To a DCM (20 ml) solution of (cis)-methyl 3-hydroxycyclobutanecarboxylate (2.00 g, 15.4 mmol) at 0° C., triethylamine (4.71 ml, 33.8 mmol) was added, followed by methanesulfonyl chloride (1.94 g, 17.0 mmol). After 3 h, the mixture was warmed to room temperature. After 1 h, a precipitate was removed by filtration, the filtrate was concentrated in vacuo, and the resulting residue was purified on silica gel, eluting with a 10% to 60% EtOAc-hexanes gradient, to afford the title compound (3.01 g, 94%), a colorless liquid. $^1$H NMR (400 MHz, CDCl$_3$) δ 2.55-2.65 (m, 2H), 2.68-2.82 (m, 3H), 3.02 (s, 3H), 3.73 (s, 3H), 4.90-5.01 (m, 1H).

B. (trans)-Methyl 3-((6-fluorobenzo[d]thiazol-4-yl)oxy)cyclobutanecarboxylate

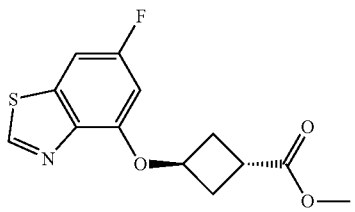 [SMILES: COC(=O)[C@H]1C[C@H](Oc2cc(F)cc3scnc23)C1]

A mixture of 6-fluorobenzo[d]thiazol-4-ol (400 mg, 2.36 mmol), (cis)-methyl 3-((methylsulfonyl)oxy)cyclobutanecarboxylate (Intermediate 59A) (492 mg, 2.36 mmol) and cesium carbonate (924 mg, 2.84 mmol) in DMF (7.5 mL) was stirred at 85° C. After stirring overnight, the reaction was cooled to room temperature, diluted with water; extracted with ethyl acetate (3×) and the combined organics were washed with brine, dried over sodium sulfate, filtered and concentrated. The resulting residue was purified on silica gel eluting with a 10%-60% EtOAc-hexanes gradient to give the title compound (370 mg, 56%) as a thick oil which slowly solidified. $^1$H NMR (400 MHz, CD$_3$OD) δ 2.57-2.69 (m, 2H), 2.80-2.91 (m, 2H), 3.25-3.33 (m, 1H), 3.76 (s, 3H), 5.14 (t, J=6 Hz, 1H), 6.71 (d, J=11 Hz, 1H), 7.39 (d, J=8 Hz, 1H), 9.12 (s, 1H); LC-MS (LC-ES) M+H=282.

C. (trans)-3-(6-Fluorobenzo[d]thiazol-4-yloxy)cyclobutanecarboxylic acid

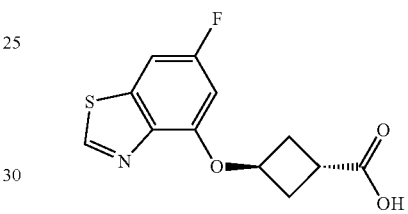

To a solution of (trans)-methyl 3-((6-fluorobenzo[d]thiazol-4-yl)oxy)cyclobutanecarboxylate (Intermediate 59B) (680 mg, 2.42 mmol) in THF (6 mL) and water (2 mL) was added LiOH (116 mg, 4.80 mmol). The reaction mixture was stirred at room temperature overnight. A portion of the solvents were removed in vacuo, and the remainder was partitioned between EtOAc and water. The aqueous layer was separated and adjusted to pH=4 with the addition of aqueous citric acid, followed by extraction with EtOAc (3×). The combined organic layers were washed with water, dried over MgSO$_4$ and concentrated to give the title compound (582 mg, 90%) as a light tan solid. $^1$H NMR (400 MHz, CD$_3$OD) δ 2.57-2.69 (m, 2H), 2.80-2.95 (m, 2H), 3.19-3.31 (m, 1H), 5.01-5.24 (m, 1H), 6.73 (d, J=11 Hz, 1H), 7.39 (d, J=7 Hz, 1H), 8.90-9.31 (m, 1H); LC-MS (LC-ES) M+H=268.

Intermediate 60: 2-(3-Aminoazetidin-1-yl)-5-methylpyridine 1-oxide hydrochloride

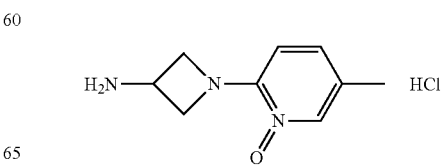

A. 2-(3-((tert-Butoxycarbonyl)amino)azetidin-1-yl)-5-methylpyridine 1-oxide

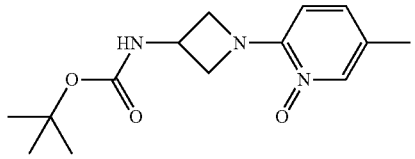

To a microwave reaction vial with tert-butyl azetidin-3-ylcarbamate hydrochloride (522 mg, 2.5 mmol) in ethanol (8 mL) was added 2-chloro-5-methylpyridine 1-oxide (359 mg, 2.5 mmol) and N,N-diisopropylethylamine (0.87 mL, 5.0 mmol). The mixture was heated in a microwave at 120° C. for 2 h, cooled, and then another portion (2.5 mmol) of both tert-butyl azetidin-3-ylcarbamate hydrochloride and N,N-diisopropylethylamine were added. The mixture was heated in a microwave at 125° C. for 3 h, cooled, and concentrated. The resulting residue was purified on silica gel eluting with a 0%-40% MeOH-DCM gradient to give the title compound (335 mg, 31%) as a white solid. $^1$H NMR (400 MHz, CD$_3$OD) δ 1.47 (s, 9H), 2.24 (s, 3H), 3.67-3.83 (m, 2H), 4.00-4.06 (m, 2H), 4.44-4.54 (m, 1H), 6.66 (d, J=9 Hz, 1H), 7.29-7.38 (m, 1H), 7.86 (s, 1H); LC-MS (LC-ES) M+H=280.

B. 2-(3-Aminoazetidin-1-yl)-5-methylpyridine 1-oxide hydrochloride

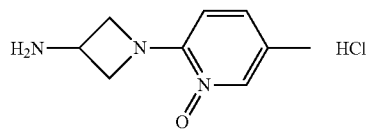

To 2-(3-((tert-butoxycarbonyl)amino)azetidin-1-yl)-5-methylpyridine 1-oxide (Intermediate 60A) (330 mg, 1.18 mmol) in MeOH (3 mL) was added 4 N HCl in dioxane (0.3 mL, 1.2 mmol). The mixture was stirred at room temperature for 1 h, and the solvent was removed in vacuo to give the title compound as a white solid (310 mg, quantitative). $^1$H NMR (400 MHz, CD$_3$OD) δ 2.32 (s, 3H), 4.28-4.40 (m, 1H), 4.57 (dd, J=11, 4 Hz, 2H), 4.83-4.89 (m, 2H), 7.00 (d, J=9 Hz, 1H), 7.89 (dd, J=9, 2 Hz, 1H), 8.09 (s, 1H); LC-MS (LC-ES) M+H=180.

Intermediate 61: 4-(Azetidin-3-yloxy)-6-fluorobenzo[d]thiazole hydrochloride

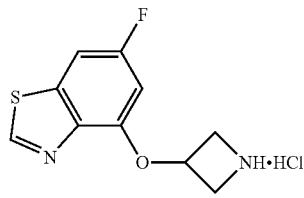

A. tert-Butyl 3-((6-fluorobenzo[d]thiazol-4-yl)oxy)azetidine-1-carboxylate

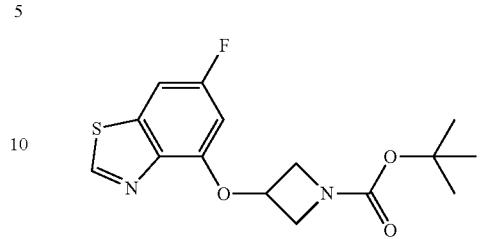

To a stirred solution of tert-butyl 3-((methylsulfonyl)oxy)azetidine-1-carboxylate (Intermediate 1) (2.67 g, 10.6 mmol) and 6-fluorobenzo[d]thiazol-4-ol (1.50 g, 8.87 mmol) in DMF (19 mL) was added cesium carbonate (3.47 g, 10.6 mmol). The mixture was heated to 85° C. overnight, poured into water and extracted with EtOAc (3×). The combined organic layers were washed with brine, dried over Na$_2$SO$_4$, filtered and concentrated. The remaining material was purified on silica gel eluting with a 20%-70% EtOAc-hexanes gradient. The appropriate fractions were combined, evaporated under reduced pressure and placed in vacuo to give the title compound contaminated with the mesylate starting material. This material was purified on silica gel eluting with a 5%-60% EtOAc-hexanes gradient to give the title compound (1.30 g, 45%) as a colorless foam. $^1$H NMR (400 MHz, CD$_3$OD) δ 1.48 (s, 9H), 4.12 (d, J=7 Hz, 2H), 4.41-4.50 (m, 2H), 5.21-5.32 (m, 1H), 6.74 (dd, J=11, 2 Hz, 1H), 7.48 (dd, J=8, 2 Hz, 1H), 9.17 (s, 1H); LC-MS (LC-ES) M+H=325.

B. 4-(Azetidin-3-yloxy)-6-fluorobenzo[d]thiazole hydrochloride

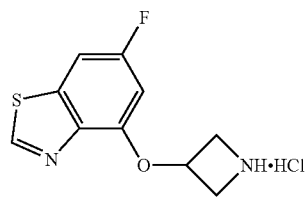

To tert-butyl 3-((6-fluorobenzo[d]thiazol-4-yl)oxy)azetidine-1-carboxylate (Intermediate 61A) (1.30 g, 4.01 mmol) in DCM (6 mL), was added 4 M HCl in dioxane (12 mL, 48 mmol). The mixture was stirred at room temperature for 1 h and the solvent was removed in vacuo to give the title compound as an off white solid (1.26 g, quantitative). $^1$H NMR (400 MHz, CD$_3$OD) δ 4.33 (dd, J=12, 4 Hz, 2H), 4.67 (dd, J=12, 7 Hz, 2H), 5.44-5.51 (m, 1H), 6.88 (dd, J=10, 2 Hz, 1H), 7.56 (dd, J=8, 2 Hz, 1H), 9.25 (s, 1H); LC-MS (LC-ES) M+H=225.

Intermediate 62: (2-(3-Aminoazetidin-1-yl)pyrimidin-5-yl)methanol dihydrochloride

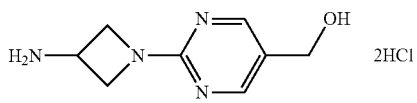

A. tert-Butyl (1-(5-(hydroxymethyl)pyrimidin-2-yl)azetidin-3-yl)carbamate

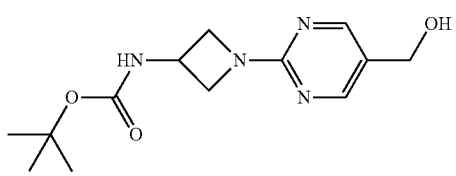 [SMILES: CC(C)(C)OC(=O)NC1CN(c2ncc(CO)cn2)C1]

To a microwave reaction vial with tert-butyl azetidin-3-ylcarbamate hydrochloride (433 mg, 2.1 mmol) in acetonitrile (10 mL) was added (2-chloropyrimidin-5-yl)methanol (300 mg, 2.1 mmol) and N,N-diisopropylethylamine (1.8 mL, 10 mmol). The mixture was heated in a microwave at 130° for 3 h, cooled and concentrated. The resulting residue was purified on silica gel eluting with a 30%-100% EtOAc: EtOH (3:1) in hexanes gradient to give the title compound (415 mg, 71%) as a white solid. $^1$H NMR (400 MHz, CD$_3$OD) δ 1.47 (s, 9H), 3.96 (dd, J=9, 6 Hz, 2H), 4.38 (t, J=8 Hz, 2H), 4.48 (s, 2H), 4.48-4.57 (m, 1H), 8.34 (s, 2H); LC-MS (LC-ES) M+H=281.

B. (2-(3-Aminoazetidin-1-yl)pyrimidin-5-yl)methanol dihydrochloride

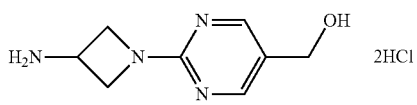 [SMILES: NC1CN(c2ncc(CO)cn2)C1]

To tert-butyl (1-(5-(hydroxymethyl)pyrimidin-2-yl)azetidin-3-yl)carbamate (Intermediate 62A) (410 mg, 1.46 mmol) in DCM (6 mL) was added 4 N HCl in dioxane (6 mL, 24 mmol). The mixture was stirred at room temperature for 3 h, and the solvent was removed in vacuo to give the title compound as a pale yellow solid (382 mg, quantitative). $^1$H NMR (400 MHz, CD$_3$OD) δ 4.31-4.51 (m, 3H), 4.61 (s, 2H), 4.71-4.79 (m, 2H), 8.64 (s, 2H); LC-MS (LC-ES) M+H=181.

Intermediate 63: Racemic 4-Nitrophenyl ((cis)-4-((1,1,1-trifluoro-3-hydroxypropan-2-yl)amino)cyclohexyl)carbamate

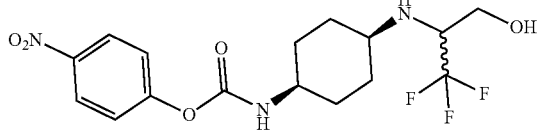

A. 4-(Dibenzylamino)cyclohexanone

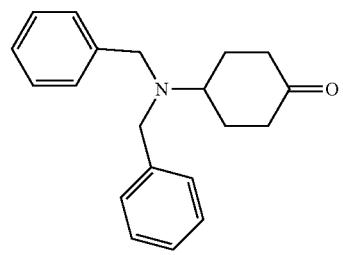 [SMILES: O=C1CCC(N(Cc2ccccc2)Cc2ccccc2)CC1]

To a DCM (160 mL) solution of oxalyl chloride (9.1 mL, 104 mmol) cooled to −78° C. was added, dropwise over 15 min, a solution of DMSO (14.5 mL, 2.04 mmol) in DCM (16 mL), keeping the reaction below −68° C. for the duration. After 15 min, a DCM (100 mL) solution of (trans)-4-(dibenzylamino)cyclohexanol (20 g, 67.7 mmol) was added dropwise over 15 min, keeping the temperature below −68° C. for the duration. After 30 min, triethylamine (30 mL, 215 mmol) was added over 15 min, keeping the temperature below −70° C. for the duration. After 1 h, the reaction was warmed to −3° C., diluted with diethyl ether (500 mL), and washed with 1:1 brine:water (2×250 mL). The organic layer was dried over MgSO$_4$, filtered, concentrated, diluted with heptane (50 mL) and concentrated again to remove residual DCM. The residue was triturated with heptane (50 mL), aged 1 h at 0° C., and the resulting solid was collected by filtration, washed with heptanes and dried to give the title compound as an off white solid (17.9 g, 90%). $^1$H NMR (400 MHz, CD$_3$SOCD$_3$) δ 1.73-1.88 (m, 2H), 2.06 (dd, J=10, 3 Hz, 2H), 2.13-2.23 (m, 2H), 2.25-2.37 (m, 2H), 2.87-2.99 (m, 1H), 3.61 (s, 4H), 7.15-7.24 (m, 2H), 7.27-7.33 (m, 4H), 7.34-7.41 (m, 4H).

B. Racemic Methyl 2-((4-(dibenzylamino)cyclohexyl)amino)-3,3,3-trifluoropropanoate

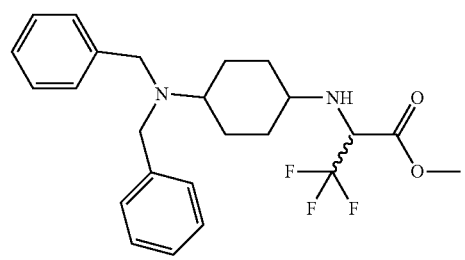 [SMILES: COC(=O)C(NC1CCC(N(Cc2ccccc2)Cc2ccccc2)CC1)C(F)(F)F]

Methyl 2-amino-3,3,3-trifluoropropanoate hydrochloride (820 mg, 4.24 mmol) was added to 4-(dibenzylamino)cyclohexanone (Intermediate 63A) (1.24 g, 4.24 mmol) in 1,2-dichloroethane (21 mL) at room temperature and stirred for 5 minutes, followed by 4 Å molecular sieves (10 g). After 2 h, sodium bicarbonate (356 mg, 4.24 mmol) and sodium triacetoxyborohydride (0.898 g, 4.24 mmol) were added, and the reaction mixture was stirred over the weekend. The reaction mixture was filtered, diluted with EtOAc, washed with saturated aqueous NaHCO$_3$ and the aqueous layer was extracted with EtOAc. The combined organics were washed with brine, dried over magnesium sulfate, filtered, and concentrated. The residue was purified by silica gel chromatography, eluting with 2:3 EtOAc:hexanes to give the title compound (730 mg, 40% yield) as a mixture of cis and trans isomers. $^1$H NMR (400 MHz, CD$_3$SOCD$_3$) δ 0.98-1.20 (m, 2H), 1.31-2.01 (m, 6H), 2.37-2.47 (m, 1H), 2.48-2.58 (m, 1H), 2.75 (br s, 1H), 3.59 (s, 2H), 3.64 (s, 2H), 3.74-3.84 (m, 1H), 3.84 (s, 3H), 7.19-7.25 (m, 2H), 7.27-7.33 (m, 4H), 7.34-7.42 (m, 4H); LC-MS (LC-ES) M+H=435.

C. Racemic 2-(((trans)-4-(Dibenzylamino)cyclohexyl)amino)-3,3,3-trifluoropropan-1-ol and 2-(((cis)-4-(Dibenzylamino)cyclohexyl)amino)-3.3.3-trifluoropropan-1-ol

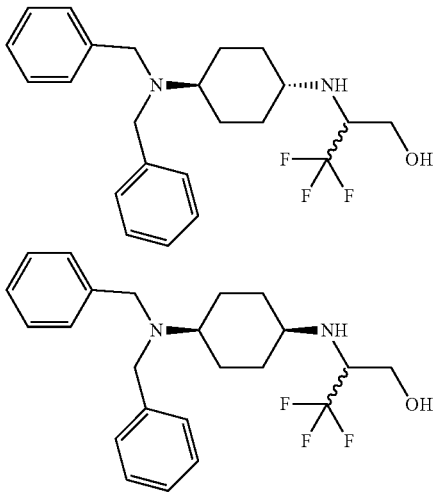

1 M Lithium aluminum hydride in diethyl ether (2.1 mL, 2.1 mmol) was added to methyl 2-((4-(dibenzylamino)cyclohexyl)amino)-3,3,3-trifluoropropanoate (Intermediate 63B) (690 mg, 1.59 mmol) in THF (10 mL). After 30 min, the mixture was quenched with water dropwise, stirred for 15 min and diluted with EtOAc. After partitioning between two layers, 1 N NaOH was added to the aqueous layer, which was further extracted with EtOAc. The combined organic layers were washed with brine, dried over MgSO$_4$ and filtered. The filtrate was concentrated and the residue was purified on silica gel, eluting with 5% to 40% EtOAc in hexanes to give 2-(((trans)-4-(dibenzylamino)cyclohexyl)amino)-3,3,3-trifluoropropan-1-ol as a white solid (284 mg, 44%) and 2-(((cis)-4-(dibenzylamino)cyclohexyl)amino)-3,3,3-trifluoropropan-1-ol as a white solid (317 mg, 49%).

2-(((trans)-4-(Dibenzylamino)cyclohexyl)amino)-3,3,3-trifluoropropan-1-ol $^1$H NMR (400 MHz, CD$_3$OD) δ 1.35 (t, J=13 Hz, 2H), 1.60 (d, J=11 Hz, 2H), 1.72-1.94 (m, 4H), 2.39-2.54 (m, 1H), 2.94 (br s, 1H), 3.17 (d, J=6 Hz, 1H), 3.55-3.69 (m, 5H), 3.78 (dd, J=12, 4 Hz, 1H), 7.13-7.20 (m, 2H), 7.26 (t, J=7 Hz, 4H), 7.35 (d, J=7 Hz, 4H); LC-MS (LC-ES) M+H=407.

2-(((cis)-4-(Dibenzylamino)cyclohexyl)amino)-3,3,3-trifluoropropan-1-ol $^1$H NMR (400 MHz, CD$_3$OD) δ 0.89-1.11 (m, 2H), 1.37-1.58 (m, 2H), 1.80-2.00 (m, 4H), 2.37-2.66 (m, 2H), 3.17-3.25 (m, 1H), 3.52-3.67 (m, 5H), 3.75 (dd, J=12, 4 Hz, 1H), 7.13-7.21 (m, 2H), 7.21-7.29 (m, 4H), 7.29-7.40 (m, 4H); LC-MS (LC-ES) M+H=407. LCMS in GADR but Not in notebook D. Racemic 2-(cis)-((4-Aminocyclohexyl)amino)-3,3,3-trifluoropropan-1-ol

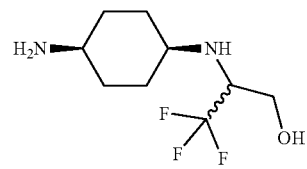 [SMILES: N[C@H]1CC[C@@H](NC(CO)C(F)(F)F)CC1]

2-(((cis)-4-(Dibenzylamino)cyclohexyl)amino)-3,3,3-trifluoropropan-1-ol (Intermediate 63C) (0.31 g, 0.76 mmol) and 20 wt % Pearlman's catalyst (53.6 mg, 0.076 mmol) were stirred in ethanol (20 mL) and purged with hydrogen on a Parr apparatus before shaking under a 40 psi hydrogen atmosphere overnight. The reaction was purged with nitrogen, filtered through a pad of Celite® and rinsed with ethyl acetate. The filtrate was concentrated under reduced pressure to give the title compound as a colorless oil (166 mg, 96%). $^1$H NMR (400 MHz, CD$_3$OD) δ 1.03-1.26 (m, 4H), 1.80-2.13 (m, 4H), 2.57-2.69 (m, 2H), 3.22-3.34 (m, 1H), 3.60-3.67 (m, 1H), 3.72-3.95 (m, 1H).

E. Racemic 4-Nitrophenyl ((cis)-4-((1,1,1-trifluoro-3-hydroxypropan-2-yl)amino)cyclohexyl)carbamate

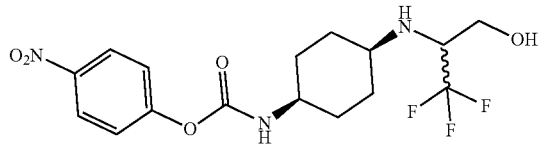 [SMILES: O=C(N[C@H]1CC[C@@H](NC(CO)C(F)(F)F)CC1)Oc1ccc([N+](=O)[O-])cc1]

To 4-nitrophenyl chloroformate (122 mg, 0.604 mmol) in acetonitrile (2 mL) at 0° C. was slowly added 2-(cis)-((4-aminocyclohexyl)amino)-3,3,3-trifluoropropan-1-ol (Intermediate 63D) (130 mg, 0.575 mmol) in acetonitrile (2 mL). After 1 h, sodium bicarbonate (97 mg, 1.2 mmol) was added, and the mixture was allowed to warm to room temperature. After stirring overnight, the solvent was removed in vacuo, and the residue was diluted with EtOAc, washed with brine, dried over MgSO$_4$, filtered and concentrated. A small amount of DCM was added to the residue, and the resulting solid was collected by filtration to afford the title compound white solid (163 mg, 73% yield). $^1$H NMR (400 MHz, CD$_3$SOCD$_3$) δ 0.90-1.35 (m, 4H), 1.75-2.01 (m, 4H), 2.44-2.54 (m, 3H), 3.16-3.30 (m, 2H), 3.43-3.57 (m, 1H), 3.62-

3.69 (m, 1H), 4.97 (br s, 1H), 7.40 (d, J=9 Hz, 2H), 8.26 (d, J=9 Hz, 2H); LC-MS (LC-ES) M+H=392.

Intermediate 64: Racemic 2-(((trans)-4-Aminocyclohexyl)amino)-3,3,3-trifluoropropan-1-ol dihydrochloride

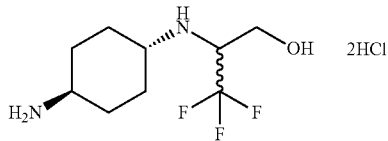 [SMILES: N[C@H]1CC[C@H](NC(CO)C(F)(F)F)CC1 ; "2HCl"]

A. Racemic Ethyl 2-(((trans)-4-((tert-butoxycarbonyl)amino)cyclohexyl)amino)-3,3,3-trifluoropropanoate

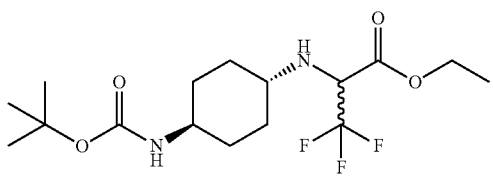 [SMILES: CCOC(=O)C(N[C@H]1CC[C@H](NC(=O)OC(C)(C)C)CC1)C(F)(F)F]

tert-Butyl ((trans)-4-aminocyclohexyl)carbamate (1.00 g, 4.67 mmol) was added to ethyl 3,3,3-trifluoro-2-oxopropanoate (1.02 g, 5.13 mmol) in 1,2-dichloroethane (23 mL) at room temperature and stirred for 5 minutes, followed by acetic acid (14 mg, 0.23 mmol) and 4 Å molecular sieves (8 g). After 2 h, sodium triacetoxyborohydride (0.989 g, 4.67 mmol) were added, and the reaction mixture was stirred overnight. The reaction mixture was filtered, diluted with EtOAc, washed with saturated aqueous NaHCO$_3$ and the aqueous layer extracted with EtOAc. The combined organics were washed with brine, dried over magnesium sulfate, filtered, and concentrated. The residue was purified by silica gel chromatography, eluting with 10%-60% EtOAc-hexanes to give the title compound (87 mg, 5% yield). $^1$H NMR (400 MHz, CD$_3$OD) δ 1.31 (d, J=10 Hz, 2H), 1.38 (t, J=7 Hz, 3H), 1.46 (s, 9H), 1.59-1.72 (m, 2H), 1.73-1.84 (m, 2H), 2.00 (d, J=11 Hz, 2H), 3.31-3.46 (m, 2H), 3.59 (t, J=5 Hz, 1H), 4.42 (q, J=7 Hz, 2H).

B. Racemic tert-butyl ((trans)-4-(1,1,1-trifluoro-3-hydroxypropan-2-yl)amino)cyclohexyl)carbamate

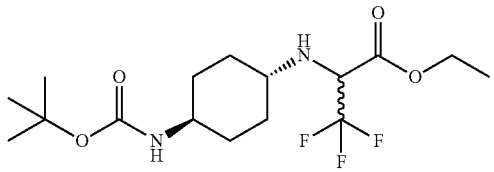 [SMILES: CCOC(=O)C(N[C@H]1CC[C@H](NC(=O)OC(C)(C)C)CC1)C(F)(F)F]

1 M Lithium aluminum hydride in diethyl ether (0.31 ml, 0.31 mmol) was added to ethyl 2-(((trans)-4-((tert-butoxycarbonyl)amino)cyclohexyl)amino)-3,3,3-trifluoropropanoate (Intermediate 64A) (87 mg, 0.24 mmol) in THF (1.5 ml) at 0° C. After 1 h, the reaction was quenched carefully with water and then 1 N aqueous NaOH. The mixture was taken up in EtOAc, dried over MgSO$_4$, concentrated and the residue was purified on silica gel, eluting with 10% to 70% EtOAc in hexanes, to afford the title compound as a white solid (84 mg, quantitative). $^1$H NMR (400 MHz, CD$_3$OD) δ 1.08-1.30 (m, 4H), 1.45 (s, 9H), 1.83-2.03 (m, 4H), 2.51-2.68 (m, 1H), 3.21-3.32 (m, 2H), 3.62 (dd, J=12, 6 Hz, 1H), 3.77 (d, J=4 Hz, 1H).

C. Racemic 2-(((trans)-4-Aminocyclohexyl)amino)-3,3,3-trifluoropropan-1-ol dihydrochloride

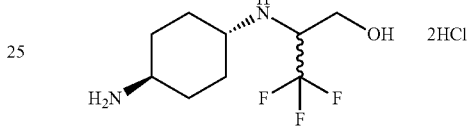

To tert-butyl ((trans)-4-((1,1,1-trifluoro-3-hydroxypropan-2-yl)amino)cyclohexyl)carbamate (Intermediate 64B) (85 mg, 0.26 mmol) in DCM (2 mL) was added 4 N HCl in dioxane (2 mL, 8 mmol). The mixture was stirred at room temperature for 2 h, and the solvent was removed in vacuo to give the title compound (79 mg, quantitative). $^1$H NMR (400 MHz, CD$_3$OD) δ 1.50-1.83 (m, 4H), 2.15-2.28 (m, 2H), 2.30-2.41 (m, 2H), 3.15-3.25 (m, 1H), 3.42-3.53 (m, 1H), 3.55-3.61 (m, 1H), 3.65-3.72 (m, 2H), 3.74-3.80 (m, 1H), 3.98-4.15 (m, 2H), 4.36-4.52 (m, 1H).

Intermediate 65: 4-Nitrophenyl ((trans)-4-(2-methoxyethoxy)cyclohexyl)carbamate

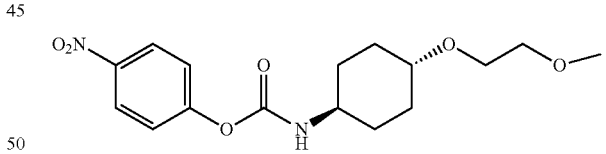

To 4-nitrophenyl chloroformate (326 mg, 1.62 mmol) in acetonitrile (5 mL) at 0° C. was slowly added (trans)-4-(2-methoxyethoxy)cyclohexanamine (Intermediate 39) (200 mg, 1.15 mmol) in acetonitrile (5 mL). After 30 min, sodium bicarbonate (194 mg, 2.31 mmol) was added, and the mixture was allowed to warm to room temperature. After 1 h, the solvent was removed in vacuo, and the residue was purified on silica gel, eluting with a 0%-60% EtOAc in hexanes gradient to give the title compound as a white solid (280 mg, 72%). $^1$H NMR (400 MHz, CD$_3$SOCD$_3$) δ 1.15-1.32 (m, 4H), 1.82-1.89 (m, 2H), 1.90-2.03 (m, 2H), 2.51 (dt, J=4, 2 Hz, 1H), 3.21-3.24 (m, 1H), 3.24 (s, 3H), 3.39-3.45 (m, 2H), 3.49-3.56 (m, 2H), 7.36-7.43 (m, 2H), 8.04 (d, J=8 Hz, 1H), 8.24-8.31 (m, 2H); LC-MS (LC-ES) M+H=339.

Intermediate 66: 4-Nitrophenyl (1-(pyrimidin-2-yl)azetidin-3-yl)carbamate

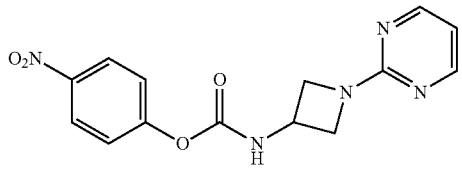 [SMILES: O=C(NC1CN(c2ncccn2)C1)Oc1ccc([N+](=O)[O-])cc1]

To 4-nitrophenyl chloroformate (172 mg, 0.853 mmol) in acetonitrile (2 mL) at 0° C. was slowly added 1-(pyrimidin-2-yl)azetidin-3-amine dihydrochloride (Intermediate 58) (136 mg, 0.61 mmol) in acetonitrile (2 mL). After 30 min, pyridine (145 mg, 1.83 mmol) was added, and the mixture was allowed to warm to room temperature. After 1 h, the solvent was removed in vacuo, and the residue was purified on silica gel, eluting with a 0%-60% EtOAc in hexanes gradient to give the title compound as a white solid (86 mg, 45%). $^1$H NMR (400 MHz, CD$_3$SOCD$_3$) δ 4.00 (dd, J=9, 6 Hz, 2H), 4.26-4.40 (m, 2H), 4.48-4.60 (m, 1H), 6.71 (t, J=5 Hz, 1H), 7.45 (d, J=9 Hz, 2H), 8.28 (d, J=9 Hz, 2H), 8.34-8.42 (m, 2H), 8.79 (d, J=8 Hz, 1H); LC-MS (LC-ES) M+H=316.

Intermediate 67: (cis)-3-Amino-1-methylcyclobutanol hydrochloride

A. tert-Butyl (cis)-3-hydroxy-3-methylcyclobutyl)carbamate

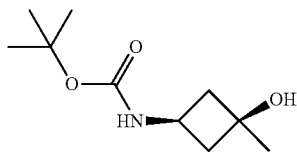

Cerium(III) chloride heptahydrate (10.06 g, 27.0 mmol) was dried at 140° C. under high vacuum for 17 h, and then was cooled to room temperature while remaining under vacuum. The solid was placed under a nitrogen atmosphere, cooled to 0° C. and THF (60 mL) was added. The ice bath was removed, and the slurry was stirred for 1 h, and then cooled to −78° C. A 1.6 M solution of methyllithium in diethyl ether (16.9 mL, 27.0 mmol) was added at a rate to keep the temperature below −70° C. After 90 minutes, tert-butyl (3-oxocyclobutyl)carbamate (2.50 g, 13.5 mmol) in THF (15 mL) was added at a rate to keep the temperature below −70° C. After 3 hours, the mixture was allowed to slowly warm to room temperature. After stirring overnight, the mixture was poured into saturated aqueous ammonium chloride (100 mL) and water (100 mL), stirred 10 min and filtered. The filtrate was extracted with ethyl acetate (2×), and the combined organics were dried over magnesium sulfate and concentrated. The residue was purified by silica gel chromatography, eluting with a 20%-100% ethyl acetate-hexanes gradient, to give the title compound as a colorless solid (1.05 g, 39%). $^1$H NMR (400 MHz, CDCl$_3$) δ 1.37 (s, 3H), 1.44 (s, 9H), 1.98 (td, J=9, 3 Hz, 2H), 2.46-2.54 (m, 2H), 3.72 (quin, J=8 Hz, 1H), 4.68 (br s, 1H).

B. (cis)-3-Amino-1-methylcyclobutanol hydrochloride

To tert-butyl (cis)-3-hydroxy-3-methylcyclobutyl)carbamate (Intermediate 67B) (1.04 g, 5.17 mmol) in methanol (18.45 mL) was added 4 N HCl in dioxane (5.81 mL, 23.3 mmol). The mixture was stirred overnight, more 4 N HCl in dioxane (1.30 mL, 5.17 mmol) was added, and after three hours, the solvent was removed in vacuo. The resulting residue was redissolved and concentrated with both dioxane and diethyl ether to give the title compound (786 mg, 99%). $^1$H NMR (400 MHz, CD$_3$SOCD$_3$) δ 1.14-1.24 (m, 3H), 1.88 (t, J=10 Hz, 2H), 2.10-2.20 (m, 2H), 3.42-3.55 (m, 1H), 4.85 (s, 1H).

Intermediate 68: Racemic 2-((trans)-5-Aminotetrahydro-2H-pyran-2-yl)propan-2-ol hydrochloride

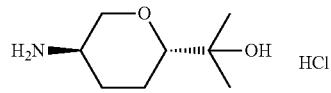

To 2-((trans)-5-(d ibenzylamino)tetrahydro-2H-pyran-2-yl)propan-2-ol (Intermediate 341) (265 mg, 0.781 mmol) and EtOH (7 mL) under a N$_2$ atmosphere was added 20% palladium hydroxide (137 mg, 0.195 mmol), and the vessel was evacuated and flushed with N$_2$ and then stirred under 40 psi H$_2$ for 24 h. The vessel was evacuated and flushed with N$_2$ and the mixture filtered through a pad of Celite® and rinsed with EtOH and EtOAc. To the filtrate, 4 N HCl in dioxane (1 mL, 4 mmol) was added. This mixture was concentrated to give the title compound as a white foam (147 mg, 96% yield). $^1$H NMR (400 MHz, CD$_3$SOCD$_3$) δ 0.98 (s, 3H), 1.04 (s, 3H), 1.24-1.38 (m, 1H), 1.41-1.54 (m, 1H), 1.75 (d, J=13 Hz, 1H), 2.06 (d, J=12 Hz, 1H), 2.87-3.04 (m, 2H), 3.22 (t, J=11 Hz, 1H), 3.95-4.07 (m, 1H); LC-MS (ES-MS) M+H=160.

Intermediate 69: (trans)-3-(5-fluoro-2-methoxyphenoxy)cyclobutanecarboxylic acid

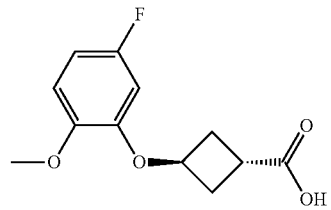 [SMILES: COc1ccc(F)cc1O[C@H]1C[C@H](C(=O)O)C1]

143

A. (trans)-Methyl 3-(5-fluoro-2-methoxyphenoxy)cyclobutanecarboxylate

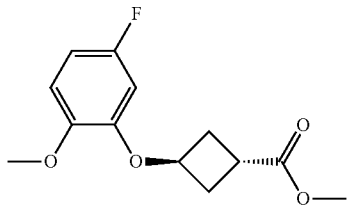

Triphenylphosphine (6.14 g, 23.4 mmol) was added to a solution of 2-methoxy-5-fluorophenol (2.25 g, 15.6 mmol) in tetrahydrofuran (40 mL). The reaction mixture was cooled to 0° C., and (cis)-methyl 3-hydroxycyclobutanecarboxylate (2.44 g, 18.7 mmol) was added, followed by DIAD (4.6 mL, 23 mmol). The reaction mixture was then warmed to room temperature, stirred for 3 days, and diluted with water and EtOAc. The mixture was partitioned, and the aqueous layer was extracted with EtOAc. The organics were washed with water, dried over sodium sulfate, filtered, and concentrated. The residue was purified on silica gel eluting with a 30%-70% EtOAc-hexanes gradient to give the title compound as a colorless, thick oil (3.6 g, 91%). $^1$H NMR (400 MHz, $CD_3SOCD_3$) δ 2.52-2.64 (m, 2H), 2.74-2.83 (m, 2H), 3.15-3.27 (m, 1H), 3.76 (s, 3H), 3.86 (s, 3H), 4.90 (t, J=7 Hz, 1H), 6.48 (dd, J=10, 3 Hz, 1H), 6.62 (td, J=8, 3 Hz, 1H), 6.81 (dd, J=9, 5 Hz, 1H); LC-MS (LC-ES) peak at T=0.78 min.

B. (trans)-3-(5-fluoro-2-methoxyphenoxy)cyclobutanecarboxylic acid

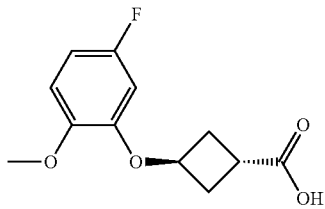 [SMILES: COc1ccc(F)cc1O[C@H]1C[C@H](C(=O)O)C1]

To a solution of (trans)-methyl 3-(2-(difluoromethoxy)-5-fluorophenoxy)cyclobutanecarboxylate (Intermediate 69A) (3.70 g, 14.6 mmol) in THF (20 mL) was added a solution of LiOH (1.83 g, 43.7 mmol) in water (10 mL). After 3 h, the mixture was adjusted to pH=5 with concentrated HCl, and the resulting solid was collected by filtration and then azeotroped with MeOH to give the title compound (2.51 g, 72%). $^1$H NMR (400 MHz, $CD_3OD$) δ 2.36-2.46 (m, 2H), 2.69 (ddd, J=13, 7, 4 Hz, 2H), 3.11 (dt, J=10, 5 Hz, 1H), 3.79 (s, 3H), 4.84 (t, J=7 Hz, 1H), 6.55-6.65 (m, 2H), 6.89 (dd, J=9, 5 Hz, 1H); LC-MS (LC-ES) M–H=239.

144

Intermediate 70: Racemic (trans)-3-(5-Fluoro-2-methoxyphenoxy)-N-(pyrrolidin-3-yl)cyclobutanecarboxamide hydrochloride

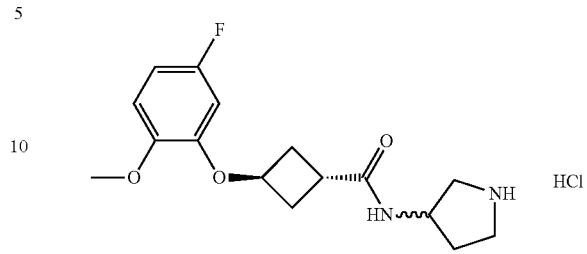

To tert-butyl 3-((trans)-3-(5-fluoro-2-methoxyphenoxy)cyclobutanecarboxamido)pyrrolidine-1-carboxylate (Example 143) (90 mg, 0.22 mmol) in DCM (1 mL) was added 4 N HCl in dioxane (3 mL, 12 mmol). The mixture was stirred for 2 h and the solvent was removed in vacuo to give the title compound (786 mg, 99%) as a light tan solid. $^1$H NMR (400 MHz, $CD_3OD$) δ 1.98-2.09 (m, 1H), 2.26-2.38 (m, 1H), 2.38-2.49 (m, 2H), 2.61-2.71 (m, 2H), 3.09-3.18 (s, 1H), 3.20-3.29 (m, 1H), 3.30-3.40 (m, 2H), 3.42-3.57 (m, 2H), 3.81 (s, 3H), 4.37-4.42 (m, 1H), 4.81-4.90 (m, 1H), 6.55 (dd, J=10, 3 Hz, 1H), 6.58-6.66 (m, 1H), 6.92 (dd, J=9, 5 Hz, 1H), 8.32 (br s, 1H); LC-MS (ES-MS) M+H=309.

Intermediate 71: (trans)-N-(Azetidin-3-yl)-3-(5-fluoro-2-methoxyphenoxy)cyclobutanecarboxamide, trifluoroacetic acid salt

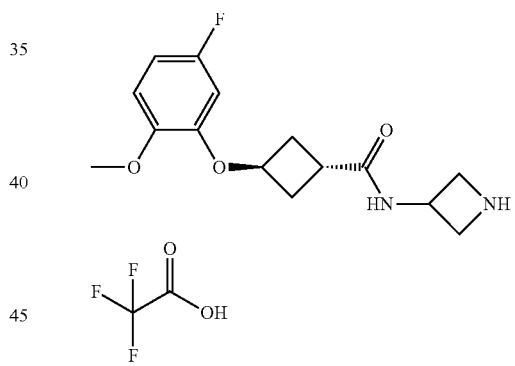

A. tert-Butyl 3-((trans)-3-(5-fluoro-2-methoxyphenoxy)cyclobutanecarboxamido)azetidine-1-carboxylate

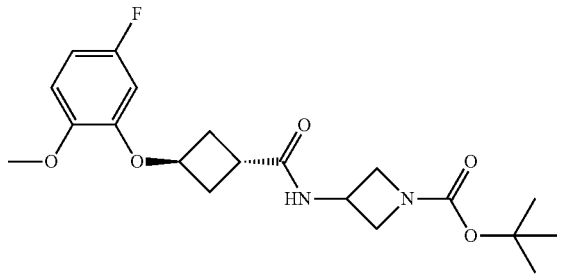 [SMILES: COc1ccc(F)cc1O[C@H]1C[C@H](C(=O)NC2CN(C(=O)OC(C)(C)C)C2)C1]

To a DMF (5 mL) solution of (trans)-3-(5-fluoro-2-methoxyphenoxy)cyclobutanecarboxylic acid (Intermediate 69) (120 mg, 0.50 mmol) was added HATU (228 mg, 0.599 mmol)) and N,N-diisopropylethylamine (0.17 mL, 1.0 mmol). After 5 minutes, tert-butyl 3-aminoazetidine-1-carboxylate (103 mg, 0.599 mmol) was added, and the mixture was stirred for 2 h, diluted with water and extracted with EtOAc. The organic extracts were washed with water and brine, dried over MgSO$_4$, filtered and concentrated. The residue was purified on silica gel eluting with a 20%-60% EtOAc/EtOH (3/1)-hexanes gradient to give the title compound as a white foam (171 mg, 87%). $^1$H NMR (400 MHz, CDCl$_3$) δ 1.42 (s, 9H), 2.48-2.52 (m, 2H), 2.69-2.73 (m, 2H), 2.95-3.05 (m, 1H), 3.72 (dd, J=9, 5 Hz, 2H), 3.82 (s, 3H), 4.25 (t, J=8 Hz, 2H), 4.59-4.68 (m, 1H), 4.91 (t, J=7 Hz, 1H), 6.25-6.31 (m, 1H), 6.46 (d, J=10 Hz, 1H), 6.55-6.62 (m, 1H), 6.77 (dd, J=9, 5 Hz, 1H); LC-MS (LC-ES) M+H=395.

B. (trans)-N-(Azetidin-3-yl)-3-(5-fluoro-2-methoxyphenoxy)cyclobutanecarboxamide, trifluoroacetic acid salt

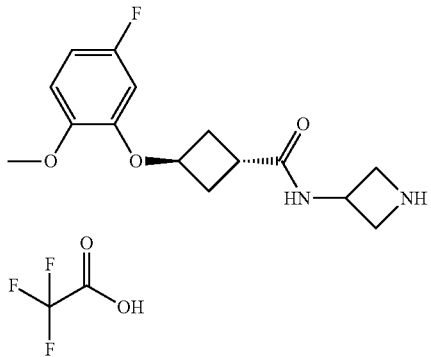

To a stirred solution of tert-butyl 3-((trans)-3-(5-fluoro-2-methoxyphenoxy)cyclobutanecarboxamido)azetidine-1-carboxylate (Intermediate 71A) (171 mg, 0.434 mmol) in DCM (2 mL) was added trifluoroacetic acid (2.0 mL, 26 mmol). After 1 h, the solvent was removed in vacuo and triturated with ether to afford the title compound as a white solid (181 mg, quantitative). $^1$H NMR (400 MHz, CD$_3$OD) δ 2.36-2.51 (m, 2H), 2.60-2.75 (m, 2H), 3.07-3.18 (m, 1H), 3.81 (s, 3H), 4.14-4.22 (m, 2H), 4.24-4.34 (m, 2H), 4.61-4.69 (m, 1H), 4.80-4.89 (m, 1H), 6.55 (dd, J=10, 3 Hz, 1H), 6.61 (d, J=3 Hz, 1H), 6.92 (dd, J=9, 5 Hz, 1H); LC-MS (LC-ES) M+H=295.

Intermediate 72: 2-(6-Amino-2-azaspiro[3.3]heptan-2-yl)isonicotinonitrile, di-trifluoroacetic acid salt

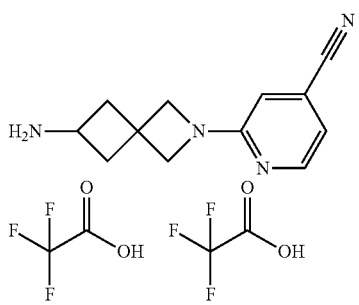

A. tert-Butyl (2-(4-cyanopyridin-2-yl)-2-azaspiro[3.3]heptan-6-yl)carbamate

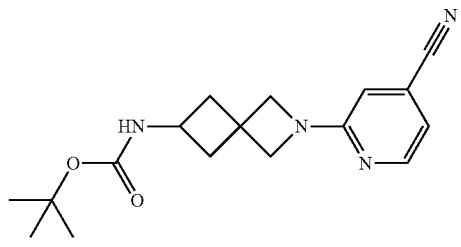 [SMILES: CC(C)(C)OC(=O)NC1CC2(C1)CN(c1cc(C#N)ccn1)C2]

To a DMF (3 mL) solution of tert-butyl 2-azaspiro[3.3]heptan-6-ylcarbamate (212 mg, 1.00 mmol) and 2-fluoroisonicotinonitrile (183 mg, 1.50 mmol) was added N,N-diisopropylethylamine (0.35 mL, 2.0 mmol). The mixture was heated to 100° C. for 3 h, cooled, diluted with water and extracted with EtOAc. The organic extracts were washed with water, dried over MgSO$_4$, filtered and concentrated. The residue was purified on silica gel eluting with a 20%-60% EtOAc/EtOH (3/1)-hexanes gradient to give the title compound as a white solid (245 mg, 78%). $^1$H NMR (400 MHz, CDCl$_3$) δ 1.44 (s, 9H), 2.04-2.14 (m, 2H), 2.59-2.67 (m, 2H), 3.97 (s, 2H), 4.04-4.11 (m, 1H), 4.07 (s, 2H), 4.61-4.71 (m, 1H), 6.41 (s, 1H), 6.72 (dd, J=5, 1 Hz, 1H), 8.22 (d, J=5 Hz, 1H); LC-MS (LC-ES) M+H=315.

B. 2-(6-Amino-2-azaspiro[3.3]heptan-2-yl)isonicotinonitrile, di-trifluoroacetic acid salt

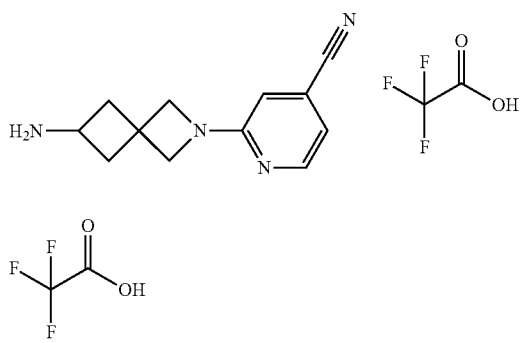

To a stirred solution of tert-butyl (2-(4-cyanopyridin-2-yl)-2-azaspiro[3.3]heptan-6-yl)carbamate (Intermediate 72A) (245 mg, 0.779 mmol) in DCM (2 mL) was added trifluoroacetic acid (2.0 mL, 26 mmol). After 1 h, the solvent was removed in vacuo and triturated with ether to afford the title compound as a pale yellow solid (413 mg, quantitative). $^1$H NMR (400 MHz, CD$_3$OD) δ 2.38-2.46 (m, 2H), 2.68-2.75 (m, 2H), 3.71-3.80 (m, 1H), 4.17 (s, 2H), 4.26 (s, 2H), 6.93-6.96 (m, 1H), 6.98 (t, J=1 Hz, 1H), 8.12 (dd, J=6, 1 Hz, 1H); LC-MS (LC-ES) M+H=215.

Intermediate 73: 4-((trans)-4-Aminocyclohexyl)morpholin-3-one

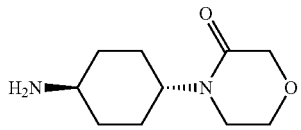

A. Benzyl ((trans)-4-(2-(2-chloroethoxy)acetamido)cyclohexyl)carbamate

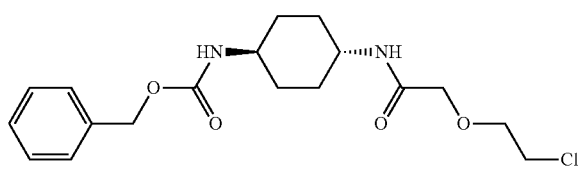 [SMILES: O=C(COCCCl)N[C@H]1CC[C@H](NC(=O)OCc2ccccc2)CC1]

To a THF solution (30 mL) of 2-(2-chloroethoxy)acetyl chloride (958 mg, 6.11 mmol) and benzyl ((trans)-4-aminocyclohexyl)carbamate (1.38 g, 5.55 mmol) was added tri-ethylamine (1.12 g, 11.1 mmol) at room temperature. After stirring overnight, the organics were taken up in CHCl$_3$, washed with water, dried over MgSO$_4$ and concentrated to give the title compound as a light yellow solid (1.90 g, 93%) which was used without further purification. $^1$H NMR (400 MHz, CD$_3$SOCD$_3$) δ 1.18-1.38 (m, 4H), 1.71-1.84 (m, 4H), 3.20-3.32 (m, 1H), 3.49-3.58 (m, 1H), 3.70-3.74 (m, 2H), 3.77-3.81 (m, 2H), 3.90 (s, 2H), 5.00 (s, 2H), 7.28-7.40 (m, 5H); LC-MS (LC-ES) M+H=369.

B. Benzyl ((trans)-4-(3-oxomorpholino)cyclohexyl)carbamate

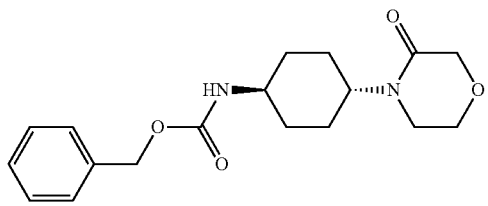 [SMILES: O=C(N[C@H]1CC[C@H](N2CCOCC2=O)CC1)OCc1ccccc1]

An acetonitrile solution (60 mL) containing benzyl ((trans)-4-(2-(2-chloroethoxy)acetamido)cyclohexyl)carbamate (Intermediate 73A) (1.88 g, 5.10 mmol) and cesium carbonate (2.49 g, 7.65 mmol) was heated to reflux. After stirring overnight, the reaction was cooled, the solvent was removed in vacuo and the residual solid taken up in CHCl$_3$ followed by careful quenching with saturated aqueous NaHSO$_4$. The organic layer was separated and the aqueous layer extracted with CHCl$_3$. The combined organic layers were dried over MgSO$_4$ and concentrated, and the residue was purified on silica gel eluting with a 0%-15% MeOH-DCM gradient to give the title compound as a light yellow solid (1.37 g, 81%). $^1$H NMR (400 MHz, CD$_3$SOCD$_3$) δ 1.31-1.22 (m, 2H), 1.48-1.62 (m, 4H), 1.82-1.91 (m, 2H), 3.20-3.26 (m, 2H), 3.26-3.32 (m, 1H), 3.76-3.82 (m, 2H), 4.01 (s, 2H), 4.12-4.22 (m, 1H), 5.01 (s, 2H), 7.27-7.39 (m, 5H); LC-MS (LC-ES) M+H=333.

C. 4-((trans)-4-Aminocyclohexyl)morpholin-3-one

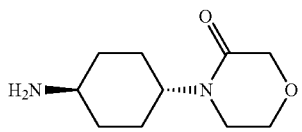

To a stirred solution of benzyl ((trans)-4-(3-oxomorpholino)cyclohexyl)carbamate (Intermediate 73B) (1.35 g, 4.06 mmol) in methanol (15 mL) under a nitrogen atmosphere was added 10% Pd/C (864 mg, 0.812 mmol). The reaction vessel was evacuated under reduced pressure and purged with hydrogen three times. The mixture was placed under a nitrogen atmosphere, fitted with a hydrogen filled balloon and stirred overnight under a hydrogen atmosphere. The mixture was filtered through a pad of Celite®, washing with DCM. The filtrate was evaporated to dryness to give the crude title compound (790 mg, 98%) as a waxy solid, which was used without further purification. $^1$H NMR (400 MHz, CD$_3$SOCD$_3$) δ 1.04-1.16 (m, 2H), 1.45-1.57 (m, 4H), 1.76-1.85 (m, 2H), 2.42-2.53 (m, 1H), 3.20-3.26 (m, 2H), 3.76-3.81 (m, 2H), 4.00 (s, 2H), 4.13-4.22 (m, 1H).

Intermediate 74: (trans)-3-(5-Fluoro-2-methoxyphenoxy)-N-(piperidin-4-yl)cyclobutanecarboxamide hydrochloride

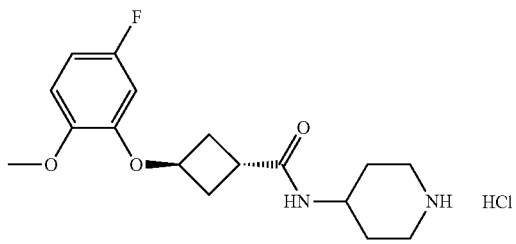 [SMILES: COc1ccc(F)cc1O[C@H]1C[C@H](C(=O)NC2CCNCC2)C1 ; Cl]

A. tert-Butyl 4-((trans)-3-(5-fluoro-2-methoxyphenoxy)cyclobutanecarboxamido)piperidine-1-carboxylate

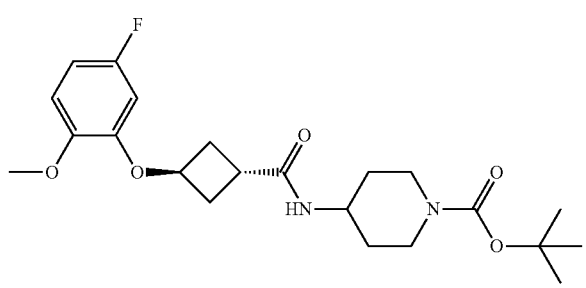 [SMILES: COc1ccc(F)cc1O[C@H]1C[C@H](C(=O)NC2CCN(C(=O)OC(C)(C)C)CC2)C1]

To a DMF (10 mL) solution of (trans)-3-(5-fluoro-2-methoxyphenoxy)cyclobutanecarboxylic acid (Intermediate 69) (300 mg, 1.25 mmol) was added HATU (570 mg, 1.50 mmol)) and N,N-diisopropylethylamine (0.44 mL, 2.5 mmol). After 5 minutes, tert-butyl 4-aminopiperidine-1-carboxylate (300 mg, 1.50 mmol) was added, and the mixture was stirred for 2 h, diluted with water and MeOH, and loaded onto a semi-prep HPLC (NH$_4$OH as modifier) to afford the title compound as a pale yellow foamy solid (370 mg, 70%). $^1$H NMR (400 MHz, CDCl$_3$) δ 1.21-1.33 (m, 2H), 1.45 (s, 9H), 1.87-1.95 (m, 2H), 2.43-2.55 (m, 2H), 2.68-2.75 (m, 2H), 2.81-2.90 (m, 2H), 2.90-2.99 (m, 1H), 3.84 (s, 3H), 3.88-3.99 (m, 1H), 3.99-4.14 (m, 2H), 4.88-4.99 (m, 1H), 5.29-5.33 (m, 1H), 6.47 (dd, J=10, 3 Hz, 1H), 6.56-6.62 (m, 1H), 6.78 (dd, J=9, 5 Hz, 1H); LC-MS (LC-ES) M+H=423.

B. (trans)-3-(5-Fluoro-2-methoxyphenoxy)-N-(piperidin-4-yl)cyclobutanecarboxamide hydrochloride

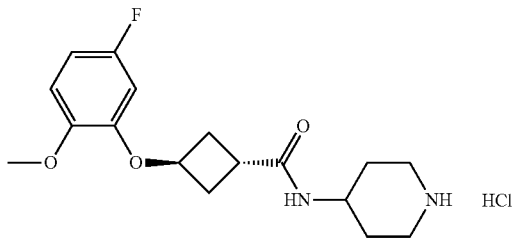 [SMILES: COc1ccc(F)cc1O[C@H]1C[C@H](C(=O)NC2CCNCC2)C1 ; Cl]

To a stirred solution of tert-butyl 4-((trans)-3-(5-fluoro-2-methoxyphenoxy)cyclobutanecarboxamido)piperidine-1-carboxylate (Intermediate 74A) (370 mg, 0.876 mmol) in DCM (1.5 mL) was added 4 N HCl in dioxane (1.5 mL, 6.0 mmol). After 15 min, a small amount of MeOH was added to facilitate solubility. After 15 min, the solvent was removed in vacuo to afford the title compound as a white foamy solid (335 mg, quantitative). $^1$H NMR (400 MHz, CD$_3$OD) δ 1.58-1.69 (m, 2H), 2.04-2.14 (m, 2H), 2.32-2.45 (m, 2H), 2.56-2.67 (m, 2H), 3.06-3.11 (m, 3H), 3.33-3.45 (m, 2H), 3.78 (s, 3H), 3.89-3.99 (m, 1H), 4.83-4.92 (m, 1H), 6.51-6.61 (m, 2H), 6.84-6.93 (m, 1H); LC-MS (LC-ES) M+H=323.

Intermediate 75: 2-((trans)-3-(5-Fluoro-2-methoxyphenoxy)cyclobutanecarboxamido)oxazole-4-carboxylic acid

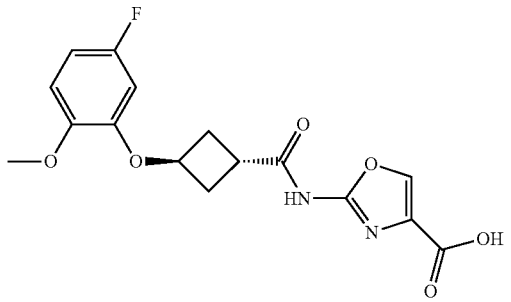 [SMILES: COc1ccc(F)cc1O[C@H]1C[C@H](C(=O)Nc2nc(C(=O)O)co2)C1]

To a DMF (12 mL) solution of (trans)-3-(5-fluoro-2-methoxyphenoxy)cyclobutanecarboxylic acid (Intermediate 69) (340 mg, 1.42 mmol) was added HATU (646 mg, 1.70 mmol) and N,N-diisopropylethylamine (0.49 mL, 2.8 mmol). After 20 minutes, 2-aminooxazole-4-carboxylic acid (272 mg, 2.12 mmol) was added, and the mixture was stirred for 2 h, diluted with water and MeOH, and loaded onto a semi-prep HPLC (TFA as modifier) to afford the title compound as a pale yellow foamy solid (370 mg, 70%). $^1$H NMR (400 MHz, CD$_3$OD) δ 2.45-2.55 (m, 2H), 2.75-2.84 (m, 2H), 3.35-3.45 (m, 1H), 3.82 (s, 3H), 4.85-4.92 (m, 1H), 6.55-6.65 (m, 2H), 6.89-6.95 (m, 1H), 8.25 (s, 1H); LC-MS (LC-ES) M+H=351.

Intermediate 76: Racemic trans-N1-(1,1,1-Trifluoropropan-2-yl)cyclohexane-1,4-diamine dihydrochloride

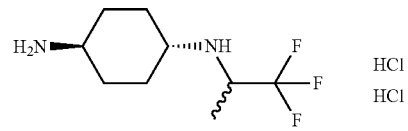

A. Racemic tert-Butyl (trans-4-((1,1,1-trifluoropropan-2-yl)amino)cyclohexyl)carbamate

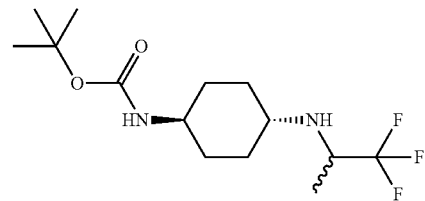 [SMILES: CC(N[C@H]1CC[C@H](NC(=O)OC(C)(C)C)CC1)C(F)(F)F]

N,N-Diisopropylethylamine (1.64 mL, 9.43 mmol) was added to tert-butyl (trans-4-aminocyclohexyl)carbamate (1.01 g, 4.71 mmol) in 1,4-dioxane (7.8 mL) at room temperature, followed by 1,1,1-trifluoropropan-2-yl trifluoromethanesulfonate (1.39 g, 5.66 mmol), and the reaction mixture was stirred at 70° C. for 16 h. The reaction mixture was concentrated and the residue was purified by silica gel chromatography, eluting with EtOAc:hexanes (1:4) to give the title compound (906 mg, 59%). $^1$H NMR (400 MHz, CD$_3$SOCD$_3$) δ 0.98 (dq, J=11 Hz, 2H), 1.11 (dq, J=13, 3 Hz, 2H), 1.11 (d, J=7 Hz, 3H), 1.35 (s, 9H), 1.66-1.82 (m, 4H), 1.82-1.90 (m, 1H), 2.30-2.44 (m, 1H), 3.06-3.18 (m, 1H), 3.28 (h, J=7 Hz, 1H), 6.66 (d, J=8 Hz, 1H); LC-MS (LC-ES) M+H=311.

B. Racemic trans-N1-(1,1,1-Trifluoropropan-2-yl)cyclohexane-1,4-diamine dihydrochloride

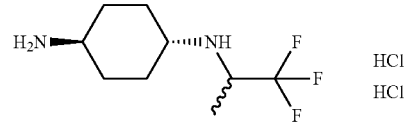

4.0 M HCl in dioxane (7.3 mL, 29 mmol) was added to tert-butyl (trans-4-((1,1,1-trifluoropropan-2-yl)amino)cyclohexyl)carbamate (Intermediate 76A) (0.91 g, 2.9 mmol) in MeOH (7.3 mL) at room temperature. After 15 h, the reaction mixture was concentrated to give the title compound (817 mg, 94%). $^1$H NMR (400 MHz, CD$_3$SOCD$_3$) δ 1.26-1.70 (m, 6H), 1.99 (br s, 3H), 2.14 (br s, 2H), 2.93 (br s, 1H), 3.15 (br s, 1H), 4.41 (br s, 1H), 8.08 (br s, 3H), 9.56 (br s, 1H), 10.25 (br s, 1H); LC-MS (LC-ES) M+H=211.

Intermediate 77: (trans)-3-(5-Fluoro-2-methoxyphenoxy)cyclobutanamine hydrochloride

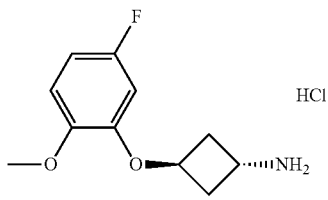

A. tert-Butyl ((trans)-3-(5-fluoro-2-methoxyphenoxy)cyclobutyl)carbamate

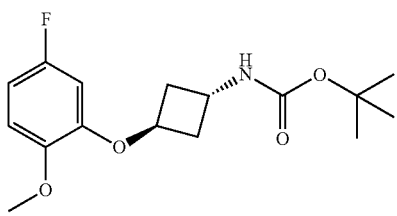 [SMILES: COc1ccc(F)cc1O[C@H]1C[C@H](NC(=O)OC(C)(C)C)C1]

Triphenylphosphine (1.04 g, 3.96 mmol) was added to a solution of 5-fluoro-2-methoxyphenol (1.85 g, 10.4 mmol) in tetrahydrofuran (10 mL). The reaction mixture was cooled to 0° C., and tert-butyl ((cis)-3-hydroxycyclobutyl)carbamate (494 mg, 2.64 mmol) was added, followed by DIAD (0.77 mL, 4.0 mmol). The reaction mixture was then warmed to room temperature, stirred for 1 week, and partially concentrated. The remaining material was diluted with water and EtOAc, partitioned, and the aqueous layer was extracted with EtOAc. The combined organics were washed with water, dried over MgSO$_4$, filtered and concentrated. The residue was purified on silica gel eluting with a 30%-80% EtOAc-hexanes gradient to give the title compound (601 mg, 73%) as a white solid. $^1$H NMR (400 MHz, CDCl$_3$) δ 1.46 (s, 9H), 2.34-2.46 (m, 2H), 2.63-2.70 (s, 2H), 3.85 (s, 3H), 4.25-4.34 (m, 1H), 4.70-4.87 (m, 2H), 6.41 (dd, J=10, 3 Hz, 1H), 6.60 (d, J=3 Hz, 1H), 6.80 (dd, J=9, 5 Hz, 1H); LC-MS (LC-ES) M+H-Boc=212.

B. (trans)-3-(5-Fluoro-2-methoxyphenoxy)cyclobutanamine hydrochloride

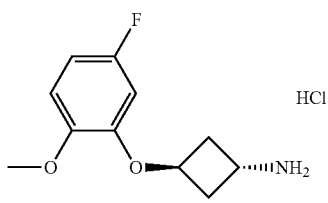

4.0 M HCl in dioxane (6 mL, 24 mmol) was added to tert-butyl ((trans)-3-(5-fluoro-2-methoxyphenoxy)cyclobutyl)carbamate (Intermediate 77A) (602 mg, 1.93 mmol) in DCM (2 mL). After 1 h, the reaction mixture was concentrated to give the title compound (481 mg, quantitative). $^1$H NMR (400 MHz, CD$_3$OD) δ 1.31 (t, J=6 Hz, 2H), 2.66 (dd, J=7, 6 Hz, 4H), 3.84 (s, 3H), 3.96-4.06 (m, 1H), 4.94-5.01 (m, 1H), 6.58 (dd, J=10, 3 Hz, 1H), 6.64-6.73 (m, 1H), 6.97 (dd, J=9, 5 Hz, 1H); LC-MS (LC-ES) M+H=212.

Intermediate 78: (trans)-4-(2-Hydroxypropan-2-yl)cyclohexanecarboxylic acid

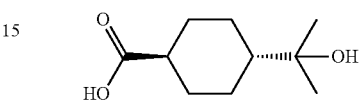

To a solution of (trans)-4-(methoxycarbonyl)cyclohexanecarboxylic acid (5.00 g, 26.9 mmol) in THF (120 mL) at −20° C. was added 3 M MeMgBr in ether (26.9 mL, 81 mmol), dropwise at such a rate that the internal temperature remained <−15° C. The mixture was slowly warmed to room temperature overnight and after 30 h was cooled to −20° C. An additional portion of MeMgBr (4.5 mL; 13.5 mmol) was added dropwise. The mixture was allowed to warm to room temperature overnight. After 40 h the mixture was cooled to 0° C. and slowly quenched by addition of 2 N aqueous HCl (50 mL). The layers were separated, and the aqueous layer was extracted with EtOAc (3×). The combined organic layers were washed with brine, dried over Na$_2$SO$_4$ and concentrated. The residue was dissolved in a minimal amount of Et$_2$O, and the product was precipitated by addition of hexanes and collected by filtration to afford the title compound as a colorless solid (4.36 g, 88%). $^1$H NMR (400 MHz, CD$_3$SOCD$_3$) δ 0.91-1.04 (m, 8H), 1.08-1.17 (m, 1H), 1.23 (qd, J=13, 3 Hz, 2H), 1.81 (dd, J=13, 3 Hz, 2H), 1.87-1.97 (m, 2H), 2.01-2.11 (m, 1H), 4.01 (s, 1H), 11.95 (s, 1H).

Intermediate 79: (trans)-3-(Quinolin-8-yloxy)cyclobutanecarboxylic acid

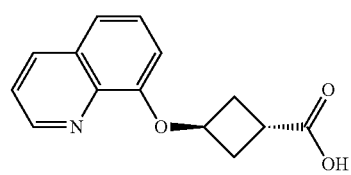 [SMILES: O=C(O)[C@H]1C[C@H](Oc2cccc3cccnc23)C1]

A. (trans)-Methyl 3-(quinolin-8-yloxy)cyclobutanecarboxylate

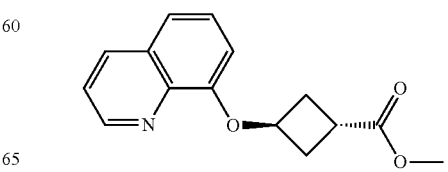

Triphenylphosphine (5.42 g, 20.7 mmol) was added to a solution of quinolin-8-ol (2.00 g, 13.8 mmol) in tetrahydrofuran (40 mL). The reaction mixture was cooled to 0° C., and (cis)-methyl 3-hydroxycyclobutanecarboxylate (2.15 g, 16.5 mmol) was added, followed by DIAD (4.0 mL, 21 mmol). The reaction mixture was then warmed to room temperature, stirred for 3 days, and diluted with water and EtOAc. The mixture was partitioned, and the aqueous layer was extracted with EtOAc. The organics were washed with water, dried over sodium sulfate, filtered, and concentrated. The residue was purified on silica gel eluting with a 30%-70% EtOAc-hexanes gradient to give the title compound as a thick oil (2.4 g, 66%). $^1$H NMR (400 MHz, CD$_3$SOCD$_3$) δ 2.74-2.84 (m, 2H), 2.86-2.96 (m, 2H), 3.23-3.31 (m, 1H), 3.78 (s, 3H), 5.14-5.23 (m, 1H), 6.91 (dd, J=7, 2 Hz, 1H), 7.41-7.52 (m, 3H), 8.16 (dd, J=8, 2 Hz, 1H), 8.98 (dd, J=4, 2 Hz, 1H); LC-MS (LC-ES) M+H=258.

B.
(trans)-3-(Quinolin-8-yloxy)cyclobutanecarboxylic acid

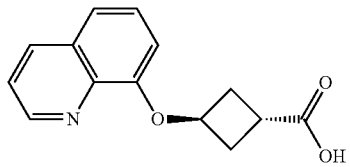

To a solution of (trans)-methyl 3-(quinolin-8-yloxy)cyclobutanecarboxylate (Intermediate 79A) (2.35 g, 9.13 mmol) in THF (15 mL) was added a solution of LiOH (1.15 g, 27.4 mmol) in water (7.5 mL). After 3 h, the mixture was adjusted to pH=4 with aqueous citric acid, and the aqueous phase was extracted with EtOAc (3×). The organic layers were combined, dried over Na$_2$SO$_4$, filtered and concentrated. The resulting yellow solid was triturated with diethyl ether to give the title compound (1.70 g, 77%). $^1$H NMR (400 MHz, CDCl$_3$) δ 2.80-2.89 (m, 2H), 2.94-3.05 (m, 2H), 3.41 (tt, J=10, 5 Hz, 1H), 5.14-5.19 (m, 1H), 6.92 (dd, J=8, 1 Hz, 1H), 7.34-7.57 (m, 3H), 8.21 (dd, J=8, 2 Hz, 1H), 9.14 (dd, J=4, 2 Hz, 1H); LC-MS (LC-ES) M+H=244.

Intermediate 80: 2-((trans)-3-(Quinolin-8-yloxy) cyclobutanecarboxamido)oxazole-4-carboxylic acid

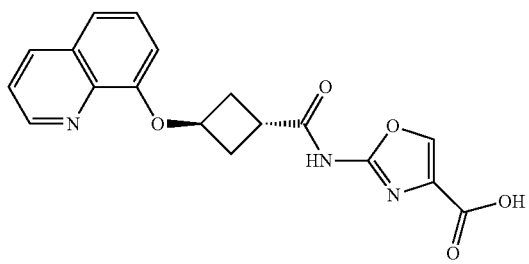 [SMILES: O=C(O)c1coc(NC(=O)[C@H]2C[C@H](Oc3cccc4cccnc34)C2)n1]

To a solution of ethyl 2-((trans)-3-(quinolin-8-yloxy)cyclobutanecarboxamido)oxazole-4-carboxylate (Example 171) (110 mg, 0.288 mmol) in THF (1.6 mL) was added a solution of LiOH (36 mg, 0.87 mmol) in water (0.80 mL). After 2 h, the reaction was concentrated and azeotroped with toluene (3×) to give the title compound as a pale yellow solid (50 mg, 49%). $^1$H NMR (400 MHz, CD$_3$SOCD$_3$) δ 2.40-2.50 (m, 2H), 2.71-2.81 (m, 2H), 3.10-3.20 (m, 1H), 5.03 (quin, J=6 Hz, 1H), 6.98 (dd, J=7, 2 Hz, 1H), 7.41-7.58 (m, 3H), 7.58-7.65 (m, 1H), 8.30 (dd, J=8, 2 Hz, 1H), 8.86 (dd, J=4, 2 Hz, 1H), 11.55-12.73 (br s, 1H); LC-MS (LC-ES) M+H=354.

Intermediate 81: 4-Cyclopropyloxazol-2-amine

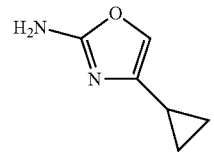

A. 1-Cyclopropyl-2-hydroxyethanone

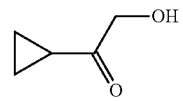

To neat 2-bromo-1-cyclopropylethanone (2 g, 12.3 mmol) was added 1 N aqueous NaOH (12.3 mL, 12.3 mmol). The mixture was stirred for 2 h and then extracted with EtOAc (5×). The organics were dried over MgSO$_4$, filtered and concentrated to give 1-cyclopropyl-2-hydroxyethane (1.1 g, 90%) as a dark liquid, which was used without further purification. $^1$H NMR (400 MHz, CDCl$_3$) δ 1.00-1.05 (m, 2H), 1.15-1.21 (m, 2H), 1.87 (tt, J=8, 5 Hz, 1H), 3.15 (s, 1H), 4.42 (d, J=5 Hz, 2H).

B. 4-Cyclopropyloxazol-2-amine

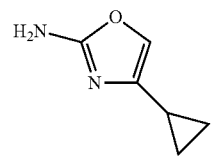

To a THF (2 mL) solution of 1-cyclopropyl-2-hydroxyethanone (450 mg, 4.49 mmol) and cyanamide (227 mg, 5.39 mmol) was added 2 M aqueous NaOH (2.92 mL, 5.84 mmol) dropwise. After stirring overnight, the mixture was partially concentrated, diluted with water, and extracted with EtOAc (5×) and chloroform (3×). The combined organics were dried over MgSO$_4$, filtered and concentrated. The residue was loaded onto a semi-prep HPLC (NH$_4$OH as modifier) to afford the title compound as a white solid (92 mg, 16%). $^1$H NMR (400 MHz, CDCl$_3$) δ 0.66-0.72 (m, 2H), 0.77-0.83 (m, 2H), 1.66 (tt, J=8, 5 Hz, 1H), 4.64 (br s, 2H), 6.92 (s, 1H); LC-MS (LC-ES) M+H=125.

Intermediate 82: 8-(Azetidin-3-yloxy)quinoline dihydrochloride

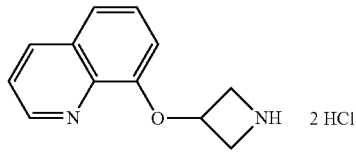 [SMILES: c1cnc2c(OC3CNC3)cccc2c1]

A. tert-Butyl 3-(quinolin-8-yloxy)azetidine-1-carboxylate

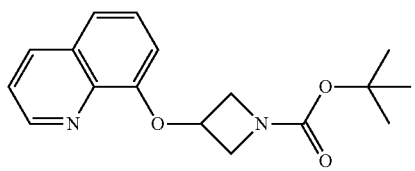 [SMILES: CC(C)(C)OC(=O)N1CC(Oc2cccc3cccnc23)C1]

To a stirred solution of tert-butyl 3-((methylsulfonyl)oxy)azetidine-1-carboxylate (Intermediate 1) (249 mg, 0.991 mmol) and quinolin-8-ol (145 mg, 0.999 mmol) in DMF (5 mL) was added cesium carbonate (360 g, 1.11 mmol). The mixture was heated to 80° C. overnight, poured into water and extracted with EtOAc (3×). The combined organic layers were washed with brine, dried over $Na_2SO_4$, filtered and concentrated. The remaining material was purified on silica gel eluting with a 0%-90% EtOAc-hexanes gradient to give the title compound (144 mg, 48%) as a white solid. $^1$H NMR (400 MHz, $CD_3SOCD_3$) δ 1.40 (s, 9H), 3.90-3.96 (m, 2H), 4.36-4.42 (m, 2H), 5.17-5.22 (m, 1H), 6.96 (d, J=8 Hz, 1H), 7.48 (t, J=6 Hz, 1H), 7.55-7.60 (m, 2H), 8.32-8.36 (m, 1H), 8.87-8.90 (m, 1H); LC-MS (LC-ES) M+H=301.

B. 8-(Azetidin-3-yloxy)quinoline dihydrochloride

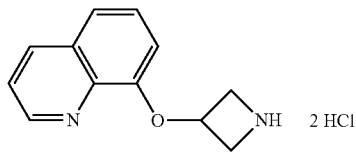 [SMILES: c1cnc2c(OC3CNC3)cccc2c1]

To tert-butyl 3-(quinolin-8-yloxy)azetidine-1-carboxylate (Intermediate 82A) (142 mg, 0.473 mmol) in methanol (1 mL), was added 4 M HCl in dioxane (4 mL, 16 mmol). The mixture was stirred at room temperature for 5 h and the solvent was removed in vacuo. The residue was diluted with diethyl ether, and the resulting precipitate was collected by filtration to give the title compound as a white solid (118 mg, 91%). $^1$H NMR (400 MHz, $CD_3OD$) δ 4.43-4.47 (m, 2H), 4.67-4.74 (m, 2H), 5.51-5.57 (m, 1H), 7.44 (d, J=8 Hz, 1H), 7.87 (t, J=6 Hz, 1H), 7.96 (d, J=8 Hz, 1H), 8.11-8.16 (m, 1H), 9.14-9.19 (m, 2H); LC-MS (LC-ES) M+H=201.

Intermediate 83: N-Methoxy-N-methyl-2-((trans)-3-(quinolin-8-yloxy)cyclobutanecarboxamido)thiazole-4-carboxamide

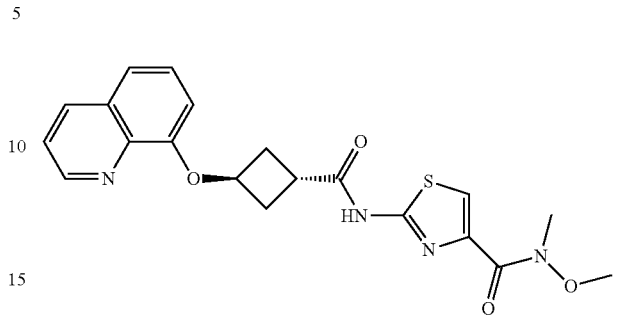

2-((trans)-3-(Quinolin-8-yloxy)cyclobutanecarboxamido)thiazole-4-carboxylic acid (Example 193) (97 mg, 0.26 mmol) was dissolved in DMF (5 mL) followed by the addition of N,N-diisopropylethylamine (0.23 mL, 1.3 mmol) and HATU (120 mg, 0.32 mmol). The reaction was stirred at room temperature for ca. 5 min, and N,O-dimethylhydroxylamine hydrochloride (38 mg, 0.39 mmol) was added. After 12 h, the reaction was quenched with water, extracted with EtOAc, dried over $Na_2SO_4$, filtered and concentrated. The residue was purified on silica gel, eluting with a 0%-100% EtOAc:EtOH (3:1)-hexanes gradient to give the title compound (34 mg, 31%). LC-MS (LC-ES) M+H=413.

Intermediate 84: 2-(2-Aminothiazol-5-yl)propan-2-ol

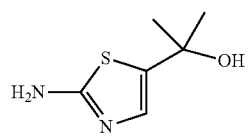

3 M methylmagnesium bromide in THF solution (1.17 mL, 3.52 mmol) was added to 1-(2-aminothiazol-5-yl)ethanone (0.10 g, 0.70 mmol) in THF (5 mL). After 3 h, the reaction mixture was poured into saturated aqueous ammonium chloride, and extracted with EtOAc. The combined organic layers were dried over $Na_2SO_4$ and evaporated under reduced pressure to give the title compound (42 mg, 36%). $^1$H NMR (400 MHz, $CD_3SOCD_3$) δ 1.39 (s, 6H), 5.11 (s, 1H), 6.55-6.66 (m, 3H); LC-MS (LC-ES) M+H=159.

Intermediate 85: 5-(Prop-1-en-2-yl)thiazol-2-amine, trifluoroacetic acid salt

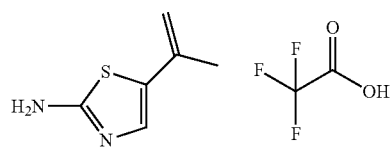

A. tert-Butyl (5-acetylthiazol-2-yl)carbamate

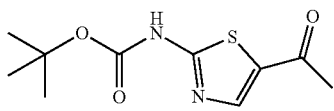 [SMILES: CC(=O)c1cnc(NC(=O)OC(C)(C)C)s1]

Boc-anhydride (0.86 mL, 3.7 mmol) was added to 1-(2-aminothiazol-5-yl)ethanone (0.50 g, 3.5 mmol), N,N-diisopropylethylamine (0.68 mL, 3.9 mmol) and DMAP (4 mg, 0.04 mmol) in THF (10 mL) at 0° C. The reaction mixture was warmed to room temperature and stirred overnight. The reaction was concentrated, and the residue was purified on silica gel, eluting with a 0%-100% EtOAc-hexanes gradient to give the title compound (409 mg, 48%). $^1$H NMR (400 MHz, CD$_3$SOCD$_3$) δ 1.47 (s, 9H), 2.44 (s, 3H), 8.22 (s, 1H), 11.95 (s, 1H); LC-MS (LC-ES) M−H=241.

B. tert-Butyl (5-(2-hydroxypropan-2-yl)thiazol-2-yl)carbamate

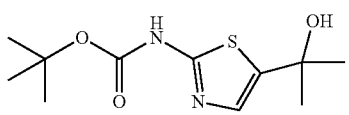 [SMILES: CC(C)(C)OC(=O)Nc1ncc(C(C)(C)O)s1]

3 M methylmagnesium bromide in THF (0.55 mL, 1.7 mmol) was added to tert-butyl (5-acetylthiazol-2-yl)carbamate (Intermediate 85A) (0.20 g, 0.83 mmol) in THF (5 mL). After 3 h, the reaction mixture was poured into saturated aqueous ammonium chloride, and extracted with EtOAc. The combined organic layers were dried over Na$_2$SO$_4$ and evaporated under reduced pressure. The residue was purified on silica gel, eluting with a 0%-100% EtOAc-hexanes gradient to give the title compound (150 mg, 68%). $^1$H NMR (400 MHz, CD$_3$SOCD$_3$) δ 1.44 (s, 15H), 3.29 (s, 1H), 5.34 (s, 1H), 7.05 (s, 1H); LC-MS (LC-ES) M−H=257.

C. 5-(Prop-1-en-2-yl)thiazol-2-amine, trifluoroacetic acid salt

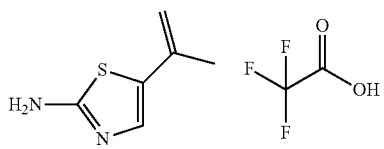

Trifluoroacetic acid (0.46 mL, 6.0 mmol) was added to a solution of tert-butyl (5-(2-hydroxypropan-2-yl)thiazol-2-yl)carbamate (Intermediate 85B) (155 mg, 0.600 mmol) in DCM (5 mL) cooled at 0° C. The reaction was allowed to warm to room temperature overnight and was concentrated. The resulting residue was triturated with hexanes to give the title compound (80 mg, 36%). $^1$H NMR (400 MHz, CD$_3$SOCD$_3$) δ 1.98 (s, 3H), 4.96 (d, J=11 Hz, 2H), 7.20 (br s, 1H); LC-MS (LC-ES) M+H=141.

Intermediate 86: 1-(2-Aminothiazol-4-yl)-2-methylpropan-2-ol hydrochloride

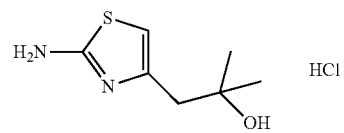

A. Methyl 2-(2-((tert-butoxycarbonyl)amino)thiazol-4-yl)acetate

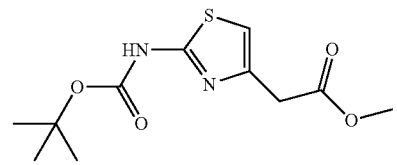 [SMILES: COC(=O)Cc1csc(NC(=O)OC(C)(C)C)n1]

Boc-anhydride (1.53 mL, 6.6 mmol) was added to methyl 2-(2-aminothiazol-4-yl)acetate (1.08 g, 6.28 mmol), N,N-diisopropylethylamine (1.21 mL, 6.91 mmol) and DMAP (8 mg, 0.06 mmol) in THF (20 mL) at 0° C. The reaction mixture was warmed to room temperature and stirred overnight, then heated to 90° C. After 2 h the reaction was concentrated, and the residue was purified on silica gel, eluting with a 0%-100% EtOAc-hexanes gradient to give the title compound (1.35 g, 79%). $^1$H NMR (400 MHz, CD$_3$SOCD$_3$) δ 1.44 (s, 9H), 1.96 (s, 2H), 3.62 (s, 3H), 6.89 (s, 1H), 11.39 (s, 1H); LC-MS (LC-ES) M−H=271.

B. tert-Butyl (4-(2-hydroxy-2-methylpropyl)thiazol-2-yl)carbamate

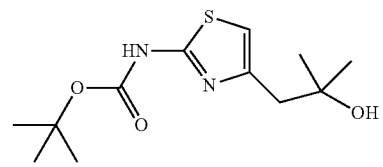 [SMILES: CC(C)(O)Cc1csc(NC(=O)OC(C)(C)C)n1]

3 M Methylmagnesium bromide in THF (0.98 mL, 2.9 mmol) was added to methyl 2-(2-((tert-butoxycarbonyl)amino)thiazol-4-yl)acetate (Intermediate 86A) (0.20 g, 0.73 mmol) in THF (5 mL). After 1 h, the reaction mixture was concentrated, and the residue was purified on silica gel, eluting with a 0%-100% EtOAc-hexanes gradient to give the title compound (159 mg, 73%). $^1$H NMR (400 MHz, CD$_3$SOCD$_3$) δ 1.04 (s, 6H), 1.44 (s, 9H), 3.57 (s, 2H), 6.89 (s, 1H), 11.38 (s, 1H); LC-MS (LC-ES) M−H=271.

C. 1-(2-Aminothiazol-4-yl)-2-methylpropan-2-ol hydrochloride

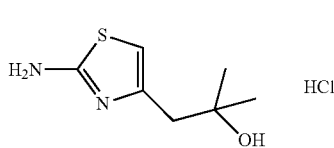

To tert-butyl (4-(2-hydroxy-2-methylpropyhthiazol-2-yl)carbamate (Intermediate 86B) (159 mg, 0.582 mmol) in DCM (2 mL), was added 4 M HCl in dioxane (0.29 mL, 1.2 mmol). The mixture was stirred at room temperature for 1 h and the solvent was removed in vacuo. The residue was purified on silica gel, eluting with a 0%-100% EtOAc-hexanes gradient to give the title compound (120 mg, 99%). $^1$H NMR (400 MHz, CD$_3$OD) δ 1.10 (s, 6H), 3.63 (s, 2H), 6.66 (s, 1H), 9.31 (br s, 2H); LC-MS (LC-ES) M+H=173.

Intermediate 87: 1-(2-Aminothiazol-5-yl)-2-methylpropan-2-ol

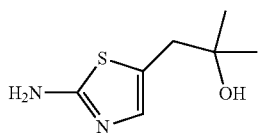

A. Ethyl 2-(2-((tert-butoxycarbonyl)amino)thiazol-5-yl)acetate

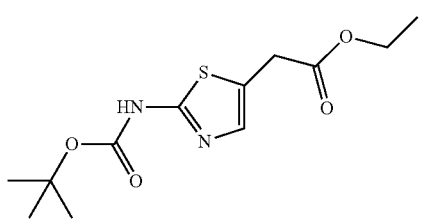 [SMILES: CCOC(=O)Cc1cnc(NC(=O)OC(C)(C)C)s1]

Boc-anhydride (1.18 mL, 5.07 mmol) was added to ethyl 2-(2-aminothiazol-5-yl)acetate (900 mg, 4.83 mmol), N,N-diisopropylethylamine (0.93 mL, 5.3 mmol) and DMAP (6 mg, 0.05 mmol) in THF (20 mL) at 0° C. The reaction mixture was warmed to room temperature. After 2 h the reaction was concentrated, and the residue was purified on silica gel, eluting with a 0%-100% EtOAc-hexanes gradient to give the title compound (1.01 g, 72%). $^1$H NMR (400 MHz, CD$_3$SOCD$_3$) δ 1.17 (t, J=7 Hz, 3H), 1.45 (s, 9H), 1.52 (s, 2H), 4.07 (q, J=7 Hz, 2H), 7.13 (s, 1H), 11.26 (br s, 1H); LC-MS (LC-ES) M−H=285.

B. tert-Butyl (5-(2-hydroxy-2-methylpropyl)thiazol-2-yl)carbamate

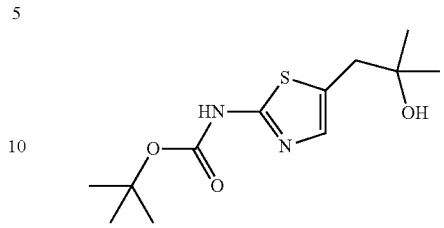

3 M Methylmagnesium bromide in THF (2.33 mL, 6.98 mmol) was added to ethyl 2-(2-((tert-butoxycarbonyl)amino)thiazol-5-yl)acetate (Intermediate 87A) (0.20 g, 0.70 mmol) in THF (5 mL). After 1 h, the reaction mixture was concentrated, and the residue was purified on silica gel, eluting with a 0%-100% EtOAc-hexanes gradient to give the title compound (159 mg, 73%). $^1$H NMR (400 MHz, CD$_3$SOCD$_3$) δ 1.05 (s, 6H), 1.44 (s, 9H), 2.71 (s, 2H), 4.49 (s, 1H), 6.98 (s, 1H), 11.08 (br s, 1H); LC-MS (LC-ES) peak at T=0.65 min.

C. 1-(2-Aminothiazol-5-yl)-2-methylpropan-2-ol

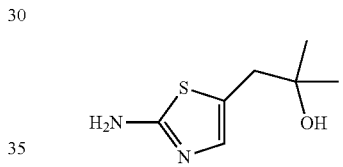

Trifluoroacetic acid (0.36 mL, 4.7 mmol) was added to a solution of tert-butyl (5-(2-hydroxy-2-methylpropyl)thiazol-2-yl)carbamate (Intermediate 87B) (0.128 g, 0.470 mmol) in DCM (5 mL) cooled at 0° C. The reaction mixture was warmed to room temperature. After stirring overnight, the solvent was removed, and the residue was basified to pH=9 by adding saturated aqueous NaHCO$_3$. The aqueous phase was extracted with ethyl acetate (3×), and the combined organic layers were washed with brine, dried over Na$_2$SO$_4$ and evaporated to give the title compound (21 mg, 26%). $^1$H NMR (400 MHz, CD$_3$OD) δ 1.04 (s, 6H), 2.57 (s, 2H), 4.35 (s, 1H), 6.53 (s, 2H), 6.56 (s, 1H); LC-MS (LC-ES) M+H=173.

Intermediate 88: (trans)-3-(Quinolin-8-ylamino)cyclobutanecarboxylic acid

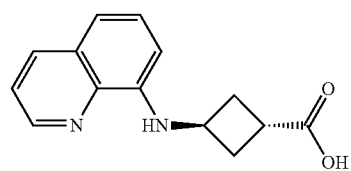

A. 4-Methyl-N-(quinolin-8-yl)benzenesulfonamide

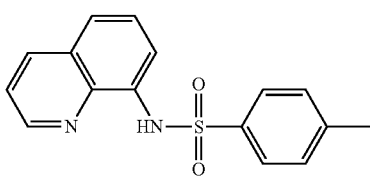 [SMILES: Cc1ccc(S(=O)(=O)Nc2cccc3cccnc23)cc1]

A solution of quinolin-8-amine (1.00 g, 6.94 mmol) and tosyl chloride (1.98 g, 10.4 mmol) in pyridine (15 mL) was heated in a microwave at 130° C. for 10 min. The reaction mixture was poured into water (100 mL), and the solid was collected and dried via vacuum filtration to give the title compound (1.88 g, 90%). $^1$H NMR (400 MHz, CD$_3$SOCD$_3$) δ 2.23 (m, 3H), 7.25 (d, J=12 Hz, 2H), 7.45-7.49 (m, 1H), 7.53-7.58 (m, 1H), 7.59-7.67 (m, 2H), 7.77 (d, J=12 Hz, 2H), 8.32 (d, J=12 Hz, 1H), 8.81-8.86 (m, 1H), 9.84 (br s, 1H); LC-MS (LC-ES) M−H=299.

B. (trans)-Methyl 3-(4-methyl-N-(quinolin-8-yl)phenyl)sulfonamido)cyclobutanecarboxylate

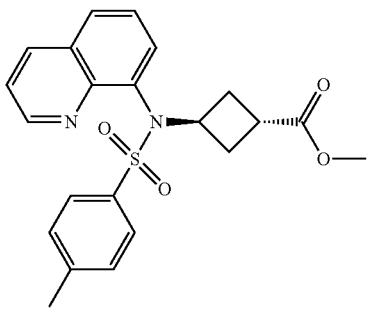 [SMILES: COC(=O)[C@H]1C[C@H](N(c2cccc3cccnc23)S(=O)(=O)c2ccc(C)cc2)C1]

Triphenylphosphine (0.948 g, 3.61 mmol) was added to a solution of 4-methyl-N-(quinolin-8-yl)benzenesulfonamide (Intermediate 88A) (1.08 g, 3.61 mmol) in tetrahydrofuran (30 mL). The reaction mixture was cooled to 0° C., and methyl 3-hydroxycyclobutanecarboxylate (0.35 mL, 3.0 mmol) was added, followed by DIAD (0.70 mL, 3.6 mmol). The reaction mixture was then warmed to room temperature, stirred overnight, and diluted with water and EtOAc. The mixture was partitioned, and the aqueous layer was extracted with EtOAc. The organics were washed with water, dried over sodium sulfate, filtered, and concentrated. The residue was purified on silica gel eluting with a 0%-100% EtOAc-hexanes gradient to give the title compound (0.691 g, 56%). $^1$H NMR (400 MHz, CD$_3$SOCD$_3$) δ 1.79-1.93 (m, 1H), 2.04 (dt, J=8, 4 Hz, 1H), 2.25-2.36 (m, 1H), 2.36-2.46 (m, 4H), 2.66-2.76 (m, 1H), 3.60 (s, 3H), 4.97 (t, J=8 Hz, 1H), 7.32 (d, J=8 Hz, 2H), 7.49-7.59 (m, 4H), 7.65 (t, J=8 Hz, 1H), 8.06 (dd, J=8, 1 Hz, 1H), 8.41 (dd, J=8, 1 Hz, 1H), 8.71 (dd, J=4, 2 Hz, 1H); LC-MS (LC-ES) M+H=411.

C. (trans)-3-(4-Methyl-N-(quinolin-8-yl)phenyl)sulfonamido)cyclobutanecarboxylic acid

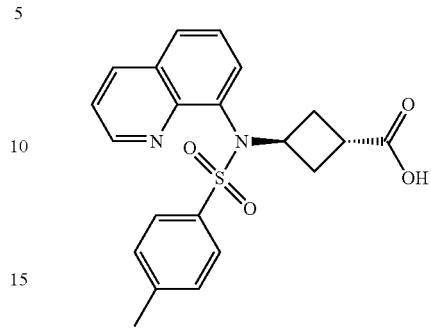

Lithium hydroxide (403 mg, 16.8 mmol) in water (5 mL) was added to a solution of (trans)-methyl 3-(4-methyl-N-(quinolin-8-yl)phenylsulfonamido)cyclobutanecarboxylate (Intermediate 88B) (690 mg, 1.68 mmol) in THF (15 mL). After 3 h, the reaction mixture was adjusted to pH 4 using saturated aqueous citric acid, and the aqueous phase was extracted with EtOAc (3×). The combined organic layers were dried over Na$_2$SO$_4$ and evaporated to give the title compound (666 mg, quantitative). $^1$H NMR (400 MHz, CD$_3$SOCD$_3$) δ 1.11-1.16 (m, 1H), 1.69-1.74 (m, 1H), 1.74-1.82 (m, 1H), 1.91-1.98 (m, 1H), 2.18-2.24 (m, 1H), 2.32 (s, 3H), 4.83-4.92 (m, 1H), 7.27 (d, J=8 Hz, 2H), 7.45-7.53 (m, 4H), 7.61 (t, J=8 Hz, 1H), 8.02 (d, J=8 Hz, 1H), 8.38 (d, J=8 Hz, 1H), 8.65-8.69 (m, 1H); LC-MS (LC-ES) M+H=397.

D. (trans)-3-(Quinolin-8-ylamino)cyclobutanecarboxylic acid

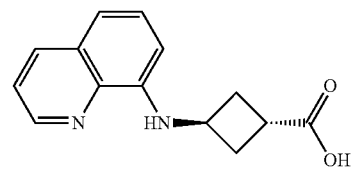 [SMILES: O=C(O)[C@H]1C[C@H](Nc2cccc3cccnc23)C1]

A solution of (trans)-3-(4-methyl-N-(quinolin-8-yl)phenylsulfonamido)cyclobutanecarboxylic acid (Intermediate 88C) (666 mg, 1.68 mmol) in concentrated aqueous H$_2$SO$_4$ (0.38 mL, 71 mmol) was stirred at 110° C. After 2 h, the reaction mixture was adjusted to neutral pH using 1 M aqueous NaOH, and the aqueous phase was extracted with EtOAc (3×). The combined organic layers were dried over Na$_2$SO$_4$, and evaporated to give the title compound (326 mg, 80%). $^1$H NMR (400 MHz, CD$_3$SOCD$_3$) δ 2.24-2.34 (m, 2H), 2.60-2.69 (m, 2H), 3.02-3.11 (m, 1H), 4.12-4.22 (m, 1H), 6.50-6.53 (m, 1H), 6.58-6.62 (m, 1H), 7.06-7.11 (m, 1H), 7.32-7.36 (m, 1H), 7.48-7.54 (m, 1H), 8.19-8.24 (m, 1H), 8.72-8.77 (m, 1H), 12.03 (br s, 1H); LC-MS (LC-ES) M+H=243.

Intermediate 89: tert-Butyl 3-(thieno[3,2-b]pyridin-3-yloxy)azetidine-1-carboxylate

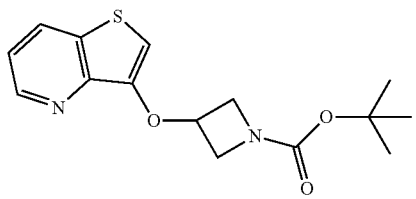 [SMILES: CC(C)(C)OC(=O)N1CC(Oc2csc3cccnc23)C1]

A. Methyl 3-hydroxythieno[3,2-b]pyridine-2-carboxylate

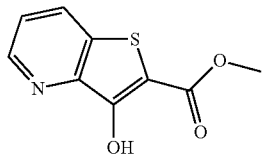

To methyl 3-chloropicolinate (1.0 g, 5.8 mmol) and sodium tert-butoxide (1.23 g, 12.8 mmol) in DMF (12 ml) was added methyl thioglycolate (0.62 ml, 7.0 mmol), and this mixture was heated to 65° C. overnight. The reaction was allowed to cool, and the mixture was stirred vigorously and diluted with water. The resulting precipitate was collected by filtration and dried under vacuum to give the title compound as a yellow solid (55 mg, 9%). $^1$H NMR (400 MHz, CD$_3$OD) δ 3.82 (s, 3H), 7.32 (dd, J=8, 4 Hz, 1H), 8.06 (d, J=8 Hz, 1H), 8.51 (d, J=4 Hz, 1H); LC-MS (LC-ES) M+H=210.

B. tert-Butyl 3-(thieno[3,2-b]pyridin-3-yloxy)azetidine-1-carboxylate

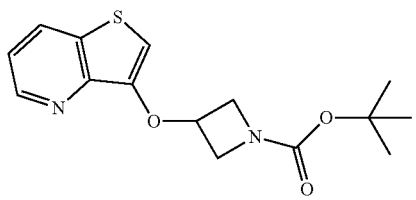 [SMILES: CC(C)(C)OC(=O)N1CC(Oc2csc3cccnc23)C1]

To a stirred solution of tert-butyl 3-((methylsulfonyl)oxy)azetidine-1-carboxylate (Intermediate 1) (107 mg, 0.426 mmol) and methyl 3-hydroxythieno[3,2-b]pyridine-2-carboxylate (Intermediate 89A) (75 mg, 0.36 mmol) in DMF (0.8 mL) was added cesium carbonate (140 g, 0.430 mmol). The mixture was heated to 110° C. overnight, poured into water and extracted with EtOAc (3×). The combined organic layers were washed with brine, dried over Na$_2$SO$_4$, filtered and concentrated. The remaining material was purified on silica gel eluting with a 30%-90% EtOAc-heptane gradient to give material that was further purified on reverse-phase silica gel, eluting with a 5%-95% acetonitrile-water (TFA additive) gradient. The appropriate fractions were concentrated, and the resulting material was diluted with ethyl acetate and washed with saturated aqueous sodium bicarbonate and brine. The organics were dried over sodium sulfate, filtered and concentrated to give the title compound (50 mg, 46%) as a yellow solid. $^1$H NMR (400 MHz, CDCl$_3$) δ 1.46 (s, 9H), 4.14-4.23 (m, 2H), 4.38 (dd, J=10, 7 Hz, 2H), 5.01-5.12 (m, 1H), 6.67 (s, 1H), 7.59 (dd, J=8, 5 Hz, 1H), 8.42 (d, J=8 Hz, 1H), 8.90 (d, J=5 Hz, 1H); LC-MS (LC-ES) M+H=307.

Intermediate 90: (trans)-3-((5-Fluorobenzofuran-7-yl)oxy)cyclobutanecarboxylic acid

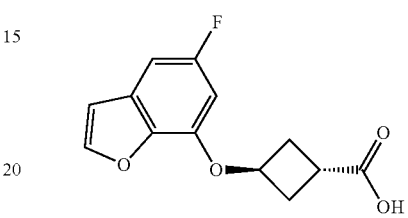

A. 2-(5-Fluorobenzofuran-7-yl)-4,4,5,5-tetramethyl-1,3,2-dioxaborolane

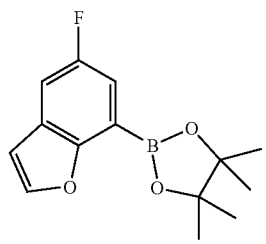 [SMILES: CC1(C)OB(c2cc(F)cc3ccoc23)OC1(C)C]

7-Bromo-5-fluorobenzofuran (0.25 g, 1.16 mmol), bis(pinacolato)diboron (0.354 g, 1.40 mmol), potassium acetate (0.285 g, 2.91 mmol), and PdCl$_2$(dppf)-CH$_2$Cl$_2$ adduct (0.095 g, 0.12 mmol) were stirred in DMSO (3.0 ml). The reaction solution was degassed and flushed with nitrogen and heated to 85° C. After 5 h, the reaction was allowed to cool overnight, and was diluted with ethyl acetate and washed with water and brine. The organic layers were dried over sodium sulfate, filtered, and concentrated. The material was purified by silica gel chromatography eluting with a 10%-60% ethyl acetate in heptanes gradient to give the title compound (237 mg, 78%) as a white crystalline solid. $^1$H NMR (400 MHz, CDCl$_3$) δ 1.41 (s, 12H), 6.73 (d, J=2 Hz, 1H), 7.31-7.35 (m, 1H), 7.45 (dd, J=9, 3 Hz, 1H), 7.76 (d, J=2 Hz, 1H); LC-MS (LC-ES) M−H=263.

B. 5-Fluorobenzofuran-7-ol

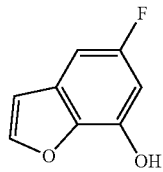 [SMILES: Oc1cc(F)cc2ccoc12]

To 2-(5-fluorobenzofuran-7-yl)-4,4,5,5-tetramethyl-1,3,2-dioxaborolane (Intermediate 90A) (0.23 g, 0.88 mmol) in ethanol (1.0 ml) at 0° C. was added 30% H$_2$O$_2$ in water (0.1 ml, 1 mmol). After 2 h, the reaction was quenched with 10% aqueous Na$_2$S$_2$O$_3$, diluted with water and extracted with ethyl acetate (2×). The combined organic layers were washed with brine, dried over sodium sulfate, filtered and concentrated to give the title compound (86 mg, 64%) as an oil which was used without further purification. $^1$H NMR (400 MHz, CD$_3$SOCD$_3$) δ 6.55 (dd, J=11, 3 Hz, 1H), 6.85 (dd, J=9, 2 Hz, 1H), 6.88 (d, J=2 Hz, 1H), 7.98 (d, J=2 Hz, 1H), 10.52 (s, 1H); LC-MS (LC-ES) M+H=153.

C. (trans)-Methyl 3-((5-fluorobenzofuran-7-yl)oxy)cyclobutanecarboxylate

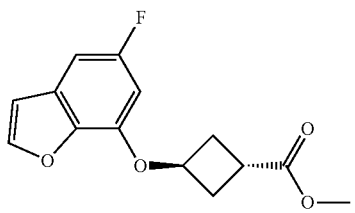 [SMILES: COC(=O)[C@H]1C[C@H](Oc2cc(F)cc3ccoc23)C1]

Triphenylphosphine (161 mg, 0.615 mmol) was added to a solution of 5-fluorobenzofuran-7-ol (Intermediate 90B) (85 mg, 0.56 mmol) in tetrahydrofuran (0.6 mL). The reaction mixture was cooled to 0° C., and (cis)-methyl 3-hydroxycyclobutanecarboxylate (87 mg, 0.67 mmol) was added, followed by DIAD (0.12 mL, 0.62 mmol). After 10 min, the reaction mixture was warmed to room temperature, stirred for 5 days, and diluted with water and EtOAc. The mixture was partitioned, and the aqueous layer was extracted with EtOAc. The organic layer was washed with water, dried over sodium sulfate, filtered, and concentrated. The residue was purified on silica gel eluting with a 10%-50% EtOAc-heptane gradient to give the title compound (71 mg, 48%). $^1$H NMR (400 MHz, CDCl$_3$) δ 2.54-2.67 (m, 2H), 2.81 (qd, J=7, 4 Hz, 2H), 3.19-3.28 (m, 1H), 3.75 (s, 3H), 5.02-5.10 (m, 1H), 6.41 (dd, J=11, 2 Hz, 1H), 6.72 (d, J=1 Hz, 1H), 6.85 (dd, J=8, 2 Hz, 1H), 7.63 (d, J=2 Hz, 1H); LC-MS (LC-ES) M+H=265.

D. (trans)-3-((5-Fluorobenzofuran-7-yl)oxy)cyclobutanecarboxylic acid

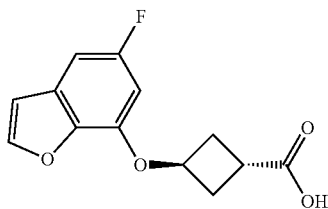 [SMILES: O=C(O)[C@H]1C[C@H](Oc2cc(F)cc3ccoc23)C1]

To a solution of (trans)-methyl 3-((5-fluorobenzofuran-7-yl)oxy)cyclobutanecarboxylate (Intermediate 90C) (70 mg, 0.27 mmol) in THF (2 mL) was added a solution of LiOH (17 mg, 0.40 mmol) in water (0.5 mL). After stirring overnight, the reaction was concentrated. The residue was treated with 1 N aqueous HCl and extracted with EtOAc (3×). The combined organic layers were dried over Na$_2$SO$_4$, filtered and concentrated to give the title compound (72 mg, quantitative) as a white solid. LC-MS (LC-ES) M−H=249.

Intermediate 91: (trans)-Methyl 3-(3-bromophenoxy)cyclobutanecarboxylate

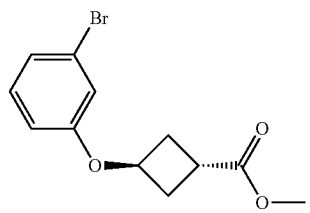 [SMILES: COC(=O)[C@H]1C[C@H](Oc2cccc(Br)c2)C1]

Triphenylphosphine (364 mg, 1.39 mmol) was added to a solution of 3-bromophenol (200 mg, 1.16 mmol) in tetrahydrofuran (1.2 mL). The reaction mixture was cooled to 0° C., and (cis)-methyl 3-hydroxycyclobutanecarboxylate (181 mg, 1.39 mmol) was added, followed by DIAD (0.25 mL, 1.3 mmol). After 10 min, the reaction mixture was warmed to room temperature, stirred for 3 days, and diluted with water and EtOAc. The mixture was partitioned, and the aqueous layer was extracted with EtOAc. The organic layer was washed with water, dried over sodium sulfate, filtered, and concentrated. The residue was purified on silica gel eluting with a 10%-60% EtOAc-heptane gradient to give the title compound (265 mg, 80%). $^1$H NMR (400 MHz, CDCl$_3$) δ 2.40-2.51 (m, 2H), 2.74 (ddd, J=14, 7, 4 Hz, 2H), 3.14-3.25 (m, 1H), 3.75 (s, 3H), 4.88 (quin, J=7 Hz, 1H), 6.73 (d, J=7 Hz, 1H), 6.95 (s, 1H), 7.05-7.18 (m, 2H); LC-MS (LC-ES) M+H=285, 287 (Br pattern).

Intermediate 92: (trans)-3-(2,5-Difluorophenoxy)cyclobutanecarboxylic acid

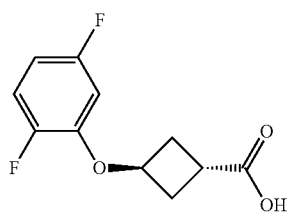 [SMILES: O=C(O)[C@H]1C[C@H](Oc2cc(F)ccc2F)C1]

A. (trans)-Methyl 3-(2,5-difluorophenoxy)cyclobutanecarboxylate

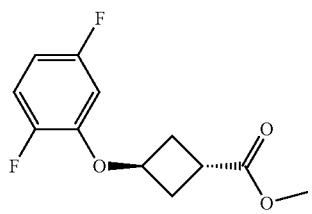 [SMILES: COC(=O)[C@H]1C[C@H](Oc2cc(F)ccc2F)C1]

Triphenylphosphine (484 mg, 1.85 mmol) was added to a solution of 2,5-difluorophenol (0.2 g, 1.537 mmol) in tetrahydrofuran (1.7 mL). The reaction mixture was cooled to 0°

C., and (cis)-methyl 3-hydroxycyclobutanecarboxylate (240 mg, 1.85 mmol) was added, followed by DIAD (0.35 mL, 1.8 mmol). After 10 min, the reaction mixture was warmed to room temperature, stirred for 3 days, and diluted with water and EtOAc. The mixture was partitioned, and the aqueous layer was extracted with EtOAc. The organic layer was washed with water, dried over sodium sulfate, filtered, and concentrated. The residue was purified on silica gel eluting with a 10%-60% EtOAc-heptane gradient to give the title compound (236 mg, 63%). $^1$H NMR (400 MHz, CDCl$_3$) δ 2.48-2.59 (m, 2H), 2.76 (ddd, J=14, 7, 4 Hz, 2H), 3.16-3.26 (m, 1H), 3.75 (s, 3H), 4.90 (quin, J=7 Hz, 1H), 6.49-6.63 (m, 2H), 7.02 (ddd, J=10, 9, 5 Hz, 1H); LC-MS (LC-ES) M+H=243.

B. (trans)-3-(2,5-Difluorophenoxy)cyclobutanecarboxylic acid

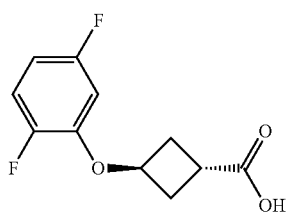

To a solution of (trans)-methyl 3-(2,5-difluorophenoxy)cyclobutanecarboxylate (Intermediate 92A) (230 mg, 0.950 mmol) in THF (4 mL), methanol (2 mL) and water (2 mL) was added LiOH (68 mg, 2.85 mmol). After stirring overnight, the reaction was concentrated. The residue was taken up in water and treated with 6 N aqueous HCl until a precipitate began to form. This solid was collected by filtration and dried under vacuum to give the title compound (185 mg, 85%) as a white solid. $^1$H NMR (400 MHz, CD$_3$SOCD$_3$) δ 2.29-2.40 (m, 2H), 2.68 (qd, J=7, 5 Hz, 2H), 3.05-3.15 (m, 1H), 4.89 (quin, J=7 Hz, 1H), 6.70-6.80 (m, 1H), 6.86 (ddd, J=10, 7, 3 Hz, 1H), 7.26 (ddd, J=11, 9, 6 Hz, 1H), 12.34 (s, 1H); LC-MS (LC-ES) M−H=227.

Intermediate 93: Lithium (trans)-3-(2-chloro-5-fluorophenoxy)cyclobutanecarboxylate

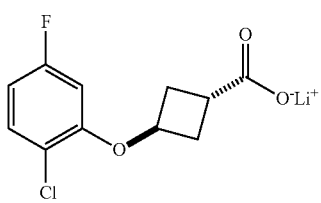

A. (trans)-Methyl 3-(2-chloro-5-fluorophenoxy)cyclobutanecarboxylate

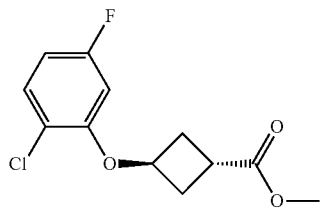 [SMILES: COC(=O)[C@H]1C[C@H](Oc2cc(F)ccc2Cl)C1]

Triphenylphosphine (430 mg, 1.64 mmol) was added to a solution of 2-chloro-5-fluorophenol (200 mg, 1.37 mmol) in tetrahydrofuran (2 mL). The reaction mixture was cooled to 0° C., and (cis)-methyl 3-hydroxycyclobutanecarboxylate (213 mg, 1.64 mmol) was added, followed by DIAD (0.32 mL, 1.6 mmol). After 10 min, the reaction mixture was warmed to room temperature, stirred for 3 days, and diluted with water and EtOAc. The mixture was partitioned, and the aqueous layer was extracted with EtOAc. The organic layer was washed with water, dried over sodium sulfate, filtered, and concentrated. The residue was purified on silica gel eluting with a 10%-50% EtOAc-heptane gradient to give the title compound (264 mg, 64%) as a yellow oil. $^1$H NMR (400 MHz, CDCl$_3$) δ 2.50-2.61 (m, 2H), 2.78 (ddd, J=14, 7, 4 Hz, 2H), 3.18-3.28 (m, 1H), 3.76 (s, 3H), 4.91 (quin, J=7 Hz, 1H), 6.49 (dd, J=10, 3 Hz, 1H), 6.63 (td, J=8, 3 Hz, 1H), 7.30 (dd, J=9, 6 Hz, 1H); LC-MS (LC-ES) M+H=259, 261 (Cl pattern).

B. Lithium (trans)-3-(2-chloro-5-fluorophenoxy)cyclobutanecarboxylate

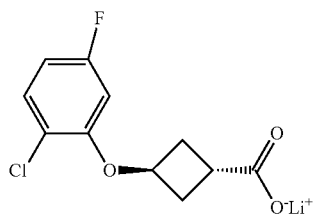

To a solution of (trans)-methyl 3-(2-chloro-5-fluorophenoxy)cyclobutanecarboxylate (Intermediate 93A) (245 mg, 0.947 mmol) in THF (4 mL), methanol (2 mL) and water (2 mL) was added LiOH (68 mg, 2.84 mmol). After stirring overnight, the reaction was concentrated to give the title compound (248 mg, quantitative) as a white solid that was used crude. $^1$H NMR (400 MHz, CD$_3$SOCD$_3$) δ 2.03-2.15 (m, 2H), 2.53-2.66 (m, 3H), 4.81-4.92 (m, 1H), 6.69 (d, J=11 Hz, 1H), 6.80 (td, J=8, 3 Hz, 1H), 7.45 (dd, J=9, 6 Hz, 1H); LC-MS (LC-ES) M−H=243, 245 (Cl pattern).

Intermediate 94: 1-(5-Methylpyridin-2-yl)azetidin-3-amine

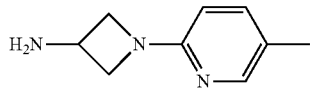

A. Benzyl (1-(5-methylpyridin-2-yl)azetidin-3-yl)carbamate

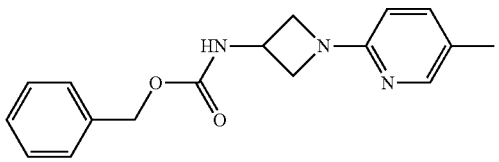

To benzyl azetidin-3-ylcarbamate (1.24 g, 6.00 mmol) and 2-chloro-5-methylpyridine (638 mg, 5.00 mmol) in toluene (8 mL) was added sodium tert-butoxide (577 mg, 6.00 mmol) followed by BINAP (78 mg, 0.13 mmol) and $Pd_2(dba)_3$ (73 mg, 0.080 mmol). The resulting mixture was heated to 70° C. overnight. The reaction was allowed to cool, ether was added and the mixture was washed with brine (3×). The washing was extracted with ether, and the organics were combined and dried over $MgSO_4$, filtered, concentrated and purified on silica gel, eluting with 20% to 85% EtOAc in hexanes to afford the title compound (640 mg, 43%), a pale yellow solid. $^1$H NMR (400 MHz, $CDCl_3$) δ 2.21 (s, 3H), 3.79 (dd, J=8, 6 Hz, 2H), 4.35 (t, J=8 Hz, 2H), 4.70 (d, J=7 Hz, 1H), 5.14 (s, 2H), 5.25 (d, J=8 Hz, 1H), 6.28 (d, J=9 Hz, 1H), 7.29-7.42 (m, 6H), 7.91-8.00 (m, 1H); LC-MS (LC-ES) M+H=298.

B. 1-(5-Methylpyridin-2-yl)azetidin-3-amine

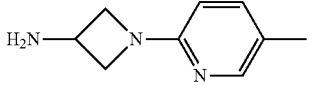

Palladium on carbon (379 mg, 0.356 mmol) was added to benzyl (1-(5-methylpyridin-2-yl)azetidin-3-yl)carbamate (Intermediate 94A) (0.530 g, 1.78 mmol) in EtOAc (5 mL) and MeOH (15 mL) under a nitrogen atmosphere. The reaction vessel was fitted with a hydrogen balloon, and the vessel was repeatedly evacuated and purged with hydrogen, then stirred for 6 h under a hydrogen atmosphere. The vessel was repeatedly evacuated and purged with nitrogen, filtered through Celite®, and concentrated to give the title compound (417 mg, quantitative). $^1$H NMR (400 MHz, $CD_3OD$) δ 2.30 (s, 3H), 4.29-4.41 (m, 3H), 4.60-4.69 (m, 2H), 6.88 (d, J=9 Hz, 1H), 7.84 (s, 1H), 7.90 (dd, J=9, 2 Hz, 1H); LC-MS (LC-ES) M+H=164.

Intermediate 95: 4-Nitrophenyl (1-(5-methylpyridin-2-yl)azetidin-3-yl)carbamate

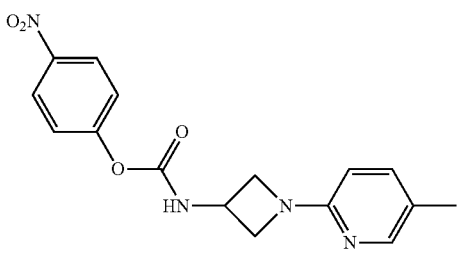 [SMILES: Cc1ccc(N2CC(NC(=O)Oc3ccc([N+](=O)[O-])cc3)C2)nc1]

To 4-nitrophenyl chloroformate (278 mg, 1.38 mmol) and 1-(5-methylpyridin-2-yl)azetidin-3-amine (Intermediate 94) (150 mg, 0.919 mmol) in DCM (5 mL) at 0° C. was added pyridine (0.11 mL, 1.4 mmol), and the mixture was allowed to warm to room temperature. After 3 h, the resulting solid was collected by filtration and washed with DCM and acetonitrile to give the title compound as a white solid (113 mg, 38%). $^1$H NMR (400 MHz, $CDCl_3$) δ 2.22 (s, 3H), 4.74-4.79 (m, 4H), 4.81-4.91 (m, 1H), 6.53 (d, J=9 Hz, 1H), 7.34 (d, J=9 Hz, 2H), 7.61-7.69 (m, 1H), 7.77 (s, 1H), 7.92 (br s, 1H), 8.27 (d, J=9 Hz, 2H); LC-MS (LC-ES) M+H=329.

Intermediate 96: Racemic 1-(6-Aminospiro[3.3]heptan-2-yl)propan-1-one hydrochloride

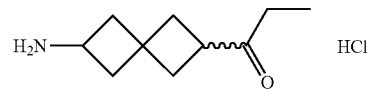

A. Racemic tert-Butyl (6-(1-hydroxycyclopropyl)spiro[3.3]heptan-2-yl)carbamate

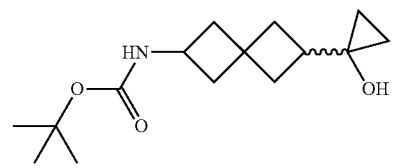 [SMILES: CC(C)(C)OC(=O)NC1CC2(C1)CC(C1(O)CC1)C2]

To a stirred solution of methyl 6-((tert-butoxycarbonyl)amino)spiro[3.3]heptane-2-carboxylate (500 mg, 1.87 mmol) and titanium(IV) isopropoxide (0.11 mL, 0.37 mmol) in diethyl ether (7 mL) was added 3 M ethylmagnesium bromide in ether (1.86 mL, 5.57 mmol) over 30 min (using water bath to keep the temperature from rising). After 1 h, the reaction was poured into water, and 10% aqueous sulfuric acid solution was added at 0° C. until the mixture was clear. The mixture was extracted with EtOAc, and the combined organics were washed with water, brine, dried over $MgSO_4$, filtered and then concentrated. The residue was purified on silica gel, eluting with 0% to 60% EtOAc in hexanes to afford the title compound (62 mg, 12%). $^1$H NMR (400 MHz, $CDCl_3$) δ 0.40-0.50 (m, 2H), 0.66-0.75 (m, 2H), 1.45 (s, 9H), 1.70-1.97 (m, 6H), 2.02-2.13 (m, 1H), 2.18-2.42 (m, 2H), 2.44-2.56 (m, 1H), 4.00 (br s, 1H), 4.61 (br s, 1H.

B. Racemic 1-(6-Aminospiro[3.3]heptan-2-yl)propan-1-one hydrochloride

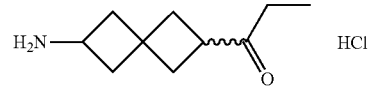

To tert-butyl (6-(1-hydroxycyclopropyl)spiro[3.3]heptan-2-yl)carbamate (Intermediate 96A) (62 mg, 0.23 mmol) in DCM (1 mL) at 0° C. was added 4 M HCl in dioxane (1 mL, 4 mmol). The mixture was stirred at room temperature for 1 h and the solvent was removed in vacuo at room temperature to give the title compound (56 mg, quantitative), which was used crude. $^1$H NMR (400 MHz, CD$_3$OD) δ 1.03 (t, J=7 Hz, 3H), 2.15-2.39 (m, 6H), 2.44 (q, J=7 Hz, 2H), 2.55 (ddd, J=12, 7, 5 Hz, 1H), 3.24-3.33 (m, 1H), 3.58-3.72 (m, 2H).

Intermediate 97: 6-(3-Aminoazetidin-1-yl)-N-(2-ethoxyethyl)pyridazine-3-carboxamide dihydrochloride

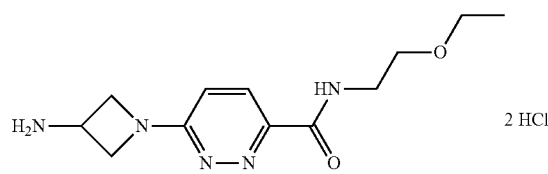 [SMILES: CCOCCNC(=O)c1ccc(N2CC(N)C2)nn1 ; "2 HCl"]

2 HCl

A.
6-Chloro-N-(2-ethoxyethyl)pyridazine-3-carboxamide

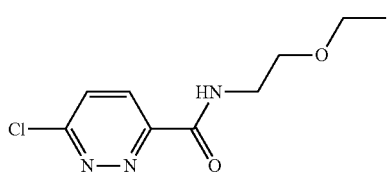

To a DMF (5 mL) solution of 6-chloropyridazine-3-carboxylic acid (430 mg, 2.71 mmol) and 2-ethoxyethanamine (508 mg, 5.70 mmol) was added, dropwise, a 50% solution of T3P in ethyl acetate (1.73 mL, 2.71 mmol). The mixture was stirred overnight, quenched with water for 10 min and extracted with EtOAc. The combined organics were washed with water and brine, dried over MgSO$_4$, filtered and then concentrated to give the title compound (536 mg, 86%) as a white solid. $^1$H NMR (400 MHz, CDCl$_3$) δ 1.17-1.30 (m, 3H), 3.57 (q, J=7 Hz, 2H), 3.61-3.68 (m, 2H), 3.70-3.79 (m, 2H), 7.71 (d, J=9 Hz, 1H), 8.30 (d, J=9 Hz, 1H), 8.37 (br s, 1H); LC-MS (LC-ES) M+H=230.

B. tert-Butyl (1-(6-((2-ethoxyethyl)carbamoyl)pyridazin-3-azetidin-3-yl)carbamate

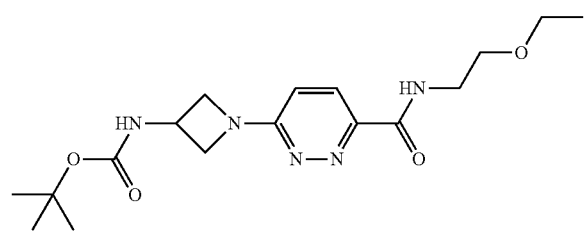 [SMILES: CCOCCNC(=O)c1ccc(N2CC(NC(=O)OC(C)(C)C)C2)nn1]

To a reaction vial with tert-butyl azetidin-3-ylcarbamate hydrochloride (360 mg, 2.09 mmol) in acetonitrile (15 mL) was added 6-chloro-N-(2-ethoxyethyl)pyridazine-3-carboxamide (Intermediate 97A) (480 mg, 2.09 mmol) and N,N-diisopropylethylamine (0.55 mL, 3.1 mmol). The mixture was heated at 105° C. overnight, cooled and concentrated. The resulting residue was purified on silica gel eluting with a 5%-25% MeOH in DCM gradient to give the title compound (535 mg, 70%) as a pale yellow solid. $^1$H NMR (400 MHz, CD$_3$OD) δ 1.21 (t, J=7 Hz, 3H), 1.48 (s, 9H), 3.52-3.68 (m, 6H), 4.06 (dd, J=9, 6 Hz, 2H), 4.49 (t, J=8 Hz, 2H), 4.62 (d, J=6 Hz, 1H), 6.90 (d, J=9 Hz, 1H), 7.94 (d, J=9 Hz, 1H); LC-MS (LC-ES) M+H=366.

C. 6-(3-Aminoazetidin-1-yl)-N-(2-ethoxyethyl)pyridazine-3-carboxamide dihydrochloride

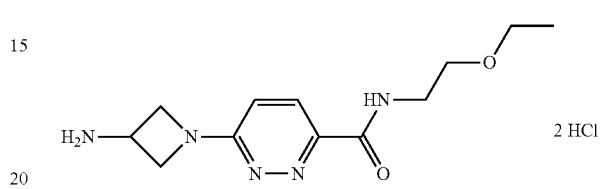

2 HCl

To tert-butyl (1-(6-((2-ethoxyethyl)carbamoyl)pyridazin-3-yl)azetidin-3-yl)carbamate (Intermediate 97B) (535 mg, 1.46 mmol) in DCM (2 mL) was added 4 N HCl in dioxane (3 mL, 12 mmol). The mixture was stirred at room temperature for 2 h, and the solvent was removed in vacuo to give the title compound as a light tan solid (388 mg, quantitative). $^1$H NMR (400 MHz, CD$_3$OD) δ 1.20 (t, J=7 Hz, 3H), 3.50-3.64 (m, 6H), 4.41-4.49 (m, 1H), 4.58 (ddd, J=11, 5, 1 Hz, 2H), 4.79-4.88 (m, 2H), 7.61 (d, J=10 Hz, 1H), 8.32 (d, J=10 Hz, 1H); LC-MS (LC-ES) M+H=266.

Intermediate 98: 1-(Pyrazin-2-yl)azetidin-3-amine dihydrochloride

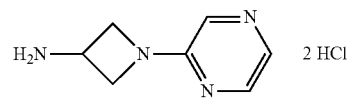 [SMILES: NC1CN(c2cnccn2)C1 ; "2 HCl"]

2 HCl

A. tert-Butyl (1-(pyrazin-2-yl)azetidin-3-yl)carbamate

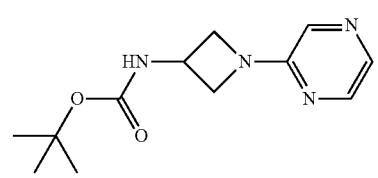 [SMILES: CC(C)(C)OC(=O)NC1CN(c2cnccn2)C1]

To a reaction vial with tert-butyl azetidin-3-ylcarbamate hydrochloride (902 mg, 5.24 mmol) in acetonitrile (15 mL) was added 2-chloropyrazine (600 mg, 5.24 mmol) and N,N-diisopropylethylamine (1.37 mL, 7.86 mmol). The mixture was heated to 100° C. for 1 h, heated to 90° C. overnight, cooled, and concentrated. The resulting residue was purified on silica gel eluting with a 5%-20% MeOH in DCM gradient to give the title compound (595 mg, 45%) as a white solid. $^1$H NMR (400 MHz, CD$_3$OD) δ 1.47 (s, 9H), 3.94 (dd, J=8, 6 Hz, 2H), 4.38 (t, J=8 Hz, 2H), 4.58 (d, J=6 Hz, 1H), 7.83 (dd, J=11, 2 Hz, 2H), 8.03 (dd, J=3, 2 Hz, 1H); LC-MS (LC-ES) M+H=251.

B. 1-(Pyrazin-2-yl)azetidin-3-amine dihydrochloride

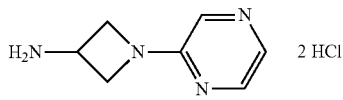

To tert-butyl (1-(pyrazin-2-yl)azetidin-3-yl)carbamate (Intermediate 98A) (590 mg, 2.36 mmol) in DCM (2 mL) was added 4 N HCl in dioxane (3 mL, 12 mmol). The mixture was stirred at room temperature for 1.5 h, and the solvent was removed in vacuo to give the title compound as a yellow solid (574 mg, quantitative). $^1$H NMR (400 MHz, CD$_3$OD) δ 4.30-4.48 (m, 3H), 4.61-4.79 (m, 2H), 8.03 (d, J=4 Hz, 1H), 8.31 (d, J=1 Hz, 1H), 8.50 (dd, J=4, 1 Hz, 1H); LC-MS (LC-ES) M+H=151.

Intermediate 99: Racemic 6-Fluoro-4-((2-methyl-azetidin-3-yl)oxy)benzo[d]thiazole hydrochloride

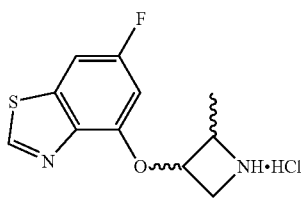

A. Racemic tert-Butyl 2-methyl-3-((methylsulfonyl)oxy)azetidine-1-carboxylate

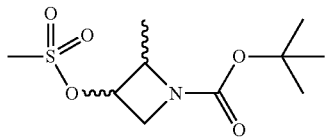 [SMILES: CC1C(OS(C)(=O)=O)CN1C(=O)OC(C)(C)C]

To a stirred, cooled (0° C.) solution of tert-butyl 3-hydroxy-2-methylazetidine-1-carboxylate (600 mg, 3.20 mmol) in DCM (10 mL) was added triethylamine (1.0 mL, 7.2 mmol) followed by methanesulfonyl chloride (0.30 mL, 3.9 mmol). The mixture was allowed to warm to room temperature and stirred overnight. The mixture was poured into 1 N aqueous HCl and extracted twice with EtOAc. The combined organic layers were washed with saturated aqueous NaHCO$_3$ and brine, dried over Na$_2$SO$_4$, filtered and concentrated to give the title compound (814 mg, 96%) as a pale yellow oil. $^1$H NMR (400 MHz, CD$_3$SOCD$_3$) δ 1.32-1.43 (m, 12H), 3.26 (s, 3H), 3.80 (dd, J=9, 4 Hz, 1H), 4.11 (t, J=8 Hz, 1H), 4.20-4.29 (m, 1H), 4.84 (d, J=5 Hz, 1H).

B. Racemic tert-Butyl 3-((6-fluorobenzo[d]thiazol-4-yl)oxy)-2-methylazetidine-1-carboxylate

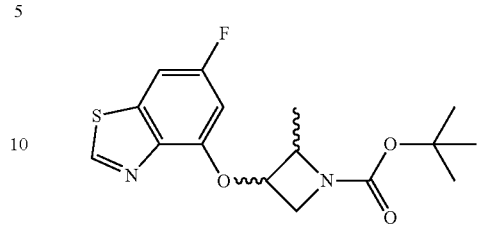

To a stirred solution of tert-butyl 2-methyl-3-((methylsulfonyl)oxy)azetidine-1-carboxylate (Intermediate 99A) (265 mg, 0.999 mmol) and 6-fluorobenzo[d]thiazol-4-ol (170 mg, 1.01 mmol) in DMF (5 mL) was added cesium carbonate (360 mg, 1.11 mmol). The mixture was heated to 100° C. overnight, then 120° C. overnight, poured into water and extracted twice with EtOAc. The combined organic layers were washed with brine, dried over Na$_2$SO$_4$, filtered and concentrated. The remaining material was purified on silica gel eluting with a 0%-40% EtOAc-hexanes gradient to give the title compound (116 mg, 34%) as a yellow oil. $^1$H NMR (400 MHz, CD$_3$SOCD$_3$) δ 1.29 (d, J=7 Hz, 3H), 1.41 (s, 9H), 3.85 (br s, 1H), 4.32 (br s, 1H), 4.70 (t, J=6 Hz, 1H), 5.28 (td, J=7, 4 Hz, 1H), 6.91 (dd, J=11, 2 Hz, 1H), 7.66 (dd, J=8, 2 Hz, 1H), 9.27 (s, 1H); LC-MS (LC-ES) M+H=339.

C. Racemic 6-Fluoro-4-((2-methylazetidin-3-yl)oxy)benzo[d]thiazole hydrochloride

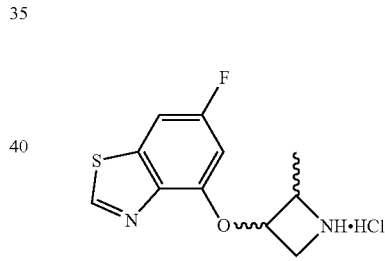

To tert-butyl 3-((6-fluorobenzo[d]thiazol-4-yl)oxy)-2-methylazetidine-1-carboxylate (Intermediate 99B) (116 mg, 0.343 mmol) in MeOH (0.5 mL) was added 4 N HCl in dioxane (2 mL, 8.0 mmol). The mixture was stirred at room temperature for 2 h, and the solvent was removed in vacuo to give material that was triturated with diethyl ether to give the title compound as a pale yellow solid (93 mg, 99%). $^1$H NMR (400 MHz, CD$_3$OD) δ 1.46 (d, J=7 Hz, 3H), 3.97-4.04 (m, 1H), 4.45 (dd, J=12, 6 Hz, 1H), 4.89-5.02 (m, 1H), 5.30-5.43 (m, 1H), 7.03 (dd, J=11, 2 Hz, 1H), 7.72 (dd, J=8, 2 Hz, 1H), 9.20 (br s, 1H), 9.30 (s, 1H); LC-MS (LC-ES) M+H=239.

Intermediate 100: 3-Methyl-1-(pyridazin-3-yl)azetidin-3-amine dihydrochloride

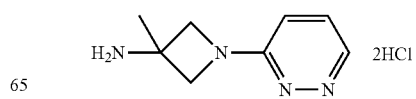

A. tert-Butyl (3-methyl-1-(pyridazin-3-yl)azetidin-3-yl)carbamate

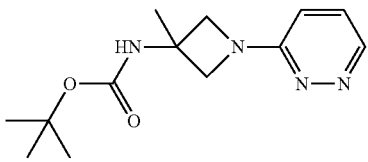

To tert-butyl (3-methylazetidin-3-yl)carbamate hydrochloride (737 mg, 3.31 mmol) in acetonitrile (15 mL) was added 3-chloropyridazine hydrochloride (500 mg, 3.31 mmol) and N,N-diisopropylethylamine (1.45 mL, 8.28 mmol). The mixture was heated to 100° C. overnight, cooled and concentrated. The resulting residue was purified on silica gel eluting with a 5%-30% MeOH in DCM gradient to give the title compound (331 mg, 38%) as a brown oil. $^1$H NMR (400 MHz, CD$_3$OD) δ 1.45 (s, 9H), 1.67 (s, 3H), 4.02 (d, J=8 Hz, 2H), 4.29 (d, J=8 Hz, 2H), 6.56 (dd, J=9, 1 Hz, 1H), 7.20 (dd, J=9, 5 Hz, 1H), 8.60 (dd, J=5, 1 Hz, 1H); LC-MS (LC-ES) M+H=265.

B. 3-Methyl-1-(pyridazin-3-yl)azetidin-3-amine dihydrochloride

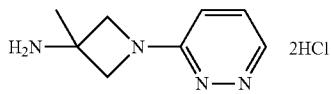

To tert-butyl (3-methyl-1-(pyridazin-3-yl)azetidin-3-yl)carbamate (Intermediate 100A) (87 mg, 0.35 mmol) in DCM (1 mL) and MeOH (1 mL) was added 4 N HCl in dioxane (1.5 mL, 6.0 mmol). The mixture was stirred at room temperature for 1 h, and the solvent was removed in vacuo to give the title compound as a tan solid (84 mg, quantitative). $^1$H NMR (400 MHz, CD$_3$OD) δ 1.78 (s, 3H), 4.41-4.50 (m, 2H), 4.53-4.63 (m, 2H), 7.63 (dd, J=9, 1 Hz, 1H), 7.96 (dd, J=9, 5 Hz, 1H), 8.65 (d, J=4 Hz, 1H); LC-MS (LC-ES) M+H=165.

Intermediate 101: 3-Methyl-1-(pyrimidin-2-yl)azetidin-3-amine dihydrochloride

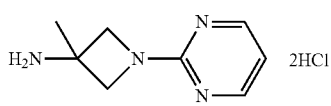

A. tert-Butyl (3-methyl-1-(pyrimidin-2-yl)azetidin-3-yl)carbamate

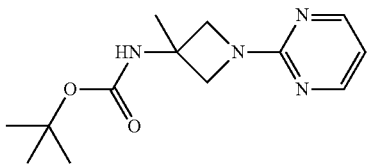

To a stirred solution of 2-chloropyrimidine (500 mg, 4.37 mmol) in acetonitrile (15 mL) was added N,N-diisopropylethylamine (2.67 mL, 15.3 mmol) followed by tert-butyl (3-methylazetidin-3-yl)carbamate hydrochloride (972 mg, 4.37 mmol). The mixture was heated to 100° C. overnight, cooled and concentrated. The resulting residue was purified on silica gel eluting with a 0%-30% MeOH in DCM gradient to give the title compound (750 mg, 65%) as a yellowish oil. $^1$H NMR (400 MHz, CDCl$_3$) δ 1.45 (s, 9H), 1.65 (s, 3H), 4.00 (d, J=9 Hz, 2H), 4.29 (d, J=8 Hz, 2H), 4.82 (br s, 1H), 6.56 (t, J=5 Hz, 1H), 8.33 (d, J=5, 1 Hz, 2H); LC-MS (LC-ES) M+H=265.

B. 3-Methyl-1-(pyrimidin-2-yl)azetidin-3-amine dihydrochloride

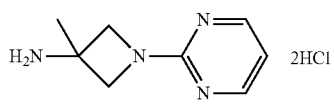

To tert-butyl (3-methyl-1-(pyrimidin-2-yl)azetidin-3-yl)carbamate (Intermediate 101A) (750 mg, 2.84 mmol) in DCM (1 mL) and MeOH (2 mL) was added 4 N HCl in dioxane (6 mL, 24 mmol). The mixture was stirred at room temperature for 1 h, and the solvent was removed in vacuo to give the title compound as a tan solid (720 mg, quantitative). $^1$H NMR (400 MHz, CD$_3$OD) δ 1.77 (s, 3H), 4.38-4.48 (m, 2H), 4.51-4.60 (m, 2H), 7.06-7.12 (m, 1H), 8.68 (d, J=5 Hz, 2H); LC-MS (LC-ES) M+H=165.

Intermediate 102: Racemic 4-((2-Methylazetidin-3-yl)oxy)benzo[d]thiazole hydrochloride

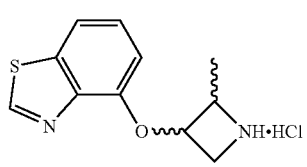

A. Racemic tert-Butyl 3-(benzo[d]thiazol-4-yloxy)-2-methylazetidine-1-carboxylate

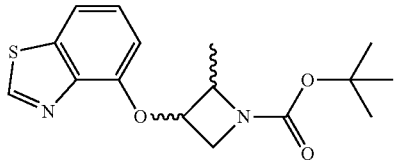

To a stirred solution of tert-butyl 2-methyl-3-((methylsulfonyl)oxy)azetidine-1-carboxylate (Intermediate 99A) (184 mg, 0.693 mmol) and benzo[d]thiazol-4-ol (105 mg, 0.693 mmol) in DMF (4 mL) was added cesium carbonate (250 mg, 0.767 mmol). The mixture was heated to 80° C. overnight, then 100° C. overnight, poured into water and extracted twice with EtOAc. The combined organic layers were washed with brine, dried over $Na_2SO_4$, filtered and concentrated. The remaining material was purified on silica gel eluting with a 0%-50% EtOAc-hexanes gradient to give the title compound (103 mg, 46%) as a colorless oil. $^1$H NMR (400 MHz, $CD_3SOCD_3$) δ 1.25-1.46 (m, 12H), 3.82-3.92 (m, 1H), 4.29 (br s, 1H), 4.84 (dt, J=7, 4 Hz, 1H), 5.27 (td, J=7, 4 Hz, 1H), 6.92 (d, J=8 Hz, 1H), 7.35-7.44 (m, 1H), 7.71-7.79 (m, 1H), 9.30 (s, 1H); LC-MS (LC-ES) M+H=321.

B. Racemic 4-((2-Methylazetidin-3-yl)oxy)benzo[d]thiazole hydrochloride

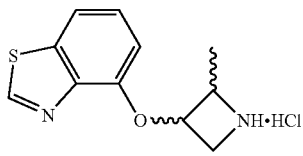

To tert-butyl 3-(benzo[d]thiazol-4-yloxy)-2-methylazetidine-1-carboxylate (Intermediate 102A) (102 mg, 0.318 mmol) in MeOH (0.5 mL) was added 4 N HCl in dioxane (2 mL, 8.0 mmol). The mixture was stirred at room temperature for 2 h, and the solvent was removed in vacuo to give material that was triturated with diethyl ether to give the title compound as a white solid (85 mg, quantitative). $^1$H NMR (400 MHz, $CD_3SOCD_3$) δ 1.43-1.55 (m, 3H), 3.93-4.09 (m, 1H), 4.35-4.45 (m, 1H), 4.85-4.99 (m, 1H), 5.30-5.44 (m, 1H), 6.99 (d, J=8 Hz, 1H), 7.42 (t, J=8 Hz, 1H), 7.81 (d, J=8 Hz, 1H), 9.29 (br s, 1H), 9.34 (s, 1H); LC-MS (LC-ES) M+H=221.

Intermediate 103: 1-(5-Methylpyridazin-3-yl)azetidin-3-amine dihydrochloride

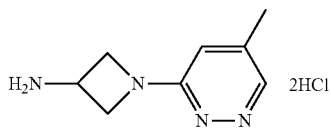

A. tert-Butyl (1-(5-methylpyridazin-3-yl)azetidin-3-yl)carbamate

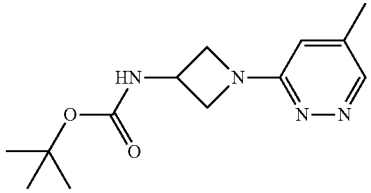 [SMILES: Cc1cnnc(N2CC(NC(=O)OC(C)(C)C)C2)c1]

To a reaction vial with 3-chloro-5-methylpyridazine (600 mg, 4.67 mmol) dissolved in acetonitrile (15 mL) was added tert-butyl azetidin-3-ylcarbamate (804 mg, 4.67 mmol) and N,N-diisopropylethylamine (1.22 mL, 7.00 mmol). The mixture was heated to 100° C. overnight, cooled, and concentrated. The resulting residue was purified on silica gel eluting with a 5%-30% MeOH in DCM gradient to give the title compound (215 mg, 17%) as a tan solid. $^1$H NMR (400 MHz, $CD_3OD$) δ 1.47 (s, 9H), 2.30 (s, 3H), 3.93 (dd, J=8, 6 Hz, 2H), 4.38 (t, J=8 Hz, 2H), 4.51-4.67 (m, 1H), 6.70 (s, 1H), 8.37 (d, J=2 Hz, 1H); LC-MS (LC-ES) M+H=265.

B. 1-(5-Methylpyridazin-3-yl)azetidin-3-amine dihydrochloride

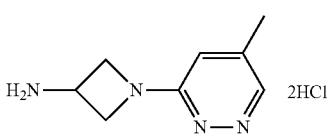

To tert-butyl (1-(5-methylpyridazin-3-yl)azetidin-3-yl)carbamate (Intermediate 103A) (210 mg, 0.794 mmol) in DCM (2 mL) was added 4 N HCl in dioxane (3 mL, 12 mmol). The mixture was stirred at room temperature for 1 h, and the solvent was removed in vacuo to give the title compound as a dark tan solid (206 mg, quantitative). $^1$H NMR (400 MHz, $CD_3OD$) δ 2.50 (d, J=1 Hz, 3H), 4.37-4.50 (m, 3H), 4.68-4.79 (m, 2H), 7.43 (s, 1H), 8.51 (s, 1H); LC-MS (LC-ES) M+H=165.

Intermediate 104: 1-(Pyridazin-3-yl)azetidin-3-amine dihydrochloride

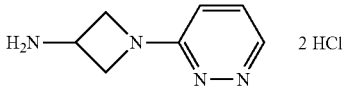

A. tert-Butyl (1-(pyridazin-3-yl)azetidin-3-yl)carbamate

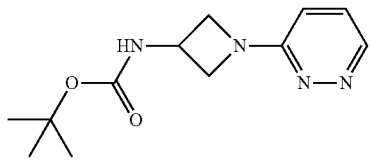 [SMILES: CC(C)(C)OC(=O)NC1CN(c2cccnn2)C1]

To a reaction vial with 3-chloropyridazine hydrochloride (150 mg, 0.993 mmol) dissolved in EtOH (5 mL) was added N,N-diisopropylethylamine (0.35 mL, 2.0 mmol) followed by tert-butyl azetidin-3-ylcarbamate (171 mg, 0.993 mmol). The mixture was heated to 90° C. overnight, cooled, and concentrated. The resulting residue was purified on silica gel eluting with a 5%-25% MeOH in DCM gradient to give the title compound (87 mg, 35%) as a tan solid. $^1$H NMR (400 MHz, CD$_3$OD) δ 1.47 (s, 9H), 3.96 (dd, J=8, 6 Hz, 2H), 4.40 (t, J=8 Hz, 2H), 4.53-4.70 (m, 1H), 6.87 (dd, J=9, 1 Hz, 1H), 7.41 (dd, J=9, 5 Hz, 1H), 8.49 (dd, J=5, 1 Hz, 1H); LC-MS (LC-ES) M+H=251.

B. 1-(Pyridazin-3-yl)azetidin-3-amine dihydrochloride

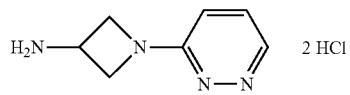 [SMILES: NC1CN(c2cccnn2)C1]

To tert-butyl (1-(pyridazin-3-yl)azetidin-3-yl)carbamate (Intermediate 104A) (87 mg, 0.35 mmol) in DCM (1 mL) and MeOH (1 mL) was added 4 N HCl in dioxane (1.5 mL, 6.0 mmol). The mixture was stirred at room temperature for 1 h, and the solvent was removed in vacuo to give the title compound as a tan solid (84 mg, quantitative). $^1$H NMR (400 MHz, CD$_3$OD) δ 4.38-4.54 (m, 3H), 4.72-4.82 (m, 2H), 7.63 (dd, J=9, 1 Hz, 1H), 7.95 (dd, J=9, 5 Hz, 1H), 8.63 (d, J=4 Hz, 1H); LC-MS (LC-ES) M+H=151.

Intermediate 105: 4-Nitrophenyl (3-methyl-1-(pyrimidin-2-yl)azetidin-3-yl)carbamate

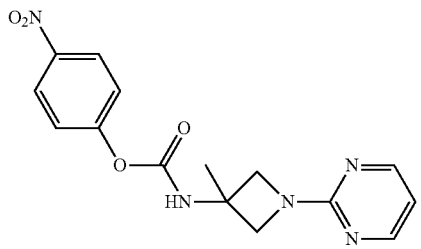 [SMILES: CC1(NC(=O)Oc2ccc([N+](=O)[O-])cc2)CN(c2ncccn2)C1]

To 4-nitrophenyl chloroformate (179 mg, 0.886 mmol) and 3-methyl-1-(pyrimidin-2-yl)azetidin-3-amine dihydrochloride (Intermediate 101) (150 mg, 0.633 mmol) in DCM (3 mL) at 0° C. was added, dropwise, pyridine (0.18 mL, 2.2 mmol) in DCM (5 mL). After 1 h, 2/3 of the reaction mixture was taken for another use, and the remaining material was diluted with EtOAc, washed with water and brine, dried over MgSO$_4$, filtered and concentrated. The residue was purified on silica gel, eluting with a 5%-90% EtOAc in hexanes gradient to give the title compound (65 mg, 31%) as a white solid. $^1$H NMR (400 MHz, CDCl$_3$) δ 1.78 (s, 3H), 4.11 (d, J=9 Hz, 2H), 4.41 (d, J=9 Hz, 2H), 5.51 (br s, 1H), 6.62 (t, J=5 Hz, 1H), 7.31-7.39 (m, 2H), 8.21-8.30 (m, 2H), 8.36 (d, J=5 Hz, 2H); LC-MS (LC-ES) M+H=330.

Intermediate 106: Racemic 8-(Azetidin-3-ylfluoromethyl)quinoline dihydrochloride

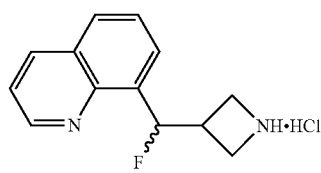

A. Racemic tert-Butyl 3-(hydroxy(quinolin-8-yl)methyl)azetidine-1-carboxylate

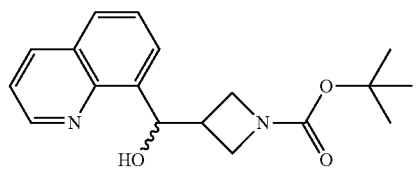 [SMILES: CC(C)(C)OC(=O)N1CC(C(O)c2cccc3cccnc23)C1]

To a THF (25 mL) solution of 8-bromoquinoline (1.00 g, 4.81 mmol) at −78° C. was added, dropwise, a 2.5 M solution of n-BuLi in hexanes (1.92 mL, 4.81 mmol). After 30 min, tert-butyl 3-formylazetidine-1-carboxylate (891 mg, 4.81 mmol) in THF (10 ml) was added. After 1 h, the reaction was warmed to 0° C. After another hour, the reaction was quenched with saturated aqueous NH$_4$Cl. The mixture was extracted with EtOAc and the combined organics were washed with brine, dried and filtered. The filtrate was concentrated in vacuo and the residue was purified on silica gel, eluting with a 0% to 30% MeOH in DCM gradient, to afford the title compound (1.25 g, 83%), as a yellowish foam. $^1$H NMR (400 MHz, CDCl$_3$) δ 1.42-1.52 (m, 9H), 3.18-3.30 (m, 1H), 3.32-3.44 (m, 1H), 3.66-4.04 (m, 4H), 7.43-7.58 (m, 3H), 7.76-7.83 (m, 1H), 8.25 (d, J=8.3 Hz, 1H), 8.83-8.91 (m, 1H); LC-MS (LC-ES) M+H=315.

B. Racemic tert-Butyl 3-(fluoro(quinolin-8-yl)methyl)azetidine-1-carboxylate

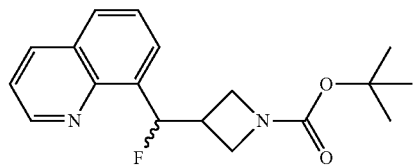 [SMILES: CC(C)(C)OC(=O)N1CC(C(F)c2cccc3cccnc23)C1]

To a DCM (2 mL) solution of tert-butyl 3-(hydroxy (quinolin-8-yl)methyl)azetidine-1-carboxylate (Intermediate 106A) (110 mg, 0.350 mmol) at 0° C. was added, dropwise, DAST (0.35 mL, 0.35 mmol). After 1.5 h, the reaction was warmed to room temperature. After 0.5 h, the mixture was diluted with DCM and saturated aqueous NH$_4$Cl. The aqueous layer was separated and extracted with DCM. The combined organic layers were washed with brine, dried over MgSO$_4$, filtered and concentrated. The remaining material was purified on silica gel eluting with a 5%-70% EtOAc-hexanes gradient to give the title compound (47 mg, 43%) as a colorless oil. $^1$H NMR (400 MHz, CDCl$_3$) δ 1.45 (s, 9H), 3.29-3.45 (m, 1H), 3.70-3.80 (m, 1H), 4.01 (t, J=8 Hz, 1H), 4.05-4.18 (m, 2H), 6.67-6.89 (m, 1H), 7.44 (d, J=3 Hz, 1H), 7.58 (d, J=7 Hz, 1H), 7.73-7.90 (m, 2H), 8.16 (d, J=8 Hz, 1H), 8.90 (s, 1H); LC-MS (LC-ES) M+H=317.

C. Racemic 8-(Azetidin-3-ylfluoromethyl)quinoline dihydrochloride

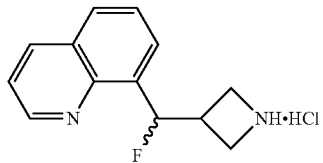

To tert-butyl 3-(fluoro(quinolin-8-yl)methyl)azetidine-1-carboxylate (Intermediate 106B) (110 mg, 0.348 mmol) in DCM (2 mL) was added 4 N HCl in dioxane (0.087 mL, 0.35 mmol). The mixture was stirred at room temperature for 1.5 h, and the solvent was removed in vacuo to give the title compound as a tan solid (106 mg, quantitative). LC-MS (LC-ES) M+H=217.

Intermediate 107: (trans)-3-(2,5-Dichlorophenoxy) cyclobutanecarboxylic acid

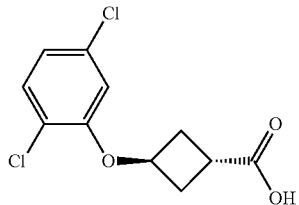 [SMILES: O=C(O)[C@H]1C[C@H](Oc2cc(Cl)ccc2Cl)C1]

A. (trans)-Methyl 3-(2,5-dichlorophenoxy)cyclobutanecarboxylate

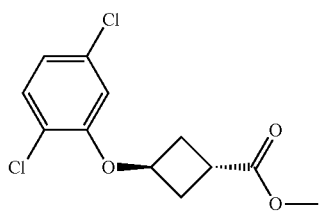 [SMILES: COC(=O)[C@H]1C[C@H](Oc2cc(Cl)ccc2Cl)C1]

Triphenylphosphine (644 mg, 2.46 mmol) was added to a solution of 2,5-dichlorophenol (300 mg, 2.05 mmol) in tetrahydrofuran (3 mL). The reaction mixture was cooled to 0° C., and (cis)-methyl 3-hydroxycyclobutanecarboxylate (320 mg, 2.46 mmol) was added, followed by DIAD (0.48 mL, 2.5 mmol). After 10 min, the reaction mixture was warmed to room temperature, stirred for 3 days, and diluted with water and EtOAc. The mixture was partitioned, and the aqueous layer was extracted with EtOAc. The organic layer was washed with water, dried over sodium sulfate, filtered, and concentrated. The residue was purified on silica gel eluting with a 10%-50% EtOAc-heptane gradient to give the title compound (275 mg, 81%) as a yellow oil. $^1$H NMR (400 MHz, CDCl$_3$) δ 2.47-2.58 (m, 2H), 2.76 (ddd, J=14, 7, 4 Hz, 2H), 3.15-3.26 (m, 1H), 3.74 (s, 3H), 4.90 (quin, J=7 Hz, 1H), 6.69 (d, J=2 Hz, 1H), 6.87 (dd, J=9, 2 Hz, 1H), 7.25 (s, 1H); LC-MS (LC-ES) M+H=275, 277, 279 (di-Cl pattern).

B. (trans)-3-(2,5-Dichlorophenoxy)cyclobutanecarboxylic acid

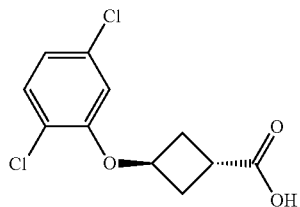

To a solution of (trans)-methyl 3-(2,5-dichlorophenoxy) cyclobutanecarboxylate (Intermediate 107A) (265 mg, 0.963 mmol) in THF (5 mL), methanol (2.5 mL) and water (2.5 mL) was added LiOH (69 mg, 2.9 mmol). After stirring overnight, the reaction was diluted with water and acidified with 6 N aqueous HCl solution. The resulting precipitate was collected by filtration and washed with water and diethyl ether to give the title compound (175 mg, 70%) as a white solid. $^1$H NMR (400 MHz, CD$_3$SOCD$_3$) δ 2.03-2.15 (m, 2H), 2.53-2.66 (m, 3H), 4.81-4.92 (m, 1H), 6.69 (d, J=11 Hz, 1H), 6.80 (td, J=8, 3 Hz, 1H), 7.45 (dd, J=9, 6 Hz, 1H); LC-MS (LC-ES) M−H=259, 261, 263 (di-Cl pattern).

Intermediate 108: 3-(2-(Trifluoromethoxy)phenoxy)azetidine hydrochloride

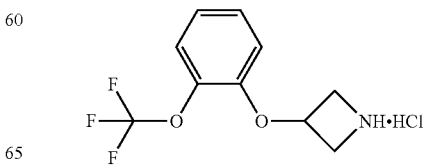

183

A. tert-Butyl 3-(2-(trifluoromethoxy)phenoxy)azetidine-1-carboxylate

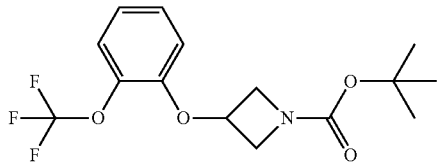

To a stirred solution of tert-butyl 3-((methylsulfonyl)oxy)azetidine-1-carboxylate (Intermediate 1) (355 mg, 1.41 mmol) and 2-(trifluoromethoxy)phenol (250 mg, 1.40 mmol) in DMF (4 mL) was added cesium carbonate (510 mg, 1.57 mmol). The mixture was heated to 80° C. overnight, poured into water and extracted twice with EtOAc. The combined organic layers were washed with brine, dried over $Na_2SO_4$, filtered and concentrated. The remaining material was purified on silica gel eluting with a 2%-20% EtOAc-hexanes gradient to give the title compound (416 mg, 89%) as a pale yellow oil. $^1$H NMR (400 MHz, $CD_3SOCD_3$) δ 1.40 (s, 9H), 3.78 (d, J=7 Hz, 2H), 4.33 (t, J=8 Hz, 2H), 5.06-5.14 (m, 1H), 6.99 (d, J=8 Hz, 1H), 7.05-7.12 (m, 1H), 7.30-7.46 (m, 2H); LC-MS (LC-ES) M-t-Bu=278.

B. 3-(2-(Trifluoromethoxy)phenoxy)azetidine hydrochloride

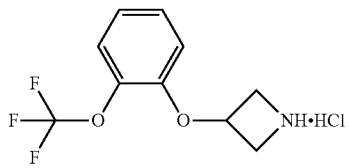

To tert-butyl 3-(2-(trifluoromethoxy)phenoxy)azetidine-1-carboxylate (Intermediate 108A) (414 mg, 1.24 mmol) in methanol (2 mL), 4 N HCl in dioxane (8 mL, 32 mmol) was added. After 3 h, the solvent was removed in vacuo and the resulting solid was triturated with diethyl ether to give the title compound as a white solid (297 mg, 89%). $^1$H NMR (400 MHz, $CD_3OD$) δ 4.01 (dd, J=12, 4 Hz, 2H), 4.46 (dd, J=12, 7 Hz, 2H), 5.17 (t, J=6 Hz, 1H), 7.04 (d, J=9 Hz, 1H), 7.10-7.19 (m, 1H), 7.37 (t, J=8 Hz, 1H), 7.43 (d, J=8 Hz, 1H), 9.07 (br s, 2H); LC-MS (LC-ES) M+H=234.

Intermediate 109: (trans)-3-(2-(Trifluoromethoxy)phenoxy)cyclobutanecarboxylic acid

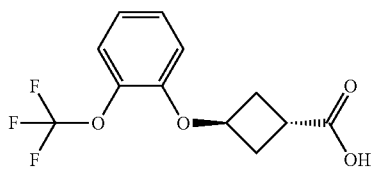 [SMILES: O=C(O)[C@H]1C[C@H](Oc2ccccc2OC(F)(F)F)C1]

184

A. (trans)-Methyl 3-(2-(trifluoromethoxy)phenoxy)cyclobutanecarboxylate

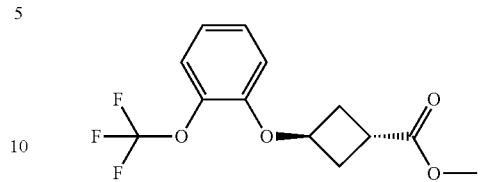

Triphenylphosphine (504 mg, 1.92 mmol) was added to a solution of 2-(trifluoromethoxy)phenol (0.21 mL, 1.6 mmol) in tetrahydrofuran (5 mL). The reaction mixture was cooled to 0° C., and (cis)-methyl 3-hydroxycyclobutanecarboxylate (250 mg, 1.92 mmol) was added, followed by DIAD (0.37 mL, 1.9 mmol). After 10 min, the reaction mixture was warmed to room temperature, stirred for 3 days, and diluted with water and EtOAc. The mixture was partitioned, and the aqueous layer was extracted with EtOAc. The organic layer was washed with water, dried over sodium sulfate, filtered, and concentrated. The residue was purified on silica gel eluting with a 0%-100% EtOAc-hexanes gradient to give the title compound (191 mg, 21%). $^1$H NMR (400 MHz, $CD_3SOCD_3$) δ 2.29-2.39 (m, 2H), 2.64-2.72 (m, 2H), 3.14-3.22 (m, 1H), 3.65 (s, 3H), 4.88-4.96 (m, 1H), 6.99-7.04 (m, 2H), 7.16-7.26 (m, 1H), 7.29-7.36 (m, 1H); LC-MS (LC-ES) M−H=289.

B. (trans)-3-(2-(Trifluoromethoxy)phenoxy)cyclobutanecarboxylic acid

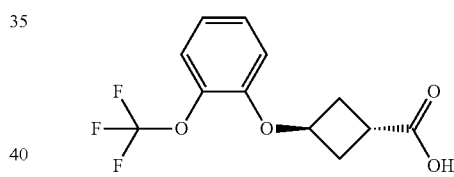

To a solution of (trans)-methyl 3-(2-(trifluoromethoxy)phenoxy)cyclobutanecarboxylate (Intermediate 109A) (191 mg, 0.658 mmol) in THF (10 mL) was added LiOH (43 mg, 2.0 mmol) in water (5 mL). After 3 h, the reaction was adjusted to pH=4 with the addition of saturated aqueous citric acid, and the mixture was extracted with EtOAc (3×). The combined organic layers were dried over $Na_2SO_4$, filtered and concentrated to give the title compound (105 mg, 49%). $^1$H NMR (400 MHz, $CD_3SOCD_3$) δ 2.29 (ddd, J=13, 10, 6 Hz, 2H), 2.64 (qd, J=7, 4 Hz, 2H), 2.97-3.12 (m, 1H), 4.88 (t, J=6 Hz, 1H), 6.91-7.06 (m, 2H), 7.19-7.40 (m, 2H), 12.32 (br s, 1H); LC-MS (LC-ES) M−H=275.

Intermediate 110: 3-(Benzofuran-7-yloxy)azetidine hydrochloride

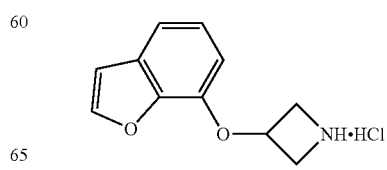

185

A. tert-Butyl 3-(benzofuran-7-yloxy)azetidine-1-carboxylate

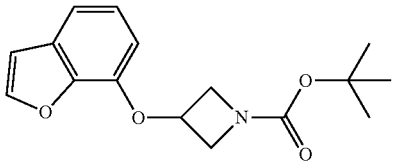

To a stirred solution of tert-butyl 3-((methylsulfonyl)oxy) azetidine-1-carboxylate (Intermediate 1) (100 mg, 0.398 mmol) and benzofuran-7-ol (50 mg, 0.373 mmol) in DMF (3 mL) was added cesium carbonate (150 mg, 0.460 mmol). The mixture was heated to 80° C. overnight, poured into water and extracted twice with EtOAc. The combined organic layers were washed with brine, dried over $Na_2SO_4$, filtered and concentrated. The remaining material was purified on silica gel eluting with a 0%-25% EtOAc-hexanes gradient to give the title compound (60 mg, 56%) as a white solid. $^1$H NMR (400 MHz, $CD_3SOCD_3$) δ 1.39 (s, 9H), 3.75-3.82 (m, 2H), 4.32-4.38 (m, 2H), 5.14-5.19 (m, 1H), 6.70 (d, J=12 Hz, 1H), 6.94-6.97 (m, 1H), 7.14 (t, J=8 Hz, 1H), 7.27 (d, J=12 Hz, 1H), 7.98-8.00 (m, 1H); LC-MS (LC-ES) M-t-Bu=234.

B. 3-(Benzofuran-7-yloxy)azetidine hydrochloride

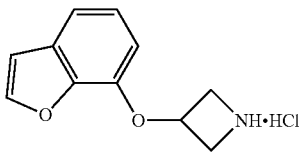

To neat tert-butyl 3-(benzofuran-7-yloxy)azetidine-1-carboxylate (Intermediate 110A) (58 mg, 0.20 mmol) was added 4 N HCl in dioxane (2 mL, 8 mmol). After 3 h, the solvent was removed in vacuo and the resulting solid was triturated with diethyl ether to give the title compound as a white solid (40 mg, 88%). $^1$H NMR (400 MHz, $CD_3SOCD_3$) δ 4.04-4.11 (m, 2H), 4.44-4.51 (m, 2H), 5.20-5.27 (m, 1H), 6.72 (d, J=12 Hz, 1H), 6.96-6.98 (m, 1H), 7.14 (t, J=8 Hz, 1H), 7.29 (d, J=12 Hz, 1H), 7.98-8.01 (m, 1H), 9.19 (br s, 2H); LC-MS (LC-ES) M+H=190.

Intermediate 111: (trans)-3-(Benzofuran-7-yloxy) cyclobutanecarboxylic acid

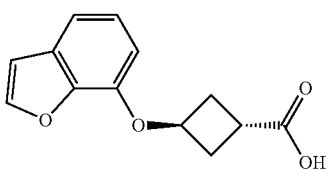 [SMILES: O=C(O)[C@H]1C[C@H](Oc2cccc3ccoc23)C1]

186

A. (trans)-Methyl 3-(benzofuran-7-yloxy)cyclobutanecarboxylate

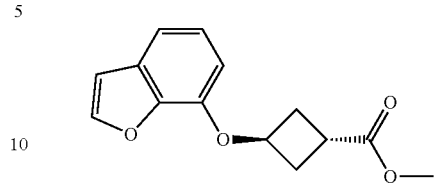

Triphenylphosphine (892 mg, 3.40 mmol) was added to a solution of benzofuran-7-ol (380 mg, 2.83 mmol) in tetrahydrofuran (7 mL). The reaction mixture was cooled to 0° C., and (cis)-methyl 3-hydroxycyclobutanecarboxylate (0.36 mL, 3.4 mmol) was added, followed by DIAD (0.66 mL, 3.4 mmol). After 10 min, the reaction mixture was warmed to room temperature, stirred for 3 days, and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give the title compound (373 mg, 45%). $^1$H NMR (400 MHz, $CD_3SOCD_3$) δ 2.34-2.46 (m, 2H), 2.65-2.73 (m, 2H), 3.15-3.25 (m, 1H), 3.63 (s, 3H), 4.90-5.01 (m, 1H), 6.69 (d, J=8 Hz, 1H), 6.87-6.91 (m, 1H), 7.10 (t, J=8 Hz, 1H), 7.20 (d, J=8 Hz, 1H), 7.90-7.93 (m, 1H); LC-MS (LC-ES) M+H=247.

B. (trans)-3-(Benzofuran-7-yloxy)cyclobutanecarboxylic acid

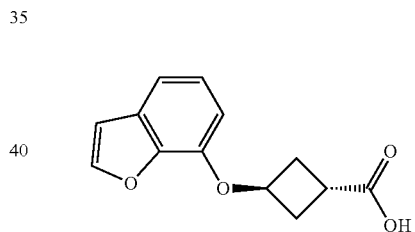

To a solution of (trans)-methyl 3-(benzofuran-7-yloxy) cyclobutanecarboxylate (Intermediate 111A) (373 mg, 1.52 mmol) in THF (10 mL) was added LiOH (109 mg, 4.54 mmol) in water (5 mL). After 3 h, the reaction was adjusted to pH=4 with the addition of saturated aqueous citric acid, and the mixture was extracted with EtOAc (3×). The combined organic layers were dried over $Na_2SO_4$, filtered and concentrated to give the title compound (332 mg, 86%). LC-MS (LC-ES) M+H=233.

Intermediate 112: (trans)-3-((3-Bromobenzofuran-7-yl)oxy)cyclobutanecarboxylic acid

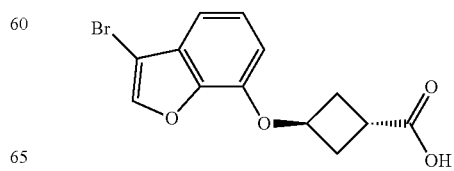

A. 3-Bromo-7-methoxybenzofuran

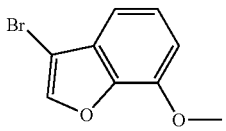

Bromine (0.33 mL, 6.4 mmol) was added dropwise to a solution of 7-methoxybenzofuran (0.70 mL, 5.4 mmol) in carbon disulfide (25 mL) cooled to 0° C. After 1 h, the reaction mixture was concentrated, and ethanol (25 mL) and sodium ethoxide (548 mg, 8.05 mmol) were added. After stirring overnight, the reaction was concentrated. The crude material was purified on silica gel, eluting with 0%-40% EtOAc in hexanes, and then reverse phase silica gel, eluting with 10%-100% MeCN in water (with 0.1% TFA) to afford the title compound (1.25 g, 83%) as a yellowish foam. $^1$H NMR (400 MHz, CD$_3$SOCD$_3$) δ 3.91 (s, 3H), 6.82-6.91 (m, 2H), 7.36 (d, J=9 Hz, 1H), 8.08 (d, J=2 Hz, 1H); LC-MS (LC-ES) M+H=226, 228 (Br pattern).

B. 3-Bromobenzofuran-7-ol

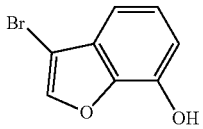

A 1 M solution of boron trichloride in DCM (8.92 mL, 8.92 mmol) was added to 3-bromo-7-methoxybenzofuran (Intermediate 112A) (0.60 mL, 3.0 mmol) and TBAI (1.32 g, 3.57 mmol) in DCM (6 mL) cooled to −78° C. After 6 h, the reaction was then quenched with iced water (50 mL). After stirring overnight, the aqueous layer was basified with 5 N aqueous NaOH (to pH=10), stirred for 1 h, neutralized with 1 N aqueous HCl (to pH=7), and extracted with DCM (3×). The combined organics were washed with brine, dried over Na$_2$SO$_4$, filtered and concentrated. The residue was purified over silica gel, eluting with 0%-100% EtOAc: EtOH (3:1) in hexanes to give the title compound (660 mg, 88%). $^1$H NMR (400 MHz, CDCl$_3$) δ 6.70 (d, J=8 Hz, 1H), 6.81 (d, J=2 Hz, 1H), 7.21 (d, J=8 Hz, 1H), 8.04 (d, J=2 Hz, 1H), 10.33 (s, 1H); LC-MS (LC-ES) M+H=213, 215 (Br pattern).

C. (trans)-Methyl 3-((3-bromobenzofuran-7-yl)oxy) cyclobutanecarboxylate

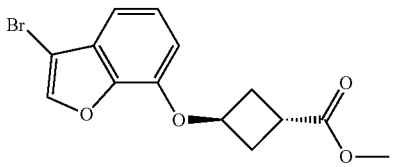 [SMILES: COC(=O)[C@H]1C[C@H](Oc2cccc3c(Br)coc23)C1]

Triphenylphosphine (443 mg, 1.69 mmol) was added to a solution of 3-bromobenzofuran-7-ol (Intermediate 112B) (300 mg, 1.41 mmol) in tetrahydrofuran (2 mL). The reaction mixture was cooled to 0° C., and (cis)-methyl 3-hydroxycyclobutanecarboxylate (0.18 mL, 1.7 mmol) was added, followed by DIAD (0.33 mL, 1.7 mmol). After 10 min, the reaction mixture was warmed to room temperature, stirred for 3 days, and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-70% EtOAc-hexanes gradient to give the title compound (343 mg, 63%). $^1$H NMR (400 MHz, CD$_3$SOCD$_3$) δ 2.30-2.44 (m, 2H), 2.69 (ddd, J=14, 7.4 Hz, 2H), 3.12-3.21 (m, 1H), 3.31 (s, 3H), 4.99 (t, J=7 Hz, 1H), 6.70 (d, J=8 Hz, 1H), 6.87 (d, J=2 Hz, 1H), 7.32 (d, J=9 Hz, 1H), 8.08 (d, J=2 Hz, 1H); LC-MS (LC-ES) M+H=325, 327 (Br pattern).

D. (trans)-3-((3-Bromobenzofuran-7-yl)oxy)cyclobutanecarboxylic acid

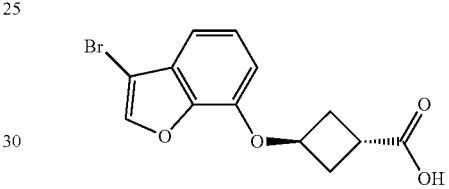

To a solution of (trans)-methyl 3-(benzofuran-7-yloxy) cyclobutanecarboxylate (Intermediate 112C) (343 mg, 1.06 mmol) in THF (5 mL) was added LiOH (76 mg, 3.2 mmol) in water (2.5 mL). After 1 h, the reaction was adjusted to pH=4 with the addition of saturated aqueous citric acid, and the mixture was extracted with EtOAc (3×). The combined organic layers were washed with brine, dried over Na$_2$SO$_4$, filtered and concentrated to give the title compound (315 mg, 88%). $^1$H NMR (400 MHz, CD$_3$SOCD$_3$) δ 2.32-2.44 (m, 2H), 2.66 (d, J=6 Hz, 2H), 3.05-3.14 (m, 1H), 4.97 (t, J=6 Hz, 1H), 6.70 (d, J=8 Hz, 1H), 6.87 (s, 1H), 7.32 (d, J=8 Hz, 1H), 8.08 (s, 1H), 12.34 (br s, 1H); LC-MS (LC-ES) M+H=311, 313 (Br pattern).

Intermediate 113: (trans)-3-(5-Chloro-2-(difluoromethoxy)phenoxy)cyclobutanecarboxylic acid

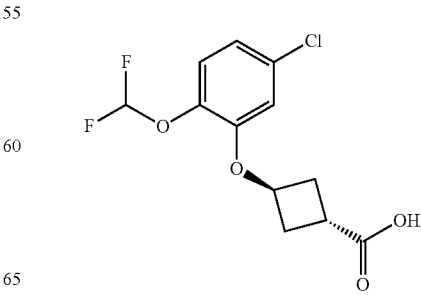

A. 2-(Benzyloxy)-4-chlorobenzaldehyde

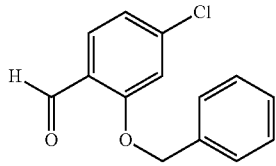 [SMILES: O=Cc1ccc(Cl)cc1OCc1ccccc1]

To a stirred solution of 4-chloro-2-hydroxybenzaldehyde (5.00 g, 12.8 mmol) in DMF (20 mL) was added potassium carbonate (2.12 g, 15.3 mmol) and benzyl bromide (1.72 mL, 15.3 mmol). After 3 h, the reaction mixture was quenched with water and extracted with ethyl acetate (3×). The organic layers were dried over $Na_2SO_4$, evaporated and dried under vacuum. The residue was purified on silica gel eluting with a 0%-40% EtOAc in hexanes gradient to give the title compound (3.17 g, 98%). $^1$H NMR (400 MHz, $CD_3SOCD_3$) δ 5.33 (s, 2H) 7.04-7.23 (m, 1H) 7.25-7.58 (m, 6H) 7.72 (d, J=8 Hz, 1H) 10.34 (s, 1H); LC-MS (LC-ES) M+H=247, 249 (Cl pattern).

B. 2-(Benzyloxy)-4-chlorophenol

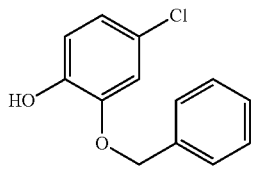

3-Chlorobenzoperoxoic acid (5.54 g, 3.21 mmol) was added to a solution of 2-(benzyloxy)-4-chlorobenzaldehyde (Intermediate 113A) (3.17 g, 12.9 mmol) in DCM (50 mL) and stirred at 40° C. overnight, cooled and washed with $NaHCO_3$ (saturated, 3×) and brine. The organic layer was dried over $Na_2SO_4$ and evaporated. The residue was dissolved in THF (50 mL) and water (25 mL), and lithium hydroxide (923 mg, 38.6 mmol) was added. The reaction mixture was stirred at room temperature for 1 h. Citric acid was added until pH neutral, and the aqueous phase was extracted with ethyl acetate (3×). The combined organic layers were washed with brine, dried over $Na_2SO_4$ and evaporated. The residue was purified on silica gel eluting with a 0%-40% EtOAc in hexanes gradient. The appropriate fractions were combined, evaporated under reduced pressure and placed in vacuo to give the title compound (2.08 g, 63%). $^1$H NMR (400 MHz, $CD_3SOCD_3$) δ 5.12 (s, 2H), 6.80 (d, J=1 Hz, 2H), 7.03 (s, 1H), 7.23-7.53 (m, 5H), 9.31 (s, 1H); LC-MS (LC-ES) M−H=233.

C. 2-(Benzyloxy)-4-chloro-1-(difluoromethoxy)benzene

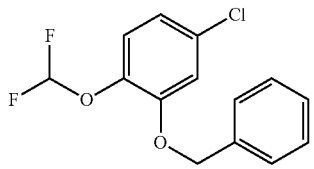 [SMILES: FC(F)Oc1ccc(Cl)cc1OCc1ccccc1]

To a stirred, cooled (−78° C.) solution of 2-(benzyloxy)-4-chlorophenol (Intermediate 113B) (2.08 g, 8.86 mmol) and potassium hydroxide (9.95 g, 177 mmol) in acetonitrile (80 mL) and water (80 mL) was added diethyl (bromodifluoromethyl)phosphonate (3.15 mL, 17.7 mmol). The cooling bath was removed and the mixture was allowed to warm to room temperature. After stirring overnight, the mixture was extracted twice with $Et_2O$. The combined organic layers were washed with brine, dried over $Na_2SO_4$, filtered and concentrated under reduced pressure. The residue was purified on silica gel eluting with a 0%-50% EtOAc in hexanes gradient to give the title compound (1.94 g, 77%). $^1$H NMR (400 MHz, $CD_3SOCD_3$) δ 5.20 (s, 2H), 6.91-7.15 (m, 2H), 7.15-7.32 (m, 1H), 7.32-7.51 (m, 6H); LC-MS (LC-ES) M−H=283, 285 (Cl pattern).

D. 5-Chloro-2-(difluoromethoxy)phenol

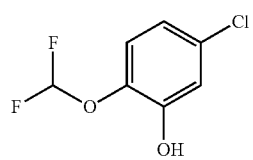 [SMILES: Oc1cc(Cl)ccc1OC(F)F]

To a stirred solution of 2-(benzyloxy)-1-(difluoromethoxy)-4-fluorobenzene (Intermediate 113C) (332 mg, 1.17 mmol) in methanol (5 mL) under a nitrogen atmosphere was added Pd/C (60 mg, 0.56 mmol). The reaction vessel was fitted with a hydrogen filled balloon and stirred overnight under a hydrogen atmosphere. The mixture was filtered through a pad of Celite®, washing with DCM and EtOH. The filtrate was evaporated to dryness to give the crude title compound (194 mg, 86%), which was used without further purification. $^1$H NMR (400 MHz, $CD_3SOCD_3$) δ 6.79-7.19 (m, 4H) 10.42 (s, 1H); LC-MS (LC-ES) M−H=193, 195 (Cl pattern).

E. (trans)-Methyl 3-(5-chloro-2-(difluoromethoxy)phenoxy)cyclobutanecarboxylate

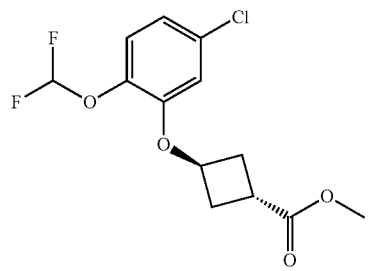 [SMILES: COC(=O)[C@H]1C[C@H](Oc2cc(Cl)ccc2OC(F)F)C1]

Triphenylphosphine (314 mg, 1.20 mmol) was added to a solution of 5-chloro-2-(difluoromethoxy)phenol (Intermediate 113D) (194 mg, 0.997 mmol) in tetrahydrofuran (1 mL). The reaction mixture was cooled to 0° C., and (cis)-methyl 3-hydroxycyclobutanecarboxylate (0.13 mL, 1.2 mmol) was added, followed by DIAD (0.23 mL, 1.2 mmol). After 10 min, the reaction mixture was warmed to room temperature, stirred for 3 days, and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-70% EtOAc-hexanes gradient to give the title compound (192 mg, 63%). ¹H NMR (400 MHz, CD₃SOCD₃) δ 2.32-2.42 (m, 2H), 2.64-2.72 (m, 2H), 3.20 (dd, J=5, 5 Hz, 1H), 3.32 (s, 3H), 4.93 (dd, J=7, 6 Hz, 1H), 6.90-7.09 (m, 3H), 7.21 (d, J=9 Hz, 1H); LC-MS (LC-ES) peak at T=0.91 min.

F. (trans)-3-(5-Chloro-2-(difluoromethoxy)phenoxy)cyclobutanecarboxylic acid

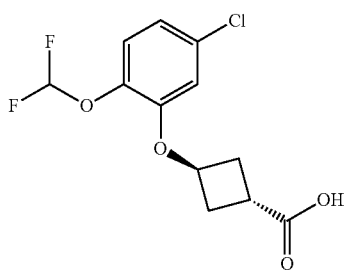 [SMILES: O=C(O)[C@H]1C[C@H](Oc2cc(Cl)ccc2OC(F)F)C1]

To a solution of (trans)-methyl 3-(5-chloro-2-(difluoromethoxy)phenoxy)cyclobutanecarboxylate (Intermediate 113E) (192 mg, 0.626 mmol) in THF (5 mL) was added LiOH (45 mg, 1.9 mmol) in water (2.5 mL). After 1 h, the reaction was adjusted to pH=4 with the addition of saturated aqueous citric acid, and the mixture was extracted with EtOAc (3×). The combined organic layers were washed with brine, dried over Na₂SO₄, filtered and concentrated to give the title compound (200 mg, quantitative). ¹H NMR (400 MHz, CD₃SOCD₃) δ 2.32-2.44 (m, 2H), 2.66 (d, J=6 Hz, 2H), 3.05-3.14 (m, 1H), 4.97 (t, J=6 Hz, 1H), 6.70 (d, J=8 Hz, 1H), 6.87 (s, 1H), 7.32 (d, J=8 Hz, 1H), 8.08 (s, 1H), 12.34 (br s, 1H); LC-MS (LC-ES) M−H=291, 293 (CI pattern).

Intermediate 114: (trans)-3-(5-Chloro-2-methoxyphenoxy)cyclobutanecarboxylic acid

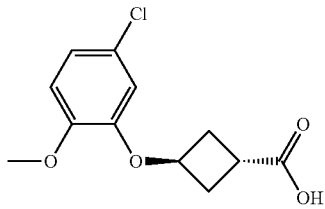 [SMILES: COc1ccc(Cl)cc1O[C@H]1C[C@H](C(=O)O)C1]

A. (trans)-Methyl 3-(5-chloro-2-methoxyphenoxy)cyclobutanecarboxylate

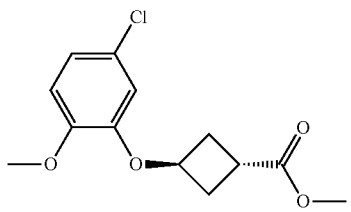

Triphenylphosphine (500 mg, 1.90 mmol) was added to a solution of 5-chloro-2-methoxyphenol (250 mg, 1.58 mmol) in tetrahydrofuran (1 mL). The reaction mixture was cooled to 0° C., and (cis)-methyl 3-hydroxycyclobutanecarboxylate (0.30 mL, 1.9 mmol) was added, followed by DIAD (0.37 mL, 1.9 mmol). After 10 min, the reaction mixture was warmed to room temperature, stirred for 12 h and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-50% EtOAc-hexanes gradient to give the title compound (228 mg, 30%). ¹H NMR (400 MHz, CD₃SOCD₃) δ 2.25-2.38 (m, 2H), 2.63 (ddd, J=13, 7, 4 Hz, 2H), 3.15 (dt, J=10, 5 Hz, 1H), 3.63 (s, 3H), 3.72 (s, 3H), 4.72-4.82 (m, 1H), 6.72 (d, J=2 Hz, 1H), 6.87-6.98 (m, 2H); LC-MS (LC-ES) M+H−OMe=239, 241 (CI pattern).

B. (trans)-3-(5-Chloro-2-methoxyphenoxy)cyclobutanecarboxylic acid

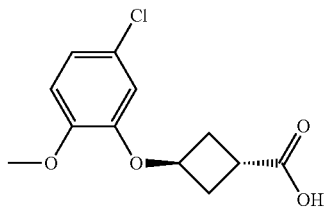 [SMILES: COc1ccc(Cl)cc1O[C@H]1C[C@H](C(=O)O)C1]

To a solution of (trans)-methyl 3-(5-chloro-2-methoxyphenoxy)cyclobutanecarboxylate (Intermediate 114A) (306 mg, 1.13 mmol) in THF (10 mL) was added LiOH (81 mg, 3.4 mmol) in water (5 mL). After 1 h, the reaction was adjusted to pH=4 with the addition of saturated aqueous citric acid, and the mixture was extracted with EtOAc (3×). The combined organic layers were dried over Na₂SO₄, filtered and concentrated to give the title compound (300 mg, 100%). ¹H NMR (400 MHz, CD₃SOCD₃) δ 2.13-2.30 (m, 2H), 2.54-2.65 (m, 2H), 2.92-3.08 (m, 1H), 3.72 (s, 3H), 4.72-4.85 (m, 1H), 6.71 (s, 1H), 6.85-6.95 (m, 2H), 12.30 (br s, 1H); LC-MS (LC-ES) M−H=255, 257 (CI pattern).

Intermediate 115: (trans)-3-(4-Fluoro-2-methoxyphenoxy)cyclobutanecarboxylic acid

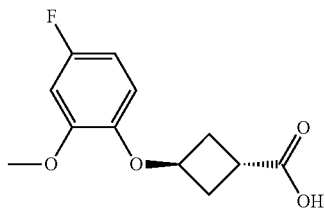

A. (trans)-Methyl 3-(4-fluoro-2-methoxyphenoxy)cyclobutanecarboxylate

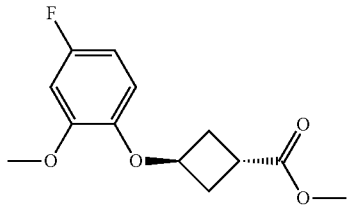

Triphenylphosphine (830 mg, 3.16 mmol) was added to a solution of 4-fluoro-2-methoxyphenol (0.300 mL, 2.63 mmol) in tetrahydrofuran (2 mL). The reaction mixture was cooled to 0° C., and (cis)-methyl 3-hydroxycyclobutanecarboxylate (0.34 mL, 3.2 mmol) was added, followed by DIAD (0.61 mL, 3.2 mmol). After 10 min, the reaction mixture was warmed to room temperature, stirred for 12 h and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-50% EtOAc-hexanes gradient to give the title compound (666 mg, 100%). $^1$H NMR (400 MHz, CD$_3$SOCD$_3$) δ 2.24-2.40 (m, 2H), 2.58 (ddd, J=13, 7, 4 Hz, 2H), 3.09-3.18 (m, 1H), 3.62 (s, 3H), 3.72 (s, 3H), 4.71 (t, J=7 Hz, 1H), 6.56-6.66 (m, 1H), 6.67-6.77 (m, 1H), 6.88 (d, J=3 Hz, 1H); LC-MS (LC-ES) M+H=255.

B. (trans)-3-(4-Fluoro-2-methoxyphenoxy)cyclobutanecarboxylic acid

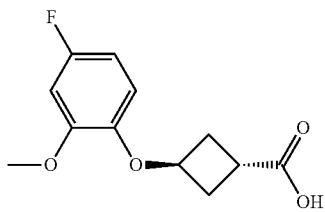 [SMILES: COc1cc(F)ccc1O[C@H]1C[C@H](C(=O)O)C1]

To a solution of (trans)-methyl 3-(4-fluoro-2-methoxyphenoxy)cyclobutanecarboxylate (Intermediate 115A) (666 mg, 2.62 mmol) in THF (15 mL) was added LiOH (190 mg, 7.86 mmol) in water (7.5 mL). After 1 h, the reaction was adjusted to pH=4 with the addition of saturated aqueous citric acid, and the mixture was extracted with EtOAc (3×). The combined organic layers were dried over Na$_2$SO$_4$, filtered and concentrated to give the title compound (690 mg, quantitative). $^1$H NMR (400 MHz, CD$_3$SOCD$_3$) δ 2.21-2.38 (m, 2H), 2.53-2.65 (m, 2H), 2.95-3.08 (m, 1H), 3.74 (s, 3H), 4.69 (t, J=7 Hz, 1H), 6.61 (td, J=9, 3 Hz, 1H), 6.66-6.72 (m, 1H), 6.89 (d, J=3 Hz, 1H), 12.27 (br s, 1H); LC-MS (LC-ES) M-H=239.

Intermediate 116: (trans)-3-(2-(Difluoromethoxy)phenoxy)cyclobutanecarboxylic acid

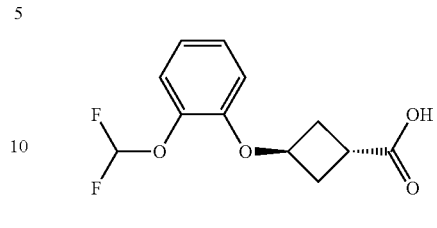

A. 2-(Benzyloxy)phenol

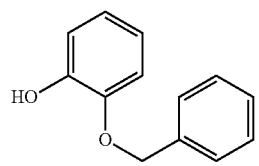 [SMILES: Oc1ccccc1OCc1ccccc1]

To a stirred solution of pyrocatechol (3.00 g, 27.2 mmol) in DMF (30 mL) was added potassium carbonate (4.14 g, 30.0 mmol) and benzyl bromide (3.89 mL, 32.7 mmol). After 3 h, the reaction mixture was quenched with water and extracted with EtOAc (3×). The combined organic layers were washed with brine, dried over Na$_2$SO$_4$ and evaporated. The residue was purified on silica gel, eluting with a 0%-30% EtOAc in hexanes gradient to give the title compound (3.56 g, 59%). $^1$H NMR (400 MHz, CD$_3$SOCD$_3$) δ 5.07 (s, 2H), 6.64-6.88 (m, 3H), 6.94 (dd, J=8, 1 Hz, 1H), 7.19-7.41 (m, 3H), 7.45 (d, J=7 Hz, 2H), 8.97 (s, 1H); LC-MS (LC-ES) M+H=201.

B. 1-(Benzyloxy)-2-(difluoromethoxy)benzene

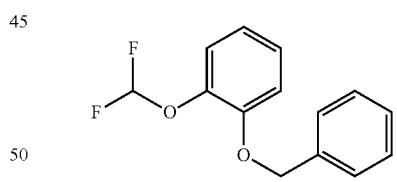

To a stirred, cooled (-78° C.) solution of 2-(benzyloxy)phenol (Intermediate 116A) (2.50 g, 12.5 mmol) and potassium hydroxide (14.0 g, 250 mmol) in acetonitrile (120 mL) and water (120 mL) was added diethyl (bromodifluoromethyl)phosphonate (4.44 mL, 25.0 mmol). The cooling bath was removed and the mixture was allowed to warm to room temperature. After stirring overnight, the mixture was extracted twice with Et$_2$O. The combined organic layers were washed with brine, dried over Na$_2$SO$_4$, filtered and concentrated. The residue was purified on silica gel eluting with a 0%-50% EtOAc in hexanes gradient to give the title compound (1.54 g, 49%). $^1$H NMR (400 MHz, CD$_3$SOCD$_3$) δ 5.15 (s, 2H), 6.87-7.00 (m, 2H), 7.07 (t, J=76 Hz, 1H), 7.12-7.49 (m, 7H); LC-MS (LC-ES) M-H=249.

C. 2-(Difluoromethoxy)phenol

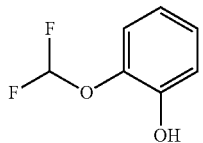

To a stirred solution of 1-(benzyloxy)-2-(difluoromethoxy)benzene (Intermediate 116B) (1.53 g, 6.11 mmol) in ethanol (15 mL) under a nitrogen atmosphere was added Pd/C (200 mg, 1.88 mmol). The reaction vessel was degassed, fitted with a hydrogen filled balloon and stirred 14 h under a hydrogen atmosphere. The mixture was filtered through a pad of Celite®, washing with DCM. The filtrate was concentrated to give the crude title compound (194 mg, 86%), which was used without further purification. LC-MS (LC-ES) M−H=159.

D. (trans)-Methyl 3-(2-(difluoromethoxy)phenoxy)cyclobutanecarboxylate

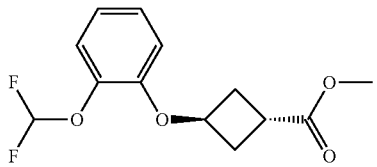 [SMILES: COC(=O)[C@H]1C[C@H](Oc2ccccc2OC(F)F)C1]

Triphenylphosphine (786 mg, 3.00 mmol) was added to a solution of 2-(difluoromethoxy)phenol (Intermediate 116C) (400 mg, 2.50 mmol) in tetrahydrofuran (2 mL). The reaction mixture was cooled to 0° C., and (cis)-methyl 3-hydroxycyclobutanecarboxylate (0.32 mL, 3.0 mmol) was added, followed by DIAD (0.58 mL, 3.0 mmol). After 10 min, the reaction mixture was warmed to room temperature, stirred for 3 days, and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-50% EtOAc-hexanes gradient to give the title compound (228 mg, 30%). $^1$H NMR (400 MHz, CD$_3$SOCD$_3$) δ 2.32-2.41 (m, 2H), 2.64-2.70 (m, 2H), 3.15-3.20 (m, 1H), 3.32 (s, 3H), 4.84-4.90 (m, 1H), 6.92-6.99 (m, 2H), 7.07 (t, J=76 Hz, 1H), 7.14-7.21 (m, 2H); LC-MS (LC-ES) peak at T=0.85 min.

E. (trans)-3-(2-(Difluoromethoxy)phenoxy)cyclobutanecarboxylic acid

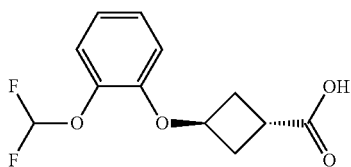 [SMILES: O=C(O)[C@H]1C[C@H](Oc2ccccc2OC(F)F)C1]

To a solution of (trans)-methyl 3-(2-(difluoromethoxy)phenoxy)cyclobutanecarboxylate (Intermediate 116D) (228 mg, 0.837 mmol) in THF (5 mL) was added LiOH (60 mg, 2.5 mmol) in water (2.5 mL). After 1 h, the reaction was adjusted to pH=4 with the addition of saturated aqueous citric acid, and the mixture was extracted with EtOAc (3×). The combined organic layers were washed with brine, dried over Na$_2$SO$_4$, filtered and concentrated to give the title compound (221 mg, 100%). $^1$H NMR (400 MHz, CD$_3$SOCD$_3$) δ 2.25-2.32 (m, 2H), 2.56-2.65 (m, 2H), 3.01-3.09 (m, 1H), 4.84 (t, J=7 Hz, 1H), 6.86-6.95 (m, 2H), 7.05 (t, J=76 Hz, 1H), 7.11-7.19 (m, 2H), 12.31 (br s, 1H); LC-MS (LC-ES) M−H=257.

Intermediate 117: (trans)-3-((3-Fluoroquinolin-8-yl)oxy)cyclobutanecarboxylic acid

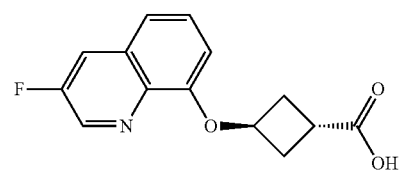 [SMILES: O=C(O)[C@H]1C[C@H](Oc2cccc3cc(F)cnc23)C1]

A. (trans)-Methyl 3-((3-fluoroquinolin-8-yl)oxy)cyclobutanecarboxylate

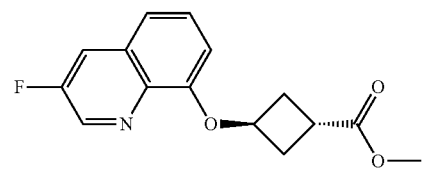 [SMILES: COC(=O)[C@H]1C[C@H](Oc2cccc3cc(F)cnc23)C1]

Triphenylphosphine (386 mg, 1.47 mmol) was added to a solution of 3-fluoroquinolin-8-ol (200 mg, 1.23 mmol) in tetrahydrofuran (5 mL). The reaction mixture was cooled to 0° C., and (cis)-methyl 3-hydroxycyclobutanecarboxylate (0.16 mL, 1.5 mmol) was added, followed by DIAD (0.29 mL, 1.5 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give the title compound (438 mg, 65%). $^1$H NMR (400 MHz, CD$_3$SOCD$_3$) δ 2.38-2.52 (m, 2H), 2.68-2.71 (m, 2H), 3.15-3.22 (m, 1H), 3.30 (s, 3H), 4.94-5.01 (m, 1H), 6.92-6.97 (m, 1H), 7.45-7.55 (m, 2H), 8.13-8.21 (m, 1H), 8.85 (s, 1H); LC-MS (LC-ES) M+H=276.

B. (trans)-3-((3-Fluoroquinolin-8-yl)oxy)cyclobutanecarboxylic acid

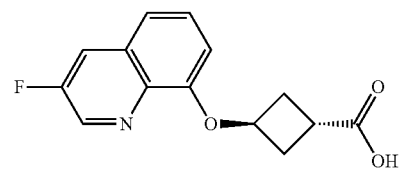 [SMILES: O=C(O)[C@H]1C[C@H](Oc2cccc3cc(F)cnc23)C1]

To a solution of (trans)-methyl 3-(4-fluoro-2-methoxyphenoxy)cyclobutanecarboxylate (Intermediate 117A) (440 mg, 1.60 mmol) in THF (20 mL) was added LiOH (115 mg, 4.80 mmol) in water (10 mL). After 1 h, the reaction was adjusted to pH=4 with the addition of saturated aqueous citric acid, and the mixture was extracted with EtOAc (3×). The combined organic layers were dried over $Na_2SO_4$, filtered and concentrated to give the title compound (430 mg, 100%). $^1$H NMR (400 MHz, $CD_3SOCD_3$) δ 2.42-2.48 (m, 2H), 2.70-2.77 (m, 2H), 3.09-3.14 (m, 1H), 4.96-5.04 (m, 1H), 6.92-6.95 (m, 1H), 7.47-7.55 (m, 2H), 8.16-8.20 (m, 1H), 8.86 (s, 1H), 12.35 (br s, 1H); LC-MS (LC-ES) M+H=262.

Intermediate 118: (trans)-3-(2-Chlorophenoxy)cyclobutanecarboxylic acid

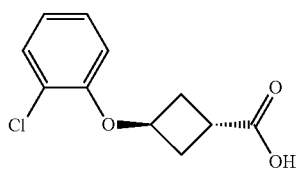

A. (trans)-Methyl 3-(2-chlorophenoxy)cyclobutanecarboxylate

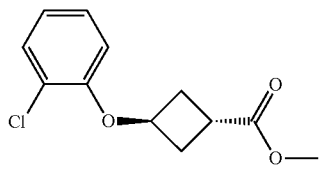 [SMILES: COC(=O)[C@H]1C[C@H](Oc2ccccc2Cl)C1]

Triphenylphosphine (504 mg, 1.92 mmol) was added to a solution of 2-chlorophenol (0.17 mL, 1.6 mmol) in tetrahydrofuran (5 mL). The reaction mixture was cooled to 0° C., and (cis)-methyl 3-hydroxycyclobutanecarboxylate (250 mg, 1.92 mmol) was added, followed by DIAD (0.37 mL, 1.9 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give the title compound (365 mg, 83%). $^1$H NMR (400 MHz, $CD_3SOCD_3$) δ 2.38 (ddd, J=13, 10, 6 Hz, 2H), 2.68 (ddd, J=13, 7, 4 Hz, 2H), 3.11-3.20 (m, 1H), 3.60 (s, 3H), 4.88 (t, J=7 Hz, 1H), 6.77-7.00 (m, 2H), 7.24 (td, J=8, 2 Hz, 1H), 7.40 (dd, J=8, 2 Hz, 1H); LC-MS (LC-ES) M+H=241, 243 (Cl pattern).

B. (trans)-3-(2-Chlorophenoxy)cyclobutanecarboxylic acid

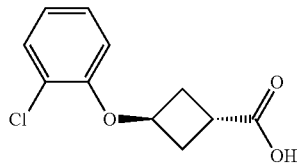 [SMILES: O=C(O)[C@H]1C[C@H](Oc2ccccc2Cl)C1]

To a solution of (trans)-methyl 3-(2-chlorophenoxy)cyclobutanecarboxylate (Intermediate 118A) (365 mg, 1.52 mmol) in THF (10 mL) was added LiOH (109 mg, 4.55 mmol) in water (5 mL). After 1 h, the reaction was adjusted to pH=4 with the addition of saturated aqueous citric acid, and the mixture was extracted with EtOAc (3×). The combined organic layers were dried over $Na_2SO_4$, filtered and concentrated to give the title compound (327 mg, 93%). $^1$H NMR (400 MHz, $CD_3SOCD_3$) δ 2.28-2.35 (m, 2H), 2.65 (ddd, J=13, 7, 4 Hz, 2H), 3.01-3.10 (m, 1H), 4.86 (t, J=7 Hz, 1H), 6.85-6.92 (m, 2H), 7.24 (td, J=8, 2 Hz, 1H), 7.40 (dd, J=8, 2 Hz, 1H), 12.32 (s, 1H); LC-MS (LC-ES) M−H=225, 227 (Cl pattern).

Intermediate 119: (trans)-3-(3,5-Difluorophenoxy)cyclobutanecarboxylic acid

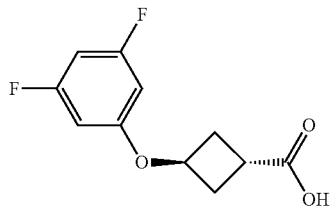

A. (trans)-Methyl 3-(3,5-difluorophenoxy)cyclobutanecarboxylate

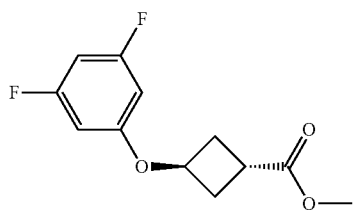 [SMILES: COC(=O)[C@H]1C[C@H](Oc2cc(F)cc(F)c2)C1]

Triphenylphosphine (504 mg, 1.92 mmol) was added to a solution of 3,5-difluorophenol (208 mg, 1.60 mmol) in tetrahydrofuran (5 mL). The reaction mixture was cooled to 0° C., and (cis)-methyl 3-hydroxycyclobutanecarboxylate (250 mg, 1.92 mmol) was added, followed by DIAD (0.37 mL, 1.9 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give the title compound (371 mg, 82%). ¹H NMR (400 MHz, CD₃SOCD₃) δ 2.22-2.39 (m, 2H), 2.63-2.72 (m, 2H), 3.17 (dd, J=5, 5 Hz, 1H), 3.61 (s, 3H), 4.83 (dd, J=7, 6 Hz, 1H), 6.56 (dd, J=9, 2 Hz, 2H), 6.72-6.89 (m, 1H); LC-MS (LC-ES) M−H=240.

B. (trans)-3-(3,5-Difluorophenoxy)cyclobutanecarboxylic acid

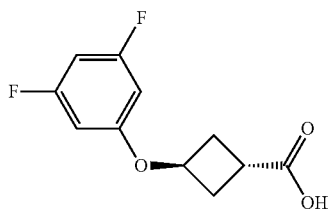

To a solution of (trans)-methyl 3-(3,5-difluorophenoxy)cyclobutanecarboxylate (Intermediate 119A) (371 mg, 1.53 mmol) in THF (10 mL) was added LiOH (110 mg, 4.60 mmol) in water (5 mL). After 3 h, the reaction was adjusted to pH=4 with the addition of saturated aqueous citric acid, and the mixture was extracted with EtOAc (3×). The combined organic layers were dried over Na₂SO₄, filtered and concentrated to give the title compound (325 mg, 91%). ¹H NMR (400 MHz, CD₃SOCD₃) δ 2.19-2.31 (m, 2H), 2.58-2.63 (m, 2H), 3.00-3.09 (m, 1H), 4.82 (dd, J=7, 6 Hz, 1H), 6.49-6.60 (m, 2H), 6.75 (tt, J=9, 2 Hz, 1H), 12.31 (br s, 1H); LC-MS (LC-ES) M−H=227.

Intermediate 120:
(trans)-3-(2-Methoxyphenoxy)cyclobutanecarboxylic acid

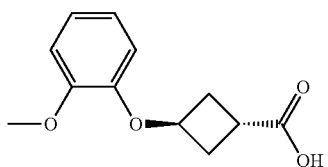 [SMILES: COc1ccccc1O[C@H]1C[C@H](C(=O)O)C1]

A. (trans)-Methyl 3-(2-methoxyphenoxy)cyclobutanecarboxylate

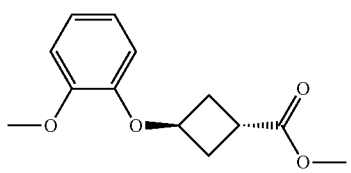

Triphenylphosphine (504 mg, 1.92 mmol) was added to a solution of 2-methoxyphenol (0.18 mL, 1.6 mmol) in tetrahydrofuran (5 mL). The reaction mixture was cooled to 0° C., and (cis)-methyl 3-hydroxycyclobutanecarboxylate (250 mg, 1.92 mmol) was added, followed by DIAD (0.37 mL, 1.9 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give the title compound (206 mg, 54%). ¹H NMR (400 MHz, CD₃SOCD₃) δ 2.30-2.40 (m, 2H), 2.58-2.67 (m, 2H), 3.10-3.20 (m, 1H), 3.63 (s, 3H), 3.73 (s, 3H), 4.71-4.79 (m, 1H), 6.68-6.81 (m, 1H), 6.78-6.89 (m, 2H), 6.91-6.95 (m, 1H); LC-MS (LC-ES) M+H−OMe=205.

B.
(trans)-3-(2-Methoxyphenoxy)cyclobutanecarboxylic acid

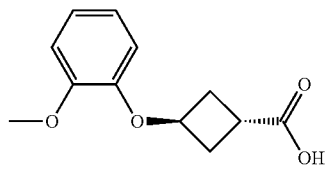

To a solution of (trans)-methyl 3-(2-methoxyphenoxy)cyclobutanecarboxylate (Intermediate 120A) (206 mg, 0.872 mmol) in THF (10 mL) was added LiOH (63 mg, 2.6 mmol) in water (5 mL). After 3 h, the reaction was adjusted to pH=4 with the addition of saturated aqueous citric acid, and the mixture was extracted with EtOAc (3×). The combined organic layers were dried over Na₂SO₄, filtered and concentrated to give the title compound (209 mg, quantitative). ¹H NMR (400 MHz, CD₃SOCD₃) δ 2.24-2.31 (m, 2H), 2.54-2.62 (m, 2H), 2.98-3.08 (m, 1H), 3.71 (s, 3H), 4.74 (t, J=7 Hz, 1H), 6.71 (dd, J=8, 2 Hz, 1H), 6.76-6.88 (m, 2H), 6.91-6.96 (m, 1H), 12.30 (br s, 1H); LC-MS (LC-ES) M−H=221.

Intermediate 121:
(trans)-3-(3-Ethylphenoxy)cyclobutanecarboxylic acid

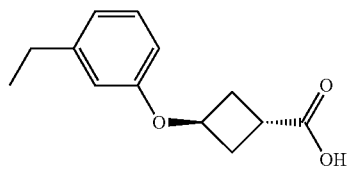 [SMILES: CCc1cccc(O[C@H]2C[C@H](C(=O)O)C2)c1]

A. (trans)-Methyl 3-(3-ethylphenoxy)cyclobutanecarboxylate

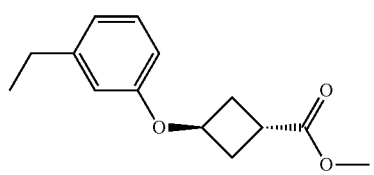 [SMILES: CCc1cccc(O[C@H]2C[C@H](C(=O)OC)C2)c1]

Triphenylphosphine (504 mg, 1.92 mmol) was added to a solution of 3-ethylphenol (0.20 mL, 1.6 mmol) in tetrahydrofuran (5 mL). The reaction mixture was cooled to 0° C., and (cis)-methyl 3-hydroxycyclobutanecarboxylate (250 mg, 1.92 mmol) was added, followed by DIAD (0.37 mL, 1.9 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give the title compound (169 mg, 41%). $^1$H NMR (400 MHz, CD$_3$SOCD$_3$) δ 1.13 (t, J=8 Hz, 3H), 2.22-2.31 (m, 2H), 2.45-2.56 (m, 2H), 2.58-2.65 (m, 2H), 3.10-3.19 (m, 1H), 3.62 (s, 3H), 4.72-4.81 (m, 1H), 6.56-6.61 (m, 2H), 6.75 (d, J=8 Hz, 1H), 7.11-7.16 (m, 1H); LC-MS (LC-ES) M+H=235.

B. (trans)-3-(3-Ethylphenoxy)cyclobutanecarboxylic acid

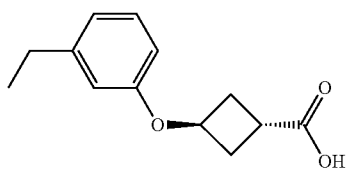 [SMILES: CCc1cccc(O[C@H]2C[C@H](C(=O)O)C2)c1]

To a solution of (trans)-methyl 3-(3-ethylphenoxy)cyclobutanecarboxylate (Intermediate 121A) (169 mg, 0.721 mmol) in THF (10 mL) was added LiOH (52 mg, 2.2 mmol) in water (5 mL). After 3 h, the reaction was adjusted to pH=4 with the addition of saturated aqueous citric acid, and the mixture was extracted with EtOAc (3×). The combined organic layers were dried over Na$_2$SO$_4$, filtered and concentrated to give the title compound (172 mg, 96%). $^1$H NMR (400 MHz, CD$_3$SOCD$_3$) δ 1.13 (t, J=8 Hz, 3H), 2.15-2.29 (m, 2H), 2.42-2.65 (m, 4H), 2.92-3.02 (m, 1H), 4.68-4.79 (m, 1H), 6.56-6.62 (m, 2H), 6.75 (d, J=8 Hz, 1H), 7.11-7.16 (m, 1H), 12.34 (br s, 1H); LC-MS (LC-ES) M−H=219.

Intermediate 122:
(trans)-3-(3-Chlorophenoxy)cyclobutanecarboxylic acid

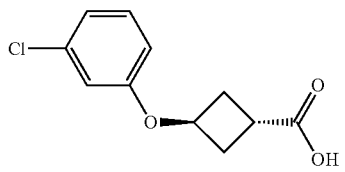

A. (trans)-Methyl 3-(3-chlorophenoxy)cyclobutanecarboxylate

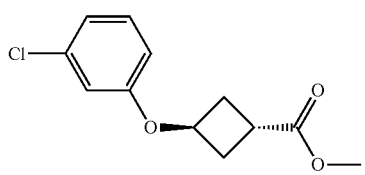 [SMILES: COC(=O)[C@H]1C[C@H](Oc2cccc(Cl)c2)C1]

Triphenylphosphine (504 mg, 1.92 mmol) was added to a solution of 3-chlorophenol (206 mg, 1.60 mmol) in tetrahydrofuran (5 mL). The reaction mixture was cooled to 0° C., and (cis)-methyl 3-hydroxycyclobutanecarboxylate (250 mg, 1.92 mmol) was added, followed by DIAD (0.37 mL, 1.9 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give the title compound (291 mg, 72%). $^1$H NMR (400 MHz, CD$_3$SOCD$_3$) δ 2.28-2.36 (m, 2H), 2.61-2.68 (m, 2H), 3.11-3.20 (m, 1H), 3.65 (s, 3H), 4.80-4.88 (m, 1H), 6.76-6.78 (m, 1H), 6.83-6.86 (m, 1H), 6.95-6.98 (m, 1H), 7.24-7.29 (m, 1H); LC-MS (LC-ES) M+H=241, 243 (Cl pattern).

B. (trans)-3-(3-Chlorophenoxy)cyclobutanecarboxylic acid

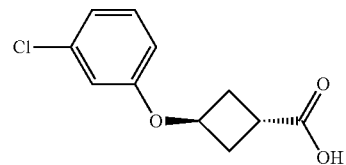 [SMILES: O=C(O)[C@H]1C[C@H](Oc2cccc(Cl)c2)C1]

To a solution of (trans)-methyl 3-(3-chlorophenoxy)cyclobutanecarboxylate (Intermediate 122A) (291 mg, 1.21 mmol) in THF (10 mL) was added LiOH (87 mg, 3.6 mmol) in water (5 mL). After 3 h, the reaction was adjusted to pH=4 with the addition of saturated aqueous citric acid, and the mixture was extracted with EtOAc (3×). The combined organic layers were dried over Na$_2$SO$_4$, filtered and concentrated to give the title compound (282 mg, quantitative). $^1$H NMR (400 MHz, CD$_3$SOCD$_3$) δ 2.24-2.32 (m, 2H), 2.58-2.65 (m, 2H), 3.01-3.10 (m, 1H), 4.78-4.86 (m, 1H), 6.76-6.79 (m, 1H), 6.83-6.86 (m, 1H), 6.94-6.98 (m, 1H), 7.24-7.30 (m, 1H), 12.44 (br s, 1H); LC-MS (LC-ES) M−H=225, 227 (Cl pattern).

Intermediate 123:
(trans)-3-(3-Fluorophenoxy)cyclobutanecarboxylic acid

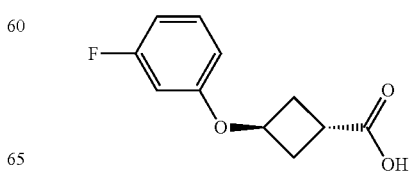

A. (trans)-Methyl 3-(3-fluorophenoxy)cyclobutanecarboxylate

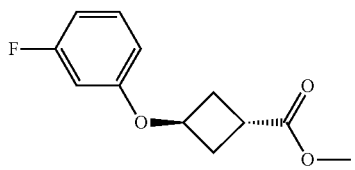 [SMILES: COC(=O)[C@H]1C[C@H](Oc2cccc(F)c2)C1]

Triphenylphosphine (504 mg, 1.92 mmol) was added to a solution of 3-fluorophenol (0.14 mL, 1.6 mmol) in tetrahydrofuran (5 mL). The reaction mixture was cooled to 0° C., and (cis)-methyl 3-hydroxycyclobutanecarboxylate (250 mg, 1.92 mmol) was added, followed by DIAD (0.37 mL, 1.9 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give the title compound (291 mg, 72%). $^1$H NMR (400 MHz, $CD_3SOCD_3$) δ 2.22-2.35 (m, 2H), 2.60-2.68 (m, 2H), 3.12-3.21 (m, 1H), 3.62 (s, 3H), 4.74-4.82 (m, 1H), 6.59-6.65 (m, 2H), 6.70-6.76 (m, 1H), 7.21-7.31 (m, 1H); LC-MS (LC-ES) M+H+$CH_3CN$=266.

B. (trans)-3-(3-Fluorophenoxy)cyclobutanecarboxylic acid

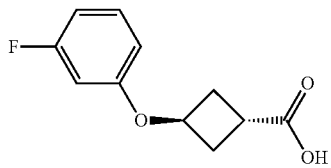 [SMILES: O=C(O)[C@H]1C[C@H](Oc2cccc(F)c2)C1]

To a solution of (trans)-methyl 3-(3-fluorophenoxy)cyclobutanecarboxylate (Intermediate 123A) (330 mg, 1.47 mmol) in THF (10 mL) was added LiOH (106 mg, 4.42 mmol) in water (5 mL). After 3 h, the reaction was adjusted to pH=4 with the addition of saturated aqueous citric acid, and the mixture was extracted with EtOAc (3×). The combined organic layers were dried over $Na_2SO_4$, filtered and concentrated to give the title compound (325 mg, quantitative). $^1$H NMR (400 MHz, $CD_3SOCD_3$) δ 2.21-2.31 (m, 2H), 2.57-2.67 (m, 2H), 3.05 (dt, J=10, 5 Hz, 1H), 4.70-4.81 (m, 1H), 6.59-6.65 (m, 2H), 6.94-6.98 (m, 1H), 7.21-7.31 (m, 1H), 12.32 (br s, 1H); LC-MS (LC-ES) M–H=209.

Intermediate 124: (trans)-3-(3-Chloro-5-fluorophenoxy)cyclobutanecarboxylic acid

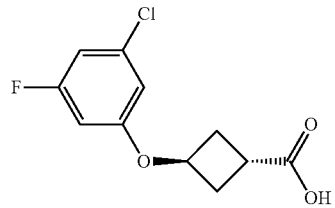 [SMILES: O=C(O)[C@H]1C[C@H](Oc2cc(F)cc(Cl)c2)C1]

A. (trans)-Methyl 3-(3-Chloro-5-fluorophenoxy)cyclobutanecarboxylate

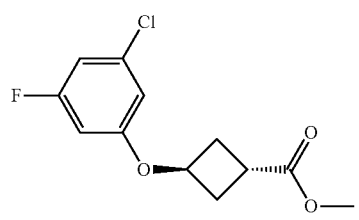 [SMILES: COC(=O)[C@H]1C[C@H](Oc2cc(F)cc(Cl)c2)C1]

Triphenylphosphine (504 mg, 1.92 mmol) was added to a solution of 3-chloro-5-fluorophenol (0.17 mL, 1.6 mmol) in tetrahydrofuran (5 mL). The reaction mixture was cooled to 0° C., and (cis)-methyl 3-hydroxycyclobutanecarboxylate (250 mg, 1.92 mmol) was added, followed by DIAD (0.37 mL, 1.9 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give the title compound (291 mg, 72%). $^1$H NMR (400 MHz, $CD_3SOCD_3$) δ 2.25-2.31 (m, 2H), 2.60-2.70 (m, 2H), 3.12-3.21 (m, 1H), 3.62 (s, 3H), 4.80-4.89 (m, 1H), 6.51-6.58 (m, 1H), 6.70-6.78 (m, 1H), 6.95-6.98 (m, 1H); LC-MS (LC-ES) M-$CO_2$Me=201, 203 (Cl pattern).

B. (trans)-3-(3-Chloro-5-fluorophenoxy)cyclobutanecarboxylic acid

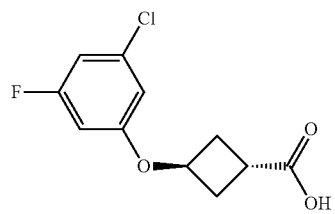

To a solution of (trans)-Methyl 3-(3-Chloro-5-fluorophenoxy)cyclobutanecarboxylate (Intermediate 124A) (295 mg, 1.14 mmol) in THF (10 mL) was added LiOH (82 mg, 3.4 mmol) in water (5 mL). After 3 h, the reaction was adjusted to pH=4 with the addition of saturated aqueous citric acid, and the mixture was extracted with EtOAc (3×). The combined organic layers were dried over Na$_2$SO$_4$, filtered and concentrated to give the title compound (244 mg, 65%). $^1$H NMR (400 MHz, CD$_3$SOCD$_3$) δ 2.19-2.30 (m, 2H), 2.58-2.67 (m, 2H), 3.01-3.11 (m, 1H), 4.84 (dd, J=7, 6 Hz, 1H), 6.68-6.75 (m, 2H), 6.94-6.98 (m, 1H), 12.30 (br s, 1H); LC-MS (LC-ES) M+H=245, 247 (Cl pattern).

Intermediate 125: (trans)-3-((5-Fluoroquinolin-8-yl)oxy)cyclobutanecarboxylic acid

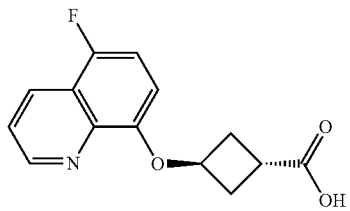 [SMILES: O=C(O)[C@H]1C[C@H](Oc2ccc(F)c3cccnc23)C1]

A. (trans)-Methyl 3-((5-fluoroquinolin-8-yl)oxy)cyclobutanecarboxylate

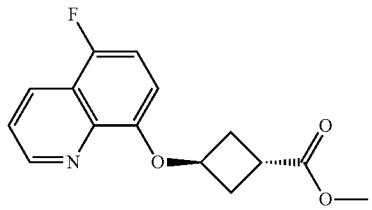 [SMILES: COC(=O)[C@H]1C[C@H](Oc2ccc(F)c3cccnc23)C1]

Triphenylphosphine (1.21 g, 4.60 mmol) was added to a solution of 5-fluoroquinolin-8-ol (500 mg, 3.06 mmol) in tetrahydrofuran (10 mL). The reaction mixture was cooled to 0° C., and methyl 3-hydroxycyclobutanecarboxylate (0.49 mL, 4.6 mmol) was added, followed by DIAD (0.89 mL, 4.6 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give a mixture of cis and trans isomers which were separated on a Whelk 0 RR 20×250 mm column eluting with 40% EtOH in hexanes to give the title compound (415 mg, 49%). $^1$H NMR (400 MHz, CD$_3$SOCD$_3$) δ 2.48-2.55 (m, 2H), 2.77 (ddd, J=13, 7, 4 Hz, 2H), 3.21-3.29 (m, 1H), 3.66 (s, 3H), 5.04 (t, J=7 Hz, 1H), 6.96 (dd, J=9, 5 Hz, 1H), 7.32 (dd, J=10, 9 Hz, 1H), 7.68 (dd, J=8, 4 Hz, 1H), 8.44 (dd, J=8, 2 Hz, 1H), 8.97 (dd, J=4, 2 Hz, 1H); LC-MS (LC-ES) M+H=276.

B. (trans)-3-((5-Fluoroquinolin-8-yl)oxy)cyclobutanecarboxylic acid

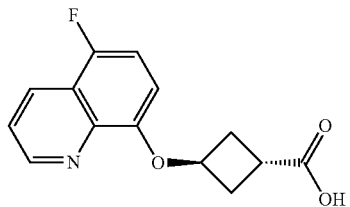 [SMILES: O=C(O)[C@H]1C[C@H](Oc2ccc(F)c3cccnc23)C1]

To a solution of (trans)-Methyl 3-((5-fluoroquinolin-8-yl)oxy)cyclobutanecarboxylate (Intermediate 125A) (415 mg, 1.51 mmol) in THF (10 mL) was added LiOH (108 mg, 4.52 mmol) in water (2 mL). After 2 h, the reaction was adjusted to pH=4 with the addition of saturated aqueous citric acid, and the mixture was extracted with EtOAc (3×). The combined organic layers were dried over Na$_2$SO$_4$, filtered and concentrated to give the title compound (400 mg, 100%). $^1$H NMR (400 MHz, CD$_3$SOCD$_3$) δ 2.38-2.50 (m, 2H), 2.66-2.75 (m, 2H), 3.05-3.12 (m, 1H), 4.92-5.01 (m, 1H), 6.89-6.93 (m, 1H), 7.23-7.31 (m, 1H), 7.61-7.66 (m, 1H), 8.38-8.42 (m, 1H), 8.91-8.95 (m, 1H), 12.38 (br s, 1H); LC-MS (LC-ES) M+H=262.

Intermediate 126: (trans)-3-((6-Fluoroquinolin-8-yl)oxy)cyclobutanecarboxylic acid

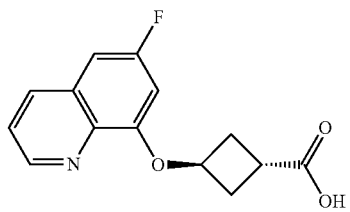 [SMILES: O=C(O)[C@H]1C[C@H](Oc2cc(F)cc3cccnc23)C1]

A. 6-Fluoroquinolin-8-ol

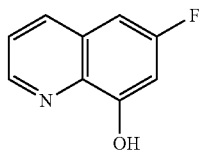 [SMILES: Oc1cc(F)cc2cccnc12]

Aluminium chloride (4.52 g, 33.9 mmol) was added to a solution of 6-fluoro-8-methoxyquinoline (2.00 g, 11.3 mmol) in 1,2-dichloroethane (20 mL), and the reaction mixture was heated to 50° C. After 3 h, the mixture was cooled to 0° C., quenched with saturated aqueous NaHCO$_3$ until pH neutral and filtered. The collected solid was retained. The aqueous layer of the filtrate was extracted with DCM (3×), and the combined organics were washed with brine, dried over Na$_2$SO$_4$, filtered and concentrated. The residue was purified on silica gel using 0%-100% EtOAc: EtOH (3:1) in hexanes to afford 186 mg of the title compound. The previously retained solid was stirred in THF (20 mL) overnight, and the mixture was filtered through Celite.

B. (trans)-Methyl 3-((6-fluoroquinolin-8-yl)oxy)cyclobutanecarboxylate

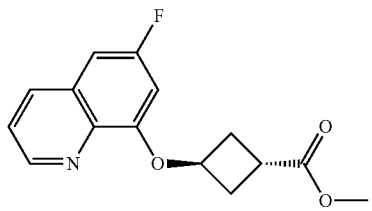 [SMILES: COC(=O)[C@H]1C[C@H](Oc2cc(F)cc3cccnc23)C1]

Triphenylphosphine (916 mg, 3.49 mmol) was added to a solution of 6-fluoroquinolin-8-ol (Intermediate 126A) (380 mg, 2.23 mmol) in tetrahydrofuran (10 mL). The reaction mixture was cooled to 0° C., and methyl 3-hydroxycyclobutanecarboxylate (0.37 mL, 3.5 mmol) was added, followed by DIAD (0.68 mL, 3.5 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc-hexanes gradient to give a mixture of cis and trans isomers which were separated on an IC 30×250 mm column eluting with 50% EtOH in hexanes to give the title compound (137 mg, 21%). $^1$H NMR (400 MHz, $CD_3SOCD_3$) δ 2.48-2.59 (m, 2H), 2.82 (ddd, J=14, 7, 5 Hz, 2H), 3.22-3.32 (m, 1H), 3.31 (s, 3H), 5.07 (t, J=7 Hz, 1H), 6.91 (dd, J=11, 3 Hz, 1H), 7.31 (dd, J=9, 3 Hz, 1H), 7.59 (dd, J=8, 4 Hz, 1H), 8.30 (dd, J=8, 2 Hz, 1H), 8.83 (dd, J=4, 2 Hz, 1H); LC-MS (LC-ES) M+H=276.

C. (trans)-3-((6-Fluoroquinolin-8-yl)oxy)cyclobutanecarboxylic acid

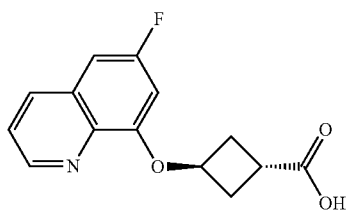 [SMILES: O=C(O)[C@H]1C[C@H](Oc2cc(F)cc3cccnc23)C1]

To a solution of (trans)-methyl 3-((6-fluoroquinolin-8-yl)oxy)cyclobutanecarboxylate (Intermediate 126B) (167 mg, 0.607 mmol) in THF (5 mL) was added LiOH (44 mg, 1.8 mmol) in water (1 mL). After 2 h, the reaction was adjusted to pH=4 with the addition of saturated aqueous citric acid, and the mixture was extracted with EtOAc (3×). The combined organic layers were dried over $Na_2SO_4$, filtered and concentrated to give the compound (155 mg, 94%). $^1$H NMR (400 MHz, $CD_3SOCD_3$) δ 2.41-2.51 (m, 2H), 2.71-2.79 (m, 2H), 3.07-3.15 (m, 1H), 4.98-5.05 (m, 1H), 6.84-6.89 (m, 1H), 7.25-7.30 (m, 1H), 7.53-7.58 (m, 1H), 8.25-8.30 (m, 1H), 8.78-8.82 (m, 1H), 12.35 (br s, 1H); LC-MS (LC-ES) M+H=262.

The filtrate was concentrated and dried under vacuum to afford an additional 500 mg the title compound (37% total yield). LC-MS (LC-ES) peak at T=0.37 min; M+H=164.

Intermediate 127:
2-(3-Aminocyclobutyl)propan-2-ol

A. 3-(2-Hydroxypropan-2-yl)cyclobutanol

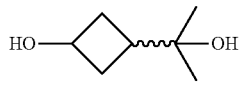

To a diethyl ether solution (30 mL) containing methyl magnesium bromide (7.63 mL of a 3.0 M diethyl ether solution) was added a diethyl ether solution (5 mL) containing ethyl 3-hydroxycyclobutane carboxylate (2.05 g, 6.94 mmol), dropwise. After 2 h the reaction was carefully quenched with 3 M aqueous HCl. $MgSO_4$ was added until the evolution of gas stopped. The solution was filtered, and the solvent removed in vacuo yielding a viscous oil which was purified by silica gel chromatography (50%-100% EtOAc in hexanes) to give the title compound (419 mg, 46%). $^1$H NMR ($CDCl_3$) δ 1.13 (s, 6H), 1.74-1.86 (m, 4H), 2.23-2.39 (m, 2H), 2.66 (br s, 1H), 4.03-4.09 (m, 1H).

B. 3-(2-Hydroxypropan-2-yl)cyclobutyl4-methylbenzenesulfonate

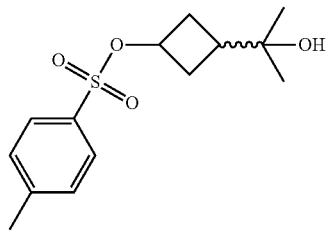 [SMILES: Cc1ccc(S(=O)(=O)OC2CC(C(C)(C)O)C2)cc1]

To a pyridine solution (15 mL) containing 3-(2-hydroxypropan-2-yl)cyclobutanol (Intermediate 127A) (415 mg, 3.19 mmol) cooled to 0° C. was added p-toluenesulfonyl chloride (638 mg, 3.35 mmol). The reaction was slowly allowed to warm to room temperature overnight, and the organics were taken up in $Et_2O$. The solution was washed with water, saturated $NaHCO_3$ and saturated $NaHSO_4$ followed by drying over $MgSO_4$. The solvent was removed in vacuo yielding the title compound (792 mg) as a viscous oil which was taken on crude. $^1$H NMR ($CDCl_3$) δ 1.08 (s, 6H), 1.71-1.88 (m, 1H), 1.98-2.11 (m, 2H), 2.12-2.23 (m, 2H), 2.45 (s, 3H), 4.65 (quin, J=8 Hz, 1H), 7.33 (d, J=8 Hz, 2H), 7.78 (d, J=8 Hz, 2H).

C. 2-(3-Azidocyclobutyl)propan-2-ol

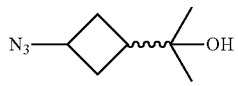

A DMF solution (40 mL) of 3-(2-hydroxypropan-2-yl)cyclobutyl 4-methylbenzenesulfonate (Intermediate 127B) (2.50 g, 8.79 mmol) and sodium azide (686 mg, 10.6 mmol) was heated to 90° C. overnight. Upon cooling, the organics were taken up in Et₂O and washed with water (2×) and saturated NaHCO₃ followed by drying over MgSO₄. The solvent was carefully removed in vacuo yielding the title compound (1.19 g) as an oil which was taken on crude. $^1$H NMR (CDCl₃) δ 1.14 (s, 6H), 2.03-2.16 (m, 2H), 2.26-2.34 (m, 2H), 2.35-2.44 (m, 1H), 3.87-4.01 (m, 1H).

D. 2-(3-Aminocyclobutyl)propan-2-ol

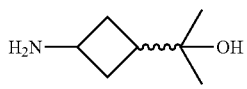

To an EtOH solution (25 mL) containing 10% Pd/C (809 mg, wet Degussa) was added an EtOH solution (5 mL) of 2-(3-azidocyclobutyl)propan-2-ol (Intermediate 127C) (1.18 g, 7.60 mmol). The flask was then evacuated under vacuum and refilled with hydrogen via a balloon. This process was repeated twice more and then the reaction was stirred under 1 atmosphere of hydrogen overnight. The catalyst was removed under vacuum filtration though a plug of Celite®. The Celite® was rinsed with DCM and the solvent removed in vacuo yielding the title compound (920 mg) as an oil. $^1$H NMR (CDCl₃) δ 1.12 (s, 6H), 1.66-1.77 (m, 2H), 2.16-2.28 (m, 2H), 2.27-2.42 (m, 1H), 3.40-3.52 (m, 1H).

Intermediate 128: (trans)-3-(Quinazolin-8-yloxy)cyclobutanecarboxylic acid

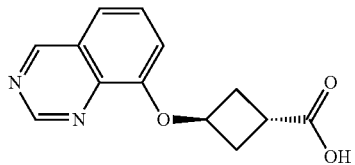 [SMILES: O=C(O)[C@H]1C[C@H](Oc2cccc3cncnc23)C1]

A. (trans)-Methyl 3-(quinazolin-8-yloxy)cyclobutanecarboxylate

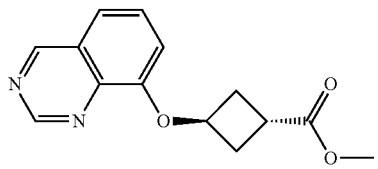 [SMILES: COC(=O)[C@H]1C[C@H](Oc2cccc3cncnc23)C1]

Triphenylphosphine (538 mg, 2.05 mmol) was added to a solution of quinazolin-8-ol (250 mg, 1.71 mmol) in tetrahydrofuran (10 mL). The reaction mixture was cooled to 0° C., and (cis)-methyl 3-hydroxycyclobutanecarboxylate (245 mg, 1.88 mmol) was added, followed by DIAD (0.40 mL, 2.1 mmol). After 10 min, the reaction mixture was warmed to room temperature, stirred for 2 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc: EtOH (3:1) in hexanes gradient to give the title compound (178 mg, 40%) as a light brown oil. $^1$H NMR (400 MHz, CDCl₃) δ 2.65-2.75 (m, 2H), 2.80-2.90 (m, 2H), 3.20-3.28 (m, 1H), 3.74 (s, 3H), 5.10-5.15 (m, 1H), 7.04-7.08 (m, 1H), 7.47-7.57 (m, 2H), 9.35-9.37 (m, 2H); LC-MS (LC-ES) M−H=258.

B. (trans)-3-(Quinazolin-8-yloxylcyclobutanecarboxylic acid

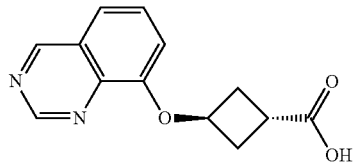 [SMILES: O=C(O)[C@H]1C[C@H](Oc2cccc3cncnc23)C1]

To a solution of (trans)-methyl 3-(quinazolin-8-yloxy)cyclobutanecarboxylate (Intermediate 128A) (175 mg, 0.678 mmol) in THF (3 mL) was added LiOH hydrate (85 mg, 2.0 mmol) in water (1.5 mL). After stirring overnight, the reaction was adjusted to pH=4.5 with the addition of 10% aqueous citric acid, and the mixture was extracted with EtOAc (3×). The combined organic layers were dried over Na₂SO₄, filtered and concentrated to give the title compound (190 mg, quantitative) as a tan solid. $^1$H NMR (400 MHz, CD₃SOCD₃) δ 2.40-2.49 (m, 2H), 2.68-2.77 (m, 2H), 3.08-3.17 (m, 1H), 4.99-5.05 (m, 1H), 7.21-7.25 (m, 1H), 7.58-7.66 (m, 2H), 9.24-9.27 (m, 1H), 9.54 (s, 1H), 12.40 (br s, 1H).

Intermediate 129: (trans)-3-Hydroxy-N-(thiazol-2-yl)cyclobutanecarboxamide

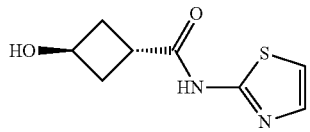 [SMILES: O=C(Nc1nccs1)[C@H]1C[C@H](O)C1]

A. (trans)-Methyl 3-((tert-butyldiphenylsilyl)oxy)cyclobutanecarboxylate

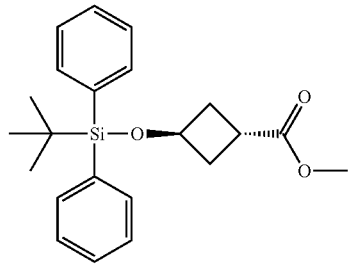 [SMILES: COC(=O)[C@H]1C[C@H](O[Si](c2ccccc2)(c2ccccc2)C(C)(C)C)C1]

To (trans)-methyl 3-hydroxycyclobutanecarboxylate (1.00 g, 7.68 mmol) and imidazole (1.15 g, 16.9 mmol) in DMF (35 mL) at 0° C. was added tert-butylchlorodiphenylsilane (2.32 g, 8.45 mmol). The reaction was warmed to room temperature overnight, and was concentrated, diluted with EtOAc, and washed with water and brine. The organic layer was separated, dried over Na$_2$SO$_4$, filtered and concentrated. The residue was purified by silica gel chromatography (0%-30% EtOAc in hexanes) to give the title compound (3.05 g, quantitative) as a clear oil. $^1$H NMR (CDCl$_3$) δ 1.01 (s, 9H), 2.28-2.44 (m, 4H), 2.92-2.98 (m, 1H), 3.59 (s, 3H), 4.50-4.56 (m, 1H), 7.32-7.42 (m, 6H), 7.59-7.66 (m, 4H).

B. (trans)-3-((tert-Butyldiphenylsilyl)oxy)cyclobutanecarboxylic acid

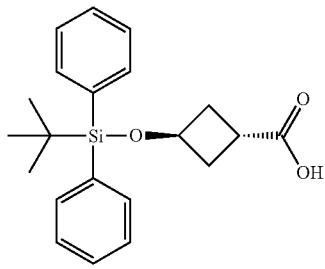 [SMILES: CC(C)(C)[Si](O[C@H]1C[C@H](C(=O)O)C1)(c1ccccc1)c1ccccc1]

To a solution of (trans)-methyl 3-((tert-butyldiphenylsilyl)oxy)cyclobutanecarboxylate (Intermediate 129A) (3.00 g, 1.84 mmol) in THF (40 mL) was added LiOH hydrate (1.03 g, 24.4 mmol) in water (20 mL). After stirring overnight, the reaction was made acidic with the addition of 1 N aqueous HCl, and the mixture was extracted with EtOAc (4×). The combined organic layers were dried over Na$_2$SO$_4$, filtered and concentrated to give the title compound (2.80 g, 97%) as an oil. $^1$H NMR (400 MHz, CDCl$_3$) δ 1.01 (s, 9H), 2.28-2.42 (m, 4H), 2.93-3.01 (m, 1H), 4.48-4.56 (m, 1H), 7.32-7.42 (m, 6H), 7.58-7.62 (m, 4H); LC-MS (LC-ES) M−H=353.

C. (trans)-3-((tert-Butyldiphenylsilyl)oxy)-N-(thiazol-2-yl)cyclobutanecarboxamide

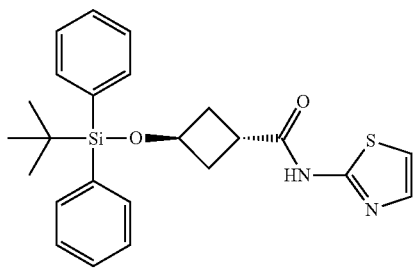 [SMILES: CC(C)(C)[Si](O[C@H]1C[C@H](C(=O)Nc2nccs2)C1)(c1ccccc1)c1ccccc1]

To a DMF (50 mL) solution of (trans)-3-((tert-butyldiphenylsilyl)oxy)cyclobutanecarboxylic acid (Intermediate 129B) (2.00 g, 5.64 mmol) was added HATU (2.68 g, 5.64 mmol) and N,N-diisopropylethylamine (2.96 mL, 16.9 mmol). After 5 minutes, thiazol-2-amine (706 mg, 7.05 mmol) was added, and the mixture was stirred for 6.5 h, poured into water, and extracted with EtOAc (3×). The combined organic layers were dried over Na$_2$SO$_4$, filtered and concentrated. This residue was purified on silica gel, eluting with 0%-65% EtOAc in hexanes to give the title compound (1.92 g, 78%) as a white foam. $^1$H NMR (400 MHz, CDCl$_3$) δ 1.03 (s, 9H), 2.38-2.46 (m, 2H), 2.52-2.60 (m, 2H), 3.12-3.20 (m, 1H), 4.61-4.68 (m, 1H), 6.96 (d, J=4 Hz, 1H), 7.33-7.44 (m, 7H), 7.61-7.65 (m, 4H), 10.90 (s, 1H); LC-MS (LC-ES) M+H=437.

D. (trans)-3-Hydroxy-N-(thiazol-2-yl)cyclobutanecarboxamide

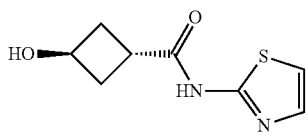 [SMILES: O=C(Nc1nccs1)[C@H]1C[C@H](O)C1]

To a THF solution (25 mL) of (trans)-3-((tert-butyldiphenylsilyhoxy)-N-(thiazol-2-yl)cyclobutanecarboxamide (Intermediate 129C) (1.92 g, 4.40 mmol) at 0° C. was added 1 M TBAF in THF (22.0 mL, 22.0 mmol). The reaction was allowed to warm to room temperature. After stirring overnight, the reaction was concentrated, and saturated aqueous NaHCO$_3$ solution (30 mL) was added. This mixture was extracted EtOAc (6×), and the combined organic layers were dried over Na$_2$SO$_4$, filtered and concentrated. The residue was purified on silica gel, eluting with 0%-75% EtOAc:EtOH (3:1) in hexanes to give the title compound (1.92 g, 78%) as a white solid. $^1$H NMR (CDCl$_3$) δ 1.90-1.95 (m, 1H), 2.26-2.35 (m, 2H), 2.68-2.74 (m, 2H), 3.18-3.26 (m, 1H), 4.62-4.70 (m, 1H), 7.00 (d, J=8 Hz, 1H), 7.43 (d, J=8 Hz, 1H), 11.20 (s, 1H); LC-MS (LC-ES) M+H=199.

Intermediate 130: (trans)-3-(2,3-Diaminophenoxy)-N-(thiazol-2-yl)cyclobutanecarboxamide

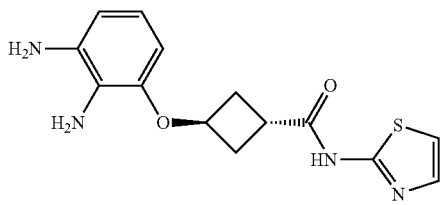 [SMILES: Nc1cccc(O[C@H]2C[C@H](C(=O)Nc3nccs3)C2)c1N]

A. 1-Azido-3-fluoro-2-nitrobenzene

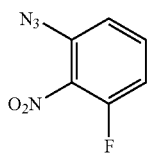 [SMILES: [N-]=[N+]=Nc1cccc(F)c1[N+](=O)[O-]]

To a solution of 1,3-difluoro-2-nitrobenzene (4.80 g, 30.2 mmol) in DMSO (35 mL) was added sodium azide (2.26 g, 34.7 mmol). After stirring overnight, the reaction was diluted with EtOAc (150 mL), washed with water (2×150 mL), dried over Na$_2$SO$_4$, filtered and concentrated to give the title compound (5.40 g, 98%) as a pale yellow solid. $^{1}$H NMR (CDCl$_3$) δ 6.99-7.11 (m, 2H), 7.46-7.52 (m, 1H).

B. (trans)-3-(3-Azido-2-nitrophenoxy)-N-(thiazol-2-yl)cyclobutanecarboxamide

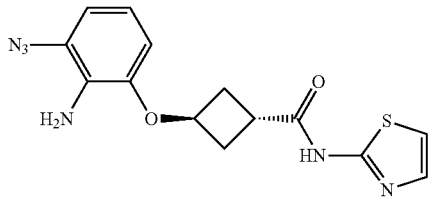 [SMILES: [N-]=[N+]=Nc1cccc(O[C@H]2C[C@H](C(=O)Nc3nccs3)C2)c1N]

To a solution of (trans)-3-hydroxy-N-(thiazol-2-yl)cyclobutanecarboxamide (Intermediate 129) (105 mg, 0.527 mmol) in THF (2 mL) was added a 60% dispersion of NaH in mineral oil (39 mg, 0.97 mmol). After 40 min, the reaction was cooled to −78° C., and 1-azido-3-fluoro-2-nitrobenzene (Intermediate 130A) (80 mg, 0.44 mmol) in THF (2.0 mL) was added. The mixture was allowed to warm to room temperature over 2 h and was quenched with saturated aqueous NH$_4$Cl solution. The mixture was extracted with EtOAc (3×), and the combined organic layers were dried over Na$_2$SO$_4$, filtered and concentrated. The residue was purified on silica gel, eluting with 0%-100% EtOAc: EtOH (3:1) in hexanes to give the title compound (30 mg, 19%) as a yellow solid. $^{1}$H NMR (400 MHz, CDCl$_3$) δ 2.49-2.57 (m, 2H), 2.80-2.89 (m, 2H), 3.31-3.39 (m, 1H), 5.04-5.11 (m, 1H), 6.63-6.66 (m, 1H), 6.84-6.86 (m, 1H), 7.04-7.06 (m, 1H), 7.35-7.39 (m, 1H), 7.44-7.46 (m, 1H), 11.20 (s, 1H); LC-MS (LC-ES) M+H=361.

C. (trans)-3-(2,3-Diaminophenoxy)-N-(thiazol-2-yl)cyclobutanecarboxamide

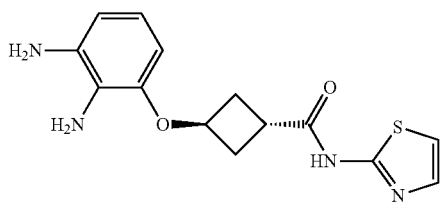 [SMILES: Nc1cccc(O[C@H]2C[C@H](C(=O)Nc3nccs3)C2)c1N]

To a MeOH solution (4 mL) containing 10% Pd/C (12 mg, 0.011 mmol) was added (trans)-3-(3-azido-2-nitrophenoxy)-N-(thiazol-2-yl)cyclobutanecarboxamide (Intermediate 130B) (27 mg, 0.075 mmol). The flask was then evacuated under vacuum and refilled with hydrogen via a balloon. The reaction was stirred under 1 atmosphere of hydrogen 5 h, filtered through a syringe filter and concentrated to give the title compound (27 mg, quantitative) as a glass. LC-MS (LC-ES) M+H=305.

Intermediate 131: (trans)-3-(Imidazo[1,2-a]pyridin-8-yloxy)cyclobutanecarboxylic acid

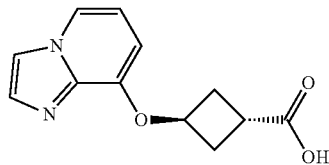 [SMILES: O=C(O)[C@H]1C[C@H](Oc2cccn3ccnc23)C1]

A. (trans)-Methyl 3-(imidazo[1,2-a]pyridin-8-yloxy)cyclobutanecarboxylate

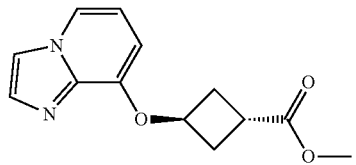 [SMILES: COC(=O)[C@H]1C[C@H](Oc2cccn3ccnc23)C1]

Triphenylphosphine (293 mg, 1.12 mmol) was added to a solution of imidazo[1,2-a]pyridin-8-ol (125 mg, 0.932 mmol) in tetrahydrofuran (4 mL). The reaction mixture was cooled to 0° C., and (cis)-methyl 3-hydroxycyclobutanecarboxylate (133 mg, 1.03 mmol) was added, followed by DIAD (0.22 mL, 1.1 mmol). After 10 min, the reaction mixture was warmed to room temperature, stirred for 3 days and diluted with water and EtOAc. The mixture was partitioned, and the aqueous layer was extracted with EtOAc (2×). The organic layer was washed with water, dried over sodium sulfate, filtered, and concentrated. The residue was purified on silica gel eluting with a 0%-100% EtOAc: EtOH (3:1) in hexanes to give the title compound (110 mg, 48%). $^{1}$H NMR (400 MHz, CDCl$_3$) δ 2.61-2.70 (m, 2H), 2.75-2.82 (m, 2H), 3.18-3.27 (m, 1H), 3.72 (s, 3H), 5.02-5.10 (m, 1H), 6.23-6.26 (m, 1H), 6.60-6.66 (m, 1H), 7.53-7.56 (m, 2H), 7.73-7.76 (m, 1H); LC-MS (LC-ES) M+H=248.

B. (trans)-3-(Imidazo[1,2-a]pyridin-8-yloxy)cyclobutanecarboxylic acid

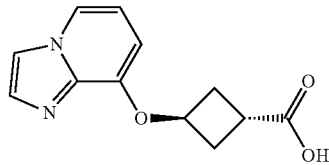 [SMILES: O=C(O)[C@H]1C[C@H](Oc2cccn3ccnc23)C1]

To a solution of (trans)-methyl 3-(imidazo[1,2-a]pyridin-8-yloxy)cyclobutanecarboxylate (Intermediate 131A) (80 mg, 0.33 mmol) in THF (4 mL) was added LiOH monohydrate (34 mg, 0.81 mmol) in water (2 mL). After stirring overnight, the reaction was adjusted to pH=4 with the addition of saturated aqueous citric acid, and the mixture was extracted with EtOAc (3×). The combined organic layers were dried over Na$_2$SO$_4$, filtered and concentrated to give the title compound (72 mg, 96%) as a tacky white solid. LC-MS (LC-ES) M+H=233.

Intermediate 132: 4-(Azetidin-3-yloxy)benzo[d]isothiazole hydrochloride

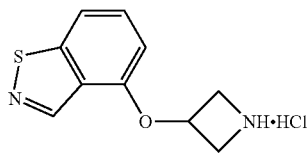

A. 2-(Benzylthio)-6-methoxybenzaldehyde

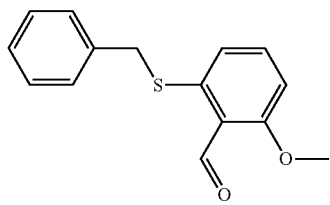 [SMILES: COc1cccc(SCc2ccccc2)c1C=O]

To a stirred, cooled (0° C.) suspension of sodium tert-butoxide (750 mg, 7.80 mmol) in THF (10 mL) was added benzyl mercaptan (0.80 mL, 6.8 mmol). After 30 minutes, 2-fluoro-6-methoxybenzaldehyde (1.00 g, 6.49 mmol) in THF (2 mL) was added dropwise. The mixture was warmed to room temperature and after 1 h poured into water (30 mL). The resulting precipitate was stirred for 5 minutes, collected via vacuum filtration and washed with water (10 mL) and Et$_2$O (10 mL) and dried in vacuo to give the title compound (1.71 g, quantitative) as a pale yellow solid. $^1$H NMR (400 MHz, CD$_3$SOCD$_3$) δ 3.91 (s, 3H), 4.21 (s, 2H), 6.98 (d, J=9 Hz, 1H), 7.11 (d, J=8 Hz, 1H), 7.29 (d, J=7 Hz, 1H), 7.32-7.38 (m, 2H), 7.40-7.47 (m, 2H), 7.56 (t, J=8 Hz, 1H), 10.45 (s, 1H); LC-MS (LC-ES) M+H=259.

B. 4-Methoxybenzo[d]isothiazole

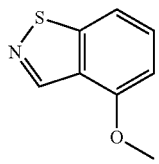

A mixture of 2-(benzylthio)-6-methoxybenzaldehyde (Intermediate 132A) (1.71 g, 6.62 mmol) and thioanisole (1.60 mL, 13.5 mmol) in acetonitrile (15 mL) and water (15 mL) was stirred for 30 minutes. To this mixture was added hydroxylamine-O-sulfonic acid (1.15 g, 10.2 mmol). After 2 h, the mixture was quenched with saturated aqueous NaHCO$_3$ (40 mL) and extracted with EtOAc. The organic layer was washed with brine, dried over Na$_2$SO$_4$, filtered and concentrated. The residue was purified on silica gel eluting with a 0%-10% EtOAc in hexanes gradient to give the title compound (682 mg, 62%) as a white solid. $^1$H NMR (400 MHz, CD$_3$SOCD$_3$) δ 4.00 (s, 3H), 6.99 (d, J=8 Hz, 1H), 7.57 (t, J=8 Hz, 1H), 7.75 (d, J=8 Hz, 1H), 9.07 (d, J=1 Hz, 1H); LC-MS (LC-ES) M+H=166.

C. Benzo[d]isothiazol-4-ol

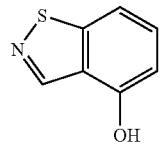

A mixture of 4-methoxybenzo[d]isothiazole (Intermediate 132B) (674 mg, 4.08 mmol) and pyridine hydrochloride (4.30 g, 37.2 mmol) was heated to 195° C. After 5 h, the reaction was cooled and diluted with water and EtOAc and stirred overnight. The mixture was poured into 1 N aqueous HCl and extracted with EtOAc. The organic layer was washed with brine, dried over Na$_2$SO$_4$ and filtered. The residue was purified on silica gel eluting with a 0%-25% EtOAc in hexanes gradient to give the title compound (480 mg, 78%) as a white solid. $^1$H NMR (400 MHz, CD$_3$SOCD$_3$) δ 6.81 (d, J=8 Hz, 1H), 7.42 (t, J=8 Hz, 1H), 7.58 (d, J=8 Hz, 1H), 9.06 (d, J=1 Hz, 1H), 10.72 (s, 1H); LC-MS (LC-ES) M+H=152.

D. tert-Butyl 3-(benzo[d]isothiazol-4-yloxy)azetidine-1-carboxylate

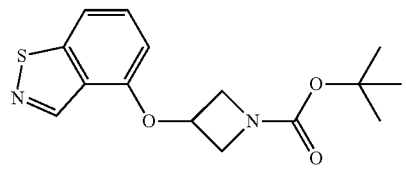 [SMILES: CC(C)(C)OC(=O)N1CC(Oc2cccc3sncc23)C1]

To a stirred solution of tert-butyl 3-((methylsulfonyl)oxy)azetidine-1-carboxylate (Intermediate 1) (260 mg, 1.04 mmol) and benzo[d]isothiazol-4-ol (Intermediate 132C) (150 mg, 0.992 mmol) in DMF (4 mL) was added cesium carbonate (360 mg, 1.11 mmol). The mixture was heated to 80° C. overnight, poured into water and extracted twice with EtOAc. The combined organic layers were washed with brine, dried over Na$_2$SO$_4$, filtered and concentrated. The remaining material was purified on silica gel eluting with a 0%-40% EtOAc-hexanes gradient to give the title compound (178 mg, 69%) as a white solid. $^1$H NMR (400 MHz, CD$_3$SOCD$_3$) δ 1.40 (s, 9H), 3.95 (d, J=7 Hz, 2H), 4.35-4.46 (m, 2H), 5.18-5.27 (m, 1H), 6.73 (d, J=8 Hz, 1H), 7.53 (t, J=8 Hz, 1H), 7.81 (d, J=8 Hz, 1H), 9.13 (s, 1H); LC-MS (LC-ES) M+H=307.

E. 4-(Azetidin-3-yloxy)benzo[d]isothiazole hydrochloride

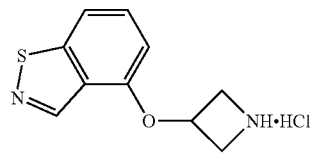

To neat tert-butyl 3-(benzo[d]isothiazol-4-yloxy)azetidine-1-carboxylate (Intermediate 132D) (177 mg, 0.578 mmol) was added 4 N HCl in dioxane (3.0 mL, 12 mmol). After 2.5 h, the mixture was diluted with diethyl ether, and the resulting solid was collected by filtration to give the title compound as a white solid (138 mg, 98%). $^1$H NMR (400 MHz, CD$_3$SOCD$_3$) δ 4.05-4.19 (m, 2H), 4.45-4.60 (m, 2H), 5.32 (t, J=5 Hz, 1H), 6.79 (d, J=8 Hz, 1H), 7.54 (t, J=8 Hz, 1H), 7.85 (d, J=8 Hz, 1H), 9.15 (s, 1H); LC-MS (LC-ES) M+H=207.

Intermediate 133: 4-(Azetidin-3-yloxy)-2-methylbenzo[d]thiazole hydrochloride

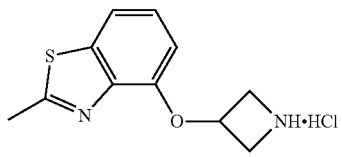

A. 2-Fluoro-6-methoxyaniline

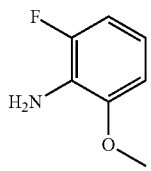

To an EtOH solution (400 mL) containing 10% Pd/C (7.46 g, 70.1 mmol) in a Parr vessel was added 1-fluoro-3-methoxy-2-nitrobenzene (40.0 g, 234 mmol). The vessel was evacuated under vacuum and refilled with hydrogen (50 psi). The reaction was shaken 5 h, filtered through Celite® and concentrated to give the title compound (30.0 g, 83%) as a colorless oil. $^1$H NMR (400 MHz, CDCl$_3$) δ 3.75 (br s, 2H), 3.86 (s, 3H), 6.58-6.71 (m, 3H); LC-MS (LC-ES) M+H=142.

B. N-(2-Fluoro-6-methoxyphenyl)acetamide

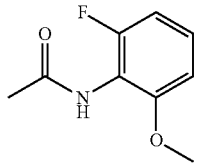

To a suspension of 2-fluoro-6-methoxyaniline (Intermediate 133A) (30.0 g, 193 mmol) in acetic anhydride (21.9 mL, 232 mmol) and DCM (200 mL) was added triethylamine (40.4 mL, 290 mmol), dropwise. After 12 h, the reaction mixture was concentrated, and the residue taken up in saturated aqueous sodium bicarbonate (250 mL). The resulting solid was collected by filtration to give the title compound (25.0 g, 65%). LC-MS (LC-ES) peak at T=1.29 min; M+H=184.

C. N-(2-Fluoro-6-methoxyphenyl)ethanethioamide

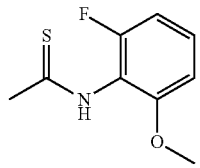

To a solution of N-(2-fluoro-6-methoxyphenyl)acetamide (Intermediate 133B) (5.00 g, 24.8 mmol) in toluene (100 mL) was added Lawesson's reagent (5.02 g, 12.4 mmol), and the reaction was heated to 120° C. After 3 h, the reaction mixture was evaporated under reduced pressure and the residue triturated with pentane (50 mL) to give the title compound (5.20 g, 77%) as an off white solid. $^1$H NMR (400 MHz, CDCl$_3$) δ 2.77 (s, 3H), 3.90 (s, 3H), 6.69-6.90 (m, 3H); LC-MS (LC-ES) M+H=200.

D. 4-Methoxy-2-methylbenzo[d]thiazole

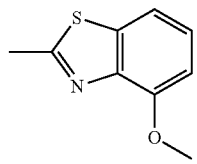

To a solution of N-(2-fluoro-6-methoxyphenyl)ethanethioamide (Intermediate 133C) (5.20 g, 19.1 mmol) in DMF (50 mL) was added a 60% dispersion of NaH in mineral oil (762 mg, 19.1 mmol). The reaction was heated to 80° C. After 12 h, the mixture was cooled to room temperature and quenched with water (200 mL) and extracted with EtOAc (2×150 mL). The combined organic layers were washed with brine (100 mL), dried over Na$_2$SO$_4$, filtered and concentrated to give the title compound (4.00 g, 86%) as a yellow solid. LC-MS (LC-ES) M+H=180.

E. 2-Methylbenzo[d]thiazol-4-ol

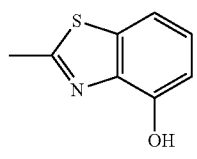

A mixture of 4-methoxy-2-methylbenzo[d]thiazole (Intermediate 133D) (4.00 g, 16.4 mmol) and pyridine hydrochloride (18.90 g, 164 mmol) was heated to 150° C. After 1 h, the reaction was cooled and diluted with ice water (100 mL) and extracted with EtOAc (2×150 mL). The combined organic layers were washed with brine, dried over Na$_2$SO$_4$, filtered and concentrated to give the title compound (3.00 g, 75%) as a yellow solid. $^1$H NMR (400 MHz, CDCl$_3$) δ 2.81 (s, 3H), 6.94-6.98 (m, 1H), 7.23-7.28 (m, 1H), 7.31-7.36 (m, 1H); LC-MS (LC-ES) M+H=166.

F. tert-Butyl 3-((2-methylbenzo[d]thiazol-4-yl)oxy)azetidine-1-carboxylate

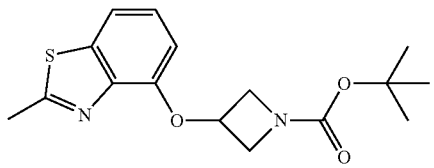 [SMILES: Cc1nc2c(OC3CN(C(=O)OC(C)(C)C)C3)cccc2s1]

To a stirred solution of tert-butyl 3-((methylsulfonyl)oxy)azetidine-1-carboxylate (Intermediate 1) (3.39 g, 13.5 mmol) and 2-methylbenzo[d]thiazol-4-ol (Intermediate 133E) (3.00 g, 12.3 mmol) in DMF (15 mL) was added cesium carbonate (5.19 g, 15.9 mmol). The mixture was heated to 80° C. for 3 h, poured into ice water (100 mL) and extracted with EtOAc (2×250 mL). The combined organic layers were washed with brine (50 mL), dried over $Na_2SO_4$, filtered and concentrated. The residue was purified on silica gel eluting with a 0%-15% EtOAc-hexanes gradient to give the title compound (800 mg, 20%) as an off white solid. $^1$H NMR (400 MHz, $CDCl_3$) δ 1.45 (s, 9H), 2.86 (s, 3H), 4.20-4.28 (m, 2H), 4.33-4.40 (m, 2H), 5.09-5.19 (m, 1H), 6.57-6.61 (m, 1H), 7.21-7.28 (m, 1H), 7.43-7.49 (m, 1H); LC-MS (LC-ES) M+H=321.

G. 4-(Azetidin-3-yloxy)-2-methylbenzo[d]thiazole hydrochloride

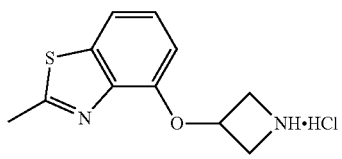

To tert-butyl 3-((2-methylbenzo[d]thiazol-4-yl)oxy)azetidine-1-carboxylate (Intermediate 133F) (800 mg, 2.49 mmol) in MeOH (8 mL) was added 4 N HCl in dioxane (2.49 mL, 9.96 mmol). After 1 h, the mixture was concentrated, and the residue was triturated with diethyl ether (20 mL) to give the title compound as an off white solid (610 mg, 94%). $^1$H NMR (400 MHz, $CD_3SOCD_3$) δ 2.79 (s, 3H), 4.05-4.15 (m, 2H), 4.43-4.52 (m, 2H), 5.26-5.35 (m, 1H), 6.86-6.89 (m, 1H), 7.29-7.35 (m, 1H), 7.63-7.70 (m, 1H), 9.49 (br s, 2H); LC-MS (LC-ES) M+H=221.

Intermediate 134: (trans)-3-(Benzo[d]thiazol-4-yloxy)-N-(1-((2-(trimethylsilyl)ethoxy)methyl)-1H-pyrazol-5-yl)cyclobutanecarboxamide

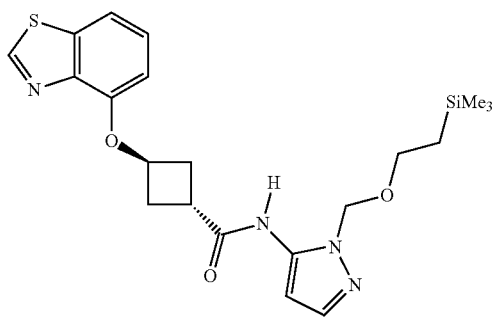 [SMILES: C[Si](C)(C)CCOCn1nccc1NC(=O)[C@H]1C[C@H](Oc2cccc3scnc23)C1]

A. 5-Nitro-1-((2-(trimethylsilyl)ethoxy)methyl-1H-pyrazole

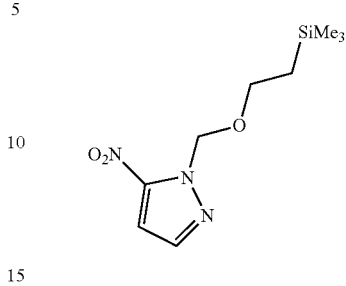

To a stirred, cooled (0° C.) solution of 5-nitro-1H-pyrazole (1.00 g, 8.84 mmol) in N,N-dimethylformamide (5 mL) was slowly added potassium carbonate (2.44 g, 17.1 mmol), followed by (2-(chloromethoxy)ethyl)trimethylsilane (1.77 g, 10.6 mmol). The progress of the reaction was monitored by TLC (silica, 30% EtOAc in hexane). Upon completion, the mixture was diluted with water (100 mL) and extracted with ethyl acetate, 3×). The combined organic layers were washed with brine, dried over sodium sulfate, filtered, and evaporated under reduced pressure to give the title compound (560 mg, 17.5%). This material was used without further purification. $^1$H NMR (400 MHz, $CDCl_3$) δ 0.08-0.01 (m, 9H), 0.84-0.96 (m, 2H), 3.54-3.64 (m, 2H), 5.43 (s, 2H), 6.96 (d, J=3 Hz, 1H) 7.60-7.73 (m, 1H); LC-MS (LC-ES) M+H=244.

B. 1-((2-(Trimethylsilyl)ethoxy)methyl-1H-pyrazol-5-amine

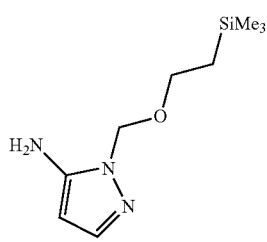 [SMILES: C[Si](C)(C)CCOCn1nccc1[N+](=O)[O-]]

To a solution of 5-nitro-1-((2-(trimethylsilyl)ethoxy)methyl)-1H-pyrazole (560 mg, 2.30 mmol) in ethyl acetate (20 mL) was added palladium on carbon (245 mg). The mixture was stirred under a hydrogen atmosphere for 12 hours, filtered through a pad of Celite® and concentrated under reduced pressure. The crude material was diluted with dichloromethane, pre-adsorbed onto silica gel, and chromatographed on silica gel, eluting with a 10-20% ethyl acetate in hexanes gradient to give the title compound (250 mg, 47%) as a light yellow solid. $^1$H NMR (400 MHz, $CDCl_3$) δ 0.09-0.02 (m, 9H), 0.80-0.99 (m, 2H), 3.47-3.63 (m, 2H), 3.86 (br s, 2H), 5.35 (s, 2H), 7.14-7.36 (m, 2H); LC-MS (LC-ES) M+H=214.

C. (trans)-3-(Benzo[d]thiazol-4-yloxy)-N-(1-((2-(trimethylsilyl)ethoxy)methyl)-1H-pyrazol-5-yl)cyclobutanecarboxamide

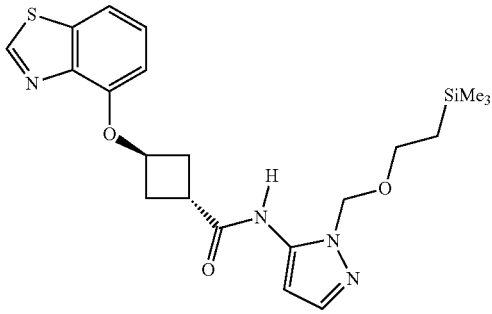 [SMILES: C[Si](C)(C)CCOCn1nccc1NC(=O)[C@H]1C[C@H](Oc2cccc3scnc23)C1]

To a stirred, cooled (0° C.) solution of (trans)-3-(benzo[d]thiazol-4-yloxy)cyclobutanecarboxylic acid (Intermediate 25) (150 mg, 0.602 mmol) in N,N-dimethylformamide (5 mL) was added N,N-diisopropylethylamine (0.315 mL, 1.805 mmol) slowly dropwise, followed by 1-((2-(trimethylsilyl)ethoxy)methyl)-1H-pyrazol-5-amine (128 mg, 0.602 mmol) and then 1-[bis(dimethylamino)methylene]-1H-1,2,3-triazolo[4,5-b]pyridinium 3-oxide hexafluorophosphate (458 mg, 1.203 mmol). The mixture was warmed to room temperature and stirred for 3 hr. The reaction mixture was diluted with cold ice water (10 mL) and extracted with ethyl acetate (3×). The combined organic layers were washed with brine, dried over sodium sulfate, filtered, and evaporated under reduced pressure to give the title compound (250 mg, 83%) as a gummy oil. $^1$H NMR (400 MHz, CD$_3$SOCD$_3$) δ 0.06-0.08 (m, 9H), 0.76-0.95 (m, 2H), 2.40-2.54 (m, 2H), 2.69-2.81 (m, 2H), 3.30-3.42 (m, 1H), 3.51-3.60 (m, 2H), 5.12-5.21 (m, 1H), 5.79 (s, 2H), 6.67 (d, J=2 Hz, 1H), 6.90 (d, J=8 Hz, 1H), 7.41-7.51 (m, 1H), 7.73 (d, J=8 Hz, 1H), 7.81 (d, J=2 Hz, 1H), 9.30 (s, 1H), 10.58 (br s, 1H); LC-MS (LC-ES) M+H=445.

Intermediate 135: (trans)-3-(Benzo[d]thiazol-4-yloxy)-N-(3-cyclopropyl-1-((2-(trimethylsilyl)ethoxy)methyl)-1H-pyrazol-5-yl)cyclobutanecarboxamide

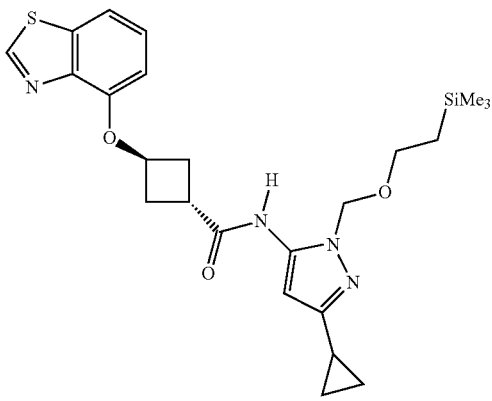 [SMILES: C[Si](C)(C)CCOCn1nc(C2CC2)cc1NC(=O)[C@H]1C[C@H](Oc2cccc3scnc23)C1]

A. 3-Cyclopropyl-5-nitro-1-((2-(trimethylsilyl)ethoxy)methyl)-1H-pyrazole

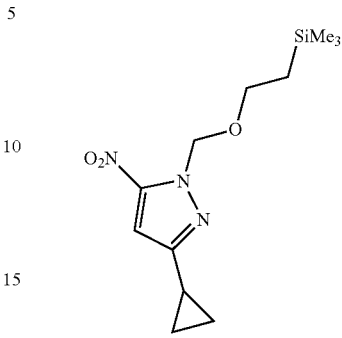

To a stirred, cooled (0° C.) solution of 3-cyclopropyl-5-nitro-1H-pyrazole (600 mg, 3.92 mmol) in tetrahydrofuran (10 mL) was added potassium carbonate (1.08 g, 7.84 mmol), followed by (2-(chloromethoxy)ethyl)trimethylsilane (719 mg, 4.31 mmol). The mixture was warmed to room temperature and stirred for 3 hours. Water (10 mL) was added to the mixture, followed by extraction with ethyl acetate (3×). The combined organic layers were washed with brine, dried over sodium sulfate, filtered, and evaporated under reduced pressure. The crude material was purified by silica gel chromatography, eluting with a 4:1 ethyl acetate in hexanes gradient to give the title compound (500 mg, 45%). $^1$H NMR (400 MHz, CDCl$_3$) δ −0.08-0.03 (m, 9H), 0.75-0.80 (m, 2H), 0.84-0.95 (m, 2H), 0.94-1.02 (m, 2H), 1.83-2.05 (m, 1H), 3.55-3.65 (m, 2H), 5.59 (s, 1H), 5.78 (s, 1H), 6.48 (s, 0.4H), 6.78 (s, 0.6H); LC-MS (LC-ES) M+H=284.

B. 3-Cyclopropyl-1-((2-(trimethylsilyl)ethoxy)methyl)-1H-pyrazole-5-amine

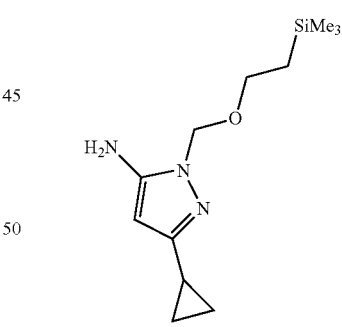

To a solution of 3-cyclopropyl-5-nitro-1-((2-(trimethylsilyl)ethoxy)methyl)-1H-pyrazole (500 mg, 0.998 mmol) in tetrahydrofuran (10 mL) was added palladium on carbon (500 mg). The mixture was stirred under a hydrogen atmosphere for 17 hours, filtered through a pad of Celite®, and concentrated under reduced pressure. The crude material was purified by silica gel chromatography, eluting with a 10-15% ethyl acetate in hexanes gradient to give the title compound (150 mg, 54%). $^1$H NMR (400 MHz, CDCl$_3$) δ −0.02 (s, 9H), 0.62-0.68 (m, 2H), 0.85-1.00 (m, 4H), 1.73-1.91 (m, 1H), 3.51-3.71 (m, 4H), 5.27 (s, 1H), 5.32 (s, 2H); LC-MS (LC-ES) M+H=254.

C. (trans)-3-(Benzo[d]thiazol-4-yloxy)-N-(3-cyclopropyl-1-((2-(trimethylsilyl)ethoxy)methyl)-1H-pyrazol-5-yl)cyclobutanecarboxamide

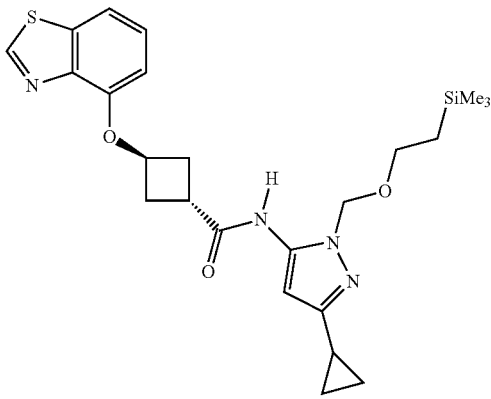 [SMILES: C[Si](C)(C)CCOCn1nc(C2CC2)cc1NC(=O)[C@H]1C[C@H](Oc2cccc3scnc23)C1]

To a stirred, cooled (0° C.) solution of (trans)-3-(benzo[d]thiazol-4-yloxy)cyclobutanecarboxylic acid (Intermediate 25) (150 mg, 0.602 mmol) in N,N-dimethylformamide (10 mL) was added 1-((2-(trimethylsilyl)ethoxy)methyl)-1H-pyrazol-5-amine (167 mg, 0.66 mmol), followed by N,N-diisopropylethylamine (0.312 mL, 1.79 mmol), and then 1-[bis(dimethylamino)methylene]-1H-1,2,3-triazolo[4,5-b]pyridinium 3-oxide hexafluorophosphate (453 mg, 1.19 mmol). The mixture was warmed to room temperature and stirred for 3 hours. The reaction mixture was diluted with cold ice water (10 mL) and extracted with ethyl acetate (3×). The combined organic layers were washed with water, brine, dried over sodium sulfate, filtered, and evaporated under reduced pressure. The crude material was purified by silica gel chromatography, eluting with a 10-15% ethyl acetate in hexanes gradient to give the title compound (220 mg, 64%). $^1$H NMR (400 MHz, CDCl$_3$) δ 0.09 (s, 9H), 0.69-0.83 (m, 2H), 0.86-1.06 (m, 2H), 1.25-1.34 (m, 3H), 2.61-2.77 (m, 2H), 2.85-2.92 (m, 2H), 3.14-3.28 (m, 1H), 3.54-3.65 (m, 2H), 5.20-5.28 (m, 1H), 5.40 (s, 2H), 6.41 (s, 1H), 6.78 (d, J=8 Hz, 1H), 7.34 (t, J=8 Hz, 1H), 7.53 (d, J=8 Hz, 1H), 7.64 (s, 1H), 8.93 (s, 1H); LC-MS (LC-ES) M+H=485.

Intermediate 136: 1-(4-Aminopiperidin-1-yl)-2-hydroxy-2-methylpropan-1-one

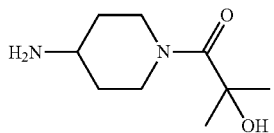

A. Benzyl (1-(2-hydroxy-2-methylpropanoyl)piperidin-4-yl)carbamate

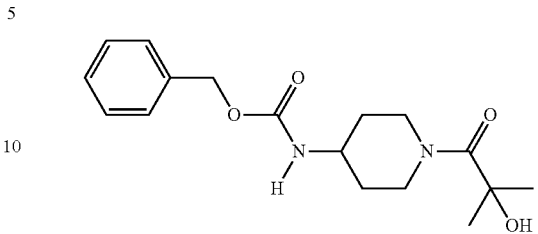

Benzyl piperidin-4-ylcarbamate (512 mg, 2.18 mmol) was added to 2-hydroxy-2-methylpropanoic acid (227 mg, 2.18 mmol) in 1,4-dioxane (11 mL) at room temperature. N,N-diisopropylethylamine (1.14 mL, 6.55 mmol) was added to the mixture and the stirring was continued for five minutes. 1-[bis(dimethylamino)methylene]-1H-1,2,3-triazolo[4,5-b]pyridinium 3-oxide hexafluorophosphate (830 mg, 2.18 mmol) was added and the reaction mixture was stirred for sixteen hours. The reaction mixture was poured into saturated sodium bicarbonate, extracted with ethyl acetate (3×), dried over magnesium sulfate, filtered, and concentrated. The reaction mixture was purified by silica gel chromatography, eluting with ethyl acetate:hexanes (1:1 to 0:1) to give the title compound (315 mg, 43% yield). $^1$H NMR (400 MHz, CD$_3$SOCD$_3$) δ 1.28 (s, 6H), 1.28-1.36 (m, 2H), 1.74 (d, J=12 Hz, 2H), 2.60-3.24 (m, 2H), 3.48-3.62 (m, 1H), 4.10-4.70 (m, 2H), 5.00 (s, 2H), 5.33 (s, 1H), 7.26-7.40 (m, 6H); LC-MS (LC-ES) M+H=321.

B. 1-(4-Aminopiperidin-1-yl)-2-hydroxy-2-methylpropan-1-one

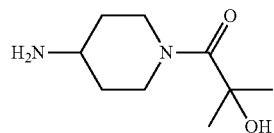

Palladium on carbon (0.105 g, 0.098 mmol) was added to benzyl (1-(2-hydroxy-2-methylpropanoyl)piperidin-4-yl)carbamate (0.315 g, 0.984 mmol) in methanol (3.3 mL) under a nitrogen atmosphere. The reaction vessel was fitted with a hydrogen balloon and the vessel was repeatedly evacuated and purged with hydrogen, then stirred for sixteen hours. The vessel was repeatedly evacuated and purged with nitrogen, filtered through Celite®, and concentrated to give the title compound (0.175 g, 91% yield). $^1$H NMR (400 MHz, CD$_3$SOCD$_3$) δ 1.00-1.80 (m, 2H), 1.29 (s, 6H), 1.54 (br s, 2H), 1.67 (d, J=12 Hz, 2H), 2.76 (p, J=5 Hz, 1H), 2.54-3.18 (m, 2H), 4.02-4.72 (m, 2H), 5.28 (s, 1H); LC-MS (LC-ES) M+H=187.

Intermediate 137: (2S,3S)-tert-Butyl 3-(benzo[d]thiazol-4-yloxy)-2-methylazetidine-1-carboxylate

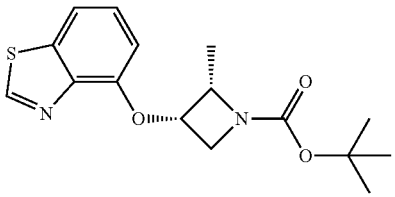 [SMILES: C[C@H]1[C@@H](Oc2cccc3scnc23)CN1C(=O)OC(C)(C)C]

and

Intermediate 138: (2R,3R)-tert-Butyl 3-(benzo[d]thiazol-4-yloxy)-2-methylazetidine-1-carboxylate

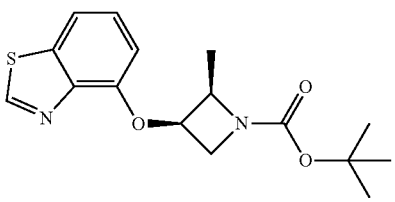 [SMILES: C[C@@H]1[C@H](Oc2cccc3scnc23)CN1C(=O)OC(C)(C)C]

To a stirred solution of tert-butyl 2-methyl-3-((methylsulfonyl)oxy)azetidine-1-carboxylate (Intermediate 99A) (1.40 g, 5.28 mmol) and benzo[d]thiazol-4-ol (0.800 g, 5.29 mmol) in N,N-dimethylformamide (20 mL) was added cesium carbonate (1.90 g, 5.83 mmol). The mixture was heated to 100° C. and stirred overnight. After cooling to room temperature, the mixture was poured into water and extracted with ethyl acetate (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 0%-50% ethyl acetate to hexanes gradient to give the desired product (1.20 g, 71%) as a mixture of diastereomers. The isomers were separated by chiral SFC on an IC column (30 mm×250 mm×5 um column with 45% IPA. Intermediate 137 (29 mg, 1.7%) was obtained as a sticky foam. $^1$H NMR (400 MHz, CD$_3$SOCD$_3$) δ 1.31 (d, J=6 Hz, 3H), 1.41 (s, 9H), 3.85 (br s, 1H), 4.30 (br s, 1H), 4.68 (t, J=6 Hz, 1H), 5.27 (td, J=7, 4 Hz, 1H), 6.92 (d, J=8 Hz, 1H), 7.40 (t, J=8 Hz, 1H), 7.75 (d, J=8 Hz, 1H), 9.30 (s, 1H); LC-MS (LC-ES) M+H=321. Intermediate 138 (18 mg, 1.1%) was obtained as a sticky foam. $^1$H NMR (400 MHz, CD$_3$SOCD$_3$) δ 1.31 (d, J=6 Hz, 3H) 1.41 (s, 9H) 3.85 (br s, 1H) 4.30 (br s, 1H) 4.68 (t, J=6 Hz, 1H) 5.27 (td, J=7, 4 Hz, 1H) 6.92 (d, J=8 Hz, 1H) 7.40 (t, J=8 Hz, 1H) 7.75 (d, J=8 Hz, 1H) 9.30 (s, 1H); LC-MS (LC-ES) M+H=321.

Intermediate 139: 4-(((2S,3S)-2-Methylazetidin-3-yl)oxy)benzo[d]thiazole hydrochloride

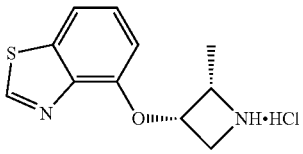

To a stirred solution of (2S,3S)-tert-butyl 3-(benzo[d]thiazol-4-yloxy)-2-methylazetidine-1-carboxylate (Intermediate 137) (29 mg, 0.091 mmol) in methanol (0.5 mL) was added 4N hydrochloric acid (0.5 mL, 2.00 mmol) in dioxane. After stirring for 3 hours, solvent was removed under reduced pressure and the remaining material was placed in vacuo to give the title compound. This material was used without further characterization. LC-MS (LC-ES) M+H=221.

Intermediate 140: 4-(((2R,3R)-2-Methylazetidin-3-yl)oxy)benzo[d]thiazole hydrochloride

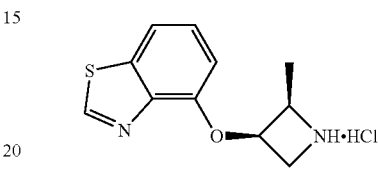

To a stirred solution of (2R,3R)-tert-butyl 3-(benzo[d]thiazol-4-yloxy)-2-methylazetidine-1-carboxylate (Intermediate 138) (18 mg, 0.056 mmol) in methanol (0.5 mL) was added 4N hydrochloric acid (0.5 mL, 2.00 mmol) in dioxane. After stirring for 3 hours, solvent was removed under reduced pressure and the remaining material was placed in vacuo to give the title compound. This material was used without further characterization. LC-MS (LC-ES) M+H=221.

Intermediate 141: 4-Nitrophenyl (3-cyclopropyl-1-methyl-1H-pyrazol-5-yl)carbamate

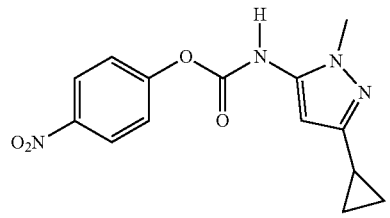 [SMILES: Cn1nc(C2CC2)cc1NC(=O)Oc1ccc([N+](=O)[O-])cc1]

A mixture of 3-cyclopropyl-1-methyl-1H-pyrazol-5-amine (100 mg, 0.729 mmol) and N,N-diisopropylethylamine (0.125 mL, 0.716 mmol) dissolved in dichloromethane (3 mL) was added to a stirred, cooled (0° C.) solution of 4-nitrophenyl chloroformate (150 mg, 0.744 mmol) in dichloromethane (5 mL) dropwise over 10 minutes. The mixture was stirred for 1.5 hours and then partitioned between water and ethyl acetate. The biphasic mixture was filtered to remove insoluble material and the aqueous layer was further extracted with ethyl acetate. The combined organic layers were washed with brine and the layers were separated. Solid material began to precipitate. Solvent was removed under reduced pressure and the remaining solid material was triturated with 1:1 ethyl acetate:hexane, collected via vacuum filtration, and dried in vacuo to give the title compound (117 mg, 53%) as a pale yellow solid. This material was used without further purification. $^1$H NMR (400 MHz, CD$_3$SOCD$_3$) δ 0.54-0.61 (m, 2H), 0.75-0.82 (m, 2H), 1.71-1.80 (m, 1H), 3.59 (s, 3H), 5.86 (s, 1H), 7.75 (d, J=9 Hz, 2H), 8.38-8.43 (m, 2H), 9.34 (br s, 1H); LC-MS (LC-ES) M+H=302.

Intermediate 142: N1-(Pyrimidin-2-yl)bicyclo[1.1.1]pentane-1,3-diamine hydrochloride

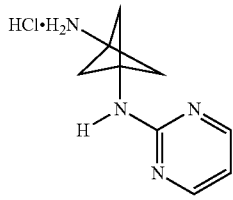

A. tert-Butyl (3-(pyrimidin-2-ylamino)bicyclo[1.1.1]pentan-1-yl)carbamate

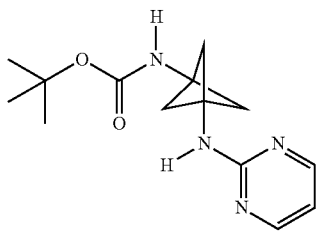 [SMILES: CC(C)(C)OC(=O)NC12CC(Nc3ncccn3)(C1)C2]

To a N,N-dimethylformamide (2 mL) solution of tert-butyl (3-aminobicyclo[1.1.1]pentan-1-yl)carbamate (140 mg, 0.706 mmol) and 2-chloropyrimidine (81 mg, 0.706 mmol) in a vial was added N,N-diisopropylethylamine (0.247 mL, 1.412 mmol). The vial was sealed and heated to 125° C. in an oil bath for 1.5 hours. After cooling to room temperature, the mixture was diluted with methanol and purified by reverse HPLC, eluting with a acetonitrile:water (1% ammonium hydroxide modifier) gradient to give the title compound (21 mg, 11%) as a pale yellow solid. $^1$H NMR (400 MHz, CDCl$_3$) δ 1.48 (s, 9H), 2.24-2.52 (m, 6H), 5.06 (br s, 1H), 5.68-6.03 (m, 1H), 6.59 (t, J=5 Hz, 1H), 8.29 (d, J=5 Hz, 2H); LC-MS (LC-ES) M+H=277.

B. N1-(Pyrimidin-2-yl)bicyclo[1.1.1]pentane-1,3-diamine hydrochloride

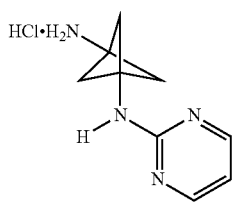

To a stirred solution of tert-butyl (3-(pyrimidin-2-ylamino)bicyclo[1.1.1]pentan-1-yl)carbamate (20 mg, 0.072 mmol) in dichloromethane (2 mL) was added 4M hydrochloric acid in dioxane (1 mL, 4.00 mmol). After stirring for 5 hours, LCMS analysis of the mixture showed the reaction was incomplete. Additional 4M hydrochloric acid in dioxane was added. Solvent was removed under reduced pressure to afford the title compound (18 mg, 117%) as a pale yellow solid. $^1$H NMR (400 MHz, CD$_3$OD) δ 2.59 (s, 6H), 7.13 (br s, 1H), 8.68 (br s, 2H); LC-MS (LC-ES) M+H=177.

Intermediate 143: 2-(3-Aminobicyclo[1.1.1]pentan-1-yl)propan-2-ol hydrochloride

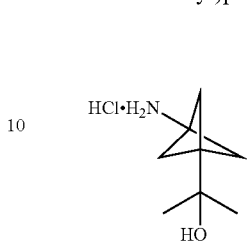

A. tert-Butyl (3-(2-hydroxypropan-2-yl)bicyclo[1.1.1]pentan-1-yl)carbamate

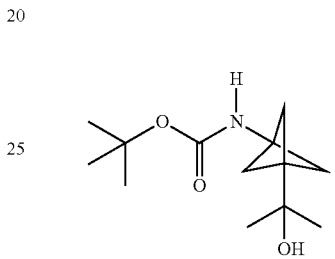

To a stirred, cooled (0° C.) solution of ethyl 3-((tert-butoxycarbonyl)amino)bicyclo[1.1.1]pentane-1-carboxylate (200 mg, 0.829 mmol) in tetrahydrofuran (3 mL) was slowly added 3M methylmagnesium bromide in diethyl ether (0.9 mL, 2.70 mmol). After stirring for ~10 minutes, the mixture was warmed to room temperature and stirred for 2 hours. The mixture was recooled to 0° C. and additional 3M methylmagnesium bromide in diethyl ether (0.9 mL, 2.70 mmol) was slowly added. The mixture was allowed to warm to room temperature, stirred for 30 minutes and then quenched with saturated aqueous ammonium chloride. The mixture was extracted with ethyl acetate and the combined organic layers were washed with brine, dried over sodium sulfate, and filtered. Solvent was removed under reduced pressure to give the title compound (176 mg, 88%) as a colorless oil. $^1$H NMR (400 MHz, CD$_3$SOCD$_3$) δ 1.03 (s, 6H), 1.37 (s, 9H), 1.70 (s, 6H), 4.11 (s, 1H), 7.38 (br s, 1H).

B. 2-(3-Aminobicyclo[1.1.1]pentan-1-yl)propan-2-ol hydrochloride

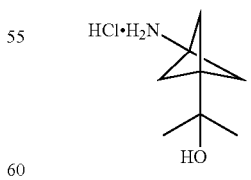

To a stirred solution of tert-butyl (3-(2-hydroxypropan-2-yl)bicyclo[1.1.1]pentan-1-yl)carbamate (170 mg, 0.704 mmol) in methanol (2.5 mL) was added 4M hydrochloric acid in dioxane (0.88 mL, 3.52 mmol). The mixture was stirred overnight. Solvent was removed under reduced pressure and the remaining colorless oil became a solid upon scratching to give the title compound (144 mg, 115% yield). ¹H NMR (400 MHz, CD₃SOCD₃) δ 1.05 (s, 6H), 1.80 (s, 6H), 3.17 (s, 1H), 8.72 (br s, 3H).

Intermediate 144: 4-(Aminocuban-1-yl)propan-2-ol hydrochloride

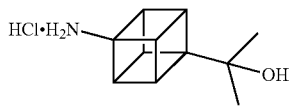

A. Methyl 4-((tert-butoxycarbonyl)amino)cubane-1-carboxylate

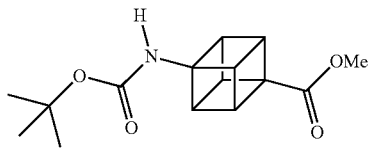 [SMILES: COC(=O)C12C3C4C1C1C2C3C41NC(=O)OC(C)(C)C]

To a stirred solution of 4-(methoxycarbonyl)cubane-1-carboxylic acid (500 mg, 2.42 mmol) in tert-butanol (10 mL) was added triethylamine (1.40 mL, 10.0 mmol), followed by diphenyl phosphoryl azide (0.80 mL, 3.71 mmol). The mixture was stirred for 1 hour at room temperature and then heated to reflux while stirring overnight. After cooling to room temperature, the mixture was evaporated under reduced pressure. The remaining residue was dissolved in ethyl acetate, washed with saturated brine (3x), dried over sodium sulfate, and filtered. Solvent was removed under reduced pressure. The remaining solid was triturated with ethyl acetate-hexane, collected by vacuum filtration and discarded. The filtrate was evaporated under reduced pressure. The remaining material was chromatographed on silica gel, eluting with a 5%-25% ethanol in hexanes gradient to give the title compound (134 mg, 20%) as a white solid. ¹H NMR (400 MHz, CD₃SOCD₃) δ 1.39 (s, 9H), 3.62 (s, 3H), 3.98 (br s, 6H).

B. tert-Butyl 4-(2-hydroxypropan-2-yl)cuban-1-yl)carbamate

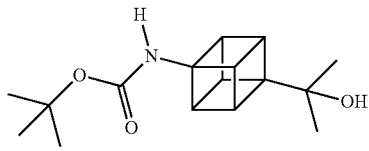 [SMILES: CC(C)(C)OC(=O)NC12C3C4C1C1C2C3C41C(C)(C)O]

To a stirred, cooled (0° C.) solution of methyl-4-((tert-butoxycarbonyl)amino)cubane-1-carboxylate (132 mg, 0.476 mmol) in tetrahydrofuran (5 mL) was added 3M methylmagnesium bromide (0.7 mL, 2.10 mmol) in diethyl ether. The mixture was allowed to warm to room temperature while stirring overnight. TLC analysis (silica gel, 1:1 ethyl acetate-hexane, PMA stain) of the mixture showed 2 major spots. The mixture was re-cooled to 0° C. and additional 3M methylmagnesium bromide (0.35 mL, 1.05 mmol) in diethyl ether was added dropwise. The mixture was allowed to warm to room temperature while stirring for 6 hours. The mixture was quenched with saturated aqueous ammonium chloride, poured into water and extracted with ethyl acetate (2x). The combined organic layers were washed with brine, dried over sodium sulfate, and filtered. Solvent was removed under reduced pressure. The remaining material dissolved in a minimal amount of dichloromethane and chromatographed on silica gel, eluting with a 0%-100% ethyl acetate in hexanes to give the title compound (58 mg, 44%) as a white solid. ¹H NMR (400 MHz, CD₃SOCD₃) δ 0.99 (s, 6H), 1.38 (s, 9H), 3.62 (br s, 3H), 3.73 (br s, 3H), 4.07 (s, 1H).

C. 4-(Aminocuban-1-yl)propan-2-ol hydrochloride

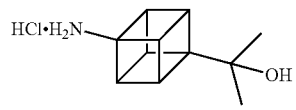

To a stirred, cooled (0° C.) solution of tert-butyl 4-(2-hydroxypropan-2-yl)cuban-1-yl)carbamate (58 mg, 0.209 mmol) in methanol (1 mL) was added 4M hydrochloric acid in dioxane (0.5 mL, 2.000 mmol). The mixture was allowed to warm to room temperature while stirring for 4 hours. Solvent was removed under reduced pressure and the remaining material was triturated with diethyl ether, evaporated under reduced pressure and triturated with hexane. Solvent was removed under reduced pressure and the remaining material was placed in vacuo to give the title compound (45 mg, 101%) as a tan solid. ¹H NMR (400 MHz, CD₃SOCD₃) δ 0.62 (s, 6H), 2.61 (t, J=5 Hz, 1H), 3.00 (dd, J=7, 5 Hz, 2H), 3.30-3.38 (m, 3H), 5.30 (s, 1H), 8.50 (br s, 3H).

Intermediate 145: Ethyl (3-aminobicyclo[1.1.1]pentan-1-yl)carbamate hydrochloride

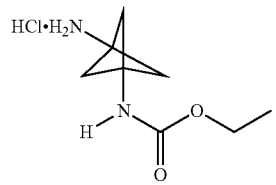

A. tert-Butyl ethyl bicyclo[1.1.1]pentane-1,3-diyldicarbamate

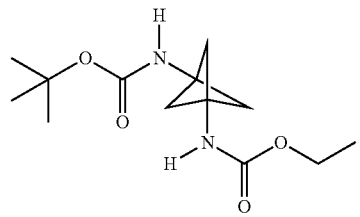 [SMILES: CCOC(=O)NC12CC(NC(=O)OC(C)(C)C)(C1)C2]

To a stirred, cooled (0° C.) solution of tert-butyl (3-aminobicyclo[1.1.1]pentan-1-yl)carbamate (200 mg, 1.01 mmol) in tetrahydrofuran (3.5 mL) was added N,N-diisopropylethylamine (0.25 mL, 1.43 mmol), followed by ethyl chloroformate (0.11 mL, 1.15 mmol). After 5 minutes, the mixture was warmed to room temperature and stirred for 2 hours. The resulting white suspension was diluted with ethyl acetate, washed with water, brine, dried over sodium sulfate, and filtered. Solvent was removed under reduced pressure to give the title compound (300 mg, 110%) as a white solid. $^1$H NMR (400 MHz, CD$_3$SOCD$_3$) δ 1.14 (t, J=7 Hz, 3H), 1.37 (s, 9H), 2.03 (s, 6H), 3.95 (q, J=7 Hz, 2H), 7.52 (br s, 1H), 7.78 (br s, 1H).

B. Ethyl (3-aminobicyclo[1.1.1]pentan-1-yl)carbamate hydrochloride

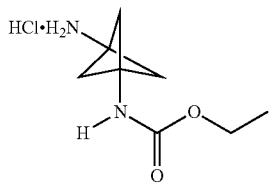

4N Hydrochloric acid in dioxane (1.5 mL, 6.00 mmol) was added to tert-butyl ethyl bicyclo[1.1.1]pentane-1,3-diyldicarbamate (300 mg, 1.11 mmol). The resulting suspension was stirred for 1.75 hours. Solvent was removed under reduced pressure and the remaining material was placed in vacuo to give the title compound (225 mg, 98%) as a white solid. $^1$H NMR (400 MHz, CD$_3$SOCD$_3$) δ 1.15 (t, J=7 Hz, 3H), 2.14 (s, 6H), 3.98 (q, J=7 Hz, 2H), 8.76 (br s, 3H).

Intermediate 146: Phenyl (5-methyl-1,3,4-thiadiazol-2-yl)carbamate

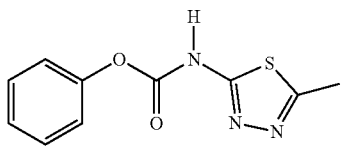 [SMILES: Cc1nnc(NC(=O)Oc2ccccc2)s1]

To a stirred, cooled (5° C.) solution of 5-methyl-1,3,4-thiadiazol-2-amine (100 mg, 0.868 mmol) in tetrahydrofuran (7 mL) was added pyridine (0.28 mL, 3.47 mmol). The mixture was stirred for 10 minutes and then phenyl chloroformate (204 mg, 1.30 mmol) was added. The mixture was allowed to warm to room temperature and stirred for 2 hours. The mixture was diluted with diethyl ether (10 mL) and stirred for 10 minutes. The resulting solid was collected by vacuum filtration, washed with diethyl ether and dried to give the title compound (185 mg, 83%) as an off-white solid. $^1$H NMR (400 MHz, CD$_3$SOCD$_3$) δ 2.61 (s, 3H), 7.20-7.34 (m, 3H), 7.42-7.51 (m, 2H), 12.45 (br s, 1H); LC-MS (LC-ES) M+H=236.

Intermediate 147: Phenyl (1-methyl-1H-pyrazol-3-yl)carbamate

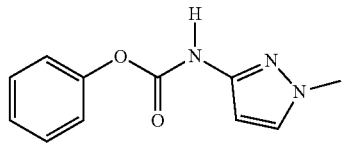 [SMILES: Cn1ccc(NC(=O)Oc2ccccc2)n1]

To a stirred, cooled (0° C.) solution of 1-methyl-1H-pyrazol-3-amine (1.00 g, 10.30 mmol) in tetrahydrofuran (20 mL) was added pyridine (3.33 mL, 41.2 mmol). The mixture was stirred for 5 minutes and then phenyl chloroformate (2.42 g, 15.5 mmol) was added. The mixture was warmed to room temperature and stirred for 5 minutes. Solvent was removed under reduced pressure to give the title compound (500 mg, 13%) in 59% purity. This material was used without further purification. $^1$H NMR (400 MHz, CD$_3$SOCD$_3$) δ 3.74 (s, 3H), 6.23 (s, 1H), 7.17 (d, J=8 Hz, 2H), 7.22-7.31 (m, 1H), 7.37-7.45 (m, 2H), 7.56 (s, 1H), 10.42 (br s, 1H); LC-MS (LC-ES) M+H=218.

Intermediate 148: Phenyl (5-methoxypyridin-3-yl)carbamate

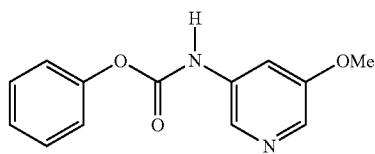 [SMILES: COc1cncc(NC(=O)Oc2ccccc2)c1]

To a stirred, cooled (0° C.) solution of 5-methoxypyridin-3-amine (100 mg, 0.806 mmol) in tetrahydrofuran (10 mL) was added pyridine (0.26 mL, 3.22 mmol). The mixture was stirred for 5 minutes and then phenyl chloroformate (189 mg, 1.21 mmol) was added. The mixture was warmed to room temperature and stirred for 3 hours. Solvent was removed under reduced pressure to give the title compound (120 mg, 45%) In 73% purity as a pink solid. This material was used without further purification. $^1$H NMR (400 MHz, CD$_3$SOCD$_3$) δ 3.84 (s, 3H), 7.20-7.53 (m, 5H), 7.73 (s, 1H), 8.13 (d, J=2 Hz, 1H), 8.38 (d, J=2 Hz, 1H), 10.70 (br s, 1H); LC-MS (LC-ES) M+H=245.

Intermediate 149: Phenyl (1-methyl-1H-pyrazol-4-yl)carbamate

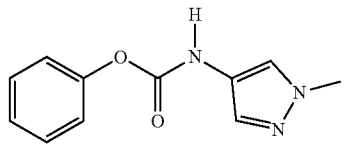 [SMILES: Cn1cc(NC(=O)Oc2ccccc2)cn1]

To a stirred, cooled (0° C.) solution of 1-methyl-1H-pyrazol-4-amine (100 mg, 1.03 mmol) in tetrahydrofuran (2 mL) was added pyridine (0.33 mL, 4.12 mmol). The mixture was stirred for 5 minutes and then phenyl chloroformate (177 mg, 1.13 mmol) was added. The mixture was warmed to room temperature and stirred for 2 hours. Solvent was removed under reduced pressure to give the title compound (200 mg, 55%) in 62% purity. This material was used without further purification. ¹H NMR (400 MHz, CD₃SOCD₃) δ ppm 3.79 (s, 3H), 7.14-7.20 (m, 2H), 7.25-7.37 (m, 4H), 7.46-7.53 (m, 1H), 9.98 (s, 1H); LC-MS (LC-ES) M+H=218.

Intermediate 150: Phenyl (1-ethyl-1H-tetrazol-5-yl)carbamate

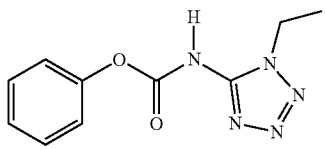 [SMILES: CCn1nnnc1NC(=O)Oc1ccccc1]

To a stirred solution of 1-ethyl-1H-tetrazol-5-amine (250 mg, 2.21 mmol) in tetrahydrofuran (20 mL) was added potassium carbonate (611 mg, 4.42 mmol), followed by phenyl chloroformate (519 mg, 3.32 mmol). The mixture was stirred for 4 hours. The solid material was collected by vacuum filtration, washed with pentane, and dried to give the title compound (180 mg, 27%) in 77% purity as an off-white solid. This material was used without further purification. ¹H NMR (400 MHz, CDCl₃) δ 1.65 (t, J=7 Hz, 3H), 4.64 (q, J=7 Hz, 2H), 7.18-7.29 (m, 3H), 7.37-7.46 (m, 2H), 7.90 (br s, 1H); LC-MS (LC-ES) M+H=234.

Intermediate 151: Phenyl (5-isopropyl-1,3,4-oxadiazol-2-yl)carbamate

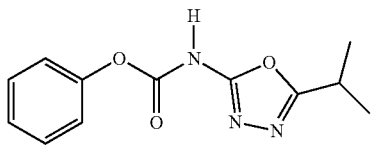 [SMILES: CC(C)c1nnc(NC(=O)Oc2ccccc2)o1]

To a stirred cooled (0° C.) solution of 5-isopropyl-1,3,4-oxadiazol-2-amine (100 mg, 0.787 mmol) in tetrahydrofuran (8 mL) was added phenyl chloroformate (135 mg, 0.865 mmol) and pyridine (0.254 mL, 3.15 mmol). The mixture was warmed to room temperature and stirred for 4 hours. Solvent was removed under reduced pressure to give the title compound (180 mg, 32%) in 34% purity. This material was used without further purification. ¹H NMR (400 MHz, CD₃SOCD₃) δ 1.16-1.35 (m, 6H), 2.94-3.03 (m, 1H), 7.17 (t, J=8 Hz, 1H), 7.26-7.41 (m, 2H), 7.46-7.58 (m, 2H), 9.40 (s, 1H); LC-MS (LC-ES) M+H=248.

Intermediate 152: Phenyl (4-cyano-3-methyl-1H-pyrazol-5-yl)carbamate

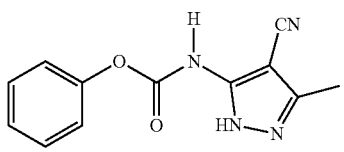 [SMILES: Cc1n[nH]c(NC(=O)Oc2ccccc2)c1C#N]

To a stirred, cooled (0° C.) solution of 5-amino-3-methyl-1H-pyrazole-4-carbonitrile (300 mg, 2.46 mmol) in tetrahydrofuran (10 mL) was added phenyl chloroformate (423 mg, 2.70 mmol) and pyridine (0.795 mL, 9.83 mmol). The mixture was warmed to room temperature and stirred for 4 hours. Solvent was removed under reduced pressure to give the title compound (245 mg, 11%) in 26% purity. This material was used without further purification. ¹H NMR (400 MHz, CD₃SOCD₃) δ 2.12 (s, 3H), 7.09-7.54 (m, 5H), 9.34 (brs, 1H), 13.15 (brs, 1H); LC-MS (LC-ES) M+H=243.

Intermediate 153: 4-((1-(((trans)-4-(2-Hydroxypropan-2-yl)cyclohexyl)carbamoyl)azetidin-3-yl)oxy)benzo[d]thiazole-6-carboxylic acid

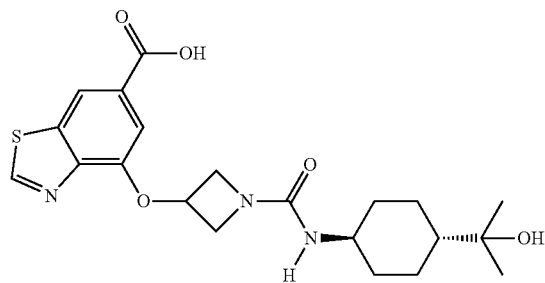 [SMILES: CC(C)(O)[C@H]1CC[C@H](NC(=O)N2CC(Oc3cc(C(=O)O)cc4scnc34)C2)CC1]

A. Methyl 2-amino-4-methoxybenzo[d]thiazole-6-carboxylate

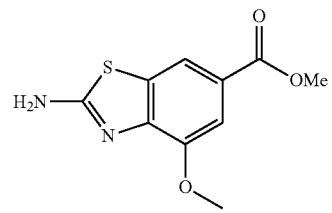 [SMILES: COC(=O)c1cc(OC)c2nc(N)sc2c1]

To a stirred solution of methyl 4-amino-3-methoxybenzoate (2.00 g, 11.04 mmol) in methanol (25 mL) was added an intimated mixture of potassium thiocyanate (10.0 g, 103 mmol) and anhydrous copper(II) sulfate (8.00 g, 50.1 mmol) in one portion. The resulting black mixture was heated to reflux for 3 hours. The reaction suspension was filtered and the filter cake was washed with methanol. The filtrate was evaporated to dryness to give a dark colored solid. This material was redissolved in methanol, diluted with water, and heated to boiling until a clear solution formed. The mixture was allowed to cool to room temperature while standing overnight. The resulting solid was collected via vacuum filtration, washed with water, and dried in vacuo to give the title compound (1.26 g, 48%) as a yellow solid. The aqueous filtrate from the previous day contained solid material and was extracted with ethyl acetate. The organic layer was dried over sodium sulfate, and filtered. Solvent was removed under reduced pressure and the remaining material was dried in vacuo to give the title compound (181 mg, 1.6%) as a yellow solid. The aqueous layer still contained solid. The solid was collected via vacuum filtration, washed with water and dried in vacuo to give additional title compound (988 mg, 9%) as a yellow solid. ¹H NMR (400

MHz, CD$_3$SOCD$_3$) δ 3.85 (s, 3H), 3.92 (s, 3H), 7.41 (s, 1H), 8.03 (br s, 1H), 8.24 (br s, 2H); LC-MS (LC-ES) M+H=239.

B. Methyl 4-methoxybenzo[d]thiazole-6-carboxylate

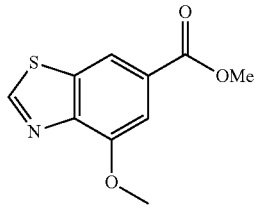

To a stirred suspension of methyl 2-amino-4-methoxybenzo[d]thiazole-6-carboxylate (200 mg, 0.839 mmol) in 1,4-dioxane (3 mL) was added isoamyl nitrite (0.60 mL, 4.46 mmol). The mixture was stirred for 6 hours, poured into water and extracted with ethyl acetate (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 5%-40% ethyl acetate in hexanes gradient to give the title compound (62 mg, 33%) as a yellow solid. $^1$H NMR (400 MHz, CD$_3$SOCD$_3$) δ 3.91 (s, 3H), 4.03 (s, 3H), 7.53 (d, J=1 Hz, 1H), 8.43 (d, J=1 Hz, 1H), 9.47 (s, 1H); LC-MS (LC-ES) M+H=224.

C. Methyl 4-hydroxybenzo[d]thiazole-6-carboxylate

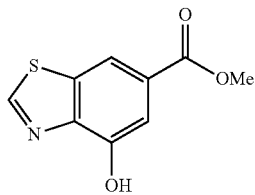 [SMILES: COC(=O)c1cc(O)c2ncsc2c1]

To a stirred, cooled (−78° C.) solution of methyl 4-methoxybenzo[d]thiazole-6-carboxylate (775 mg, 3.47 mmol) in dichloromethane (20 mL) was added 1M boron tribromide (16.5 mL, 16.5 mmol) in dichloromethane dropwise. The mixture was stirred for 3 hours at −78° C. and then allowed to warm to room temperature, while stirring overnight. Solvent was removed under reduced pressure. Methanol (20 mL) was added dropwise to the residue with stirring for 5 minutes and then evaporated under reduced pressure. The remaining material was triturated with water and the solid was collected via vacuum filtration, washed with water, and dried in vacuo to give the title compound (157 mg, 22%) as a yellow solid. Additional solid was obtained from the filtrate and recrystallized from methanol, while standing for 3 days, to give additional title compound (44 mg, 6%) as a yellow solid. $^1$H NMR (400 MHz, CD$_3$SOCD$_3$) δ 3.88 (s, 3H), 7.47 (d, J=2 Hz, 1H), 8.24 (d, J=2 Hz, 1H), 9.42 (s, 1H); LC-MS (LC-ES) M+H=210.

D. Methyl 4-((1-(tert-butoxycarbonyl)azetidin-3-yl)oxy)benzo[d]thiazole-6-carboxylate

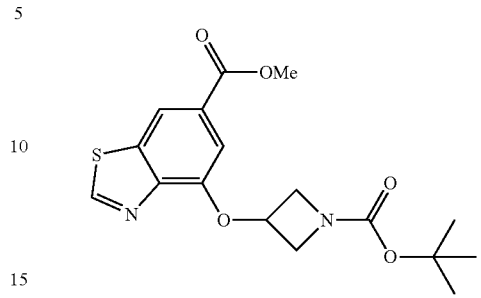

To a stirred solution of tert-butyl 3-((methylsulfonyl)oxy)azetidine-1-carboxylate (Intermediate 1) (265 mg, 1.055 mmol) and methyl 4-hydroxybenzo[d]thiazole-6-carboxylate (198 mg, 0.946 mmol) in N,N-dimethylformamide (5 mL) was added cesium carbonate (340 mg, 1.044 mmol). The mixture was heated to 80° C. and stirred overnight. The mixture was poured into water and extracted with ethyl acetate (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 5%-50% ethyl acetate in hexanes gradient to give the title compound (199 mg, 58%) as an oil that slowly solidified. $^1$H NMR (400 MHz, CD$_3$SOCD$_3$) δ 1.41 (s, 9H), 3.91 (s, 3H), 3.94 (d, J=5 Hz, 2H), 4.38 (br s, 2H), 5.32-5.38 (m, 1H), 7.27 (d, J=1 Hz, 1H), 8.49 (d, J=1 Hz, 1H), 9.51 (s, 1H); LC-MS (LC-ES) M+H=365.

E. Methyl 4-(azetidin-3-yloxy)benzo[d]thiazole-6-carboxylate hydrochloride

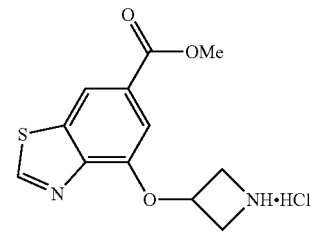

To a stirred solution of methyl 4-((1-(tert-butoxycarbonyl)azetidin-3-yl)oxy)benzo[d]thiazole-6-carboxylate (197 mg, 0.541 mmol) in methanol (2 mL) was added 4M hydrochloric acid in dioxane (2 mL, 8.00 mmol). The mixture was stirred for 2 hours during which time a yellow precipitate formed. Solvent was removed under reduced pressure and the remaining material was dried in vacuo to give the title compound (183 mg, 113%) as a yellow solid. This material was used without further purification. LC-MS (LC-ES) M+H=301.

F. Methyl 4-((1-(((trans)-4-(2-hydroxypropan-2-yl)cyclohexyl)carbamoyl)azetidin-3-yl)oxy)benzo[d]thiazole-6-carboxylate

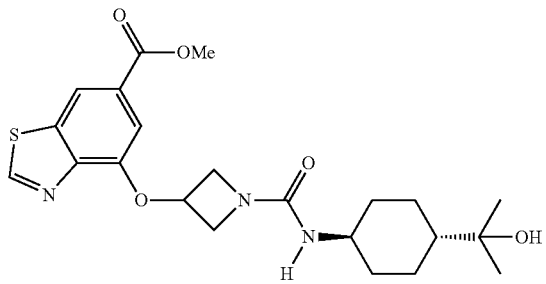 [SMILES: COC(=O)c1cc(OC2CN(C(=O)N[C@H]3CC[C@H](C(C)(C)O)CC3)C2)c2ncsc2c1]

To a stirred mixture of methyl 4-(azetidin-3-yloxy)benzo[d]thiazole-6-carboxylate hydrochloride (163 mg, 0.542 mmol) in dichloromethane (5 mL) was added N,N-diisopropylethylamine (0.30 mL, 1.718 mmol), followed by 4-nitrophenyl ((trans)-4-(2-hydroxypropan-2-yl)cyclohexyl)carbamate (Intermediate 3) (200 mg, 0.620 mmol). The resulting yellow mixture was stirred overnight. The mixture was poured into 1N aqueous sodium hydroxide and extracted with dichloromethane (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 5%-80% ethyl acetate:ethanol (3:1 v/v) in hexanes gradient to give the title compound (151 mg, 62%) as a pale yellow solid. $^1$H NMR (400 MHz, CD$_3$SOCD$_3$) δ 1.02 (s, 6H), 1.06-1.15 (m, 5H), 1.79 (t, J=11 Hz, 4H), 3.25 (m, 1H), 3.86 (dd, J=9, 4 Hz, 2H), 3.91 (s, 3H), 4.00-4.07 (m, 1H), 4.31 (dd, J=9, 6 Hz, 2H), 5.30 (t, J=4 Hz, 1H), 6.23 (d, J=8 Hz, 1H), 7.26 (d, J=1 Hz, 1H), 8.48 (d, J=1 Hz, 1H), 9.51 (s, 1H); LC-MS (LC-ES) M+H=448.

G. 4-((1-(((trans)-4-(2-Hydroxypropan-2-yl)cyclohexyl)carbamoyl)azetidin-3-yl)oxy)benzo[d]thiazole-6-carboxylic acid

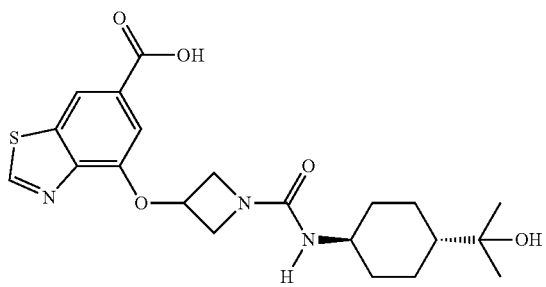

To a stirred mixture of methyl 4-((1-(((trans)-4-(2-hydroxypropan-2-yl)cyclohexyl)carbamoyl)azetidin-3-yl)oxy)benzo[d]thiazole-6-carboxylate (136 mg, 0.304 mmol) in tetrahydrofuran (3 mL) and methanol (1 mL) was added 1M aqueous lithium hydroxide (1 mL, 1.000 mmol). The mixture was stirred 1.5 hours and then evaporated under reduced pressure. The remaining material was diluted with water, poured into 1N aqueous hydrochloric acid and extracted with ethyl acetate. A white gelatinous suspension formed in the aqueous layer. The aqueous layer was separated and extraction with dichloromethane was attempted. The mixture remained a gelatinous suspension and was vacuum filtered. The collected solid was placed in vacuo to give the title compound (84 mg, 64%) as a white solid. The ethyl acetate layer from the initial extraction was washed with brine, dried over sodium sulfate, and filtered. Solvent was removed under reduced pressure and the remaining solid was placed in vacuo to give additional title compound (30 mg, 23%) as a yellow solid. The two aqueous work up layers were combined and further extracted with ethyl acetate. The organic layer was washed with brine, dried over sodium sulfate, and filtered. Solvent was removed under reduced pressure and the remaining solid was placed in vacuo to give additional title compound (17 mg, 13%) as a white solid. $^1$H NMR (400 MHz, CD$_3$SOCD$_3$) δ $^1$H NMR (400 MHz, DMSO-d$_6$) δ 1.02 (s, 6H), 1.06-1.18 (m, 5H), 1.74-1.84 (m, 4H), 3.29 (br s, 1H), 3.86 (dd, J=9, 3 Hz, 2H), 4.30 (dd, J=9, 6 Hz, 2H), 5.29 (br s, 1H), 6.22 (d, J=8 Hz, 1H), 7.25 (d, J=1 Hz, 1H), 8.43 (d, J=1 Hz, 1H), 9.49 (s, 1H); LC-MS (LC-ES) M+H=434.

EXAMPLES

Example 1

3-(2-(Difluoromethoxy)-5-fluorophenoxy)-N-((trans)-4-(2-hydroxypropan-2-yl)cyclohexyl)azetidine-1-carboxamide

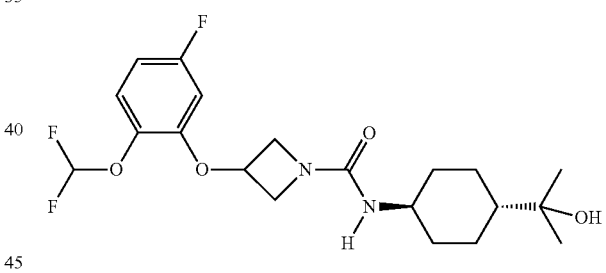

To a stirred mixture of 3-(2-(difluoromethoxy)-5-fluorophenoxy)azetidine hydrochloride (Intermediate 2) (21 mg, 0.08 mmol) in DCM (2 mL) was added N,N-diisopropylethylamine (0.05 mL, 0.3 mmol), followed by 4-nitrophenyl ((trans)-4-(2-hydroxypropan-2-yl)cyclohexyl)carbamate (Intermediate 3) (27 mg, 0.084 mmol). The mixture was stirred overnight, poured into 1 N aqueous NaOH and extracted twice with DCM. The combined organic layers were washed with brine, dried over Na$_2$SO$_4$ and filtered. Solvent was removed under reduced pressure. The remaining material was purified on silica gel, eluting with a 0%-50% EtOAc-EtOH (3:1) in hexanes gradient. The appropriate fractions were combined, evaporated under reduced pressure and placed in vacuo to give the title compound (25 mg, 77%) as a white solid. $^1$H NMR (400 MHz, CD$_3$SOCD$_3$) δ 0.99 (s, 6H), 1.01-1.16 (m, 5H), 1.71-1.79 (m, 4H), 3.18-3.28 (m, 1H), 3.70 (dd, J=12, 8 Hz, 2H), 3.97 (s, 1H), 4.20 (dd, J=12, 8 Hz, 2H), 4.97-5.03 (m, 1H), 6.13 (d, J=12 Hz, 1H), 6.78-6.87 (m, 2H), 7.03 (s, 1H), 7.21-7.26 (m, 1H); LC-MS (LC-ES) M+H=417.

Example 2

(trans)-N-(1-Butyl-1H-tetrazol-5-yl)-3-(2-(difluoromethoxy)-5-fluorophenoxy)cyclobutanecarboxamide

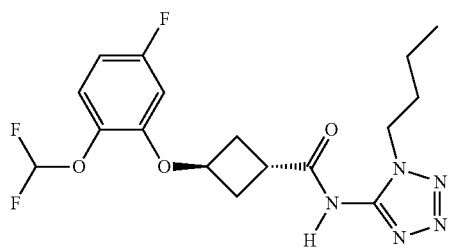 [SMILES: CCCCn1nnnc1NC(=O)[C@H]1C[C@H](Oc2cc(F)ccc2OC(F)F)C1]

To a DMF (3 mL) solution of (trans)-3-(2-(difluoromethoxy)-5-fluorophenoxy)cyclobutanecarboxylic acid (Intermediate 4) (75 mg, 0.27 mmol) was added 1-n-butyl-1H-tetrazol-5-amine (19 mg, 0.2 mmol) and N,N-diisopropylethylamine (0.14 mL, 0.8 mmol), followed by the dropwise addition of a 50% solution of T3P in EtOAc (346 mg, 0.54 mmol). The resulting mixture was stirred overnight, diluted with MeOH and loaded onto a semi-prep HPLC (NH$_4$OH as modifier) to afford the title compound (5 mg, 5%). $^1$H NMR (400 MHz, CD$_3$SOCD$_3$) δ 0.97 (t, J=7 Hz, 3H), 1.38 (dq, J=15, 7 Hz, 2H), 1.82-1.96 (m, 2H), 2.52-2.70 (m, 2H), 2.76-2.95 (m, 2H), 3.57 (br s, 1H,) 4.42 (t, J=7 Hz, 2H), 4.90-4-95 (m, 1H), 6.50 (t, J=76 Hz, 1H), 6.50-6.54 (m, 1H), 6.59-6.66 (m, 1H), 7.13 (dd, J=9, 6 Hz, 1H); LC-MS (LC-ES) M+H=400.

Example 3

(trans)-3-(2-(Difluoromethoxy)-5-fluorophenoxy)-N-(1-methyl-1H-tetrazol-5-yl)cyclobutanecarboxamide

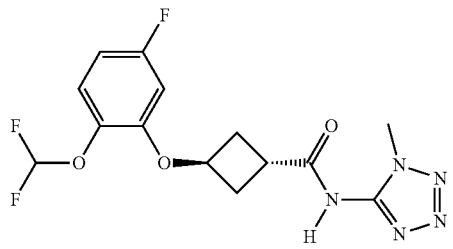 [SMILES: Cn1nnnc1NC(=O)[C@H]1C[C@H](Oc2cc(F)ccc2OC(F)F)C1]

To a DMF (3 mL) solution of (trans)-3-(2-(difluoromethoxy)-5-fluorophenoxy)cyclobutanecarboxylic acid (Intermediate 4) (75 mg, 0.27 mmol) was added 1-methyl-1H-tetrazol-5-amine (19 mg, 0.2 mmol) and N,N-diisopropylethylamine (0.14 mL, 0.82 mmol) followed by the dropwise addition of T3P (346 mg, 0.54 mmol) (50% solution in EtOAc).

The resulting mixture was stirred overnight, diluted with MeOH and loaded onto a semi-prep HPLC (NH$_4$OH as modifier) to afford the title compound (5 mg, 5%). $^1$H NMR (400 MHz, CDCl$_3$) δ 2.57-2.73 (m, 2H), 2.76-2.87 (m, 2H), 3.46-3.85 (m, 1H), 4.10 (s, 3H), 4.90-4.96 (m, 1H), 6.50 (t, J=72 Hz, 1H), 6.49-6.53 (m, 1H), 6.57-6.65 (m, 1H), 7.14 (dd, J=9, 6 Hz, 1H); LC-MS (LC-ES) M+H=358.

Example 4

(trans)-N-(1-(5-Cyanothiazol-2-yl)azetidin-3-yl)-3-(2-(difluoromethoxy)-5-fluorophenoxy)cyclobutanecarboxamide, Methyl 2-(3-((trans)-3-(2-(difluoromethoxy)-5-fluorophenoxy)cyclobutanecarboxamido)azetidin-1-yl)thiazole-5-carbimidate, and 2-(3-((trans)-3-(2-(Difluoromethoxy)-5-fluorophenoxy)cyclobutanecarboxamido)azetidin-1-yl)thiazole-5-carboxamide

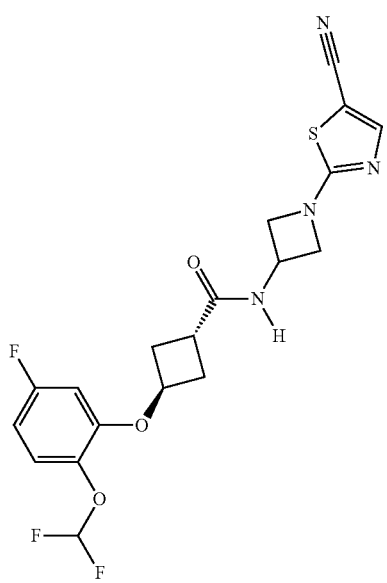

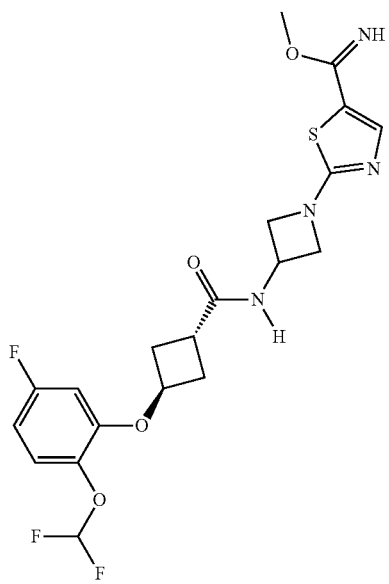

241

-continued

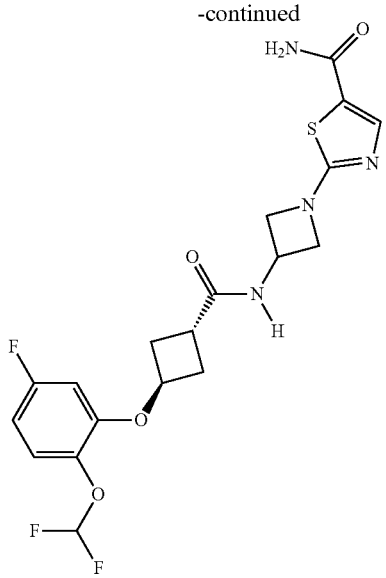

To a DMF (3 mL) solution of (trans)-3-(2-(difluoromethoxy)-5-fluorophenoxy)cyclobutanecarboxylic acid (Intermediate 4) (75 mg, 0.27 mmol) was added 2-(3-aminoazetidin-1-yl)thiazole-5-carbonitrile dihydrochloride (crude, Intermediate 5) (69 mg, ~0.27 mmol), methyl 2-(3-aminoazetidin-1-yl)thiazole-5-carbimidate dihydrochloride (crude, Intermediate 5) (77 mg, ~0.27 mmol), 2-(3-aminoazetidin-1-yl)thiazole-5-carboxamide dihydrochloride (crude, Intermediate 5) (74 mg, ~0.27 mmol), and N,N-diisopropylethylamine (0.14 mL, 0.82 mmol), followed by the dropwise addition of a 50% solution of T3P in EtOAc (346 mg, 0.54 mmol). The resulting mixture was stirred for 20 minutes, diluted with water and MeOH and loaded onto a semi-prep HPLC (NH$_4$OH as modifier) to afford (trans)-N-(1-(5-cyanothiazol-2-yl)azetidin-3-yl)-3-(2-(difluoromethoxy)-5-fluorophenoxy)cyclobutanecarboxamide (42 mg, 35%), methyl 2-(3-((trans)-3-(2-(difluoromethoxy)-5-fluorophenoxy)cyclobutanecarboxamido)azetidin-1-yl)thiazole-5-carbimidate (8 mg, 6%), and 2-(3-((trans)-3-(2-(difluoromethoxy)-5-fluorophenoxy)cyclobutanecarboxamido)azetidin-1-yl)thiazole-5-carboxamide (30 mg, 24%).

(trans)-N-(1-(5-Cyanothiazol-2-yl)azetidin-3-yl)-3-(2-(difluoromethoxy)-5-fluorophenoxy)cyclobutanecarboxamide $^1$H NMR (400 MHz, CD$_3$OD) δ 2.29-2.51 (m, 2H), 2.61-2.74 (m, 2H), 3.04-3.25 (m, 1H), 4.01-4.11 (m, 2H), 4.46-4.50 (m, 2H), 4.78-4.85 (m, 1H), 4.86-4.97 (m, 1H), 6.64-6.68 (m, 2H), 6.67 (t, J=72 Hz, 1H), 7.07-7.29 (m, 1H), 7.80 (s, 1H); LC-MS (LC-ES) M+H=439.

Methyl 2-(3-((trans)-3-(2-(difluoromethoxy)-5-fluorophenoxy)cyclobutanecarboxamido)azetidin-1-yl)thiazole-5-carbimidate $^1$H NMR (400 MHz, CD$_3$OD) δ 2.33-2.51 (m, 2H), 2.66-2.73 (m, 2H), 3.09-3.22 (m, 1H), 3.81 (s, 3H), 3.95-4.02 (m, 2H), 4.36-4.42 (m, 2H), 4.77-4.85 (m, 1H), 4.89-4.98 (m, 1H), 6.62-6.69 (m, 2H), 6.67 (t, J=72 Hz, 1H), 7.12-7.17 (m, 1H), 7.74 (s, 1H); LC-MS (LC-ES) M+H=471.

242

2-(3-((trans)-3-(2-(Difluoromethoxy)-5-fluorophenoxy)cyclobutanecarboxamido)azetidin-1-yl)thiazole-5-carboxamide $^1$H NMR (400 MHz, CD$_3$OD) δ 2.36-2.52 (m, 2H), 2.63-2.76 (m, 2H), 3.08-3.24 (m, 1H), 3.96-4.02 (m, 2H), 4.39-4.44 (m, 2H), 4.74-4.85 (m, 1H), 4.89-5.01 (m, 1H), 6.60-6.69 (m, 2H), 6.67 (t, J=72 Hz, 1H), 7.13 (s, 1H), 7.76 (s, 1H); LC-MS (LC-ES) M+H=457.

Example 5

2-(3-((trans)-3-(2-(Difluoromethoxy)-5-fluorophenoxy)cyclobutanecarboxamido)azetidin-1-yl)pyrimidine-4-carboxamide, and (trans)-N-(1-(4-Cyanopyrimidin-2-yl)azetidin-3-yl)-3-(2-(difluoromethoxy)-5-fluorophenoxy)cyclobutanecarboxamide

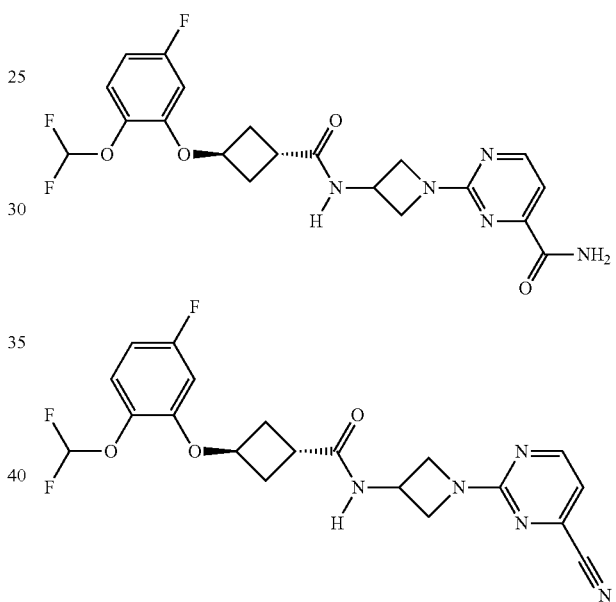

To a DMF (3 mL) solution of (trans)-3-(2-(difluoromethoxy)-5-fluorophenoxy)cyclobutanecarboxylic acid (Intermediate 4) (75 mg, 0.27 mmol) was added 2-(3-aminoazetidin-1-yl)pyrimidine-4-carboxamide dihydrochloride (crude, Intermediate 6) (33 mg, ~0.12 mmol), 2-(3-aminoazetidin-1-yl)pyrimidine-4-carbonitrile dihydrochloride (crude, Intermediate 6) (47 mg, ~0.19 mmol), and N,N-diisopropylethylamine (0.14 mL, 0.82 mmol), followed by the dropwise addition of a 50% solution of T3P in EtOAc (346 mg, 0.54 mmol). The resulting mixture was stirred for 20 minutes, diluted with water and MeOH and loaded onto a semi-prep HPLC (NH$_4$OH as modifier) to afford 2-(3-((trans)-3-(2-(difluoromethoxy)-5-fluorophenoxy)cyclobutanecarboxamido)azetidin-1-yl)pyrimidine-4-carboxamide (60 mg, 49%) and (trans)-N-(1-(4-cyanopyrimidin-2-yl)azetidin-3-yl)-3-(2-(difluoromethoxy)-5-fluorophenoxy)cyclobutanecarboxamide (35 mg, 30%).

2-(3-((trans)-3-(2-(Difluoromethoxy)-5-fluorophenoxy)cyclobutanecarboxamido)azetidin-1-yl)pyrimidine-4-carboxamide ¹H NMR (400 MHz, CDCl₃) δ 2.40-2.51 (m, 2H), 2.70-2.79 (m, 2H), 2.94-3.14 (m, 1H), 3.94-4.00 (m, 2H), 4.48-4.57 (m, 2H), 4.81-4.90 (m, 1H), 4.91-5.00 (m, 1H), 5.57 (br s, 1H), 6.08 (d, J=7 Hz, 1H), 6.47 (t, J=76 Hz, 1H), 6.48-6.55 (m, 1H), 6.56-6.66 (m, 1H), 7.12 (dd, J=9, 6 Hz, 1H), 7.36 (d, J=5 Hz, 1H), 7.62 (br s, 1H), 8.54 (d, J=5 Hz, 1H); LC-MS (LC-ES) M+H=452.

(trans)-N-(1-(4-Cyanopyrimidin-2-yl)azetidin-3-yl)-3-(2-(difluoromethoxy)-5-fluorophenoxy)cyclobutanecarboxamide ¹H NMR (400 MHz, CDCl₃) δ 2.40-2.52 (m, 2H), 2.71-2.81 (m, 2H), 2.92-3.13 (m, 1H), 3.85-4.06 (m, 2H), 4.48-4.58 (m, 2H), 4.81-4.88 (m, 1H), 4.88-5.00 (m, 1H), 5.83-5.96 (m, 1H), 6.47 (t, J=76 Hz, 1H), 6.50-6.56 (m, 1H), 6.59-6.65 (m, 1H), 6.84 (d, J=4 Hz, 1H), 7.06-7.16 (m, 1H), 8.47 (d, J=4 Hz, 1H); LC-MS (LC-ES) M+H=434.

Example 6

(trans)-N-(1-(2-Chloropyrimidin-4-yl)azetidin-3-yl)-3-(2-(difluoromethoxy)-5-fluorophenoxy)cyclobutanecarboxamide

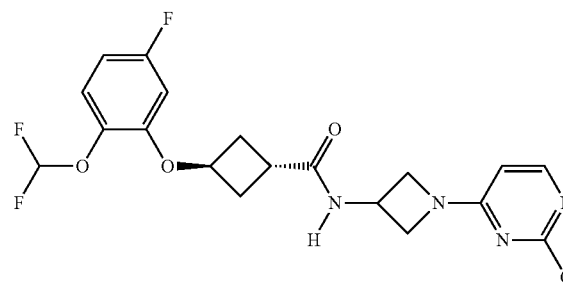

To a DMF (2 mL) solution of (trans)-3-(2-(difluoromethoxy)-5-fluorophenoxy)cyclobutanecarboxylic acid (Intermediate 4) (50 mg, 0.18 mmol) was added 1-(2-chloropyrimidin-4-yl)azetidin-3-amine dihydrochloride (Intermediate 7) (40 mg, 0.18 mmol) and N,N-diisopropylethylamine (0.095 mL, 0.54 mmol), followed by the dropwise addition of a 50% solution of T3P in EtOAc (230 mg, 0.36 mmol). The resulting mixture was stirred for 2 h, diluted with water and MeOH and loaded onto a semi-prep HPLC (NH₄OH as modifier) to afford the title compound (48 mg, 60%). ¹H NMR (400 MHz, CDCl₃) δ 2.31-2.51 (m, 2H), 2.64-2.79 (m, 2H), 2.96-3.11 (m, 1H), 3.86-4.04 (m, 2H), 4.36-4.56 (m, 2H), 4.75-5.06 (m, 2H), 6.04-6.31 (m, 2H), 6.44-6.66 (m, 3H), 7.04-7.16 (m, 1H), 7.95-8.11 (m, 1H); LC-MS (LC-ES) M+H=443, 445 (CI pattern).

Example 7

(trans)-N-(1-(4-Chloropyrimidin-2-yl)azetidin-3-yl)-3-(2-(difluoromethoxy)-5-fluorophenoxy)cyclobutanecarboxamide

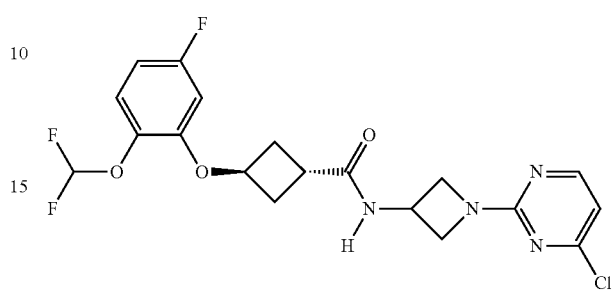

To a DMF (1 mL) solution of (trans)-3-(2-(difluoromethoxy)-5-fluorophenoxy)cyclobutanecarboxylic acid (Intermediate 4) (25 mg, 0.09 mmol) was added 1-(4-chloropyrimidin-2-yl)azetidin-3-amine hydrochloride (Intermediate 8) (20 mg, 0.09 mmol) and N,N-diisopropylethylamine (0.05 mL, 0.3 mmol), followed by the dropwise addition of a 50% solution of T3P in EtOAc (115 mg, 0.18 mmol). The resulting mixture was stirred for 1 h, diluted with water and MeOH, and loaded onto a semi-prep HPLC (NH₄OH as modifier) to afford the title compound (37 mg, 92%). ¹H NMR (400 MHz, CDCl₃) δ 2.37-2.55 (m, 2H), 2.67-2.84 (m, 2H), 2.96-3.07 (m, 1H), 3.93-3.99 (m, 2H), 4.46-4.55 (m, 2H), 4.81-4.87 (m, 1H), 4.92-5.00 (m, 1H), 5.86-5.94 (m, 1H), 6.47 (t, J=76 Hz, 1H), 6.52-6.56 (m, 1H), 6.59-6.66 (m, 2H), 7.12 (dd, J=9, 6 Hz, 1H), 8.18 (d, J=6 Hz, 1H); LC-MS (LC-ES) M+H=443, 445 (CI pattern).

Example 8

(trans)-3-(2-(Difluoromethoxy)-5-fluorophenoxy)-N-(1-(5-fluoropyrimidin-2-yl)azetidin-3-yl)cyclobutanecarboxamide

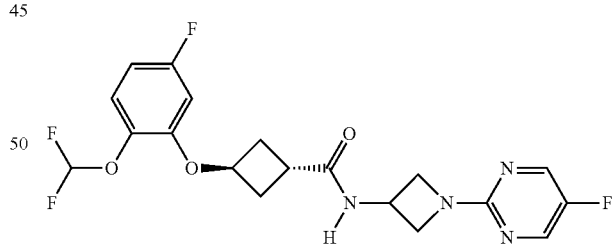

To a DMF (2 mL) solution of (trans)-3-(2-(difluoromethoxy)-5-fluorophenoxy)cyclobutanecarboxylic acid (Intermediate 4) (40 mg, 0.15 mmol) was added 1-(5-fluoropyrimidin-2-yl)azetidin-3-amine dihydrobromide (Intermediate 9) (48 mg, 0.15 mmol) and N,N-diisopropylethylamine (0.08 mL, 0.4 mmol), followed by the dropwise addition of a 50% solution of T3P in EtOAc (184 mg, 0.29 mmol). The resulting mixture was stirred for 2 h, diluted with water and MeOH, and loaded onto a semi-prep HPLC (NH₄OH as modifier) to afford the title compound as a white solid (11 mg, 18%). ¹H NMR (400 MHz, CDCl₃) δ 2.40-2.50 (m, 2H), 2.71-2.79 (m, 2H), 2.95-3.04 (m, 1H), 3.89-

3.94 (m, 2H), 4.44-4.51 (m, 2H), 4.80-4.90 (m, 1H), 4.91-5.00 (m, 1H), 5.89-5.96 (m, 1H), 6.47 (t, J=76 Hz, 1H), 6.53-6.56 (m, 1H), 6.56-6.65 (m, 1H), 7.12 (dd, J=9, 6 Hz, 1H), 8.22 (s, 2H); LC-MS (LC-ES) M+H=427.

Example 9

Racemic (trans)-N-((trans)-4-(2-Cyclopropyl-2-hydroxyethoxy)cyclohexyl)-3-(2-(difluoromethoxy)-5-fluorophenoxy)cyclobutanecarboxamide

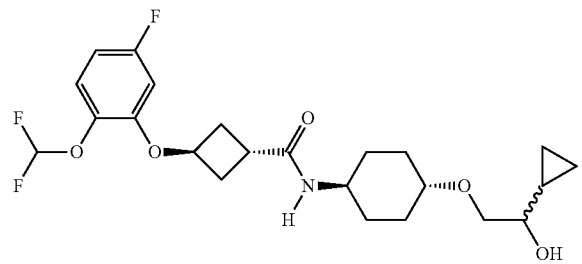 [SMILES: O=C(N[C@H]1CC[C@H](OCC(O)C2CC2)CC1)[C@H]1C[C@H](Oc2cc(F)ccc2OC(F)F)C1]

To a DMF (2 mL) solution of (trans)-3-(2-(difluoromethoxy)-5-fluorophenoxy)cyclobutanecarboxylic acid (Intermediate 4) (40 mg, 0.15 mmol) was added 2-(((trans)-4-aminocyclohexyl)oxy)-1-cyclopropylethanol (Intermediate 10) (35 mg, 0.17 mmol) and N,N-diisopropylethylamine (0.08 mL, 0.4 mmol), followed by the dropwise addition of a 50% solution of T3P in EtOAc (184 mg, 0.29 mmol). The resulting mixture was stirred for 18 h, diluted with water and MeOH, and loaded onto a semi-prep HPLC (NH$_4$OH as modifier) to afford the title compound as a white solid (48 mg, 73%). $^1$H NMR (400 MHz, CDCl$_3$) δ 0.21 (dq, J=10, 5 Hz, 1H), 0.37 (dq, J=10, 5 Hz, 1H), 0.43-0.59 (m, 2H), 0.76-0.93 (m, 1H), 1.31-1.49 (m, 2H), 1.33-1.44 (m, 2H), 1.95-2.14 (m, 4H), 2.31-2.51 (m, 2H), 2.72 (ddd, J=13, 7, 4 Hz, 2H), 2.84-2.97 (m, 1H), 3.03 (td, J=8, 3 Hz, 1H), 3.18-3.33 (m, 1H), 3.36-3.45 (m, 1H), 3.63 (dd, J=9, 3 Hz, 1H), 3.71-3.88 (m, 1H), 4.95 (quin, J=6 Hz, 1H), 5.28 (d, J=8 Hz, 1H), 6.47 (t, J=76 Hz, 1H), 6.50-6.55 (m, 1H), 6.61-6.67 (m, 1H), 7.11 (dd, J=9, 6 Hz, 1H); LC-MS (LC-ES) M+H=458.

Example 10

(trans)-3-(2-(Difluoromethoxy)-5-fluorophenoxy)-N-((trans)-4-(pyrimidin-2-ylamino)cyclohexyl)cyclobutanecarboxamide

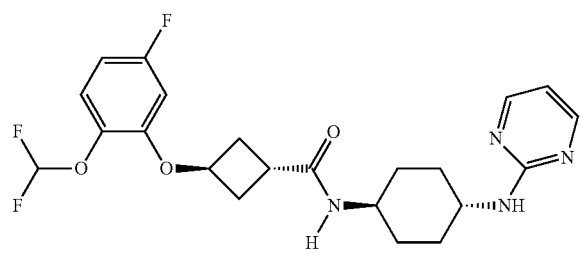 [SMILES: O=C(N[C@H]1CC[C@H](Nc2ncccn2)CC1)[C@H]1C[C@H](Oc2cc(F)ccc2OC(F)F)C1]

To a DMF (2 mL) solution of (trans)-3-(2-(difluoromethoxy)-5-fluorophenoxy)cyclobutanecarboxylic acid (Intermediate 4) (50 mg, 0.18 mmol) was added (trans)-N1-(pyrimidin-2-yl)cyclohexane-1,4-diamine dihydrobromide (Intermediate 11) (64 mg, 0.18 mmol) and N,N-diisopropylethylamine (0.10 mL, 0.5 mmol), followed by the dropwise addition of a 50% solution of T3P in EtOAc (230 mg, 0.36 mmol). The resulting mixture was stirred for 1 h, diluted with water and MeOH and loaded onto a semi-prep HPLC (NH$_4$OH as modifier) to afford the title compound as a white solid (47 mg, 58%). $^1$H NMR (400 MHz, CDCl$_3$) δ 1.19-1.51 (m, 4H), 2.10 (d, J=12 Hz, 2H), 2.20 (d, J=12 Hz, 2H), 2.34-2.55 (m, 2H), 2.66-2.82 (m, 2H), 2.89-3.07 (m, 1H), 3.77-3.90 (m, 2H), 4.91-5.05 (m, 1H), 5.32 (d, J=8 Hz, 1H), 5.46 (br s, 1H), 6.50 (t, J=72 Hz, 1H), 6.59-6.66 (m, 3H), 7.14 (dd, J=8, 6 Hz, 1H), 8.32 (br s, 2H); LC-MS (LC-ES) M+H=451.

Example 11

Racemic (trans)-N-((trans)-4-(2-Cyclopropyl-2-hydroxypropoxy)cyclohexyl)-3-(2-(difluoromethoxy)-5-fluorophenoxy)cyclobutanecarboxamide

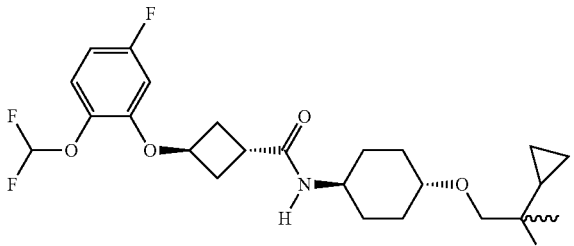

To a DMF (2 mL) solution of (trans)-3-(2-(difluoromethoxy)-5-fluorophenoxy)cyclobutanecarboxylic acid (Intermediate 4) (40 mg, 0.15 mmol) was added 1-(((trans)-4-aminocyclohexyl)oxy)-2-cyclopropylpropan-2-ol (Intermediate 12) (37 mg, 0.17 mmol) and N,N-diisopropylethylamine (0.08 mL, 0.4 mmol), followed by the dropwise addition of a 50% solution of T3P in EtOAc (184 mg, 0.29 mmol). The resulting mixture was stirred for 1 h, diluted with water and MeOH, and loaded onto a semi-prep HPLC (NH$_4$OH as modifier) to afford the title compound as a white solid (46 mg, 67%). $^1$H NMR (400 MHz, CDCl$_3$) δ 0.29-0.37 (m, 3H), 0.40-0.46 (m, 1H), 0.79-0.93 (m, 1H), 1.09 (s, 3H), 1.11-1.27 (m, 2H), 1.33-1.50 (m, 2H), 2.03 (d, J=9 Hz, 4H), 2.34-2.49 (m, 2H), 2.67-2.77 (m, 2H), 2.89-2.96 (m, 1H), 3.20-3.31 (m, 1H), 3.32-3.40 (m, 2H), 3.67-3.92 (m, 1H), 4.85-5.05 (m, 1H), 5.26 (d, J=8 Hz, 1H), 6.47 (t, J=76 Hz, 1H), 6.53 (dd, J=10, 3 Hz, 1H), 6.60 (td, J=8, 3 Hz, 1H), 7.11 (dd, J=8, 3 Hz, 1H); LC-MS (LC-ES) M−H=470.

Example 12

(trans)-3-(2-(Difluoromethoxy)-5-fluorophenoxy)-N-(5-(hydroxymethyl)thiazol-2-yl)cyclobutanecarboxamide

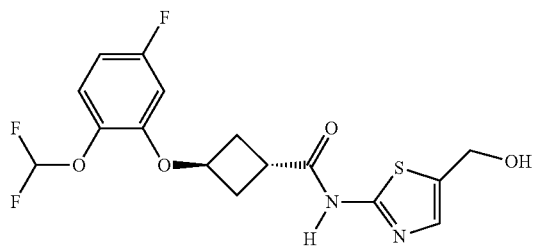 [SMILES: O=C(Nc1ncc(CO)s1)[C@H]1C[C@H](Oc2cc(F)ccc2OC(F)F)C1]

To a DMF (2 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol), followed by N,N-diisopropylethylamine (0.08 mL, 0.4 mmol). After 10 minutes, (2-aminothiazol-5-yl)methanol (24 mg, 0.18 mmol) was added, and the mixture was stirred for 18 h, diluted with water and MeOH, and loaded onto a semi-prep HPLC (NH$_4$OH as modifier) to afford the title compound as a white solid (24 mg, 34%). $^1$H NMR (400 MHz, CDCl$_3$) δ 2.48-2.66 (m, 2H), 2.82-2.97 (m, 2H), 3.36-3.43 (m, 1H), 4.86 (s, 2H), 4.94-5.04 (m, 1H), 6.50 (t, J=76 Hz, 1H), 6.54-6.59 (m, 1H), 6.61-6.66 (m, 1H), 7.14 (dd, J=9, 6 Hz, 1H), 7.36 (br s, 1H); LC-MS (LC-ES) M+H=389.

Example 13

(trans)-(2-((trans)-3-(2-(Difluoromethoxy)-5-fluorophenoxy)cyclobutanecarboxamido)thiazol-4-yl)methyl 3-(2-(difluoromethoxy)-5-fluorophenoxy)cyclobutanecarboxylate

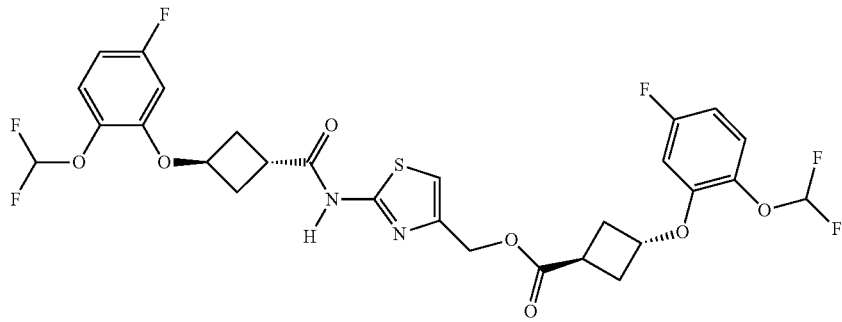 [SMILES: O=C(Nc1nc(COC(=O)[C@H]2C[C@H](Oc3cc(F)ccc3OC(F)F)C2)cs1)[C@H]1C[C@H](Oc2cc(F)ccc2OC(F)F)C1]

To a DMF (2 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol) and N,N-diisopropylethylamine (0.08 mL, 0.4 mmol). After 10 minutes, (2-aminothiazol-4-yl)methanol (24 mg, 0.18 mmol) was added. The mixture was stirred for 2 h, diluted with water and MeOH, and loaded onto a semi-prep HPLC (NH$_4$OH as modifier) to afford the title compound as a white solid (16 mg, 13%) as well as (trans)-3-(2-(Difluoromethoxy)-5-fluorophenoxy)-N-(5-(hydroxymethyl)thiazol-2-yl)cyclobutanecarboxamide (19 mg, 27%, see Example 14) and trans-(2-aminothiazol-4-yl) methyl 3-(2-(difluoromethoxy)-5-fluorophenoxy)cyclobutanecarboxylate (16 mg, 23%, see Example 14). $^1$H NMR (400 MHz, CDCl$_3$) δ 2.43-2.63 (m, 4H), 2.75 (qd, J=7, 4 Hz, 2H), 2.87 (ddd, J=14, 7, 4 Hz, 2H), 3.13-3.41 (m, 2H), 4.81-4.91 (m, 1H), 4.96-5.06 (m, 1H), 5.16 (s, 2H), 6.46 (s, 1H), 6.47 (t, J=76 Hz, 1H), 6.48-6.56 (m, 2H), 6.61-6.68 (m, 2H), 6.98 (s, 1H), 7.08-7.19 (m, 2H), 9.22 (br s, 1H); LC-MS (LC-ES) M+H=647.

Example 14

(trans)-(2-Aminothiazol-4-yl)methyl 3-(2-(difluoromethoxy)-5-fluorophenoxy)cyclobutanecarboxylate, and (trans)-3-(2-(Difluoromethoxy)-5-fluorophenoxy)-N-(4-(hydroxymethyl)thiazol-2-yl)cyclobutanecarboxamide

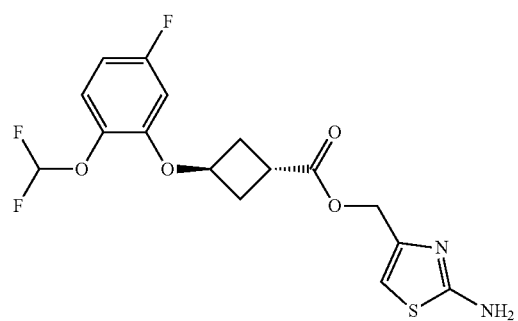

-continued

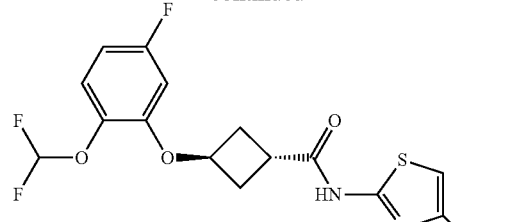

To a DMF (2 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol) and N,N-diisopropylethylamine (0.063 mL, 0.36 mmol). After 10 minutes, (2-aminothiazol-4-yl)methanol (24 mg, 0.18 mmol) was added. The mixture was stirred for 18 h, diluted with water and MeOH, and loaded onto a semi-prep HPLC (NH$_4$OH as modifier) to afford (trans)-(2-aminothiazol-4-yl)methyl 3-(2-(difluoromethoxy)-5-fluorophenoxy)cyclobutanecarboxylate as a white solid (16 mg, 22%) as well as trans-3-(2-(difluoromethoxy)-5-fluorophenoxy)-N-(4-(hydroxymethyl)thiazol-2-yl)cyclobutanecarboxamide (9 mg, 13%) as a white solid.

(trans)-(2-Aminothiazol-4-yl)methyl 3-(2-(difluoromethoxy)-5-fluorophenoxy)cyclobutanecarboxylate $^1$H NMR (400 MHz, CDCl$_3$) δ 2.39-2.57 (m, 2H), 2.71-2.79 (m, 2H), 3.14-3.31 (m, 1H), 4.84-4.92 (m, 1H), 5.02 (s, 2H), 5.15 (br s, 2H), 6.46 (t, J=76 Hz, 1H), 6.47-6.51 (m, 1H), 6.52 (s, 1H), 6.58-6.64 (m, 1H), 7.11 (dd, J=9, 6 Hz, 1H); LC-MS (LC-ES) M+H=389.

(trans)-3-(2-(Difluoromethoxy)-5-fluorophenoxy)-N-(4-(hydroxymethyl)thiazol-2-yl)cyclobutanecarboxamide $^1$H NMR (400 MHz, CDCl$_3$) δ 2.44-2.56 (m, 2H), 2.79-2.88 (m, 2H), 3.21-3.31 (m, 1H), 4.65 (s, 2H), 4.91-5.05 (m, 1H), 6.48 (t, J=72 Hz, 1H), 6.51-6.56 (m, 1H), 6.59-6.68 (m, 1H), 6.83 (s, 1H), 7.13 (dd, J=9, 6 Hz, 1H); LC-MS (LC-ES) M+H=389.

Example 15

(trans)-N-(1-(2,2-Difluoroethyl)azetidin-3-yl)-3-(2-(difluoromethoxy)-5-fluorophenoxy)cyclobutanecarboxamide

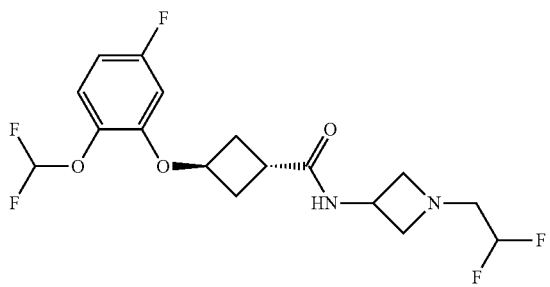 [SMILES: O=C(NC1CN(CC(F)F)C1)[C@H]1C[C@H](Oc2cc(F)ccc2OC(F)F)C1]

To a dioxane (2 mL) solution of (trans)-N-(azetidin-3-yl)-3-(2-(difluoromethoxy)-5-fluorophenoxy)cyclobutanecarboxamide trifluoroacetic acid salt (30 mg, 0.07 mmol) (Intermediate 13) was added N,N-diisopropylethylamine (0.04 mL, 0.2 mmol) and 2,2-difluoroethyl trifluoromethanesulfonate (29 mg, 0.14 mmol). The reaction was stirred for 18 h, concentrated and loaded onto a semi-prep HPLC (NH$_4$OH as modifier) to afford the title compound as an off-white solid (8 mg, 30%). $^1$H NMR (400 MHz, CDCl$_3$) δ 2.29-2.43 (m, 2H), 2.61-2.71 (m, 2H), 2.84-2.94 (m, 1H), 3.04-3.07 (m, 2H), 3.62-3.68 (m, 2H), 4.45-4.61 (m, 1H), 4.86-4.91 (m, 1H), 5.54-5.91 (m, 2H), 6.40 (t, J=76 Hz, 1H), 6.44-6.49 (m, 1H), 6.50-6.60 (m, 1H), 7.03-7.08 (m, 1H); LC-MS (LC-ES) M+H=395.

Example 16

(trans)-N-(5-(tert-Butyl)-1,3,4-oxadiazol-2-yl)-3-(2-(difluoromethoxy)-5-fluorophenoxy)cyclobutanecarboxamide

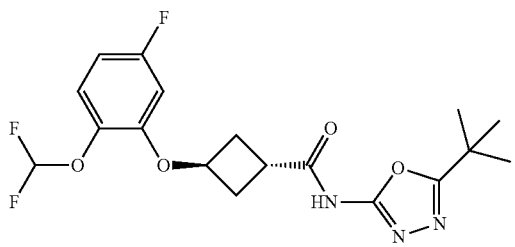 [SMILES: CC(C)(C)c1nnc(NC(=O)[C@H]2C[C@H](Oc3cc(F)ccc3OC(F)F)C2)o1]

To a DMF (2 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol) and N,N-diisopropylethylamine (0.06 mL, 0.4 mmol). After 10 minutes, 5-(tert-butyl)-1,3,4-oxadiazol-2-amine (26 mg, 0.18 mmol) was added, and the mixture was stirred for 2 h, diluted with water and MeOH, and loaded onto a semi-prep HPLC (TFA as modifier) to afford the title compound as a white solid (39 mg, 54%). $^1$H NMR (400 MHz, CDCl$_3$) δ 1.44 (s, 9H), 2.56-2.70 (m, 2H), 2.81-2.87 (m, 2H), 3.45-3.60 (m, 1H), 4.89-5.00 (m, 1H), 6.50 (t, J=76 Hz, 1H), 6.51-6.56 (m, 1H), 6.59-6.63 (m, 1H), 7.13 (dd, J=9, 6 Hz, 1H); LC-MS (LC-ES) M+H=400.

Example 17

(trans)-3-(2-(Difluoromethoxy)-5-fluorophenoxy)-N-(1-(pyrimidin-2-yl)azetidin-3-yl)cyclobutanecarboxamide

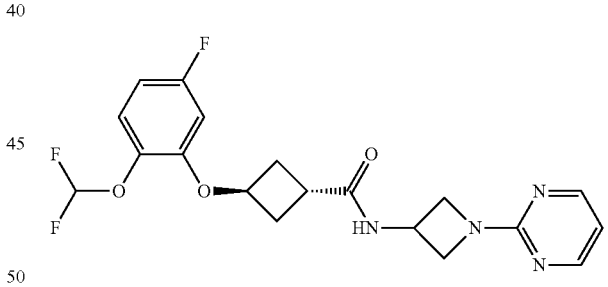

To an NMP (1 mL) solution of (trans)-N-(azetidin-3-yl)-3-(2-(difluoromethoxy)-5-fluorophenoxy)cyclobutanecarboxamide, trifluoroacetic acid salt (Intermediate 13) (33 mg, 0.07 mmol) and 2-chloropyrimidine (17 mg, 0.15 mmol) in a microwave reaction vial was added N,N-diisopropylethylamine (0.04 mL, 0.2 mmol). The reaction was heated in a microwave (150° C.) for 90 minutes, concentrated and loaded onto a semi-prep HPLC (TFA as modifier) for purification. The appropriate fractions were collected, concentrated and partitioned between DCM and saturated aqueous NaHCO$_3$ solution. The DCM phase was dried over MgSO$_4$, filtered and concentrated to afford the title compound as a white solid (19 mg, 63%). $^1$H NMR (400 MHz, CDCl$_3$) δ 2.41-2.52 (m, 2H), 2.71-2.81 (m, 2H), 2.99-3.06 (m, 1H), 3.91-3.96 (m, 2H), 4.48-4.54 (m, 2H), 4.83-4.89 (m, 1H), 4.90-5.00 (m, 1H), 5.91-5.99 (m, 1H), 6.47 (t, J=72

Hz, 1H), 6.53-6.56 (m, 1H), 6.61-6.67 (m, 2H), 7.12 (dd, J=9, 6 Hz, 1H), 8.33 (d, J=5 Hz, 1H); LC-MS (LC-ES) M+H=409.

Example 18

(trans)-3-(2-(Difluoromethoxy)-5-fluorophenoxy)-N-(1-(pyridin-2-yl)azetidin-3-yl)cyclobutanecarboxamide

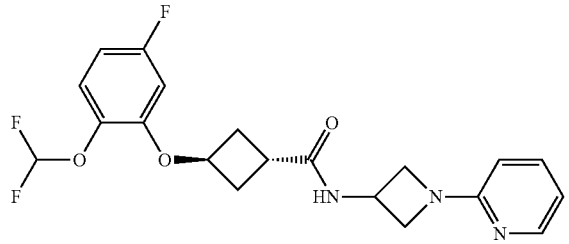 [SMILES: O=C(NC1CN(c2ccccn2)C1)[C@H]1C[C@H](Oc2cc(F)ccc2OC(F)F)C1]

To an NMP (1 mL) solution of (trans)-N-(azetidin-3-yl)-3-(2-(difluoromethoxy)-5-fluorophenoxy)cyclobutanecarboxamide, trifluoroacetic acid salt (Intermediate 13) (80 mg, 0.2 mmol) and 2-fluoropyridine (22 mg, 0.23 mmol) in a microwave reaction vial was added N,N-diisopropylethylamine (0.1 mL, 0.6 mmol). The reaction was heated in a microwave (120° C.) for 2 h, concentrated and loaded onto a semi-prep HPLC (NH$_4$OH as modifier) to afford the title compound as a tan solid (6 mg, 12%). $^1$H NMR (400 MHz, CD$_3$OD) δ 2.43-2.52 (m, 2H), 2.66-2.76 (m, 2H), 3.17-3.24 (m, 1H), 4.21-4.27 (m, 2H), 4.59-4.66 (m, 2H), 4.79-4.88 (m, 1H), 4.91-5.03 (m, 2H), 6.64-6.76 (m, 3H), 6.86-6.99 (m, 2H), 7.13-7.20 (m, 1H), 7.93 (d, J=6 Hz, 1H), 7.95-8.03 (m, 1H); LC-MS (LC-ES) M+H=408.

Example 19

(trans)-N-((trans)-4-(3,3-Difluoroazetidin-1-yl)cyclohexyl)-3-(2-(difluoromethoxy)-5-fluorophenoxy)cyclobutanecarboxamide

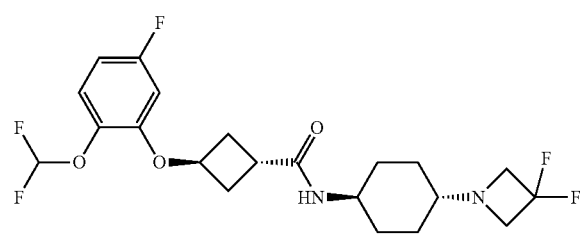 [SMILES: O=C(N[C@H]1CC[C@H](N2CC(F)(F)C2)CC1)[C@H]1C[C@H](Oc2cc(F)ccc2OC(F)F)C1]

To a DMF (3 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol) and N,N-diisopropylethylamine (0.06 mL, 0.4 mmol). After 10 minutes, trans-4-(3,3-difluoroazetidin-1-yl)cyclohexanamine (Intermediate 14) (34 mg, 0.18 mmol) was added, and the mixture was stirred for 2 h, diluted with water and MeOH, and loaded onto a semi-prep HPLC (NH$_4$OH as modifier) to afford the title compound as a white solid (54 mg, 67%). $^1$H NMR (400 MHz, CDCl$_3$) δ 1.05-1.29 (m, 4H), 1.72-1.83 (m, 2H), 1.99-2.11 (m, 3H), 2.29-2.44 (m, 2H), 2.64-2.75 (m, 2H), 2.80-2.94 (m, 1H), 3.47-3.57 (m, 4H), 3.66-3.81 (m, 1H), 4.89-4.99 (m, 1H), 5.24 (d, J=7 Hz, 1H), 6.46 (t, J=76 Hz, 1H), 6.48-6.54 (m, 1H), 6.56-6.63 (m, 1H), 7.10 (dd, J=9, 6 Hz, 1H); LC-MS (LC-ES) M+H=449.

Example 20

(trans)-3-(2-(Difluoromethoxy)-5-fluorophenoxy)-N-((trans)-4-(((S)-1,1,1-trifluoro-3-hydroxypropan-2-yl)amino)cyclohexyl)cyclobutanecarboxamide

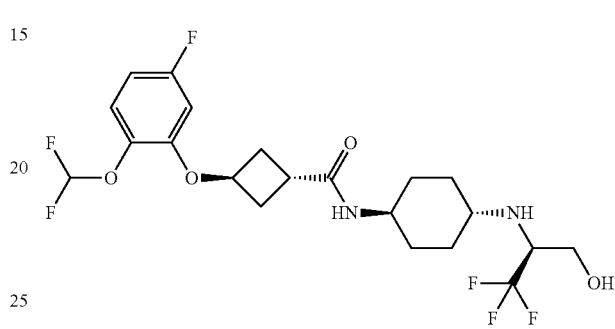

To a DMF (2 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol) and N,N-diisopropylethylamine (0.06 mL, 0.4 mmol). After 10 minutes, (S)-2-((trans-4-aminocyclohexyl)amino)-3,3,3-trifluoropropan-1-ol (Intermediate 15) (31 mg, 0.18 mmol) was added, and the mixture was stirred for 2 h, diluted with water and MeOH, and loaded onto a semi-prep HPLC (NH$_4$OH as modifier) to afford the title compound as a white solid (43 mg, 49%). $^1$H NMR (400 MHz, CDCl$_3$) δ 1.09-1.29 (m, 3H), 1.29-1.39 (m, 2H), 1.86-1.92 (m, 1H), 1.99-2.08 (m, 3H), 2.39-2.46 (m, 2H), 2.46-2.52 (m, 1H), 2.66-2.76 (m, 3H), 2.93 (tt, J=9, 5 Hz, 1H), 3.24-3.31 (m, 1H), 3.45-3.51 (m, 1H), 3.72-3.81 (m, 2H), 4.94-5.00 (m, 1H), 5.26 (d, J=8 Hz, 1H), 6.47 (t, J=80 Hz, 1H), 6.50-6.57 (m, 1H), 6.59-6.66 (m, 1H), 7.11 (dd, J=9, 6 Hz, 1H); LC-MS (LC-ES) M+H=485.

Example 21

Racemic (trans)-3-(2-(Difluoromethoxy)-5-fluorophenoxy)-N-(1-(1,1-difluoropropan-2-yl)piperidin-4-yl)cyclobutanecarboxamide

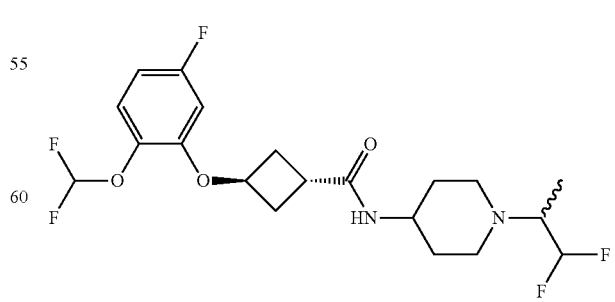

To a DMF (3 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol) and N,N-diisopropylethylamine (0.06 mL, 0.4 mmol). After 10 minutes, 1-(1,1-difluoropropan-2-yl)piperidin-4-amine (Intermediate 16) (32 mg, 0.18 mmol) was added, and the mixture was stirred for 2 h, diluted with water and MeOH and loaded onto a semi-prep HPLC (NH$_4$OH as modifier) to afford the title compound as a sticky oil (49 mg, 61%). $^1$H NMR (400 MHz, CDCl$_3$) δ 1.13 (d, J=7 Hz, 3H), 1.36-1.48 (m, 2H), 1.89-1.99 (m, 2H), 2.41-2.50 (m, 3H), 2.48-2.59 (m, 2H), 2.70-2.79 (m, 2H), 2.81-2.91 (m, 2H), 2.89-3.03 (m, 2H), 3.75-3.87 (m, 1H), 4.93-5.03 (m, 1H), 5.29-5.38 (m, 1H), 5.80 (dt, J=4, 56 Hz, 1H), 6.50 (t, J=76 Hz, 1H), 6.54-6.57 (m, 1H), 6.59-6.66 (m, 1H), 7.14 (dd, J=9, 6 Hz, 1H); LC-MS (LC-ES) M+H=437.

Example 22

(trans)-3-(2-(Difluoromethoxy)-5-fluorophenoxy)-N-(pyrimidin-5-yl)cyclobutanecarboxamide

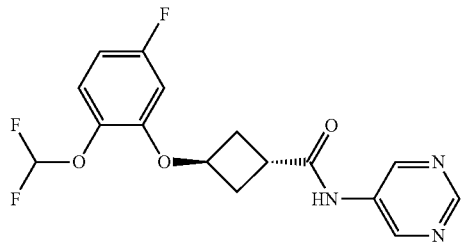 [SMILES: O=C(Nc1cncnc1)[C@H]1C[C@H](Oc2cc(F)ccc2OC(F)F)C1]

To a DMF (2 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol) and N,N-diisopropylethylamine (0.06 mL, 0.4 mmol). After 10 minutes, pyrimidin-5-amine (21 mg, 0.22 mmol) was added. The mixture was stirred for 2 h, diluted with water and MeOH, and loaded onto a semi-prep HPLC (NH$_4$OH as modifier) to afford the title compound as a tan solid (43 mg, 67%). $^1$H NMR (400 MHz, CDCl$_3$) δ 2.49-2.59 (m, 2H), 2.82-2.92 (m, 2H), 3.24-3.31 (m, 1H), 4.95-5.02 (m, 1H), 6.48 (t, J=72 Hz, 1H), 6.51-6.59 (m, 1H), 6.61-6.69 (m, 1H), 7.13 (dd, J=9, 6 Hz, 1H), 7.65 (br s, 1H), 9.00 (s, 1H), 9.04 (s, 2H); LC-MS (LC-ES) M+H=354.

Example 23

Racemic (trans)-3-(2-(Difluoromethoxy)-5-fluorophenoxy)-N-((trans)-4-((1,1-difluoropropan-2-yl)amino)cyclohexyl)cyclobutanecarboxamide

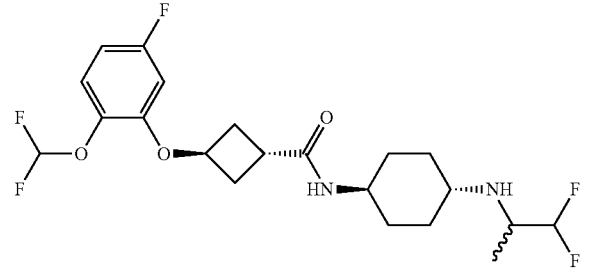 [SMILES: CC(N[C@H]1CC[C@H](NC(=O)[C@H]2C[C@H](Oc3cc(F)ccc3OC(F)F)C2)CC1)C(F)F]

To a DMF (3 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol) and N,N-diisopropylethylamine (0.06 mL, 0.4 mmol). After 10 minutes, (trans)-N1-(1,1-difluoropropan-2-yl)cyclohexane-1,4-diamine (Intermediate 17) (42 mg, 0.22 mmol) was added, and the mixture was stirred for 2 h, diluted with water and MeOH, and loaded onto a semi-prep HPLC (NH$_4$OH as modifier) to afford the title compound as a white solid (47 mg, 58%). $^1$H NMR (400 MHz, CDCl$_3$) δ 1.12 (d, J=4 Hz, 3H), 1.12-1.29 (m, 4H), 1.90-1.98 (m, 2H), 1.98-2.07 (m, 2H), 2.35-2.46 (m, 2H), 2.52-2.62 (m, 1H), 2.68-2.74 (m, 2H), 2.87-2.97 (m, 1H), 2.97-3.09 (m, 1H), 3.69-3.81 (m, 1H), 4.92-5.00 (m, 1H), 5.26 (br d, J=8 Hz, 1H), 5.59 (dt, J=4, 56 Hz, 1H), 6.47 (t, J=72 Hz, 1H), 6.52 (dd, J=10, 3 Hz, 1H), 6.60 (td, J=8, 3 Hz, 1H), 7.11 (dd, J=9, 6 Hz, 1H); LC-MS (LC-ES) M+H=451.

Example 24

Racemic (trans)-3-(2-(Difluoromethoxy)-5-fluorophenoxy)-N-(2-oxoindolin-3-yl)cyclobutanecarboxamide

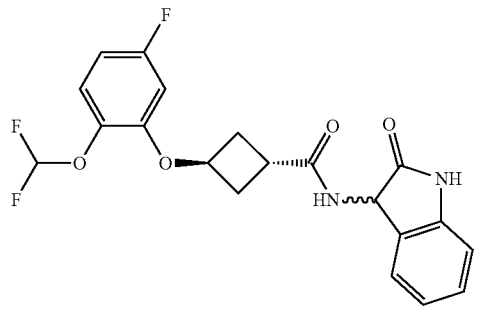 [SMILES: O=C1Nc2ccccc2C1NC(=O)[C@H]1C[C@H](Oc2cc(F)ccc2OC(F)F)C1]

To a DMF (3 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol) and N,N-diisopropylethylamine (0.06 mL, 0.4 mmol). After 10 minutes, 3-aminoindolin-2-one hydrochloride (33 mg, 0.18 mmol) was added, and the mixture was stirred for 2 h, diluted with water and MeOH, and loaded onto a semi-prep HPLC (TFA as modifier) to afford the product, which was further purified by silica gel chromatography, eluting with 10-60% EtOAc in EtOAc:hexanes (3:1) to give the title compound as a white solid (27 mg, 37% yield). $^1$H NMR (400 MHz, CDCl$_3$) δ 2.44-2.54 (m, 2H), 2.74-2.84 (m, 2H), 3.05-3.16 (m, 1H), 4.91-5.02 (m, 1H), 5.29 (d, J=8 Hz, 1H), 6.12-6.18 (m, 1H), 6.47 (t, J=76 Hz, 1H), 6.49-6.55 (m, 1H), 6.59-6.66 (m, 1H), 6.88 (d, J=8 Hz, 1H), 7.04-7.13 (m, 2H), 7.25-7.34 (m, 2H), 7.65 (s, 1H); LC-MS (LC-ES) M+H=407.

Example 25

Racemic (trans)-3-(2-(Difluoromethoxy)-5-fluorophenoxy)-N-(2-oxo-1,2,3,4-tetrahydroquinolin-4-yl)cyclobutanecarboxamide

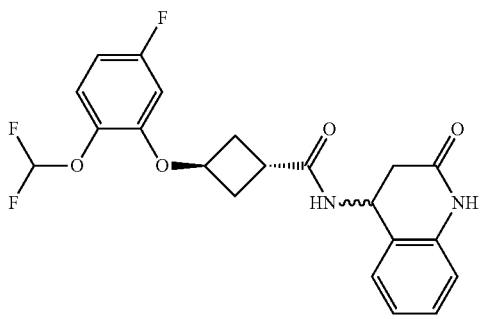 [SMILES: O=C1CC(NC(=O)[C@H]2C[C@H](Oc3cc(F)ccc3OC(F)F)C2)c2ccccc2N1]

To a DMF (3 mL) solution of (trans)-3-(2-(difluoromethoxy)-5-fluorophenoxy)cyclobutanecarboxylic acid (Intermediate 4) (50 mg, 0.18 mmol) was added HATU (103 mg, 0.27 mmol) and N,N-diisopropylethylamine (0.10 mL, 0.54 mmol). After 10 minutes, 4-amino-3,4-dihydroquinolin-2(1H)-one hydrochloride (36 mg, 0.18 mmol) was added, and the mixture was stirred for 2 h, diluted with water and MeOH and loaded onto a semi-prep HPLC (NH$_4$OH as modifier) to afford the title compound as a white solid (53 mg, 70% yield). $^1$H NMR (400 MHz, CDCl$_3$) δ 2.36-2.48 (m, 2H), 2.69-2.79 (m, 2H), 2.89 (dd, J=5, 2 Hz, 1H), 2.89-3.01 (m, 1H), 3.49 (d, J=6 Hz, 2H), 4.90-5.01 (m, 1H), 5.29-5.39 (m, 1H), 5.66-5.76 (m, 1H), 6.46 (t, J=72 Hz, 1H), 6.53 (dd, J=10, 3 Hz, 1H), 6.57-6.68 (m, 1H), 6.81 (d, J=8 Hz, 1H), 7.04-7.14 (m, 2H), 7.27-7.40 (m, 1H), 7.74-7.87 (m, 1H); LC-MS (LC-ES) M+H=421.

Example 26

Racemic (trans)-3-(2-(Difluoromethoxy)-5-fluorophenoxy)-N-(trans)-4-(1-hydroxyethyl)cyclohexyl)cyclobutanecarboxamide

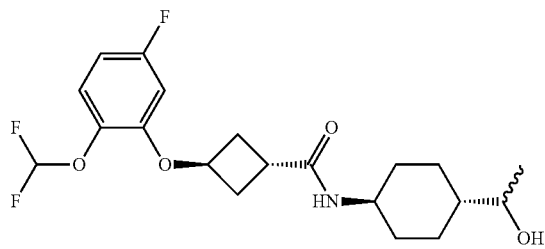 [SMILES: CC(O)[C@H]1CC[C@H](NC(=O)[C@H]2C[C@H](Oc3cc(F)ccc3OC(F)F)C2)CC1]

To a DMF (1.2 mL) solution of (trans)-3-(2-(difluoromethoxy)-5-fluorophenoxy)cyclobutanecarboxylic acid (Intermediate 4) (0.10 g, 0.36 mmol), (R,S)-1-((trans)-4-aminocyclohexyl)ethanol hydrochloride (Intermediate 18) (0.078 g, 0.43 mmol) and N,N-diisopropylethylamine (0.25 mL, 1.4 mmol) was added, dropwise, a 50% solution of T3P in ethyl acetate (0.33 mL, 0.56 mmol). The mixture was stirred 18 hours, quenched with saturated aqueous sodium bicarbonate, and extracted with ethyl acetate (2×). The combined organics were washed with water, followed by brine, then dried over sodium sulfate, filtered and concentrated under reduce pressure. The residue was purified by silica gel chromatography, eluting with a 10-60% ethyl acetate in heptanes gradient. The appropriate fractions were concentrated under reduced pressure to afford the title compound as a white solid (40 mg, 26%). $^1$H NMR (400 MHz, CDCl$_3$) δ 1.06-1.32 (m, 9H), 1.68-1.76 (m, 1H), 1.88-1.96 (m, 3H), 2.34-2.46 (m, 2H), 2.60-2.68 (m, 2H), 3.10 (dt, J=9, 5 Hz, 1H), 3.49 (t, J=6 Hz, 1H), 3.55-3.64 (m, 1H), 4.94 (t, J=6 Hz, 1H), 6.61-6.73 (m, 2H), 6.67 (t, J=76 Hz, 1H), 7.14 (dd, J=9, 6 Hz, 1H); LC-MS (LC-ES) M+H=402.

Example 27

Racemic (trans)-N-((trans)-4-(Cyclopropyl(hydroxy)methyl)cyclohexyl)-3-(2-(difluoromethoxy)-5-fluorophenoxy)cyclobutanecarboxamide

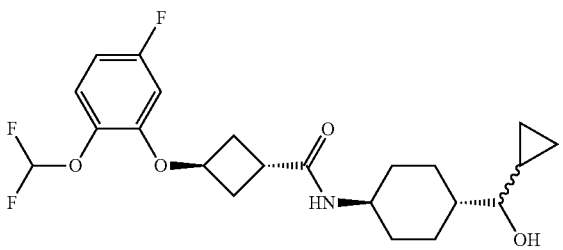 [SMILES: O=C(N[C@H]1CC[C@H](C(O)C2CC2)CC1)[C@H]1C[C@H](Oc2cc(F)ccc2OC(F)F)C1]

To a DMF (1.2 mL) solution of (trans)-3-(2-(difluoromethoxy)-5-fluorophenoxy)cyclobutanecarboxylic acid (Intermediate 4) (0.08 g, 0.3 mmol), ((trans)-4-aminocyclohexyl)(cyclopropyl)methanol (Intermediate 19) (0.068 g, 0.40 mmol) and N,N-diisopropylethylamine (0.20 mL, 1.1 mmol) was added, dropwise, a 50% solution of T3P in ethyl acetate (0.26 mL, 0.44 mmol). The mixture was stirred 17 hours, quenched with saturated aqueous sodium bicarbonate to a pH of 8-9. The reaction was extracted with ethyl acetate (2×). The combined organics were washed with water, followed by brine, then dried over sodium sulfate, filtered and concentrated under reduce pressure. The residue was purified by silica gel chromatography, eluting with a 10-50% ethyl acetate in heptanes gradient. The appropriate fractions were concentrated under reduced pressure to afford the title compound (95 mg, 76%). $^1$H NMR (400 MHz, CD$_3$OD) δ 0.16-0.30 (m, 2H), 0.41-0.57 (m, 2H), 0.79-0.92 (m, 1H), 1.15-1.31 (m, 4H), 1.39-1.50 (m, 1H), 1.84-2.05 (m, 4H), 2.33-2.44 (m, 2H), 2.57 (dd, J=9.6 Hz, 1H), 2.66 (ddd, J=13, 7, 4 Hz, 2H), 3.10 (tt, J=10, 5 Hz, 1H), 3.62 (d, J=4 Hz, 1H), 4.94 (quin, J=6 Hz, 1H), 6.44-6.89 (m, 3H), 7.14 (dd, J=9, 6 Hz, 1H), 7.84 (d, J=8 Hz, 1H); LC-MS (LC-ES) M+H=428.

Example 28

Racemic (trans)-3-(2-(Difluoromethoxy)-5-fluorophenoxy)-N-((trans)-4-(1,1,1-trifluoro-2-hydroxypropan-2-yl)cyclohexyl)cyclobutanecarboxamide

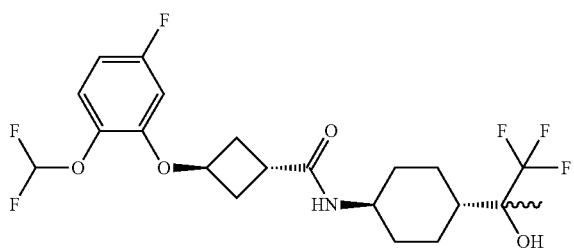 [SMILES: CC(O)([C@H]1CC[C@H](NC(=O)[C@H]2C[C@H](Oc3cc(F)ccc3OC(F)F)C2)CC1)C(F)(F)F]

To a DMF (2 mL) solution of (trans)-3-(2-(difluoromethoxy)-5-fluorophenoxy)cyclobutanecarboxylic acid (Intermediate 4) (0.15 g, 0.54 mmol), 2-((trans)-4-aminocyclohexyl)-1,1,1-trifluoropropan-2-ol (Intermediate 20) (0.126 g, 0.597 mmol) and N,N-diisopropylethylamine (0.38 mL, 2.2 mmol) was added, dropwise, a 50% solution of T3P in ethyl acetate (0.49 mL, 0.82 mmol). The mixture was stirred 17 hours, quenched with saturated aqueous sodium bicarbonate to a pH of 8-9. The reaction was extracted with ethyl acetate (2×). The combined organics were washed with water, followed by brine, then dried over sodium sulfate, filtered and concentrated under reduce pressure. The residue was purified by silica gel chromatography, eluting with a 10-50% ethyl acetate in heptanes gradient. The appropriate fractions were concentrated under reduced pressure to afford the title compound (190 mg, 67%). $^1$H NMR (400 MHz, CD$_3$OD) δ 1.14-1.37 (m, 7H), 1.66 (t, J=11 Hz, 1H), 1.90 (d, J=11 Hz, 1H), 1.94-2.05 (m, 3H), 2.31-2.47 (m, 2H), 2.66 (ddd, J=13, 7, 4 Hz, 2H), 3.05-3.14 (m, 1H), 3.56-3.68 (m, 1H), 4.94 (quin, J=6 Hz, 1H), 6.63-6.72 (m, 2H), 6.67 (t, J=76 Hz, 1H), 7.14 (dd, J=9, 6 Hz, 1H); LC-MS (LC-ES) M+H=470.

Example 29

(trans)-3-(2-(Difluoromethoxy)-5-fluorophenoxy)-N-((trans)-4-hydroxy-4-methylcyclohexyl)cyclobutanecarboxamide

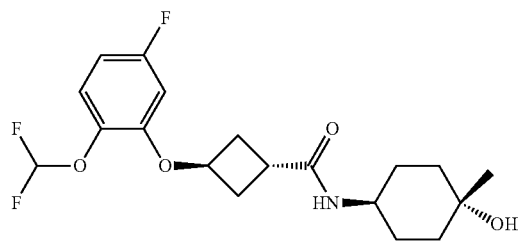 [SMILES: C[C@]1(O)CC[C@H](NC(=O)[C@H]2C[C@H](Oc3cc(F)ccc3OC(F)F)C2)CC1]

To a DMF (1 mL) solution of (trans)-3-(2-(difluoromethoxy)-5-fluorophenoxy)cyclobutanecarboxylic acid (Intermediate 4) (75 mg, 0.27 mmol), (trans)-4-amino-1-methylcyclohexanol (39 mg, 0.30 mmol) and N,N-diisopropylethylamine (0.19 mL, 1.1 mmol) was added, dropwise, a 50% solution of T3P in ethyl acetate (0.25 mL, 0.42 mmol). The mixture was stirred 17 hours, quenched with saturated aqueous sodium bicarbonate to a pH of 8-9. The reaction was extracted with ethyl acetate (2×). The combined organics were washed with water, followed by brine, then dried over sodium sulfate, filtered and concentrated under reduce pressure. The residue was purified by silica gel chromatography, eluting with a 10-50% ethyl acetate in heptanes gradient. The appropriate fractions were concentrated under reduced pressure to afford the title compound (54 mg, 51%). $^1$H NMR (400 MHz, CD$_3$OD) δ 1.23 (s, 3H), 1.34-1.46 (m, 2H), 1.50-1.60 (m, 2H), 1.63-1.72 (m, 2H), 1.80-1.92 (m, 2H), 2.36-2.46 (m, 2H), 2.59-2.70 (m, 2H), 3.06-3.18 (m, 1H), 3.70-3.82 (m, 1H), 4.93 (quin, J=6 Hz, 1H), 6.61-6.71 (m, 2H), 6.66 (t, J=72 Hz, 1H), 7.14 (dd, J=9, 6 Hz, 1H), 7.86 (d, J=8 Hz, 1H); LC-MS (LC-ES) M+H=388.

Example 30

(trans)-3-(2-(Difluoromethoxy)-5-fluorophenoxy)-N-((trans)-3-hydroxy-3-methylcyclobutyl)cyclobutanecarboxamide (trans)-3-(2-(Difluoromethoxy)-5-fluorophenoxy)-N-((cis)-3-hydroxy-3-methylcyclobutyl)cyclobutanecarboxamide, and (trans)-3-(2-(Difluoromethoxy)-5-fluorophenoxy)-N-(3-hydroxy-3-methylcyclobutyl)cyclobutanecarboxamide

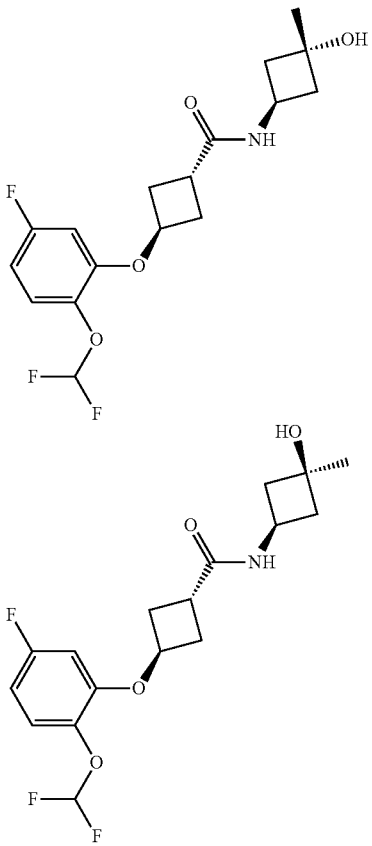

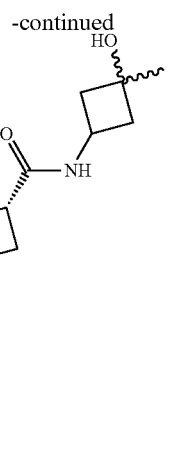

(trans)-3-(2-(Difluoromethoxy)-5-fluorophenoxy)cyclobutanecarboxylic acid (Intermediate 4) (0.05 g, 0.2 mmol) was dissolved in DMF (1.8 mL) followed by the addition of N,N-diisopropylethylamine (0.03 mL, 0.2 mmol) and HATU (0.083 g, 0.22 mmol). The reaction was stirred at room temperature for ca. 2 min, and 3-amino-1-methylcyclobutanol hydrochloride (Intermediate 21) (0.030 g, 0.22 mmol) was added. The reaction was allowed to stir at room temperature 15 h before purifying by reverse phase HPLC eluting with a gradient from 20-95% ACN:H$_2$O:0.1% NH$_4$OH to afford the title compounds (trans)-3-(2-(difluoromethoxy)-5-fluorophenoxy)-N-((trans)-3-hydroxy-3-methylcyclobutyl)cyclobutanecarboxamide (9 mg, 11%), (trans)-3-(2-(difluoromethoxy)-5-fluorophenoxy)-N-((cis)-3-hydroxy-3-methylcyclobutyl)cyclobutanecarboxamide (12 mg, 14%) and mixture (trans)-3-(2-(difluoromethoxy)-5-fluorophenoxy)-N-(3-hydroxy-3-methylcyclobutyl)cyclobutanecarboxamide (40 mg, 55%).

(trans)-3-(2-(Difluoromethoxy)-5-fluorophenoxy)-N-((trans)-3-hydroxy-3-methylcyclobutyl)cyclobutanecarboxamide $^1$H NMR (CDCl$_3$) δ 1.43 (s, 3H), 1.94-2.03 (m, 2H), 2.36-2.48 (m, 2H), 2.50-2.59 (m, 2H), 2.74 (ddd, J=13, 7, 4 Hz, 2H), 2.91-3.00 (m, 1H), 4.53 (sxt, J=8 Hz, 1H), 4.96 (quin, J=6 Hz, 1H), 5.55 (d, J=5 Hz, 1H), 6.46 (t, J=72 Hz, 1H), 6.54 (dd, J=10, 3 Hz, 1H), 6.61 (ddd, J=9, 8, 3 Hz, 1H), 7.12 (dd, J=9, 6 Hz, 1H); LC-MS (LC-ES) M+H=360.

(trans)-3-(2-(Difluoromethoxy)-5-fluorophenoxy)-N-((cis)-3-hydroxy-3-methylcyclobutyl)cyclobutanecarboxamide $^1$H NMR (CDCl$_3$) δ 1.39 (s, 3H), 2.00-2.09 (m, 2H), 2.38-2.47 (m, 2H), 2.52-2.58 (m, 2H), 2.73 (ddd, J=13, 7, 4 Hz, 2H), 2.91-3.01 (m, 1H), 4.02 (sxt, J=8 Hz, 1H), 4.95 (quin, J=6 Hz, 1H), 5.77 (d, J=7 Hz, 1H), 6.47 (t, J=76 Hz, 1H), 6.54 (dd, J=10, 3 Hz, 1H), 6.61 (ddd, J=9, 8, 3 Hz, 1H), 7.11 (dd, J=9, 6 Hz, 1H); LC-MS (LC-ES) M+H=360.

(trans)-3-(2-(Difluoromethoxy)-5-fluorophenoxy)-N-(3-hydroxy-3-methylcyclobutyl)cyclobutanecarboxamide $^1$H NMR (CD$_3$OD) δ 1.34 (s, 3H), 1.94-2.06 (m, 2H), 2.37-2.44 (m, 4H), 2.65 (ddd, J=13, 7, 5 Hz, 2H), 3.06-3.17 (m, 1H), 3.89-3.98 (m, 1H), 4.30-4.41 (m, 1H), 4.89-4.97 (m, 1H), 6.42 (t, J=76 Hz, 1H), 6.45-6.59 (m, 2H), 7.13 (dd, J=9, 6 Hz, 1H); LC-MS (LC-ES) M+H=360.

Example 31

Ethyl 2-((trans)-3-(2-(difluoromethoxy)-5-fluorophenoxy)cyclobutanecarboxamido)thiazole-4-carboxylate

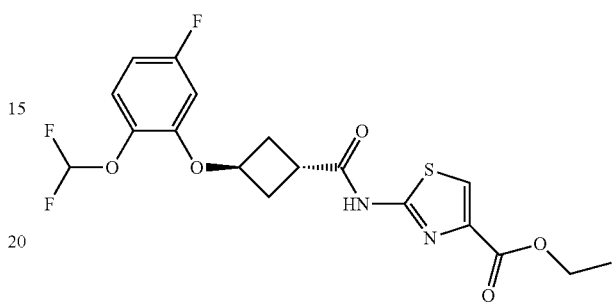

To a DMF (8 mL) solution of (trans)-3-(2-(difluoromethoxy)-5-fluorophenoxy)cyclobutanecarboxylic acid (Intermediate 4) (200 mg, 0.73 mmol) was added HATU (330 mg, 0.87 mmol) and N,N-diisopropylethylamine (0.38 mL, 2.2 mmol). After 5 minutes, ethyl 2-aminothiazole-4-carboxylate (15 mg, 0.87 mmol) was added, and the mixture was stirred for 12 h, diluted with water and extracted with EtOAc (3×). The combined organic layers were dried over Na$_2$SO$_4$ and concentrated. The residue was purified on silica gel, eluting with a 0%-100% EtOAc-EtOH (3:1) in hexanes gradient. The appropriate fractions were combined, evaporated under reduced pressure and placed in vacuo to give the title compound (70 mg, 23%). $^1$H NMR (400 MHz, CD$_3$SOCD$_3$) δ 1.21-1.29 (t, J=7 Hz, 3H), 2.29-2.45 (m, 2H), 2.68-2.77 (m, 2H), 3.23-3.33 (m, 1H), 4.25 (q, J=7 Hz, 2H), 4.82-4.91 (m, 1H), 6.70-6.80 (m, 2H), 7.03 (t, J=72 Hz, 1H), 7.12-7.20 (m, 1H), 8.05 (s, 1H); LC-MS (LC-ES) M+H=431.

Example 32

(trans)-N-(4-(Cyclopropanecarbonyl)thiazol-2-yl)-3-(2-(difluoromethoxy)-5-fluorophenoxy)cyclobutanecarboxamide

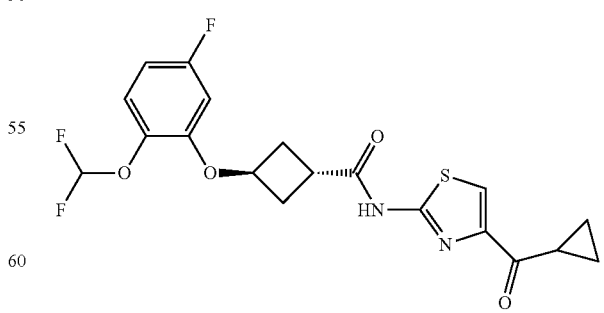

To 2-((trans)-3-(2-(difluoromethoxy)-5-fluorophenoxy)cyclobutanecarboxamido)-N-methoxy-N-methylthiazole-4-carboxamide (Intermediate 22) (15 mg, 0.03 mmol) in THF (5 mL) at 0° C. was added a 1.0 M solution of cyclopropylmagnesium bromide in 2-methylTHF (0.034 mL, 0.34 mmol). The reaction mixture was heated to 65° C. for 1 h, cooled to room temperature and quenched with saturated aqueous NH₄Cl. The mixture was extracted with EtOAc (3×), and the combined organic extracts dried over sodium sulfate, filtered, and concentrated under reduced pressure. The residue was purified on silica gel, eluting with a 0%-100% EtOAc:EtOH (3:1) in hexanes gradient. The appropriate fractions were combined, evaporated under reduced pressure and placed in vacuo to give the title compound (10 mg, 73%). (400 MHz, CD₃SOCD₃) δ 1.10-1.21 (m, 2H), 1.21-1.58 (m, 2H), 2.30-2.41 (m, 2H), 2.66-2.77 (m, 2H), 2.89-2.94 (m, 1H), 3.35-3.41 (m, 1H), 4.94-4.97 (m, 1H), 6.76-6.80 (m, 1H), 6.81-6.89 (m, 1H), 7.05 (t, J=76 Hz, 1H), 7.18-7.25 (m, 1H), 8.12 (s, 1H); LC-MS (LC-ES) M+H=427.

Example 33

(trans)-3-(2-(Difluoromethoxy)-5-fluorophenoxy)-N-((trans)-4-(2-hydroxy-2-methylpropoxy)cyclohexyl)cyclobutanecarboxamide

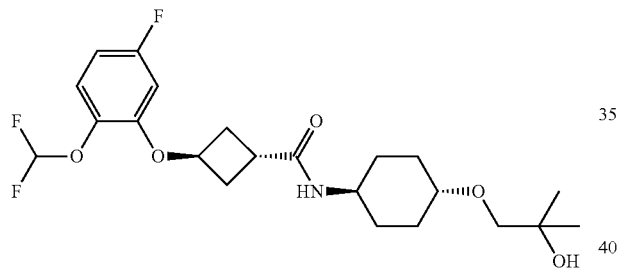

To a DMF (5 mL) solution of (trans)-3-(2-(difluoromethoxy)-5-fluorophenoxy)cyclobutanecarboxylic acid (Intermediate 4) (80 mg, 0.29 mmol) was added HATU (147 mg, 0.39 mmol) and N,N-diisopropylethylamine (0.17 mL, 0.96 mmol). After 5 minutes, 1-(((trans)-4-aminocyclohexyl)oxy)-2-methylpropan-2-ol (Intermediate 23) (60 mg, 0.32 mmol) was added, and the mixture was stirred for 12 h, diluted with water and extracted with EtOAc (3×). The combined organic layers were dried over Na₂SO₄ and concentrated. The residue was purified on silica gel, eluting with a 0%-100% EtOAc:EtOH (3:1) in hexanes gradient. The appropriate fractions were combined, evaporated under reduced pressure and placed in vacuo to give the title compound (104 mg, 73%). ¹H NMR (400 MHz, CD₃SOCD₃) δ 1.05 (s, 6H), 1.12-1.31 (m, 4H), 1.79 (d, J=9 Hz, 2H), 1.95 (d, J=9 Hz, 2H), 2.11-2.36 (m, 2H), 2.54-2.64 (m, 1H), 3.01 (dt, J=10, 5 Hz, 1H), 3.15 (s, 2H), 3.16-3.22 (m, 1H), 3.54 (dd, J=8, 4 Hz, 1H), 4.87 (t, J=6 Hz, 1H), 6.68-6.93 (m, 2H), 7.02 (t, J=76 Hz, 1H), 7.17-7.29 (m, 1H), 7.72 (d, J=8 Hz, 1H); LC-MS (LC-ES) M+H=446.

Example 34

(trans)-3-(2-(Difluoromethoxy)-5-fluorophenoxy)-N-((trans)-4-(2-hydroxypropan-2-yl)cyclohexyl)cyclobutanecarboxamide

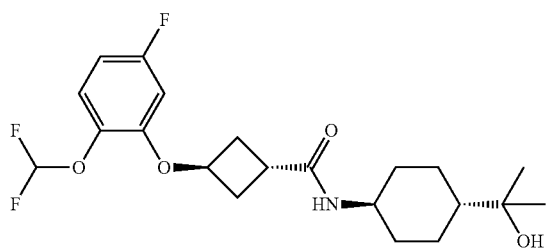 [SMILES: CC(C)(O)[C@H]1CC[C@H](NC(=O)[C@H]2C[C@H](Oc3cc(F)ccc3OC(F)F)C2)CC1]

To a DMF (5 mL) solution of (trans)-3-(2-(difluoromethoxy)-5-fluorophenoxy)cyclobutanecarboxylic acid (Intermediate 4) (80 mg, 0.29 mmol) was added HATU (147 mg, 0.39 mmol) and N,N-diisopropylethylamine (0.17 mL, 0.96 mmol). After 5 minutes, 2-((trans)-4-aminocyclohexyl)propan-2-ol (50 mg, 0.32 mmol) was added, and the mixture was stirred for 12 h, diluted with water and extracted with EtOAc (3×). The combined organic layers were dried over Na₂SO₄ and concentrated. The residue was purified on silica gel, eluting with a 0%-100% EtOAc:EtOH (3:1) in hexanes gradient. The appropriate fractions were combined, evaporated under reduced pressure and placed in vacuo to give the title compound (69 mg, 52%). ¹H NMR (400 MHz, CD₃SOCD₃) δ 1.02 (s, 6H), 1.03-1.10 (m, 5H), 1.72-1.93 (m, 4H), 2.24 (ddd, J=13, 10, 6 Hz, 2H), 2.56 (ddd, J=13, 7, 6 Hz, 2H), 2.91-3.07 (m, 1H), 3.38-3.45 (m, 1H), 4.88 (t, J=6 Hz, 1H), 6.71-6.81 (m, 2H), 7.02 (t, J=76 Hz, 1H), 7.13-7.36 (m, 1H), 7.69 (d, J=8 Hz, 1H); LC-MS (LC-ES) M+H=416.

Example 35

(trans)-N-(4-Acetylthiazol-2-yl)-3-(2-(difluoromethoxy)-5-fluorophenoxy)cyclobutanecarboxamide

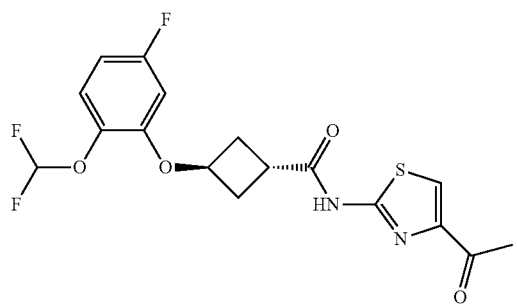 [SMILES: CC(=O)c1csc(NC(=O)[C@H]2C[C@H](Oc3cc(F)ccc3OC(F)F)C2)n1]

To a DMF (5 mL) solution of (trans)-3-(2-(difluoromethoxy)-5-fluorophenoxy)cyclobutanecarboxylic acid (Intermediate 4) (80 mg, 0.29 mmol) was added HATU (132 mg, 0.35 mmol) and N,N-diisopropylethylamine (0.15 mL, 0.87 mmol). After 5 minutes, 1-(2-aminothiazol-4-yl)ethanone (45 mg, 0.32 mmol) was added, and the mixture was stirred for 12 h, diluted with water and extracted with EtOAc (3×). The combined organic layers were dried over Na₂SO₄ and concentrated. The residue was purified on silica gel, eluting with a 0%-100% EtOAc:EtOH (3:1) in hexanes gradient. The appropriate fractions were combined, evaporated under reduced pressure and placed in vacuo to give the title compound (50 mg, 41%). $^1$H NMR (400 MHz, CD$_3$SOCD$_3$) δ 2.25-2.44 (m, 2H), 2.74 (ddd, J=13, 7, 4 Hz, 2H), 3.30 (s, 3H), 3.36-3.49 (m, 1H), 4.91 (t, J=6 Hz, 1H), 6.65-6.71 (m, 1H), 6.72-6.88 (m, 1H), 7.03 (t, J=76 Hz, 1H), 7.15-7.21 (m, 1H), 8.07 (s, 1H); LC-MS (LC-ES) M+H=401.

Example 36

6-(3-((trans)-3-(Benzo[d]thiazol-4-yloxy)cyclobutanecarboxamido)azetidin-1-yl)nicotinamide

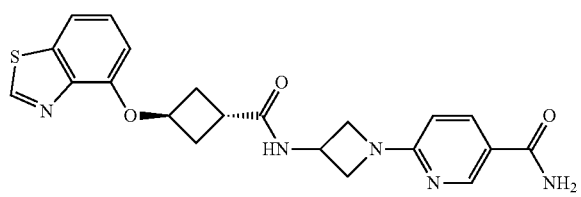 [SMILES: NC(=O)c1ccc(N2CC(NC(=O)[C@H]3C[C@H](Oc4cccc5scnc45)C3)C2)nc1]

To a DMF (2 mL) solution of (trans)-3-(benzo[d]thiazol-4-yloxy)cyclobutanecarboxylic acid (Intermediate 25) (20 mg, 0.08 mmol), 6-(3-aminoazetidin-1-yl)nicotinamide dihydrochloride (Intermediate 24) (21 mg, 0.08 mmol) and N,N-diisopropylethylamine (0.05 mL, 0.3 mmol) was added, dropwise, a 50% solution of T3P in ethyl acetate (102 mg, 0.16 mmol). The mixture was stirred 15 min, quenched with water, and loaded onto a semi-prep HPLC (NH$_4$OH as modifier) to afford the title compound (21 mg, 62%). $^1$H NMR (400 MHz, CD$_3$SOCD$_3$) δ 2.25-2.46 (m, 2H), 2.61-2.78 (m, 2H), 3.02-3.15 (m, 1H), 3.84 (dd, J=9, 5 Hz, 2H), 4.29 (t, J=8 Hz, 2H), 4.58-4.76 (m, 1H), 5.07 (quin, J=6 Hz, 1H), 6.41 (d, J=9 Hz, 1H), 6.84 (d, J=8 Hz, 1H), 7.16 (br s, 1H), 7.39 (t, J=8 Hz, 1H), 7.70 (d, J=8 Hz, 1H), 7.78 (br s, 1H), 7.96 (dd, J=9, 2 Hz, 1H), 8.60 (d, J=2 Hz, 1H), 8.63 (d, J=7 Hz, 1H), 9.26 (s, 1H); LC-MS (LC-ES) M+H=424.

Example 37

(trans)-3-(Benzo[d]thiazol-4-yloxy)-N-(1-(5-cyanopyridin-2-yl)azetidin-3-yl)cyclobutanecarboxamide

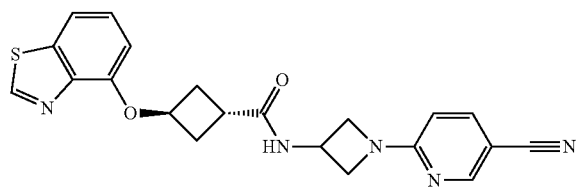 [SMILES: N#Cc1ccc(N2CC(NC(=O)[C@H]3C[C@H](Oc4cccc5scnc45)C3)C2)nc1]

To a DMF (2 mL) solution of (trans)-3-(benzo[d]thiazol-4-yloxy)cyclobutanecarboxylic acid (Intermediate 25) (20 mg, 0.08 mmol), 6-(3-aminoazetidin-1-yl)nicotinamide dihydrochloride (Intermediate 24) (21 mg, 0.08 mmol) and N,N-diisopropylethylamine (0.05 mL, 0.3 mmol) was added, dropwise, a 50% solution of T3P in ethyl acetate (102 mg, 0.16 mmol). The mixture was stirred 3 h, quenched with water, and loaded onto a semi-prep HPLC (NH$_4$OH as modifier) to afford the title compound (16 mg, 49%). $^1$H NMR (400 MHz, CD$_3$OD) δ 2.51-2.66 (m, 2H), 2.79 (qd, J=7, 5 Hz, 2H), 3.25 (tt, J=10, 5 Hz, 1H), 4.01 (dd, J=10, 5 Hz, 2H), 4.46 (t, J=9 Hz, 2H), 4.80 (tt, J=8, 5 Hz, 1H), 5.17 (quin, J=6 Hz, 1H), 6.48 (d, J=9 Hz, 1H), 6.89 (d, J=8 Hz, 1H), 7.42 (t, J=8 Hz, 1H), 7.63 (d, J=8 Hz, 1H), 7.75 (dd, J=9, 2 Hz, 1H), 8.38 (d, J=2 Hz, 1H), 9.18 (s, 1H); LC-MS (LC-ES) M+H=406.

Example 38

6-(3-((trans)-3-(Benzo[d]thiazol-4-yloxy)cyclobutanecarboxamido)azetidin-1-yl)-N-methylnicotinamide

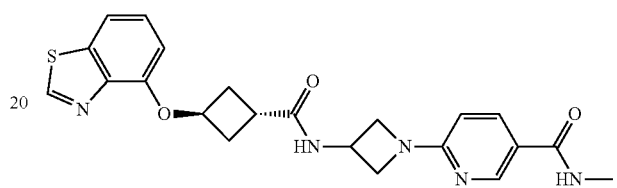

To a DMF (2 mL) solution of (trans)-3-(benzo[d]thiazol-4-yloxy)cyclobutanecarboxylic acid (Intermediate 25) (30 mg, 0.12 mmol), 6-(3-aminoazetidin-1-yl)-N-methylnicotinamide dihydrochloride (Intermediate 26) (34 mg, 0.12 mmol) and N,N-diisopropylethylamine (0.07 mL, 0.4 mmol) was added, dropwise, a 50% solution of T3P in ethyl acetate (153 mg, 0.24 mmol). The mixture was stirred 20 min, quenched with water, and loaded onto a semi-prep HPLC (NH$_4$OH as modifier) to afford the title compound (41 mg, 78%). $^1$H NMR (400 MHz, CD$_3$SOCD$_3$) δ 2.34-2.45 (m, 2H), 2.68 (ddd, J=13, 7, 4 Hz, 2H), 2.75 (d, J=5 Hz, 3H), 3.11 (tt, J=10, 5 Hz, 1H), 3.84 (dd, J=9, 5 Hz, 2H), 4.29 (t, J=9 Hz, 2H), 4.60-4.77 (m, 1H), 5.07 (quin, J=7 Hz, 1H), 6.42 (d, J=9 Hz, 1H), 6.84 (d, J=8 Hz, 1H), 7.39 (t, J=8 Hz, 1H), 7.70 (d, J=8 Hz, 1H), 7.93 (dd, J=9, 2 Hz, 1H), 8.23 (d, J=5 Hz, 1H), 8.56 (d, J=2 Hz, 1H), 8.63 (d, J=7 Hz, 1H), 9.26 (s, 1H); LC-MS (LC-ES) M+H=438.

Example 39

(trans)-3-(Benzo[d]thiazol-4-yloxy)-N-(1-(5-methylpyrimidin-2-yl)azetidin-3-yl)cyclobutanecarboxamide

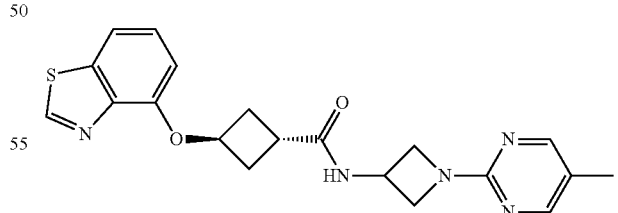

To a DMF (2 mL) solution of (trans)-3-(benzo[d]thiazol-4-yloxy)cyclobutanecarboxylic acid (Intermediate 25) (40 mg, 0.16 mmol), 1-(5-methylpyrimidin-2-yl)azetidin-3-amine dihydrochloride (Intermediate 27) (46 mg, 0.19 mmol) and N,N-diisopropylethylamine (0.10 mL, 0.56 mmol) was added, dropwise, a 50% solution of T3P in ethyl acetate (204 mg, 0.32 mmol). The reaction was stirred 20 min, quenched with water, and loaded onto a semi-prep HPLC (NH₄OH as modifier) to afford the title compound as a white solid (10.1 mg, 15.7%). ¹H NMR (400 MHz, CDCl₃) δ 2.15 (s, 3H), 2.60-2.72 (m, 2H), 2.87 (ddd, J=13, 7, 4 Hz, 2H), 3.04-3.19 (m, 1H), 3.93 (dd, J=9, 5 Hz, 2H), 4.49 (t, J=9 Hz, 2H), 4.82-4.96 (m, 1H), 5.22 (quin, J=7 Hz, 1H), 6.18 (d, J=7 Hz, 1H), 6.79 (d, J=8 Hz, 1H), 7.36 (t, J=8 Hz, 1H), 7.54 (d, J=8 Hz, 1H), 8.19 (s, 2H), 8.93 (s, 1H); LC-MS (LC-ES) M+H=396.

Example 40

Racemic 3-(Benzo[d]thiazol-4-yloxy)-N-((trans)-4-((1,1-difluoropropan-2-yl)amino)cyclohexyl)azetidine-1-carboxamide

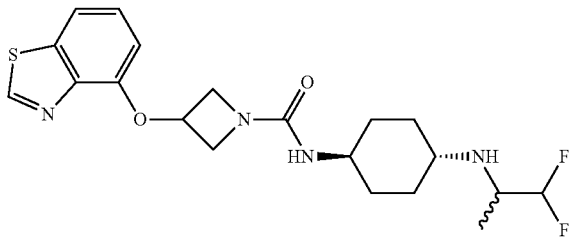 [SMILES: CC(N[C@H]1CC[C@H](NC(=O)N2CC(Oc3cccc4scnc34)C2)CC1)C(F)F]

To 4-nitrophenyl chloroformate (42 mg, 0.21 mmol) in DCM (1 mL) at 0° C. was slowly added (trans)-N1-(1,1-difluoropropan-2-yl)cyclohexane-1,4-diamine (Intermediate 17) (40 mg, 0.21 mmol) in DCM (3 mL). After one hour, N,N-diisopropylethylamine (0.04 mL, 0.2 mmol) was added, and after 3 h the solvent was removed in vacuo. To the residue was added DMF (1 mL), then 4-(azetidin-3-yloxy)benzo[d]thiazole hydrochloride (Intermediate 28) (43 mg, 0.21 mmol) and N,N-diisopropylethylamine (0.11 mL, 0.62 mmol). The mixture was stirred for 18 h and loaded onto a semi-prep HPLC (NH₄OH as modifier) to afford the title compound (31 mg, 35% yield) as a light tan solid. ¹H NMR (400 MHz, CD₃OD) δ 1.07-1.36 (m, 7H), 1.77-2.09 (m, 4H), 2.60 (t, J=11 Hz, 1H), 2.97-3.19 (m, 1H), 3.51 (t, J=11 Hz, 1H), 4.09 (dd, J=9, 4 Hz, 2H), 4.32-4.50 (m, 2H), 5.17-5.36 (m, 1H), 5.68 (dt, J=56, 4 Hz, 1H), 6.85 (d, J=8 Hz, 1H), 7.43 (t, J=8 Hz, 1H), 7.69 (d, J=8 Hz, 1H), 9.19 (s, 1H); LC-MS (LC-ES) M+H=425.

Example 41

(trans)-3-(Benzo[d]thiazol-4-yloxy)-N-(1-(5-fluoropyrimidin-2-yl)piperidin-4-yl)cyclobutanecarboxamide

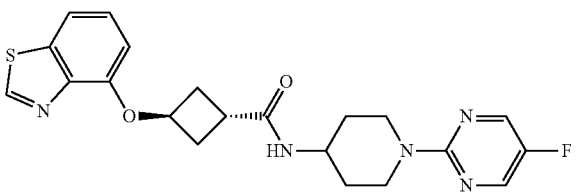 [SMILES: O=C(NC1CCN(c2ncc(F)cn2)CC1)[C@H]1C[C@H](Oc2cccc3scnc23)C1]

To a DMF (2 mL) solution of (trans)-3-(benzo[d]thiazol-4-yloxy)cyclobutanecarboxylic acid (Intermediate 25) (40 mg, 0.16 mmol), 1-(5-fluoropyrimidin-2-yl)piperidin-4-amine dihydrochloride (Intermediate 29) (43 mg, 0.16 mmol) and N,N-diisopropylethylamine (0.06 mL, 0.3 mmol) was added, dropwise, a 50% solution of T3P in ethyl acetate (204 mg, 0.32 mmol). The reaction was stirred 30 min, quenched with water, and loaded onto a semi-prep HPLC (NH₄OH as modifier) to afford the title compound as an off-white solid (37 mg, 54%). ¹H NMR (400 MHz, CDCl₃) δ 1.33 (d, J=11 Hz, 2H), 1.82 (d, J=11 Hz, 2H), 2.29-2.41 (m, 2H), 2.55-2.69 (m, 2H), 3.02-3.17 (m, 3H), 3.84-3.93 (m, 1H), 4.43 (d, J=13 Hz, 2H), 5.03-5.11 (m, 1H), 6.84 (d, J=8 Hz, 1H), 7.31-7.47 (m, 1H), 7.69 (d, J=8 Hz, 1H), 7.84 (d, J=8 Hz, 1H), 8.44 (s, 2H), 9.25 (s, 1H); LC-MS (LC-ES) M+H=428.

Example 42

3-(Benzo[d]thiazol-7-yloxy)-N-(1-(5-fluoropyrimidin-2-yl)piperidin-4-yl)azetidine-1-carboxamide

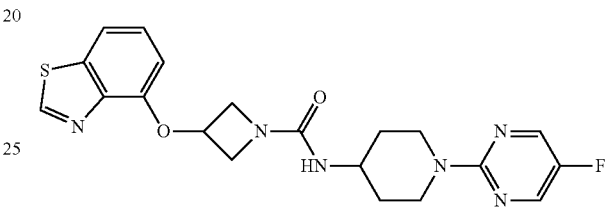

To 4-nitrophenyl (1-(5-fluoropyrimidin-2-yl)piperidin-4-yl)carbamate (Intermediate 30) (145 mg, 0.40 mmol) in DMF (1 mL) was added 4-(azetidin-3-yloxy)benzo[d]thiazole (Intermediate 28) (16 mg, 0.06 mmol) and N,N-diisopropylethylamine (0.03 mL, 0.2 mmol). The reaction was stirred 18 h and loaded onto a semi-prep HPLC (NH₄OH as modifier) to afford the title compound (20 mg, 81% yield) a white solid. ¹H NMR (400 MHz, CD₃OD) δ 1.35-1.56 (m, 2H), 1.92 (d, J=12 Hz, 2H), 3.00 (t, J=12 Hz, 2H), 3.80 (t, J=11 Hz, 1H), 4.11 (dd, J=9, 3 Hz, 2H), 4.37-4.51 (m, 2H), 4.67 (d, J=13 Hz, 2H), 5.29 (br s, 1H), 6.85 (d, J=8 Hz, 1H), 7.43 (t, J=8 Hz, 1H), 7.69 (d, J=8 Hz, 1H), 8.26 (s, 2H), 9.19 (s, 1H); LC-MS (LC-ES) M+H=429.

Example 43

3-(Benzo[d]thiazol-7-yloxy)-N-(1-(5-fluoropyridin-2-yl)azetidin-3-yl)azetidine-1-carboxamide

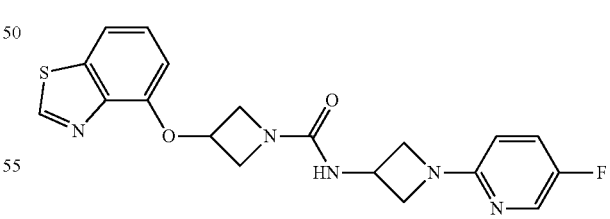

To 4-nitrophenyl (1-(5-fluoropyridin-2-yl)azetidin-3-yl)carbamate (Intermediate 31) (19 mg, 0.06 mmol) in DMF (1 mL) was added 4-(azetidin-3-yloxy)benzo[d]thiazole (Intermediate 28) (16 mg, 0.06 mmol) and N,N-diisopropylethylamine (22 mg, 0.2 mmol). The reaction was stirred 18 h and loaded onto a semi-prep HPLC (NH₄OH as modifier) to afford the title compound (21 mg, 90% yield) as a white solid. ¹H NMR (400 MHz, CDCl₃) δ 3.63-3.88 (m, 2H), 4.22-4.29 (m, 2H), 4.32 (t, J=8 Hz, 2H), 4.44 (t, J=8 Hz, 2H), 4.69-4.81 (m, 1H), 4.85 (d, J=8 Hz, 1H), 5.27 (br s, 1H), 6.26 (dd, J=9, 3 Hz, 1H), 6.68 (d, J=8 Hz, 1H), 7.20-7.30 (m, 1H), 7.33-7.43 (m, 1H), 7.61 (d, J=8 Hz, 1H), 8.01 (br s, 1H), 8.95 (s, 1H); LC-MS (LC-ES) M+H=400.

Example 44

(trans)-3-(Benzo[d]thiazol-4-yloxy)-N-(1-(5-fluoro-pyridin-2-yl)azetidin-3-yl)cyclobutanecarboxamide

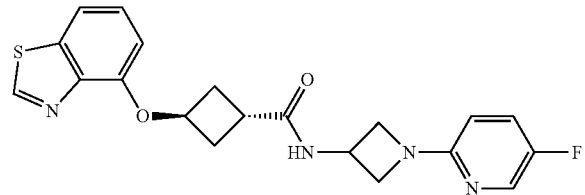 [SMILES: O=C(NC1CN(c2ccc(F)cn2)C1)[C@H]1C[C@H](Oc2cccc3scnc23)C1]

To a DMF (1 mL) solution of (trans)-3-(benzo[d]thiazol-4-yloxy)cyclobutanecarboxylic acid (Intermediate 25) (18 mg, 0.072 mmol), 1-(5-fluoropyridin-2-yl)azetidin-3-amine (Intermediate 31B) (12 mg, 0.072 mmol) and N,N-diisopropylethylamine (0.03 mL, 0.1 mmol) was added, dropwise, a 50% solution of T3P in ethyl acetate (91 mg, 0.14 mmol). The reaction was stirred 10 min, quenched with water, and loaded onto a semi-prep HPLC (NH$_4$OH as modifier) to afford the title compound as a foam (21 mg, 73%). $^1$H NMR (400 MHz, CD$_3$OD) δ 2.44-2.66 (m, 2H), 2.71-2.81 (m, 2H), 3.15-3.30 (m, 1H), 3.75-3.97 (m, 2H), 4.32 (t, J=8 Hz, 2H), 4.69-4.80 (m, 1H), 5.10-5.29 (m, 1H), 6.33-6.57 (m, 1H), 6.88 (d, J=8 Hz, 1H), 7.31-7.48 (m, 2H), 7.62 (d, J=8 Hz, 1H), 7.94 (br s, 1H), 9.16 (s, 1H); LC-MS (LC-ES) M+H=399.

Example 45

Methyl 2-(3-((trans)-3-(benzo[d]thiazol-4-yloxy)cyclobutanecarboxamido)azetidin-1-yl)oxazole-4-carboxylate

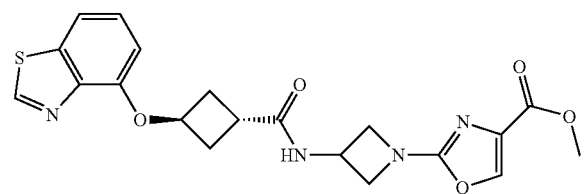 [SMILES: COC(=O)c1coc(N2CC(NC(=O)[C@H]3C[C@H](Oc4cccc5scnc45)C3)C2)n1]

To (trans)-N-(azetidin-3-yl)-3-(benzo[d]thiazol-4-yloxy)cyclobutanecarboxamide hydrochloride (Intermediate 32) (100 mg, 0.27 mmol) and N,N-diisopropylethylamine (0.14 mL, 0.80 mmol) in acetonitrile (15 mL), methyl 2-chlorooxazole-4-carboxylate (45 mg, 0.28 mmol) was added. The mixture was heated in a microwave at 125° C. for 2 h, concentrated, and the residue was purified on silica gel, eluting with a 5%-20% MeOH in DCM gradient to give the title compound as a yellow solid (46 mg, 40%). $^1$H NMR (400 MHz, CD$_3$OD) δ 2.48-2.65 (m, 2H), 2.70-2.84 (m, 2H), 3.24 (dt, J=10, 5 Hz, 1H), 3.85 (s, 3H), 4.07 (dd, J=8, 6 Hz, 2H), 4.47 (t, J=8 Hz, 2H), 4.74-4.82 (m, 1H), 5.05-5.24 (m, 1H), 6.88 (d, J=8 Hz, 1H), 7.41 (t, J=8 Hz, 1H), 7.62 (d, J=8 Hz, 1H), 8.05 (s, 1H), 9.16 (s, 1H); LC-MS (LC-ES) M+H=429.

Example 46

Racemic (trans)-3-(Benzo[d]thiazol-4-yloxy)-N-((trans)-4-((1,1-difluoropropan-2-yl)amino)cyclohexyl)cyclobutanecarboxamide

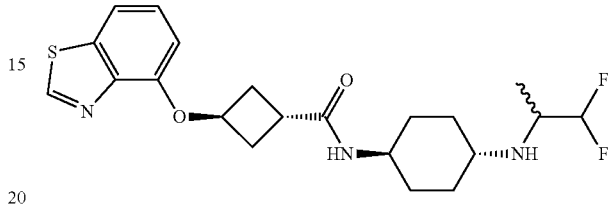

To a DMF (2 mL) solution of (trans)-3-(benzo[d]thiazol-4-yloxy)cyclobutanecarboxylic acid (Intermediate 25) (50 mg, 0.20 mmol), (trans)-N1-(1,1-difluoropropan-2-yl)cyclohexane-1,4-diamine (Intermediate 17) (39 mg, 0.20 mmol) and N,N-diisopropylethylamine (0.07 mL, 0.4 mmol) was added, dropwise, a 50% solution of T3P in ethyl acetate (255 mg, 0.40 mmol). The reaction was stirred 30 min, quenched with water, and loaded onto a semi-prep HPLC (NH$_4$OH as modifier) to afford the title compound as an off-white solid (54 mg, 64%). $^1$H NMR (400 MHz, CD$_3$OD) δ 1.14 (d, J=6.5 Hz, 3H), 1.17-1.39 (m, 4H), 1.89-2.04 (m, 4H), 2.50-2.59 (m, 2H), 2.59-2.67 (m, 1H), 2.74 (ddd, J=13, 7, 4 Hz, 2H), 3.08 (ddd, J=10, 7, 3 Hz, 1H), 3.16 (td, J=10, 5 Hz, 1H), 3.67 (ddd, J=11, 7, 4 Hz, 1H), 5.12-5.20 (m, 1H), 5.71 (t, J=56 Hz, 1H), 6.87 (d, J=8 Hz, 1H), 7.41 (t, J=8 Hz, 1H), 7.61 (d, J=8 Hz, 1H), 9.16 (s, 1H); LC-MS (LC-ES) M+H=424.

Example 47

(trans)-N-(1-(4-Acetyloxazol-2-yl)azetidin-3-yl)-3-(benzo[d]thiazol-4-yloxy)cyclobutanecarboxamide

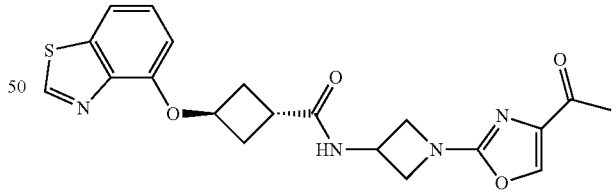

Methyl 2-(3-((trans)-3-(benzo[d]thiazol-4-yloxy)cyclobutanecarboxamido)azetidin-1-yl)oxazole-4-carboxylate (Example 45) (40 mg, 0.09 mmol) was stirred in THF (3.5 mL), and a 3.0 M solution of methylmagnesium bromide (0.07 mL, 0.2 mmol) in diethyl ether was added. The reaction was stirred 1 h, quenched with water, extracted with EtOAc, and the organic extracts dried over MgSO$_4$, filtered, and concentrated under reduced pressure. The residue was loaded onto a semi-prep HPLC to afford the title compound (3.5 mg, 9%). $^1$H NMR (CD$_3$OD) δ 2.41 (s, 3H), 2.54-2.64 (m, 2H), 2.72-2.80 (m, 2H), 3.16-3.29 (m, 1H), 3.98-4.13 (m, 2H), 4.47 (t, J=8 Hz, 2H), 4.75-4.81 (m, 1H), 5.16 (t, J=6

Hz, 1H), 6.89 (d, J=8 Hz, 1H), 7.42 (t, J=8 Hz, 1H), 7.62 (d, J=8 Hz, 1H), 8.23 (s, 1H), 9.16 (s, 1H); LC-MS (LC-ES) M+H=413.

Example 48

Ethyl 2-(3-((trans)-3-(benzo[d]thiazol-4-yloxy)cyclobutanecarboxamido)azetidin-1-yl)oxazole-5-carboxylate

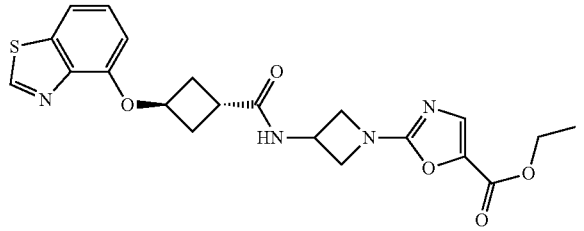 [SMILES: CCOC(=O)c1cnc(N2CC(NC(=O)[C@H]3C[C@H](Oc4cccc5scnc45)C3)C2)o1]

To (trans)-N-(azetidin-3-yl)-3-(benzo[d]thiazol-4-yloxy)cyclobutanecarboxamide hydrochloride (Intermediate 32) (100 mg, 0.27 mmol) and N,N-diisopropylethylamine (0.14 mL, 0.80 mmol) in acetonitrile (15 mL), ethyl 2-chlorooxazole-5-carboxylate (56 mg, 0.34 mmol) was added. The mixture was heated in a microwave at 125° C. for 2 h, concentrated, and the residue was purified on silica gel, eluting with a 5%-20% MeOH in DCM gradient to give the title compound (96 mg, 82%). $^1$H NMR (400 MHz, CD$_3$OD) δ 1.35 (t, J=7 Hz, 3H), 2.49-2.66 (m, 2H), 2.71-2.87 (m, 2H), 3.18-3.29 (m, 1H), 4.14 (dd, J=8, 6 Hz, 2H), 4.14 (dd, J=8, 6 Hz, 2H), 4.32 (q, J=7 Hz, 2H), 4.54 (t, J=8 Hz, 2H), 5.11-5.21 (m, 1H), 6.89 (d, J=8 Hz, 1H), 7.42 (t, J=8 Hz, 1H), 7.53-7.72 (m, 2H), 9.16 (s, 1H); LC-MS (LC-ES) M+H=443.

Example 49

(trans)-3-(Benzo[d]thiazol-4-yloxy)-N-(1-(5-(2-hydroxypropan-2-yl)oxazol-2-yl)azetidin-3-yl)cyclobutanecarboxamide

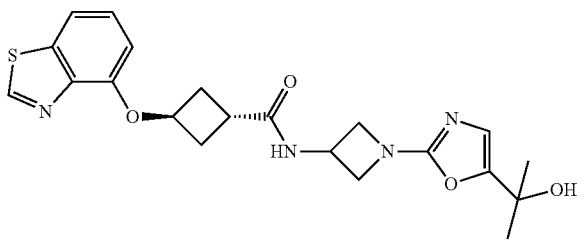 [SMILES: CC(C)(O)c1cnc(N2CC(NC(=O)[C@H]3C[C@H](Oc4cccc5scnc45)C3)C2)o1]

Ethyl 2-(3-((trans)-3-(benzo[d]thiazol-4-yloxy)cyclobutanecarboxamido)azetidin-1-yl)oxazole-5-carboxylate (Example 48) (40 mg, 0.09 mmol) was stirred in THF (2 mL) at 0° C., and a 3.0 M solution of methylmagnesium bromide (0.07 mL, 0.2 mmol) in diethyl ether was added. The reaction was slowly warmed to room temperature over 1 h, quenched with water, extracted with EtOAc, and the organic extracts dried over MgSO$_4$, filtered, and concentrated under reduced pressure. The residue was loaded onto a semi-prep HPLC (NH$_4$OH as modifier) to afford the title compound (6 mg, 15%). $^1$H NMR (CD$_3$OD) δ 1.52 (s, 6H), 2.47-2.66 (m, 2H), 2.69-2.86 (m, 2H), 3.16-3.29 (m, 1H), 3.94-4.07 (m, 2H), 4.42 (t, J=8 Hz, 2H), 4.74-4.83 (m, 1H), 5.17 (t, J=6 Hz, 1H), 6.61 (s, 1H), 6.89 (d, J=8 Hz, 1H), 7.42 (t, J=8 Hz, 1H), 7.62 (d, J=8 Hz, 1H), 9.16 (s, 1H); LC-MS (LC-ES) M+H—H$_2$O=411.

Example 50

(trans)-3-(Benzo[d]thiazol-4-yloxy)-N-(1-(2-methylpyrimidin-4-yl)azetidin-3-yl)cyclobutanecarboxamide

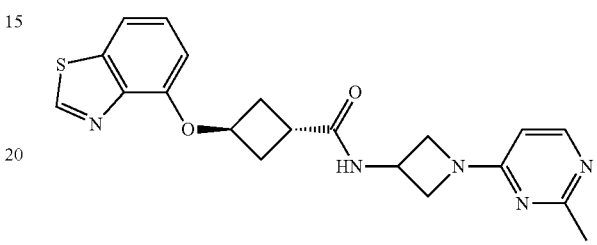

To a DMF (2 mL) solution of (trans)-3-(benzo[d]thiazol-4-yloxy)cyclobutanecarboxylic acid (Intermediate 25) (35 mg, 0.14 mmol), 1-(2-methylpyrimidin-4-yl)azetidin-3-amine (Intermediate 33) (23 mg, 0.14 mmol) and N,N-diisopropylethylamine (0.05 mL, 0.3 mmol) was added, dropwise, a 50% solution of T3P in ethyl acetate (179 mg, 0.28 mmol). The reaction was stirred 30 min, quenched with water, and loaded onto a semi-prep HPLC (NH$_4$OH as modifier) to afford the title compound as an off-white solid (39 mg, 70%). $^1$H NMR (CD$_3$OD) δ 2.45 (s, 3H), 2.49-2.66 (m, 2H), 2.79 (ddd, J=13, 7, 4 Hz, 2H), 3.25 (tt, J=10, 5 Hz, 1H), 4.00 (dd, J=9, 5 Hz, 2H), 4.45 (t, J=9 Hz, 2H), 4.79 (tt, J=8, 5 Hz, 1H), 5.17 (quin, J=6 Hz, 1H), 6.27 (d, J=6 Hz, 1H), 6.90 (d, J=8 Hz, 1H), 7.42 (t, J=8 Hz, 1H), 7.62 (s, 1H), 8.05 (d, J=6 Hz, 1H), 9.18 (s, 1H); LC-MS (LC-ES) M+H=396.

Example 51

Racemic (trans)-3-(Benzo[d]thiazol-4-yloxy)-N-((trans)-6-(2-hydroxypropan-2-yl)tetrahydro-2H-pyran-3-yl)cyclobutanecarboxamide

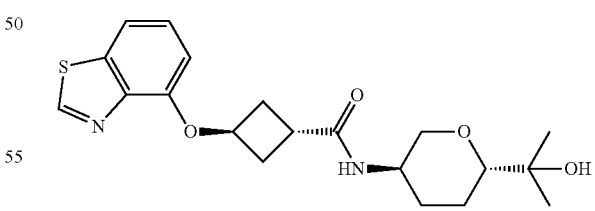

To a DMF (2 mL) solution of (trans)-3-(benzo[d]thiazol-4-yloxy)cyclobutanecarboxylic acid (Intermediate 25) (40 mg, 0.16 mmol), 2-((trans)-5-aminotetrahydro-2H-pyran-2-yl)propan-2-ol (Intermediate 34) (26 mg, 0.16 mmol) and N,N-diisopropylethylamine (0.06 mL, 0.3 mmol) was added, dropwise, a 50% solution of T3P in ethyl acetate (204 mg, 0.32 mmol). The reaction mixture was stirred 30 min, quenched with water, and loaded onto a semi-prep HPLC (NH$_4$OH as modifier) to afford the title compound as an off-white solid (36 mg, 58%). ¹H NMR (400 MHz, CD₃OD) δ 1.18 (d, J=7 Hz, 6H), 1.42-1.59 (m, 2H), 1.78-1.88 (m, 1H), 1.99-2.11 (m, 1H), 2.47-2.61 (m, 2H), 2.69-2.78 (m, 2H), 3.00-3.23 (m, 3H), 3.71-3.91 (m, 1H), 3.96-4.15 (m, 1H), 5.11-5.20 (m, 1H), 6.87 (d, J=8 Hz, 1H), 7.41 (t, J=8 Hz, 1H), 7.61 (d, J=8 Hz, 1H), 9.17 (s, 1H); LC-MS (LC-ES) M+H=391.

Example 52

3-(Benzo[d]thiazol-4-yloxy)-N-(1-(4-cyanopyridin-2-yl)azetidin-3-yl)azetidine-1-carboxamide

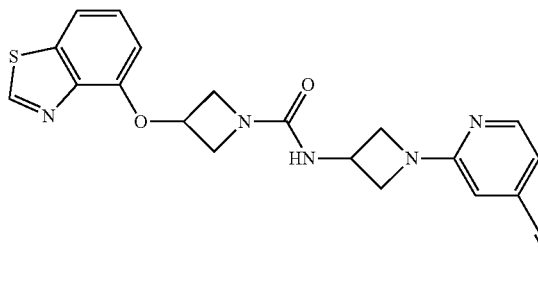

To 4-nitrophenyl chloroformate (12 mg, 0.06 mmol) in DCM (1 mL) at 0° C. was slowly added 2-(3-aminoazetidin-1-yl)isonicotinonitrile (Intermediate 35) (10 mg, 0.06 mmol). After 3 h, N,N-diisopropylethylamine (0.03 mL, 0.2 mmol) and 4-(azetidin-3-yloxy)benzo[d]thiazole hydrochloride (Intermediate 28) (16 mg, 0.06 mmol) in DCM (1 mL) were added. The reaction was stirred 3 h and loaded onto a semi-prep HPLC (NH₄OH as modifier) to afford the title compound (6 mg, 26% yield) as a white solid. ¹H NMR (400 MHz, CDCl₃) δ 3.86 (dd, J=9, 5 Hz, 2H), 4.26 (dd, J=9, 4 Hz, 2H), 4.34-4.51 (m, 4H), 4.66 (d, J=8 Hz, 1H), 4.73-4.88 (m, 1H), 5.14-5.36 (m, 1H), 6.45 (s, 1H), 6.67 (d, J=8 Hz, 1H), 6.76 (d, J=5 Hz, 1H), 7.36 (t, J=8 Hz, 1H), 7.54-7.72 (m, 1H), 8.24 (d, J=5 Hz, 1H), 8.95 (s, 1H); LC-MS (LC-ES) M+H=407.

Example 53

3-(Benzo[d]thiazol-4-yloxy)-N-((trans)-4-(((S)-1,1,1-trifluoro-3-hydroxypropan-2-yl)amino)cyclohexyl)azetidine-1-carboxamide

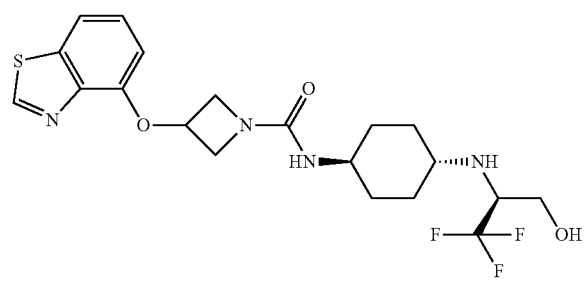 [SMILES: O=C(N[C@H]1CC[C@H](N[C@@H](CO)C(F)(F)F)CC1)N1CC(Oc2cccc3scnc23)C1]

To a stirred solution of triphosgene (9.6 mg, 0.032 mmol) in DCM (1 mL) was added a mixture of (S)-2-(((trans)-4-aminocyclohexyl)amino)-3,3,3-trifluoropropan-1-ol (Intermediate 15) (24 mg, 0.11 mmol) and N,N-diisopropylethylamine (0.03 mL, 0.2 mmol) in DCM (1.5 mL) dropwise over 5 minutes. The mixture was stirred an additional 10 minutes, and then a mixture of 4-(azetidin-3-yloxy)benzo[d]thiazole hydrochloride (Intermediate 28) (30 mg, 0.11 mmol) and N,N-diisopropylethylamine (0.06 mL, 0.3 mmol) in DCM (1 mL) was added in one portion. After 18 h, the mixture was loaded onto a semi-prep HPLC (NH₄OH as modifier) to afford the title compound (12 mg, 24%), as a white solid. ¹H NMR (400 MHz, CDCl₃) δ 1.09-1.21 (m, 4H), 1.96-2.07 (m, 4H), 2.60-2.72 (m, 1H), 3.20-3.30 (m, 1H), 3.44-3.52 (m, 1H), 3.52-3.66 (m, 1H), 3.71-3.81 (m, 1H), 3.95 (d, J=8 Hz, 1H), 4.19 (dd, J=9, 4 Hz, 2H), 4.32-4.40 (m, 2H), 5.14-5.30 (m, 1H), 6.66 (d, J=8 Hz, 1H), 7.35 (t, J=8 Hz, 1H), 7.59 (d, J=8 Hz, 1H), 8.94 (s, 1H); LC-MS (LC-ES) M+H=459.

Example 54

3-(Benzo[d]thiazol-4-yloxy)-N-(1-(pyridin-2-yl)azetidin-3-yl)azetidine-1-carboxamide

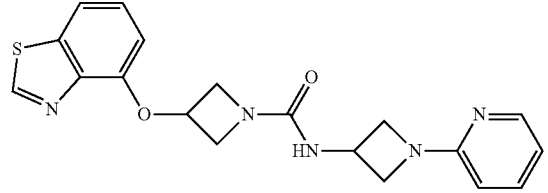 [SMILES: O=C(NC1CN(c2ccccn2)C1)N1CC(Oc2cccc3scnc23)C1]

To a stirred solution of triphosgene (21 mg, 0.070 mmol) in DCM (1 mL) was added a mixture of 1-(pyridin-2-yl)azetidin-3-amine dihydrochloride (Intermediate 37) (50 mg, 0.23 mmol) and N,N-diisopropylethylamine (0.12 mL, 0.70 mmol) in DCM (1.5 mL) dropwise over 5 minutes. The mixture was stirred an additional 10 minutes, and then a mixture of 4-(azetidin-3-yloxy)benzo[d]thiazole hydrochloride (Intermediate 28) (65 mg, 0.23 mmol) and N,N-diisopropylethylamine (0.12 mL, 0.70 mmol) in DCM (1 mL) was added in one portion. After 18 h, the reaction was loaded onto a semi-prep HPLC (NH₄OH as modifier) to afford the title compound (46 mg, 52%), as a white solid. ¹H NMR (400 MHz, CDCl₃) δ 3.76 (dd, J=9, 5 Hz, 2H), 4.24 (dd, J=9, 4 Hz, 2H), 4.34 (t, J=8 Hz, 2H), 4.42 (dd, J=9, 7 Hz, 2H), 4.70-4.80 (m, 1H), 4.81-4.89 (m, 1H), 5.18-5.28 (m, 1H), 6.27 (d, J=9 Hz, 1H), 6.57-6.63 (m, 1H), 6.65 (d, J=8 Hz, 1H), 7.31-7.36 (m, 1H), 7.39-7.48 (m, 1H), 7.59 (d, J=8 Hz, 1H), 8.13 (d, J=5 Hz, 1H), 8.93 (s, 1H); LC-MS (LC-ES) M+H=382.

Example 55

(trans)-3-(Benzo[d]thiazol-4-yloxy)-N-(4-(2-hydroxypropan-2-yl)thiazol-2-yl)cyclobutanecarboxamide

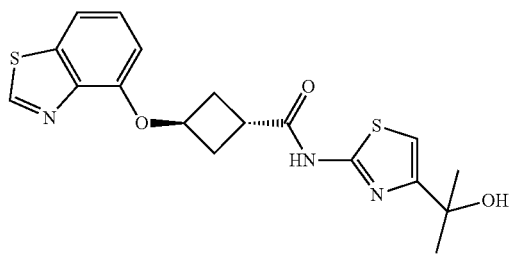 [SMILES: CC(C)(O)c1csc(NC(=O)[C@H]2C[C@H](Oc3cccc4scnc34)C2)n1]

To a DMF (2 mL) solution of (trans)-3-(benzo[d]thiazol-4-yloxy)cyclobutanecarboxylic acid (Intermediate 25) (50 mg, 0.20 mmol), 2-(2-aminothiazol-4-yl)propan-2-ol trifluoroacetic acid salt (Intermediate 38) (55 mg, 0.20 mmol) and N,N-diisopropylethylamine (0.09 mL, 0.5 mmol) was added, dropwise, a 50% solution of T3P in ethyl acetate (255 mg, 0.40 mmol). The reaction was stirred 1 h and loaded onto a semi-prep HPLC (NH₄OH as modifier) to afford the title compound as a white solid (33 mg, 42%). $^1$H NMR (400 MHz, CD₃OD) δ 1.53 (s, 6H), 2.61-2.69 (m, 2H), 2.80-2.96 (m, 2H), 3.39-3.53 (m, 1H), 5.18-5.25 (m, 1H), 6.74-7.00 (m, 2H), 7.39-7.44 (m, 1H), 7.62 (d, J=8 Hz, 1H), 9.16 (s, 1H); LC-MS (LC-ES) M+H=390.

Example 56

3-(Benzo[d]thiazol-4-yloxy)-N-(4-(2-hydroxypropan-2-yl)thiazol-2-yl)azetidine-1-carboxamide

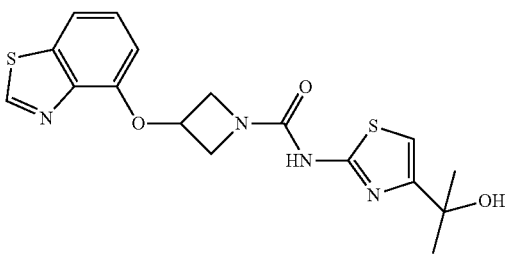 [SMILES: CC(C)(O)c1csc(NC(=O)N2CC(Oc3cccc4scnc34)C2)n1]

To 4-nitrophenyl chloroformate (120 mg, 0.60 mmol) in DCM (10 mL) at 0° C. was slowly added 2-(2-aminothiazol-4-yl)propan-2-ol trifluoroacetic acid salt (Intermediate 38) (136 mg, 0.50 mmol) and N,N-diisopropylethylamine (0.3 mL, 2 mmol). After 30 min, THF (10 mL), N,N-diisopropylethylamine (0.3 mL, 2 mmol) and 4-(azetidin-3-yloxy)benzo[d]thiazole hydrochloride (Intermediate 28) (133 mg, 0.5 mmol) were added. The reaction was stirred 2 h, diluted with EtOAc, washed with water, and the aqueous layer extracted with EtOAc. The combined organic layers were washed with water (2×) and brine, dried over MgSO₄, filtered and concentrated. The resulting solid was triturated with DCM and collected by filtration to give the title compound as a white solid (10.5 mg, 5.6%). $^1$H NMR (400 MHz, CD₃OD) δ 1.51 (s, 6H), 4.11-4.36 (m, 2H), 4.52-4.69 (m, 2H), 5.24-5.44 (m, 1H), 6.75 (s, 1H), 6.84-6.97 (m, 1H), 7.34-7.49 (m, 1H), 7.64-7.87 (m, 1H), 9.20 (s, 1H); LC-MS (LC-ES) M+H=391.

Example 57

3-(Benzo[d]thiazol-4-yloxy)-N-((trans)-4-(3,3-difluoroazetidin-1-yl)cyclohexyl)azetidine-1-carboxamide

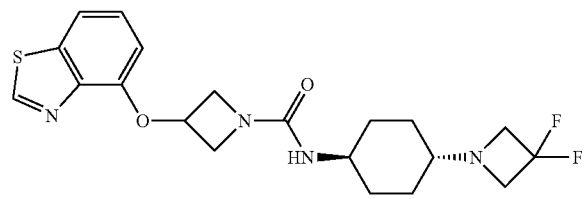 [SMILES: O=C(N[C@H]1CC[C@H](N2CC(F)(F)C2)CC1)N1CC(Oc2cccc3scnc23)C1]

To a stirred solution of triphosgene (31 mg, 0.11 mmol) in DCM (1 mL) was added a mixture of (trans)-4-(3,3-difluoroazetidin-1-yl)cyclohexanamine (Intermediate 14) (68 mg, 0.36 mmol) and N,N-diisopropylethylamine (0.07 mL, 0.4 mmol) in DCM (1 mL) dropwise over 5 minutes. The mixture was stirred an additional 10 minutes, and then a mixture of 4-(azetidin-3-yloxy)benzo[d]thiazole hydrochloride (Intermediate 28) (100 mg, 0.36 mmol) and N,N-diisopropylethylamine (0.19 mL, 1.1 mmol) in DCM (1 mL) was added in one portion. After 18 h, the reaction was loaded onto a semi-prep HPLC (NH₄OH as modifier) to afford the title compound (38 mg, 25%) as a white solid. $^1$H NMR (400 MHz, CDCl₃) δ 0.99-1.32 (m, 4H), 1.76 (d, J=13 Hz, 2H), 1.99-2.08 (m, 3H), 3.43-3.69 (m, 5H), 3.93 (d, J=8 Hz, 1H), 4.20 (dd, J=9, 4 Hz, 2H), 4.38 (dd, J=9, 7 Hz, 2H), 5.17-5.25 (m, 1H), 6.66 (d, J=8 Hz, 1H), 7.31-7.41 (m, 1H), 7.59 (d, J=8 Hz, 1H), 8.94 (s, 1H); LC-MS (LC-ES) M+H=423.

Example 58

(trans)-3-(Benzo[d]thiazol-4-yloxy)-N-((trans)-4-(2-methoxyethoxy)cyclohexyl)cyclobutanecarboxamide

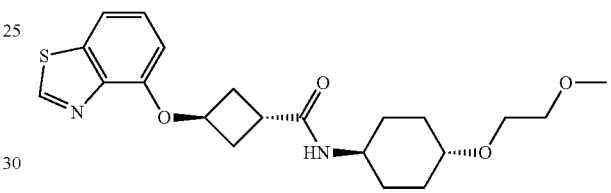

To a DMF (1.5 mL) solution of (trans)-3-(benzo[d]thiazol-4-yloxy)cyclobutanecarboxylic acid (Intermediate 25) (50 mg, 0.20 mmol), (trans)-4-(2-methoxyethoxy)cyclohexanamine (Intermediate 39) (42 mg, 0.24 mmol) and N,N-diisopropylethylamine (0.09 mL, 0.5 mmol) was added, dropwise, a 50% solution of T3P in ethyl acetate (255 mg, 0.40 mmol). The reaction was stirred 1 h, diluted with water and MeOH, and loaded onto a semi-prep HPLC (NH₄OH as modifier) to afford partially pure product which was purified by silica gel chromatography, eluting with a 10-70% 3:1 EtOAc:EtOH in hexanes gradient to afford the title compound as a white solid (59 mg, 73% yield). $^1$H NMR (400 MHz, CDCl₃) δ 0.94-1.17 (m, 2H), 1.25-1.46 (m, 2H), 1.87-2.09 (m, 4H), 2.48-2.61 (m, 2H), 2.67-2.76 (m, 2H), 2.85-2.97 (m, 1H), 3.11-3.24 (m, 1H), 3.30 (s, 3H), 3.41-3.48 (m, 2H), 3.50-3.59 (m, 2H), 3.64-3.83 (m, 1H), 5.06-5.15 (m, 1H), 5.28 (d, J=8 Hz, 1H), 6.70 (d, J=8 Hz, 1H), 7.26 (m, 1H), 7.44 (d, J=8 Hz, 1H), 8.83 (s, 1H); LC-MS (LC-ES) M+H=405.

Example 59

3-(Benzo[d]thiazol-4-yloxy)-N-((trans)-4-(2-methoxyethoxy)cyclohexyl)azetidine-1-carboxamide

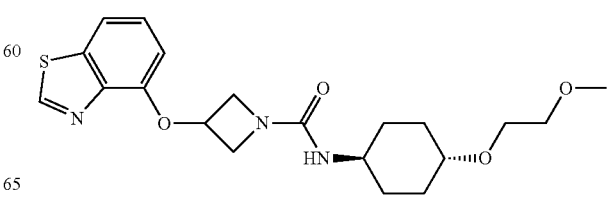

To a stirred solution of triphosgene (26 mg, 0.09 mmol) in DCM (1 mL) was added a mixture of (trans)-4-(2-methoxyethoxy)cyclohexanamine (Intermediate 39) (50 mg, 0.29 mmol) and N,N-diisopropylethylamine (0.06 mL, 0.3 mmol) in DCM (1 mL) dropwise over 5 minutes. The mixture was stirred an additional 10 minutes, and then a mixture of 4-(azetidin-3-yloxy)benzo[d]thiazole hydrochloride (Intermediate 28) (80 mg, 0.29 mmol) and N,N-diisopropylethylamine (0.15 mL, 0.9 mmol) in DCM (1 mL) was added in one portion. After 18 h, the reaction was loaded onto a semi-prep HPLC (NH₄OH as modifier) to afford the title compound (68 mg, 59%). ¹H NMR (400 MHz, CDCl₃) δ 1.05-1.19 (m, 2H), 1.31-1.47 (m, 2H), 1.88-2.16 (m, 4H), 3.16-3.30 (m, 1H), 3.37 (s, 3H), 3.46-3.54 (m, 2H), 3.56-3.65 (m, 3H), 3.92 (d, J=8 Hz, 1H), 4.15-4.20 (m, 2H), 4.34-4.40 (m, 2H), 5.14-5.28 (m, 1H), 6.65 (d, J=8 Hz, 1H), 7.31-7.37 (m, 1H), 7.59 (d, J=8 Hz, 1H), 8.93 (s, 1H); LC-MS (LC-ES) M+H=406.

Example 60

3-(Benzo[d]thiazol-4-yloxy)-N-(1-(2-chloropyrimidin-4-yl)azetidin-3-yl)azetidine-1-carboxamide

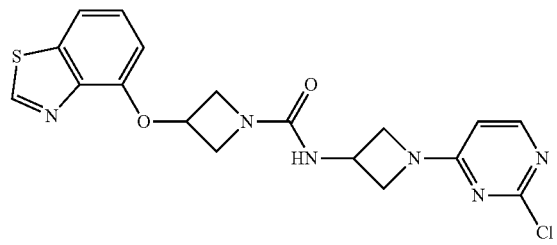 [SMILES: O=C(NC1CN(c2ccnc(Cl)n2)C1)N1CC(Oc2cccc3scnc23)C1]

To 4-nitrophenyl chloroformate (70 mg, 0.35 mmol) in DCM (2 mL) at 0° C. was slowly added a suspension of 1-(2-chloropyrimidin-4-yl)azetidin-3-amine dihydrochloride (Intermediate 7) (75 mg, 0.30 mmol) and potassium carbonate (80 mg, 0.58 mmol) in THF (2 mL). After 2 h, N,N-diisopropylethylamine (0.08 mL, 0.4 mmol) and 4-(azetidin-3-yloxy)benzo[d]thiazole hydrochloride (Intermediate 28) (60 mg, 0.29 mmol) in DCM were added. The reaction was stirred 18 h and loaded onto a semi-prep HPLC (NH₄OH as modifier) to afford the title compound (55 mg, 45% yield) as a white solid. ¹H NMR (400 MHz, CDCl₃) δ 3.91 (dd, J=9, 5 Hz, 2H), 4.25 (dd, J=9, 5 Hz, 2H), 4.36-4.50 (m, 4H), 4.73-4.81 (m, 1H), 5.18-5.28 (m, 1H), 5.31 (d, J=8 Hz, 1H), 6.03 (d, J=6 Hz, 1H), 6.66 (d, J=8 Hz, 1H), 7.31-7.37 (m, 1H), 7.59 (d, J=8 Hz, 1H), 7.97 (d, J=6 Hz, 1H, 8.93 (s, 1H); LC-MS (LC-ES) M+H=417.

Example 61

3-(Benzo[d]thiazol-4-yloxy)-N-(1-(5-fluoropyrimidin-2-yl)azetidin-3-yl)azetidine-1-carboxamide

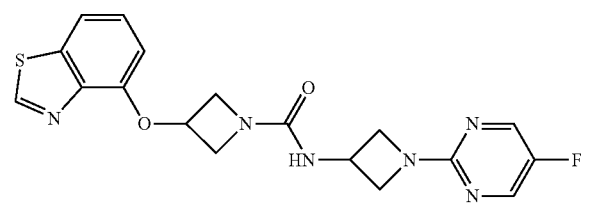 [SMILES: O=C(NC1CN(c2ncc(F)cn2)C1)N1CC(Oc2cccc3scnc23)C1]

To 4-nitrophenyl chloroformate (40 mg, 0.20 mmol) in DCM (1 mL) at 0° C. was slowly added a mixture of 1-(5-fluoropyrimidin-2-yl)azetidin-3-amine dihydrochloride (Intermediate 9) (40 mg, 0.17 mmol) and N,N-diisopropylethylamine (0.09 mL, 0.5 mmol) in DCM (1 mL). After 2 h, N,N-diisopropylethylamine (0.09 mL, 0.5 mmol) and 4-(azetidin-3-yloxy)benzo[d]thiazole hydrochloride (Intermediate 28) (34 mg, 0.17 mmol) in DCM (1 mL) were added. The reaction was stirred 2.5 h, concentrated, taken up in MeOH and loaded onto a semi-prep HPLC (NH₄OH as modifier) to afford the title compound (24 mg, 36% yield) as a white solid. ¹H NMR (400 MHz, CD₃OD) δ 3.92-4.01 (m, 2H), 4.10-4.19 (m, 2H), 4.31-4.40 (m, 2H), 4.42-4.51 (m, 2H), 4.56-4.68 (m, 1H), 5.20-5.40 (m, 1H), 6.75-6.96 (m, 1H), 7.32-7.53 (m, 1H), 7.61-7.81 (m, 1H), 8.29 (s, 2H), 9.19 (s, 1H); LC-MS (LC-ES) M+H=401.

Example 62

N-(4-Acetylthiazol-2-yl)-3-(benzo[d]thiazol-4-yloxy)azetidine-1-carboxamide

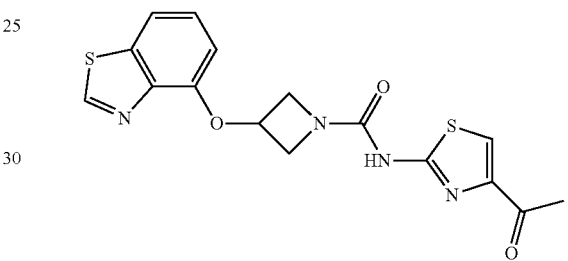

To 4-nitrophenyl chloroformate (102 mg, 0.51 mmol) in DCM (1 mL) at 0° C. was slowly added a suspension of 1-(2-aminothiazol-4-yl)ethanone (60 mg, 0.42 mmol) and sodium carbonate (1.03 g, 9.71 mmol) in THF (1 mL). After 3 h, the reaction was filtered, the filtrate concentrated and the residue dissolved in DCM (1 mL). N,N-diisopropylethylamine (0.22 mL, 1.3 mmol) and 4-(azetidin-3-yloxy)benzo[d]thiazole hydrochloride (Intermediate 28) (118 mg, 0.42 mmol) in DCM (1 mL) were added. The reaction was stirred 18 h and loaded onto a semi-prep HPLC (NH₄OH as modifier) to afford the title compound (7 mg, 4% yield) as a white solid. ¹H NMR (400 MHz, CDCl₃) δ 2.56 (s, 3H), 4.41 (dd, J=9, 4 Hz, 2H), 4.58-4.65 (m, 2H), 5.33-5.42 (m, 1H), 6.70-6.77 (m, 1H), 7.35-7.44 (m, 1H), 7.63-7.68 (m, 1H), 7.70 (s, 1H), 8.98 (s, 1H); LC-MS (LC-ES) M+H=375.

Example 63

3-(Benzo[d]thiazol-4-yloxy)-N-(pyridin-4-yl)azetidine-1-carboxamide

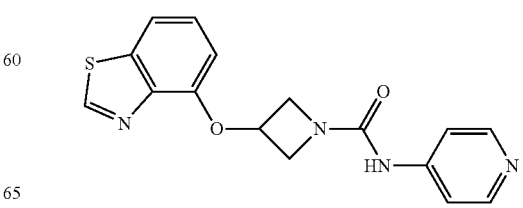

To 4-(azetidin-3-yloxy)benzo[d]thiazole hydrochloride (Intermediate 28) (25 mg, 0.09 mmol) in DCM (2 mL) was added N,N-diisopropylethylamine (0.05 mL, 0.3 mmol) and 4-isocyanatopyridine (14 mg, 0.12 mmol). After 18 h, the reaction was concentrated and loaded onto a semi-prep HPLC (NH$_4$OH as modifier) to afford partially pure product, which was purified by silica gel chromatography, eluting with a 10-80% 3:1 EtOAc:EtOH in hexanes gradient to afford the title compound as a white solid (10 mg, 34% yield). $^1$H NMR (400 MHz, CD$_3$OD) δ 4.24 (dd, J=10, 4 Hz, 2H), 4.57 (dd, J=10, 7 Hz, 2H), 5.27-5.35 (m, 1H), 6.84 (d, J=8 Hz, 1H), 7.35-7.44 (m, 1H), 7.55 (d, J=7 Hz, 2H), 7.66 (d, J=8 Hz, 1H), 8.26 (d, J=7 Hz, 2H), 9.16 (s, 1H); LC-MS (LC-ES) M+H=327.

Example 64

3-(Benzo[d]thiazol-4-yloxy)-N-cyclohexylazetidine-1-carboxamide

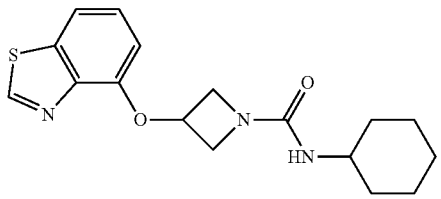 [SMILES: O=C(NC1CCCCC1)N1CC(Oc2cccc3scnc23)C1]

To 4-(azetidin-3-yloxy)benzo[d]thiazole hydrochloride (Intermediate 28) (25 mg, 0.09 mmol) in DCM (2 mL) was added N,N-diisopropylethylamine (0.05 mL, 0.3 mmol) and isocyanatocyclohexane (15 mg, 0.12 mmol). After 0.5 h, the reaction was concentrated and loaded onto a semi-prep HPLC (NH$_4$OH as modifier) to afford the title compound as a white solid (23 mg, 77% yield). $^1$H NMR (400 MHz, CD$_3$OD) δ 0.99-1.45 (m, 5H), 1.56-1.98 (m, 5H), 3.47 (t, J=4 Hz, 1H), 4.08 (dd, J=10, 4 Hz, 2H), 4.41 (dd, J=10, 6 Hz, 2H), 5.16-5.43 (m, 1H), 6.83 (d, J=8 Hz, 1H), 7.39-7.44 (m, 1H), 7.67 (d, J=8 Hz, 1H), 9.18 (s, 1H); LC-MS (LC-ES) M+H=332.

Example 65

(trans)-3-(Benzo[d]thiazol-4-yloxy)-N-(1-((E)-N'-cyano-N-methylcarbamimidoyl)azetidin-3-yl)cyclobutanecarboxamide

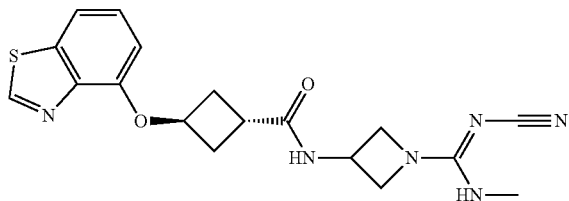 [SMILES: CN/C(=N\C#N)N1CC(NC(=O)[C@H]2C[C@H](Oc3cccc4scnc34)C2)C1]

To (trans)-N-(azetidin-3-yl)-3-(benzo[d]thiazol-4-yloxy)cyclobutanecarboxamide hydrochloride (Intermediate 32) (70 mg, 0.19 mmol) and triethylamine (0.08 mL, 0.6 mmol) in EtOH (15 mL), (E)-methyl N'-cyano-N-methylcarbamimidothioate (24 mg, 0.19 mmol) was added. The mixture was heated in a microwave at 150° C. for 3 h, then at 160° C. for 5 h, diluted with MeOH and loaded onto a semi-prep HPLC (NH$_4$OH as modifier) to afford the title compound as a white solid (7 mg, 10% yield). $^1$H NMR (400 MHz, CD$_3$OD) δ 2.52-2.61 (m, 2H), 2.70-2.84 (m, 5H), 3.19-3.27 (m, 1H), 4.06-4.17 (m, 2H), 4.51-4.59 (m, 2H), 4.59-4.69 (m, 1H), 5.10-5.19 (m, 1H), 6.87 (d, J=8 Hz, 1H), 7.38-7.43 (m, 1H), 7.61 (d, J=8 Hz, 1H), 9.15 (s, 1H); LC-MS (LC-ES) peak at 0.45 min.

Example 66 tert-Butyl ((trans)-3-((trans)-3-(benzo[d]thiazol-4-yloxy)cyclobutanecarboxamido)cyclobutyl)carbamate

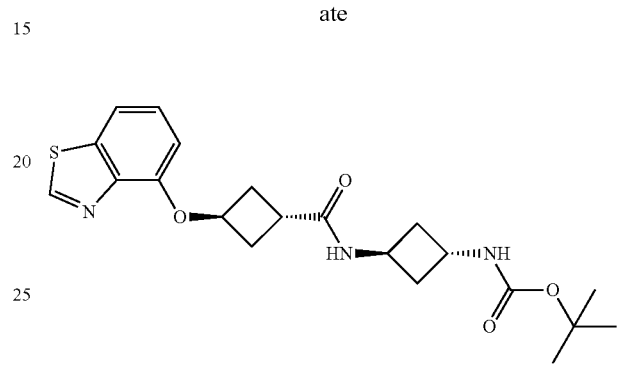

To a DMF (2 mL) solution of (trans)-3-(benzo[d]thiazol-4-yloxy)cyclobutanecarboxylic acid (Intermediate 25) (150 mg, 0.60 mmol), tert-butyl ((trans)-3-aminocyclobutyl)carbamate hydrochloride (174 mg, 0.78 mmol) and N,N-diisopropylethylamine (0.32 mL, 1.8 mmol) was added, dropwise, a 50% solution of T3P in ethyl acetate (766 mg, 1.20 mmol). The reaction was stirred 30 min, diluted with water and MeOH, and loaded onto a semi-prep HPLC (NH$_4$OH as modifier) to give the title compound as a white solid (191 mg, 76% yield). $^1$H NMR (400 MHz, CDCl$_3$) δ 1.44 (s, 9H), 2.13-2.41 (m, 4H), 2.51-2.69 (m, 2H), 2.74-2.85 (m, 2H), 2.95-3.05 (m, 1H), 4.14-4.26 (m, 1H), 4.39-4.46 (m, 1H), 4.74-4.83 (m, 1H), 5.16-5.24 (m, 1H), 5.67-5.76 (m, 1H), 6.77 (d, J=8 Hz, 1H), 7.32-7.40 (m, 1H), 7.52 (d, J=8 Hz, 1H), 8.91 (s, 1H); LC-MS (LC-ES) M+H=418.

Example 67

(trans)-3-(Benzo[d]thiazol-4-yloxy)-N-((trans)-3-(3-cyclohexylureido)cyclobutyl)cyclobutanecarboxamide

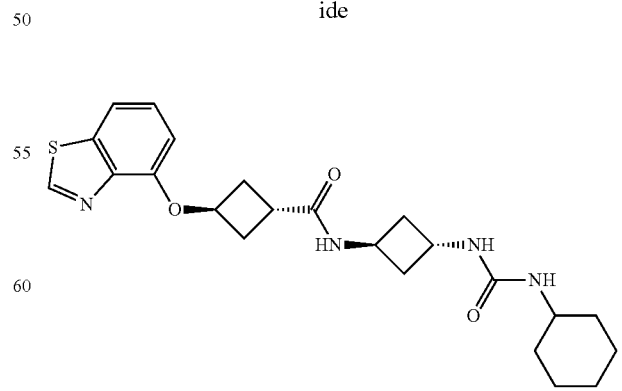

To (trans)-N-((trans)-3-aminocyclobutyl)-3-(benzo[d]thiazol-4-yloxy)cyclobutanecarboxamide hydrochloride (Intermediate 40) (60 mg, 0.15 mmol) in DCM (2 mL) was added N,N-diisopropylethylamine (0.08 mL, 0.5 mmol) and isocyanatocyclohexane (19 mg, 0.15 mmol). After 0.5 h, the reaction was concentrated and loaded onto a semi-prep HPLC (NH$_4$OH as modifier) to afford the title compound as a white solid (31 mg, 46% yield). $^1$H NMR (400 MHz, CD$_3$OD) δ 1.06-1.25 (m, 4H), 1.27-1.44 (m, 2H), 1.55-1.66 (m, 1H), 1.67-1.78 (m, 2H), 1.79-1.90 (m, 2H), 2.15-2.37 (m, 3H), 2.49-2.59 (m, 2H), 2.68-2.78 (m, 2H), 3.11-3.23 (m, 1H), 3.40-3.52 (m, 1H), 4.16-4.25 (m, 1H), 4.26-4.35 (m, 1H), 5.09-5.16 (m, 1H), 6.86 (d, J=8 Hz, 1H), 7.35-7.41 (m, 1H), 7.60 (d, J=8 Hz, 1H), 9.15 (s, 1H); LC-MS (LC-ES) M+H=443.

Example 68

(trans)-N-(4-Acetylthiazol-2-yl)-3-(benzo[d]thiazol-4-yloxy)cyclobutanecarboxamide

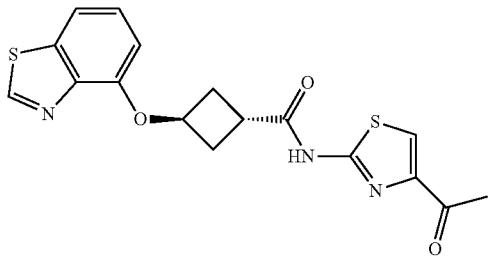 [SMILES: CC(=O)c1csc(NC(=O)[C@H]2C[C@H](Oc3cccc4scnc34)C2)n1]

To a solution of (trans)-3-(benzo[d]thiazol-4-yloxy)cyclobutanecarboxylic acid (Intermediate 25) (3.48 g, 13.2 mmol) in THF (40 mL) and water (15 mL) was added lithium hydroxide (0.790 g, 33.0 mmol). The mixture was stirred at room temperature for 2 h, solvents were removed in vacuo and the resulting residue was triturated with ether affording the lithium salt as a white solid. To a portion of the lithium salt (70 mg, 0.27 mmol), 1-(2-aminothiazol-4-yl)ethanone (39 mg, 0.27 mmol) and N,N-diisopropylethylamine (0.14 mL, 0.8 mmol) in DMF (2 mL) was added, dropwise, T3P (50% in ethyl acetate)(348 mg, 0.55 mmol). The reaction was stirred 18 h, diluted with MeOH and loaded onto a semi-prep HPLC (NH$_4$OH as modifier) to afford partially pure product which was purified by silica gel chromatography, eluting with a 10-70% 3:1 EtOAc:EtOH in hexanes gradient to afford the title compound (10 mg, 10% yield). $^1$H NMR (400 MHz, CD$_3$OD) δ 2.57 (s, 3H), 2.61-2.78 (m, 2H), 2.83-3.00 (m, 2H), 3.41-3.50 (m, 1H), 5.14-5.22 (m, 1H), 6.90 (d, J=8 Hz, 1H), 7.35-7.43 (m, 1H), 7.62 (d, J=8 Hz, 1H), 8.00 (s, 1H), 9.17 (s, 1H); LC-MS (LC-ES) M+H=374.

Example 69

(trans)-3-(Benzo[d]thiazol-4-yloxy)-N-(1-(2-chloropyrimidin-4-yl)azetidin-3-yl)cyclobutanecarboxamide

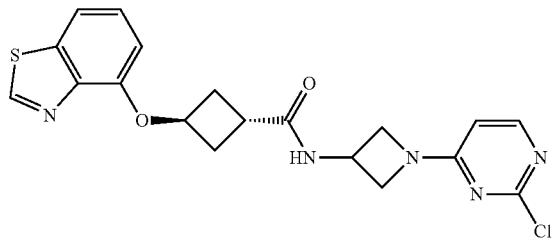 [SMILES: O=C(NC1CN(c2ccnc(Cl)n2)C1)[C@H]1C[C@H](Oc2cccc3scnc23)C1]

To a DMF (3 mL) solution of (trans)-3-(benzo[d]thiazol-4-yloxy)cyclobutanecarboxylic acid (Intermediate 25) (75 mg, 0.30 mmol), 1-(2-chloropyrimidin-4-yl)azetidin-3-amine dihydrochloride (Intermediate 7) (42 mg, 0.24 mmol) and N,N-diisopropylethylamine (0.16 mL, 0.9 mmol) was added, dropwise, a 50% solution of T3P in ethyl acetate (383 mg, 0.60 mmol). The reaction was stirred 1 h, diluted with water and MeOH, and loaded onto a semi-prep HPLC (NH$_4$OH as modifier) to afford the title compound as a white solid (101 mg, 81% yield). $^1$H NMR (400 MHz, CDCl$_3$) δ 2.67 (ddd, J=13, 10, 6 Hz, 2H), 2.84 (ddd, J=13, 7, 4 Hz, 2H), 3.06-3.14 (m, 1H), 3.94-4.01 (m, 2H), 4.44-4.54 (m, 2H), 4.81-4.90 (m, 1H), 5.19-5.25 (m, 1H), 6.04-6.11 (m, 2H), 6.77 (d, J=8 Hz, 1H), 7.32-7.38 (m, 1H), 7.54 (d, J=8 Hz, 1H), 8.03 (d, J=6 Hz, 1H), 8.92 (s, 1H); LC-MS (LC-ES) M+H=416, 418 (Cl pattern).

Example 70

(trans)-3-(Benzo[d]thiazol-4-yloxy)-N-(1-(2-(isopropylamino)pyrimidin-4-yl)azetidin-3-yl)cyclobutanecarboxamide

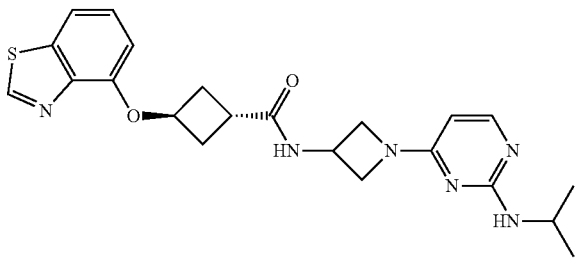 [SMILES: CC(C)Nc1nccc(N2CC(NC(=O)[C@H]3C[C@H](Oc4cccc5scnc45)C3)C2)n1]

To an acetonitrile (2.5 mL) solution of (trans)-3-(benzo[d]thiazol-4-yloxy)-N-(1-(2-chloropyrimidin-4-yl)azetidin-3-yl)cyclobutanecarboxamide (Example 69) (21 mg, 0.05 mmol) was added propan-2-amine (38 mg, 0.64 mmol). The reaction was heated in a microwave at 135° C. for 3 h, diluted with MeOH and loaded onto a semi-prep HPLC (NH$_4$OH as modifier) to afford the title compound as a white solid (4 mg, 18% yield). $^1$H NMR (400 MHz, CD$_3$OD) δ 1.18 (d, J=7 Hz, 6H), 2.51-2.61 (m, 2H), 2.76 (ddd, J=13, 7, 5 Hz, 2H), 3.16-3.25 (m, 1H), 3.88 (dd, J=9, 5 Hz, 2H), 3.97-4.11 (m, 1H), 4.30-4.38 (m, 2H), 4.65-4.76 (m, 1H), 5.11-5.20 (m, 1H), 5.67 (d, J=6 Hz, 1H), 6.86 (d, J=8

1H), 7.35-7.41 (m, 1H), 7.60 (d, J=8 Hz, 1H), 7.73 (d, J=6 Hz, 1H), 9.14 (s, 1H); LC-MS (LC-ES) M+H=439.

Example 71

(trans)-3-(Benzo[d]thiazol-4-yloxy)-N-(1-(5-cyanothiazol-2-yl)azetidin-3-yl)cyclobutanecarboxamide, and 2-(3-((trans)-3-(Benzo[d]thiazol-4-yloxy)cyclobutanecarboxamido)azetidin-1-yl)thiazole-5-carboxamide

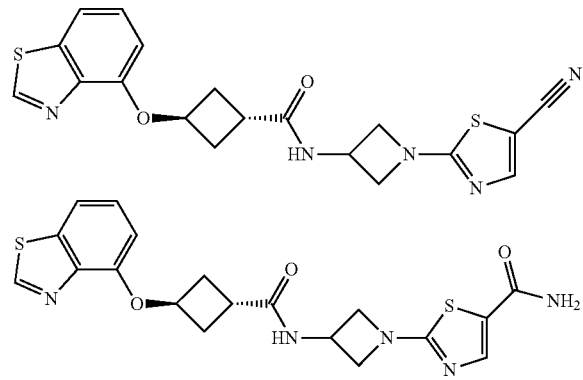

To a DMF (3 mL) solution of (trans)-3-(benzo[d]thiazol-4-yloxy)cyclobutanecarboxylic acid (Intermediate 25) (100 mg, 0.40 mmol), 2-(3-aminoazetidin-1-yl)thiazole-5-carbonitrile dihydrochloride (Intermediate 5) (102 mg, 0.40 mmol), 2-(3-aminoazetidin-1-yl)thiazole-5-carboxamide dihydrochloride (Intermediate 5) (109 mg, 0.40 mmol), and N,N-diisopropylethylamine (0.28 mL, 1.6 mmol) was added, dropwise, a 50% solution of T3P in ethyl acetate (522 mg, 0.80 mmol). The reaction was stirred 20 min, diluted with water and MeOH, and loaded onto a semi-prep HPLC (NH$_4$OH as modifier) to afford (trans)-3-(benzo[d]thiazol-4-yloxy)-N-(1-(5-cyanothiazol-2-yl)azetidin-3-yl)cyclobutanecarboxamide as a white solid (31 mg, 19% yield) and 2-(3-((trans)-3-(benzo[d]thiazol-4-yloxy)cyclobutanecarboxamido)azetidin-1-yl)thiazole-5-carboxamide and as a white solid (13 mg, 8% yield).

(trans)-3-(Benzo[d]thiazol-4-yloxy)-N-(1-(5-cyanothiazol-2-yl)azetidin-3-yl)cyclobutanecarboxamide $^1$H NMR (400 MHz, CDCl$_3$) δ 2.63-2.70 (m, 2H), 2.78-2.89 (m, 2H), 3.04-3.19 (m, 1H), 4.06 (dd, J=9, 5 Hz, 2H), 4.48-4.55 (m, 2H), 4.90-5.02 (m, 1H), 5.15-5.23 (m, 1H), 6.06 (d, J=7 Hz, 1H), 6.76 (d, J=8 Hz, 1H), 7.30-7.38 (m, 1H), 7.54 (d, J=8 Hz, 1H), 7.67 (s, 1H), 8.92 (s, 1H); LC-MS (LC-ES) M+H=412.

2-(3-((trans)-3-(Benzo[d]thiazol-4-yloxy)cyclobutanecarboxamido)azetidin-1-yl)thiazole-5-carboxamide $^1$H NMR (400 MHz, CD$_3$OD) δ 2.53-2.64 (m, 2H), 2.72-2.86 (m, 2H), 3.21-3.27 (m, 1H), 4.03 (dd, J=9, 6 Hz, 2H), 4.39-4.49 (m, 2H), 4.78-4.84 (m, 1H), 5.10-5.19 (m, 1H), 6.87 (d, J=8 Hz, 1H), 7.38-7.46 (m, 1H), 7.61 (d, J=8 Hz, 1H), 7.76 (s, 1H), 9.15 (s, 1H); LC-MS (LC-ES) M+H=430.

Example 72

(trans)-3-(Benzo[d]thiazol-4-yloxy)-N-(1-(2-((2-methoxyethyl)amino)pyrimidin-4-yl)azetidin-3-yl)cyclobutanecarboxamide

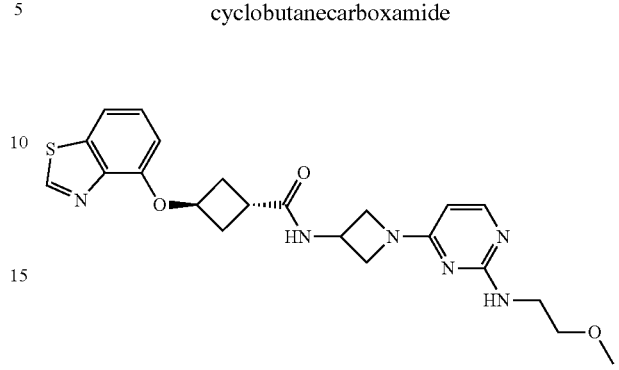

To an acetonitrile (2.5 mL) solution of (trans)-3-(benzo[d]thiazol-4-yloxy)-N-(1-(2-chloropyrimidin-4-yl)azetidin-3-yl)cyclobutanecarboxamide (Example 69) (21 mg, 0.05 mmol) was added 2-methoxyethanamine (38 mg, 0.51 mmol). The reaction was heated in a microwave at 130° C. for 2 h. Additional amine (20 eq) was added, and the reaction was heated in a microwave at 140° C. for 5 h, diluted with MeOH and loaded onto a semi-prep HPLC (NH$_4$OH as modifier) to afford the title compound as a white solid (19 mg, 83% yield). $^1$H NMR (400 MHz, CDCl$_3$) δ 2.56-2.72 (m, 2H), 2.83 (ddd, J=14, 7, 4 Hz, 2H), 3.02-3.16 (m, 1H), 3.36 (s, 3H), 3.50-3.62 (m, 4H), 3.80 (dd, J=9, 5 Hz, 2H), 4.30-4.31 (m, 2H), 4.79-4.90 (m, 1H), 5.08-5.15 (m, 1H), 5.19-5.23 (m, 1H), 5.57 (d, J=6 Hz, 1H), 6.21 (br s, 1H), 6.77 (d, J=8 Hz, 1H), 7.32-7.38 (m, 1H), 7.53 (d, J=8 Hz, 1H), 7.86 (d, J=6 Hz, 1H), 8.91 (s, 1H); LC-MS (LC-ES) M+H=455.

Example 73

(trans)-3-(Benzo[d]thiazol-4-yloxy)-N-((trans)-3-(pyrimidin-2-ylamino)cyclobutyl)cyclobutanecarboxamide

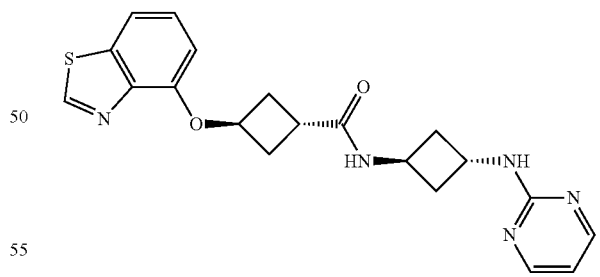

To (trans)-N-((trans)-3-aminocyclobutyl)-3-(benzo[d]thiazol-4-yloxy)cyclobutanecarboxamide hydrochloride (Intermediate 40) (40 mg, 0.10 mmol) in acetonitrile (2 mL) was added N,N-diisopropylethylamine (0.05 mL, 0.3 mmol) and 2-chloropyrimidine (18 mg, 0.15 mmol). The reaction was heated in a microwave at 150° C. for 5 h, diluted with MeOH and loaded onto a semi-prep HPLC (NH$_4$OH as modifier) to afford the title compound as a white solid (22 mg, 54% yield). $^1$H NMR (400 MHz, CDCl$_3$) δ 2.36-2.44 (m, 4H), 2.57-2.70 (m, 2H), 2.79-2.86 (m, 2H), 3.02-3.09 (m, 1H), 4.46-4.56 (m, 2H), 5.16-5.24 (m, 1H), 5.44-5.51 (m, 1H), 5.81 (d, J=7 Hz, 1H), 6.56 (t, J=5 Hz, 1H), 6.77 (d, J=8 Hz, 1H), 7.30-7.38 (m, 1H), 7.52 (d, J=8 Hz, 1H), 8.28 (d, J=5 Hz, 2H), 8.91 (s, 1H); LC-MS (LC-ES) M+H=396.

Example 74

(trans)-3-(Benzo[d]thiazol-4-yloxy)-N-(1-(4-chloropyrimidin-2-yl)azetidin-3-yl)cyclobutanecarboxamide

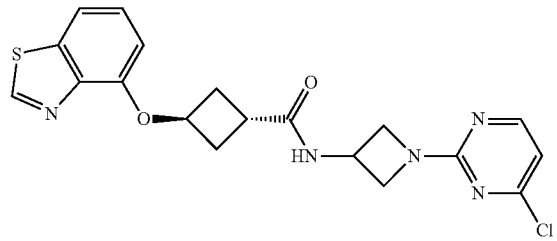 [SMILES: O=C(NC1CN(c2nccc(Cl)n2)C1)[C@H]1C[C@H](Oc2cccc3scnc23)C1]

To a DMF (2 mL) solution of (trans)-3-(benzo[d]thiazol-4-yloxy)cyclobutanecarboxylic acid (Intermediate 25) (30 mg, 0.12 mmol), 1-(4-chloropyrimidin-2-yl)azetidin-3-amine hydrochloride (Intermediate 8) (27 mg, 0.12 mmol) and N,N-diisopropylethylamine (0.06 mL, 0.4 mmol) was added, dropwise, a 50% solution of T3P in ethyl acetate (153 mg, 0.24 mmol). The reaction was stirred 1 h, diluted with water and MeOH and loaded onto a semi-prep HPLC (NH$_4$OH as modifier) to afford the title compound as a white solid (34 mg, 68% yield). $^1$H NMR (400 MHz, CDCl$_3$) δ 2.60-2.70 (m, 2H), 2.80-2.88 (m, 2H), 3.06-3.14 (m, 1H), 3.98 (dd, J=10, 5 Hz, 2H), 4.49-4.58 (m, 2H), 4.77-4.91 (m, 1H), 5.16-5.26 (m, 1H), 5.92 (d, J=7 Hz, 1H), 6.60 (d, J=5 Hz, 1H), 6.78 (d, J=8 Hz, 1H), 7.35 (t, J=8 Hz, 1H), 7.53 (d, J=8 Hz, 1H), 8.17 (d, J=5 Hz, 1H), 8.92 (s, 1H); LC-MS (LC-ES) M+H=416, 418 (Cl pattern).

Example 75

(trans)-3-(Benzo[d]thiazol-4-yloxy)-N-(1-(4-(dimethylamino)pyrimidin-2-yl)azetidin-3-yl)cyclobutanecarboxamide

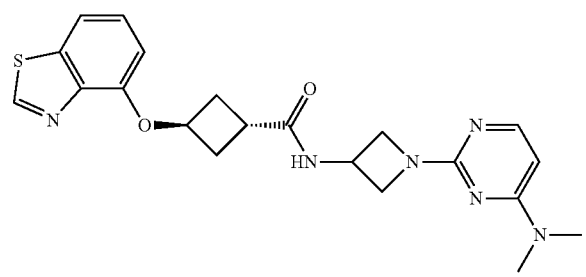 [SMILES: CN(C)c1ccnc(N2CC(NC(=O)[C@H]3C[C@H](Oc4cccc5scnc45)C3)C2)n1]

To an acetonitrile (1 mL) solution of (trans)-3-(benzo[d]thiazol-4-yloxy)-N-(1-(4-chloropyrimidin-2-yl)azetidin-3-yl)cyclobutanecarboxamide (Example 74) (10 mg, 0.02 mmol) was added dimethylamine (0.12 mL, 0.24 mmol). The reaction was heated in a microwave at 130° C. for 2 h, diluted with MeOH and loaded onto a semi-prep HPLC (NH$_4$OH as modifier) to afford the title compound as a white solid (8 mg, 74% yield). $^1$H NMR (400 MHz, CDCl$_3$) δ 2.55-2.69 (m, 2H), 2.84 (ddd, J=14, 7, 4 Hz, 2H), 3.03 (s, 6H), 3.05-3.14 (m, 1H), 3.85 (dd, J=9, 5 Hz, 2H), 4.40-4.48 (m, 2H), 4.74-4.81 (m, 1H), 5.16-5.24 (m, 1H), 5.84 (d, J=6 Hz, 1H), 6.12 (d, J=8 Hz, 1H), 6.77 (d, J=8 Hz, 1H), 7.31-7.35 (m, 1H), 7.52 (d, J=8 Hz, 1H), 7.88 (d, J=6 Hz, 1H), 8.91 (s, 1H); LC-MS (LC-ES) M+H=425.

Example 76

(trans)-3-(Benzo[d]thiazol-4-yloxy)-N-(1-(2-(dimethylamino)pyrimidin-4-yl)azetidin-3-yl)cyclobutanecarboxamide

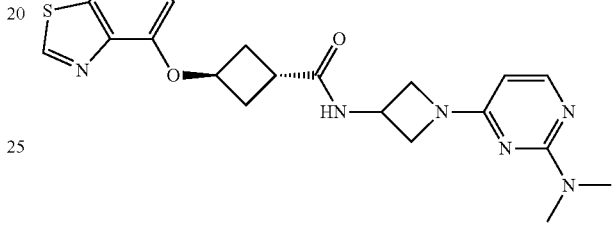

To an acetonitrile (2.5 mL) solution of (trans)-3-(benzo[d]thiazol-4-yloxy)-N-(1-(2-chloropyrimidin-4-yl)azetidin-3-yl)cyclobutanecarboxamide (Example 69) (25 mg, 0.06 mmol) was added dimethylamine (0.3 mL, 0.6 mmol). The reaction was heated in a microwave at 130° C. for 2 h, diluted with MeOH and loaded onto a semi-prep HPLC (NH$_4$OH as modifier) to afford the title compound as a white solid (18 mg, 70% yield). $^1$H NMR (400 MHz, CDCl$_3$) δ 2.59-2.70 (m, 2H), 2.84 (ddd, J=14, 7, 4 Hz, 2H), 3.78 (dd, J=9, 5 Hz, 2H), 2.98-3.22 (m, 7H), 4.31-4.39 m, 2H), 4.81-4.89 (m, 1H), 5.19-5.23 (m, 1H), 5.50 (d, J=6 Hz, 1H), 6.47 (d, J=8 Hz, 1H), 6.77 (d, J=8 Hz, 1H), 7.29-7.36 (m, 1H), 7.52 (d, J=8 Hz, 1H), 7.90 (d, J=6 Hz, 1H), 8.91 (s, 1H); LC-MS (LC-ES) M+H=425.

Example 77

2-(3-(((trans)-3-(Benzo[d]thiazol-4-yloxy)cyclobutanecarboxamido)azetidin-1-yl)pyrimidine-4-carboxamide, and (trans)-3-(Benzo[d]thiazol-4-yloxy)-N-(1-(4-cyanopyrimidin-2-yl)azetidin-3-yl)cyclobutanecarboxamide

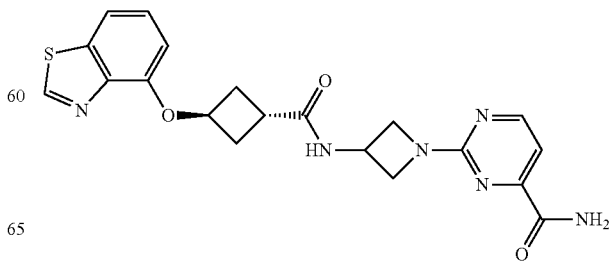

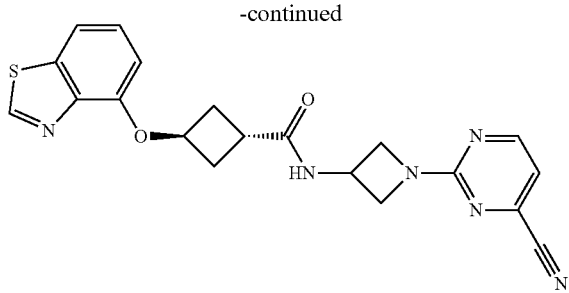

To a DMF (2 mL) solution of (trans)-3-(benzo[d]thiazol-4-yloxy)cyclobutanecarboxylic acid (Intermediate 25) (130 mg, 0.52 mmol), 2-(3-aminoazetidin-1-yl)pyrimidine-4-carboxamide dihydrochloride (Intermediate 6) (139 mg, 0.52 mmol), 2-(3-aminoazetidin-1-yl)pyrimidine-4-carbonitrile dihydrochloride (Intermediate 6) (129 mg, 0.52 mmol), and N,N-diisopropylethylamine (0.27 mL, 1.6 mmol) was added, dropwise, a 50% solution of T3P in ethyl acetate (664 mg, 1.04 mmol). The reaction was stirred 20 min, diluted with water and MeOH, and loaded onto a semi-prep HPLC (NH4OH as modifier) to afford 2-(3-((trans)-3-(benzo[d]thiazol-4-yloxy)cyclobutanecarboxamido)azetidin-1-yl)pyrimidine-4-carboxamide as a white solid (110 mg, 50% yield) and (trans)-3-(benzo[d]thiazol-4-yloxy)-N-(1-(4-cyanopyrimidin-2-yl)azetidin-3-yl)cyclobutanecarboxamide as a white solid (58 mg, 27% yield).

2-(3-((trans)-3-(Benzo[d]thiazol-4-yloxy)cyclobutanecarboxamido)azetidin-1-yl)pyrimidine-4-carboxamide $^1$H NMR (400 MHz, CD$_3$SOCD$_3$) δ 2.34-2.45 (m, 2H), 2.63-2.70 (m, 2H), 3.04-3.15 (m, 1H), 3.94 (dd, J=9, 5 Hz, 2H), 4.34-4.41 (m, 2H), 4.61-4.69 (m, 1H), 5.04-5.14 (m, 1H), 6.84 (d, J=8 Hz, 1H), 7.16 (d, J=5 Hz, 1H), 7.35-7.42 (m, 1H), 7.69 (d, J=8 Hz, 1H), 7.74-7.85 (m, 1H), 7.94-8.04 (m, 1H), 8.56 (d, J=5 Hz, 1H), 8.61 (d, J=7 Hz, 1H), 9.25 (s, 1H); LC-MS (LC-ES) M+H=425.

(trans)-3-(Benzo[d]thiazol-4-yloxy)-N-(1-(4-cyanopyrimidin-2-yl)azetidin-3-yl)cyclobutanecarboxamide $^1$H NMR (400 MHz, CD$_3$SOCD$_3$) δ 2.32-2.45 (m, 2H), 2.62-2.77 (m, 2H), 3.05-3.14 (m, 1H), 3.94 (dd, J=10, 5 Hz, 2H), 4.31-4.38 (m, 2H), 4.61-4.71 (m, 1H), 5.03-5.11 (m, 1H), 6.84 (d, J=8 Hz, 1H), 7.22 (d, J=5 Hz, 1H), 7.36-7.43 (m, 1H), 7.69 (d, J=8 Hz, 1H), 8.53-8.73 (m, 2H), 9.25 (s, 1H); LC-MS (LC-ES) M+H=407.

Example 78

(trans)-3-(Benzo[d]thiazol-4-yloxy)-N-(1-(5-fluoropyrimidin-2-yl)azetidin-3-yl)cyclobutanecarboxamide

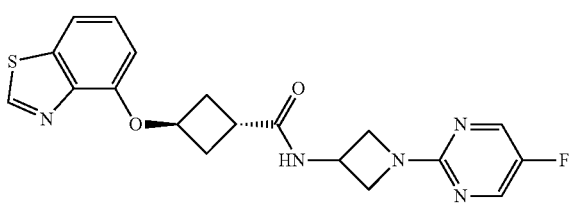 [SMILES: O=C(NC1CN(c2ncc(F)cn2)C1)[C@H]1C[C@H](Oc2cccc3scnc23)C1]

To a DMF (2 mL) solution of (trans)-3-(benzo[d]thiazol-4-yloxy)cyclobutanecarboxylic acid (Intermediate 25) (20 mg, 0.08 mmol), 1-(5-fluoropyrimidin-2-yl)azetidin-3-amine dihydrobromide (Intermediate 9) (27 mg, 0.08 mmol) and N,N-diisopropylethylamine (0.04 mL, 0.2 mmol) was added, dropwise, a 50% solution of T3P in ethyl acetate (102 mg, 0.16 mmol). The reaction was stirred 18 h, diluted with water and MeOH, and loaded onto a semi-prep HPLC (NH4OH as modifier) to afford the title compound as a white solid (3 mg, 9% yield). $^1$H NMR (400 MHz, CDCl$_3$) δ 2.59-2.70 (m, 2H), 2.85 (ddd, J=14, 7, 4 Hz, 2H), 3.05-3.14 (m, 1H), 3.93 (dd, J=10, 5.0 Hz, 2H), 4.45-4.54 (m, 2H), 4.84-4.91 (m, 1H), 5.16-5.25 (m, 1H), 5.97 (d, J=8 Hz, 1H), 6.77 (d, J=8 Hz, 1H), 7.31-7.38 (m, 1H), 7.53 (d, J=8 Hz, 1H), 8.22 (s, 2H), 8.92 (s, 1H); LC-MS (LC-ES) M+H=400.

Example 79

(trans)-3-(Benzo[d]thiazol-4-yloxy)-N-(5-methyl-1,3,4-oxadiazol-2-yl)cyclobutanecarboxamide

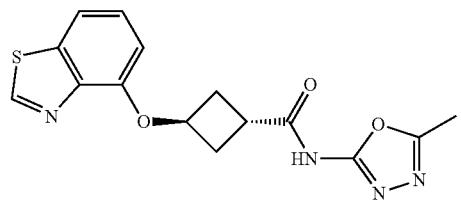 [SMILES: Cc1nnc(NC(=O)[C@H]2C[C@H](Oc3cccc4scnc34)C2)o1]

(trans)-3-(Benzo[d]thiazol-4-yloxy)cyclobutanecarboxylic acid (Intermediate 25) (50 mg, 0.20 mmol), was dissolved in DMF (2 mL) followed by the addition of N,N-diisopropylethylamine (0.07 mL, 0.4 mmol) and HATU (92 mg, 0.24 mmol). The reaction was stirred at room temperature for ca. 5 min, and 5-methyl-1,3,4-oxadiazol-2-amine (20 mg, 0.20 mmol) was added. After 2 h, the reaction was quenched with water and MeOH, and loaded onto a semi-prep HPLC (NH4OH as modifier) to afford the title compound as a white solid (29 mg, 44% yield). $^1$H NMR (CDCl$_3$) δ 2.54 (s, 3H), 2.73-2.84 (s, 2H), 2.89-2.96 (m, 2H), 3.51-3.63 (m, 1H), 5.19-5.27 (m, 1H), 6.75-6.80 (m, 1H), 7.34-7.38 (s, 1H), 7.50-7.56 (m, 1H), 8.96 (s, 1H); LC-MS (LC-ES) M+H=331.

Example 80

(trans)-3-(Benzo[d]thiazol-4-yloxy)-N-(1-(pyrimidin-2-yl)azetidin-3-yl)cyclobutanecarboxamide

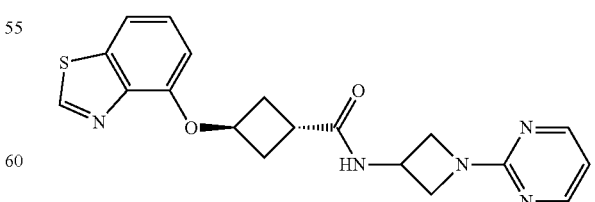

To an NMP (2 mL) solution of (trans)-N-(azetidin-3-yl)-3-(benzo[d]thiazol-4-yloxy)cyclobutanecarboxamide hydrochloride (Intermediate 32) (22 mg, 0.07 mmol) was added 2-chloropyrimidine (10 mg, 0.08 mmol). The reaction was heated in a microwave at 145° C. for 2.5 h, diluted with MeOH and loaded onto a semi-prep HPLC (NH₄OH as modifier) to afford the title compound as a light tan solid (17 mg, 70% yield). ¹H NMR (400 MHz, CDCl₃) δ 2.60-2.70 (m, 2H), 2.85 (ddd, J=13, 7, 4 Hz, 2H), 3.05-3.20 (m, 1H), 3.99 (dd, J=10, 5 Hz, 2H), 4.46-4.55 (m, 2H), 4.86-4.95 (m, 1H), 5.18-5.26 (m, 1H), 6.10 (d, J=8 Hz, 1H), 6.59 (t, J=5 Hz, 1H), 6.78 (d, J=8 Hz, 1H), 7.30-7.37 (m, 1H), 7.49-7.56 (m, 1H), 8.34 (d, J=5 Hz, 2H), 8.91 (s, 1H); LC-MS (LC-ES) M+H=382.

Example 81

(trans)-3-(Benzo[d]thiazol-4-yloxy)-N-(1-(pyridin-2-yl)azetidin-3-yl)cyclobutanecarboxamide

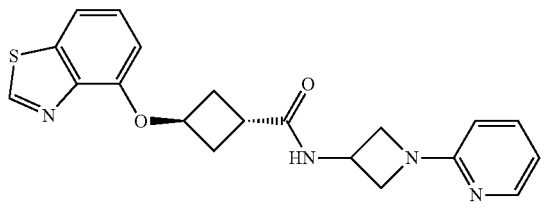 [SMILES: O=C(NC1CN(c2ccccn2)C1)[C@H]1C[C@H](Oc2cccc3scnc23)C1]

(trans)-3-(Benzo[d]thiazol-4-yloxy)cyclobutanecarboxylic acid (Intermediate 25) (50 mg, 0.20 mmol), was dissolved in DMF (8 mL) followed by the addition of N,N-diisopropylethylamine (0.07 mL, 0.4 mmol) and HATU (92 mg, 0.24 mmol). The reaction was stirred at room temperature for ca. 5 min, and 1-(pyridin-2-yl)azetidin-3-amine (Intermediate 41) (30 mg, 0.20 mmol) was added. After 1 h, the reaction was quenched with water and MeOH, and loaded onto a semi-prep HPLC (NH₄OH as modifier) to afford the title compound as a white solid (49 mg, 64% yield). ¹H NMR (CDCl₃) δ 2.58-2.72 (m, 2H), 2.78-2.88 (m, 2H), 3.06-3.14 (m, 1H), 3.82 (dd, J=9, 5 Hz, 2H), 4.36-4.42 (m, 2H), 4.86-4.94 (m, 1H), 5.16-5.24 (m, 1H), 6.13 (d, J=7 Hz, 1H), 6.31 (d, J=8 Hz, 1H), 6.64 (dd, J=7, 6 Hz, 1H), 6.78 (d, J=8 Hz, 1H), 7.35 (m, 1H), 7.43-7.50 (m, 1H), 7.53 (d, J=8 Hz, 1H), 8.15 (d, J=4 Hz, 1H), 8.92 (s, 1H); LC-MS (LC-ES) M+H=381.

Example 82

Racemic (trans)-3-(Benzo[d]thiazol-4-yloxy)-N-(1-(pyridin-2-yl)pyrrolidin-3-yl)cyclobutanecarboxamide

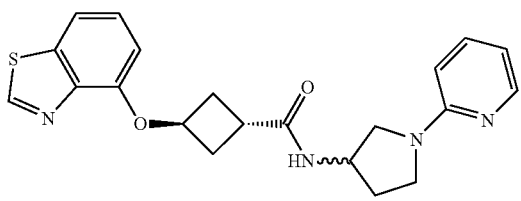 [SMILES: O=C(NC1CCN(c2ccccn2)C1)[C@H]1C[C@H](Oc2cccc3scnc23)C1]

To an NMP (1 mL) solution of (trans)-3-(benzo[d]thiazol-4-yloxy)-N-(pyrrolidin-3-yl)cyclobutanecarboxamide hydrochloride (Intermediate 42) (30 mg, 0.09 mmol) was added 2-fluoropyridine (25 mg, 0.25 mmol) and N,N-diisopropylethylamine (0.04 mL, 0.3 mmol). The reaction was heated in a microwave at 120° C. for 2 h, then at 150° C. for 2 h and loaded onto a semi-prep HPLC (NH₄OH as modifier) to afford the title compound as a white solid (2 mg, 6% yield). ¹H NMR (400 MHz, CD₃OD) δ 1.97-2.10 (m, 1H), 2.24-2.38 (m, 1H), 2.47-2.63 (m, 2H), 2.68-2.84 (m, 2H), 3.16-3.25 (m, 1H), 3.30-3.47 (m, 1H), 3.45-3.66 (m, 2H), 3.71-3.78 (m, 1H), 4.45-4.61 (m, 1H), 5.10-5.24 (m, 1H), 6.45-6.54 (m, 1H), 6.56-6.63 (m, 1H), 6.82-6.92 (m, 1H), 7.33-7.43 (m, 1H), 7.49-7.55 (m, 1H), 7.58-7.64 (m, 1H), 7.96-8.07 (m, 1H), 9.14 (s, 1H); LC-MS (LC-ES) M+H=395.

Example 83

Racemic (trans)-3-(Benzo[d]thiazol-4-yloxy)-N-(6-(2-hydroxypropan-2-yl)spiro[3.3]heptan-2-yl)cyclobutanecarboxamide

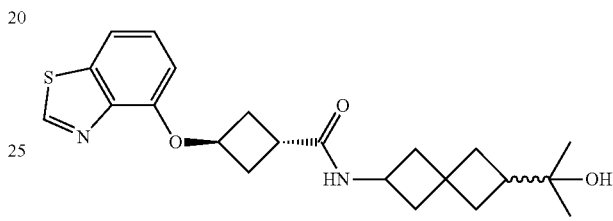

(trans)-3-(Benzo[d]thiazol-4-yloxy)cyclobutanecarboxylic acid (Intermediate 25) (50 mg, 0.20 mmol), was dissolved in DMF (2 mL) followed by the addition of N,N-diisopropylethylamine (0.07 mL, 0.4 mmol) and HATU (114 mg, 0.30 mmol). The reaction was stirred at room temperature for ca. 10 min, and 2-(6-aminospiro[3.3]heptan-2-yl)propan-2-ol (Intermediate 43) (41 mg, 0.24 mmol) was added. After 2 h, the reaction was loaded onto a semi-prep HPLC (NH₄OH as modifier) to afford the title compound as a white solid (15 mg, 19% yield). ¹H NMR (CDCl₃) δ 1.03-1.09 (m, 6H), 1.71-2.07 (m, 6H), 2.15-2.38 (m, 2H), 2.49-2.68 (m, 2H), 2.76-2.88 (m, 2H), 2.93-3.02 (m, 1H), 4.23-4.39 (m, 1H), 5.14-5.23 (m, 1H), 5.52 (d, J=8 Hz, 1H), 6.78 (d, J=8 Hz, 1H), 7.34 (t, J=8 Hz, 1H), 7.52 (d, J=8 Hz, 1H), 8.91 (s, 1H); LC-MS (LC-ES) M+H=401.

Example 84

Racemic (trans)-3-(Benzo[d]thiazol-4-yloxy)-N-(2-oxo-1,2,3,4-tetrahydroquinolin-4-yl)cyclobutanecarboxamide

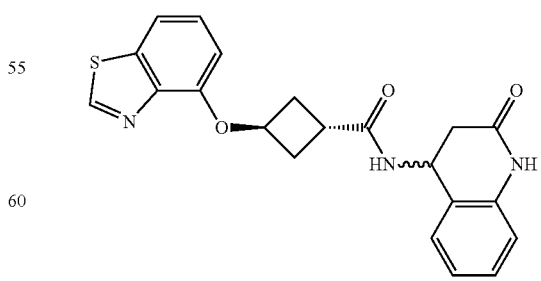

To a DMF (2 mL) solution of (trans)-3-(benzo[d]thiazol-4-yloxy)cyclobutanecarboxylic acid (Intermediate 25) (50 mg, 0.18 mmol) was added HATU (114 mg, 0.30 mmol) and N,N-diisopropylethylamine (0.07 mL, 0.4 mmol). After 10 minutes, 4-amino-3,4-dihydroquinolin-2(1H)-one hydrochloride (48 mg, 0.24 mmol) was added, and the mixture was stirred for 2 h, diluted with water and MeOH, and loaded onto a semi-prep HPLC (NH₄OH as modifier) to afford the title compound as a light tan solid (13 mg, 17% yield). $^1$H NMR (400 MHz, CDCl₃) δ 2.56-2.67 (m, 2H), 2.78-2.86 (m, 2H), 2.89 (d, J=5 Hz, 2H), 3.02 (td, J=10, 5 Hz, 1H), 5.22 (quin, J=7 Hz, 1H), 5.32-5.42 (m, 1H), 5.90 (br s, 1H), 6.76-6.82 (m, 2H), 7.04-7.10 (m, 1H), 7.20-7.29 (m, 1H), 7.30-7.39 (m, 2H), 7.53 (d, J=8 Hz, 1H), 8.23 (br s, 1H), 8.90 (s, 1H); LC-MS (LC-ES) M+H=394.

Example 85

(trans)-3-(Benzo[d]thiazol-4-yloxy)-N-((trans)-4-(2-hydroxypropan-2-yl)cyclohexyl)cyclobutanecarboxamide

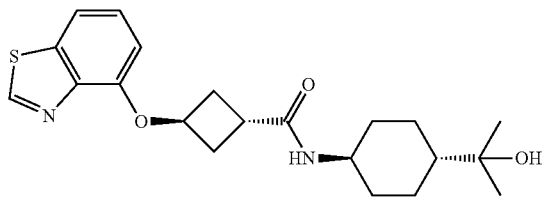 [SMILES: CC(C)(O)[C@H]1CC[C@H](NC(=O)[C@H]2C[C@H](Oc3cccc4scnc34)C2)CC1]

To a DMF (32.1 mL) solution of (trans)-3-(benzo[d]thiazol-4-yloxy)cyclobutanecarboxylic acid (Intermediate 25) (2.80 g, 11.2 mmol), 2-((trans)-4-aminocyclohexyl)propan-2-ol (2.12 g, 13.5 mmol) and N,N-diisopropylethylamine (4.90 mL, 28.1 mmol) was added, dropwise, a 50% solution of T3P in ethyl acetate (14.3 g, 22.5 mmol). The reaction was stirred 1 h, diluted with water and a white solid precipitated, which was collected by filtration. The filtrate was extracted with EtOAc (3×), the organic layers combined, dried over MgSO₄, filtered and concentrated, and the residue, along with the previously harvested solid product, was purified on silica gel, eluting with a 10%-70% 3:1 EtOAc/EtOH in hexanes gradient. The appropriate fractions were combined, evaporated under reduced pressure and placed in vacuo to give the title compound (3.88 g, 89%) as a white solid. $^1$H NMR (400 MHz, CD₃OD) δ 1.15 (s, 6H), 1.16-1.30 (m, 5H), 1.89-1.94 (m, 2H), 1.95-2.04 (m, 2H), 2.49-2.59 (m, 2H), 2.70-2.73 (m, 2H), 3.11-3.24 (m, 1H), 3.55-3.69 (m, 1H), 5.10-5.19 (m, 1H), 6.87 (d, J=8 Hz, 1H), 7.35-7.42 (m, 1H), 7.60 (d, J=8 Hz, 1H), 7.86 (d, J=8 Hz, 1H), 9.15 (s, 1H); LC-MS (LC-ES) M+H=389.

Example 86

Racemic 3-(Benzo[d]thiazol-4-yloxy)-N-(1-(1,1,1-trifluoropropan-2-yl)piperidin-4-yl)azetidine-1-carboxamide

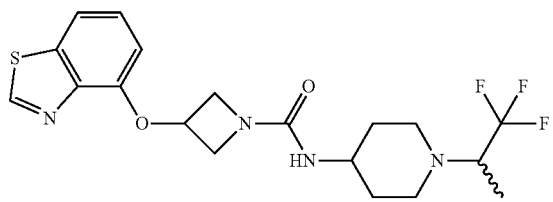 [SMILES: CC(N1CCC(NC(=O)N2CC(Oc3cccc4scnc34)C2)CC1)C(F)(F)F]

To 4-(azetidin-3-yloxy)benzo[d]thiazole hydrochloride (Intermediate 28) (15 mg, 0.06 mmol) in DCM (2 mL) was added N,N-diisopropylethylamine (0.04 mL, 0.2 mmol) and 4-nitrophenyl (1-(1,1,1-trifluoropropan-2-yl)piperidin-4-yl) carbamate (Intermediate 44) (21 mg, 0.06 mmol). After 18 h, the reaction was poured into 1 N aqueous NaOH and extracted with DCM (2×). The combined organic layers were washed with brine, dried over Na₂SO₄, filtered, concentrated and purified by silica gel chromatography, eluting with a 10-75% 3:1 EtOAc:EtOH in hexanes gradient to afford the title compound as a white solid (16 mg, 60% yield). $^1$H NMR (400 MHz, CD₃SOCD₃) δ 1.15 (d, J=7 Hz, 3H), 1.37 (dt, J=11, 6 Hz, 2H), 1.70 (br s, 2H), 2.30-2.48 (m, 2H), 2.84 (t, J=12 Hz, 2H), 3.38-3.54 (m, 1H), 3.84 (dd, J=9, 4 Hz, 2H), 4.23-4.35 (m, 2H), 5.22 (br s, 1H), 6.25 (d, J=8 Hz, 1H), 6.86 (d, J=8 Hz, 1H), 7.41 (t, J=8 Hz, 1H), 7.76 (d, J=8 Hz, 1H), 9.30 (s, 1H); LC-MS (LC-ES) M+H=429.

Example 87

Racemic 3-(Benzo[d]thiazol-4-yloxy)-N-(1-(pyridin-2-yl)pyrrolidin-3-yl)azetidine-1-carboxamide

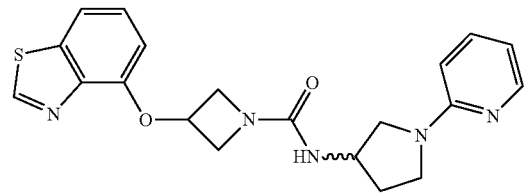 [SMILES: O=C(NC1CCN(c2ccccn2)C1)N1CC(Oc2cccc3scnc23)C1]

To 4-nitrophenyl chloroformate (45 mg, 0.22 mmol) in DCM (2 mL) at 0° C. was slowly added a mixture of 1-(pyridin-2-yl)pyrrolidin-3-amine (35 mg, 0.21 mmol) and N,N-diisopropylethylamine (0.04 mL, 0.2 mmol) in DCM (2 mL). After 30 min, the mixture was allowed to warm to rt. After 3 h, N,N-diisopropylethylamine (0.09 mL, 0.5 mmol) and 4-(azetidin-3-yloxy)benzo[d]thiazole hydrochloride (Intermediate 28) (50 mg, 0.21 mmol) in DCM (2 mL) were added. After 18 h, the reaction was poured into 1 N aqueous NaOH and extracted with DCM (2×). The combined organic layers were washed with brine, dried over Na₂SO₄, filtered, concentrated and purified by silica gel chromatography, eluting with a 10-100% 3:1 EtOAc:EtOH in hexanes gradient to afford the title compound as a yellow solid (46 mg, 54% yield). $^1$H NMR (400 MHz, CD₃SOCD₃) δ 1.81-1.93 (m, 1H), 2.14 (dd, J=13, 6 Hz, 1H), 3.14-3.25 (m, 1H), 3.37-3.67 (m, 3H), 3.89 (d, J=10 Hz, 2H), 4.17-4.39 (m, 3H), 5.24 (br s, 1H), 6.41 (d, J=8 Hz, 1H), 6.48-6.57 (m, 1H), 6.64 (d, J=7 Hz, 1H), 6.86 (d, J=8 Hz, 1H), 7.35-7.54 (m, 2H), 7.76 (d, J=8 Hz, 1H), 8.06 (d, J=4 Hz, 1H), 9.30 (s, 1H); LC-MS (LC-ES) M+H=396.

Example 88

3-(Benzo[d]thiazol-4-yloxy)-N-(1-(pyridin-2-yl)piperidin-4-yl)azetidine-1-carboxamide

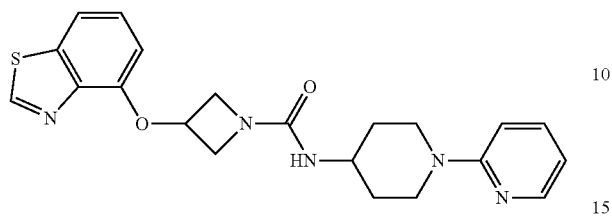

To 4-nitrophenyl chloroformate (45 mg, 0.22 mmol) in DCM (2 mL) at 0° C. was slowly added a mixture of 1-(pyridin-2-yl)piperidin-4-amine (40 mg, 0.23 mmol) and N,N-diisopropylethylamine (0.04 mL, 0.2 mmol) in DCM (2 mL). After 30 min, the reaction was let warm to rt. After 3 h, N,N-diisopropylethylamine (0.09 mL, 0.5 mmol) and 4-(azetidin-3-yloxy)benzo[d]thiazole hydrochloride (Intermediate 28) (50 mg, 0.21 mmol) in DCM (2 mL) were added. After 18 h, the reaction was poured into 1 N aqueous NaOH and extracted with DCM (2×). The combined organic layers were washed with brine, dried over $Na_2SO_4$, filtered, concentrated and purified by silica gel chromatography, eluting with a 5-100% 3:1 EtOAc:EtOH in hexanes gradient to afford the title compound as a yellow solid (43 mg, 47% yield). $^1$H NMR (400 MHz, $CD_3SOCD_3$) δ 1.30-1.45 (m, 2H), 1.71-1.83 (m, 2H), 2.87 (t, J=12 Hz, 2H), 3.68 (br s, 1H), 3.81-3.91 (m, 2H), 4.18-4.38 (m, 4H), 5.23 (br s, 1H), 6.28 (d, J=8 Hz, 1H), 6.53-6.64 (m, 1H), 6.80-6.91 (m, 2H), 7.40 (t, J=8 Hz, 1H), 7.50 (t, J=8 Hz, 1H), 7.76 (d, J=8 Hz, 1H), 8.10 (br s, 1H), 9.30 (s, 1H); LC-MS (LC-ES) M+H=410.

Example 89

Benzyl 4-(3-(benzo[d]thiazol-4-yloxy)azetidine-1-carboxamido)piperidine-1-carboxylate

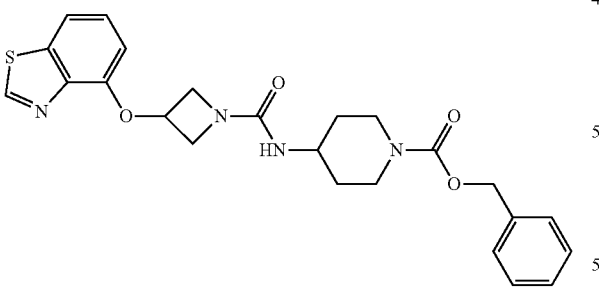

To 4-(azetidin-3-yloxy)benzo[d]thiazole hydrochloride (Intermediate 28) (75 mg, 0.31 mmol) in DCM (2 mL) was added N,N-diisopropylethylamine (0.17 mL, 0.97 mmol) and benzyl 4-(((4-nitrophenoxy)carbonyl)amino)piperidine-1-carboxylate (Intermediate 45) (125 mg, 0.31 mmol). After 18 h, the reaction was poured into 1 N aqueous NaOH and extracted with DCM (2×). The combined organic layers were washed with brine, dried over $Na_2SO_4$, filtered, concentrated and purified by silica gel chromatography, eluting with a 5-75% 3:1 EtOAc:EtOH in hexanes gradient to afford the title compound as a yellow solid (98 mg, 68% yield). $^1$H NMR (400 MHz, $CD_3SOCD_3$) δ 1.22-1.36 (m, 2H), 1.68-1.80 (m, 2H), 2.91 (br s, 2H), 3.59 (br s, 1H), 3.85 (d, J=8 Hz, 2H), 3.95 (d, J=13 Hz, 2H), 4.25-4.37 (m, 2H), 5.08 (s, 2H), 5.23 (br s, 1H), 6.29 (d, J=8 Hz, 1H), 6.86 (d, J=7 Hz, 1H), 7.28-7.45 (m, 5H), 7.76 (d, J=8 Hz, 1H), 9.30 (s, 1H); LC-MS (LC-ES), M+H=467.

Example 90

Racemic 3-(Benzo[d]thiazol-4-yloxy)-N-(tetrahydro-2H-pyran-3-yl)azetidine-1-carboxamide

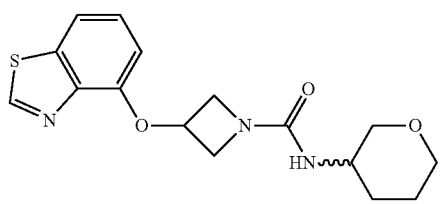 [SMILES: O=C(NC1CCCOC1)N1CC(Oc2cccc3scnc23)C1]

To 4-nitrophenyl chloroformate (42 mg, 0.21 mmol) in DCM (2 mL) at 0° C. was slowly added a mixture of tetrahydro-2H-pyran-3-amine (20 mg, 0.20 mmol) and N,N-diisopropylethylamine (0.04 mL, 0.2 mmol) in DCM (2 mL). After 15 min, the mixture was allowed to warm to rt. After 3 h, N,N-diisopropylethylamine (0.09 mL, 0.5 mmol) and 4-(azetidin-3-yloxy)benzo[d]thiazole hydrochloride (Intermediate 28) (50 mg, 0.21 mmol) in DCM (2 mL) were added. After 18 h, the reaction was poured into 1 N aqueous NaOH and extracted with DCM (2×). The combined organic layers were washed with brine, dried over $Na_2SO_4$, filtered, concentrated and loaded onto a semi-prep HPLC (TFA as modifier) to afford the title compound as a white solid (8.5 mg, 13% yield). $^1$H NMR (400 MHz, $CD_3SOCD_3$) δ 1.34-1.56 (m, 2H), 1.61-1.69 (m, 1H), 1.78-1.87 (m, 1H), 3.01 (t, J=10 Hz, 1H), 3.18-3.26 (m, 1H), 3.45-3.55 (m, 1H), 3.71 (d, J=11 Hz, 2H), 3.86 (d, J=7 Hz, 2H), 4.26-4.36 (m, 2H), 5.23 (br s, 1H), 6.24 (d, J=8 Hz, 1H), 6.86 (d, J=8 Hz, 1H), 7.41 (t, J=8 Hz, 1H), 7.76 (d, J=8 Hz, 1H), 9.30 (s, 1H); LC-MS (LC-ES) M+H=334.

Example 91

3-(Benzo[d]thiazol-4-yloxy)-N-(1-(2,2,2-trifluoroethyl)piperidin-4-yl)azetidine-1-carboxamide

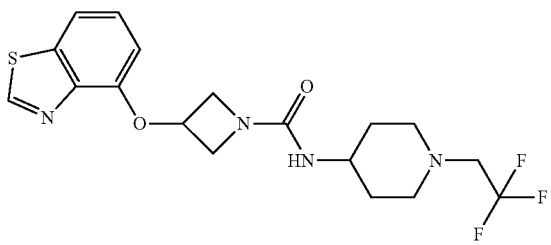 [SMILES: O=C(NC1CCN(CC(F)(F)F)CC1)N1CC(Oc2cccc3scnc23)C1]

To 4-(azetidin-3-yloxy)benzo[d]thiazole hydrochloride (Intermediate 28) (55 mg, 0.23 mmol) in DCM (2 mL) was added N,N-diisopropylethylamine (0.13 mL, 0.72 mmol) and 4-nitrophenyl (1-(2,2,2-trifluoroethyl)piperidin-4-yl)carbamate (Intermediate 46) (80 mg, 0.23 mmol). After 18 h, the reaction was poured into 1 N aqueous NaOH and extracted with DCM (2×). The combined organic layers were washed with brine, dried over Na$_2$SO$_4$, filtered, concentrated and loaded onto a semi-prep HPLC (TFA as modifier) to afford the title compound as a white solid (32 mg, 35% yield). $^1$H NMR (400 MHz, CD$_3$SOCD$_3$) δ 1.37-1.48 (m, 2H) 1.69 (d, J=11 Hz, 2H), 2.36 (t, J=11 Hz, 2H), 2.88 (d, J=11 Hz, 2H), 3.13 (q, J=10 Hz, 2H), 3.33-3.43 (m, 1H), 3.85 (dd, J=9, 3 Hz, 2H), 4.24-4.36 (m, 2H), 5.23 (br s, 1H), 6.23 (d, J=8 Hz, 1H), 6.86 (d, J=8 Hz, 1H), 7.41 (t, J=8 Hz, 1H), 7.76 (d, J=8 Hz, 1H), 9.30 (s, 1H); LC-MS (LC-ES), M+H=415.

Example 92

Racemic N-(1-Acetylpiperidin-3-yl)-3-(benzo[d]thiazol-4-yloxy)azetidine-1-carboxamide

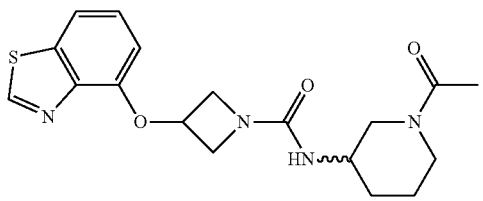 [SMILES: CC(=O)N1CCCC(NC(=O)N2CC(Oc3cccc4scnc34)C2)C1]

To 1-(3-aminopiperidin-1-yl)ethanone hydrochloride (Intermediate 48) (50 mg, 0.28 mmol) in DMSO (1 mL) was added N,N-diisopropylethylamine (0.07 mL, 0.4 mmol) and 4-nitrophenyl 3-(benzo[d]thiazol-4-yloxy)azetidine-1-carboxylate (Intermediate 47) (40 mg, 0.11 mmol). The reaction was heated to 80° C. for 18 h, poured into 1 N aqueous NaOH and extracted with EtOAc (2×). The combined organic layers were washed with brine, dried over Na$_2$SO$_4$, filtered, concentrated and loaded onto a semi-prep HPLC (NH$_4$OH as modifier) to afford the title compound as a beige solid (6 mg, 14% yield). NMR showed a mixture of rotamers. $^1$H NMR (400 MHz, CD$_3$SOCD$_3$) δ 1.22-1.32 (m, 1H), 1.35-1.49 (m, 1H), 1.62-1.72 (m, 1H), 1.79-1.86 (m, 1H), 1.95 (s, 1.5H), 1.99 (s, 1.5H), 2.62-2.74 (m, 1H), 2.85-2.93 (m, 1H), 3.35-3.46 (m, 1H), 3.64-3.74 (m, 1H), 3.82-3.89 (m, 2H), 3.93-4.00 (m, 1H), 4.26-4.38 (m, 2H), 5.19-5.26 (m, 1H), 6.31 (d, J=12 Hz, 0.5H), 6.41 (d, J=12 Hz, 0.5H), 6.85 (d, J=12 Hz, 1H), 7.40 (t, J=8 Hz, 1H), 7.75 (d, J=12 Hz, 1H), 9.29 (s, 1H); LC-MS (LC-ES), M+H=375.

Example 93

Racemic Methyl 3-(3-(benzo[d]thiazol-4-yloxy)azetidine-1-carboxamido)piperidine-1-carboxylate

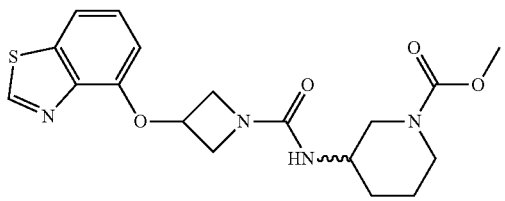 [SMILES: COC(=O)N1CCCC(NC(=O)N2CC(Oc3cccc4scnc34)C2)C1]

To methyl 3-aminopiperidine-1-carboxylate hydrochloride (Intermediate 49) (80 mg, 0.41 mmol) in DMSO (1 mL) was added N,N-diisopropylethylamine (0.10 mL, 0.57 mmol) and 4-nitrophenyl 3-(benzo[d]thiazol-4-yloxy)azetidine-1-carboxylate (Intermediate 47) (50 mg, 0.14 mmol). The reaction was heated to 80° C. for 66 h and loaded onto a semi-prep HPLC (NH$_4$OH as modifier) to afford the title compound as a beige solid (14 mg, 27% yield). $^1$H NMR (400 MHz, CD$_3$SOCD$_3$) δ 1.31-1.39 (m, 2H), 1.62-1.71 (m, 1H), 1.75-1.82 (m, 1H), 2.55-2.67 (m, 2H), 2.70-2.79 (m, 1H), 3.34-3.45 (m, 1H), 3.57 (s, 3H), 3.73-3.81 (m, 1H), 3.82-3.90 (m, 2H), 4.28-4.35 (m, 2H), 5.19-5.26 (m, 1H), 6.34 (d, J=12 Hz, 1H), 6.85 (d, J=8 Hz, 1H), 7.39 (t, J=8 Hz, 1H), 7.75 (d, J=8 Hz, 1H), 9.29 (s, 1H); LC-MS (LC-ES), M+H=391.

Example 94

Racemic Methyl 2-((3-(benzo[d]thiazol-4-yloxy)azetidine-1-carboxamido)methyl)morpholine-4-carboxylate

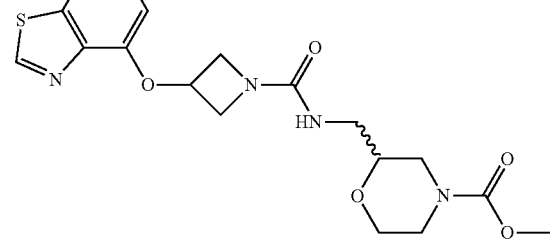

To a solution of 3-(benzo[d]thiazol-4-yloxy)-N-(morpholin-2-ylmethyl)azetidine-1-carboxamide (Intermediate 50) (18 mg, 0.05 mmol) in DCM (1 mL) was added triethylamine (0.03 mL, 0.2 mmol) followed by methyl chloroformate (0.01 mL, 0.1 mmol). After 18 h, the reaction was concentrated and loaded onto a semi-prep HPLC (NH$_4$OH as modifier) to afford the title compound as a white solid (8 mg, 39% yield). $^1$H NMR (400 MHz, CD$_3$SOCD$_3$) δ 2.52-2.65 (m, 1H), 2.82-2.96 (m, 1H), 2.99-3.14 (m, 2H), 3.30-3.39 (m, 2H), 3.60 (s, 3H), 3.69-3.74 (m, 1H), 3.78-3.89 (m, 4H), 4.28-4.36 (m, 2H), 5.20-5.27 (m, 1H), 6.63 (t, J=12 Hz, 1H), 6.86 (d, J=8 Hz, 1H), 7.40 (t, J=8 Hz, 1H), 7.76 (d, J=8 Hz, 1H), 9.29 (s, 1H); LC-MS (LC-ES), M+H=407.

Example 95

3-(Benzo[d]thiazol-4-yloxy)-N-((trans)-4-(2-hydroxypropan-2-yl)cyclohexyl) azetidine-1-carbothioamide

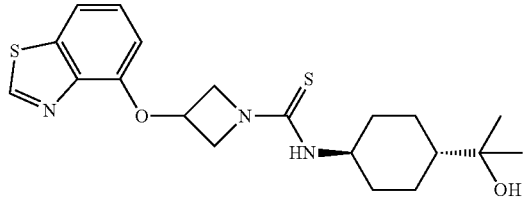 [SMILES: CC(C)(O)[C@H]1CC[C@H](NC(=S)N2CC(Oc3cccc4scnc34)C2)CC1]

To a stirred solution of 2-((trans)-4-isothiocyanatocyclohexyl)propan-2-ol (Intermediate 51) (51 mg, 0.256 mmol) in DCM (3 mL) was added triethylamine (0.04 mL, 0.3 mmol)

followed by 4-(azetidin-3-yloxy)benzo[d]thiazole hydrochloride (Intermediate 28) (60 mg, 0.25 mmol). After 18 h, the mixture was poured into water and extracted twice with EtOAc. The combined organic layers were washed with brine, dried over Na$_2$SO$_4$ and filtered. Solvent was removed under reduced pressure. The remaining material was purified on silica gel, eluting with a 10%-75% EtOAc-EtOH (3:1) in hexanes gradient. The appropriate fractions were combined, evaporated under reduced pressure and placed in vacuo to give the title compound (23 mg, 23%) as a white solid. $^1$H NMR (400 MHz, CD$_3$SOCD$_3$) δ 1.02 (s, 6H), 1.04-1.25 (m, 5H), 1.76-1.84 (m, 2H), 1.86-1.93 (m, 2H), 3.87-3.95 (m, 1H), 3.95-4.02 (m, 2H), 4.44-4.49 (m, 2H), 5.23-5.28 (m, 1H), 6.89 (d, J=12 Hz, 1H), 7.32 (d, J=8 Hz, 1H), 7.41 (t, J=8 Hz, 1H), 7.77 (d, J=8 Hz, 1H), 9.30 (s, 1H); LC-MS (LC-ES) M+H=406.

Example 96 tert-Butyl 4-(3-(benzo[d]thiazol-4-yloxy)azetidine-1-carboxamido)piperidine-1-carboxylate

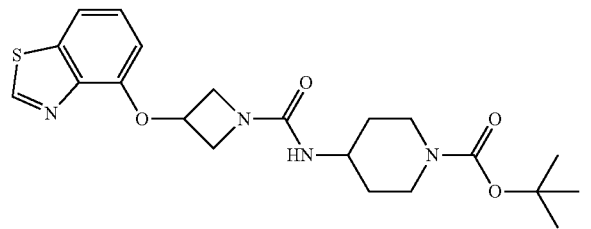 [SMILES: CC(C)(C)OC(=O)N1CCC(NC(=O)N2CC(Oc3cccc4scnc34)C2)CC1]

To 4-(azetidin-3-yloxy)benzo[d]thiazole hydrochloride (Intermediate 28) (145 mg, 0.597 mmol) in DCM (5 mL) was added N,N-diisopropylethylamine (0.35 mL, 2.0 mmol) and tert-butyl 4-(((4-nitrophenoxy)carbonyl)amino)piperidine-1-carboxylate (Intermediate 52) (237 mg, 0.649 mmol). After 18 h, the reaction was poured into saturated aqueous NaHCO$_3$ and extracted with DCM (2×). The combined organic layers were washed with brine, dried over Na$_2$SO$_4$, filtered, concentrated, and the residue was purified on silica gel, eluting with 0% to 75% EtOAc:EtOH (3:1) in hexanes to afford the title compound as a white solid (195 mg, 75% yield). $^1$H NMR (400 MHz, CD$_3$SOCD$_3$) δ 1.20-1.29 (m, 2H), 1.39 (s, 9H), 1.65-1.72 (m, 2H), 2.71-2.82 (m, 2H), 3.52-3.59 (m, 1H), 3.82-3.90 (m, 4H), 4.28-4.32 (m, 2H), 5.19-5.24 (m, 1H), 6.28 (d, J=8 Hz, 1H), 6.84 (d, J=8 Hz, 1H), 7.39 (t, J=8 Hz, 1H), 7.75 (d, J=8 Hz, 1H), 9.29 (s, 1H); LC-MS (LC-ES), M+H=433.

Example 97

3-(Benzo[d]thiazol-4-yloxy)-N-(1-(methylsulfonyl)piperidin-4-yl)azetidine-1-carboxamide

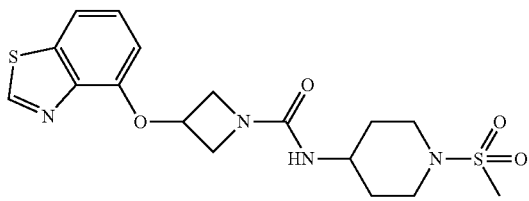 [SMILES: CS(=O)(=O)N1CCC(NC(=O)N2CC(Oc3cccc4scnc34)C2)CC1]

To a solution of 3-(benzo[d]thiazol-4-yloxy)-N-(piperidin-4-yl)azetidine-1-carboxamide (Intermediate 53) (30 mg, 0.09 mmol) in DCM (2 mL) was added triethylamine (0.04 mL, 0.3 mmol) followed by methanesulfonyl chloride (0.02 mL, 0.2 mmol). After 1 h, the solvent was removed under reduced pressure, and the remaining material was partitioned between EtOAc and 0.5 N aqueous HCl. The aqueous layer was further extracted with EtOAc and the combined organic layers were washed with saturated NaHCO$_3$ and brine, dried over Na$_2$SO$_4$, concentrated and loaded onto a semi-prep HPLC (NH$_4$OH as modifier) to afford the title compound as a white solid (10 mg, 27% yield). $^1$H NMR (400 MHz, CD$_3$SOCD$_3$) δ 1.36-1.49 (m, 2H), 1.78-1.86 (m, 2H), 2.72-2.82 (m, 2H), 2.86 (s, 3H), 3.45-3.56 (m, 3H), 3.82-3.88 (m, 2H), 4.29-4.35 (m, 2H), 5.19-5.26 (m, 1H), 6.37 (d, J=8 Hz, 1H), 6.85 (d, J=8 Hz, 1H), 7.40 (t, J=8 Hz, 1H), 7.75 (d, J=8 Hz, 1H), 9.29 (s, 1H); LC-MS (LC-ES), M+H=411.

Example 98

3-(Benzo[d]thiazol-4-yloxy)-N-(4-(methylsulfonyl)cyclohexyl)azetidine-1-carboxamide

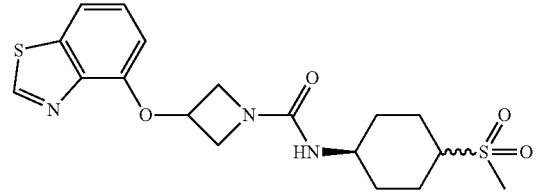

To 4-(methylsulfonyl)cyclohexanamine hydrochloride (50 mg, 0.23 mmol) in NMP (0.5 mL) was added N,N-diisopropylethylamine (0.06 mL, 0.3 mmol) and 4-nitrophenyl 3-(benzo[d]thiazol-4-yloxy)azetidine-1-carboxylate (Intermediate 47) (40 mg, 0.11 mmol). The reaction was heated to 80° C. for 18 h, and additional 4-(methylsulfonyl)cyclohexanamine, hydrochloride (50 mg, 0.23 mmol) and N,N-diisopropylethylamine (0.06 mL, 0.3 mmol) were added. The reaction was heated to 100° C. for 4 h, dissolved in MeOH, and loaded onto a semi-prep HPLC (NH$_4$OH as modifier) to afford the title compound as a beige solid (16 mg, 35% yield). $^1$H NMR (400 MHz, CD$_3$SOCD$_3$) δ 1.42-1.55 (m, 2H), 1.73-1.85 (m, 6H), 2.89 (s, 3H), 2.98-3.07 (m, 1H), 3.62-3.69 (m, 1H), 3.81-3.89 (m, 2H), 4.29-4.36 (m, 2H), 5.17-5.23 (m, 1H), 6.21 (d, J=12 Hz, 1H), 6.83 (d, J=12 Hz, 1H), 7.38 (t, J=8 Hz, 1H), 7.74 (d, J=12 Hz, 1H), 9.28 (s, 1H); LC-MS (LC-ES), M+H=410.

Example 99

(S)-3-(Benzo[d]thiazol-4-yloxy)-N-(2-oxopyrrolidin-3-yl)azetidine-1-carboxamide

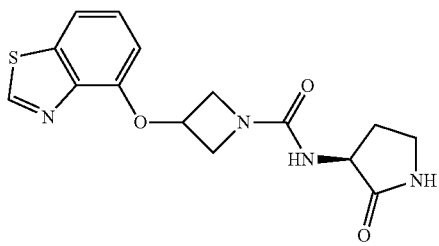 [SMILES: O=C1NCC[C@@H]1NC(=O)N1CC(Oc2cccc3scnc23)C1]

To a stirred solution of triphosgene (20 mg, 0.07 mmol) in DCM (1 mL) was added a mixture of (S)-3-aminopyrrolidin-2-one (22 mg, 0.22 mmol) and N,N-diisopropylethylamine (0.05 mL, 0.3 mmol) in DCM (1 mL) dropwise over 5 minutes. The mixture was stirred an additional 5 minutes, and then a mixture of 4-(azetidin-3-yloxy)benzo[d]thiazole hydrochloride (Intermediate 28) (50 mg, 0.21 mmol) and N,N-diisopropylethylamine (0.08 mL, 0.5 mmol) in DCM (1 mL) was added in one portion. After 18 h, the reaction was concentrated, diluted with MeOH (4 mL) and loaded onto a semi-prep HPLC (NH$_4$OH as modifier) to afford the title compound as a white solid (31 mg, 45%). $^1$H NMR (400 MHz, CD$_3$SOCD$_3$) δ 1.73-1.88 (m, 1H), 2.18-2.27 (m, 1H), 3.09-3.17 (m, 2H), 3.81-3.89 (m, 2H), 4.11-4.19 (m, 1H), 4.28-4.35 (m, 2H), 5.19-5.26 (m, 1H), 6.67 (d, J=8 Hz, 1H), 6.85 (d, J=8 Hz, 1H), 7.38 (t, J=8 Hz, 1H), 7.69 (br s, 1H), 7.73 (d, J=8 Hz, 1H), 9.27 (s, 1H); LC-MS (LC-ES) M+H=333.

Example 100

Racemic 3-(Benzo[d]thiazol-4-yloxy)-N-((trans)-4-(2-cyclopropyl-2-hydroxypropoxy)cyclohexyl)azetidine-1-carboxamide

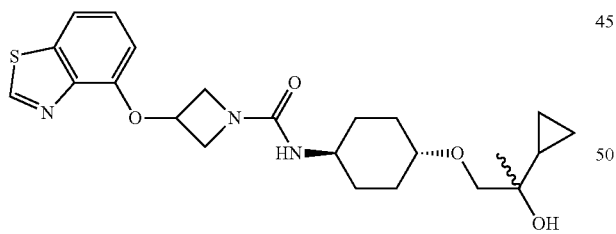

To a stirred solution of triphosgene (20 mg, 0.07 mmol) in DCM (1 mL) was added a mixture of 1-(((trans)-4-aminocyclohexyl)oxy)-2-cyclopropylpropan-2-ol (Intermediate 12) (38 mg, 0.18 mmol) and N,N-diisopropylethylamine (0.04 mL, 0.2 mmol) in DCM (1 mL) dropwise over 5 minutes. The mixture was stirred an additional 10 minutes, and then a mixture of 4-(azetidin-3-yloxy)benzo[d]thiazole hydrochloride (Intermediate 28) (40 mg, 0.17 mmol) and N,N-diisopropylethylamine (0.07 mL, 0.4 mmol) in DCM (1 mL) was added in one portion. After 18 h, the reaction was concentrated, diluted with MeOH (4 mL) and loaded onto a semi-prep HPLC (NH$_4$OH as modifier) to afford the title compound as a white solid (24 mg, 32%). $^1$H NMR (400 MHz, CD$_3$SOCD$_3$) δ 0.07-0.21 (m, 2H), 0.22-0.35 (m, 2H), 0.78-0.90 (m, 1H), 1.03 (s, 3H), 1.13-1.21 (m, 4H), 1.75 (br s, 2H), 1.84-1.96 (m, 2H), 3.12-3.22 (m, 3H), 3.81 (dd, J=9, 3 Hz, 2H), 3.85 (s, 1H), 4.27 (dd, J=9, 6 Hz, 2H), 5.15-5.23 (m, 1H), 6.17 (d, J=8 Hz, 1H), 6.83 (d, J=8 Hz, 1H), 7.38 (t, J=8 Hz, 1H), 7.73 (d, J=8 Hz, 1H), 9.27 (s, 1H); LC-MS (LC-ES) M+H=446.

Example 101

3-(Benzo[d]thiazol-4-yloxy)-N-((trans)-4-(1,1-dioxidoisothiazolidin-2-yl)cyclohexyl)azetidine-1-carboxamide

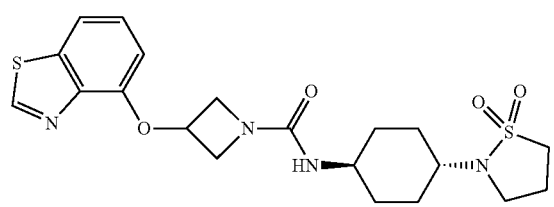 [SMILES: O=C(N[C@H]1CC[C@H](N2CCCS2(=O)=O)CC1)N1CC(Oc2cccc3scnc23)C1]

To a stirred solution of triphosgene (20 mg, 0.07 mmol) in DCM (1 mL) was added a mixture of 2-((trans)-4-aminocyclohexyl)isothiazolidine 1,1-dioxide (Intermediate 54) (40 mg, 0.18 mmol) and N,N-diisopropylethylamine (0.05 mL, 0.3 mmol) in DCM (2 mL) dropwise over 5 minutes. The mixture was stirred an additional 10 minutes, and then a mixture of 4-(azetidin-3-yloxy)benzo[d]thiazole hydrochloride (Intermediate 28) (44 mg, 0.18 mmol) and N,N-diisopropylethylamine (0.08 mL, 0.5 mmol) in DCM (1 mL) was added in one portion. After 18 h, the reaction was concentrated, diluted with MeOH (4 mL) and loaded onto a semi-prep HPLC (NH$_4$OH as modifier) to afford the title compound as a white solid (43 mg, 53%). $^1$H NMR (400 MHz, CD$_3$SOCD$_3$) δ 1.18-1.30 (m, 2H), 1.44-1.58 (m, 2H), 1.71-1.83 (m, 4H), 2.11-2.20 (m, 2H), 3.18-3.21 (m, 5H), 3.26-3.38 (m, 1H), 3.78-3.83 (m, 2H), 4.23-4.30 (m, 2H), 5.15-5.22 (m, 1H), 6.22 (d, J=8 Hz, 1H), 6.82 (d, J=8 Hz, 1H), 7.39 (t, J=8 Hz, 1H), 7.73 (d, J=8 Hz, 1H), 9.28 (s, 1H); LC-MS (LC-ES) M+H=451.

Example 102

3-(Benzo[d]thiazol-4-yloxy)-N-((trans)-4-(3-methyl-2-oxoimidazolidin-1-yl)cyclohexyl)azetidine-1-carboxamide

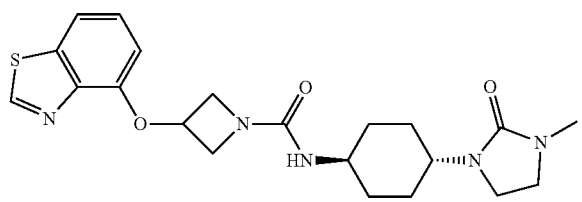 [SMILES: CN1CCN([C@H]2CC[C@H](NC(=O)N3CC(Oc4cccc5scnc45)C3)CC2)C1=O]

To a stirred solution of triphosgene (20 mg, 0.07 mmol) in DCM (1 mL) was added a mixture of 2-((trans)-4-aminocyclohexyl)-3-methylimidazolidin-2-one (Intermediate 55) (41 mg, 0.21 mmol) and N,N-diisopropylethylamine (0.05 mL, 0.3 mmol) in DCM (2 mL) dropwise over 5 minutes. The mixture was stirred an additional 10 minutes, and then a mixture of 4-(azetidin-3-yloxy)benzo[d]thiazole hydrochloride (Intermediate 28) (50 mg, 0.21 mmol) and N,N-diisopropylethylamine (0.08 mL, 0.5 mmol) in DCM (1 mL) was added in one portion. After 18 h, the reaction was concentrated, diluted with MeOH (4 mL) and loaded onto a semi-prep HPLC (NH$_4$OH as modifier) to afford the title compound as a white solid (49 mg, 55%). $^1$H NMR (400 MHz, CD$_3$SOCD$_3$) δ 1.18-1.31 (m, 2H), 1.41-1.58 (m, 4H), 1.77-1.85 (m, 2H), 2.61 (s, 3H), 3.14-3.22 (m, 4H), 3.28-3.37 (m, 1H), 3.38-3.49 (m, 1H), 3.80-3.86 (m, 2H), 4.25-4.32 (m, 2H), 5.19-5.24 (m, 1H), 6.24 (d, J=8 Hz, 1H), 6.85 (d, J=8 Hz, 1H), 7.40 (t, J=8 Hz, 1H), 7.75 (d, J=8 Hz, 1H), 9.30 (s, 1H); LC-MS (LC-ES) M+H=430.

Example 103

3-(Benzo[d]thiazol-4-yloxy)-N-((trans)-4-(2-oxooxa-zolidin-3-yl)cyclohexyl)azetidine-1-carboxamide

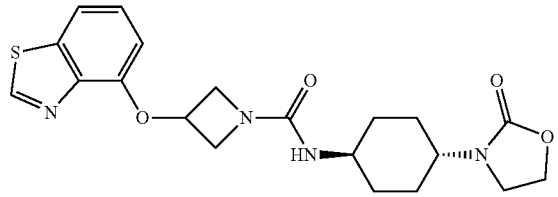 [SMILES: O=C(N[C@H]1CC[C@H](N2CCOC2=O)CC1)N1CC(Oc2cccc3scnc23)C1]

To a stirred solution of triphosgene (20 mg, 0.07 mmol) in DCM (1 mL) was added a mixture of 3-(trans-4-amino-cyclohexyl)oxazolidin-2-one (Intermediate 56) (38 mg, 0.21 mmol) and N,N-diisopropylethylamine (0.05 mL, 0.3 mmol) in DCM (2 mL) dropwise over 5 minutes. The mixture was stirred an additional 10 minutes, and then a mixture of 4-(azetidin-3-yloxy)benzo[d]thiazole hydrochloride (Intermediate 28) (50 mg, 0.21 mmol) and N,N-diisopropylethylamine (0.08 mL, 0.5 mmol) in DCM (1 mL) was added in one portion. After 18 h, the reaction was concentrated, diluted with MeOH (4 mL) and loaded onto a semi-prep HPLC (NH$_4$OH as modifier) to afford the title compound as a white solid (43 mg, 50%). $^1$H NMR (400 MHz, CD$_3$SOCD$_3$) δ 1.19-1.31 (m, 2H), 1.45-1.58 (m, 2H), 1.59-1.68 (m, 2H), 1.77-1.85 (m, 2H), 3.31-3.41 (m, 2H), 3.42-3.50 (m, 2H), 3.79-3.85 (m, 2H), 4.18-4.24 (m, 2H), 4.25-4.32 (m, 2H), 5.17-5.22 (m, 1H), 6.23 (d, J=8 Hz, 1H), 6.83 (d, J=8 Hz, 1H), 7.39 (t, J=8 Hz, 1H), 7.73 (d, J=8 Hz, 1H), 9.27 (s, 1H); LC-MS (LC-ES) M+H=417.

Example 104

Racemic 3-(Benzo[d]thiazol-4-yloxy)-N-((trans)-6-(2-hydroxypropan-2-yl)tetrahydro-2H-pyran-3-yl)azetidine-1-carboxamide

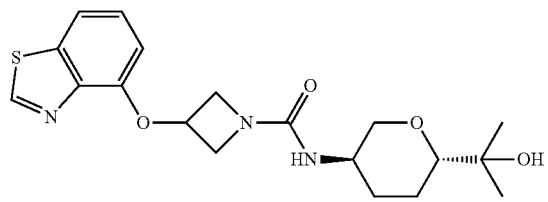 [SMILES: CC(C)(O)[C@@H]1CC[C@@H](NC(=O)N2CC(Oc3cccc4scnc34)C2)CO1]

To a stirred solution of triphosgene (20 mg, 0.07 mmol) in DCM (1 mL) was added a mixture of 2-((trans)-5-aminotetrahydro-2H-pyran-2-yl)propan-2-ol (Intermediate 34) (35 mg, 0.22 mmol) and N,N-diisopropylethylamine (0.05 mL, 0.3 mmol) in DCM (2 mL) dropwise over 5 minutes. The mixture was stirred an additional 10 minutes, and then a mixture of 4-(azetidin-3-yloxy)benzo[d]thiazole hydrochloride (Intermediate 28) (50 mg, 0.21 mmol) and N,N-diisopropylethylamine (0.08 mL, 0.5 mmol) in DCM (1 mL) was added in one portion. After 18 h, the reaction was partitioned between DCM and 0.5 N aqueous HCl. The aqueous layer was further extracted with DCM and the combined organic layers were washed with saturated NaHCO$_3$ and brine, dried over Na$_2$SO$_4$, concentrated and purified by silica gel chromatography, eluting with a 10%-100% EtOAc:EtOH (3:1) hexanes gradient, to give the title compound as a white solid (41 mg, 51%). $^1$H NMR (400 MHz, CD$_3$SOCD$_3$) δ 0.99 (s, 3H), 1.03 (s, 3H), 1.23-1.42 (m, 2H), 1.69-1.75 (m, 1H), 1.81-1.87 (m, 1H), 2.85-2.96 (m, 2H), 3.36-3.47 (m, 1H), 3.77-3.86 (m, 3H), 4.17 (s, 1H), 4.26-4.31 (m, 2H), 5.16-5.22 (m, 1H), 6.20 (d, J=8 Hz, 1H), 6.82 (d, J=8 Hz, 1H), 7.38 (t, J=8 Hz, 1H), 7.72 (d, J=8 Hz, 1H), 9.27 (s, 1H); LC-MS (LC-ES) M+H=392.

Example 105

3-(Benzo[d]thiazol-4-yloxy)-N-((trans)-4-hydroxy-4-methylcyclohexyl)azetidine-1-carboxamide

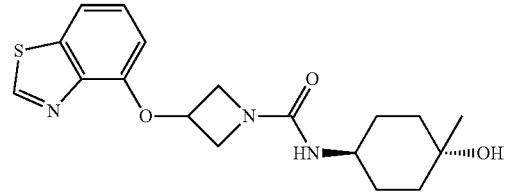 [SMILES: C[C@]1(O)CC[C@H](NC(=O)N2CC(Oc3cccc4scnc34)C2)CC1]

To a stirred solution of triphosgene (20 mg, 0.07 mmol) in DCM (1 mL) was added a mixture of trans-4-amino-1-methylcyclohexanol (Intermediate 57) (30 mg, 0.23 mmol) and N,N-diisopropylethylamine (0.05 mL, 0.3 mmol) in DCM (2 mL) dropwise over 5 minutes. The mixture was stirred an additional 10 minutes, and then a mixture of 4-(azetidin-3-yloxy)benzo[d]thiazole hydrochloride (Intermediate 28) (50 mg, 0.21 mmol) and N,N-diisopropylethylamine (0.08 mL, 0.5 mmol) in DCM (1 mL) was added in one portion. After 18 h, the reaction was partitioned between DCM and 0.5 N aqueous HCl. The aqueous layer was further extracted with DCM and the combined organic layers were washed with saturated NaHCO$_3$ and brine, dried over Na$_2$SO$_4$, concentrated and purified by silica gel chromatography, eluting with a 10%-100% EtOAc:EtOH (3:1) in hexanes gradient, to give the title compound as a white solid (28 mg, 38%). $^1$H NMR (400 MHz, CD$_3$SOCD$_3$) δ 1.08 (s, 3H), 1.20-1.39 (m, 4H), 1.44-1.52 (m, 2H), 1.59-1.67 (m, 2H), 3.32-3.40 (m, 1H), 3.78-3.84 (m, 2H), 4.19 (s, 1H), 4.25-4.30 (m, 2H), 5.16-5.22 (m, 1H), 6.10 (d, J=8 Hz, 1H), 6.82 (d, J=8 Hz, 1H), 7.38 (t, J=8 Hz, 1H), 7.72 (d, J=8 Hz, 1H), 9.27 (s, 1H); LC-MS (LC-ES) M+H=362.

Example 106

3-(Benzo[d]thiazol-4-yloxy)-N-((trans)-4-(2-hydroxy-2-methylpropoxy)cyclohexyl)azetidine-1-carboxamide

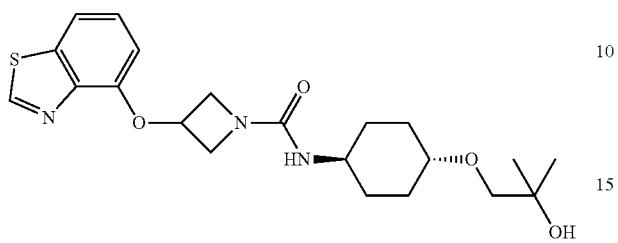

To a stirred solution of triphosgene (20 mg, 0.07 mmol) in DCM (1 mL) was added a mixture of 1-(((trans)-4-aminocyclohexyl)oxy)-2-methylpropan-2-ol (Intermediate 23) (40 mg, 0.21 mmol) and N,N-diisopropylethylamine (0.05 mL, 0.3 mmol) in DCM (1 mL) dropwise over 5 minutes. The mixture was stirred an additional 10 minutes, and then a mixture of 4-(azetidin-3-yloxy)benzo[d]thiazole hydrochloride (Intermediate 28) (50 mg, 0.21 mmol) and N,N-diisopropylethylamine (0.08 mL, 0.5 mmol) in DCM (1 mL) was added in one portion. After 18 h, the reaction was partitioned between DCM and 0.5 N aqueous HCl. The aqueous layer was further extracted with DCM and the combined organic layers were washed with saturated NaHCO$_3$ and brine, dried over Na$_2$SO$_4$, concentrated and purified by silica gel chromatography, eluting with a 0%-75% EtOAc:EtOH (3:1) in hexanes gradient, to give the title compound as a white solid (41 mg, 47%). $^1$H NMR (400 MHz, CD$_3$SOCD$_3$) δ 1.01 (s, 6H), 1.11-1.22 (m, 4H), 1.71-1.78 (m, 2H), 1.89-1.95 (m, 2H), 3.11 (s, 2H), 3.11-3.18 (m, 1H), 3.28-3.35 (m, 1H), 3.79-3.84 (m, 2H), 4.18 (s, 1H), 4.23-4.29 (m, 2H), 5.16-5.22 (m, 1H), 6.17 (d, J=8 Hz, 1H), 6.83 (d, J=8 Hz, 1H), 7.39 (t, J=8 Hz, 1H), 7.73 (d, J=8 Hz, 1H), 9.28 (s, 1H); LC-MS (LC-ES) M+H=420.

Example 107

3-(Benzo[d]thiazol-4-yloxy)-N-(1-(pyrimidin-2-yl)azetidin-3-yl)azetidine-1-carboxamide

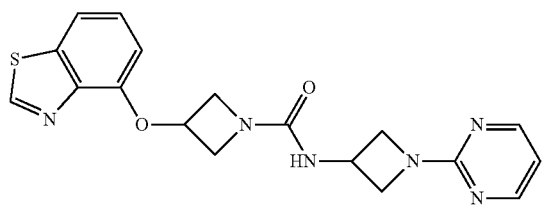 [SMILES: O=C(NC1CN(c2ncccn2)C1)N1CC(Oc2cccc3scnc23)C1]

To a stirred solution of triphosgene (20 mg, 0.07 mmol) in DCM (1 mL) was added a mixture of 1-(pyrimidin-2-yl)azetidin-3-amine dihydrochloride (Intermediate 58) (60 mg, 0.22 mmol) and N,N-diisopropylethylamine (0.12 mL, 0.69 mmol) in DCM (1 mL) dropwise over 5 minutes. The mixture was stirred an additional 10 minutes, and then a mixture of 4-(azetidin-3-yloxy)benzo[d]thiazole hydrochloride (Intermediate 28) (50 mg, 0.21 mmol) and N,N-diisopropylethylamine (0.08 mL, 0.5 mmol) in DCM (1 mL) was added in one portion. After 18 h, the solvent was removed under reduced pressure, and the residue was diluted with MeOH (4 mL) and loaded onto a semi-prep HPLC (NH$_4$OH as modifier) to afford the title compound as a white solid (44 mg, 56%). $^1$H NMR (400 MHz, CD$_3$SOCD$_3$) δ 3.81-3.89 (m, 4H), 4.17-4.23 (m, 2H), 4.29-4.36 (m, 2H), 4.46-4.55 (m, 1H), 5.18-5.25 (m, 1H), 6.63 (t, J=8 Hz, 1H), 6.83 (d, J=8 Hz, 1H), 7.19 (d, J=8 Hz, 1H), 7.38 (t, J=8 Hz, 1H), 7.74 (d, J=8 Hz, 1H), 8.32 (d, J=8 Hz, 2H), 9.27 (s, 1H); LC-MS (LC-ES) M+H=383.

Example 108

3-(Benzo[d]thiazol-4-yloxy)-N-((trans)-4-(2-hydroxypropan-2-yl)cyclohexyl)azetidine-1-carboxamide

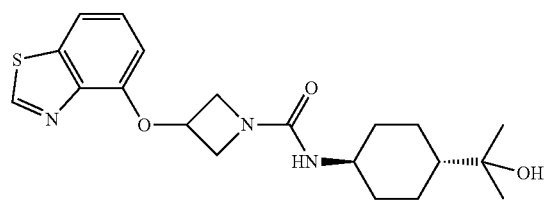 [SMILES: CC(C)(O)[C@H]1CC[C@H](NC(=O)N2CC(Oc3cccc4scnc34)C2)CC1]

To a stirred mixture of 4-(azetidin-3-yloxy)benzo[d]thiazole hydrochloride (Intermediate 28) (4.85 g, 20.0 mmol) in DCM (100 mL) was added N,N-diisopropylethylamine (11.0 mL, 63.0 mmol) followed by 4-nitrophenyl ((trans)-4-(2-hydroxypropan-2-yl)cyclohexyl)carbamate (Intermediate 3) (6.50 g, 20.2 mmol). The mixture was stirred overnight, poured into 1 N aqueous NaOH and extracted twice with DCM. The combined organic layers were washed with brine, dried over Na$_2$SO$_4$ and filtered. Solvent was removed under reduced pressure. The remaining material was purified on silica gel, eluting with a 10%-75% EtOAc-EtOH (3:1) in hexanes gradient. The appropriate fractions were combined, evaporated under reduced pressure and placed in vacuo to give the title compound (5.36 g, 69%) as a pale yellow solid. $^1$H NMR (400 MHz, CD$_3$SOCD$_3$) δ 0.97-1.02 (m, 6H), 1.06-1.22 (m, 4H), 1.79 (t, J=12 Hz, 4H), 3.23-3.32 (m, 1H), 3.45 (t, J=6 Hz, 1H), 3.83 (dd, J=9, 3 Hz, 2H), 4.00 (s, 1H), 4.24-4.33 (m, 2H), 5.22 (br s, 1H), 6.18 (d, J=8 Hz, 1H), 6.85 (d, J=8 Hz, 1H), 7.41 (t, J=8 Hz, 1H), 7.76 (d, J=8 Hz, 1H), 9.30 (s, 1H); LC-MS (LC-ES) M+H=390.

Example 109

(trans)-3-(Benzo[d]thiazol-4-yloxy)-N-((trans)-4-(2-hydroxypropan-2-yl)cyclohexyl)cyclobutanecarboxamide

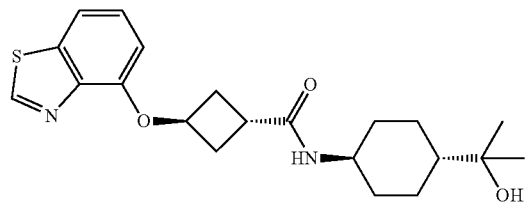 [SMILES: CC(C)(O)[C@H]1CC[C@H](NC(=O)[C@H]2C[C@H](Oc3cccc4scnc34)C2)CC1]

(trans)-3-(Benzo[d]thiazol-4-yloxy)cyclobutanecarboxylic acid (Intermediate 25) (200 mg, 0.80 mmol) was dissolved in DMF (5 mL) followed by the addition of N,N-diisopropylethylamine (0.42 mL, 2.4 mmol) and HATU (366 mg, 0.963 mmol). The reaction was stirred at room temperature for ca. 5 min, and 2-((trans)-4-aminocyclohexyl)propan-2-ol (139 mg, 0.883 mmol) was added. After 18 h, the reaction was quenched with water and extracted with EtOAc (4×). The combined organics were dried over Na$_2$SO$_4$, filtered and concentrated, and the residue was purified on silica gel, eluting with a 0%-65% EtOAc-EtOH (3:1) in hexanes gradient. The appropriate fractions were combined, evaporated under reduced pressure and placed in vacuo to give the title compound (44 mg, 14%) as a tan foam. $^1$H NMR (CD$_3$SOCD$_3$) δ 1.00 (s, 6H), 1.01-1.18 (m, 5H), 1.73-1.88 (m, 4H), 2.29-2.37 (m, 2H), 2.57-2.65 (m, 2H), 2.98-3.07 (m, 1H), 3.41-3.50 (m, 1H), 4.01 (s, 1H), 5.02-5.09 (m, 1H), 6.82 (d, J=8 Hz, 1H), 7.37 (t, J=8 Hz, 1H), 7.66-7.74 (m, 2H), 9.25 (s, 1H); LC-MS (LC-ES) M+H=389.

Example 110

6-(3-((trans)-3-(6-Fluorobenzo[d]thiazol-4-yloxy) cyclobutanecarboxamido)azetidin-1-yl)nicotinamide

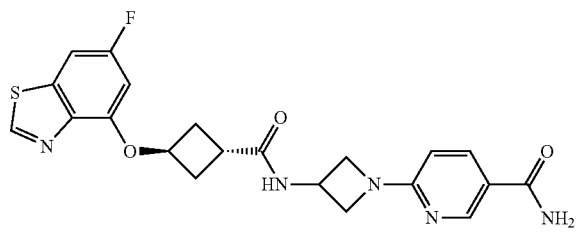 [SMILES: NC(=O)c1ccc(N2CC(NC(=O)[C@H]3C[C@H](Oc4cc(F)cc5scnc45)C3)C2)nc1]

To a DMF (2 mL) solution of (trans)-3-(6-fluorobenzo[d] thiazol-4-yloxy)cyclobutanecarboxylic acid (Intermediate 59) (30 mg, 0.11 mmol), 6-(3-aminoazetidin-1-yl)nicotinamide dihydrochloride (Intermediate 24) (30 mg, 0.11 mmol) and N,N-diisopropylethylamine (0.07 mL, 0.4 mmol) was added, dropwise, a 50% solution of T3P in ethyl acetate (143 mg, 0.22 mmol). The mixture was stirred 30 min, quenched with water, and loaded onto a semi-prep HPLC (NH$_4$OH as modifier) to afford the title compound (33 mg, 67%) as a white solid. $^1$H NMR (400 MHz, CD$_3$OD) δ 2.60 (ddd, J=13, 10, 6 Hz, 2H), 2.81 (ddd, J=13, 7, 5 Hz, 2H), 3.21-3.28 (m, 1H), 3.37 (s, 2H), 3.99 (dd, J=9, 5 Hz, 2H), 4.45 (t, J=8 Hz, 2H), 4.77-4.85 (m, 1H), 5.16 (t, J=6 Hz, 1H), 6.47 (d, J=9 Hz, 1H), 6.76 (dd, J=11, 2 Hz, 1H), 7.40 (dd, J=8, 2 Hz, 1H), 8.02 (dd, J=9, 2 Hz, 1H), 8.61 (d, J=2 Hz, 1H), 9.14 (s, 1H); LC-MS (LC-ES) M+H=442.

Example 111

2-(3-((trans)-3-((6-Fluorobenzo[d]thiazol-4-yl)oxy) cyclobutanecarboxamido)azetidin-1-yl)-5-methylpyridine 1-oxide

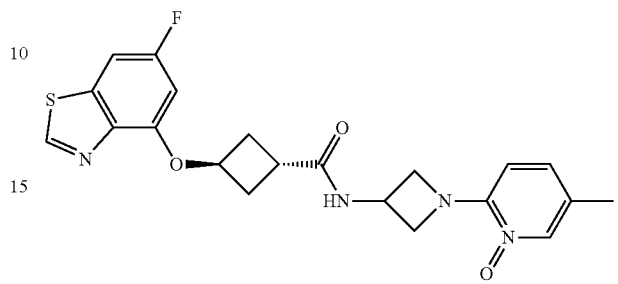

To a DMF (1 mL) solution of (trans)-3-(6-fluorobenzo[d] thiazol-4-yloxy)cyclobutanecarboxylic acid (Intermediate 59) (25 mg, 0.094 mmol), 2-(3-aminoazetidin-1-yl)-5-methylpyridine 1-oxide hydrochloride (Intermediate 60) (25 mg, 0.12 mmol) and N,N-diisopropylethylamine (0.06 mL, 0.3 mmol) was added, dropwise, a 50% solution of T3P in ethyl acetate (119 mg, 0.19 mmol). The mixture was stirred 30 min, quenched with water, and loaded onto a semi-prep HPLC (NH$_4$OH as modifier) to afford the title compound (14 mg, 35%) as a white solid. $^1$H NMR (400 MHz, CD$_3$OD) δ 2.24 (s, 3H), 2.52-2.65 (m, 2H), 2.80 (ddd, J=13, 7, 5 Hz, 2H), 3.25 (dt, J=10, 5 Hz, 1H), 4.12 (dd, J=9, 6 Hz, 2H), 4.62 (t, J=8 Hz, 2H), 4.67-4.80 (m, 1H), 5.15 (t, J=6 Hz, 1H), 6.68 (d, J=9 Hz, 1H), 6.74 (dd, J=11, 2 Hz, 1H), 7.34 (dd, J=9, 1 Hz, 1H), 7.40 (dd, J=8, 2 Hz, 1H), 7.87 (s, 1H), 9.14 (s, 1H); LC-MS (LC-ES) M+H=429.

Example 112

(trans)-3-((6-Fluorobenzo[d]thiazol-4-yl)oxy)-N-(1-(5-methylpyrimidin-2-yl)azetidin-3-yl)cyclobutanecarboxamide

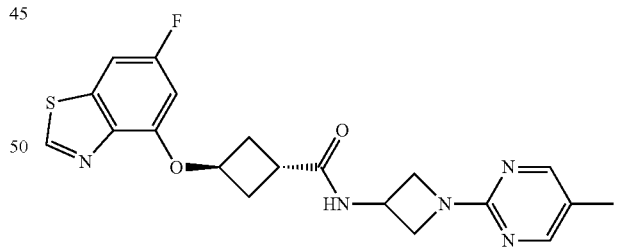

To a DMF (2 mL) solution of (trans)-3-(6-fluorobenzo[d] thiazol-4-yloxy)cyclobutanecarboxylic acid (Intermediate 59) (40 mg, 0.15 mmol), 1-(5-methylpyrimidin-2-yl)azetidin-3-amine dihydrochloride (Intermediate 27) (43 mg, 0.18 mmol) and N,N-diisopropylethylamine (0.09 mL, 0.5 mmol) was added, dropwise, a 50% solution of T3P in ethyl acetate (190 mg, 0.30 mmol). The mixture was stirred 30 min, quenched with water, and loaded onto a semi-prep HPLC (NH$_4$OH as modifier) to afford the title compound (27 mg, 44%) as a white solid. $^1$H NMR (400 MHz, CDCl$_3$) δ 2.16 (s, 3H), 2.56-2.75 (m, 2H), 2.82-2.96 (m, 2H), 3.06-3.19 (m, 1H), 3.94 (dd, J=9, 5 Hz, 2H), 4.44-4.57 (m, 2H), 4.81-4.98

(m, 1H), 5.15-5.25 (m, 1H), 6.09 (d, J=7 Hz, 1H), 6.52-6.65 (m, 1H), 7.23 (dd, J=8, 2 Hz, 1H), 8.20 (s, 2H), 8.84-8.94 (m, 1H); LC-MS (LC-ES) M+H=414.

Example 113

3-(((6-Fluorobenzo[d]thiazol-4-yl)oxy)-N-(1-(5-(hydroxymethyl)pyrimidin-2-yl)azetidin-3-yl)azetidine-1-carboxamide

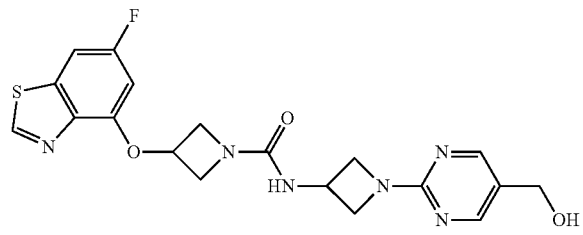 [SMILES: O=C(NC1CN(c2ncc(CO)cn2)C1)N1CC(Oc2cc(F)cc3scnc23)C1]

To 4-nitrophenyl chloroformate (38 mg, 0.19 mmol) in DCM (1 mL) at 0° C. was slowly added (2-(3-aminoazetidin-1-yl)pyrimidin-5-yl)methanol dihydrochloride (Intermediate 62) (34 mg, 0.14 mmol) and N,N-diisopropylethylamine (0.07 mL, 0.4 mmol) in DCM (1 mL). After one hour, the mixture was warmed to rt, and concentrated after another hour. To the residue was added DMF (1 mL), then 4-(azetidin-3-yloxy)-6-fluorobenzo[d]thiazole hydrochloride (Intermediate 61) (40 mg, 0.14 mmol) and N,N-diisopropylethylamine (0.07 mL, 0.4 mmol). The mixture was stirred for 3 h and loaded onto a semi-prep HPLC (NH$_4$OH as modifier) to afford the title compound (19 mg, 33% yield) as a pale yellow solid. $^1$H NMR (400 MHz, CD$_3$OD) δ 4.02 (dd, J=10, 6 Hz, 2H), 4.14 (dd, J=10, 4 Hz, 2H), 4.41 (t, J=9 Hz, 2H), 4.45-4.54 (m, 2H), 4.48 (s, 2H), 4.60-4.75 (m, 1H), 5.23-5.40 (m, 1H), 6.75 (dd, J=11, 2 Hz, 1H), 7.47 (dd, J=8, 2 Hz, 1H), 8.34 (s, 2H), 9.17 (s, 1H); LC-MS (LC-ES) M+H=431.

Example 114

(trans)-3-((6-Fluorobenzo[d]thiazol-4-yl)oxy)-N-(1-(5-(hydroxymethyl)pyrimidin-2-yl)azetidin-3-yl)cyclobutanecarboxamide

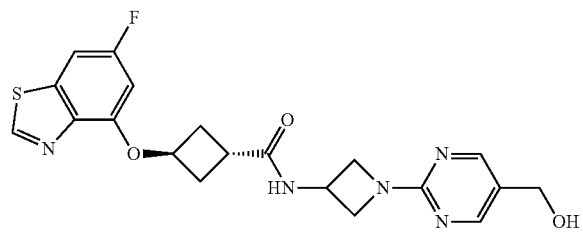 [SMILES: O=C(NC1CN(c2ncc(CO)cn2)C1)[C@H]1C[C@H](Oc2cc(F)cc3scnc23)C1]

To a DMF (1 mL) solution of (trans)-3-(6-fluorobenzo[d]thiazol-4-yloxy)cyclobutanecarboxylic acid (Intermediate 59) (25 mg, 0.094 mmol), (2-(3-aminoazetidin-1-yl)pyrimidin-5-yl)methanol dihydrochloride (Intermediate 62) (46 mg, 0.18 mmol) and N,N-diisopropylethylamine (0.09 mL, 0.5 mmol) was added, dropwise, a 50% solution of T3P in ethyl acetate (119 mg, 0.19 mmol). The mixture was stirred 30 min, quenched with water, and loaded onto a semi-prep HPLC (NH$_4$OH as modifier) to afford the title compound (42 mg, 65%) as a white solid. $^1$H NMR (400 MHz, CD$_3$OD) δ 2.45-2.65 (m, 2H), 2.80 (ddd, J=14, 7, 4 Hz, 2H), 3.20-3.27 (m, 1H), 4.01 (dd, J=9, 5 Hz, 2H), 4.41-4.51 (m, 2H), 4.49 (s, 2H), 4.65-4.82 (m, 1H), 5.16 (t, J=6 Hz, 1H), 6.75 (dd, J=11, 2 Hz, 1H), 7.40 (dd, J=8, 2 Hz, 1H), 8.36 (s, 2H), 9.14 (s, 1H); LC-MS (LC-ES) M+H=430.

Example 115

(trans)-3-((6-Fluorobenzo[d]thiazol-4-yl)oxy)-N-((trans)-4-(2-methoxyethoxy)cyclohexyl)cyclobutanecarboxamide

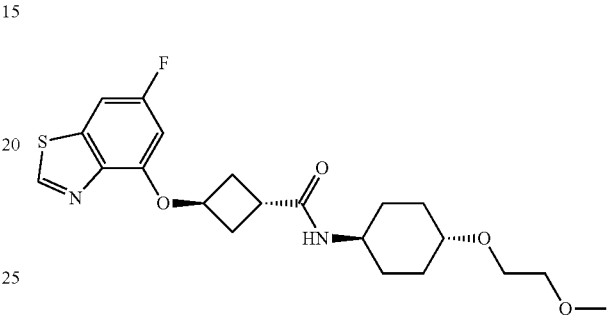

To a DMF (1 mL) solution of (trans)-3-(6-fluorobenzo[d]thiazol-4-yloxy)cyclobutanecarboxylic acid (Intermediate 59) (40 mg, 0.15 mmol), (trans)-4-(2-methoxyethoxy)cyclohexanamine (Intermediate 39) (26 mg, 0.15 mmol) and N,N-diisopropylethylamine (0.08 mL, 0.4 mmol) was added, dropwise, a 50% solution of T3P in ethyl acetate (190 mg, 0.30 mmol). The mixture was stirred 30 min, quenched with water, and loaded onto a semi-prep HPLC (NH$_4$OH as modifier) to afford the title compound (39 mg, 62%) as an off white solid. $^1$H NMR (400 MHz, CDCl$_3$) δ 1.06-1.28 (m, 2H), 1.33-1.54 (m, 2H), 1.97-2.21 (m, 4H), 2.50-2.70 (m, 2H), 2.76-2.89 (m, 2H), 2.93-3.08 (m, 1H), 3.28 (t, J=10 Hz, 1H), 3.40 (s, 3H), 3.51-3.58 (m, 2H), 3.60-3.67 (m, 2H), 3.73-3.91 (m, 1H), 5.13-5.21 (m, 1H), 5.31 (d, J=8 Hz, 1H), 6.58 (d, J=11 Hz, 1H), 7.22 (d, J=7 Hz, 1H), 8.87 (s, 1H); LC-MS (LC-ES) M+H=423.

Example 116

Racemic (trans)-3-((6-Fluorobenzo[d]thiazol-4-yl)oxy)-N-(6-(2-hydroxypropan-2-yl)spiro[3.3]heptan-2-yl)cyclobutanecarboxamide

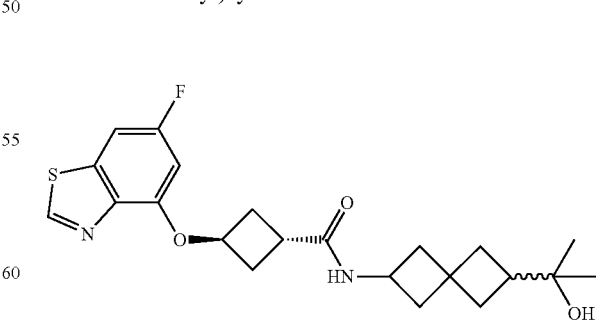

To a DMF (1 mL) solution of (trans)-3-(6-fluorobenzo[d]thiazol-4-yloxy)cyclobutanecarboxylic acid (Intermediate 59) (31 mg, 0.12 mmol), 2-(6-aminospiro[3.3]heptan-2-yl)propan-2-ol (Intermediate 43) (20 mg, 0.12 mmol) and N,N-diisopropylethylamine (0.06 mL, 0.3 mmol) was added, dropwise, a 50% solution of T3P in ethyl acetate (148 mg, 0.23 mmol). The mixture was stirred 30 min, quenched with water, and loaded onto a semi-prep HPLC (NH$_4$OH as modifier) to afford the title compound (39 mg, 80%) as an off white solid. $^1$H NMR (400 MHz, CDCl$_3$) δ 1.10 (d, J=5 Hz, 6H), 1.61-2.08 (m, 6H), 2.14-2.39 (m, 2H), 2.48-2.65 (m, 3H), 2.81 (d, J=4 Hz, 2H), 2.92-3.09 (m, 1H), 4.16-4.40 (m, 1H), 5.16 (t, J=6 Hz, 1H), 5.70 (d, J=7 Hz, 1H), 6.57 (d, J=11 Hz, 1H), 7.20 (d, J=8 Hz, 1H), 8.86 (s, 1H); LC-MS (LC-ES) M+H=419.

Example 117

(trans)-3-((6-Fluorobenzo[d]thiazol-4-yl)oxy)-N-(1-(5-fluoropyrimidin-2-yl)piperidin-4-yl)cyclobutanecarboxamide

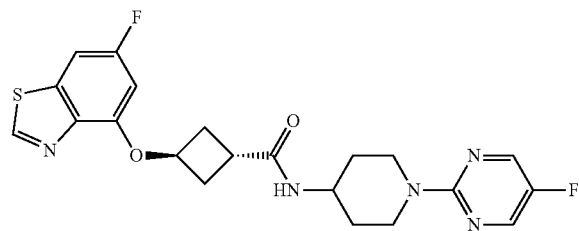 [SMILES: O=C(NC1CCN(c2ncc(F)cn2)CC1)[C@H]1C[C@H](Oc2cc(F)cc3scnc23)C1]

To a DMF (2 mL) solution of (trans)-3-(6-fluorobenzo[d]thiazol-4-yloxy)cyclobutanecarboxylic acid (Intermediate 59) (40 mg, 0.16 mmol), 1-(5-fluoropyrimidin-2-yl)piperidin-4-amine dihydrochloride (Intermediate 29) (40 mg, 0.15 mmol) and N,N-diisopropylethylamine (0.06 mL, 0.3 mmol) was added, dropwise, a 50% solution of T3P in ethyl acetate (204 mg, 0.32 mmol). The mixture was stirred 30 min, quenched with water, and loaded onto a semi-prep HPLC (NH$_4$OH as modifier) to afford the title compound as an off white solid (18.6 mg, 27.9%). $^1$H NMR (400 MHz, CD$_3$OD) δ 1.33-1.50 (m, 2H), 1.93 (d, J=12 Hz, 2H), 2.44-2.62 (m, 2H), 2.66-2.82 (m, 2H), 3.08 (t, J=13 Hz, 2H), 3.14-3.24 (m, 1H), 3.97 (t, J=10 Hz, 1H), 4.62 (d, J=13 Hz, 2H), 5.15 (t, J=6 Hz, 1H), 6.72 (d, J=11 Hz, 1H), 7.37 (d, J=8 Hz, 1H), 8.26 (s, 2H), 9.11 (s, 1H); LC-MS (LC-ES) M+H=446.

Example 118

3-((6-Fluorobenzo[d]thiazol-4-yl)oxy)-N-(1-(5-fluoropyrimidin-2-yl)piperidin-4-yl)azetidine-1-carboxamide

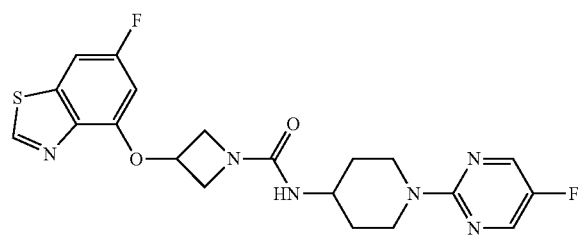 [SMILES: O=C(NC1CCN(c2ncc(F)cn2)CC1)N1CC(Oc2cc(F)cc3scnc23)C1]

To 4-nitrophenyl (1-(5-fluoropyrimidin-2-yl)piperidin-4-yl)carbamate (Intermediate 30) (145 mg, 0.40 mmol) in DMF (1 mL) was added 4-(azetidin-3-yloxy)-6-fluorobenzo[d]thiazole hydrochloride (Intermediate 61) (30 mg, 0.10 mmol) and N,N-diisopropylethylamine (39 mg, 0.30 mmol). The reaction was stirred 3 h and loaded onto a semi-prep HPLC (NH$_4$OH as modifier) to afford the title compound (22 mg, 49% yield) a light tan solid. $^1$H NMR (400 MHz, CDCl$_3$) δ 1.29-1.44 (m, 2H), 2.04 (d, J=12 Hz, 2H), 2.96-3.11 (m, 2H), 3.85-3.98 (m, 1H), 4.03 (d, J=8 Hz, 1H), 4.23 (dd, J=9, 4 Hz, 2H), 4.43 (t, J=8 Hz, 2H), 4.61 (d, J=14 Hz, 2H), 5.24 (br s, 1H), 6.48 (d, J=10 Hz, 1H), 7.30 (d, J=8 Hz, 1H), 8.20 (s, 2H), 8.90 (s, 1H); LC-MS (LC-ES) M+H=447.

Example 119

3-((6-Fluorobenzo[d]thiazol-4-yl)oxy)-N-(1-(5-fluoropyridin-2-yl)azetidin-3-yl)azetidine-1-carboxamide

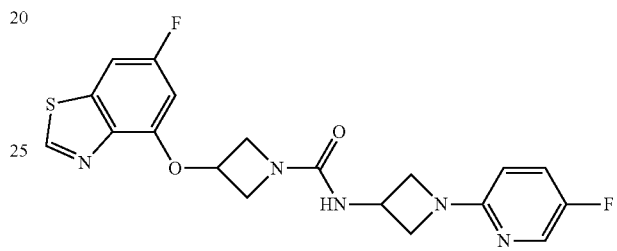

To 4-nitrophenyl (1-(5-fluoropyridin-2-yl)azetidin-3-yl)carbamate (Intermediate 31) (18 mg, 0.05 mmol) in DMF (1 mL) was added 4-(azetidin-3-yloxy)-6-fluorobenzo[d]thiazole hydrochloride (Intermediate 61) (16 mg, 0.05 mmol) and N,N-diisopropylethylamine (21 mg, 0.16 mmol). The reaction was stirred 18 h and loaded onto a semi-prep HPLC (NH$_4$OH as modifier) to afford the title compound (17 mg, 77% yield) as a white solid. $^1$H NMR (400 MHz, CDCl$_3$) δ 3.77-3.84 (m, 2H), 4.27 (dd, J=9, 4 Hz, 2H), 4.37 (t, J=8 Hz, 2H), 4.47 (t, J=8 Hz, 2H), 4.68 (d, J=8 Hz, 1H), 4.74-4.85 (m, 1H), 5.28 (br s, 1H), 6.26-6.38 (m, 1H), 6.50 (d, J=10 Hz, 1H), 7.24-7.38 (m, 1H), 8.03 (br s, 1H), 8.91 (s, 1H); LC-MS (LC-ES) M+H=418.

Example 120

(trans)-3-((6-Fluorobenzo[d]thiazol-4-yl)oxy)-N-(1-(5-fluoropyridin-2-yl)azetidin-3-yl)cyclobutanecarboxamide

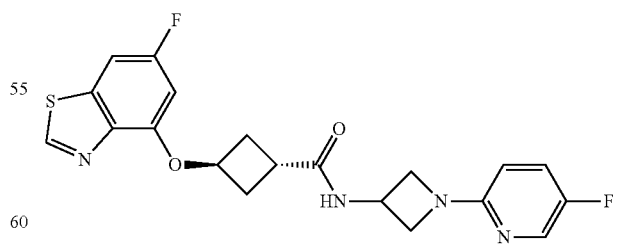

To a DMF (1 mL) solution of (trans)-3-((6-fluorobenzo[d]thiazol-4-yl)oxy)cyclobutanecarboxylic acid (Intermediate 59) (40 mg, 0.15 mmol), 1-(5-fluoropyridin-2-yl)azetidin-3-amine (Intermediate 31B) (30 mg, 0.18 mmol) and N,N-diisopropylethylamine (0.05 mL, 0.3 mmol) was added, dropwise, a 50% solution of T3P in ethyl acetate (190 mg, 0.30 mmol). The reaction was stirred 10 min, quenched with water, and loaded onto a semi-prep HPLC (NH₄OH as modifier) to afford the title compound as a white solid (37 mg, 59%). ¹H NMR (400 MHz, CDCl₃) δ 2.60-2.72 (m, 2H), 2.81-2.93 (m, 2H), 3.05-3.18 (m, 1H), 3.74-3.89 (m, 2H), 4.31-4.45 (m, 2H), 4.81-4.95 (m, 1H), 5.14-5.24 (m, 1H), 6.06 (d, J=8 Hz, 1H), 6.30 (d, J=8 Hz, 1H), 6.58 (d, J=11 Hz, 1H), 7.21-7.30 (m, 2H), 8.04 (br s, 1H), 8.87 (s, 1H); LC-MS (LC-ES) M+H=417.

Example 121

Racemic (trans)-N-((trans)-4-((1,1-Difluoropropan-2-yl)amino)cyclohexyl)-3-((6-fluorobenzo[d]thiazol-4-yl)oxy)cyclobutanecarboxamide

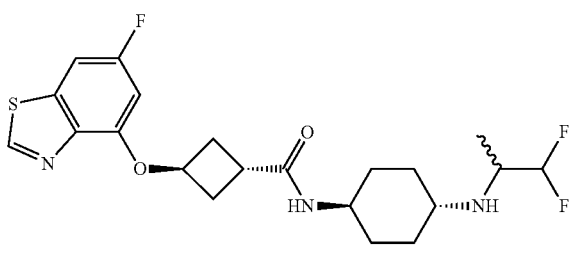 [SMILES: CC(N[C@H]1CC[C@H](NC(=O)[C@H]2C[C@H](Oc3cc(F)cc4scnc34)C2)CC1)C(F)F]

To a DMF (2 mL) solution of (trans)-3-((6-fluorobenzo[d]thiazol-4-yl)oxy)cyclobutanecarboxylic acid (Intermediate 59) (20 mg, 0.075 mmol), (trans)-N1-(1,1-difluoropropan-2-yl)cyclohexane-1,4-diamine (Intermediate 17) (14 mg, 0.075 mmol) and N,N-diisopropylethylamine (0.03 mL, 0.2 mmol) was added, dropwise, a 50% solution of T3P in ethyl acetate (95 mg, 0.15 mmol). The reaction was stirred 30 min, quenched with water, and loaded onto a semi-prep HPLC (NH₄OH as modifier) to afford the title compound as an off-white solid (27 mg, 80%). ¹H NMR (400 MHz, CD₃OD) δ 1.14 (d, J=7 Hz, 3H), 1.19-1.35 (m, 4H), 1.90-2.05 (m, 4H), 2.47-2.59 (m, 2H), 2.59-2.69 (m, 1H), 2.70-2.81 (m, 2H), 3.03-3.12 (m, 1H), 3.13-3.23 (m, 1H), 3.63-3.73 (m, 1H), 5.10-5.19 (m, 1H), 5.71 (t, J=56 Hz, 1H), 6.72 (d, J=11 Hz, 1H), 7.38 (d, J=8 Hz, 1H), 9.12 (s, 1H); LC-MS (LC-ES) M+H=442.

Example 122

3-((6-Fluorobenzo[d]thiazol-4-yl)oxy)-N-(1-(2-methylpyrimidin-4-yl)azetidin-3-yl)azetidine-1-carboxamide

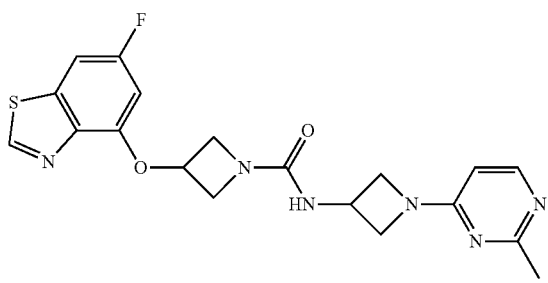 [SMILES: Cc1nccc(N2CC(NC(=O)N3CC(Oc4cc(F)cc5scnc45)C3)C2)n1]

To 4-nitrophenyl chloroformate (59 mg, 0.29 mmol) in acetonitrile (5 mL) at 0° C. was slowly added 1-(2-methylpyrimidin-4-yl)azetidin-3-amine (Intermediate 33) (40 mg, 0.24 mmol) in acetonitrile (5 mL). After one hour, N,N-diisopropylethylamine (0.04 mL, 0.2 mmol) was added, and the reaction was allowed to warm to room temperature for 18 h. To this mixture was added 4-(azetidin-3-yloxy)-6-fluorobenzo[d]thiazole hydrochloride (Intermediate 61) (72 mg, 0.24 mmol). The mixture was stirred for 4 h, concentrated, diluted with MeOH, concentrated to reduce the volume and loaded onto a semi-prep HPLC (NH₄OH as modifier) to afford the title compound (19 mg, 19% yield) as an off white solid. ¹H NMR (400 MHz, CD₃OD) δ 2.44 (s, 3H), 3.96-4.06 (m, 2H), 4.15 (dd, J=9, 3 Hz, 2H), 4.41 (t, J=9 Hz, 2H), 4.46-4.55 (m, 2H), 4.69 (t, J=6 Hz, 1H), 5.33 (br s, 1H), 6.25 (d, J=6 Hz, 1H), 6.75 (d, J=11 Hz, 1H), 7.47 (d, J=8 Hz, 1H), 8.02 (d, J=6 Hz, 1H), 9.16 (s, 1H); LC-MS (LC-ES) M+H=415.

Example 123

(trans)-3-((6-Fluorobenzo[d]thiazol-4-yl)oxy)-N-(1-(2-methylpyrimidin-4-yl)azetidin-3-yl)cyclobutanecarboxamide

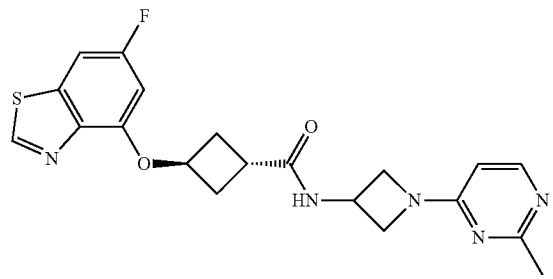 [SMILES: Cc1nccc(N2CC(NC(=O)[C@H]3C[C@H](Oc4cc(F)cc5scnc45)C3)C2)n1]

To a DMF (2 mL) solution of (trans)-3-((6-fluorobenzo[d]thiazol-4-yl)oxy)cyclobutanecarboxylic acid (Intermediate 59) (28 mg, 0.11 mmol), 1-(2-methylpyrimidin-4-yl)azetidin-3-amine (Intermediate 33) (17 mg, 0.11 mmol) and N,N-diisopropylethylamine (0.04 mL, 0.2 mmol) was added, dropwise, a 50% solution of T3P in ethyl acetate (133 mg, 0.21 mmol). The reaction was stirred 30 min, quenched with water, and loaded onto a semi-prep HPLC (NH₄OH as modifier) to afford the title compound as an off-white solid (31 mg, 72%). ¹H NMR (400 MHz, CD₃OD) δ 2.45 (s, 3H), 2.53-2.68 (m, 2H), 2.74-2.85 (m, 2H), 3.21-3.30 (m, 1H), 3.92-4.03 (m, 2H), 4.45 (t, J=9 Hz, 2H), 4.76-4.83 (m, 1H), 5.16 (t, J=6 Hz, 1H), 6.26 (d, J=6 Hz, 1H), 6.75 (dd, J=11, 2 Hz, 1H), 7.40 (dd, J=8, 2 Hz, 1H), 8.01-8.06 (m, 1H), 9.14 (s, 1H); LC-MS (LC-ES) M+H=414.

Example 124

Racemic 3-((6-Fluorobenzo[d]thiazol-4-yl)oxy)-N-((cis)-4-((1,1,1-trifluoro-3-hydroxypropan-2-yl)amino)cyclohexyl)azetidine-1-carboxamide

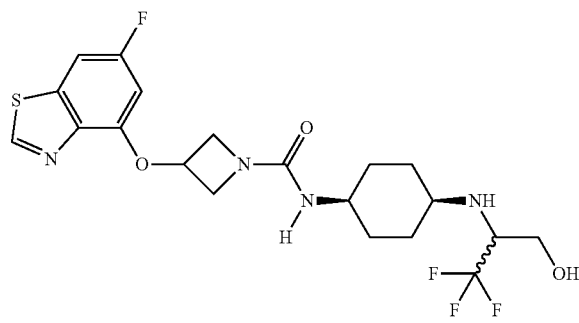 [SMILES: O=C(N[C@H]1CC[C@@H](NC(CO)C(F)(F)F)CC1)N1CC(Oc2cc(F)cc3scnc23)C1]

To a mixture of 4-(azetidin-3-yloxy)-6-fluorobenzo[d]thiazole hydrochloride (Intermediate 61) (35 mg, 0.12 mmol) in DMF (1 mL) was added N,N-diisopropylethylamine (46 mg, 0.35 mmol) followed by 4-nitrophenyl ((cis)-4-((1,1,1-trifluoro-3-hydroxypropan-2-yl)amino)cyclohexyl)carbamate (Intermediate 63) (46 mg, 0.12 mmol). The mixture was stirred 18 h and then loaded onto a semi-prep HPLC (NH$_4$OH as modifier) to afford the title compound as a pale yellow solid (37 mg, 66%). $^1$H NMR (400 MHz, CD$_3$OD) δ 1.07-1.23 (m, 2H), 1.23-1.40 (m, 2H), 1.89 (d, J=12 Hz, 1H), 1.96-2.10 (m, 3H), 2.61-2.72 (m, 1H), 3.18-3.36 (m, 1H), 3.40-3.52 (m, 1H), 3.55-3.72 (m, 1H), 3.73-3.84 (m, 1H), 3.92-4.02 (m, 1H), 4.19 (dd, J=9, 4 Hz, 2H), 4.27-4.44 (m, 2H), 5.21 (br s, 1H), 6.46 (d, J=9 Hz, 1H), 7.28 (d, J=8 Hz, 1H), 8.88 (s, 1H); LC-MS (LC-ES) M+H=477.

Example 125

Racemic (trans)-3-((6-Fluorobenzo[d]thiazol-4-yl)oxy)-N-((cis)-4-((1,1,1-trifluoro-3-hydroxypropan-2-yl)amino)cyclohexyl)cyclobutanecarboxamide

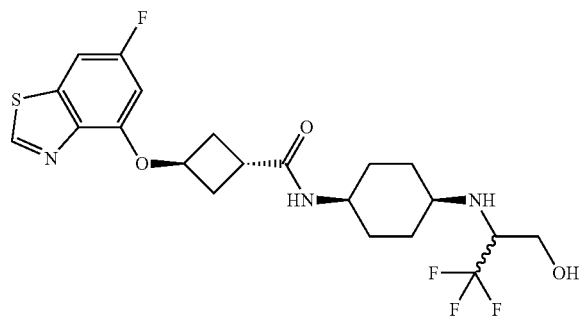 [SMILES: O=C(N[C@H]1CC[C@@H](NC(CO)C(F)(F)F)CC1)[C@H]1C[C@H](Oc2cc(F)cc3scnc23)C1]

To a DMF (2 mL) solution of (trans)-3-((6-fluorobenzo[d]thiazol-4-yl)oxy)cyclobutanecarboxylic acid (Intermediate 59) (25 mg, 0.094 mmol), 2-(cis)-((4-aminocyclohexyl)amino)-3,3,3-trifluoropropan-1-ol (Intermediate 63D) (21 mg, 0.094 mmol) and N,N-diisopropylethylamine (24 mg, 0.2 mmol) was added, dropwise, a 50% solution of T3P in ethyl acetate (119 mg, 0.19 mmol). The reaction was stirred 30 min, quenched with water, and loaded onto a semi-prep HPLC (NH$_4$OH as modifier) to afford the title compound as an off-white solid (37 mg, 83%). $^1$H NMR (400 MHz, CD$_3$OD) δ 1.18-1.37 (m, 4H), 1.86-2.12 (m, 4H), 2.49-2.60 (m, 2H), 2.60-2.69 (m, 1H), 2.71-2.82 (m, 2H), 3.17 (s, 1H), 3.26-3.32 (m, 1H), 3.58-3.73 (m, 2H), 3.78 (d, J=4 Hz, 1H), 5.10-5.21 (m, 1H), 6.74 (dd, J=11, 2 Hz, 1H), 7.39 (dd, J=8, 2 Hz, 1H), 9.13 (s, 1H); LC-MS (LC-ES) M+H=476.

Example 126

Racemic (trans)-3-((6-Fluorobenzo[d]thiazol-4-yl)oxy)-N-((trans)-4-((1,1,1-trifluoro-3-hydroxypropan-2-yl)amino)cyclohexyl)cyclobutanecarboxamide

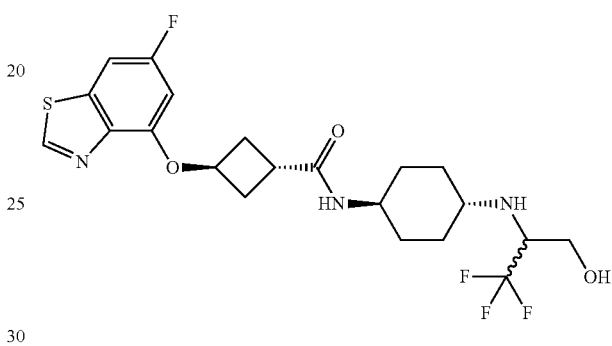

To a DMF (1 mL) solution of (trans)-3-((6-fluorobenzo[d]thiazol-4-yl)oxy)cyclobutanecarboxylic acid (Intermediate 59) (22 mg, 0.082 mmol), 2-(((trans)-4-aminocyclohexyl)amino)-3,3,3-trifluoropropan-1-ol dihydrochloride (Intermediate 64) (19 mg, 0.082 mmol) and N,N-diisopropylethylamine (0.04 mL, 0.2 mmol) was added, dropwise, a 50% solution of T3P in ethyl acetate (105 mg, 0.17 mmol). The reaction was stirred 30 min, quenched with water, and loaded onto a semi-prep HPLC (NH$_4$OH as modifier) to afford the title compound as a white solid (18 mg, 46%). $^1$H NMR (400 MHz, CDCl$_3$) δ 1.08-1.56 (m, 4H), 2.02-2.23 (m, 4H), 2.55-2.70 (m, 2H), 2.75-2.83 (m, 3H), 2.95-3.10 (m, 1H), 3.33-3.40 (m, 1H), 3.49-3.64 (m, 1H), 3.77-3.90 (m, 2H), 5.11-5.23 (m, 1H), 6.59 (d, J=11 Hz, 1H), 7.23 (d, J=8 Hz, 1H), 8.88 (s, 1H); LC-MS (LC-ES) M+H=476.

Example 127

Racemic 3-((6-Fluorobenzo[d]thiazol-4-yl)oxy)-N-((trans)-6-(2-hydroxypropan-2-yl)tetrahydro-2H-pyran-3-yl)azetidine-1-carboxamide

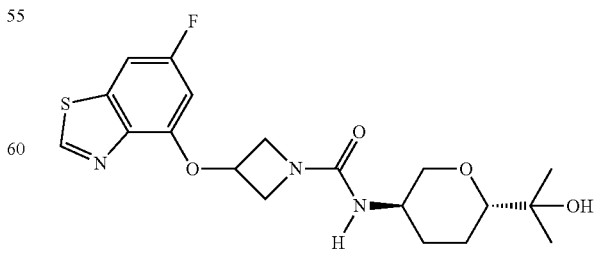

To a mixture of 4-(azetidin-3-yloxy)-6-fluorobenzo[d]thiazole hydrochloride (Intermediate 61) (35 mg, 0.12 mmol) in DMF (1 mL) was added N,N-diisopropylethylamine (46 mg, 0.35 mmol) followed by 4-nitrophenyl ((trans)-6-(2-hydroxypropan-2-yl)tetrahydro-2H-pyran-3-yl)carbamate (Intermediate 36) (38 mg, 0.12 mmol). The mixture was stirred 1 h and then loaded onto a semi-prep HPLC (NH₄OH as modifier) to afford the title compound as a pale yellow solid (32 mg, 66%). ¹H NMR (400 MHz, CD₃OD) δ 1.17 (d, J=8 Hz, 6H), 1.48 (t, J=10 Hz, 2H), 1.81 (d, J=8 Hz, 1H), 2.05 (d, J=6 Hz, 1H), 3.00-3.17 (m, 2H), 3.57-3.74 (m, 1H), 4.01 (dd, J=11, 3 Hz, 1H), 4.09 (dd, J=10, 3 Hz, 2H), 4.40-4.49 (m, 2H), 5.25-5.34 (m, 1H), 6.74 (d, J=11 Hz, 1H), 7.47 (d, J=8 Hz, 1H), 9.16 (s, 1H); LC-MS (LC-ES) M+H=410.

Example 128

3-((6-Fluorobenzo[d]thiazol-4-yl)oxy)-N-((trans)-4-(2-methoxyethoxy)cyclohexyl)azetidine-1-carboxamide

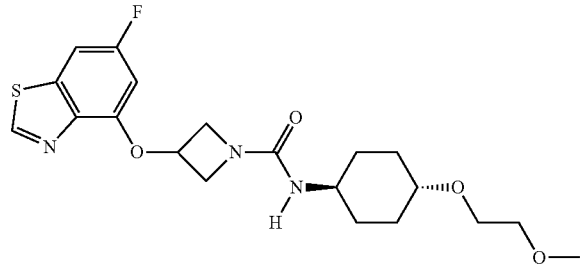 [SMILES: COCCO[C@H]1CC[C@H](NC(=O)N2CC(Oc3cc(F)cc4scnc34)C2)CC1]

To a mixture of 4-(azetidin-3-yloxy)-6-fluorobenzo[d]thiazole hydrochloride (Intermediate 61) (70 mg, 0.24 mmol) in acetonitrile (5 mL) was added N,N-diisopropylethylamine (91 mg, 0.71 mmol) followed by 4-nitrophenyl ((trans)-6-(2-hydroxypropan-2-yl)tetrahydro-2H-pyran-3-yl)carbamate (Intermediate 65) (80 mg, 0.24 mmol). The mixture was stirred 1 h and then loaded onto a semi-prep HPLC (NH₄OH as modifier) to afford the title compound as a solid (46 mg, 46%). ¹H NMR (400 MHz, CDCl₃) δ 1.05-1.21 (m, 2H), 1.31-1.50 (m, 2H), 2.04 (d, J=10 Hz, 4H), 3.24 (ddd, J=11, 7, 4 Hz, 1H), 3.39 (s, 3H), 3.51-3.56 (m, 2H), 3.57-3.70 (m, 3H), 4.00 (d, J=8 Hz, 1H), 4.20 (dd, J=9, 4 Hz, 2H), 4.32-4.44 (m, 2H), 5.16-5.24 (m, 1H), 6.46 (dd, J=10, 2 Hz, 1H), 7.25-7.31 (m, 1H), 8.90 (s, 1H); LC-MS (LC-ES) M+H=424.

Example 129

3-((6-Fluorobenzo[d]thiazol-4-yl)oxy)-N-(1-(pyrimidin-2-yl)azetidin-3-yl)azetidine-1-carboxamide

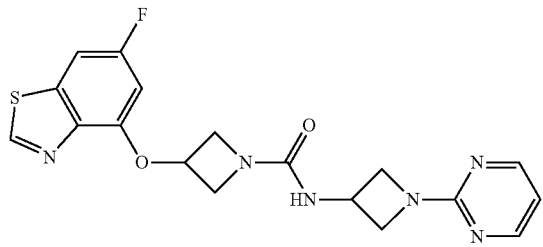 [SMILES: O=C(NC1CN(c2ncccn2)C1)N1CC(Oc2cc(F)cc3scnc23)C1]

To a mixture of 4-(azetidin-3-yloxy)-6-fluorobenzo[d]thiazole hydrochloride (Intermediate 61) (35 mg, 0.12 mmol) in acetonitrile (5 mL) was added N,N-diisopropylethylamine (46 mg, 0.35 mmol) followed by 4-nitrophenyl (1-(pyrimidin-2-yl)azetidin-3-yl)carbamate (Intermediate 66) (37 mg, 0.12 mmol). The mixture was stirred 1 h and then loaded onto a semi-prep HPLC (NH₄OH as modifier) to afford the title compound as a white solid (29 mg, 62%). ¹H NMR (400 MHz, CDCl₃) δ 3.97 (dd, J=9, 5 Hz, 2H), 4.27 (dd, J=9, 4 Hz, 2H), 4.44-4.60 (m, 4H), 4.75-4.91 (m, 2H), 5.21-5.30 (m, 1H), 6.48 (dd, J=10, 2 Hz, 1H), 6.59 (t, J=5 Hz, 1H), 7.31 (dd, J=8, 2 Hz, 1H), 8.34 (d, J=5 Hz, 2H), 8.91 (s, 1H); LC-MS (LC-ES) M+H=401.

Example 130

N-(1-(2-Chloropyrimidin-4-yl)azetidin-3-yl)-3-((6-fluorobenzo[d]thiazol-4-yl)oxy)azetidine-1-carboxamide

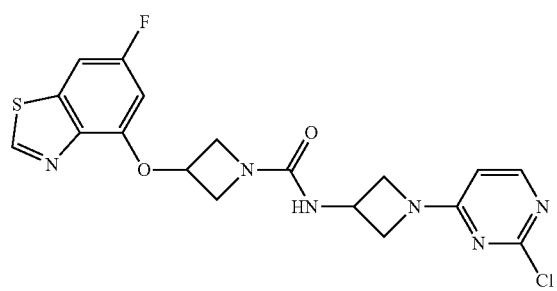 [SMILES: O=C(NC1CN(c2ccnc(Cl)n2)C1)N1CC(Oc2cc(F)cc3scnc23)C1]

To 4-nitrophenyl chloroformate (77 mg, 0.38 mmol) in DCM (1 mL) at 0° C. was slowly added 1-(2-chloropyrimidin-4-yl)azetidin-3-amine dihydrochloride (Intermediate 7) (70 mg, 0.27 mmol) and N,N-diisopropylethylamine (0.14 mL, 0.82 mmol) in DCM (1.5 mL). After 2 h, 4-(azetidin-3-yloxy)-6-fluorobenzo[d]thiazole hydrochloride (Intermediate 61) (71 mg, 0.27 mmol) and N,N-diisopropylethylamine (0.14 mL, 0.82 mmol) were added. The mixture was warmed to rt, stirred for 30 min, concentrated and loaded onto a semi-prep HPLC (NH₄OH as modifier) to afford the title compound (42 mg, 36% yield) as a white solid. ¹H NMR (400 MHz, CDCl₃) δ 3.93 (dd, J=10, 5 Hz, 2H), 4.25 (dd, J=9, 4 Hz, 2H), 4.36-4.52 (m, 4H), 4.71-4.82 (m, 1H), 4.87 (d, J=7 Hz, 1H), 5.25 (br s, 1H), 6.07 (d, J=6 Hz, 1H), 6.47 (d, J=11 Hz, 1H), 7.30 (d, J=8 Hz, 1H), 8.01 (d, J=6 Hz, 1H), 8.88 (s, 1H); LC-MS (LC-ES) M+H=435, 437 (Cl pattern).

Example 131

(trans)-3-((6-Fluorobenzo[d]thiazol-4-yl)oxy)-N-((cis)-3-hydroxy-3-methylcyclobutyl)cyclobutanecarboxamide

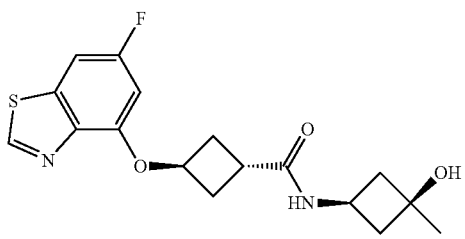 [SMILES: C[C@]1(O)C[C@@H](NC(=O)[C@H]2C[C@H](Oc3cc(F)cc4scnc34)C2)C1]

To a DMF (2 mL) solution of (trans)-3-((6-fluorobenzo[d]thiazol-4-yl)oxy)cyclobutanecarboxylic acid (Intermediate 59) (40 mg, 0.15 mmol), (cis)-3-amino-1-methylcyclobutanol hydrochloride (Intermediate 67) (21 mg, 0.15 mmol) and N,N-diisopropylethylamine (0.07 mL, 0.4 mmol) was added, dropwise, a 50% solution of T3P in ethyl acetate (190 mg, 0.30 mmol). The reaction was stirred 30 min, quenched with water, and loaded onto a semi-prep HPLC (NH$_4$OH as modifier) to afford the title compound as a white solid (29 mg, 55%). $^1$H NMR (400 MHz, CD$_3$OD) δ 1.35 (s, 3H), 1.91-2.05 (m, 2H), 2.34-2.45 (m, 2H), 2.45-2.60 (m, 2H), 2.68-2.74 (m, 2H), 3.10-3.24 (m, 1H), 3.81-3.95 (m, 1H), 5.10-5.21 (m, 1H), 6.66-6.74 (m, 1H), 7.32-7.40 (m, 1H), 9.11 (s, 1H); LC-MS (LC-ES) M+H=351.

Example 132

3-((6-Fluorobenzo[d]thiazol-4-yl)oxy)-N-(1-(pyridin-2-yl)azetidin-3-yl)azetidine-1-carboxamide

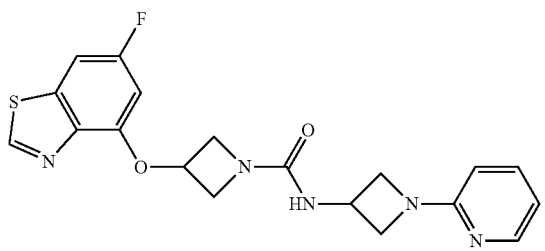

To 4-nitrophenyl chloroformate (64 mg, 0.32 mmol) in DCM (1 mL) at 0° C. was slowly added 1-(pyridin-2-yl)azetidin-3-amine dihydrochloride (Intermediate 37) (59 mg, 0.23 mmol) and N,N-diisopropylethylamine (87 mg, 0.68 mmol) in DCM (2 mL). After 1 h, 4-(azetidin-3-yloxy)-6-fluorobenzo[d]thiazole hydrochloride (Intermediate 61) (59 mg, 0.23 mmol) and N,N-diisopropylethylamine (0.18 mL, 0.68 mmol) were added. The mixture was warmed to rt, stirred for 1 h, concentrated and loaded onto a semi-prep HPLC (NH$_4$OH as modifier) to afford the title compound (43 mg, 48% yield) as a white solid. $^1$H NMR (400 MHz, CDCl$_3$) δ 3.77 (dd, J=8, 5 Hz, 2H), 4.23 (dd, J=9, 4 Hz, 2H), 4.35 (t, J=8 Hz, 2H), 4.40-4.45 (m, 2H), 4.74-4.86 (m, 2H), 5.20-5.26 (m, 1H), 6.28 (d, J=8 Hz, 1H), 6.41-6.50 (m, 1H), 6.60-6.69 (m, 1H), 7.25-7.31 (m, 1H), 7.44 (t, J=8 Hz, 1H), 8.13 (d, J=5 Hz, 1H), 8.87 (s, 1H); LC-MS (LC-ES) M+H=400.

Example 133

(trans)-3-((6-Fluorobenzo[d]thiazol-4-yl)oxy)-N-(1-(pyrimidin-2-yl)azetidin-3-yl)cyclobutanecarboxamide

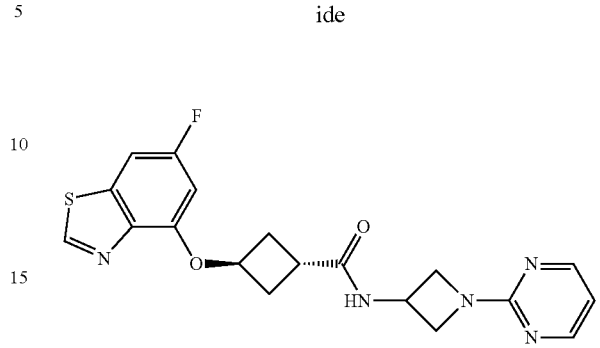

To a DMF (2 mL) solution of (trans)-3-((6-fluorobenzo[d]thiazol-4-yl)oxy)cyclobutanecarboxylic acid (Intermediate 59) (40 mg, 0.15 mmol), 1-(pyrimidin-2-yl)azetidin-3-amine dihydrochloride (Intermediate 58) (33 mg, 0.15 mmol) and N,N-diisopropylethylamine (0.07 mL, 0.4 mmol) was added, dropwise, a 50% solution of T3P in ethyl acetate (190 mg, 0.30 mmol). The reaction was stirred 30 min, quenched with water, and loaded onto a semi-prep HPLC (NH$_4$OH as modifier) to afford the title compound (46 mg, 77%). $^1$H NMR (400 MHz, CD$_3$SOCD$_3$) δ 2.30-2.44 (m, 2H), 2.65-2.74 (m, 2H), 3.06-3.19 (s, 1H), 3.87 (dd, J=9, 6 Hz, 2H), 4.25-4.34 (m, 2H), 4.59-4.68 (m, 1H), 5.04-5.11 (m, 1H), 6.69 (t, J=5 Hz, 1H), 6.74 (d, J=11 Hz, 1H), 7.59 (d, J=8 Hz, 1H), 8.35 (d, J=5 Hz, 2H), 8.59 (d, J=7 Hz, 1H), 9.22 (s, 1H); LC-MS (LC-ES) M+H=400.

Example 134

N-(1-(4-Cyanopyridin-2-yl)azetidin-3-yl))-3-((6-fluorobenzo[d]thiazol-4-yl)oxy)azetidine-1-carboxamide

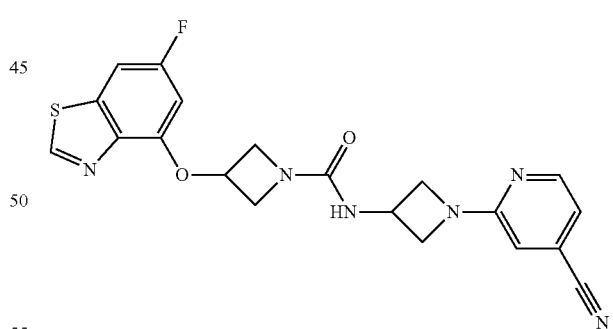

To 4-nitrophenyl chloroformate (57 mg, 0.28 mmol) in DCM (1 mL) at 0° C. was slowly added 2-(3-aminoazetidin-1-yl)isonicotinonitrile dihydrochloride (Intermediate 35) (50 mg, 0.20 mmol) and N,N-diisopropylethylamine (0.11 mL, 0.61 mmol) in DCM (1 mL). After 1 h, 4-(azetidin-3-yloxy)-6-fluorobenzo[d]thiazole hydrochloride (Intermediate 61) (57 mg, 0.20 mmol) and N,N-diisopropylethylamine (0.11 mL, 0.61 mmol) were added. The mixture was warmed to rt, stirred for 1 h, concentrated and loaded onto a semi-prep HPLC (NH$_4$OH as modifier) to afford the title compound (28 mg, 33% yield) as a white solid. $^1$H NMR (400 MHz, CDCl₃) δ 3.86 (dd, J=9, 5 Hz, 2H), 4.25 (dd, J=9, 4 Hz, 2H), 4.40 (t, J=8 Hz, 2H), 4.43-4.49 (m, 2H), 4.65 (d, J=8 Hz, 1H), 4.76-4.87 (m, 1H), 5.21-5.32 (m, 1H), 6.45-6.52 (m, 2H), 6.77 (d, J=5 Hz, 1H), 7.28-7.33 (m, 1H), 8.25 (d, J=5 Hz, 1H), 8.89 (s, 1H); LC-MS (LC-ES) M+H=425.

Example 135

3-((6-Fluorobenzo[d]thiazol-4-yl)oxy)-N-(1-(5-fluoropyrimidin-2-yl)azetidin-3-yl)azetidine-1-carboxamide

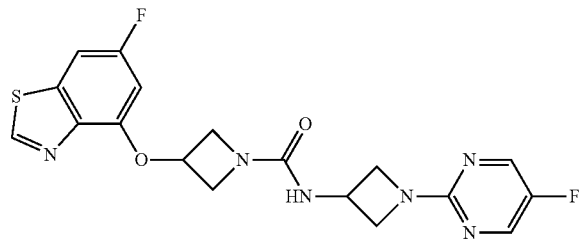 [SMILES: O=C(NC1CN(c2ncc(F)cn2)C1)N1CC(Oc2cc(F)cc3scnc23)C1]

To 4-nitrophenyl chloroformate (70 mg, 0.35 mmol) in DCM (1 mL) at 0° C. was slowly added 1-(5-fluoropyrimidin-2-yl)azetidin-3-amine dihydrochloride (Intermediate 9) (60 mg, 0.25 mmol) and N,N-diisopropylethylamine (0.13 mL, 0.75 mmol) in DCM (1 mL). After 1 h, 4-(azetidin-3-yloxy)-6-fluorobenzo[d]thiazole hydrochloride (Intermediate 61) (65 mg, 0.25 mmol) and N,N-diisopropylethylamine (0.11 mL, 0.61 mmol) were added. The mixture was warmed to rt, stirred for 1 h, concentrated and loaded onto a semi-prep HPLC (NH₄OH as modifier) to afford the title compound (49 mg, 47% yield) as a white solid. ¹H NMR (400 MHz, CDCl₃) δ 3.89 (dd, J=9, 5 Hz, 2H), 4.25 (dd, J=9, 4 Hz, 2H), 4.40-4.51 (m, 4H), 4.63 (d, J=8 Hz, 1H), 4.71-4.81 (m, 1H), 5.20-5.30 (m, 1H), 6.47 (dd, J=10, 2 Hz, 1H), 7.29 (dd, J=8, 2 Hz, 1H), 8.21 (s, 2H), 8.88 (s, 1H); LC-MS (LC-ES) M+H=419.

Example 136

(trans)-3-((6-Fluorobenzo[d]thiazol-4-yl)oxy)-N-(1-(5-fluoropyrimidin-2-yl)azetidin-3-yl)cyclobutanecarboxamide

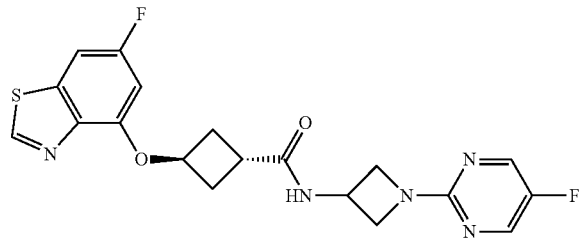 [SMILES: O=C(NC1CN(c2ncc(F)cn2)C1)[C@H]1C[C@H](Oc2cc(F)cc3scnc23)C1]

To a DMF (2 mL) solution of (trans)-3-((6-fluorobenzo[d]thiazol-4-yl)oxy)cyclobutanecarboxylic acid (Intermediate 59) (40 mg, 0.15 mmol), 1-(5-fluoropyrimidin-2-yl)azetidin-3-amine dihydrochloride (Intermediate 9) (36 mg, 0.15 mmol) and N,N-diisopropylethylamine (0.07 mL, 0.4 mmol) was added, dropwise, a 50% solution of T3P in ethyl acetate (190 mg, 0.30 mmol). The reaction was stirred 20 min, quenched with water, and loaded onto a semi-prep HPLC (NH₄OH as modifier) to afford the title compound (44 mg, 70%). ¹H NMR (400 MHz, CD₃SOCD₃) δ 2.32-2.46 (m, 2H), 2.63-2.81 (m, 2H), 3.05-3.19 (m, 1H), 3.88 (dd, J=9, 5 Hz, 2H), 4.22-4.36 (m, 2H), 4.57-4.72 (m 1H), 5.07 (t, J=6 Hz, 1H), 6.75 (dd, J=11, 2 Hz, 1H), 7.60 (dd, J=8, 2 Hz, 1H), 8.46 (s, 2H), 8.58 (d, J=7 Hz, 1H), 9.22 (s, 1H); LC-MS (LC-ES) M+H=418.

Example 137

(trans)-3-((6-Fluorobenzo[d]thiazol-4-yl)oxy)-N-(1-(pyridin-2-yl)azetidin-3-yl)cyclobutanecarboxamide

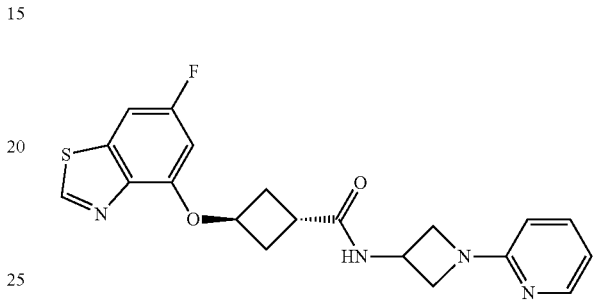

To a DMF (2 mL) solution of (trans)-3-((6-fluorobenzo[d]thiazol-4-yl)oxy)cyclobutanecarboxylic acid (Intermediate 59) (40 mg, 0.15 mmol), 1-(pyridin-2-yl)azetidin-3-amine dihydrochloride (Intermediate 37) (33 mg, 0.15 mmol) and N,N-diisopropylethylamine (0.08 mL, 0.4 mmol) was added, dropwise, a 50% solution of T3P in ethyl acetate (190 mg, 0.30 mmol). The reaction was stirred 30 min, quenched with water, and loaded onto a semi-prep HPLC (NH₄OH as modifier) to afford the title compound (49 mg, 82%). ¹H NMR (400 MHz, CDCl₃) δ 2.59-2.71 (m, 2H), 2.79-2.89 (m, 2H), 3.03-3.17 (m, 1H), 3.76-3.84 (m, 2H), 4.35-4.46 (m, 2H), 4.80-4.93 (m, 1H), 5.12-5.21 (m, 1H), 6.00 (d, J=7 Hz, 1H), 6.28-6.35 (m, 1H), 6.57 (d, J=11 Hz, 1H), 6.61-6.70 (m, 1H), 7.21 (d, J=6 Hz, 1H), 7.47 (t, J=7 Hz, 1H), 8.16 (d, J=5 Hz, 1H), 8.85 (s, 1H); LC-MS (LC-ES) M+H=399.

Example 138

(trans)-3-(Benzo[d]thiazol-4-yloxy)-N-(4-cyclopropylthiazol-2-yl)cyclobutanecarboxamide

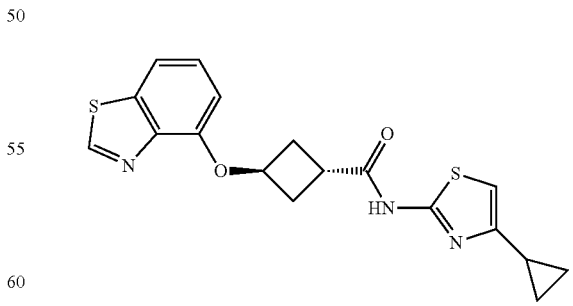

To a DMF (2 mL) solution of (trans)-3-(benzo[d]thiazol-4-yloxy)cyclobutanecarboxylic acid, lithium salt (Intermediate 25C) (50 mg, 0.20 mmol), 4-cyclopropylthiazol-2-amine (27 mg, 0.20 mmol) and N,N-diisopropylethylamine (0.10 mL, 0.59 mmol) was added, dropwise, a 50% solution of T3P in ethyl acetate (248 mg, 0.390 mmol). The reaction was stirred 18 h, diluted with MeOH and loaded onto a semi-prep HPLC (NH₄OH as modifier) to afford the title compound (8 mg, 11%) as a white solid. ¹H NMR (400 MHz, CD₃OD) δ 0.74-0.92 (m, 4H), 1.90-1.99 (m, 1H), 2.60-2.69 (m, 2H), 2.79-2.88 (m, 2H), 3.37-3.46 (m, 1H), 5.14-5.22 (m, 1H), 6.62 (s, 1H), 6.85 (d, J=8 Hz, 1H), 7.41 (t, J=8 Hz, 1H), 7.62 (d, J=8 Hz, 1H), 9.16 (s, 1H); LC-MS (LC-ES) M+H=372.

Example 139

Racemic (trans)-3-((6-Fluorobenzo[d]thiazol-4-yl)oxy)-N-((trans)-6-(2-hydroxypropan-2-yl)tetrahydro-2H-pyran-3-yl)cyclobutanecarboxamide

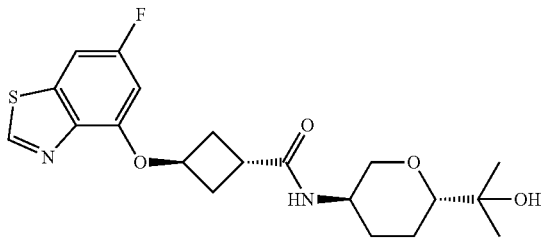 [SMILES: CC(C)(O)[C@@H]1CC[C@@H](NC(=O)[C@H]2C[C@H](Oc3cc(F)cc4scnc34)C2)CO1]

To an EtOAc (1 mL) solution of (trans)-3-((6-fluorobenzo[d]thiazol-4-yl)oxy)cyclobutanecarboxylic acid (Intermediate 59) (25 mg, 0.094 mmol), 2-((trans)-5-aminotetrahydro-2H-pyran-2-yl)propan-2-ol hydrochloride (Intermediate 68) (24 mg, 0.12 mmol) and N,N-diisopropylethylamine (0.1 mL, 0.6 mmol) was added, dropwise, a 50% solution of T3P in ethyl acetate (0.1 mL, 0.2 mmol). The reaction was stirred 1 h, diluted with ethyl acetate, and washed with saturated aqueous sodium bicarbonate, water and brine. The organics were dried over sodium sulfate, filtered, concentrated and purified on silica gel, eluting with a gradient from 20-70% ethyl acetate:ethanol (3:1) in heptanes, to give the title compound as a yellow oil (23 mg, 57%). ¹H NMR (400 MHz, CDCl₃) δ 1.18 (d, J=11 Hz, 6H), 1.32-1.40 (m, 1H), 1.46 (d, J=7 Hz, 1H), 1.48-1.60 (m, 1H), 1.75 (d, J=13 Hz, 1H), 2.15 (d, J=12 Hz, 1H), 2.59-2.68 (m, 2H), 2.83 (qd, J=7, 4 Hz, 2H), 2.98-3.12 (m, 3H), 3.88-4.03 (m, 1H), 4.17-4.22 (m, 1H), 5.14-5.20 (m, 1H), 6.58 (dd, J=11, 2 Hz, 1H), 7.22 (dd, J=8, 2 Hz, 1H), 8.88 (s, 1H); LC-MS (LC-ES) M+H=409.

Example 140

(trans)-3-((6-Fluorobenzo[d]thiazol-4-yl)oxy)-N-((trans)-4-(2-hydroxypropan-2-yl)cyclohexyl)cyclobutanecarboxamide

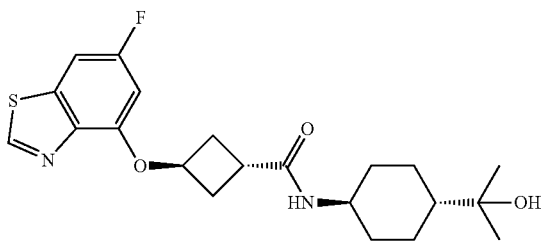 [SMILES: CC(C)(O)[C@H]1CC[C@H](NC(=O)[C@H]2C[C@H](Oc3cc(F)cc4scnc34)C2)CC1]

To an EtOAc (1 mL) solution of (trans)-3-((6-fluorobenzo[d]thiazol-4-yl)oxy)cyclobutanecarboxylic acid (Intermediate 59) (37 mg, 0.14 mmol), 2-((trans)-4-aminocyclohexyl)propan-2-ol (28 mg, 0.18 mmol) and N,N-diisopropylethylamine (0.1 mL, 0.6 mmol) was added, dropwise, a 50% solution of T3P in ethyl acetate (0.2 mL, 0.3 mmol). The reaction was stirred 1 h, diluted with ethyl acetate, and washed with saturated aqueous sodium bicarbonate, water and brine. The organics were dried over sodium sulfate, filtered and concentrated to give the title compound as a tan solid (69 mg, 91%). ¹H NMR (400 MHz, CDCl₃) δ 1.04-1.20 (m, 11H), 1.88 (d, J=11 Hz, 2H), 2.06 (d, J=11 Hz, 2H), 2.55-2.66 (m, 2H), 2.76-2.85 (m, 2H), 2.95-3.03 (m, 1H), 3.68-3.77 (m, 1H), 5.16 (quin, J=6 Hz, 1H), 5.49 (br s, 1H), 6.56 (d, J=11 Hz, 1H), 7.18 (d, J=8 Hz, 1H), 8.84 (s, 1H); LC-MS (LC-ES) M+H=407.

Example 141

3-((6-Fluorobenzo[d]thiazol-4-yl)oxy)-N-((trans)-4-(2-hydroxypropan-2-yl)cyclohexyl)azetidine-1-carboxamide

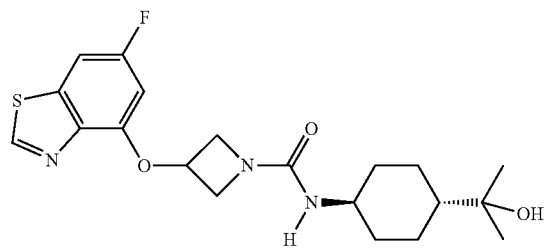 [SMILES: CC(C)(O)[C@H]1CC[C@H](NC(=O)N2CC(Oc3cc(F)cc4scnc34)C2)CC1]

To a stirred mixture of 4-(azetidin-3-yloxy)-6-fluorobenzo[d]thiazole hydrochloride (Intermediate 61) (115 mg, 0.441 mmol) in DCM (3.5 mL) was added N,N-diisopropylethylamine (0.4 mL, 2 mmol), followed by 4-nitrophenyl ((trans)-4-(2-hydroxypropan-2-yl)cyclohexyl)carbamate (Intermediate 3) (156 mg, 0.485 mmol). The mixture was stirred 1 h, diluted with DCM, washed with 1 N aqueous NaOH, water and brine, dried over Na₂SO₄ and filtered. Solvent was removed under reduced pressure. The residue was purified on silica gel, eluting with a 10%-50% EtOAc-EtOH (3:1) in hexanes gradient. The appropriate fractions were combined, evaporated under reduced pressure and placed in vacuo to give the title compound (128 mg, 71%). ¹H NMR (400 MHz, CD₃OD) δ 1.14 (s, 6H), 1.15-1.24 (m, 5H), 1.89 (d, J=12 Hz, 2H), 1.95 (d, J=12 Hz, 2H), 4.07 (dd, J=9, 4 Hz, 2H), 4.42 (dd, J=9, 6 Hz, 2H), 5.24-5.31 (m, 1H), 6.25 (d, J=8 Hz, 1H), 6.73 (dd, J=11, 2 Hz, 1H), 7.45 (dd, J=8, 2 Hz, 1H), 9.14 (s, 1H); LC-MS (LC-ES) M+H=408.

Example 142

Racemic N-((trans)-4-((1,1-Difluoropropan-2-yl)amino)cyclohexyl)-3-((6-fluorobenzo[d]thiazol-4-yl)oxy)azetidine-1-carboxamide

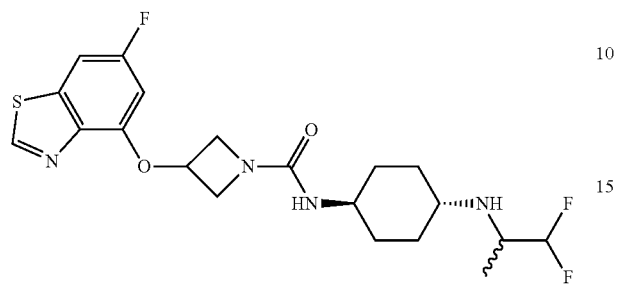

To 4-nitrophenyl chloroformate (103 mg, 0.51 mmol) in acetonitrile (3 mL) at 0° C. was slowly added (trans)-N1-(1,1-difluoropropan-2-yl)cyclohexane-1,4-diamine (Intermediate 17) (70 mg, 0.36 mmol) in acetonitrile (3 mL). After one hour, N,N-diisopropylethylamine (0.08 mL, 0.4 mmol) was added, and after 5 h the solvent was removed in vacuo. To the residue was added DMF (2 mL), then 4-(azetidin-3-yloxy)-6-fluorobenzo[d]thiazole hydrochloride (Intermediate 61) (108 mg, 0.36 mmol) and N,N-diisopropylethylamine (0.08 mL, 0.4 mmol). The mixture was stirred for 18 h and loaded onto a semi-prep HPLC (NH$_4$OH as modifier) to afford the title compound as a light tan solid (43.4 mgs, 26.9%). $^1$H NMR (400 MHz, CDCl$_3$) δ 1.04-1.23 (m, 8H), 1.78-1.90 (m, 2H), 1.91-2.07 (m, 2H), 2.53 (br s, 1H), 2.90-3.08 (m, 1H), 3.55-3.65 (m, 1H), 3.99 (d, J=8 Hz, 1H), 4.17 (dd, J=9, 4 Hz, 2H), 4.32-4.40 (m, 2H), 5.15-5.25 (m, 1H), 5.57 (td, J=56, 4 Hz 1H), 6.44 (d, J=10 Hz, 1H), 7.26 (d, J=8 Hz, 1H), 8.86 (s, 1H); LC-MS (LC-ES) M+H=443.

Example 143

Racemic tert-Butyl 3-((trans)-3-(5-fluoro-2-methoxyphenoxy)cyclobutanecarboxamido)pyrrolidine-1-carboxylate

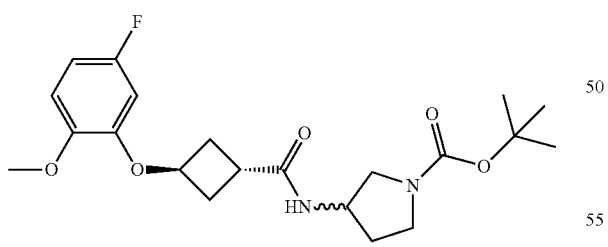

To a DMF (2 mL) solution of (trans)-3-(5-fluoro-2-methoxyphenoxy)cyclobutanecarboxylic acid (Intermediate 69) (115 mg, 0.479 mmol) was added HATU (273 mg, 0.718 mmol) and N,N-diisopropylethylamine (0.25 mL, 1.4 mmol). After 5 minutes, tert-butyl 3-aminopyrrolidine-1-carboxylate (134 mg, 7.18 mmol) was added, and the mixture was stirred for 2 h, diluted with water and MeOH, and loaded onto a semi-prep HPLC (NH$_4$OH as modifier) to afford the title compound as a white solid (39 mg, 54%). $^1$H NMR (400 MHz, CDCl$_3$) δ 1.46 (s, 9H), 1.74-1.90 (m, 1H), 2.10-2.20 (m, 1H), 2.44-2.54 (m, 2H), 2.69-2.78 (m, 2H), 2.94-3.00 (m, 1H), 3.10-3.29 (m, 1H), 3.32-3.47 (m, 2H), 3.59-3.68 (m, 1H), 3.84 (s, 3H), 4.43-4.52 (m, 1H), 4.89-5.00 (m, 1H), 5.56 (d, J=8 Hz, 1H), 6.48 (dd, J=10, 3 Hz, 1H), 6.59 (td, J=8, 3 Hz, 1H), 6.78 (dd, J=9, 5 Hz, 1H); LC-MS (LC-ES) M+H=409.

Example 144

Racemic (trans)-N-(1-(5-Cyanothiazol-2-yl)pyrrolidin-3-yl)-3-(5-fluoro-2-methoxyphenoxy)cyclobutanecarboxamide

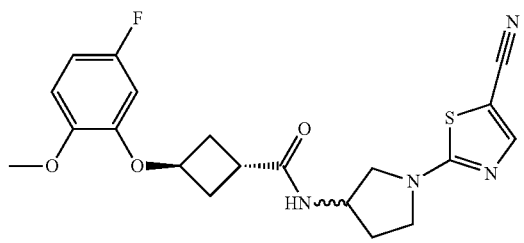 [SMILES: COc1ccc(F)cc1O[C@H]1C[C@H](C(=O)NC2CCN(c3ncc(C#N)s3)C2)C1]

To an NMP (1 mL) solution of (trans)-3-(5-fluoro-2-methoxyphenoxy)-N-(pyrrolidin-3-yl)cyclobutanecarboxamide hydrochloride (Intermediate 70) (38 mg, 0.11 mmol) and 2-chlorothiazole-5-carbonitrile (16 mg, 0.11 mmol) in a microwave reaction vial was added N,N-diisopropylethylamine (0.08 mL, 0.4 mmol). The reaction was heated in a microwave (135° C.) for 3.5 h, concentrated and loaded onto a semi-prep HPLC (NH$_4$OH as modifier) for purification to afford the title compound as a tan solid (31 mg, 62%). $^1$H NMR (400 MHz, CDCl$_3$) δ 2.09 (dd, J=13, 7 Hz, 1H), 2.42 (dd, J=13, 6 Hz, 1H), 2.46-2.58 (m, 2H), 2.74 (ddd, J=14, 7, 4 Hz, 2H), 2.95-3.04 (m, 1H), 3.40 (dd, J=11, 4 Hz, 1H), 3.57-3.69 (m, 2H), 3.81-3.89 (m, 1H), 3.84 (s, 3H), 4.64-4.74 (m, 1H), 4.94 (t, J=7 Hz, 1H), 5.59-5.72 (m, 1H), 6.47 (dd, J=10, 3 Hz, 1H), 6.59 (td, J=8, 3 Hz, 1H), 6.78 (dd, J=9, 5 Hz, 1H), 7.71 (s, 1H); LC-MS (LC-ES) M+H=417.

Example 145

Racemic (trans)-N-(1-(4-Cyanopyridin-2-yl)pyrrolidin-3-yl)-3-(5-fluoro-2-methoxyphenoxy)cyclobutanecarboxamide

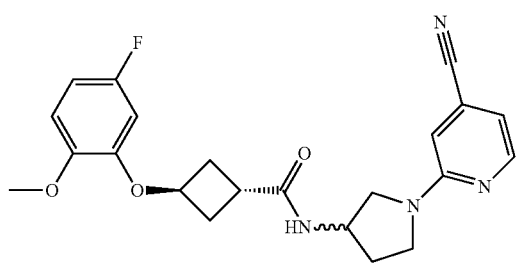 [SMILES: COc1ccc(F)cc1O[C@H]1C[C@H](C(=O)NC2CCN(c3cc(C#N)ccn3)C2)C1]

To an NMP (1 mL) solution of (trans)-3-(5-fluoro-2-methoxyphenoxy)-N-(pyrrolidin-3-yl)cyclobutanecarboxamide hydrochloride (Intermediate 70) (38 mg, 0.11 mmol) and 2-fluoroisonicotinonitrile (20 mg, 0.16 mmol) in a microwave reaction vial was added N,N-diisopropylethylamine (0.08 mL, 0.4 mmol). The reaction was heated in a microwave (120° C.) for 2 h, concentrated and loaded onto a semi-prep HPLC (NH₄OH as modifier) for purification to afford the title compound as a tan solid (31 mg, 69%). ¹H NMR (400 MHz, CDCl₃) δ 1.96-2.11 (m, 1H), 2.28-2.31 (m, 1H), 2.46-2.57 (m, 2H), 2.75 (ddd, J=12, 8, 4 Hz, 2H), 2.92-3.00 (m, 1H), 3.37 (dd, J=11, 4 Hz, 1H), 3.52-3.60 (m, 2H), 3.79 (dd, J=11, 6 Hz, 1H), 3.83 (s, 3H), 4.59-4.70 (m, 1H), 4.92-4.99 (m, 1H), 5.62 (d, J=7 Hz, 1H), 6.47 (dd, J=10, 3 Hz, 1H), 6.54 (s, 1H), 6.59 (td, J=8, 3 Hz, 1H), 6.73 (d, J=5 Hz, 1H), 6.78 (dd, J=9, 5 Hz, 1H), 8.26 (d, J=5 Hz, 1H); LC-MS (LC-ES) M+H=411.

Example 146

(trans)-3-(5-Fluoro-2-methoxyphenoxy)-N-(indolin-1-yl)cyclobutanecarboxamide

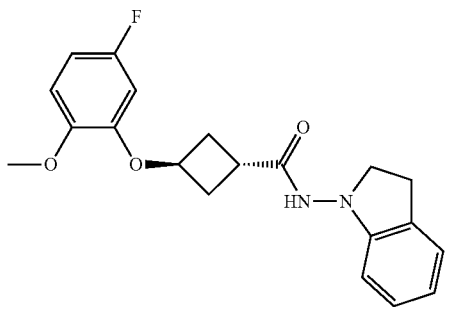 [SMILES: COc1ccc(F)cc1O[C@H]1C[C@H](C(=O)NN2CCc3ccccc32)C1]

To a DMF (2 mL) solution of (trans)-3-(5-fluoro-2-methoxyphenoxy)cyclobutanecarboxylic acid (Intermediate 69) (50 mg, 0.21 mmol) was added HATU (119 mg, 0.312 mmol) and N,N-diisopropylethylamine (0.11 mL, 0.62 mmol). After 5 minutes, indolin-1-amine hydrochloride (53 mg, 0.34 mmol) was added, and the mixture was stirred for 2 h, diluted with water and MeOH, and loaded onto a semi-prep HPLC (NH₄OH as modifier) to afford the title compound as a pale yellow foam (49 mg, 66%). ¹H NMR (400 MHz, CDCl₃) showed a mixture of tautomers: δ 2.45-2.60 (m, 2H), 2.77-2.89 (m, 2H), 2.93-3.19 (m, 3H), 3.56-3.80 (m, 2H), 3.81-3.92 (m, 3H), 4.79-5.02 (m, 1H), 6.42-6.64 (m, 3H), 6.65-6.97 (m, 3H), 7.08-7.21 (m, 2H); LC-MS (LC-ES) M+H=357.

Example 147

(trans)-N-(1-(5-Cyanothiazol-2-yl)azetidin-3-yl)-3-(5-fluoro-2-methoxyphenoxy)cyclobutanecarboxamide

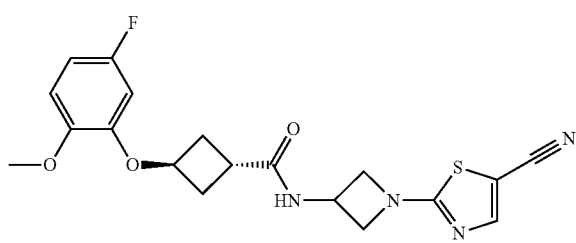 [SMILES: COc1ccc(F)cc1O[C@H]1C[C@H](C(=O)NC2CN(c3ncc(C#N)s3)C2)C1]

To an NMP (1 mL) solution of (trans)-N-(azetidin-3-yl)-3-(5-fluoro-2-methoxyphenoxy)cyclobutanecarboxamide, trifluoroacetic acid salt (Intermediate 71) (27 mg, 0.066 mmol) and 2-chlorothiazole-5-carbonitrile (14 mg, 0.099 mmol) in a microwave reaction vial was added N,N-diisopropylethylamine (0.04 mL, 0.2 mmol). The reaction was heated in a microwave (145° C.) for 1.5 h, concentrated and loaded onto a semi-prep HPLC (TFA as modifier) for purification. The purified sample was dissolved in DCM, washed with saturated aqueous NaHCO₃ solution, and then concentrated to afford the title compound as a pale yellow solid (22 mg, 84%). ¹H NMR (400 MHz, CDCl₃) δ 2.53 (ddd, J=13, 10, 6 Hz, 2H), 2.75 (ddd, J=14, 7, 4 Hz, 2H), 2.96-3.09 (s, 1H), 3.82 (s, 3H), 4.04 (dd, J=10, 5 Hz, 2H), 4.50 (t, J=9 Hz, 2H), 4.92-5.01 (m, 2H), 5.96 (d, J=7 Hz, 1H), 6.46 (dd, J=10, 3 Hz, 1H), 6.60 (td, J=8, 3 Hz, 1H), 6.79 (dd, J=9, 5 Hz, 1H), 7.68 (s, 1H); LC-MS (LC-ES) M+H=403.

Example 148

(trans)-N-(2-(4-Cyanopyridin-2-yl)-2-azaspiro[3.3]heptan-6-yl)-3-(5-fluoro-2-methoxyphenoxy)cyclobutanecarboxamide

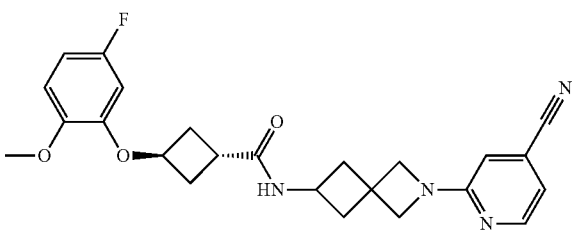 [SMILES: COc1ccc(F)cc1O[C@H]1C[C@H](C(=O)NC2CC3(C2)CN(c2cc(C#N)ccn2)C3)C1]

To a DMF (2 mL) solution of (trans)-3-(5-fluoro-2-methoxyphenoxy)cyclobutanecarboxylic acid (Intermediate 69) (50 mg, 0.21 mmol) was added HATU (95 mg, 0.25 mmol)) and N,N-diisopropylethylamine (0.15 mL, 0.83 mmol). After 5 minutes, 2-(6-amino-2-azaspiro[3.3]heptan-2-yl)isonicotinonitrile, di-trifluoroacetic acid salt (Intermediate 72) (120 mg, 0.27 mmol) was added, and the mixture was stirred for 1 h, diluted with water and extracted with DCM. The organic extracts were washed with water and saturated aqueous NaHCO₃ solution, dried over MgSO₄, filtered and concentrated. The residue was purified on silica gel, eluting with a 25%-60% EtOAc/EtOH (3/1) in hexanes gradient to give the title compound as a white solid (50 mg, 55%). ¹H NMR (400 MHz, CDCl₃) δ 2.11-2.22 (m, 2H), 2.44-2.55 (m, 2H), 2.68-2.79 (m, 4H), 2.86-2.96 (m, 1H), 3.84 (s, 3H), 3.99 (s, 2H), 4.11 (s, 2H), 4.31-4.41 (m, 1H), 4.93 (t, J=7 Hz, 1H), 5.55 (d, J=7 Hz, 1H), 6.42 (s, 1H), 6.47 (dd, J=10, 3 Hz, 1H), 6.59 (td, J=8, 3 Hz, 1H), 6.72-6.84 (m, 2H), 8.23 (d, J=5 Hz, 1H); LC-MS (LC-ES) M+H=437.

Example 149

(trans)-N-(1-(4-Cyanopyridin-2-yl)azetidin-3-yl)-3-(5-fluoro-2-methoxyphenoxy)cyclobutanecarboxamide

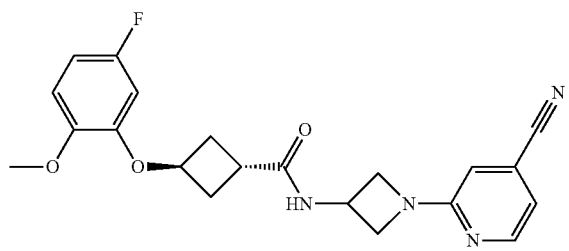 [SMILES: COc1ccc(F)cc1O[C@H]1C[C@H](C(=O)NC2CN(c3cc(C#N)ccn3)C2)C1]

To an NMP (1 mL) solution of (trans)-N-(azetidin-3-yl)-3-(5-fluoro-2-methoxyphenoxy)cyclobutanecarboxamide, trifluoroacetic acid salt (Intermediate 71) (80 mg, 0.20 mmol) and 2-fluoroisonicotinonitrile (48 mg, 0.39 mmol) in a microwave reaction vial was added N,N-diisopropylethylamine (0.10 mL, 0.59 mmol). The reaction was heated in a microwave (110° C.) for 80 min, concentrated and loaded onto a semi-prep HPLC (TFA as modifier) for purification. The purified sample was dissolved in DCM, washed with saturated aqueous NaHCO$_3$ solution, and then concentrated to afford the title compound as a white solid (75 mg, 97%). $^1$H NMR (400 MHz, CDCl$_3$) δ 2.53 (ddd, J=13, 10, 6 Hz, 2H), 2.77 (ddd, J=14, 7, 4 Hz, 2H), 2.96-3.05 (m, 1H), 3.84 (s, 3H), 3.88 (dd, J=9, 5 Hz, 2H), 4.42 (t, J=8 Hz, 2H), 4.85-4.96 (m, 2H), 5.91 (d, J=7 Hz, 1H), 6.46-6.50 (m, 2H), 6.59 (td, J=8, 3 Hz, 1H), 6.76-6.81 (m, 2H), 8.26 (dd, J=5, 1 Hz, 1H); LC-MS (LC-ES) M+H=397.

Example 150

(trans)-3-(5-Fluoro-2-methoxyphenoxy)-N-((trans)-4-methoxycyclohexyl)cyclobutanecarboxamide

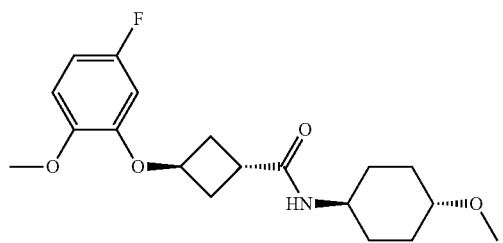

To a DMF (2 mL) solution of (trans)-3-(5-fluoro-2-methoxyphenoxy)cyclobutanecarboxylic acid (Intermediate 69) (43 mg, 0.18 mmol) was added HATU (102 mg, 0.268 mmol) and N,N-diisopropylethylamine (0.09 mL, 0.5 mmol). After 10 minutes, (trans)-4-methoxycyclohexanamine (23 mg, 0.18 mmol) was added, and the mixture was stirred for 2 h, diluted with water and MeOH, and loaded onto a semi-prep HPLC (NH$_4$OH as modifier) to afford the title compound as a white solid (36 mg, 58%). $^1$H NMR (400 MHz, CDCl$_3$) δ 1.06-1.20 (m, 2H), 1.26-1.46 (m, 2H), 1.91-2.14 (m, 4H), 2.41-2.56 (m, 2H), 2.66-2.81 (m, 2H), 2.82-3.00 (m, 1H), 3.06-3.18 (m, 1H), 3.34 (s, 3H), 3.71-3.85 (m, 1H), 3.84 (s, 3H), 4.89-5.05 (m, 1H), 5.18-5.31 (m, 1H), 6.45-6.52 (m, 1H), 6.52-6.65 (m, 1H), 6.68-6.83 (m, 1H); LC-MS (LC-ES) M+H=352.

Example 151

(trans)-3-(5-Fluoro-2-methoxyphenoxy)-N-((trans)-4-(3-oxomorpholino)cyclohexyl)cyclobutanecarboxamide

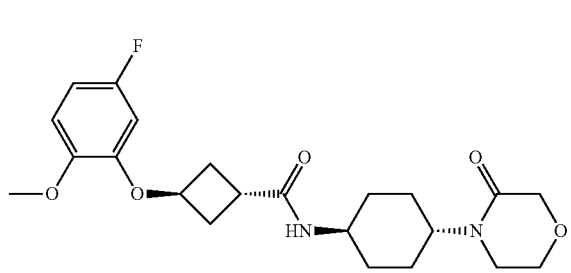 [SMILES: COc1ccc(F)cc1O[C@H]1C[C@H](C(=O)N[C@H]2CC[C@H](N3CCOCC3=O)CC2)C1]

To a DMF (2 mL) solution of (trans)-3-(5-fluoro-2-methoxyphenoxy)cyclobutanecarboxylic acid (Intermediate 69) (50 mg, 0.21 mmol) was added HATU (119 mg, 0.312 mmol) and N,N-diisopropylethylamine (0.11 mL, 0.62 mmol). After 10 minutes, 4-((trans)-4-aminocyclohexyl)morpholin-3-one (Intermediate 73) (41 mg, 0.21 mmol) was added, and the mixture was stirred for 2 h, diluted with water and MeOH, and loaded onto a semi-prep HPLC (NH$_4$OH as modifier) to afford the title compound as a light tan solid (43 mg, 49%). $^1$H NMR (400 MHz, CD$_3$OD) δ 1.26-1.41 (m, 2H), 1.60-1.70 (m, 4H), 1.90-1.99 (m, 2H), 2.29-2.41 (m, 2H), 2.59 (ddd, J=13, 7, 4 Hz, 2H), 3.04 (dt, J=10, 5 Hz, 1H), 3.27 (dt, J=3, 2 Hz, 2H), 3.29-3.34 (m, 2H), 3.56-3.62 (m, 1H), 3.77 (s, 3H), 3.80-3.86 (m, 2H), 4.08 (s, 2H), 4.25-4.34 (m, 1H), 6.48-6.61 (m, 2H), 6.87 (dd, J=9, 5 Hz, 1H); LC-MS (LC-ES) M+H=421.

Example 152

(trans)-3-(5-Fluoro-2-methoxyphenoxy)-N-(1-(1-methyl-1H-tetrazol-5-yl)piperidin-4-yl)cyclobutanecarboxamide

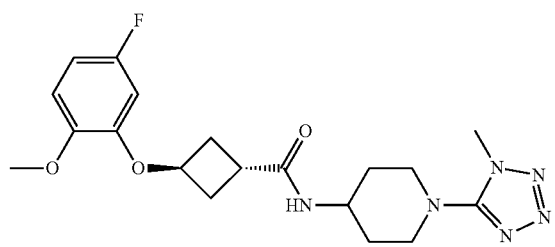 [SMILES: COc1ccc(F)cc1O[C@H]1C[C@H](C(=O)NC2CCN(c3nnnn3C)CC2)C1]

To a DMF (6 mL) solution of (trans)-3-(5-fluoro-2-methoxyphenoxy)cyclobutanecarboxylic acid (Intermediate 69) (133 mg, 0.554 mmol) was added HATU (316 mg, 0.830 mmol) and N,N-diisopropylethylamine (0.29 mL, 1.7 mmol). After 10 minutes, 1-(1-methyl-1H-tetrazol-5-yl)piperidin-4-amine (61 mg, 0.33 mmol) was added, and the mixture was stirred for 2 h, diluted with water and MeOH, and loaded onto a semi-prep HPLC (NH$_4$OH as modifier) to afford the title compound as a light tan solid (62 mg, 46%). $^1$H NMR (400 MHz, CDCl$_3$) δ 1.55-1.66 (m, 2H), 2.07 (d, J=10 Hz, 2H), 2.46-2.55 (m, 2H), 2.74 (ddt, J=10, 7, 4, 4 Hz, 2H), 2.90-3.00 (m, 1H), 3.14-3.23 (m, 2H), 3.58 (d, J=13 Hz, 2H), 3.84 (s, 3H), 3.88 (s, 3H), 4.03-4.11 (m, 1H), 4.89-5.00 (m, 1H), 5.46 (d, J=8 Hz, 1H), 6.47 (dd, J=10, 3 Hz, 1H), 6.59 (td, J=8, 3 Hz, 1H), 6.78 (dd, J=9, 5 Hz, 1H); LC-MS (LC-ES) M+H=405.

Example 153

Racemic (trans)-3-(5-Fluoro-2-methoxyphenoxy)-N-(2-oxo-1,2,3,4-tetrahydroquinolin-4-yl)cyclobutanecarboxamide

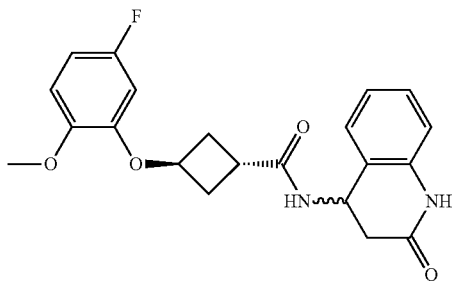 [SMILES: COc1ccc(F)cc1O[C@H]1C[C@H](C(=O)NC2CC(=O)Nc3ccccc32)C1]

To a DMF (6 mL) solution of (trans)-3-(5-fluoro-2-methoxyphenoxy)cyclobutanecarboxylic acid (Intermediate 69) (120 mg, 0.500 mmol) was added HATU (285 mg, 0.749 mmol) and N,N-diisopropylethylamine (0.26 mL, 1.5 mmol). After 10 minutes, 4-amino-3,4-dihydroquinolin-2 (1H)-one (81 mg, 0.50 mmol) was added, and the mixture was stirred for 2 h, diluted with water and MeOH, and loaded onto a semi-prep HPLC (NH$_4$OH as modifier) to afford the title compound as a light tan solid (89 mg, 46%). $^1$H NMR (400 MHz, CDCl$_3$) δ 2.43-2.52 (m, 2H), 2.68-2.82 (m, 2H), 2.88 (d, J=5 Hz, 2H), 2.91-3.02 (m, 1H), 3.82 (s, 3H), 4.89-5.01 (m, 1H), 5.29-5.38 (m, 1H), 5.73 (d, J=7 Hz, 1H), 6.48 (dd, J=10, 3 Hz, 1H), 6.59 (td, J=8, 3 Hz, 1H), 6.75-6.86 (m, 2H), 7.05-7.12 (m, 1H), 7.27-7.31 (m, 1H), 7.36 (m, J=7 Hz, 1H), 7.98 (br s, 1H); LC-MS (LC-ES) M+H=385.

Example 154

(trans)-3-(5-Fluoro-2-methoxyphenoxy)-N-(1-(thiazol-2-yl)piperidin-4-yl)cyclobutanecarboxamide

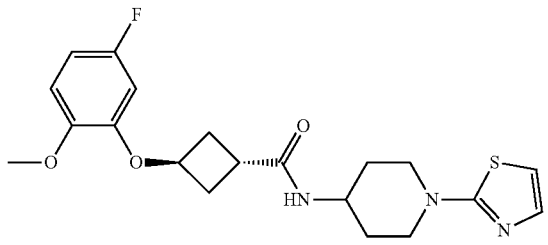 [SMILES: COc1ccc(F)cc1O[C@H]1C[C@H](C(=O)NC2CCN(c3nccs3)CC2)C1]

To an NMP (1 mL) solution of (trans)-3-(5-fluoro-2-methoxyphenoxy)-N-(piperidin-4-yl)cyclobutanecarboxamide hydrochloride (Intermediate 74) (30 mg, 0.093 mmol) and 2-chlorothiazole (16.69 mg, 0.140 mmol) in a microwave reaction vial was added triethylamine (0.06 mL, 0.5 mmol). The reaction was heated in a microwave at 130° C. for 3 h, then at 140° C. for 2 h, concentrated and loaded onto a semi-prep HPLC (NH$_4$OH as modifier) to afford the title compound as a light tan solid (16 mg, 42%). $^1$H NMR (400 MHz, CDCl$_3$) δ 1.45-1.68 (m, 2H), 2.06 (d, J=12 Hz, 2H), 2.42-2.58 (m, 2H), 2.70-2.79 (m, 2H), 2.90-3.01 (m, 1H), 3.10-3.25 (m, 2H), 3.84 (s, 3H), 3.95-4.08 (m, 3H), 4.95 (t, J=6 Hz, 1H), 5.34 (d, J=8 Hz, 1H), 6.42-6.51 (m, 1H), 6.54-6.64 (m, 2H), 6.78 (dd, J=9, 5 Hz, 1H), 7.18 (d, J=3 Hz, 1H); LC-MS (LC-ES) M+H=406.

Example 155

(trans)-N-(1-(4-Cyanopyridin-2-yl)piperidin-4-yl)-3-(5-fluoro-2-methoxyphenoxy)cyclobutanecarboxamide

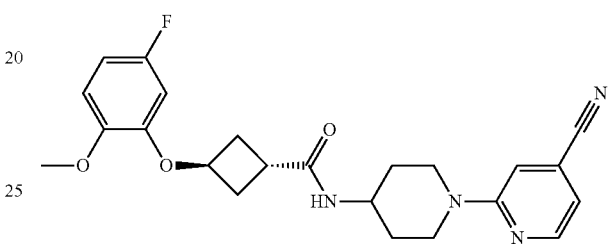

To an NMP (1 mL) solution of (trans)-3-(5-fluoro-2-methoxyphenoxy)-N-(piperidin-4-yl)cyclobutanecarboxamide hydrochloride (Intermediate 74) (40 mg, 0.12 mmol) and 2-fluoroisonicotinonitrile (23 mg, 0.19 mmol) in a microwave reaction vial was added triethylamine (0.09 mL, 0.6 mmol). The reaction was heated in a microwave at 120° C. for 2 h and loaded onto a semi-prep HPLC (NH$_4$OH as modifier) to afford the title compound as a tan solid (18 mg, 34%). $^1$H NMR (400 MHz, CDCl$_3$) δ 1.33-1.48 (m, 2H), 2.07 (d, J=10 Hz, 2H), 2.50 (ddd, J=13, 10, Hz, 2H), 2.75 (ddd, J=14, 7, 4 Hz, 2H), 2.90-3.00 (m, 1H), 3.06 (t, J=12 Hz, 2H), 3.84 (s, 3H), 4.08 (dt, J=7, 4 Hz, 1H), 4.28 (d, J=14 Hz, 2H), 4.90-5.02 (m, 1H), 5.31 (d, J=8 Hz, 1H), 6.48 (dd, J=10, 3 Hz, 1H), 6.59 (td, J=8, 3 Hz, 1H), 6.72-6.81 (m, 2H), 6.84 (s, 1H), 8.27 (d, J=5 Hz, 1H); LC-MS (LC-ES) M+H=425.

Example 156

(trans)-N-(1-(3-Chloro-4-methoxybenzyl)piperidin-4-yl)-3-(5-fluoro-2-methoxyphenoxy)cyclobutanecarboxamide

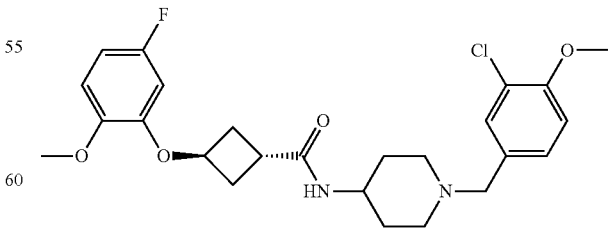

To a DMF (10 mL) solution of (trans)-3-(5-fluoro-2-methoxyphenoxy)-N-(piperidin-4-yl)cyclobutanecarboxamide hydrochloride (Intermediate 74) (100 mg, 0.279 mmol) and 4-(bromomethyl)-2-chloro-1-methoxybenzene (79 mg, 0.33 mmol) was added triethylamine (0.19 mL, 1.4 mmol). After 3 h, the mixture was loaded onto a semi-prep HPLC (NH4OH as modifier) to afford the title compound as a light tan solid (92 mg, 69%). $^1$H NMR (400 MHz, CDCl$_3$) δ 1.40-1.52 (m, 2H), 1.92 (d, J=11 Hz, 2H), 2.06-2.18 (m, 2H), 2.44-2.55 (m, 2H), 2.69-2.84 (m, 4H), 2.88-2.95 (m, 1H), 3.41 (s, 2H), 3.75-3.83 (m, 1H), 3.84 (s, 3H), 3.89 (s, 3H), 4.89-4.97 (m, 1H), 5.29 (d, J=8 Hz, 1H), 6.48 (dd, J=10, 3 Hz, 1H), 6.58 (td, J=8, 3 Hz, 1H), 6.77 (dd, J=9, 5 Hz, 1H), 6.86 (d, J=8 Hz, 1H), 7.14 (dd, J=8, 2 Hz, 1H), 7.34 (d, J=2 Hz, 1H); LC-MS (LC-ES) M+H=477.

Example 157

(trans)-3-(5-Fluoro-2-methoxyphenoxy)-N-(1-(pyridin-2-yl)piperidin-4-yl)cyclobutanecarboxamide

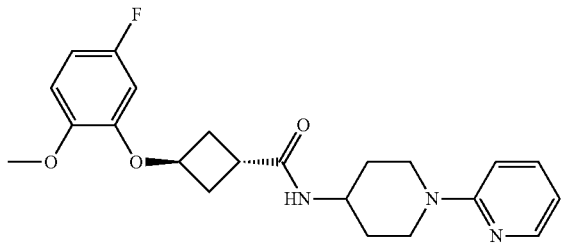 [SMILES: COc1ccc(F)cc1O[C@H]1C[C@H](C(=O)NC2CCN(c3ccccn3)CC2)C1]

To a DMF (10 mL) solution of (trans)-3-(5-fluoro-2-methoxyphenoxy)cyclobutanecarboxylic acid (Intermediate 69) (63 mg, 0.26 mmol) was added HATU (150 mg, 0.393 mmol) and N,N-diisopropylethylamine (0.12 mL, 0.66 mmol). After 1 h, 1-(pyridin-2-yl)piperidin-4-amine (35 mg, 0.20 mmol) was added, and the mixture was stirred for 2 days, diluted with water and MeOH, and loaded onto a semi-prep HPLC (NH4OH as modifier) to afford the title compound as a light tan solid (40 mg, 38%). $^1$H NMR (400 MHz, CDCl$_3$) δ 1.36-1.49 (m, 2H), 2.05 (d, J=11 Hz, 2H), 2.41-2.53 (m, 2H), 2.66-2.77 (m, 2H), 2.89-3.06 (m, 3H), 3.81 (s, 3H), 4.00-4.10 (m, 1H), 4.25 (d, J=14 Hz, 1H), 4.89-5.03 (m, 1H), 5.29-5.34 (m, 1H), 6.49 (d, J=10 Hz, 1H), 6.60-6.64 (m, 2H), 6.68 (d, J=8 Hz, 1H), 6.74-6.83 (m, 1H), 7.42-7.53 (m, 1H), 8.18 (s, 1H); LC-MS (LC-ES) M+H=400.

Example 158

2-((trans)-3-(5-Fluoro-2-methoxyphenoxy)cyclobutanecarboxamido)-N,N-dimethyloxazole-4-carboxamide

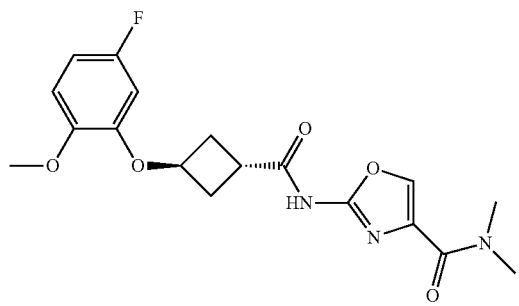

To a DMF (2 mL) solution of 2-((trans)-3-(5-fluoro-2-methoxyphenoxy)cyclobutanecarboxamido)oxazole-4-carboxylic acid (Intermediate 75) (30 mg, 0.086 mmol) was added HATU (39 mg, 0.10 mmol) and N,N-diisopropylethylamine (0.03 mL, 0.2 mmol). After 5 minutes, dimethylamine (0.05 mL, 0.1 mmol) was added, and the mixture was stirred for 2 h and was loaded onto a semi-prep HPLC (NH4OH as modifier) to afford the title compound as a tan solid (2 mg, 6%). $^1$H NMR (400 MHz, CD$_3$OD) δ 2.45-2.56 (m, 2H), 2.72-2.84 (m, 2H), 3.04-3.16 (m, 2H), 3.31 (s, 3H), 3.35 (s, 3H), 3.82 (s, 3H), 4.81-4.90 (m, 1H), 6.54-6.66 (m, 2H), 6.86-6.96 (m, 1H), 8.07 (s, 1H); LC-MS (LC-ES) M+H=378.

Example 159

(trans)-N-(6-Cyanopyridin-2-yl)-3-(5-fluoro-2-methoxyphenoxy)cyclobutanecarboxamide

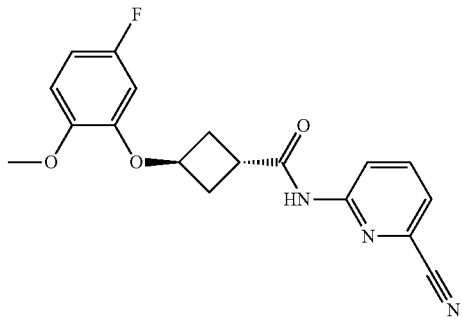 [SMILES: COc1ccc(F)cc1O[C@H]1C[C@H](C(=O)Nc2cccc(C#N)n2)C1]

To a DMF (4 mL) solution of (trans)-3-(5-fluoro-2-methoxyphenoxy)cyclobutanecarboxylic acid (Intermediate 69) (80 mg, 0.33 mmol) was added HATU (152 mg, 0.400 mmol) and N,N-diisopropylethylamine (0.12 mL, 0.66 mmol). After 1 h, 6-aminopicolinonitrile (59.5 mg, 0.500 mmol) was added, and the mixture was stirred for 18 h, diluted with water and MeOH, and loaded onto a semi-prep HPLC (NH4OH as modifier) to afford the title compound as a light tan solid (9 mg, 8%). $^1$H NMR (400 MHz, CD$_3$OD) δ 2.41-2.52 (m, 2H), 2.66-2.77 (m, 2H), 3.30-3.38 (m, 1H), 3.82 (s, 3H), 4.78-4.90 (m, 1H), 6.54-6.65 (m, 2H), 6.89-6.96 (m, 1H), 7.83 (d, J=9 Hz, 1H), 8.35-8.42 (m, 1H), 8.85 (s, 1H); LC-MS (LC-ES) M+H=342.

Example 160

Racemic (trans)-3-(5-Fluoro-2-methoxyphenoxy)-N-(6-(2-hydroxypropan-2-yl)spiro[3.3]heptan-2-yl)cyclobutanecarboxamide

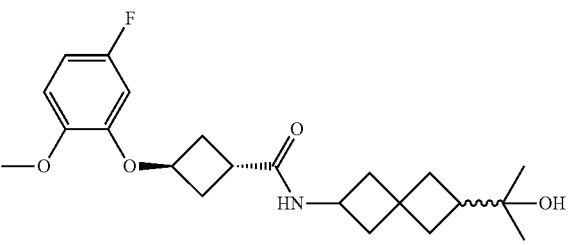 [SMILES: COc1ccc(F)cc1O[C@H]1C[C@H](C(=O)NC2CC3(C2)CC(C(C)(C)O)C3)C1]

To a DMF (2 mL) solution of (trans)-3-(5-fluoro-2-methoxyphenoxy)cyclobutanecarboxylic acid (Intermediate 69) (50 mg, 0.21 mmol) was added HATU (95 mg, 0.25 mmol) and N,N-diisopropylethylamine (0.07 mL, 0.4 mmol). After 5 minutes, 2-(6-aminospiro[3.3]heptan-2-yl)propan-2-ol (Intermediate 43) (42 mg, 0.25 mmol) was added, and the mixture was stirred for 2 h and was loaded onto a semi-prep HPLC (NH$_4$OH as modifier) to afford the title compound as a pale yellow solid (31 mg, 38%). $^1$H NMR (400 MHz, CDCl$_3$) δ 1.11 (d, J=4 Hz, 6H), 1.70-2.08 (m, 6H), 2.15-2.38 (m, 2H), 2.40-2.61 (m, 3H), 2.66-2.80 (m, 2H), 2.85-2.96 (m, 1H), 3.85 (s, 3H), 4.22-4.39 (m, 1H), 4.86-5.0 (m, 1H), 5.58 (d, J=7 Hz, 1H), 6.49 (d, J=10 Hz, 1H), 6.59 (t, J=7 Hz, 1H), 6.74-6.84 (m, 1H); LC-MS (LC-ES) M+H=392.

Example 161

Racemic (trans)-3-(5-Fluoro-2-methoxyphenoxy)-N-((trans)-4-((1,1,1-trifluoropropan-2-yl)amino)cyclohexyl)cyclobutanecarboxamide

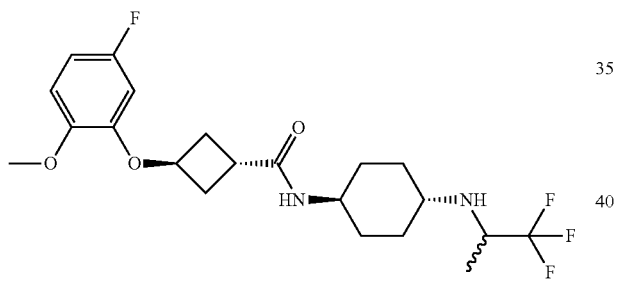

To a DMF (2 mL) solution of (trans)-3-(5-fluoro-2-methoxyphenoxy)cyclobutanecarboxylic acid (Intermediate 69) (40 mg, 0.17 mmol) was added HATU (76 mg, 0.20 mmol) and N,N-diisopropylethylamine (0.09 mL, 0.5 mmol). After 5 minutes, (trans)-N1-(1,1,1-trifluoropropan-2-yl)cyclohexane-1,4-diamine dihydrochloride (Intermediate 76) (47 mg, 0.17 mmol) was added, and the mixture was stirred for 2 h and loaded onto a semi-prep HPLC (NH$_4$OH as modifier) to afford the title compound as a pale yellow solid (42 mg, 58%). $^1$H NMR (400 MHz, CD$_3$OD) δ 1.16-1.30 (m, 7H), 1.87-2.01 (m, 4H), 2.34-2.41 (m, 2H), 2.54-2.65 (m, 3H), 3.06-3.11 (m, 1H), 3.29-3.34 (m, 1H), 3.57-3.68 (m, 1H), 3.80 (s, 3H), 4.84-4.90 (m, 1H), 6.54-6.64 (m, 2H), 6.83-6.84 (m, 1H); LC-MS (LC-ES) M+H=433.

Example 162

(trans)-N-((trans)-3-(5-Fluoro-2-methoxyphenoxy)cyclobutyl)-4-(2-hydroxypropan-2-yl)cyclohexanecarboxamide

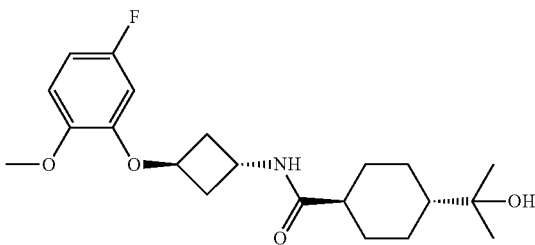 [SMILES: COc1ccc(F)cc1O[C@H]1C[C@H](NC(=O)[C@H]2CC[C@H](C(C)(C)O)CC2)C1]

To a DMF (3 mL) solution of (trans)-4-(2-hydroxypropan-2-yl)cyclohexanecarboxylic acid (Intermediate 78) (60 mg, 0.32 mmol) was added HATU (147 mg, 0.387 mmol) and N,N-diisopropylethylamine (0.14 mL, 0.77 mmol). After 5 minutes, (trans)-3-(5-fluoro-2-methoxyphenoxy)cyclobutanamine hydrochloride (Intermediate 77) (96 mg, 0.39 mmol) was added, and the mixture was stirred for 2 h and loaded onto a semi-prep HPLC (NH$_4$OH as modifier) to afford the title compound as a white solid (99 mg, 81%). $^1$H NMR (400 MHz, CD$_3$OD) δ 1.01-1.14 (m, 2H), 1.14 (s, 6H), 1.30 (d, J=12 Hz, 1H), 1.46 (dd, J=12, 3 Hz, 2H), 1.83-1.95 (m, 4H), 2.06-2.15 (m, 1H), 2.36-2.46 (m, 2H), 2.48-2.61 (m, 2H), 3.81 (s, 3H), 4.43 (t, J=6 Hz, 1H), 4.78-4.85 (m, 1H), 6.53 (dd, J=10, 3 Hz, 1H), 6.61 (td, J=9, 3 Hz, 1H), 6.92 (dd, J=9, 5 Hz, 1H); LC-MS (LC-ES) M+H=380.

Example 163

(trans)-N-(4-Acetylthiazol-2-yl)-3-(5-fluoro-2-methoxyphenoxy)cyclobutanecarboxamide

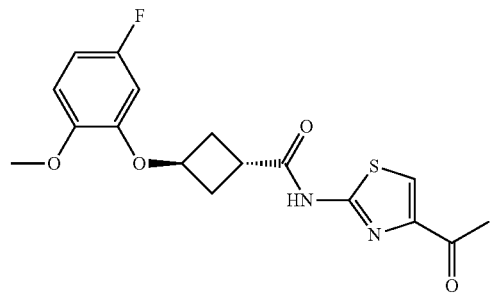 [SMILES: COc1ccc(F)cc1O[C@H]1C[C@H](C(=O)Nc2nc(C(C)=O)cs2)C1]

To a DMF (4 mL) solution of (trans)-3-(5-fluoro-2-methoxyphenoxy)cyclobutanecarboxylic acid (Intermediate 69) (100 mg, 0.416 mmol) was added HATU (190 mg, 0.500 mmol) and N,N-diisopropylethylamine (0.22 mL, 1.2 mmol). After 5 minutes, 1-(2-aminothiazol-4-yl)ethanone (65 mg, 0.46 mmol) was added, and the mixture was stirred for 12 h, quenched with water, extracted with EtOAc, dried over Na$_2$SO$_4$, filtered and concentrated. The residue was purified on silica gel, eluting with a 0%-100% EtOAc:EtOH (3:1) in hexanes gradient to give the title compound (108 mg, 64%). $^1$H NMR (400 MHz, CD$_3$SOCD$_3$) δ 2.22-2.40 (m, 2H), 2.37 (m, 3H), 2.67-2.81 (m, 2H), 3.39 (d, J=5 Hz, 1H), 3.73 (s, 3H), 4.81 (t, J=6 Hz, 1H), 6.61-6.70 (m, 2H), 6.93 (dd, J=9, 5 Hz, 1H), 8.06 (s, 1H), 12.44 (s, 1H); LC-MS (LC-ES) M+H=365.

Example 164

(trans)-N-(5-Acetylthiazol-2-yl)-3-(5-fluoro-2-methoxyphenoxy)cyclobutanecarboxamide

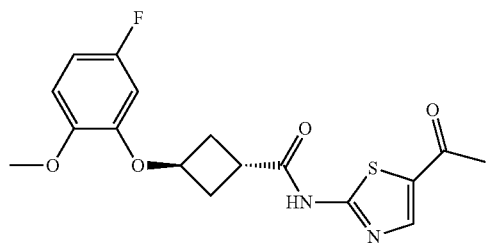 [SMILES: COc1ccc(F)cc1O[C@H]1C[C@H](C(=O)Nc2ncc(C(C)=O)s2)C1]

To a DMF (5 mL) solution of (trans)-3-(5-fluoro-2-methoxyphenoxy)cyclobutanecarboxylic acid (Intermediate 69) (100 mg, 0.416 mmol) was added HATU (190 mg, 0.500 mmol) and N,N-diisopropylethylamine (0.22 mL, 1.2 mmol). After 5 minutes, 1-(2-aminothiazol-5-yl)ethanone (59 mg, 0.42 mmol) was added, and the mixture was stirred for 3 h, quenched with water, extracted with EtOAc, dried over $Na_2SO_4$, filtered and concentrated. The residue was purified on silica gel, eluting with a 0%-100% EtOAc:EtOH (3:1) in hexanes gradient to give the title compound (65 mg, 42%). $^1$H NMR (400 MHz, $CD_3SOCD_3$) δ 2.29-2.35 (m, 2H), 2.48 (s, 3H), 2.72 (ddd, J=13, 7, 5 Hz, 2H), 3.35-3.42 (m, 1H), 3.73 (s, 3H), 4.74-4.83 (m, 1H), 6.59-6.67 (m, 2H), 6.93 (dd, J=9, 5 Hz, 1H), 8.33 (s, 1H), 12.55 (s, 1H); LC-MS (LC-ES) M+H=365.

Example 165

(trans)-3-(5-Fluoro-2-methoxyphenoxy)-N-(5-(2-hydroxypropan-2-yl)thiazol-2-yl)cyclobutanecarboxamide

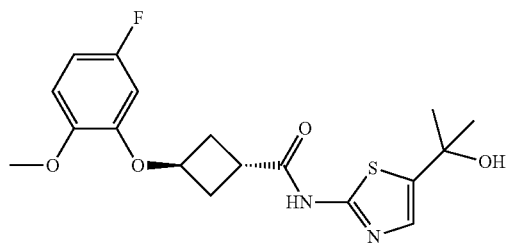 [SMILES: COc1ccc(F)cc1O[C@H]1C[C@H](C(=O)Nc2ncc(C(C)(C)O)s2)C1]

(trans)-N-(5-Acetylthiazol-2-yl)-3-(5-fluoro-2-methoxyphenoxy)cyclobutanecarboxamide (Example 164) (33 mg, 0.091 mmol) was stirred in THF (5 mL) at 0° C., and a 3.0 M solution of methylmagnesium bromide (0.06 mL, 0.2 mmol) in diethyl ether was added. The reaction was stirred 1 h, quenched with saturated aqueous $NH_4Cl$, extracted with EtOAc, and the organic extracts dried over $Na_2SO_4$, filtered, and concentrated under reduced pressure. The residue was purified on silica gel, eluting with a 0%-100% EtOAc:EtOH (3:1) in hexanes gradient to give the title compound (25 mg, 66%). $^1$H NMR ($CD_3OD$) δ 1.47 (s, 6H), 2.25-2.39 (m, 2H), 2.61-2.72 (m, 2H), 3.31-3.40 (m, 1H), 3.73 (s, 3H), 4.79-4.83 (m, 1H), 5.41 (s, 1H), 6.54-6.76 (m, 2H), 6.93 (dd, J=9, 6 Hz, 1H), 7.17 (s, 1H), 11.87 (s, 1H); LC-MS (LC-ES) M+H=381.

Example 166

(trans)-3-(5-Fluoro-2-methoxyphenoxy)-N-(5-methyl-1,3,4-thiadiazol-2-yl)cyclobutanecarboxamide

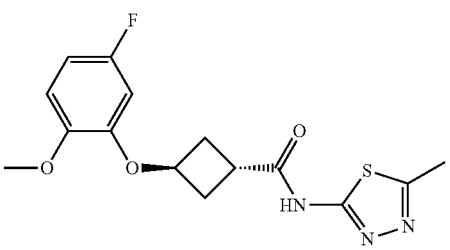

To a DMF (2 mL) solution of (trans)-3-(5-fluoro-2-methoxyphenoxy)cyclobutanecarboxylic acid (Intermediate 69) (50 mg, 0.21 mmol) was added HATU (95 mg, 0.25 mmol) and N,N-diisopropylethylamine (0.11 mL, 0.62 mmol). After 5 minutes, 5-methyl-1,3,4-thiadiazol-2-amine (24 mg, 0.21 mmol) was added, and the mixture was stirred for 3 h, quenched with water, extracted with EtOAc, dried over $Na_2SO_4$, filtered and concentrated. The residue was purified on silica gel, eluting with a 0%-100% EtOAc:EtOH (3:1) in hexanes gradient to give the title compound (42 mg, 60%). $^1$H NMR (400 MHz, $CD_3SOCD_3$) δ 2.25-2.39 (m, 2H), 2.59 (s, 3H), 2.70 (ddd, J=13, 7, 5 Hz, 2H), 3.30 (s, 3H), 3.41 (dt, J=10, 5 Hz, 1H), 4.80 (t, J=6 Hz, 1H), 6.54-6.69 (m, 2H), 6.93 (dd, J=9, 5 Hz, 1H), 12.37 (s, 1H); LC-MS (LC-ES) M+H=338.

Example 167

(trans)-N-(4-Cyclopropylthiazol-2-yl)-3-(5-fluoro-2-methoxyphenoxy)cyclobutanecarboxamide

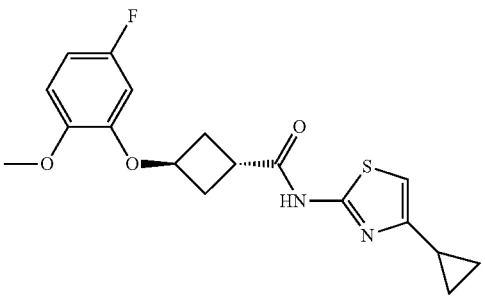 [SMILES: COc1ccc(F)cc1O[C@H]1C[C@H](C(=O)Nc2nc(C3CC3)cs2)C1]

To a DMF (2 mL) solution of (trans)-3-(5-fluoro-2-methoxyphenoxy)cyclobutanecarboxylic acid (Intermediate 69) (50 mg, 0.21 mmol) was added HATU (95 mg, 0.25 mmol) and N,N-diisopropylethylamine (0.11 mL, 0.62 mmol). After 5 minutes, 4-cyclopropylthiazol-2-amine (29 mg, 0.21 mmol) was added, and the mixture was stirred for 3 h, and quenched with water. The resulting solid was collected by filtration and dried to give the title compound (30 mg, 38%). $^1$H NMR (400 MHz, CD$_3$SOCD$_3$) δ 0.65-0.71 (m, 2H), 0.78-0.88 (m, 2H), 1.91-1.99 (m, 1H), 2.26-2.38 (m, 2H), 2.59-2.75 (m, 2H), 3.30 (s, 3H), 3.31-3.39 (m, 1H), 4.79 (t, J=6 Hz, 1H), 6.56-6.70 (m, 2H), 6.76 (s, 1H), 6.93 (dd, J=9, 6 Hz, 1H), 12.02 (s, 1H); LC-MS (LC-ES) M+H=363.

Example 168

(trans)-3-(5-Fluoro-2-methoxyphenoxy)-N-((trans)-4-(2-hydroxypropan-2-yl)cyclohexyl)cyclobutanecarboxamide

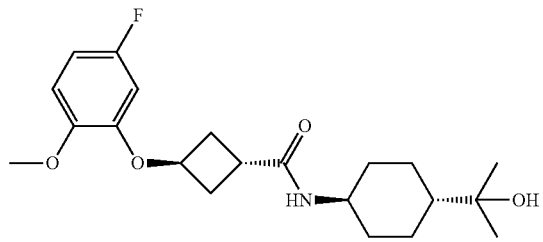 [SMILES: COc1ccc(F)cc1O[C@H]1C[C@H](C(=O)N[C@H]2CC[C@H](C(C)(C)O)CC2)C1]

To a DMF (5 mL) solution of (trans)-3-(5-fluoro-2-methoxyphenoxy)cyclobutanecarboxylic acid (Intermediate 69) (100 mg, 0.416 mmol) was added HATU (190 mg, 0.500 mmol) and N,N-diisopropylethylamine (0.22 mL, 1.2 mmol). After 5 minutes 2-((trans)-4-aminocyclohexyl)propan-2-ol (72 mg, 0.46 mmol)) was added, and the mixture was stirred for 12 h, quenched with water, extracted with EtOAc, dried over Na$_2$SO$_4$, filtered and concentrated. The residue was purified on silica gel, eluting with a 0%-100% EtOAc:EtOH (3:1) in hexanes gradient to give the title compound (118 mg, 75%). $^1$H NMR (400 MHz, CD$_3$SOCD$_3$) δ 0.82-1.12 (m, 5H), 1.00 (s, 6H), 1.63-1.76 (m, 4H), 2.12-2.21 (m, 2H), 2.47-2.51 (m, 2H), 2.89-3.00 (m, 1H), 3.46-3.52 (m, 1H), 3.66 (s, 3H), 3.99 (s, 1H), 4.76 (t, J=6 Hz, 1H), 6.45-6.51 (m, 1H), 6.66 (td, J=9, 3 Hz, 1H), 6.91 (dd, J=9, 6 Hz, 1H), 7.65 (d, J=8 Hz, 1H); LC-MS (LC-ES) M+H=380.

Example 169

(trans)-3-(5-Fluoro-2-methoxyphenoxy)-N-((trans)-4-(2-hydroxy-2-methylpropoxy)cyclohexyl)cyclobutanecarboxamide

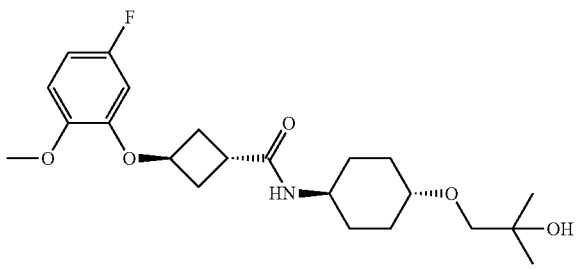 [SMILES: COc1ccc(F)cc1O[C@H]1C[C@H](C(=O)N[C@H]2CC[C@H](OCC(C)(C)O)CC2)C1]

To a DMF (5 mL) solution of (trans)-3-(5-fluoro-2-methoxyphenoxy)cyclobutanecarboxylic acid (Intermediate 69) (100 mg, 0.416 mmol) was added HATU (198 mg, 0.520 mmol) and N,N-diisopropylethylamine (0.22 mL, 1.2 mmol). After 5 minutes 1-(((trans)-4-aminocyclohexyl)oxy)-2-methylpropan-2-ol (Intermediate 23) (97 mg, 0.52 mmol) was added, and the mixture was stirred for 18 h, quenched with water, extracted with EtOAc, dried over Na$_2$SO$_4$, filtered and concentrated. The residue was purified on silica gel, eluting with a 0%-100% EtOAc:EtOH (3:1) in hexanes gradient to give the title compound (118 mg, 69%) as a white solid. $^1$H NMR (400 MHz, CD$_3$SOCD$_3$) δ 1.03 (s, 6H), 1.10-1.22 (m, 4H), 1.71-1.79 (m, 2H), 1.89-1.96 (m, 2H), 2.14-2.24 (m, 2H), 2.50-2.56 (m, 2H), 2.92-3.00 (m, 1H), 3.12 (s, 2H), 3.13-3.19 (m, 1H), 3.45-3.54 (m, 1H), 3.71 (s, 3H), 4.18 (s, 1H), 4.72-4.79 (m, 1H), 6.51-6.58 (m, 1H), 6.62-6.71 (m, 1H), 6.87-6.95 (m, 1H), 7.65-7.73 (m, 1H); LC-MS (LC-ES) M+H=410.

Example 170

Racemic (trans)-N-(6-(2-Hydroxypropan-2-yl)spiro[3.3]heptan-2-yl)-3-(quinolin-8-yloxy)cyclobutanecarboxamide

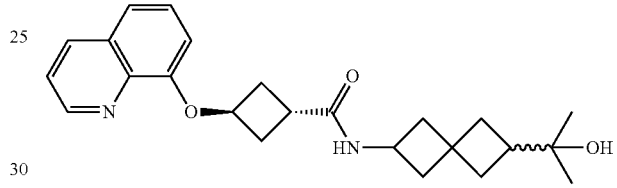

To a DMF (2 mL) solution of (trans)-3-(5-fluoro-2-methoxyphenoxy)cyclobutanecarboxylic acid (Intermediate 79) (50 mg, 0.21 mmol) was added HATU (94 mg, 0.25 mmol) and N,N-diisopropylethylamine (0.07 mL, 0.4 mmol). After 15 minutes 2-(6-aminospiro[3.3]heptan-2-yl)propan-2-ol (Intermediate 43) (42 mg, 0.25 mmol) was added, and the mixture was stirred for 2 h and then loaded onto a semi-prep HPLC (NH$_4$OH as modifier) to afford the title compound as a pale yellow solid (43 mg, 53%). $^1$H NMR (400 MHz, CDCl$_3$) δ0 1.07 (d, J=5 Hz, 6H), 1.72-2.04 (m, 6H), 2.16-2.26 (m, 1H), 2.26-2.31 (m, 1H), 2.48-2.58 (m, 1H), 2.60-2.75 (m, 2H), 2.83 (ddd, J=13, 7, 4 Hz, 2H), 2.93-3.02 (m, 1H), 4.24-4.34 (m, 1H), 5.19 (t, J=7 Hz, 1H), 5.59 (d, J=7 Hz, 1H), 6.89 (dd, J=7, 1 Hz, 1H), 7.35-7.46 (m, 3H), 8.11 (dd, J=8, 2 Hz, 1H), 8.93 (dd, J=4, 2 Hz, 1H); LC-MS (LC-ES) M+H=395.

Example 171

Ethyl 2-((trans)-3-(quinolin-8-yloxy)cyclobutanecarboxamido)oxazole-4-carboxylate

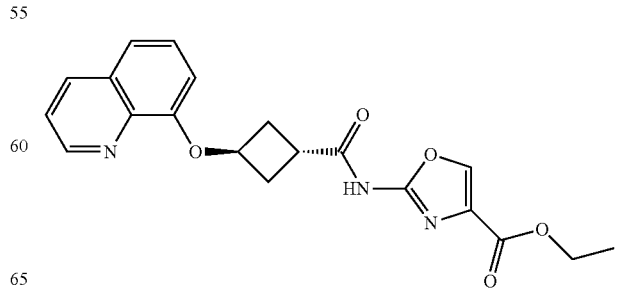

To a DMF (15 mL) solution of (trans)-3-(quinolin-8-yloxy)cyclobutanecarboxylic acid (Intermediate 79) (400 mg, 1.64 mmol) was added HATU (750 mg, 1.97 mmol)) and N,N-diisopropylethylamine (0.57 mL, 3.3 mmol). After 15 min, ethyl 2-aminooxazole-4-carboxylate (385 mg, 2.47 mmol) was added, and after 2 h the mixture was loaded onto a semi-prep HPLC (NH$_4$OH as modifier) to afford the title compound as a white (95 mg, 15%). $^1$H NMR (400 MHz, CDCl$_3$) δ 1.36 (t, J=7 Hz, 3H), 2.75-2.88 (m, 2H), 2.95-3.02 (m, 2H), 3.50-3.60 (m, 1H), 4.36 (q, J=7 Hz, 2H), 5.21 (t, J=7 Hz, 1H), 6.91 (dd, J=7, 2 Hz, 1H), 7.39-7.50 (m, 3H), 8.05 (s, 1H), 8.16 (dd, J=8, 2 Hz, 1H), 8.97 (dd, J=4, 2 Hz, 1H); LC-MS (LC-ES) M+H=382.

Example 172

N,N-Dimethyl-2-((trans)-3-(quinolin-8-yloxy)cyclobutanecarboxamido)oxazole-4-carboxamide

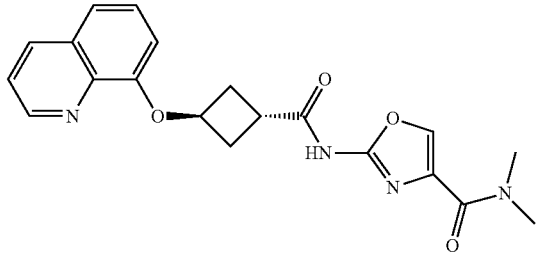 [SMILES: CN(C)C(=O)c1coc(NC(=O)[C@H]2C[C@H](Oc3cccc4cccnc34)C2)n1]

To a DMF (2 mL) solution of 2-((trans)-3-(quinolin-8-yloxy)cyclobutanecarboxamido)oxazole-4-carboxylic acid (Intermediate 80) (50 mg, 0.14 mmol) was added HATU (65 mg, 0.17 mmol) and N,N-diisopropylethylamine (0.05 mL, 0.3 mmol). After 5 minutes, dimethylamine (0.085 mL, 0.170 mmol) was added, and the mixture was stirred for 2 h and then loaded onto a semi-prep HPLC (NH$_4$OH as modifier) to afford the title compound as a pale yellow foamy solid (10 mg, 19%). $^1$H NMR (400 MHz, CDCl$_3$) δ 2.66-2.79 (m, 2H), 2.85-2.95 (m, 2H), 2.95 (s, 3H), 3.07 (s, 3H), 3.41-3.57 (m, 1H), 5.10-5.19 (m, 1H), 7.02 (dd, J=6, 3 Hz, 1H), 7.48-7.52 (m, 2H), 7.56 (dd, J=8, 4 Hz, 1H), 8.06 (s, 1H), 8.32 (dd, J=8, 2 Hz, 1H), 8.84 (d, J=3 Hz, 1H); LC-MS (LC-ES) M+H=381.

Example 173

Racemic (trans)-3-(Quinolin-8-yloxy)-N-((trans)-4-((1,1,1-trifluoropropan-2-yl)amino)cyclohexyl)cyclobutanecarboxamide

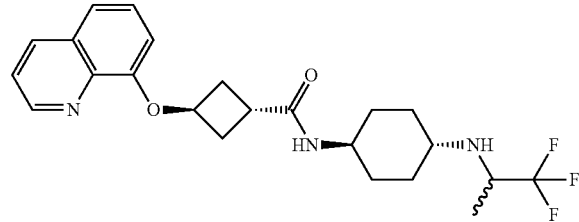 [SMILES: CC(N[C@H]1CC[C@H](NC(=O)[C@H]2C[C@H](Oc3cccc4cccnc34)C2)CC1)C(F)(F)F]

To a DMF (3 mL) solution of (trans)-3-(quinolin-8-yloxy)cyclobutanecarboxylic acid (Intermediate 79) (70 mg, 0.29 mmol) was added HATU (131 mg, 0.345 mmol) and N,N-diisopropylethylamine (0.10 mL, 0.58 mmol). After 5 minutes, (trans)-N1-(1,1,1-trifluoropropan-2-yl)cyclohexane-1,4-diamine dihydrochloride (Intermediate 76) (98 mg, 0.35 mmol) was added, and the mixture was stirred for 2 h and then loaded onto a semi-prep HPLC (NH$_4$OH as modifier) to afford the title compound as a pale yellow solid (73 mg, 58%). $^1$H NMR (400 MHz, CDCl$_3$) δ 1.07-1.34 (m, 7H), 1.90-2.10 (m, 4H), 2.55-2.77 (m, 3H), 2.81-2.92 (m, 2H), 2.94-3.09 (m, 1H), 3.24 (dt, J=14, 7 Hz, 1H), 3.72-3.87 (m, 1H), 5.19-5.31 (m, 3H), 6.93 (d, J=7 Hz, 1H), 7.36-7.49 (m, 3H), 8.15 (d, J=8 Hz, 1H), 8.97 (d, J=3 Hz, 1H); LC-MS (LC-ES) M+H=436.

Example 174

(trans)-N-(5-Acetyloxazol-2-yl)-3-(quinolin-8-yloxy)cyclobutanecarboxamide

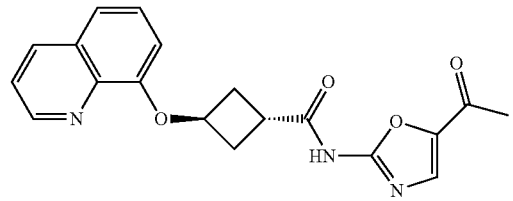 [SMILES: CC(=O)c1cnc(NC(=O)[C@H]2C[C@H](Oc3cccc4cccnc34)C2)o1]

To a DMF (1.5 mL) solution of (trans)-3-(quinolin-8-yloxy)cyclobutanecarboxylic acid (Intermediate 79) (30 mg, 0.12 mmol) was added HATU (56 mg, 0.15 mmol) and N,N-diisopropylethylamine (0.04 mL, 0.2 mmol). After 15 minutes, 1-(2-aminooxazol-5-yl)ethanone (19 mg, 0.15 mmol) was added, and the mixture was stirred for 2 h and then loaded onto a semi-prep HPLC (NH$_4$OH as modifier) to afford the title compound as a white solid (7 mg, 15%). $^1$H NMR (400 MHz, CD$_3$OD) δ 2.44 (m, 3H), 2.66-2.75 (m, 2H), 2.89-2.96 (m, 2H), 3.49 (d, J=5 Hz, 1H), 5.09-5.21 (m, 1H), 6.95-7.03 (m, 1H), 7.48-7.51 (m, 2H), 7.55 (dd, J=8, 4 Hz, 1H), 7.91 (s, 1H), 8.31 (dd, J=8, 2 Hz, 1H), 8.83 (dd, J=4, 2 Hz, 1H); LC-MS (LC-ES) M+H=352.

Example 175

(trans)-N-(4,5-Dimethyloxazol-2-yl)-3-(quinolin-8-yloxy)cyclobutanecarboxamide

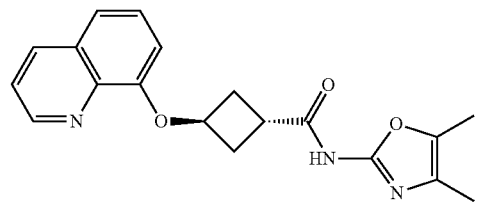 [SMILES: Cc1nc(NC(=O)[C@H]2C[C@H](Oc3cccc4cccnc34)C2)oc1C]

To a DMF (1.5 mL) solution of (trans)-3-(quinolin-8-yloxy)cyclobutanecarboxylic acid (Intermediate 79) (40 mg, 0.16 mmol) was added HATU (75 mg, 0.20 mmol) and N,N-diisopropylethylamine (0.06 mL, 0.3 mmol). After 15 minutes, 4,5-dimethyloxazol-2-amine (22 mg, 0.20 mmol) was added, and the mixture was stirred for 2 h and then loaded onto a semi-prep HPLC (NH$_4$OH as modifier) to

Example 176

Ethyl 5-((trans)-3-(quinolin-8-yloxy)cyclobutanecarboxamido)-4H-1,2,4-triazole-3-carboxylate

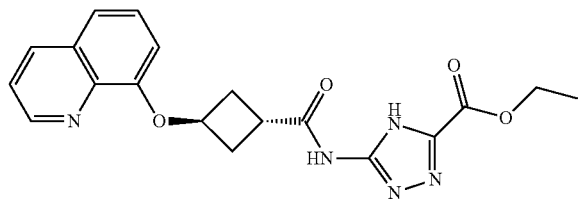 [SMILES: CCOC(=O)c1nnc(NC(=O)[C@H]2C[C@H](Oc3cccc4cccnc34)C2)[nH]1]

To a DMF (1.5 mL) solution of (trans)-3-(quinolin-8-yloxy)cyclobutanecarboxylic acid (Intermediate 79) (40 mg, 0.16 mmol) was added HATU (75 mg, 0.20 mmol) and N,N-diisopropylethylamine (0.06 mL, 0.3 mmol). After 15 minutes, ethyl 5-amino-4H-1,2,4-triazole-3-carboxylate (39 mg, 0.25 mmol) was added, and the mixture was stirred for 2 h and then loaded onto a semi-prep HPLC (NH$_4$OH as modifier) to afford the title compound as a tan solid (32 mg, 51%). $^1$H NMR (400 MHz, CD$_3$OD) δ 1.40 (t, J=7 Hz, 3H), 2.68-2.76 (m, 2H), 2.92-2.99 (m, 2H), 3.42-3.52 (m, 1H), 4.41 (q, J=7 Hz, 2H), 5.23-5.28 (m, 1H), 7.16-7.23 (m, 1H), 7.64 (d, J=5 Hz, 2H), 7.73-7.80 (m, 1H), 8.61-8.66 (m, 1H), 8.92-8.96 (m, 1H); LC-MS (LC-ES) M+H=382.

Example 177

(trans)-N-(5-Methyloxazol-2-yl)-3-(quinolin-8-yloxy)cyclobutanecarboxamide

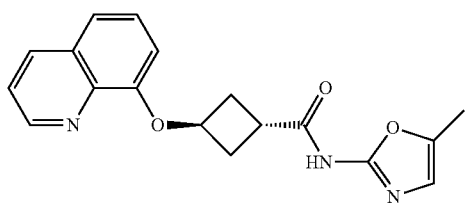 [SMILES: Cc1cnc(NC(=O)[C@H]2C[C@H](Oc3cccc4cccnc34)C2)o1]

To a DMF (15 mL) solution of (trans)-3-(quinolin-8-yloxy)cyclobutanecarboxylic acid (Intermediate 79) (40 mg, 0.16 mmol) was added HATU (75 mg, 0.20 mmol)) and N,N-diisopropylethylamine (0.06 mL, 0.3 mmol). After 15 min, 5-methyloxazol-2-amine (24 mg, 0.25 mmol) was added, and after 2 h the mixture was loaded onto a semi-prep HPLC (NH$_4$OH as modifier) to afford the title compound as a white solid (31 mg, 58%). $^1$H NMR (400 MHz, CDCl$_3$) δ 2.27 (s, 3H), 2.61-2.71 (m, 2H), 2.82-2.92 (m, 2H), 3.31-3.43 (m, 1H), 5.09-5.18 (m, 1H), 6.64 (s, 1H), 6.96-7.02 (m, 1H), 7.42-7.50 (m, 2H), 7.50-7.57 (m, 1H), 8.39 (d, J=8 Hz, 1H), 8.78-8.84 (m, 1H); LC-MS (LC-ES) M+H=324.

Example 178

(trans)-N-(4-Cyclopropyloxazol-2-yl)-3-(quinolin-8-yloxy)cyclobutanecarboxamide

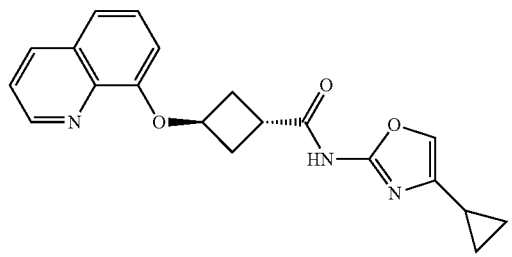

To a DMF (1.5 mL) solution of (trans)-3-(quinolin-8-yloxy)cyclobutanecarboxylic acid (Intermediate 79) (50 mg, 0.21 mmol) was added HATU (94 mg, 0.25 mmol) and N,N-diisopropylethylamine (0.07 mL, 0.4 mmol). After 15 minutes, 4-cyclopropyloxazol-2-amine (Intermediate 81) (31 mg, 0.25 mmol) was added, and the mixture was stirred for 2 h and then loaded onto a semi-prep HPLC (NH$_4$OH as modifier) to afford the title compound as a white solid (31 mg, 43%). $^1$H NMR (400 MHz, CDCl$_3$) δ 0.65-0.74 (m, 2H), 0.79-0.87 (m, 2H), 1.69-1.79 (m, 1H), 2.70-2.79 (m, 2H), 2.94-3.01 (m, 2H), 3.45-3.51 (m, 1H), 4.92-5.40 (m, 1H), 5.14-5.24 (m, 1H), 6.90 (d, J=7 Hz, 1H), 7.17 (s, 1H), 7.37-7.47 (m, 3H), 8.14 (dd, J=8, 1 Hz, 1H), 8.91-8.97 (m, 1H); LC-MS (LC-ES) M+H=350.

Example 179

(trans)-N-(5-(tert-Butyl)-1,3,4-oxadiazol-2-yl)-3-(quinolin-8-yloxy)cyclobutanecarboxamide

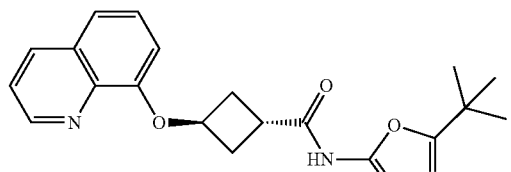

To a DMF (15 mL) solution of (trans)-3-(quinolin-8-yloxy)cyclobutanecarboxylic acid (Intermediate 79) (40 mg, 0.16 mmol) was added HATU (75 mg, 0.20 mmol)) and N,N-diisopropylethylamine (0.06 mL, 0.3 mmol). After 15 min, 5-(tert-butyl)-1,3,4-oxadiazol-2-amine (35 mg, 0.25 mmol) was added, and after 2 h the mixture was loaded onto a semi-prep HPLC (NH$_4$OH as modifier) to afford the title compound as a white solid (35 mg, 58%). $^1$H NMR (400 MHz, CDCl$_3$) δ 1.30 (s, 9H), 2.67-2.77 (m, 2H), 2.84 (td, J=7, 4 Hz, 2H), 3.39-3.51 (m, 1H), 5.06-5.15 (m, 1H), 5.73 (br s, 1H), 6.79 (dd, J=7, 2 Hz, 1H), 7.23-7.32 (m, 3H), 7.99 (dd, J=8, 2 Hz, 1H), 8.81 (dd, J=4, 2 Hz, 1H); LC-MS (LC-ES) M+H=367.

--- afford the title compound as a tan solid (34 mg, 61%). $^1$H NMR (400 MHz, CDCl$_3$) δ 1.93 (s, 3H), 2.10 (s, 3H), 2.55-2.72 (m, 2H), 2.85 (ddt, J=10, 7, 3 Hz, 2H), 3.14-3.31 (m, 1H), 5.04-5.15 (m, 1H), 6.74-6.79 (m, 1H), 7.24-7.32 (m, 3H), 8.01 dd, J=8, 2 Hz, 1H), 8.82 (dd, J=4, 2 Hz, 1H); LC-MS (LC-ES) M+H=338.

Example 180

Racemic (trans)-N-((trans)-4-((1,1-Difluoropropan-2-yl)amino)cyclohexyl)-3-(quinolin-8-yloxy)cyclobutanecarboxamide

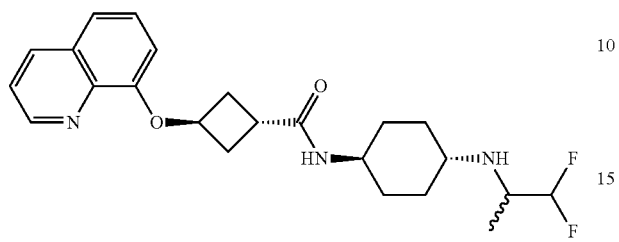

To a DMF (1 mL) solution of (trans)-3-(quinolin-8-yloxy)cyclobutanecarboxylic acid (Intermediate 79) (50 mg, 0.21 mmol) was added HATU (103 mg, 0.271 mmol) and N,N-diisopropylethylamine (0.08 mL, 0.5 mmol). After 15 minutes, (trans)-N1-(1,1-difluoropropan-2-yl)cyclohexane-1,4-diamine (Intermediate 17) (65 mg, 0.34 mmol) was added, and the mixture was stirred for 2 h and then loaded onto a semi-prep HPLC (NH$_4$OH as modifier) to afford the title compound as a white solid (94 mg, quantitative). $^1$H NMR (400 MHz, CDCl$_3$) δ 1.12 (d, J=7 Hz, 3H), 1.14-1.29 (m, 4H), 1.90-1.99 (m, 2H), 2.00-2.09 (m, 2H), 2.54-2.61 (m, 1H), 2.63-2.72 (m, 2H), 2.78-2.89 (m, 2H), 2.92-3.07 (m, 2H), 3.72-3.84 (m, 1H), 5.18-5.28 (m, 1H), 5.32 (d, J=8 Hz, 1H), 5.59 (td, 56, 4 Hz, 1H), 6.91 (dd, J=7, 2 Hz, 1H), 7.35-7.45 (m, 3H), 8.12 (dd, J=8, 2 Hz, 1H), 8.94 (dd, J=4, 2 Hz, 1H); LC-MS (LC-ES) M+H=418.

Example 181

(trans)-N-(6-Methylpyridin-2-yl)-3-(quinolin-8-yloxy)cyclobutanecarboxamide

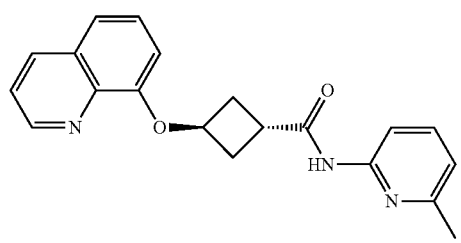 [SMILES: Cc1cccc(NC(=O)[C@H]2C[C@H](Oc3cccc4cccnc34)C2)n1]

To a DMF (2 mL) solution of (trans)-3-(quinolin-8-yloxy)cyclobutanecarboxylic acid (Intermediate 79) (51 mg, 0.21 mmol) was added HATU (96 mg, 0.25 mmol) and N,N-diisopropylethylamine (0.07 mL, 0.4 mmol). After 15 minutes, 6-methylpyridin-2-amine (34 mg, 0.31 mmol) was added, and the mixture was stirred for 18 h and then loaded onto a semi-prep HPLC (NH$_4$OH as modifier) to afford the title compound as a white solid (44 mg, 63%). $^1$H NMR (400 MHz, CDCl$_3$) δ 2.46 (s, 3H), 2.75-2.82 (m, 2H), 3.00 (ddd, J=14, 7, 4 Hz, 2H), 3.23-3.34 (m, 1H), 5.18-5.26 (m, 1H), 6.90-6.94 (m, 2H), 7.39-7.44 (m, 3H), 7.62 (t, J=8 Hz, 1H), 7.86 (br s, 1H), 8.06 (d, J=8 Hz, 1H), 8.11-8.15 (m, 1H), 8.97 (dd, J=4, 2 Hz, 1H); LC-MS (LC-ES) M+H=334.

Example 182

(trans)-N-((trans)-4-Hydroxy-4-methylcyclohexyl)-3-(quinolin-8-yloxy)cyclobutanecarboxamide

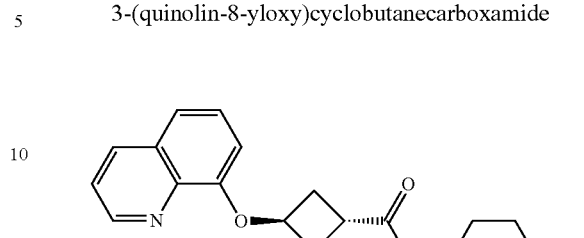

To a DMF (1.5 mL) solution of (trans)-3-(quinolin-8-yloxy)cyclobutanecarboxylic acid (Intermediate 79) (35 mg, 0.14 mmol) was added HATU (66 mg, 0.17 mmol) and N,N-diisopropylethylamine (0.05 mL, 0.3 mmol). After 15 minutes, (trans)-4-amino-1-methylcyclohexanol (Intermediate 57) (30 mg, 0.22 mmol) was added, and the mixture was stirred for 18 h and then loaded onto a semi-prep HPLC (NH$_4$OH as modifier) to afford the title compound as a white solid (31 mg, 61%). $^1$H NMR (400 MHz, CD$_3$OD) δ 1.24 (s, 3H), 1.36-1.7 (m, 2H), 1.51-1.61 (m, 2H), 1.62-1.72 (m, 2H), 1.81-1.91 (m, 2H), 2.55-2.65 (m, 2H), 2.69-2.80 (m, 2H), 3.19 (dq, J=10, 5 Hz, 1H), 3.78 (dt, J=9, 5 Hz, 1H), 5.13-5.19 (m, 1H), 6.98 (dd, J=7, 2 Hz, 1H), 7.43-7.49 (m, 2H), 7.53 (dd, J=8, 4 Hz, 1H), 8.29 (dd, J=8, 2 Hz, 1H), 8.81 (dd, J=4, 2 Hz, 1H); LC-MS (LC-ES) M+H=355.

Example 183

(trans)-N-(Pyridin-2-yl)-3-(quinolin-8-yloxy)cyclobutanecarboxamide

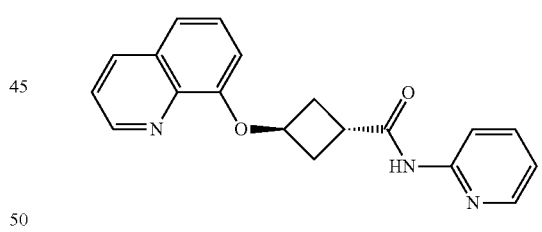

To a DMF (2 mL) solution of (trans)-3-(quinolin-8-yloxy)cyclobutanecarboxylic acid (Intermediate 79) (54 mg, 0.22 mmol) was added HATU (101 mg, 0.266 mmol) and N,N-diisopropylethylamine (0.08 mL, 0.4 mmol). After 15 minutes, pyridin-2-amine (31 mg, 0.33 mmol) was added, and the mixture was stirred for 18 h and then loaded onto a semi-prep HPLC (NH$_4$OH as modifier) to afford the title compound as a white solid (46 mg, 65%). $^1$H NMR (400 MHz, CDCl$_3$) δ 2.72-2.84 (m, 2H), 2.92-3.02 (m, 2H), 3.24.3.33 (m, 1H), 5.18-5.27 (m, 1H), 6.92 (dd, J=7, 1 Hz, 1H), 7.02-7.10 (m, 1H), 7.39-7.49 (m, 2H), 7.74 (t, J=8 Hz, 1H), 8.14 (dd, J=8, 1 Hz, 1H), 8.24-8.34 (m, 3H), 8.96 (br s, 1H); LC-MS (LC-ES) M+H=320.

Example 184 trans-3-(8-Quinolinyloxy)-N-1,3-thiazol-2-ylcyclobutanecarboxamide

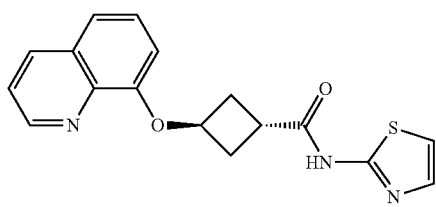

To a stirred mixture of 3-(quinolin-8-yloxy)cyclobutane-1-carboxylic acid (Intermediate 79) (100 mg, 0.411 mmol) and 2-aminothiazole (45 mg, 0.449 mmol) in dichloromethane (3 mL) was added HATU (190 mg, 0.500 mmol) followed by N,N-diisopropylethylamine (0.075 mL, 0.429 mmol). The resulting suspension was stirred for 70 h, diluted with water (1 mL), stirred for 3 minutes and filtered to give a pasty solid. This material was transferred to a mixture of dichloromethane-diethyl ether and stirred for 5 minutes. The isolated solid was dissolved in DMF (5 mL) and purified by reverse phase HPLC (C18, 6×0.9 mL injections) eluting with a 20%-95% acetonitrile-water gradient containing a 0.1% ammonium hydroxide modifier with detection at 230 nM. The appropriate fractions were combined, evaporated under reduced pressure and placed in vacuo to give the title compound (39 mg, 29%) as a white solid. $^1$H NMR (400 MHz, CDCl$_3$) δ 2.47-2.59 (m, 2H), 2.83 (ddd, J=13, 7, 5 Hz, 2H), 3.49 (dt, J=10, 5 Hz, 1H), 5.03-5.14 (m, 1H), 7.01 (dd, J=7, 2 Hz, 1H), 7.24 (d, J=4 Hz, 1H), 7.41-7.61 (m, 4H), 8.32 (dd, J=8, 2 Hz, 1H), 8.88 (dd, J=4, 2 Hz, 1H), 12.17 (br s, 1H); LC-MS (LC-ES) M+H=326.

Example 185

N-((trans)-4-(2-Hydroxypropan-2-yl)cyclohexyl)-3-(quinolin-8-yloxy)azetidine-1-carboxamide

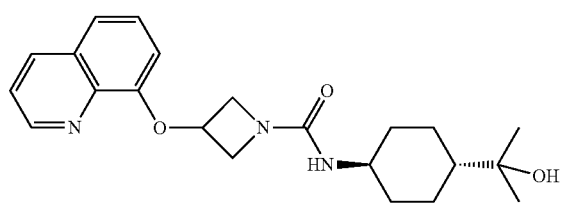 [SMILES: CC(C)(O)[C@H]1CC[C@H](NC(=O)N2CC(Oc3cccc4cccnc34)C2)CC1]

To a stirred mixture of 8-(azetidin-3-yloxy)quinoline dihydrochloride (Intermediate 82) (50 mg, 0.18 mmol) in DCM (2 mL) was added N,N-diisopropylethylamine (0.13 mL, 0.74 mmol) followed by 4-nitrophenyl ((trans)-4-(2-hydroxypropan-2-yl)cyclohexyl)carbamate (Intermediate 3) (60 mg, 0.19 mmol). The mixture was stirred overnight, poured into 1 N aqueous NaOH and extracted twice with DCM. The combined organic layers were washed with brine, dried over Na$_2$SO$_4$ and filtered. Solvent was removed under reduced pressure. The remaining material was purified on silica gel, eluting with a 0%-75% EtOAc in hexanes gradient. The appropriate fractions were combined, evaporated under reduced pressure and placed in vacuo to give the title compound (48 mg, 68%) as a light pink solid. $^1$H NMR (400 MHz, CD$_3$SOCD$_3$) δ 1.00 (s, 6H), 1.00-1.20 (m, 5H), 1.66-1.80 (m, 4H), 3.20-3.28 (m, 1H), 3.80-3.84 (m, 2H), 3.97 (s, 1H), 4.27-4.32 (m, 2H), 5.12-5.17 (m, 1H), 6.14 (d, J=8 Hz, 1H), 6.93 (d, J=8 Hz, 1H), 7.44 (t, J=6 Hz, 1H), 7.51-7.56 (m, 2H), 8.29-8.33 (m, 1H), 8.83-8.87 (m, 1H); LC-MS (LC-ES) M+H=384.

Example 186 trans-N-(4-Acetylthiazol-2-yl)-3-(quinolin-8-yloxy)cyclobutanecarboxamide

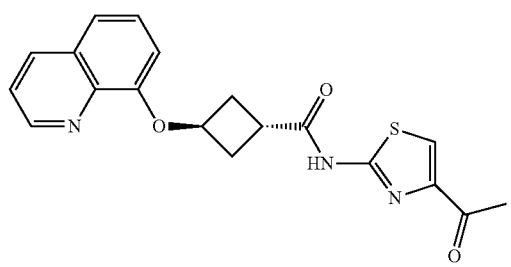 [SMILES: CC(=O)c1csc(NC(=O)[C@H]2C[C@H](Oc3cccc4cccnc34)C2)n1]

To a DMF (5 mL) solution of (trans)-3-(quinolin-8-yloxy)cyclobutanecarboxylic acid (Intermediate 79) (150 mg, 0.617 mmol) was added HATU (281 mg, 0.740 mmol) and N,N-diisopropylethylamine (0.32 mL, 1.9 mmol). After 5 minutes, 1-(2-aminothiazol-4-yl)ethanone (96 mg, 0.68 mmol) was added, and the mixture was stirred for 12 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (133 mg, 53%). $^1$H NMR (400 MHz, CD$_3$SOCD$_3$) δ 2.41-2.55 (m, 5H), 2.75-2.85 (m, 2H), 3.40-3.51 (m, 1H), 5.00-5.05 (m, 1H), 6.98 (dd, J=7, 2 Hz, 1H), 7.18-7.22 (m, 1H), 7.41-7.52 (m, 2H), 8.08 (s, 1H), 8.29 (dd, J=8, 2 Hz, 1H), 8.85 (dd, J=4, 2 Hz, 1H), 12.50 (s, 1H); LC-MS (LC-ES) M+H=368.

Example 187

Racemic (trans)-3-(Quinolin-8-yloxy)-N-(4-(1,1,1-trifluoro-2-hydroxypropan-2-yl)thiazol-2-yl)cyclobutanecarboxamide

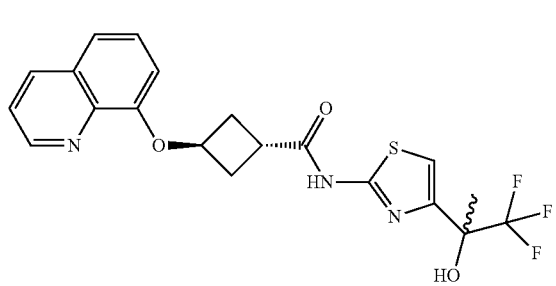 [SMILES: CC(O)(c1csc(NC(=O)[C@H]2C[C@H](Oc3cccc4cccnc34)C2)n1)C(F)(F)F]

Trimethyl(trifluoromethyl)silane (0.06 mL, 0.4 mmol) was added to a solution of (trans)-N-(4-acetylthiazol-2-yl)-3-(quinolin-8-yloxy)cyclobutanecarboxamide (Example 186) (80 mg, 0.22 mmol) and cesium fluoride (99 mg, 0.65 mmol) in THF (5 mL) cooled at 0° C. The reaction mixture was warmed to room temperature for 3 h, and a solution of 1 N TBAF in THF (0.218 mL, 0.218 mmol) was added. After 30 min., the mixture was poured into 1 N aqueous HCl, extracted with EtOAc, dried over Na₂SO₄, filtered and concentrated. The residue was purified on silica gel, eluting with a 0%-100% EtOAc:EtOH (3:1)-hexanes gradient to give the title compound (25 mg, 26%). ¹H NMR (400 MHz, CD₃SOCD₃) δ 2.51-2.59 (m, 2H), 2.78-2.85 (m, 2H), 3.02 (s, 3H), 3.51-3.57 (m, 1H), 5.01-5.08 (m, 1H), 6.61-6.65 (m, 1H), 6.95-7.01 (m, 1H), 7.28 (s, 1H), 7.48-7.58 (m, 2H), 8.30 (d, J=8 Hz, 1H), 8.85 (dd, J=4, 1 Hz, 1H), 12.31 (s, 1H); LC-MS (LC-ES) M+H=438.

Example 188

(trans)-N-(4-Cyanothiazol-2-yl)-3-(quinolin-8-yloxy)cyclobutanecarboxamide, trifluoroacetic acid salt

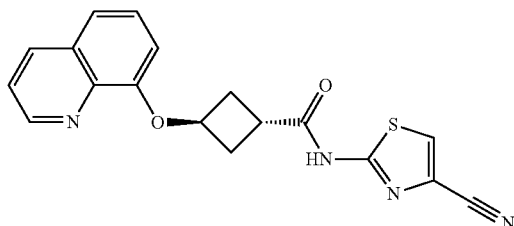

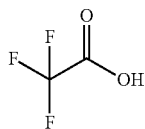

To a DMF (5 mL) solution of (trans)-3-(quinolin-8-yloxy)cyclobutanecarboxylic acid (Intermediate 79) (150 mg, 0.617 mmol) was added HATU (281 mg, 0.740 mmol) and N,N-diisopropylethylamine (0.32 mL, 1.9 mmol). After 5 minutes, 2-aminothiazole-4-carbonitrile (85 mg, 0.68 mmol) was added, and the mixture was stirred for 12 h, quenched with water, extracted with EtOAc, dried over Na₂SO₄, filtered and concentrated. The residue was purified on reverse-phase silica gel, eluting with a 10%-100% acetonitrile-water (TFA additive) gradient to give the title compound (46 mg, 14%). ¹H NMR (400 MHz, CD₃SOCD₃) δ 2.49-2.58 (m, 2H), 2.79-2.89 (m, 2H), 3.65-3.75 (m, 1H), 5.02-5.10 (m, 1H), 7.04-7.10 (m, 1H), 7.48-7.60 (m, 2H), 7.63-7.71 (m, 1H), 8.36 (s, 1H), 8.45-8.54 (m, 1H), 8.91-8.95 (m, 1H), 12.60 (s, 1H); LC-MS (LC-ES) M+H=351.

Example 189

2-((trans)-3-(Quinolin-8-yloxy)cyclobutanecarboxamido)thiazole-4-carboxamide, trifluoroacetic acid salt

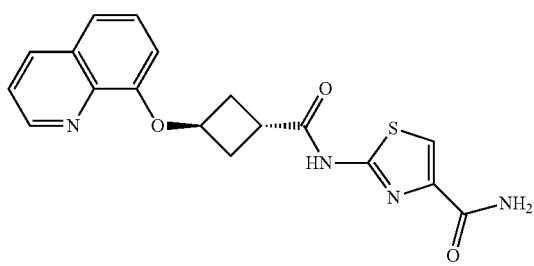

-continued

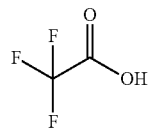

A solution of (trans)-N-(4-cyanothiazol-2-yl)-3-(quinolin-8-yloxy)cyclobutanecarboxamide (Example 188) (46 mg, 0.13 mmol) in DMSO (0.500 mL) and ethanol (2 mL) was treated with 1 N aqueous NaOH (0.13 mL, 0.13 mmol) and H₂O₂ (0.01 mL, 0.1 mmol). After 1 h, the reaction was quenched with water, extracted with EtOAc, dried over Na₂SO₄, filtered and concentrated. The residue was purified on reverse-phase silica gel, eluting with a 10%-100% acetonitrile-water (TFA additive) gradient to give the title compound (15 mg, 23%). ¹H NMR (400 MHz, CD₃SOCD₃) δ 2.54 (ddd, J=13, 10, 6 Hz, 2H), 2.76-2.92 (m, 2H), 3.45-3.55 (m, 1H), 5.04-5.13 (m, 1H), 7.12-7.18 (m, 1H), 7.18-7.23 (m, 1H), 7.52-7.65 (m, 2H), 7.71-7.79 (m, 1H), 7.79 (s, 1H), 8.65 (d, J=8 Hz, 1H), 8.99 (dd, J=4, 1 Hz, 1H), 12.33 (s, 1H); LC-MS (LC-ES) M+H=369.

Example 190

(trans)-N-(5-Cyanothiazol-2-yl)-3-(quinolin-8-yloxy)cyclobutanecarboxamide

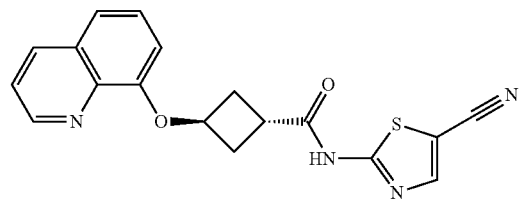 [SMILES: N#Cc1cnc(NC(=O)[C@H]2C[C@H](Oc3cccc4cccnc34)C2)s1]

To a DMF (4 mL) solution of (trans)-3-(quinolin-8-yloxy)cyclobutanecarboxylic acid (Intermediate 79) (53 mg, 0.22 mmol) was added HATU (99 mg, 0.26 mmol) and N,N-diisopropylethylamine (0.11 mL, 0.65 mmol). After 5 minutes, 2-aminothiazole-5-carbonitrile (30 mg, 0.24 mmol) was added, and the mixture was stirred for 12 h, quenched with water, extracted with EtOAc, dried over Na₂SO₄, filtered and concentrated. The residue was purified on silica gel, eluting with a 0%-100% EtOAc:EtOH (3:1)-hexanes gradient to give the title compound (59 mg, 54%). ¹H NMR (400 MHz, CD₃SOCD₃) δ 2.52-2.64 (m, 2H), 2.79-2.89 (m, 2H), 3.45-3.54 (m, 1H), 5.02-5.10 (m, 1H), 7.01 (dd, J=7, 1 Hz, 1H), 7.42-7.54 (m, 2H), 8.11-8.18 (m, 1H), 8.32 (dd, J=8, 2 Hz, 1H), 8.39 (s, 1H), 8.87 (dd, J=4, 2 Hz, 1H), 13.01 (s, 1H); LC-MS (LC-ES) M+H=351.

Example 191

2-((trans)-3-(Quinolin-8-yloxy)cyclobutanecarboxamido)thiazole-5-carboxamide

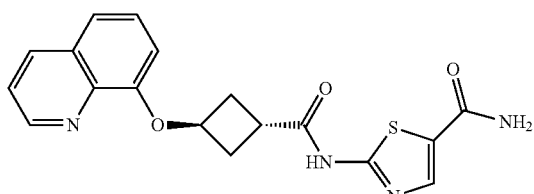

A solution of (trans)-N-(5-cyanothiazol-2-yl)-3-(quinolin-8-yloxy)cyclobutanecarboxamide (Example 190) (37 mg, 0.11 mmol) in DMSO (0.500 mL) and ethanol (2 mL) was treated with 1 N aqueous NaOH (0.11 mL, 0.11 mmol) and $H_2O_2$ (0.01 mL, 0.1 mmol). After 1 h, the reaction was quenched with saturated aqueous $NH_4Cl$, and the resulting precipitate was collected by filtration to give the title compound (12 mg, 30%). $^1$H NMR (400 MHz, $CD_3SOCD_3$) δ 2.48-2.55 (m, 2H), 2.85 (qd, J=7, 4 Hz, 2H), 3.41-3.52 (m, 1H), 5.07-5.15 (m, 1H), 7.21 (d, J=7 Hz, 1H), 7.38-7.48 (m, 1H), 7.62-7.74 (m, 2H), 7.81 (dd, J=8, 5 Hz, 1H), 7.91-7.98 (m, 1H), 8.04 (s, 1H), 8.71 (d, J=8 Hz, 1H), 9.01 (d, J=4 Hz, 1H), 12.38 (s, 1H); LC-MS (LC-ES) M+H=369.

Example 192

Ethyl 2-((trans)-3-(quinolin-8-yloxy)cyclobutanecarboxamido)thiazole-4-carboxylate

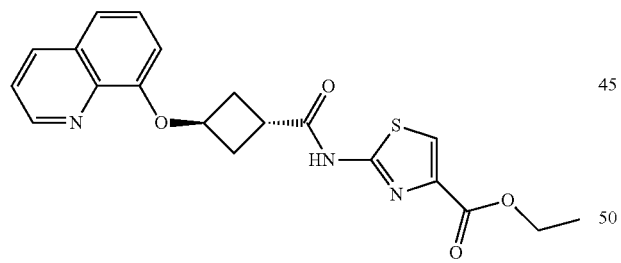

To a DMF (8 mL) solution of (trans)-3-(quinolin-8-yloxy)cyclobutanecarboxylic acid (Intermediate 79) (210 mg, 0.863 mmol) was added HATU (394 mg, 1.04 mmol) and N,N-diisopropylethylamine (0.45 mL, 2.6 mmol). After 5 minutes, ethyl 2-aminothiazole-4-carboxylate (164 mg, 0.950 mmol) was added, and the mixture was stirred for 12 h, quenched with water, and the resulting precipitate was collected by filtration to give the title compound (260 mg, 72%). $^1$H NMR (400 MHz, $CD_3SOCD_3$) δ 1.16-1.29 (m, 3H), 2.40-2.51 (m, 2H), 2.75-2.82 (m, 2H), 3.39-3.49 (m, 1H), 4.25 (q, J=7 Hz, 2H), 5.02-5.11 (m, 1H), 6.98 (dd, J=7, 2 Hz, 1H), 7.42-7.56 (m, 3H), 8.05 (s, 1H), 8.29 (dd, J=8, 2 Hz, 1H), 8.85 (dd, J=4, 2 Hz, 1H), 12.59 (s, 1H); LC-MS (LC-ES) M+H=398.

Example 193

2-((trans)-3-(Quinolin-8-yloxy)cyclobutanecarboxamido)thiazole-4-carboxylic acid

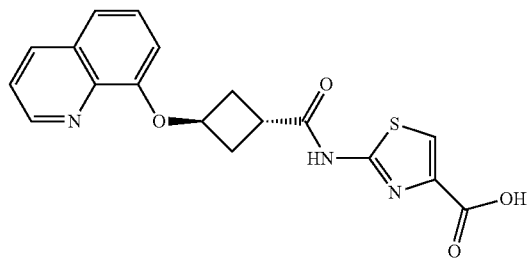 [SMILES: O=C(O)c1csc(NC(=O)[C@H]2C[C@H](Oc3cccc4cccnc34)C2)n1]

To a solution of ethyl 2-((trans)-3-(quinolin-8-yloxy)cyclobutanecarboxamido)thiazole-4-carboxylate (Example 192) (0.260 g, 0.654 mmol) in THF (20 mL) was added lithium hydroxide (0.047 g, 2.0 mmol) in water (10 mL). After 3 h, the pH was adjusted to pH 4 using saturated aqueous citric acid, and the aqueous phase was extracted with ethyl acetate (3×). The combined organics were dried over $Na_2SO_4$, filtered and concentrated. The residue was purified on silica gel, eluting with a 0%-100% EtOAc:EtOH (3:1)-hexanes gradient to give the title compound (280 mg, quantitative). $^1$H NMR (400 MHz, $CD_3SOCD_3$) δ 2.40-2.49 (m, 2H), 2.79-2.85 (m, 2H), 3.39-3.45 (m, 1H), 5.02-5.08 (m, 1H), 6.96-7.00 (m, 1H), 7.46-7.52 (m, 3H), 7.98 (s, 1H), 8.28-8.34 (m, 1H), 8.84-8.87 (m, 1H), 12.20-12.45 (br s, 1H), 12.50 (s, 1H); LC-MS (LC-ES) M+H=370.

Example 194

(trans)-N-(4-(Cyclopropanecarbonyl)thiazol-2-yl)-3-(quinolin-8-yloxy)cyclobutanecarboxamide

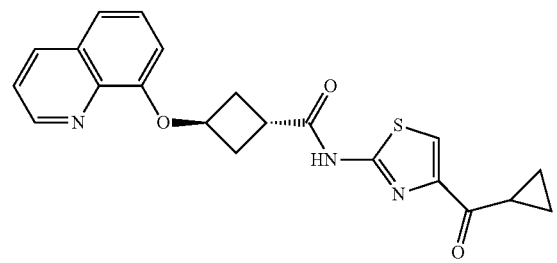 [SMILES: O=C(c1csc(NC(=O)[C@H]2C[C@H](Oc3cccc4cccnc34)C2)n1)C1CC1]

To N-methoxy-N-methyl-2-((trans)-3-(quinolin-8-yloxy)cyclobutanecarboxamido)thiazole-4-carboxamide (Intermediate 83) (34 mg, 0.082 mmol) in THF (2 mL) at 0° C. was added a 1.0 M solution of cyclopropylmagnesium bromide in 2-methylTHF (0.12 mL, 0.25 mmol). After 1 h, the reaction was warmed to rt, quenched with saturated aqueous $NH_4Cl$ and extracted with EtOAc (3×). The combined organic extracts dried over sodium sulfate, filtered, and concentrated under reduced pressure. The residue was purified on silica gel, eluting with a 0%-100% EtOAc:EtOH (3:1) in hexanes gradient. The appropriate fractions were combined, evaporated under reduced pressure and placed in vacuo to give the title compound (10 mg, 24%). $^1$H NMR (400 MHz, $CD_3SOCD_3$) δ 0.90-1.02 (m, 4H), 2.57 (ddd, J=13, 10, 6 Hz, 2H), 2.78-3.00 (m, 3H), 3.42-3.51 (m, 1H), 5.09-5.20 (m, 1H), 7.21 (d, J=7 Hz, 1H), 7.59-7.70 (m, 2H), 7.81 (dd, J=8, 5 Hz, 1H), 8.12 (s, 1H), 8.72 (d, J=8 Hz, 1H), 9.01-9.09 (m, 1H), 12.52 (s, 1H); LC-MS (LC-ES) M+H=394.

Example 195

Racemic (trans)-N-((trans)-6-(2-Hydroxypropan-2-yl)tetrahydro-2H-pyran-3-yl)-3-(quinolin-8-yloxy)cyclobutanecarboxamide

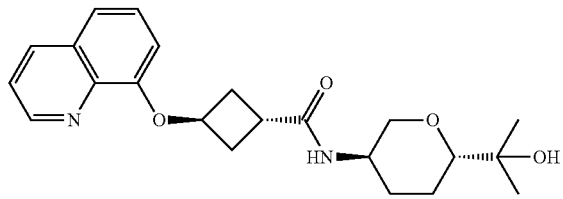

To a DMF (4 mL) solution of (trans)-3-(quinolin-8-yloxy)cyclobutanecarboxylic acid (Intermediate 79) (62 mg, 0.26 mmol) was added HATU (117 mg, 0.307 mmol) and N,N-diisopropylethylamine (0.13 mL, 0.77 mmol). After 5 minutes, 2-((trans)-5-aminotetrahydro-2H-pyran-2-yl)propan-2-ol (Intermediate 34) (45 mg, 0.28 mmol) was added, and the mixture was stirred for 12 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (10 mg, 10%). $^1$H NMR (400 MHz, CD$_3$SOCD$_3$) δ 0.71-0.82 (m, 2H), 0.98-1.05 (m, 6H), 1.19-1.24 (m, 1H), 1.33 (d, J=9 Hz, 2H), 2.29-2.42 (m, 2H), 2.63 (dd, J=6, 4 Hz, 2H), 2.85-2.95 (m, 2H), 2.98-3.09 (m, 1H), 3.80-3.88 (m, 1H), 4.95-5.05 (m, 1H), 6.92 (dd, J=7, 2 Hz, 1H), 7.46-7.51 (m, 2H), 7.51-7.55 (m, 1H), 7.72 (d, J=8 Hz, 1H), 8.28 (dd, J=8, 2 Hz, 1H), 8.83 (dd, J=4, 2 Hz, 1H); LC-MS (LC-ES) M+H=385.

Example 196

N-Methyl-2-((trans)-3-(quinolin-8-yloxy)cyclobutanecarboxamido)thiazole-4-carboxamide, trifluoroacetic acid salt

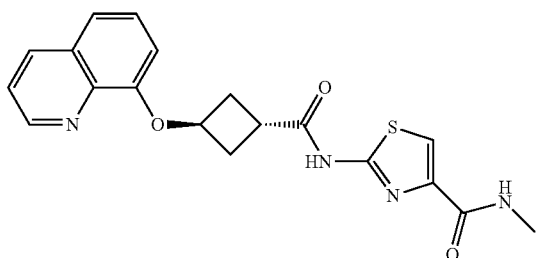
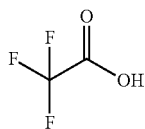

To a DMF (5 mL) solution of 2-((trans)-3-(quinolin-8-yloxy)cyclobutanecarboxamido)thiazole-4-carboxylic acid (Example 193) (80 mg, 0.22 mmol) was added HATU (99 mg, 0.26 mmol) and N,N-diisopropylethylamine (0.11 mL, 0.65 mmol). After 5 minutes, 2 M methylamine in THF (0.54 mL, 1.1 mmol) was added, and the mixture was stirred for 12 h, quenched with water, extracted with EtOAc, dried over Na$_2$SO$_4$, filtered and concentrated. The residue was purified on reverse-phase silica gel, eluting with a 10%-100% acetonitrile-water (TFA additive) gradient to give the title compound (15 mg, 13%). $^1$H NMR (400 MHz, CD$_3$SOCD$_3$) δ 2.52-2.61 (m, 2H), 2.80 (m, 3H), 2.82-2.95 (m, 2H), 3.45-3.58 (m, 1H), 5.11-5.21 (m, 1H), 7.23 (d, J=7 Hz, 1H), 7.60-7.70 (m, 2H), 7.78 (s, 1H), 7.78-7.90 (m, 2H), 8.73 (d, J=8 Hz, 1H), 9.04 (dd, J=5, 2 Hz, 1H), 12.29 (s, 1H); LC-MS (LC-ES) M+H=383.

Example 197

N,N-Dimethyl-2-((trans)-3-(quinolin-8-yloxy)cyclobutanecarboxamido)thiazole-4-carboxamide, trifluoroacetic acid salt

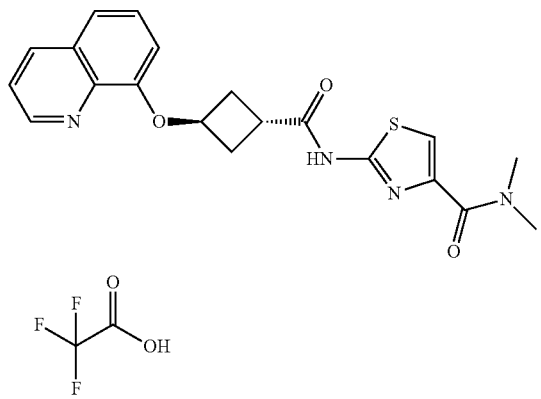

To a DMF (5 mL) solution of 2-((trans)-3-(quinolin-8-yloxy)cyclobutanecarboxamido)thiazole-4-carboxylic acid (Example 193) (80 mg, 0.22 mmol) was added HATU (99 mg, 0.26 mmol) and N,N-diisopropylethylamine (0.11 mL, 0.65 mmol). After 5 minutes, 2 M dimethylamine in THF (0.54 mL, 1.1 mmol) was added, and the mixture was stirred for 12 h, quenched with water, extracted with EtOAc, dried over Na$_2$SO$_4$, filtered and concentrated. The residue was purified on reverse-phase silica gel, eluting with a 10%-100% acetonitrile-water (TFA additive) gradient to give the title compound (15 mg, 13%). $^1$H NMR (400 MHz, CD$_3$SOCD$_3$) δ 2.45-2.52 (m, 2H), 2.76-2.82 (m, 2H), 2.95 (br s, 3H), 3.09 (br s, 3H), 5.03-5.12 (m, 1H), 7.04 (d, J=7 Hz, 1H), 7.45-7.56 (m, 3H), 7.58-7.63 (m, 1H), 8.40 (d, J=8 Hz, 1H), 8.89 (d, J=4 Hz, 1H), 12.32 (s, 1H); LC-MS (LC-ES) M+H=397.

Example 198

(trans)-N-(5-Isopropyl-1,3,4-thiadiazol-2-yl)-3-(quinolin-8-yl)oxy)cyclobutanecarboxamide

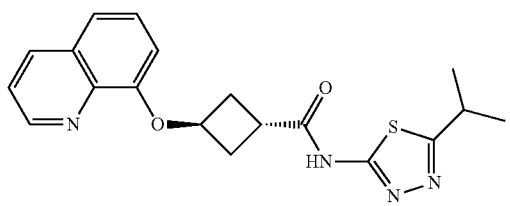

To a DMF (4 mL) solution of (trans)-3-(quinolin-8-yloxy)cyclobutanecarboxylic acid (Intermediate 79) (50 mg, 0.21 mmol) was added HATU (94 mg, 0.25 mmol) and N,N-diisopropylethylamine (0.11 mL, 0.62 mmol). After 5 minutes, 5-isopropyl-1,3,4-thiadiazol-2-amine (35 mg, 0.25 mmol) was added, and the mixture was stirred for 3 h, quenched with water, and the resulting precipitate was collected by filtration to give the title compound (53 mg, 67%). $^1$H NMR (400 MHz, $CD_3SOCD_3$) δ 1.33 (d, J=7 Hz, 6H), 2.48-2.58 (m, 2H), 2.76-2.85 (m, 2H), 3.25-3.31 (m, 1H), 3.41-3.51 (m, 1H), 5.01-5.04 (m, 1H), 6.97 (dd, J=7, 1 Hz, 1H), 7.38-7.52 (m, 3H), 8.29 (dd, J=8, 2 Hz, 1H), 8.85 (dd, J=4, 2 Hz, 1H), 12.45 (s, 1H); LC-MS (LC-ES) M+H=369.

Example 199

(trans)-N-(5-Cyclopropyl-1,3,4-thiadiazol-2-yl)-3-(quinolin-8-yloxy)cyclobutanecarboxamide

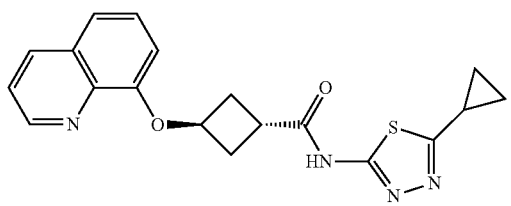 [SMILES: O=C(Nc1nnc(C2CC2)s1)[C@H]1C[C@H](Oc2cccc3cccnc23)C1]

To a DMF (4 mL) solution of (trans)-3-(quinolin-8-yloxy)cyclobutanecarboxylic acid (Intermediate 79) (50 mg, 0.21 mmol) was added HATU (94 mg, 0.25 mmol) and N,N-diisopropylethylamine (0.11 mL, 0.62 mmol). After 5 minutes, 5-cyclopropyl-1,3,4-thiadiazol-2-amine (35 mg, 0.25 mmol) was added, and the mixture was stirred for 3 h, quenched with water, and the resulting precipitate was collected by filtration to give the title compound (41 mg, 54%). $^1$H NMR (400 MHz, $CD_3SOCD_3$) δ 0.89-1.01 (m, 2H), 1.08-1.15 (m, 2H), 2.34-2.40 (m, 1H), 2.48-2.53 (m, 2H), 2.71-2.82 (m, 2H), 3.43-3.50 (m, 1H), 5.02-5.10 (m, 1H), 6.96 (dd, J=7, 2 Hz, 1H), 7.41-7.55 (m, 3H), 8.29 (dd, J=8, 2 Hz, 1H), 8.85 (dd, J=4, 2 Hz, 1H), 12.43 (s, 1H); LC-MS (LC-ES) M+H=367.

Example 200

(trans)-N-(4-(2-Hydroxypropan-2-yl)thiazol-2-yl)-3-(quinolin-8-yloxy)cyclobutanecarboxamide

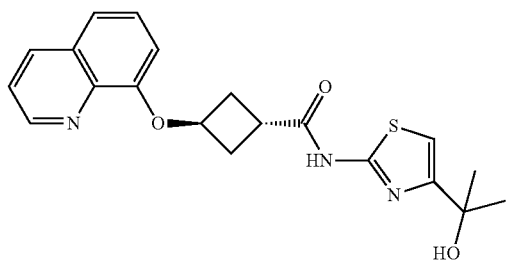 [SMILES: CC(C)(O)c1csc(NC(=O)[C@H]2C[C@H](Oc3cccc4cccnc34)C2)n1]

To a solution of (trans)-N-(4-acetylthiazol-2-yl)-3-(quinolin-8-yloxy)cyclobutanecarboxamide (Example 186) (57 mg, 0.16 mmol) in THF (5 mL) cooled to 0° C. was added 3 M methylmagnesium bromide in ether (0.10 mL, 0.31 mmol). After 1 h, the mixture was poured into saturated aqueous $NH_4Cl$, extracted with EtOAc (3×), dried over $Na_2SO_4$, filtered and concentrated. The residue was purified on silica gel, eluting with a 0%-100% EtOAc:EtOH (3:1)-hexanes gradient to give the title compound (18 mg, 29%). $^1$H NMR (400 MHz, $CD_3SOCD_3$) δ 1.39 (s, 6H), 2.39-2.46 (m, 2H), 2.72-2.79 (m, 2H), 3.35-3.46 (m, 1H), 5.01 (s, 1H), 5.02-5.10 (m, 1H), 6.86 (s, 1H), 6.97 (dd, J=7, 2 Hz, 1H), 7.41-7.56 (m, 3H), 8.29 (dd, J=8, 2 Hz, 1H), 8.85 (dd, J=4, 2 Hz, 1H), 12.64 (s, 1H); LC-MS (LC-ES) M+H=384.

Example 201

(trans)-3-(Quinolin-8-yloxy)-N-(4-(trifluoromethyl)thiazol-2-yl)cyclobutanecarboxamide

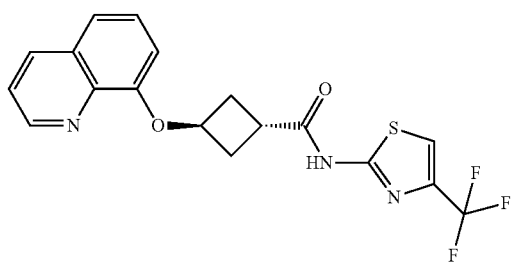 [SMILES: O=C(Nc1nc(C(F)(F)F)cs1)[C@H]1C[C@H](Oc2cccc3cccnc23)C1]

To a DMF (4 mL) solution of (trans)-3-(quinolin-8-yloxy)cyclobutanecarboxylic acid (Intermediate 79) (100 mg, 0.411 mmol) was added HATU (188 mg, 0.493 mmol) and N,N-diisopropylethylamine (0.22 mL, 1.2 mmol). After 5 minutes, 4-(trifluoromethyl)thiazol-2-amine (83 mg, 0.49 mmol) was added, and the mixture was stirred for 3 h, quenched with water, extracted with EtOAc, dried over $Na_2SO_4$, filtered and concentrated. The residue was purified on silica gel, eluting with a 0%-100% EtOAc:EtOH (3:1)-hexanes gradient to give the title compound (20 mg, 10%). $^1$H NMR (400 MHz, $CD_3SOCD_3$) δ 2.48-2.55 (m, 2H), 2.69-2.81 (m, 2H), 3.42-3.50 (m, 1H), 4.89-5.09 (m, 1H), 6.92-7.02 (m, 1H), 7.41-7.66 (m, 4H), 8.28-8.35 (m, 1H), 8.84-8.88 (m, 1H), 12.65 (s, 1H); LC-MS (LC-ES) M+H=394.

Example 202

(trans)-N-(5-Acetylthiazol-2-yl)-3-(quinolin-8-yloxy)cyclobutanecarboxamide

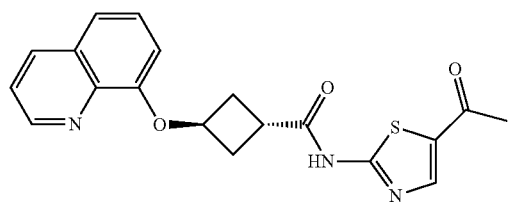

To a DMF (4 mL) solution of (trans)-3-(quinolin-8-yloxy)cyclobutanecarboxylic acid (Intermediate 79) (100 mg, 0.411 mmol) was added HATU (188 mg, 0.493 mmol) and N,N-diisopropylethylamine (0.22 mL, 1.2 mmol). After 5 minutes, 1-(2-aminothiazol-5-yl)ethanone (70 mg, 0.49 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (75 mg, 38%). $^1$H NMR (400 MHz, CD$_3$SOCD$_3$) δ 2.31 (s, 3H), 2.42-2.52 (m, 2H), 2.78-2.85 (m, 2H), 3.45-3.55 (m, 1H), 5.02-5.10 (m, 1H), 6.94-7.00 (m, 1H), 7.41-7.59 (m, 3H), 7.91-7.99 (m, 1H), 8.26-8.31 (m, 1H), 8.85 (br s, 1H), 12.60 (s, 1H); LC-MS (LC-ES) M+H=368.

Example 203

(trans)-N-(5-Methyl-1,3,4-thiadiazol-2-yl)-3-(quinolin-8-yloxy)cyclobutanecarboxamide

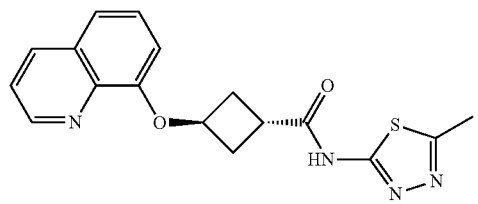 [SMILES: Cc1nnc(NC(=O)[C@H]2C[C@H](Oc3cccc4cccnc34)C2)s1]

To a DMF (4 mL) solution of (trans)-3-(quinolin-8-yloxy)cyclobutanecarboxylic acid (Intermediate 79) (45 mg, 0.19 mmol) was added HATU (84 mg, 0.22 mmol) and N,N-diisopropylethylamine (0.1 mL, 0.6 mmol). After 5 minutes, 5-methyl-1,3,4-thiadiazol-2-amine (26 mg, 0.22 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (30 mg, 46%). $^1$H NMR (400 MHz, CD$_3$SOCD$_3$) δ 2.41-2.49 (m, 1H), 2.60 (s, 3H), 2.72-2.83 (m, 2H), 3.41-3.51 (m, 1H), 4.98-5.03 (m, 1H), 6.97 (dd, J=7, 2 Hz, 1H), 7.41-7.51 (m, 3H), 8.29 (dd, J=8, 2 Hz, 1H), 8.85 (dd, J=4, 2 Hz, 1H), 12.41 (s, 1H); LC-MS (LC-ES) M+H=341.

Example 204

(trans)-N-(5-(2-Hydroxypropan-2-yl)thiazol-2-yl)-3-(quinolin-8-yloxy)cyclobutanecarboxamide

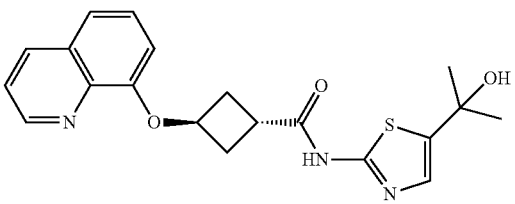 [SMILES: CC(C)(O)c1cnc(NC(=O)[C@H]2C[C@H](Oc3cccc4cccnc34)C2)s1]

To a DMF (4 mL) solution of (trans)-3-(quinolin-8-yloxy)cyclobutanecarboxylic acid (Intermediate 79) (45 mg, 0.19 mmol) was added HATU (84 mg, 0.22 mmol) and N,N-diisopropylethylamine (0.1 mL, 0.6 mmol). After 5 minutes, 2-(2-aminothiazol-5-yl)propan-2-ol (Intermediate 84) (35 mg, 0.22 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (27 mg, 37%). $^1$H NMR (400 MHz, CD$_3$SOCD$_3$) δ 1.48 (s, 6H), 2.43-2.53 (m, 2H), 2.71-2.80 (m, 2H), 3.38-3.47 (m, 1H), 5.02-5.08 (m, 1H), 5.42 (s, 1H), 6.97 (dd, J=7, 2 Hz, 1H), 7.18 (s, 1H), 7.41-7.54 (m, 3H), 8.29 (dd, J=8, 2 Hz, 1H), 8.85 (dd, J=4, 2 Hz, 1H), 11.92 (s, 1H); LC-MS (LC-ES) M+H=384.

Example 205

(trans)-N-(5-(Prop-1-en-2-yl)thiazol-2-yl)-3-(quinolin-8-yloxy)cyclobutanecarboxamide

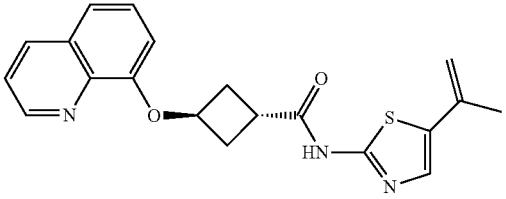 [SMILES: C=C(C)c1cnc(NC(=O)[C@H]2C[C@H](Oc3cccc4cccnc34)C2)s1]

To a DMF (2 mL) solution of (trans)-3-(quinolin-8-yloxy)cyclobutanecarboxylic acid (Intermediate 79) (40 mg, 0.16 mmol) was added HATU (75 mg, 0.20 mmol) and N,N-diisopropylethylamine (0.17 mL, 1.0 mmol). After 5 minutes, 5-(prop-1-en-2-yl)thiazol-2-amine, trifluoroacetic acid salt (Intermediate 85) (50 mg, 0.20 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (31 mg, 49%). $^1$H NMR (400 MHz, CD$_3$SOCD$_3$) δ 2.06 (s, 3H), 2.41-2.53 (m, 2H), 2.79 (ddd, J=13, 7, 5 Hz, 2H), 3.45 (dd, J=10, 5 Hz, 1H), 4.96 (s, 1H), 5.01-5.11 (m, 1H), 5.18 (s, 1H), 6.97 (dd, J=7, 2 Hz, 1H), 7.41-7.61 (m, 4H), 8.29 (dd, J=8, 2 Hz, 1H), 8.84 (dd, J=4, 2 Hz, 1H), 12.16 (s, 1H); LC-MS (LC-ES) M+H=366.

Example 206

(trans)-N-(4-Isopropylthiazol-2-yl)-3-(quinolin-8-yloxy)cyclobutanecarboxamide

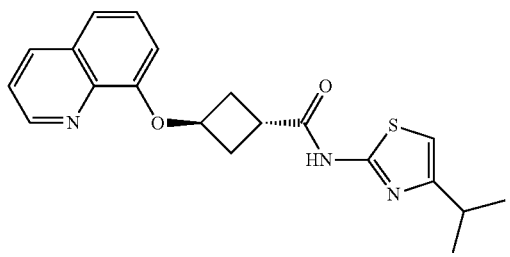 [SMILES: CC(C)c1csc(NC(=O)[C@H]2C[C@H](Oc3cccc4cccnc34)C2)n1]

To a DMF (4 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, 4-isopropylthiazol-2-amine (56.1 mg, 0.395 mmol) was added, and the mixture was stirred for 3 h, quenched with water, extracted with EtOAc, dried over $Na_2SO_4$, filtered and concentrated. The residue was purified on silica gel, eluting with a 0%-100% EtOAc:EtOH (3:1)-hexanes gradient to give the title compound (55 mg, 41%). $^1$H NMR (400 MHz, $CD_3SOCD_3$) δ 1.19 (d, J=7 Hz, 6H), 2.39-2.51 (m, 2H), 2.71-2.79 (m, 2H), 2.87 (q, J=7 Hz, 1H), 3.38-3.48 (m, 1H), 4.95-5.03 (m, 1H), 6.73 (s, 1H), 6.97 (dd, J=7, 2 Hz, 1H), 7.42-7.54 (m, 3H), 8.29 (dd, J=8, 2 Hz, 1H), 8.85 (dd, J=4, 2 Hz, 1H), 12.11 (s, 1H); LC-MS (LC-ES) M+H=368.

Example 207

(trans)-N-(4-Cyclopropylthiazol-2-yl)-3-(quinolin-8-yloxy)cyclobutanecarboxamide

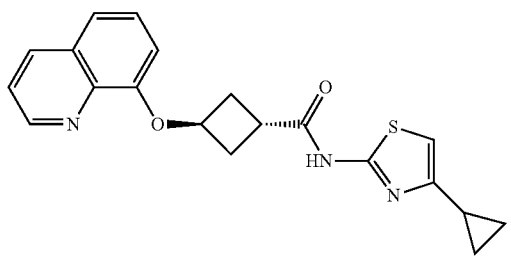 [SMILES: O=C(Nc1nc(C2CC2)cs1)[C@H]1C[C@H](Oc2cccc3cccnc23)C1]

To a DMF (4 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, 4-cyclopropylthiazol-2-amine (55.3 mg, 0.395 mmol) was added, and the mixture was stirred for 3 h, quenched with water, extracted with EtOAc, dried over $Na_2SO_4$, filtered and concentrated. The residue was purified on silica gel, eluting with a 0%-100% EtOAc:EtOH (3:1)-hexanes gradient to give the title compound (25 mg, 21%). $^1$H NMR (400 MHz, $CD_3SOCD_3$) δ 0.63-0.71 (m, 2H), 0.82-0.90 (m, 2H), 1.96-2.00 (m, 1H), 2.41-2.51 (m, 2H), 2.69-2.85 (m, 2H), 3.39-3.45 (m, 1H), 5.01-5.09 (m, 1H), 6.77 (s, 1H), 6.96 (dd, J=7, 2 Hz, 1H), 7.41-7.56 (m, 3H), 8.29 (dd, J=8, 2 Hz, 1H), 8.84 (dd, J=4, 2 Hz, 1H), 12.06 (s, 1H); LC-MS (LC-ES) M+H=366.

Example 208

(trans)-N-(Oxazol-2-yl)-3-(quinolin-8-yloxy)cyclobutanecarboxamide

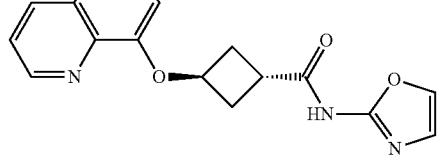

To a DMF (4 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, oxazol-2-amine (33 mg, 0.40 mmol) was added, and the mixture was stirred for 3 h, quenched with water, extracted with EtOAc, dried over $Na_2SO_4$, filtered and concentrated. The residue was purified on silica gel, eluting with a 0%-100% EtOAc:EtOH (3:1)-hexanes gradient to give the title compound (35 mg, 33%). $^1$H NMR (400 MHz, $CD_3SOCD_3$) δ 2.38-2.49 (m, 1H), 2.72-2.83 (m, 2H), 3.30-3.52 (m, 1H), 4.89-5.04 (m, 1H), 6.95 (d, J=6 Hz, 1H), 7.08 (s, 1H), 7.41-7.69 (m, 3H), 7.85 (s, 1H), 8.28 (dd, J=8, 1 Hz, 1H), 8.84 (dd, J=4, 1 Hz, 1H), 11.20 (s, 1H); LC-MS (LC-ES) M+H=310.

Example 209

(trans)-N-(4-(2-Hydroxy-2-methylpropyl)thiazol-2-yl)-3-(quinolin-8-yloxy)cyclobutanecarboxamide trifluoroacetic acid salt

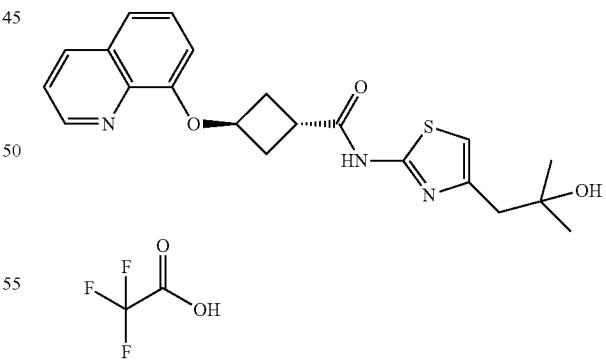

To a DMF (3 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, 1-(2-aminothiazol-4-yl)-2-methylpropan-2-ol hydrochloride (Intermediate 86) (82 mg, 0.40 mmol) was added, and the mixture was stirred for 3 h, quenched with water, extracted with EtOAc, dried over $Na_2SO_4$, filtered and concentrated. The residue was purified on silica gel, eluting with a 0%-100% EtOAc:EtOH (3:1)-hexanes gradient to give impure product which was purified on reverse-phase silica gel, eluting with a 10%-100% acetonitrile-water (TFA additive) gradient to give the title compound (20 mg, 11%). $^1$H NMR (400 MHz, CD$_3$SOCD$_3$) δ 1.08 (s, 6H), 2.50-2.62 (m, 2H), 2.68 (s, 2H), 2.82 (ddd, J=13, 7, 4 Hz, 2H), 3.38-3.47 (m, 1H), 5.09-5.18 (m, 1H), 6.81 (s, 1H), 7.20 (d, J=7 Hz, 1H), 7.60-7.69 (m, 3H), 7.81 (dd, J=8, 5 Hz, 1H), 8.71 (d, J=8 Hz, 1H), 9.01 (dd, J=5, 1 Hz, 1H), 12.12 (br s, 1H); LC-MS (LC-ES) M+H=398.

Example 210

(trans)-N-(5-(Hydroxymethyl)thiazol-2-yl)-3-(quinolin-8-yloxy)cyclobutanecarboxamide

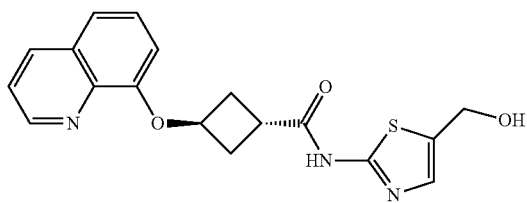 [SMILES: O=C(Nc1ncc(CO)s1)[C@H]1C[C@H](Oc2cccc3cccnc23)C1]

To a DMF (4 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, (2-aminothiazol-5-yl)methanol (51.4 mg, 0.395 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (26 mg, 21%). $^1$H NMR (400 MHz, CD$_3$SOCD$_3$) δ 2.39-2.51 (m, 2H), 2.79 (qd, J=7, 5 Hz, 2H), 3.40-3.48 (m, 1H), 4.57 (d, J=5 Hz, 2H), 5.00-5.10 (m, 1H), 5.35 (t, J=5 Hz, 1H), 6.97 (dd, J=7, 2 Hz, 1H), 7.26 (s, 1H), 7.42-7.59 (m, 3H), 8.29 (dd, J=8, 2 Hz, 1H), 8.84 (dd, J=4, 2 Hz, 1H), 12.00 (s, 1H); LC-MS (LC-ES) M+H=356.

Example 211

(trans)-N-(4-(tert-Butyl)thiazol-2-yl)-3-(quinolin-8-yloxy)cyclobutanecarboxamide

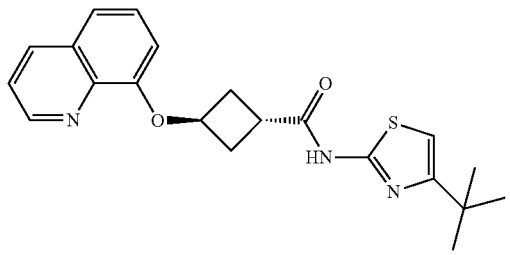 [SMILES: CC(C)(C)c1csc(NC(=O)[C@H]2C[C@H](Oc3cccc4cccnc34)C2)n1]

To a DMF (4 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, 4-(tert-butyl)thiazol-2-amine (62 mg, 0.40 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (48 mg, 36%). $^1$H NMR (400 MHz, CD$_3$SOCD$_3$) δ 1.24 (s, 9H), 2.36-2.50 (m, 2H), 2.67-2.80 (m, 2H), 3.38-3.45 (m, 1H), 4.96-5.04 (s, 1H), 6.73 (s, 1H), 6.96 (dd, J=7, 2 Hz, 1H), 7.42-7.56 (m, 3H), 8.29 (dd, J=8, 2 Hz, 1H), 8.84 (dd, J=4, 2 Hz, 1H), 12.12 (s, 1H); LC-MS (LC-ES) M+H=382.

Example 212

Racemic (trans)-N-(2,3-Dihydro-1H-inden-1-yl)-3-(quinolin-8-yloxy)cyclobutanecarboxamide

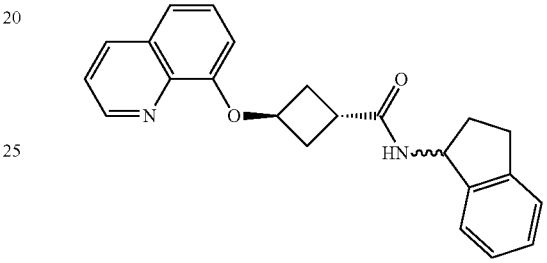

To a DMF (3 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, 1-aminoindane (0.05 mL, 0.4 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (48 mg, 36%). $^1$H NMR (400 MHz, CD$_3$SOCD$_3$) δ 1.68-1.79 (m, 1H), 2.31-2.45 (m, 3H), 2.59-2.97 (m, 4H), 3.05-3.12 (m, 1H), 5.02-5.10 (m, 1H), 5.29-5.35 (m, 1H), 6.92-6.99 (m, 1H), 7.12-7.22 (m, 4H), 7.45-7.58 (m, 3H), 8.21-8.30 (m, 2H), 8.83 (dd, J=4, 2 Hz, 1H); LC-MS (LC-ES) M+H=359.

Example 213

(trans)-N-(5-(2-Hydroxy-2-methylpropyl)thiazol-2-yl)-3-(quinolin-8-yloxy)cyclobutanecarboxamide

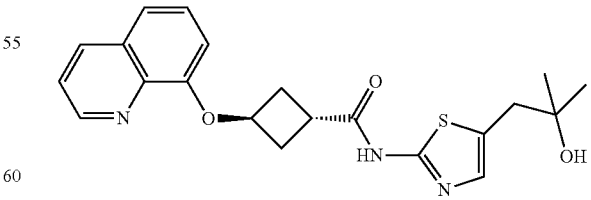

To a DMF (2 mL) solution of (trans)-3-(quinolin-8-yloxy)cyclobutanecarboxylic acid (Intermediate 79) (24 mg, 0.10 mmol) was added HATU (44 mg, 0.12 mmol) and N,N-diisopropylethylamine (0.05 mL, 0.3 mmol). After 5 minutes, 1-(2-aminothiazol-5-yl)-2-methylpropan-2-ol (Intermediate 87) (20 mg, 0.12 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (48 mg, 36%). $^1$H NMR (400 MHz, CD$_3$SOCD$_3$) δ 1.07 (s, 6H), 2.39-2.49 (m, 2H), 2.71-2.83 (m, 4H), 3.39-3.45 (m, 1H), 4.53 (s, 1H), 5.05-5.14 (m, 1H), 6.97 (dd, J=7, 2 Hz, 1H), 7.11 (s, 1H), 7.44-7.55 (m, 3H), 8.28 (dd, J=8, 2 Hz, 1H), 8.84 (dd, J=4, 2 Hz, 1H), 11.88 (s, 1H); LC-MS (LC-ES) M+H=398.

Example 214

(trans)-N-(3-Cyclopropyl-1-methyl-1H-pyrazol-5-yl)-3-(quinolin-8-yloxy)cyclobutanecarboxamide

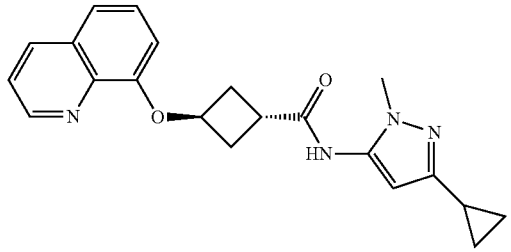 [SMILES: Cn1nc(C2CC2)cc1NC(=O)[C@H]1C[C@H](Oc2cccc3cccnc23)C1]

To a DMF (3 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, 3-cyclopropyl-1-methyl-1H-pyrazol-5-amine (54 mg, 0.40 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (48 mg, 36%). $^1$H NMR (400 MHz, CD$_3$SOCD$_3$) δ 0.45-0.53 (m, 2H), 0.72-0.80 (m, 2H), 1.74 (dd, J=9, 4 Hz, 1H), 2.39-2.54 (m, 2H), 2.71-2.80 (m, 2H), 3.02-3.15 (m, 3H), 3.53-3.62 (m, 1H), 4.99-5.09 (m, 1H), 6.98 (d, J=6 Hz, 1H), 7.40-7.59 (m, 3H), 8.13 (br s, 1H), 8.33 (d, J=8 Hz, 1H), 8.85 (d, J=3 Hz, 1H), 9.86 (s, 1H); LC-MS (LC-ES) M−H=361.

Example 215

(trans)-N-(4-(Hydroxymethyl)thiazol-2-yl)-3-(quinolin-8-yloxy)cyclobutanecarboxamide

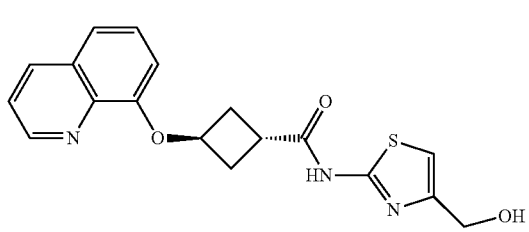 [SMILES: O=C(Nc1nc(CO)cs1)[C@H]1C[C@H](Oc2cccc3cccnc23)C1]

To a DMF (3 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, (2-aminothiazol-4-yl)methanol (51 mg, 0.40 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (30 mg, 19%). $^1$H NMR (400 MHz, CD$_3$SOCD$_3$) δ 2.49-2.53 (m, 2H), 2.72-2.81 (m, 2H), 3.44 (tt, J=10, 5 Hz, 1H), 4.43 (d, J=1 Hz, 2H), 5.08-5.16 (m, 1H), 6.88-6.91 (m, 1H), 7.11-7.18 (m, 1H), 7.51-7.60 (m, 3H), 7.71-7.79 (m, 1H), 8.59-8.69 (m, 1H), 8.92-8.97 (m, 1H), 12.10 (s, 1H); LC-MS (LC-ES) M+H=356.

Example 216

(trans)-3-(Quinolin-8-yloxy)-N-(1,3,4-thiadiazol-2-yl)cyclobutanecarboxamide

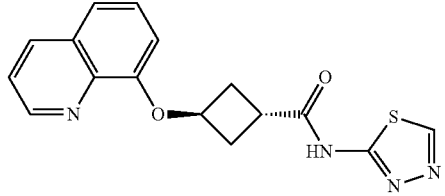 [SMILES: O=C(Nc1nncs1)[C@H]1C[C@H](Oc2cccc3cccnc23)C1]

To a DMF (3 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, 1,3,4-thiadiazol-2-amine (40 mg, 0.40 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (91 mg, 83%). $^1$H NMR (400 MHz, CD$_3$SOCD$_3$) δ 2.42-2.53 (m, 2H), 2.71-2.85 (m, 2H), 3.42-3.53 (m, 1H), 4.98-5.07 (m, 1H), 6.97 (dd, J=7, 2 Hz, 1H), 7.16 (br s, 1H), 7.42-7.59 (m, 3H), 8.29 dd, J=8, 2 Hz, 1H), 8.84 (dd, J=4, 2 Hz, 1H), 12.61 (s, 1H); LC-MS (LC-ES) M+H=327.

Example 217

(trans)-N-(5-Methylthiazol-2-yl)-3-(quinolin-8-yloxy)cyclobutanecarboxamide

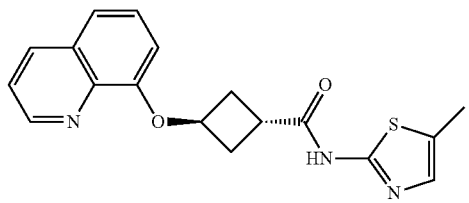 [SMILES: Cc1cnc(NC(=O)[C@H]2C[C@H](Oc3cccc4cccnc34)C2)s1]

To a DMF (3 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, 5-methylthiazol-2-amine (45 mg, 0.40 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (67 mg, 60%). $^1$H NMR (400 MHz, CD$_3$SOCD$_3$) δ 2.32 (s, 3H), 2.49-2.50 (m, 2H), 2.72-2.80 (m, 2H), 3.38-3.45 (m, 1H), 5.00-5.08 (m, 1H), 6.96 (d, J=8 Hz, 1H), 7.10 (s, 1H), 7.41-7.51 (m, 3H), 8.29 (dd, J=8, 4 Hz, 1H), 8.82-8.86 (m, 1H), 11.93 (s, 1H); LC-MS (LC-ES) M+H=340.

Example 218

(trans)-N-(4-Methylthiazol-2-yl)-3-(quinolin-8-yloxy)cyclobutanecarboxamide

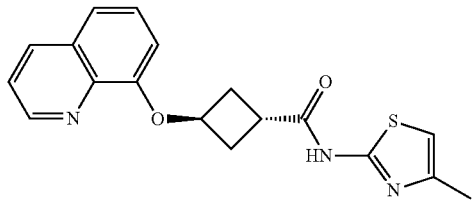 [SMILES: Cc1csc(NC(=O)[C@H]2C[C@H](Oc3cccc4cccnc34)C2)n1]

To a DMF (3 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, 4-methylthiazol-2-amine (45 mg, 0.40 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (42 mg, 38%). $^1$H NMR (400 MHz, CD$_3$SOCD$_3$) δ 2.23 (m, 3H), 2.39-2.51 (m, 2H), 2.72-2.82 (m, 2H), 3.42 (tt, J=10, 5 Hz, 1H), 5.01-5.10 (m, 1H), 6.74 (s, 1H), 6.96 (dd, J=7, 2 Hz, 1H), 7.40-7.59 (m, 3H), 8.28 (dd, J=8, 2 Hz, 1H), 8.84 (dd, J=4, 2 Hz, 1H), 12.05 (s, 1H); LC-MS (LC-ES) M+H=340.

Example 219

(trans)-N-(1-(Methylsulfonyl)piperidin-4-yl)-3-(quinolin-8-yloxy)cyclobutanecarboxamide

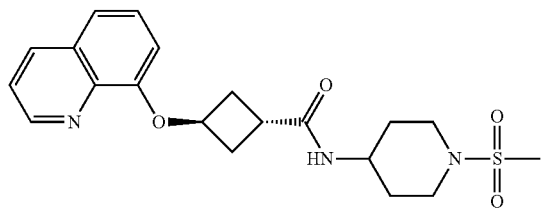 [SMILES: CS(=O)(=O)N1CCC(NC(=O)[C@H]2C[C@H](Oc3cccc4cccnc34)C2)CC1]

To a DMF (3 mL) solution of (trans)-3-(quinolin-8-yloxy)cyclobutanecarboxylic acid (Intermediate 79) (80 mg, 0.33 mmol) was added HATU (150 mg, 0.395 mmol) and N,N-diisopropylethylamine (0.17 mL, 1.0 mmol). After 5 minutes, 1-(methylsulfonyl)piperidin-4-amine (70 mg, 0.40 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)- hexanes gradient to give the title compound (27 mg, 19%). $^1$H NMR (400 MHz, CD$_3$SOCD$_3$) δ 1.32-1.45 (m, 2H), 1.78-1.86 (m, 2H), 2.31-2.41 (m, 2H), 2.59-2.68 (m, 2H), 2.80-2.85 (m, 1H), 2.84 (s, 3H), 3.01-3.13 (m, 3H), 3.55-3.62 (m, 2H), 4.95-5.01 (m, 1H), 6.91-6.95 (m, 1H), 7.44-7.48 (m, 1H), 7.51-7.56 (m, 1H), 7.87-7.91 (m, 1H), 8.13 (br s, 1H), 8.30 (d, J=12 Hz, 1H), 8.83-8.86 (m, 1H); LC-MS (LC-ES) M+H=404.

Example 220

(trans)-N-((trans)-4-(2-Hydroxy-2-methylpropoxy)cyclohexyl)-3-(quinolin-8-yloxy)cyclobutanecarboxamide

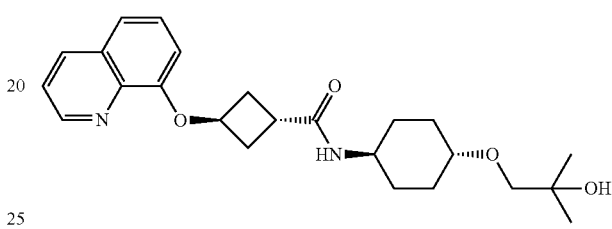

To a DMF (3 mL) solution of (trans)-3-(quinolin-8-yloxy)cyclobutanecarboxylic acid (Intermediate 79) (65 mg, 0.27 mmol) was added HATU (122 mg, 0.320 mmol) and N,N-diisopropylethylamine (0.28 mL, 1.6 mmol). After 5 minutes, 1-(((trans)-4-aminocyclohexyl)oxy)-2-methylpropan-2-ol acid (Intermediate 23) (60 mg, 0.32 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (45 mg, 41%). $^1$H NMR (400 MHz, CD$_3$SOCD$_3$) δ 1.01 (s, 6H), 1.13-1.19 (m, 4H), 1.72-1.80 (m, 2H), 1.89-1.96 (m, 2H), 2.29-2.39 (m, 2H), 2.58-2.65 (m, 2H), 2.99-3.08 (m, 1H), 3.08-3.15 (m, 3H), 3.54-3.62 (m, 1H), 4.18 (br s, 1H), 4.92-5.02 (m, 1H), 6.89-6.93 (m, 1H), 7.44-7.47 (m, 1H), 7.49-7.54 (m, 1H), 7.69-7.74 (m, 1H), 8.13 (br s, 1H), 8.27 (d, J=12 Hz, 1H), 8.81-8.85 (m, 1H); LC-MS (LC-ES) M+H=413.

Example 221

(trans)-3-(Quinolin-8-ylamino)-N-(thiazol-2-yl)cyclobutanecarboxamide

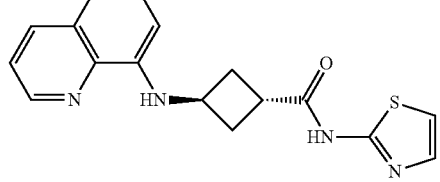

To a DMF (4 mL) solution of (trans)-3-(quinolin-8-ylamino)cyclobutanecarboxylic acid (Intermediate 88) (80 mg, 0.33 mmol) was added HATU (151 mg, 0.396 mmol) and N,N-diisopropylethylamine (0.17 mL, 1.0 mmol). After 5 minutes, thiazol-2-amine (36 mg, 0.36 mmol) was added, and the mixture was stirred for 3 h, quenched with water, extracted with EtOAc, dried over Na$_2$SO$_4$, filtered and concentrated. The residue was triturated with hexanes, filtered and dried under vacuum to give the title compound (62 mg, 58%). $^1$H NMR (400 MHz, CD$_3$SOCD$_3$) δ 2.28-2.34 (m, 2H), 2.62-2.71 (m, 2H), 3.31-3.40 (m, 1H), 4.15-4.24 (m, 1H), 6.50-6.53 (m, 1H), 6.59-6.63 (m, 1H), 7.04-7.09 (m, 1H), 7.18-7.20 (m, 1H), 7.30-7.36 (m, 1H), 7.42-7.45 (m, 1H), 7.46-7.50 (m, 1H), 8.18-8.21 (m, 1H), 8.72-8.76 (m, 1H), 12.00 (s, 1H); LC-MS (LC-ES) M+H=325.

Example 222

(trans)-N-((trans)-4-(2-Hydroxypropan-2-yl)cyclohexyl)-3-(quinolin-8-ylamino)cyclobutanecarboxamide

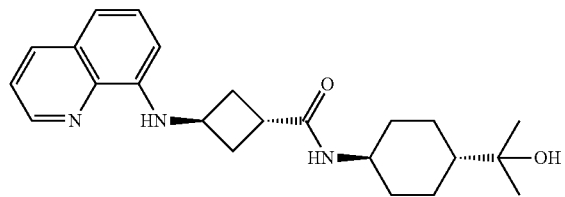 [SMILES: CC(C)(O)[C@H]1CC[C@H](NC(=O)[C@H]2C[C@H](Nc3cccc4cccnc34)C2)CC1]

To a DMF (4 mL) solution of (trans)-3-(quinolin-8-ylamino)cyclobutanecarboxylic acid (Intermediate 88) (80 mg, 0.33 mmol) was added HATU (151 mg, 0.396 mmol) and N,N-diisopropylethylamine (0.17 mL, 1.0 mmol). After 5 minutes, 2-((trans)-4-aminocyclohexyl)propan-2-ol (57 mg, 0.36 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give the title compound (95 mg, 75%). $^1$H NMR (400 MHz, CD$_3$SOCD$_3$) δ 0.96 (s, 6H), 0.96-1.13 (m, 5H), 1.70-1.81 (m, 4H), 2.11-2.20 (m, 2H), 2.48-2.55 (m, 2H), 2.92-2.98 (m, 1H), 3.40-3.48 (m, 1H), 3.98 (s, 1H), 4.11-4.19 (m, 1H), 6.42-6.49 (m, 1H), 6.49-6.52 (m, 1H), 7.02-7.07 (m, 1H), 7.20-7.25 (m, 1H), 7.45-7.50 (m, 1H), 7.55-7.61 (m, 1H), 8.16-8.21 (m, 1H), 8.69-8.74 (m, 1H); LC-MS (LC-ES) M+H=382.

Example 223

(trans)-N-((trans)-3-(2-Hydroxypropan-2-yl)cyclobutyl)-3-(quinolin-8-yloxy)cyclobutanecarboxamide

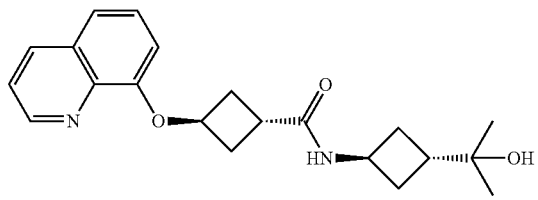 [SMILES: CC(C)(O)[C@H]1C[C@H](NC(=O)[C@H]2C[C@H](Oc3cccc4cccnc34)C2)C1]

To a DMF (4 mL) solution of (trans)-3-(quinolin-8-yloxy)cyclobutanecarboxylic acid (Intermediate 79) (60 mg, 0.25 mmol) was added HATU (113 mg, 0.296 mmol) and N,N-diisopropylethylamine (0.13 mL, 0.74 mmol). After 5 minutes, 2-(3-aminocyclobutyl)propan-2-ol (35 mg, 0.27 mmol) was added, and the mixture was stirred for 3 h, quenched with water, extracted with EtOAc, dried over Na$_2$SO$_4$, filtered and concentrated. The residue was purified on silica gel, eluting with a 0%-100% acetonitrile-water (TFA additive) gradient to give the product as a mixture of isomers. This mixture was dissolved in EtOAc (2 mL) and stirred with saturated aqueous NaHCO$_3$ solution (2 mL) for 2 h. The aqueous phase was separated and extracted with EtOAc, and the combined organic layers were dried over Na$_2$SO$_4$, filtered and concentrated. The resulting solid was purified on an IC column with 50% EtOH in hexanes as the mobile phase to give the title compound (6 mg, 7%). $^1$H NMR (400 MHz, CD$_3$SOCD$_3$) δ 1.03 (s, 6H), 1.76-1.91 (m, 2H), 2.12-2.30 (m, 3H), 2.33-2.45 (m, 2H), 2.66 (ddd, J=13, 7, 4 Hz, 2H), 3.08 (dt, J=10, 5 Hz, 1H), 4.04-4.20 (m, 1H), 4.17 (s, 1H), 4.99-5.07 (m, 1H), 6.95 (dd, J=7, 2 Hz, 1H), 7.43-7.52 (m, 2H), 7.55 (dd, J=8, 4 Hz, 1H), 8.12 (d, J=7 Hz, 1H), 8.31 (dd, J=8, 2 Hz, 1H), 8.87 (dd, J=4, 2 Hz, 1H); LC-MS (LC-ES) M+H=355.

Example 224

(trans)-3-(Quinolin-8-yloxy)-N-(1-(2,2,2-trifluoroethyl)piperidin-4-yl)cyclobutanecarboxamide

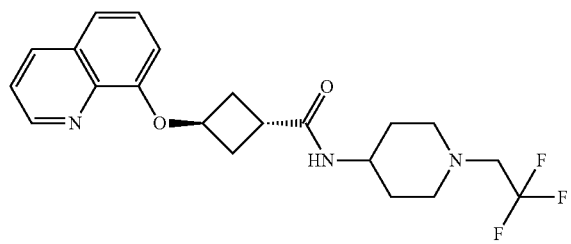 [SMILES: O=C(NC1CCN(CC(F)(F)F)CC1)[C@H]1C[C@H](Oc2cccc3cccnc23)C1]

To a DMF (3 mL) solution of (trans)-3-(quinolin-8-yloxy)cyclobutanecarboxylic acid (Intermediate 79) (60 mg, 0.25 mmol) was added HATU (113 mg, 0.296 mmol) and N,N-diisopropylethylamine (0.26 mL, 1.5 mmol). After 5 minutes, 1-(2,2,2-trifluoroethyl)piperidin-4-amine dihydrochloride (Intermediate 46B) (69 mg, 0.27 mmol) was added, and the mixture was stirred for 3 h, quenched with water, extracted with EtOAc, dried over Na$_2$SO$_4$, filtered and concentrated. The residue was purified on silica gel, eluting with a 0%-100% acetonitrile-water (TFA additive) gradient to give the product as a TFA salt, which was dissolved in EtOAc (2 mL) and stirred with saturated aqueous NaHCO$_3$ solution (2 mL) for 2 h. The aqueous phase was separated and extracted with EtOAc, and the combined organic layers were dried over Na$_2$SO$_4$, filtered and concentrated to give the title compound (78 mg, 78%). $^1$H NMR (400 MHz, CD$_3$SOCD$_3$) δ 1.30-1.43 (m, 2H), 1.66-1.74 (m, 2H), 2.28-2.40 (m, 4H), 2.59-2.67 (m, 2H), 2.81-2.89 (m, 2H), 3.00-3.09 (m, 1H), 3.09-3.18 (m, 2H), 3.48-3.60 (m, 1H), 4.97-5.04 (m, 1H), 6.89-6.95 (m, 1H), 7.44-7.48 (m, 2H), 7.49-7.54 (m, 1H), 7.76-7.80 (m, 1H), 8.26-8.30 (m, 1H), 8.81-8.85 (m, 1H); LC-MS (LC-ES) M+H=408.

Example 225

N-((trans)-4-(2-Hydroxypropan-2-yl)cyclohexyl)-3-(quinolin-8-yloxy)cyclobutanecarboxamide

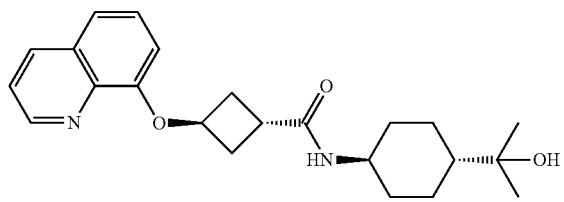 [SMILES: CC(C)(O)[C@H]1CC[C@H](NC(=O)[C@H]2C[C@H](Oc3cccc4cccnc34)C2)CC1]

To a DMF (4 mL) solution of (trans)-3-(quinolin-8-yloxy)cyclobutanecarboxylic acid (Intermediate 79) (80 mg, 0.33 mmol) was added HATU (152 mg, 0.40 mmol) and N,N-diisopropylethylamine (0.17 mL, 1.0 mmol). After 5 minutes, 2-((trans)-4-aminocyclohexyl)propan-2-ol (63 mg, 0.53 mmol) was added, and the mixture was stirred for 3 h, quenched with water, extracted with EtOAc, dried over Na$_2$SO$_4$, filtered and concentrated. The residue was purified on silica gel, eluting with a 0%-100% EtOAc:EtOH (3:1)-hexanes gradient to give an oil that was crystallized under hexane:DCM (2:1) that was slowly evaporated overnight to give the title compound (64 mg, 50%). $^1$H NMR (400 MHz, CD$_3$SOCD$_3$) δ 1.04 (s, 6H), 1.05-1.22 (m, 5H), 1.74-1.90 (m, 4H), 2.32-2.45 (m, 2H), 2.66 (ddd, J=13, 7, 4 Hz, 2H), 3.01-3.12 (m, 1H), 3.43-3.54 (m, 1H), 4.02 (s, 1H), 5.00-5.08 (m, 1H), 6.95 (dd, J=7, 2 Hz, 1H), 7.43-7.51 (m, 2H), 7.55 (dd, J=8, 4 Hz, 1H), 7.71 (d, J=8 Hz, 1H), 8.31 (dd, J=8, 2 Hz, 1H), 8.86 (dd, J=4, 2 Hz, 1H); LC-MS (LC-ES) M+H=383.

Example 226

N-((trans)-4-(2-Hydroxypropan-2-yl)cyclohexyl)-3-(thieno[3,2-b]pyridin-3-yloxy)azetidine-1-carboxamide

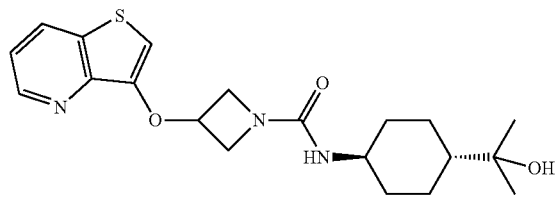 [SMILES: CC(C)(O)[C@H]1CC[C@H](NC(=O)N2CC(Oc3csc4cccnc34)C2)CC1]

To tert-butyl 3-(thieno[3,2-b]pyridin-3-yloxy)azetidine-1-carboxylate (Intermediate 89) (50 mg, 0.16 mmol) in 1,4-dioxane (0.5 mL), was added 4 M HCl in dioxane (0.1 mL, 0.4 mmol). The mixture was stirred at room temperature for 1 h and the solvent was removed in vacuo and the resulting material was triturated with diethyl ether to give a yellow solid. To a stirred mixture of this crude material in DCM (0.5 mL) was added N,N-diisopropylethylamine (0.1 mL, 0.6 mmol) followed by 4-nitrophenyl ((trans)-4-(2-hydroxypropan-2-yl)cyclohexyl)carbamate (Intermediate 3) (63 mg, 0.20 mmol). The mixture was stirred 1 h, diluted with EtOAc, washed with 1 N aqueous NaOH and brine, dried over Na$_2$SO$_4$ and filtered. Solvent was removed under reduced pressure. The remaining material was purified on reverse-phase silica gel, eluting with a 5%-95% acetonitrile-water (TFA additive) gradient. The appropriate fractions were concentrated, and the resulting material was diluted with ethyl acetate and washed with saturated aqueous sodium bicarbonate and brine. The organics were dried over sodium sulfate, filtered and concentrated to give the title compound (12 mg, 19%). $^1$H NMR (400 MHz, CDCl$_3$) δ 1.02-1.23 (m, 4H), 1.16 (s, 6H), 1.80-1.91 (m, 3H), 2.03-2.10 (m, 2H), 3.55 (dt, J=7, 4 Hz, 1H), 4.00 (d, J=7 Hz, 1H), 4.22 (dd, J=9, 4 Hz, 2H), 4.37 (dd, J=9, 7 Hz, 2H), 5.13 (tt, J=6.4 Hz, 1H), 6.46 (s, 1H), 7.32 (dd, J=8, 5 Hz, 1H), 8.12 (dd, J=8, 2 Hz, 1H), 8.72 (dd, J=5, 1 Hz, 1H); LC-MS (LC-ES) M+H=390.

Example 227

(trans)-3-((5-Fluorobenzofuran-7-yl)oxy)-N-((trans)-4-(2-hydroxypropan-2-yl)cyclohexyl)cyclobutanecarboxamide

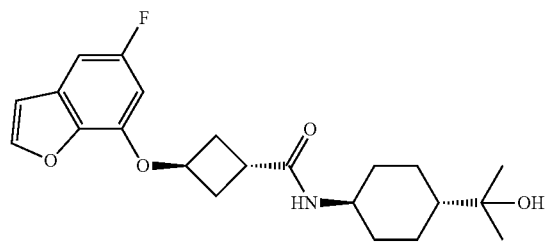 [SMILES: CC(C)(O)[C@H]1CC[C@H](NC(=O)[C@H]2C[C@H](Oc3cc(F)cc4ccoc34)C2)CC1]

To a DMF (3 mL) solution of (trans)-3-((5-fluorobenzofuran-7-yl)oxy)cyclobutanecarboxylic acid (Intermediate 90) (60 mg, 0.24 mmol), 2-((trans)-4-aminocyclohexyl)propan-2-ol (45 mg, 0.29 mmol) and N,N-diisopropylethylamine (0.17 mL, 0.96 mmol) was added, dropwise, a 50% solution of T3P in ethyl acetate (229 mg, 0.360 mmol). The reaction was stirred 3 h, quenched with saturated aqueous sodium bicarbonate solution and extracted with EtOAc (3×). The organic layers were combined, dried over MgSO$_4$, filtered and concentrated, and the residue was purified on silica gel, eluting with a 10%-60% EtOAc in heptane gradient to give the title compound (56 mg, 60%) as a white solid. $^1$H NMR (400 MHz, CD$_3$OD) δ 1.13 (s, 6H), 1.16-1.33 (m, 5H), 1.82-1.99 (m, 4H), 2.41-2.51 (m, 2H), 2.64-2.74 (m, 2H), 3.12 (tt, J=9, 4 Hz, 1H), 3.61 (d, J=4 Hz, 1H), 5.08 (quin, J=6 Hz, 1H), 6.50 (dd, J=11, 2 Hz, 1H), 6.79 (d, J=2 Hz, 1H), 6.87 (dd, J=8, 2 Hz, 1H), 7.75 (d, J=2 Hz, 1H), 7.82 (d, J=8 Hz, 1H); LC-MS (LC-ES) M+H=390.

Example 228

(trans)-3-(3-Bromophenoxy)-N-((trans)-4-(2-hydroxypropan-2-yl)cyclohexyl)cyclobutanecarboxamide

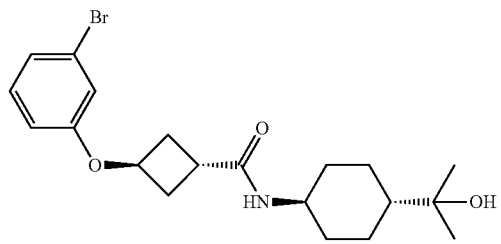 [SMILES: CC(C)(O)[C@H]1CC[C@H](NC(=O)[C@H]2C[C@H](Oc3cccc(Br)c3)C2)CC1]

To a solution of (trans)-methyl 3-(3-bromophenoxy)cyclobutanecarboxylate (Intermediate 91) (245 mg, 0.859 mmol) in THF (4 mL) and methanol (2 mL) was added water (2 mL) and LiOH (62 mg, 2.58 mmol). After 18 h, the reaction was concentrated. The residue was taken up in water and treated with 6 N aqueous HCl until a precipitate began to form. This solid was collected by filtration and dried under vacuum. DMF (5 mL) was added, and then HATU (327 mg, 0.859 mmol) and N,N-diisopropylethylamine (0.45 mL, 2.6 mmol). After 2 minutes, 2-((trans)-4-aminocyclohexyl)propan-2-ol (162 mg, 1.03 mmol) was added, and the mixture was stirred for 18 h, quenched with water, extracted with EtOAc, dried over Na$_2$SO$_4$, filtered and concentrated. The resulting material was purified on reverse-phase silica gel, eluting with a 20%-95% acetonitrile-water (TFA additive) gradient to give the title compound (170 mg, 48%). $^1$H NMR (400 MHz, CD$_3$OD) δ 1.10-1.33 (m, 11H), 1.85-2.00 (m, 4H), 2.28-2.39 (m, 2H), 2.62 (ddd, J=13, 7, 4 Hz, 2H), 3.03-3.11 (m, 1H), 3.53-3.65 (m, 1H), 4.87-4.92 (m, 1H), 6.76 (d, J=8 Hz, 1H), 6.96 (s, 1H), 7.05 (d, J=8 Hz, 1H), 7.09-7.20 (m, 1H); LC-MS (LC-ES) M+H=410, 412 (Br pattern).

Example 229

(trans)-3-(2,5-Difluorophenoxy)-N-((trans)-4-(2-hydroxypropan-2-yl)cyclohexyl)cyclobutanecarboxamide

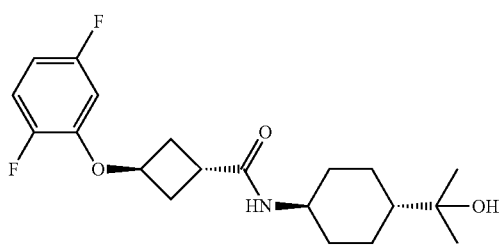 [SMILES: CC(C)(O)[C@H]1CC[C@H](NC(=O)[C@H]2C[C@H](Oc3cc(F)ccc3F)C2)CC1]

To a DMF (8 mL) solution of (trans)-3-(2,5-difluorophenoxy)cyclobutanecarboxylic acid (Intermediate 92) (185 mg, 0.811 mmol) was added HATU (308 mg, 0.811 mmol) and N,N-diisopropylethylamine (0.43 mL, 2.5 mmol). After 2 minutes, 2-((trans)-4-aminocyclohexyl)propan-2-ol (127 mg, 0.811 mmol) was added, and the mixture was stirred for 15 h, quenched with water, extracted with EtOAc, dried over Na$_2$SO$_4$, filtered and concentrated. The residue was purified on reverse-phase silica gel, eluting with a 20%-95% acetonitrile-water (NH$_4$OH additive) gradient to give the title compound (164 mg, 52%) as a white solid. $^1$H NMR (400 MHz, CD$_3$OD) δ 1.14 (s, 6H), 1.16-1.34 (m, 5H), 1.85-2.00 (m, 4H), 2.34-2.46 (m, 2H), 2.65 (qd, J=7, 4 Hz, 2H), 3.10 (tt, J=9, 4 Hz, 1H), 3.50-3.67 (m, 1H), 4.89-4.99 (m, 1H), 6.56-6.72 (m, 2H), 7.06 (ddd, J=11, 9, 5 Hz, 1H); LC-MS (LC-ES) M+H=368.

Example 230

(trans)-3-(2-Chloro-5-fluorophenoxy)-N-((trans)-4-(2-hydroxypropan-2-yl)cyclohexyl)cyclobutanecarboxamide

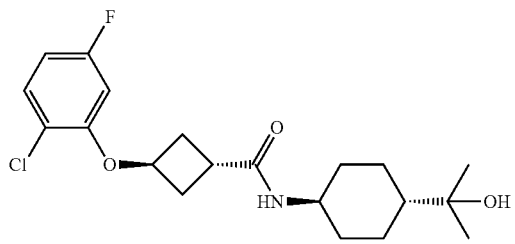

To a DMF (5 mL) solution of lithium (trans)-3-(2-chloro-5-fluorophenoxy)cyclobutanecarboxylate (Intermediate 93) (248 mg, 1.01 mmol) was added HATU (432 mg, 1.14 mmol) and N,N-diisopropylethylamine (0.50 mL, 2.9 mmol). After 10 minutes, 2-((trans)-4-aminocyclohexyl)propan-2-ol (179 mg, 1.14 mmol) was added, and the mixture was stirred for 15 h, quenched with water, extracted with EtOAc, dried over Na$_2$SO$_4$, filtered and concentrated. The residue was purified on reverse-phase silica gel, eluting with a 20%-95% acetonitrile-water (NH$_4$OH additive) gradient to give the title compound (45 mg, 12%). $^1$H NMR (400 MHz, CD$_3$OD) δ 1.14 (s, 6H), 1.16-1.31 (m, 5H), 1.85-2.02 (m, 4H), 2.35-2.45 (m, 2H), 2.66 (ddd, J=13, 7, 4 Hz, 2H), 3.06-3.16 (m, 1H), 3.54-3.64 (m, 1H), 4.93 (quin, J=6 Hz, 1H), 6.62-6.71 (m, 2H), 7.33 (dd, J=9, 6 Hz, 1H); LC-MS (LC-ES) M+H=385, 387 (Cl pattern).

Example 231

(trans)-3-((6-Fluorobenzo[d]thiazol-4-yl)oxy)-N-(1-(5-methylpyridin-2-yl)azetidin-3-yl)cyclobutanecarboxamide

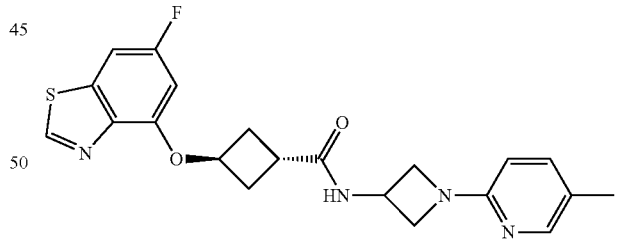

To a DMF (2 mL) solution of (trans)-3-(6-fluorobenzo[d]thiazol-4-yloxy)cyclobutanecarboxylic acid (Intermediate 59) (30 mg, 0.11 mmol), 1-(5-methylpyridin-2-yl)azetidin-3-amine (Intermediate 94) (18 mg, 0.11 mmol) and N,N-diisopropylethylamine (0.07 mL, 0.4 mmol) was added, dropwise, a 50% solution of T3P in ethyl acetate (143 mg, 0.224 mmol). The mixture was stirred 30 min, quenched with water, and loaded onto a semi-prep HPLC (NH$_4$OH as modifier) to afford the title compound (43 mg, 93%) as a white solid. $^1$H NMR (400 MHz, CDCl$_3$) δ 2.18 (s, 3H), 2.55-2.68 (m, 2H), 2.84 (ddd, J=14, 7, 4 Hz, 2H), 3.09 (td, J=10, 5 Hz, 1H), 3.77 (dd, J=9, 5 Hz, 2H), 4.33 (t, J=8 Hz, 2H), 4.80-4.92 (m, 1H), 5.15 (quin, J=7 Hz, 1H), 6.24 (d,

Example 232

3-((6-Fluorobenzo[d]thiazol-4-yl)oxy)-N-(1-(5-methylpyridin-2-yl)azetidin-3-yl)azetidine-1-carboxamide

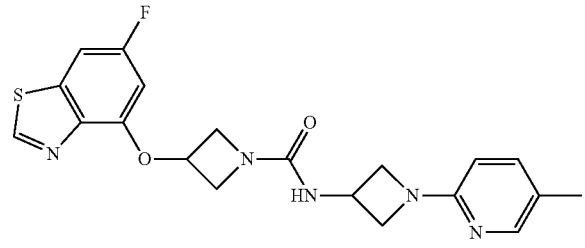 [SMILES: Cc1ccc(N2CC(NC(=O)N3CC(Oc4cc(F)cc5scnc45)C3)C2)nc1]

To a stirred mixture of 4-(azetidin-3-yloxy)-6-fluorobenzo[d]thiazole hydrochloride (Intermediate 61) (40 mg, 0.14 mmol) in DMF (2 mL) was added N,N-diisopropylethylamine (0.07 mL, 0.4 mmol) and 4-nitrophenyl (1-(5-methylpyridin-2-yl)azetidin-3-yl)carbamate (Intermediate 95) (44 mg, 0.14 mmol). The mixture was stirred 20 min, diluted with water and MeOH and loaded onto a semi-prep HPLC (NH$_4$OH as modifier) to afford the title compound (48 mg, 86%). $^1$H NMR (400 MHz, CD$_3$OD) δ 2.19 (s, 3H), 3.83 (dd, J=8, 6 Hz, 2H), 4.13 (dd, J=10, 4 Hz, 2H), 4.27 (t, J=8 Hz, 2H), 4.48 (dd, J=10, 7 Hz, 2H), 4.60-4.70 (m, 1H), 5.22-5.31 (m, 1H), 6.38 (d, J=8 Hz, 1H), 6.73 (dd, J=11, 2 Hz, 1H), 7.37-7.49 (m, 2H), 7.84 (s, 1H), 9.16 (s, 1H); LC-MS (LC-ES) M+H=414.

Example 233

(trans)-3-((6-Fluorobenzo[d]thiazol-4-yl)oxy)-N-(6-propionylspiro[3.3]heptan-2-yl)cyclobutanecarboxamide

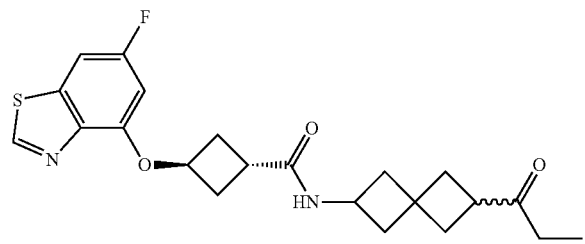 [SMILES: CCC(=O)C1CC2(CC(NC(=O)[C@H]3C[C@H](Oc4cc(F)cc5scnc45)C3)C2)C1]

To a DMF (2 mL) solution of (trans)-3-(6-fluorobenzo[d]thiazol-4-yloxy)cyclobutanecarboxylic acid (Intermediate 59) (20 mg, 0.075 mmol), 1-(6-aminospiro[3.3]heptan-2-yl)propan-1-one hydrochloride (Intermediate 96) (15 mg, 0.075 mmol) and N,N-diisopropylethylamine (0.03 mL, 0.2 mmol) was added, dropwise, a 50% solution of T3P in ethyl acetate (95 mg, 0.15 mmol). The mixture was stirred 30 min, quenched with water, and loaded onto a semi-prep HPLC (NH$_4$OH as modifier) to afford material which was further purified by silica gel chromatography, eluting with 0%-30% MeOH in DCM to give the title compound (22 mg, 71%) as a white solid. $^1$H NMR (400 MHz, CD$_3$OD) δ 1.03 (t, J=7 Hz, 3H), 1.89 (dd, J=11, 9 Hz, 1H), 2.00 (dd, J=11, 9 Hz, 1H), 2.09-2.36 (m, 5H), 2.36-2.62 (m, 5H), 2.74 (ddd, J=13, 7, 5 Hz, 2H), 3.10-3.19 (m, 1H), 4.20 (t, J=8 Hz, 1H), 5.14 (t, J=6 Hz, 1H), 6.73 (dd, J=11, 2 Hz, 1H), 7.39 (dd, J=8, 2 Hz, 1H), 9.13 (s, 1H); LC-MS (LC-ES) M+H=417.

Example 234

N-(2-Ethoxyethyl)-6-(3-((trans)-3-((6-fluorobenzo[d]thiazol-4-yl)oxy)cyclobutanecarboxamido)azetidin-1-yl)pyridazine-3-carboxamide

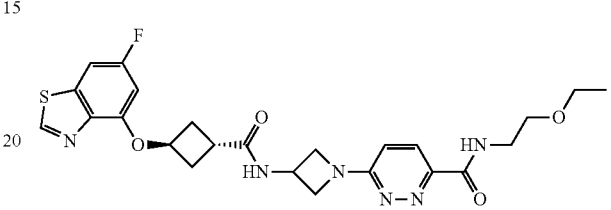

To a DMF (2 mL) solution of (trans)-3-(6-fluorobenzo[d]thiazol-4-yloxy)cyclobutanecarboxylic acid (Intermediate 59) (30 mg, 0.11 mmol), 6-(3-aminoazetidin-1-yl)-N-(2-ethoxyethyl)pyridazine-3-carboxamide dihydrochloride (Intermediate 97) (38 mg, 0.11 mmol) and N,N-diisopropylethylamine (0.06 mL, 0.3 mmol) was added, dropwise, a 50% solution of T3P in ethyl acetate (143 mg, 0.224 mmol). The mixture was stirred 30 min, quenched with water, and loaded onto a semi-prep HPLC (NH$_4$OH as modifier) to give the title compound (47 mg, 81%) as a white solid. $^1$H NMR (400 MHz, CDCl$_3$) δ 1.23 (t, J=7 Hz, 3H), 2.70 (ddd, J=13, 10, 6 Hz, 2H), 2.89 (qd, J=7, 4 Hz, 2H), 3.10-3.24 (m, 1H), 3.49-3.56 (m, 2H), 3.58-3.63 (m, 2H), 3.66-3.77 (m, 2H), 4.10-4.24 (m, 2H), 4.65 (t, J=9 Hz, 2H), 4.95-5.07 (m, 1H), 5.20 (t, J=7 Hz, 1H), 6.23-6.43 (m, 1H), 6.59 (dd, J=11, 2 Hz, 1H), 6.68 (d, J=9 Hz, 1H), 7.24 (dd, J=8, 2 Hz, 1H), 8.07 (d, J=9 Hz, 1H), 8.15 (br s, 1H), 8.89 (s, 1H); LC-MS (LC-ES) M+H=515.

Example 235

(trans)-3-((6-Fluorobenzo[d]thiazol-4-yl)oxy)-N-(1-(pyrazin-2-yl)azetidin-3-yl)cyclobutanecarboxamide

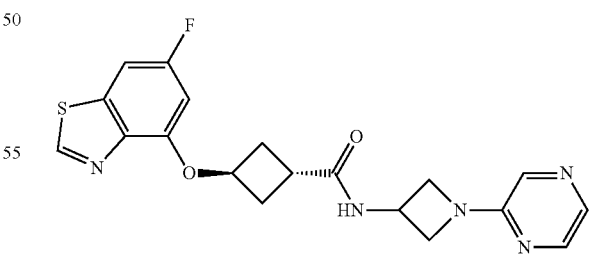

To a DMF (2 mL) solution of (trans)-3-(6-fluorobenzo[d]thiazol-4-yloxy)cyclobutanecarboxylic acid (Intermediate 59) (25 mg, 0.094 mmol), 1-(pyrazin-2-yl)azetidin-3-amine dihydrochloride (Intermediate 98) (25 mg, 0.11 mmol) and N,N-diisopropylethylamine (0.06 mL, 0.3 mmol) was added, dropwise, a 50% solution of T3P in ethyl acetate (119 mg, 0.187 mmol). The mixture was stirred 30 min, quenched with water, and loaded onto a semi-prep HPLC (NH₄OH as modifier) to give the title compound (34 mg, 91%) as a white solid. ¹H NMR (400 MHz, CDCl₃) δ 2.60-2.74 (m, 2H), 2.88 (qd, J=7, 4 Hz, 2H), 3.12 (td, J=9, 5 Hz, 1H), 3.94 (dd, J=9, 5 Hz, 2H), 4.41-4.53 (m, 2H), 4.90-5.04 (m, 1H), 5.19 (t, J=7 Hz, 1H), 6.20 (d, J=7 Hz, 1H), 6.58 (dd, J=11, 2 Hz, 1H), 7.23 (dd, J=8, 2 Hz, 1H), 7.77-7.85 (m, 1H), 7.91 (d, J=3 Hz, 1H), 8.05 (dd, J=3, 2 Hz, 1H), 8.88 (s, 1H); LC-MS (LC-ES) M+H=400.

Example 236

Racemic 3-((6-Fluorobenzo[d]thiazol-4-yl)oxy)-N-((trans)-4-(2-hydroxypropan-2-yl)cyclohexyl)-2-methylazetidine-1-carboxamide

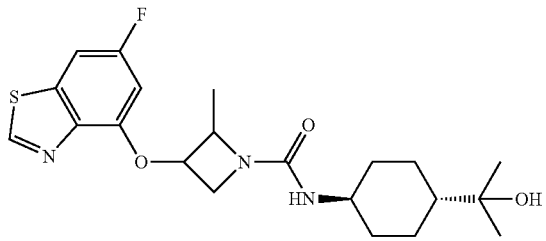 [SMILES: CC1C(Oc2cc(F)cc3scnc23)CN1C(=O)N[C@H]1CC[C@H](C(C)(C)O)CC1]

To a stirred mixture of 6-fluoro-4-((2-methylazetidin-3-yl)oxy)benzo[d]thiazole hydrochloride (Intermediate 99) (92 mg, 0.34 mmol) in DCM (3 mL) was added N,N-diisopropylethylamine (0.18 mL, 1.0 mmol) and 4-nitrophenyl ((trans)-4-(2-hydroxypropan-2-yl)cyclohexyl)carbamate (Intermediate 3) (110 mg, 0.341 mmol). The mixture was stirred 18 h, poured into 1 N aqueous NaOH and extracted twice with DCM. The combined organic layers were washed with brine, dried over Na₂SO₄, filtered and concentrated. The residue was purified on silica gel, eluting with a 5%-75% EtOAc:EtOH (3:1)-hexanes gradient to afford the title compound (116 mg, 82%) as a white solid. ¹H NMR (400 MHz, CD₃SOCD₃) δ 0.94-1.20 (m, 11H), 1.26 (d, J=7 Hz, 3H), 1.73-1.85 (m, 4H), 3.24-3.36 (m, 1H), 3.85 (dd, J=9, 4 Hz, 1H), 4.02 (s, 1H), 4.21 (dd, J=10, 7 Hz, 1H), 4.65 (t, J=7 Hz, 1H), 5.26 (td, J=7, 4 Hz, 1H), 6.04 (d, J=8 Hz, 1H), 6.90 (dd, J=11, 2 Hz, 1H), 7.65 (dd, J=8, 2 Hz, 1H), 9.26 (s, 1H); LC-MS (LC-ES) M+H=422.

Example 237

(trans)-3-((6-Fluorobenzo[d]thiazol-4-yl)oxy)-N-(3-methyl-1-(pyridazin-3-yl)azetidin-3-yl)cyclobutanecarboxamide

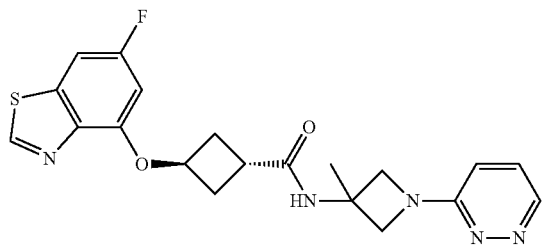 [SMILES: CC1(NC(=O)[C@H]2C[C@H](Oc3cc(F)cc4scnc34)C2)CN(c2cccnn2)C1]

To a DMF (2 mL) solution of (trans)-3-(6-fluorobenzo[d]thiazol-4-yloxy)cyclobutanecarboxylic acid (Intermediate 59) (30 mg, 0.11 mmol), 3-methyl-1-(pyridazin-3-yl)azetidin-3-amine dihydrochloride (Intermediate 100) (27 mg, 0.11 mmol) and N,N-diisopropylethylamine (0.07 mL, 0.4 mmol) was added, dropwise, a 50% solution of T3P in ethyl acetate (143 mg, 0.224 mmol). The mixture was stirred 30 min, quenched with water, and loaded onto a semi-prep HPLC (NH₄OH as modifier) to give the title compound (32 mg, 69%) as a white solid. ¹H NMR (400 MHz, CDCl₃) δ 1.74 (s, 3H), 2.47-2.67 (m, 2H), 2.82 (ddd, J=14, 7, 4 Hz, 2H), 3.07-3.23 (m, 1H), 4.03-4.12 (m, 2H), 4.34 (d, J=9 Hz, 2H), 5.15 (quin, J=7 Hz, 1H), 6.51-6.62 (m, 2H), 7.14-7.27 (m, 3H), 8.55 (d, J=4 Hz, 1H), 8.85 (s, 1H); LC-MS (LC-ES) M+H=414.

Example 238

(trans)-3-((6-Fluorobenzo[d]thiazol-4-yl)oxy)-N-(3-methyl-1-(pyrimidin-2-yl)azetidin-3-yl)cyclobutanecarboxamide

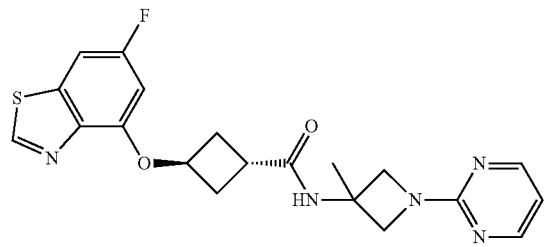 [SMILES: CC1(NC(=O)[C@H]2C[C@H](Oc3cc(F)cc4scnc34)C2)CN(c2ncccn2)C1]

To a DMF (2 mL) solution of (trans)-3-(6-fluorobenzo[d]thiazol-4-yloxy)cyclobutanecarboxylic acid (Intermediate 59) (30 mg, 0.11 mmol), 3-methyl-1-(pyrimidin-2-yl)azetidin-3-amine dihydrochloride (Intermediate 101) (27 mg, 0.11 mmol) and N,N-diisopropylethylamine (0.07 mL, 0.4 mmol) was added, dropwise, a 50% solution of T3P in ethyl acetate (143 mg, 0.224 mmol). The mixture was stirred 30 min, quenched with water, and loaded onto a semi-prep HPLC (NH₄OH as modifier) to give the title compound (33 mg, 71%) as a white solid. ¹H NMR (400 MHz, CDCl₃) δ 1.71 (s, 3H), 2.52-2.69 (m, 2H), 2.75-2.89 (m, 2H), 2.97-3.16 (m, 1H), 4.00-4.14 (m, 2H), 4.27-4.38 (m, 2H), 5.15 (quin, J=6 Hz, 1H), 6.03 (br s, 1H), 6.48-6.64 (m, 2H), 7.20 (dd, J=8, 2 Hz, 1H), 8.32 (d, J=5 Hz, 2H), 8.85 (s, 1H); LC-MS (LC-ES) M+H=414.

Example 239

(trans)-3-(Benzo[d]thiazol-4-yloxy)-N-(1-(5-methylpyridin-2-yl)azetidin-3-yl)cyclobutanecarboxamide

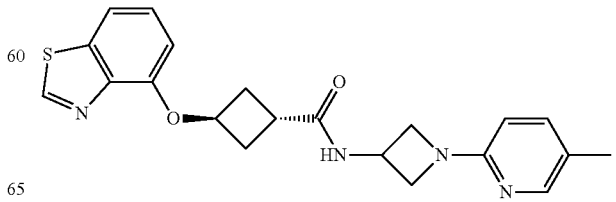

373

To a DMF (2 mL) solution of (trans)-3-(benzo[d]thiazol-4-yloxy)cyclobutanecarboxylic acid (Intermediate 25) (50 mg, 0.20 mmol), 1-(5-methylpyridin-2-yl)azetidin-3-amine (Intermediate 94) (33 mg, 0.20 mmol) and N,N-diisopropylethylamine (0.12 mL, 0.70 mmol) was added, dropwise, a 50% solution of T3P in ethyl acetate (255 mg, 0.401 mmol). The mixture was stirred 30 min, quenched with water, and loaded onto a semi-prep HPLC (NH$_4$OH as modifier) to afford the title compound (58 mg, 73%) as a white solid. $^1$H NMR (400 MHz, CD$_3$OD) δ 2.21 (s, 3H), 2.50-2.65 (m, 2H), 2.79 (ddd, J=13, 7, 5 Hz, 2H), 3.24 (tt, J=10, 5 Hz, 1H), 3.83 (dd, J=8, 6 Hz, 2H), 4.32 (t, J=8 Hz, 2H), 4.70-4.82 (m, 1H), 5.17 (quin, J=6 Hz, 1H), 6.42 (d, J=9 Hz, 1H), 6.89 (d, J=8 Hz, 1H), 7.42-7.50 (m, 2H), 7.63 (d, J=8 Hz, 1H), 7.87 (s, 1H), 9.17 (s, 1H); LC-MS (LC-ES) M+H=395.

Example 240

Racemic 3-(Benzo[d]thiazol-4-yloxy)-N-((trans)-4-(2-hydroxypropan-2-yl)cyclohexyl)-2-methylazetidine-1-carboxamide

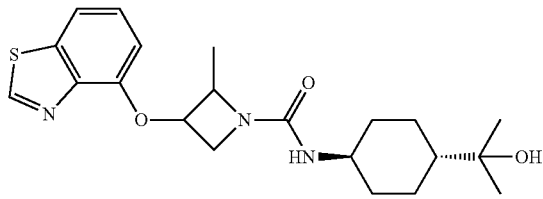 [SMILES: CC1C(Oc2cccc3scnc23)CN1C(=O)N[C@H]1CC[C@H](C(C)(C)O)CC1]

To a stirred mixture of 4-((2-methylazetidin-3-yl)oxy)benzo[d]thiazole hydrochloride (Intermediate 102) (82 mg, 0.32 mmol) in DCM (3 mL) was added N,N-diisopropylethylamine (0.18 mL, 1.0 mmol) and 4-nitrophenyl ((trans)-4-(2-hydroxypropan-2-yl)cyclohexyl)carbamate (Intermediate 3) (105 mg, 0.326 mmol). The mixture was stirred 18 h, poured into 1 N aqueous NaOH and extracted twice with DCM. The combined organic layers were washed with brine, dried over Na$_2$SO$_4$, filtered and concentrated. The residue was purified on silica gel, eluting with a 5%-75% EtOAc:EtOH (3:1)-hexanes gradient to afford the title compound (41 mg, 32%) as a white solid. $^1$H NMR (400 MHz, CD$_3$SOCD$_3$) δ 1.03 (s, 6H), 1.08-1.20 (m, 5H), 1.27 (d, J=7 Hz, 3H), 1.73-1.86 (m, 4H), 3.22-3.29 (m, 1H), 3.87 (dd, J=9, 4 Hz, 1H), 3.99 (s, 1H), 4.19 (t, J=8 Hz, 1H), 4.64 (t, J=7 Hz, 1H), 5.25 (d, J=4 Hz, 1H), 5.99 (d, J=8 Hz, 1H), 6.91 (d, J=8 Hz, 1H), 7.34-7.46 (m, 1H), 7.74 (d, J=8 Hz, 1H), 9.29 (s, 1H); LC-MS (LC-ES) M+H=404.

Example 241

(trans)-3-(Benzo[d]thiazol-4-yloxy)-N-(1-(5-methylpyridazin-3-yl)azetidin-3-yl)cyclobutanecarboxamide, trifluoroacetic acid salt

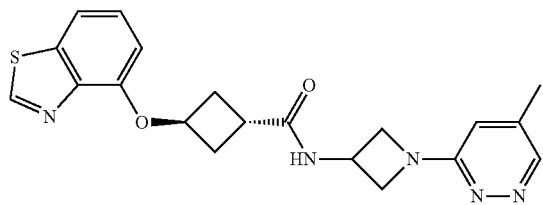

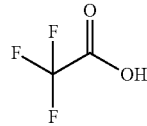

To a DMF (1.5 mL) solution of (trans)-3-(benzo[d]thiazol-4-yloxy)cyclobutanecarboxylic acid (Intermediate 25) (30 mg, 0.12 mmol), 1-(5-methylpyridazin-3-yl)azetidin-3-amine dihydrochloride (Intermediate 103) (29 mg, 0.12 mmol) and N,N-diisopropylethylamine (0.06 mL, 0.4 mmol) was added, dropwise, a 50% solution of T3P in ethyl acetate (153 mg, 0.241 mmol). The mixture was stirred 30 min, quenched with water, and loaded onto a semi-prep HPLC (TFA as modifier) to afford the title compound (49 mg, 80%) as a white solid. $^1$H NMR (400 MHz, CD$_3$OD) δ 2.46 (d, J=1 Hz, 3H), 2.55-2.67 (m, 2H), 2.80 (ddd, J=13, 7, 5 Hz, 2H), 3.27 (tt, J=10, 5 Hz, 1H), 4.32 (dd, J=10, 5 Hz, 2H), 4.68 (t, J=9 Hz, 2H), 4.79-4.88 (m, 1H), 5.17 (quin, J=6 Hz, 1H), 6.89 (d, J=8 Hz, 1H), 7.31 (s, 1H), 7.42 (t, J=8 Hz, 1H), 7.64 (d, J=8 Hz, 1H), 8.35 (d, J=2 Hz, 1H), 9.12-9.24 (m, 1H); LC-MS (LC-ES) M+H=396.

Example 242

(trans)-3-(Benzo[d]thiazol-4-yloxy)-N-(4-(methylsulfonyl)phenyl)cyclobutanecarboxamide

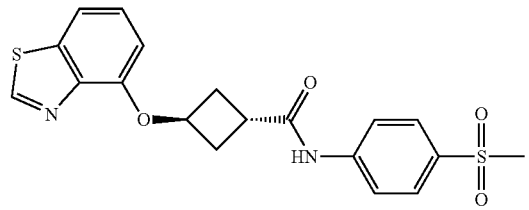 [SMILES: CS(=O)(=O)c1ccc(NC(=O)[C@H]2C[C@H](Oc3cccc4scnc34)C2)cc1]

To (trans)-3-(benzo[d]thiazol-4-yloxy)cyclobutanecarboxylic acid (Intermediate 25) (150 mg, 0.599 mmol) was added oxalyl chloride (3.0 mL, 34 mmol), and the reaction was heated to 70° C. After 2 h, the reaction was cooled and concentrated to afford the acid chloride. In a separate flask, to a stirred solution of 4-(methylsulfonyl)aniline (154 mg, 0.898 mmol) in THF (2.5 mL) was added K$_2$CO$_3$ (248 mg, 1.80 mmol). After 10 minutes, the above freshly prepared acid chloride in THF (2.5 mL) was added. After two hours, the reaction was diluted with water (50 mL), extracted with EtOAc (3×50 mL), and the combined organic layers were washed with brine (100 mL), dried over Na$_2$SO$_4$, filtered and concentrated. The residue was purified on silica gel, eluting with a 45%-80% EtOAc in petroleum ether gradient, to afford the title compound (65 mg, 27%) as an off-white solid. $^1$H NMR (400 MHz, CD$_3$SOCD$_3$) δ 2.42-2.55 (m, 2H), 2.75-2.82 (m, 2H), 3.17 (s, 3H), 3.53-3.62 (m, 1H), 5.08-5.18 (m, 1H), 6.88-6.92 (m, 1H), 7.38-7.43 (m, 1H), 7.68-7.73 (m, 1H), 7.85-7.92 (m, 4H), 9.28 (s, 1H); LC-MS (LC-ES) M+H=403.

Example 243

(trans)-3-(Benzo[d]thiazol-4-yloxy)-N-(4-morpholinophenyl)cyclobutanecarboxamide

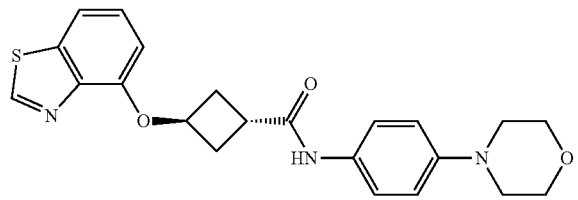 [SMILES: O=C(Nc1ccc(N2CCOCC2)cc1)[C@H]1C[C@H](Oc2cccc3scnc23)C1]

To a DMF (5 mL) solution of (trans)-3-(benzo[d]thiazol-4-yloxy)cyclobutanecarboxylic acid (Intermediate 25) (40 mg, 0.16 mmol) at 5° C. was added HATU (91 mg, 0.24 mmol) and N,N-diisopropylethylamine (0.08 mL, 0.5 mmol). After 10 minutes, 4-morpholinoaniline (28 mg, 0.16 mmol) was added, and the mixture was warmed to rt. After 18 h, the reaction was quenched into ice water, and the resulting brown solid was collected by filtration to give the title compound (60 mg, 91%). $^1$H NMR (400 MHz, CD$_3$SOCD$_3$) δ 2.40-2.50 (m, 2H), 2.69-2.78 (m, 2H), 3.03-3.09 (m, 4H), 3.26-3.35 (m, 1H), 3.72-3.78 (m, 4H), 5.08-5.16 (m, 1H), 6.85-6.95 (m, 3H), 7.39-7.43 (m, 1H), 7.47-7.52 (m, 2H), 7.67-7.75 (m, 1H), 9.25 (s, 1H); LC-MS (LC-ES) M+H=410.

Example 244

3-(Benzo[d]thiazol-4-yloxy)-N-(1-(5-methylpyridin-2-4azetidin-3-yl)azetidine-1-carboxamide

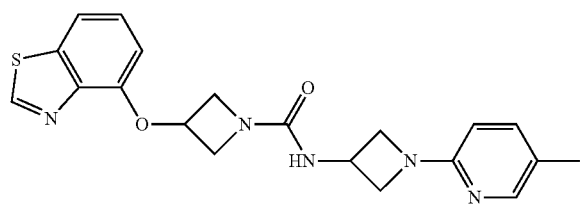 [SMILES: Cc1ccc(N2CC(NC(=O)N3CC(Oc4cccc5scnc45)C3)C2)nc1]

To a stirred mixture of 4-(azetidin-3-yloxy)benzo[d]thiazole hydrochloride (Intermediate 28) (30 mg, 0.12 mmol) in DMF (2 mL) was added N,N-diisopropylethylamine (0.025 mL, 0.15 mmol) and 4-nitrophenyl (1-(5-methylpyridin-2-yl)azetidin-3-yl)carbamate (Intermediate 95) (48 mg, 0.15 mmol). The mixture was stirred 30 min, diluted with water and MeOH and loaded onto a semi-prep HPLC (NH$_4$OH as modifier) to afford the title compound (39 mg, 68%) as a white solid. $^1$H NMR (400 MHz, CD$_3$OD) δ 2.19 (s, 3H), 3.83 (dd, J=8, 6 Hz, 2H), 4.14 (dd, J=10, 4 Hz, 2H), 4.27 (t, J=8 Hz, 2H), 4.47 (dd, J=9, 7 Hz, 2H), 4.61-4.72 (m, 1H), 5.22-5.36 (m, 1H), 6.38 (d, J=9 Hz, 1H), 6.84 (d, J=8 Hz, 1H), 7.36-7.49 (m, 2H), 7.68 (d, J=8 Hz, 1H), 7.84 (s, 1H), 9.19 (s, 1H); LC-MS (LC-ES) M+H=396.

Example 245

(trans)-3-(Benzo[d]thiazol-4-yloxy)-N-(1-(pyridazin-3-yl)azetidin-3-yl)cyclobutanecarboxamide

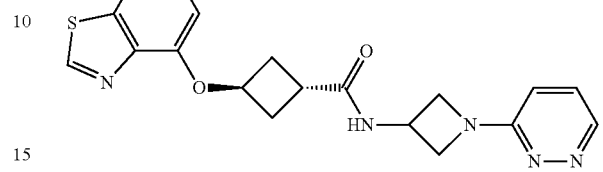

To a DMF (2 mL) solution of (trans)-3-(benzo[d]thiazol-4-yloxy)cyclobutanecarboxylic acid (Intermediate 25) (18 mg, 0.072 mmol), 1-(pyridin-2-yl)azetidin-3-amine dihydrochloride (Intermediate 104) (19 mg, 0.087 mmol) and N,N-diisopropylethylamine (0.04 mL, 0.3 mmol) was added, dropwise, a 50% solution of T3P in ethyl acetate (92 mg, 0.14 mmol). The mixture was stirred 30 min, quenched with water, and loaded onto a semi-prep HPLC (NH$_4$OH as modifier) to afford the title compound (18 mg, 65%) as a white solid. $^1$H NMR (400 MHz, CD$_3$OD) δ 2.52-2.67 (m, 2H), 2.80 (ddd, J=13, 7, 5 Hz, 2H), 3.19-3.30 (m, 1H), 4.01 (dd, J=9, 5 Hz, 2H), 4.47 (t, J=8 Hz, 2H), 4.79-4.87 (m, 1H), 5.13-5.21 (m, 1H), 6.85-6.94 (m, 2H), 7.37-7.47 (m, 2H), 7.63 (d, J=8 Hz, 1H), 8.51 (dd, J=5, 1 Hz, 1H), 9.17 (s, 1H); LC-MS (LC-ES) M+H=382.

Example 246

(trans)-3-(Benzo[d]thiazol-4-yloxy)-N-(1-(pyrazin-2-yl)azetidin-3-yl)cyclobutanecarboxamide

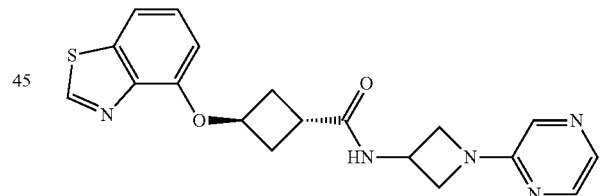

To a DMF (2 mL) solution of (trans)-3-(benzo[d]thiazol-4-yloxy)cyclobutanecarboxylic acid (Intermediate 25) (25 mg, 0.10 mmol), 1-(pyrazin-2-yl)azetidin-3-amine dihydrochloride (Intermediate 98) (27 mg, 0.12 mmol) and N,N-diisopropylethylamine (0.06 mL, 0.4 mmol) was added, dropwise, a 50% solution of T3P in ethyl acetate (128 mg, 0.201 mmol). The mixture was stirred 30 min, quenched with water, and loaded onto a semi-prep HPLC (NH$_4$OH as modifier) to afford the title compound (31 mg, 81%) as a white solid. $^1$H NMR (400 MHz, CDCl$_3$) δ 2.60-2.73 (m, 2H), 2.87 (ddd, J=13, 7, 4 Hz, 2H), 3.09-3.17 (m, 1H), 3.94 (dd, J=9, 5 Hz, 2H), 4.43-4.52 (m, 2H), 4.90-5.02 (m, 1H), 5.23 (quin, J=6 Hz, 1H), 6.19 (d, J=7 Hz, 1H), 6.79 (d, J=8 Hz, 1H), 7.36 (t, J=8 Hz, 1H), 7.55 (d, J=8 Hz, 1H), 7.83 (s, 1H), 7.91 (d, J=3 Hz, 1H), 8.06 (d, J=2 Hz, 1H), 8.94 (s, 1H); LC-MS (LC-ES) M+H=382.

Example 247

(trans)-3-(Benzo[d]thiazol-4-yloxy)-N-(2-fluoro-4-(methylsulfonyl)phenyl)cyclobutanecarboxamide

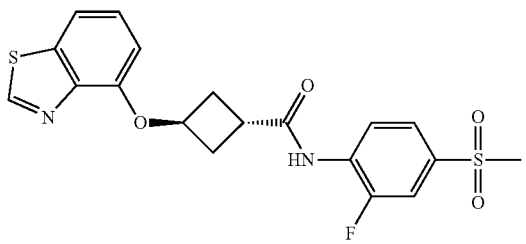 [SMILES: CS(=O)(=O)c1ccc(NC(=O)[C@H]2C[C@H](Oc3cccc4scnc34)C2)c(F)c1]

To (trans)-3-(benzo[d]thiazol-4-yloxy)cyclobutanecarboxylic acid (Intermediate 25) (150 mg, 0.599 mmol) was added oxalyl chloride (1.0 mL, 11 mmol), and the reaction was heated to 70° C. After 2 h, the reaction was cooled and concentrated to afford the acid chloride. In a separate flask, to a stirred solution of 2-fluoro-4-(methylsulfonyl)aniline (170 mg, 0.898 mmol) in THF (2.5 mL) was added $K_2CO_3$ (248 mg, 1.80 mmol). After 10 minutes, the above freshly prepared acid chloride in THF (2.5 mL) was added. After two hours, the reaction was diluted with water (50 mL), extracted with EtOAc (3×50 mL), and the combined organic layers were washed with brine (100 mL), dried over $Na_2SO_4$, filtered and concentrated. The residue was purified on silica gel, eluting with a 45%-80% EtOAc in petroleum ether gradient, to afford the title compound (185 mg, 72%). $^1$H NMR (400 MHz, $CD_3SOCD_3$) δ 2.43-2.56 (m, 2H), 2.76-2.82 (m, 2H), 3.24 (s, 3H), 3.53-3.60 (m, 1H), 5.07-5.15 (m, 1H), 6.88-6.92 (m, 1H), 7.37-7.43 (m, 1H), 7.68-7.72 (m, 1H), 7.74-7.79 (m, 1H), 7.80-7.85 (m, 1H), 8.54-8.62 (m, 1H), 9.27 (s, 1H); LC-MS (LC-ES) M+H=421.

Example 248

(trans)-3-(Benzo[d]thiazol-4-yloxy)-N-(3-morpholinophenyl)cyclobutanecarboxamide

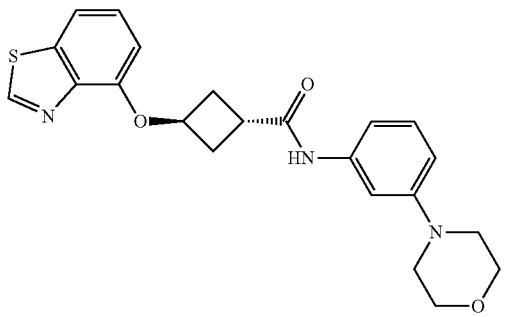 [SMILES: O=C(Nc1cccc(N2CCOCC2)c1)[C@H]1C[C@H](Oc2cccc3scnc23)C1]

To a DMF (5 mL) solution of (trans)-3-(benzo[d]thiazol-4-yloxy)cyclobutanecarboxylic acid (Intermediate 25) (150 mg, 0.594 mmol) at 0° C. was added 3-morpholinoaniline hydrochloride (128 mg, 0.594 mmol), HATU (452 mg, 1.19 mmol) and N,N-diisopropylethylamine (0.311 mL, 1.8 mmol), and the mixture was warmed to rt. After 2 h, the reaction was quenched into ice water (10 mL) and extracted with EtOAc (4×10 mL). The organic layers were combined, washed with water (20 mL) and brine (15 mL), and concentrated. The resulting material was triturated with n-pentane (15 mL) and diethyl ether (10 mL), and dried to give the title compound (83 mg, 34%) as an off-white solid. $^1$H NMR (400 MHz, $CD_3SOCD_3$) δ 2.40-2.50 (m, 2H), 2.70-2.80 (m, 2H), 3.02-3.10 (m, 4H), 3.28-3.33 (m, 1H), 3.71-3.78 (m, 4H), 5.08-5.15 (m, 1H), 6.63-6.69 (m, 1H), 6.85-6.89 (m, 1H), 7.03-7.07 (m, 1H), 7.13-7.18 (m, 1H), 7.38-7.42 (m, 2H), 7.67-7.75 (m, 1H), 9.28 (s, 1H) 9.87 (s, 1H); LC-MS (LC-ES) M+H=410.

Example 249

(trans)-3-(Benzo[d]thiazol-4-yloxy)-N-(1-methyl-1H-pyrazol-5-yl)cyclobutanecarboxamide

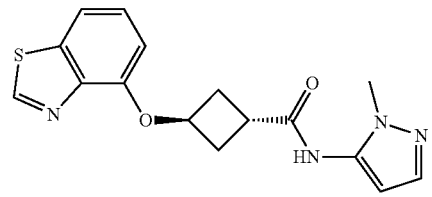 [SMILES: Cn1nccc1NC(=O)[C@H]1C[C@H](Oc2cccc3scnc23)C1]

To a DMF (5 mL) solution of (trans)-3-(benzo[d]thiazol-4-yloxy)cyclobutanecarboxylic acid (Intermediate 25) (150 mg, 0.593 mmol) at 0° C. was added 1-methyl-1H-pyrazol-5-amine (58 mg, 0.59 mmol), HATU (451 mg, 1.19 mmol) and N,N-diisopropylethylamine (0.311 mL, 1.8 mmol), and the mixture was warmed to rt. After 3 h, the reaction was quenched into ice water (10 mL) and extracted with EtOAc (3×20 mL). The organic layers were combined, washed with brine (20 mL), dried over $Na_2SO_4$, filtered and concentrated. The resulting material was triturated with n-pentane (10 mL) and dried to give the title compound (55 mg, 28%) as a white solid. $^1$H NMR (400 MHz, $CD_3SOCD_3$) δ 2.46-2.56 (m, 2H), 2.75-2.82 (m, 2H), 3.38-3.45 (m, 1H), 3.68 (s, 3H), 5.06-5.15 (m, 1H), 6.23-6.26 (m, 1H), 6.87-6.93 (m, 1H), 7.34-7.38 (m, 1H), 7.40-7.47 (m, 1H), 7.68-7.73 (m, 1H), 9.25 (s, 1H); LC-MS (LC-ES) M+H=329.

Example 250

(trans)-3-(Benzo[d]thiazol-4-yloxy)-N-(thiophen-2-yl)methyl)cyclobutanecarboxamide

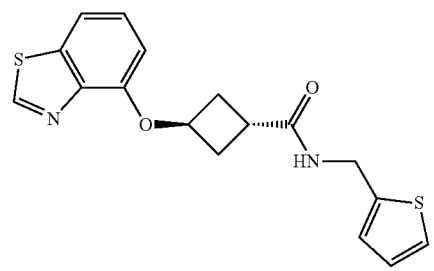 [SMILES: O=C(NCc1cccs1)[C@H]1C[C@H](Oc2cccc3scnc23)C1]

To a DMF (6 mL) solution of (trans)-3-(benzo[d]thiazol-4-yloxy)cyclobutanecarboxylic acid (Intermediate 25) (120 mg, 0.476 mmol), thiophen-2-ylmethanamine (54 mg, 0.48 mmol) and N,N-diisopropylethylamine (0.25 mL, 1.4 mmol) at 0° C. was added, dropwise, a 50% solution of T3P in ethyl acetate (0.57 mL, 0.95 mmol). The mixture was warmed to room temperature for 4 h, quenched with ice cold water (50 mL) and extracted with EtOAc (3×30 mL). The organic layers were combined, washed with brine (50 mL), dried over Na$_2$SO$_4$, filtered and concentrated. The resulting material was triturated with n-pentane (5 mL) and diethyl ether (5 mL), and dried to give the title compound (78 mg, 46%) as an off-white solid. $^1$H NMR (400 MHz, CD$_3$SOCD$_3$) δ 2.34-2.42 (m, 2H), 2.63-2.71 (m, 2H), 3.08-3.18 (m, 1H), 4.45-4.50 (m, 2H), 5.08-5.13 (m, 1H), 6.81-6.86 (m, 1H), 6.92-6.99 (m, 2H), 7.38-7.42 (m, 2H), 7.65-7.73 (m, 1H), 8.51-8.56 (m, 1H), 9.25 (s, 1H); LC-MS (LC-ES) M+H=345.

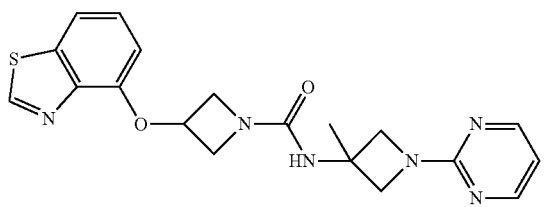 [SMILES: CC1(NC(=O)N2CC(Oc3cccc4scnc34)C2)CN(c2ncccn2)C1]

To 4-(azetidin-3-yloxy)benzo[d]thiazole, trifluoroacetic acid salt (Intermediate 28C) (64 mg, 0.20 mmol) was added crude (4-nitrophenyl (3-methyl-1-(pyrimidin-2-yl)azetidin-3-yl)carbamate (66 mg, 0.20 mmol) (Intermediate 105) in DCM (2.6 mL) and pyridine (0.060 mL, 0.74 mmol). After 66 h, the reaction mixture was concentrated and N,N-diisopropylethylamine (0.11 mL, 0.60 mmol) was added, stirred 1 h, diluted with water and MeOH and loaded onto a semi-prep HPLC (NH$_4$OH as modifier) to afford the title compound (35 mg, 44%) as a light tan solid. $^1$H NMR (400 MHz, CDCl$_3$) δ 1.68 (s, 3H), 4.03 (d, J=9 Hz, 2H), 4.23 (dd, J=9, 4 Hz, 2H), 4.30 (d, J=9 Hz, 2H), 4.42 (dd, J=9, 7 Hz, 2H), 4.57 (s, 1H), 5.18-5.31 (m, 1H), 6.50-6.57 (m, 1H), 6.67 (d, J=8 Hz, 1H), 7.36 (t, J=8 Hz, 1H), 7.61 (d, J=8 Hz, 1H), 8.26-8.38 (m, 2H), 8.95 (s, 1H); LC-MS (LC-ES) M+H=397.

Example 252

(trans)-3-(Benzo[d]thiazol-4-yloxy)-N-(thiophen-3-yl)methyl)cyclobutanecarboxamide

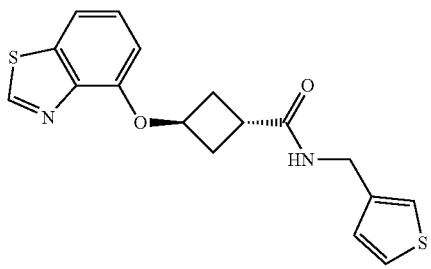 [SMILES: O=C(NCc1ccsc1)[C@H]1C[C@H](Oc2cccc3scnc23)C1]

To a DMF (5 mL) solution of (trans)-3-(benzo[d]thiazol-4-yloxy)cyclobutanecarboxylic acid (Intermediate 25) (150 mg, 0.602 mmol), thiophen-3-ylmethanamine (68 mg, 0.60 mmol) and N,N-diisopropylethylamine (0.32 mL, 1.8 mmol) at 0° C. was added, dropwise, a 50% solution of T3P in ethyl acetate (0.72 mL, 1.2 mmol). The mixture was warmed to room temperature for 2 h, quenched with ice cold water (50 mL) and extracted with EtOAc (3×30 mL). The organic layers were combined, washed with brine (50 mL), dried over Na$_2$SO$_4$, filtered and concentrated. The residue was purified on silica gel, eluting with a 90% EtOAc in hexane, to afford the title compound (64 mg, 31%) as an off-white solid. $^1$H NMR (400 MHz, CD$_3$SOCD$_3$) δ 2.32-2.42 (m, 2H), 2.63-2.72 (m, 2H), 3.11-3.21 (m, 1H), 4.28-4.34 (m, 2H), 5.05-5.15 (m, 1H), 6.83-6.88 (m, 1H), 7.02-7.07 (m, 1H), 7.29 (s, 1H), 7.38-7.42 (m, 1H), 7.48-7.53 (m, 1H), 7.68-7.72 (m, 1H), 8.40-8.46 (m, 1H), 9.23 (s, 1H); LC-MS (LC-ES) M+H=345.

Example 253

(trans)-3-(Benzo[d]thiazol-4-yloxy)-N-cyclohexyl)cyclobutanecarboxamide

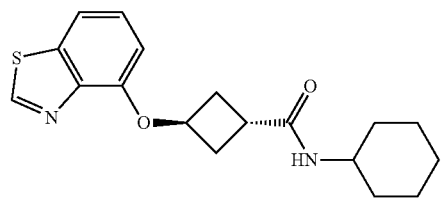 [SMILES: O=C(NC1CCCCC1)[C@H]1C[C@H](Oc2cccc3scnc23)C1]

To a DMF (6 mL) solution of (trans)-3-(benzo[d]thiazol-4-yloxy)cyclobutanecarboxylic acid (Intermediate 25) (120 mg, 0.476 mmol), cyclohexanamine (82 mg, 0.48 mmol) and N,N-diisopropylethylamine (0.25 mL, 1.4 mmol) at 0° C. was added, dropwise, a 50% solution of T3P in ethyl acetate (0.57 mL, 0.95 mmol). The mixture was warmed to room temperature for 2 h, quenched with ice cold water (20 mL) and the resulting solid was collected by filtration to afford the title compound (100 mg, 63%) as an off-white solid. $^1$H NMR (400 MHz, CD$_3$SOCD$_3$) δ 1.07-1.35 (m, 5H), 1.55-1.79 (m, 5H), 2.35-2.42 (m, 2H), 2.59-2.68 (m, 2H), 3.04-3.14 (m, 1H), 3.50-3.60 (m, 1H), 5.03-5.12 (m, 1H), 6.83-6.88 (m, 1H), 7.39-7.43 (m, 1H), 7.67-7.70 (m, 1H), 9.22 (s, 1H); LC-MS (LC-ES) M+H=331.

Example 254

Racemic (trans)-3-(Benzo[d]thiazol-4-yloxy)-N-(1,1-dioxidotetrahydrothiophen-3-yl)cyclobutanecarboxamide

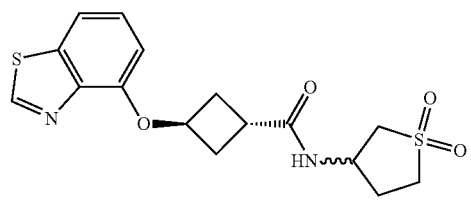 [SMILES: O=C(NC1CCS(=O)(=O)C1)[C@H]1C[C@H](Oc2cccc3scnc23)C1]

To a DMF (5 mL) solution of (trans)-3-(benzo[d]thiazol-4-yloxy)cyclobutanecarboxylic acid (Intermediate 25) (150 mg, 0.599 mmol), 3-aminotetrahydrothiophene 1,1-dioxide hydrochloride (103 mg, 0.599 mmol) and N,N-diisopropylethylamine (0.31 mL, 1.8 mmol) at 0° C. was added, dropwise, a 50% solution of T3P in ethyl acetate (0.71 mL, 1.2 mmol). The mixture was warmed to room temperature for 2 h, quenched with ice cold water (10 mL) and extracted with EtOAc (3×10 mL). The organic layers were combined, washed with water (20 mL) and brine (15 mL), dried over Na$_2$SO$_4$, filtered and concentrated. The resulting material was triturated with n-pentane (15 mL) and diethyl ether (10 mL), and dried to give the title compound (85 mg, 38%) as an off-white solid. $^1$H NMR (400 MHz, CD$_3$SOCD$_3$) δ 2.05-2.15 (m, 1H), 2.35-2.44 (m, 3H), 2.65-2.72 (m, 2H), 2.91-2.99 (m, 1H), 3.09-3.20 (m, 2H), 3.26-3.34 (m, 1H), 3.42-3.50 (m, 1H), 4.46-4.55 (m, 1H), 5.02-5.10 (m, 1H), 6.85-6.89 (m, 1H), 7.38-7.45 (m, 1H), 7.68-7.73 (m, 1H), 9.21 (s, 1H); LC-MS (LC-ES) M+H=367.

Example 255

(trans)-3-(Benzo[d]thiazol-4-yloxy)-N-((5-methylfuran-2-yl)methyl)cyclobutanecarboxamide

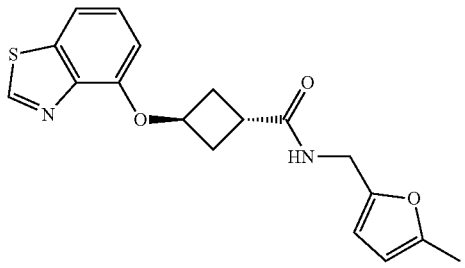 [SMILES: Cc1ccc(CNC(=O)[C@H]2C[C@H](Oc3cccc4scnc34)C2)o1]

To a DMF (5 mL) solution of (trans)-3-(benzo[d]thiazol-4-yloxy)cyclobutanecarboxylic acid (Intermediate 25) (100 mg, 0.396 mmol), (5-methylfuran-2-yl)methanamine (44 mg, 0.40 mmol) and N,N-diisopropylethylamine (0.07 mL, 0.4 mmol) at 0° C. was added T3P (126 mg, 0.396 mmol). The mixture was warmed to room temperature for 4 h, quenched with ice cold water (50 mL) and extracted with EtOAc (3×30 mL). The organic layers were combined, washed with water and brine (50 mL), dried over Na$_2$SO$_4$, filtered and concentrated. The residue was purified on silica gel, eluting with a 10%-80% EtOAc in petroleum ether gradient, to afford the title compound (65 mg, 47%). $^1$H NMR (400 MHz, CD$_3$SOCD$_3$) δ 2.25 (s, 3H), 2.35-2.45 (m, 2H), 2.63-2.72 (m, 2H), 3.10-3.20 (m, 1H), 4.22-4.29 (m, 2H), 5.05-5.13 (m, 1H), 5.98-6.02 (m, 1H), 6.12-6.16 (m, 1H), 6.83-6.89 (m, 1H), 7.39-7.45 (m, 1H), 7.68-7.73 (m, 1H), 9.25 (s, 1H); LC-MS (LC-ES) M+H=343.

Example 256

Racemic 3-(Fluoro(quinolin-8-yl)methyl)-N-((trans)-4-(2-hydroxypropan-2-yl)cyclohexyl)azetidine-1-carboxamide

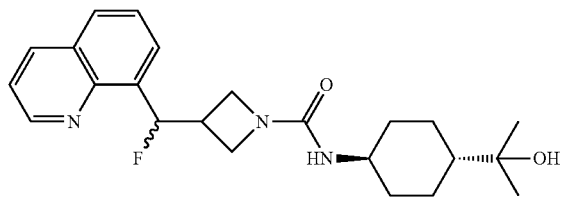 [SMILES: CC(C)(O)[C@H]1CC[C@H](NC(=O)N2CC(C(F)c3cccc4cccnc34)C2)CC1]

To 8-(azetidin-3-ylfluoromethyl)quinoline dihydrochloride (Intermediate 106) (36 mg, 0.12 mmol) and 4-nitrophenyl ((trans)-4-(2-hydroxypropan-2-yl)cyclohexyl)carbamate (66 mg, 0.20 mmol) (Intermediate 3) in 1,4-dioxane (10 mL) was added N,N-diisopropylethylamine (16 mg, 0.12 mmol). After 30 min, the reaction was diluted with water and MeOH and loaded onto a semi-prep HPLC (NH$_4$OH as modifier) to afford the title compound (23 mg, 46%) as a white solid. $^1$H NMR (400 MHz, CDCl$_3$) δ 1.01-1.31 (m, 11H), 1.87 (d, J=11 Hz, 2H), 2.04-2.15 (m, 2H), 3.36-3.63 (m, 2H), 3.75 (t, J=8 Hz, 1H), 3.88 (d, J=8 Hz, 1H), 4.00 (t, J=8 Hz, 1H), 4.05-4.15 (m, 2H), 6.68-6.95 (m, 1H), 7.46 (dd, J=8, 4 Hz, 1H), 7.55-7.68 (m, 1H), 7.79-7.91 (m, 2H), 8.19 (dd, J=8, 2 Hz, 1H), 8.91 (dd, J=4, 2 Hz, 1H); LC-MS (LC-ES) M+H=400.

Example 257

(trans)-3-(2,5-Dichlorophenoxy)-N-((trans)-4-(2-hydroxypropan-2-yl)cyclohexyl)cyclobutanecarboxamide

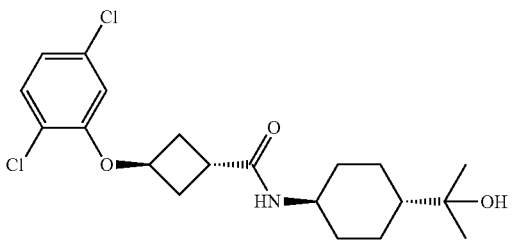 [SMILES: CC(C)(O)[C@H]1CC[C@H](NC(=O)[C@H]2C[C@H](Oc3cc(Cl)ccc3Cl)C2)CC1]

To a DMF (2 mL) solution of (trans)-3-(2,5-dichlorophenoxy)cyclobutanecarboxylic acid (Intermediate 107) (50 mg, 0.19 mmol) was added HATU (87 mg, 0.23 mmol) and N,N-diisopropylethylamine (0.10 mL, 0.57 mmol). After 10 minutes, 2-((trans)-4-aminocyclohexyl)propan-2-ol (36 mg, 0.23 mmol) was added, and the mixture was stirred for 18 h, poured into saturated aqueous sodium bicarbonate, extracted with EtOAc, dried over Na$_2$SO$_4$, filtered and concentrated. The residue was purified on reverse-phase silica gel, eluting with a 20%-95% acetonitrile-water (NH$_4$OH additive) gradient to give the title compound (49 mg, 60%). $^1$H NMR (400 MHz, CDCl$_3$) δ 1.08-1.34 (m, 11H), 1.87-1.95 (m, 2H), 2.06-2.13 (m, 2H), 2.43-2.52 (m, 2H), 2.76 (ddd, J=13, 7, 4 Hz, 2H), 2.92-3.01 (m, 1H), 3.75 (tdt, J=12, 8, 4 Hz, 1H), 5.01 (quin, J=6 Hz, 1H), 5.32 (d, J=8 Hz, 1H), 6.76 (d, J=2 Hz, 1H), 6.88 (dd, J=9, 2 Hz, 1H), 7.29 (d, J=2 Hz, 1H); LC-MS (LC-ES) M+H=400, 402, 404 (di-Cl pattern).

Example 258

N-((trans-4-(2-Hydroxypropan-2-yl)cyclohexyl)-3-(2-(trifluoromethoxy)phenoxy)azetidine-1-carboxamide

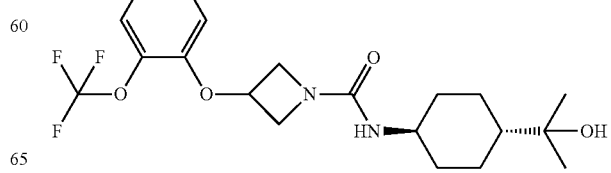

To 3-(2-(trifluoromethoxy)phenoxy)azetidine hydrochloride (Intermediate 108) (100 mg, 0.371 mmol) and 4-nitrophenyl ((trans)-4-(2-hydroxypropan-2-yl)cyclohexyl)carbamate (120 mg, 0.371 mmol) (Intermediate 3) in DCM (3 mL) was added N,N-diisopropylethylamine (0.20 mL, 1.1 mmol). After 18 h, the reaction was poured into 1 N aqueous NaOH solution and extracted twice with DCM. The combined organic layers were washed with brine, dried over $Na_2SO_4$, filtered and concentrated. The residue was purified on silica gel, eluting with a 5%-75% EtOAc:EtOH (3:1)-hexanes gradient, to give the title compound (88 mg, 57%) as a white solid. $^1$H NMR (400 MHz, $CDCl_3$) δ 0.96-1.19 (m, 5H), 1.03 (s, 6H), 1.72-1.86 (m, 4H), 3.21-3.27 (m, 1H), 3.66-3.77 (m, 2H), 3.98 (s, 1H), 4.19-4.29 (m, 2H), 5.07 (br s, 1H), 6.14 (d, J=8 Hz, 1H), 7.00 (d, J=8 Hz, 1H), 7.07 (t, J=8 Hz, 1H), 7.31-7.43 (m, 2H); LC-MS (LC-ES) M+H=417.

Example 259

(trans)-N-((trans)-4-(2-Hydroxypropan-2-yl)cyclohexyl)-3-(2-(trifluoromethoxy)phenoxy)cyclobutanecarboxamide

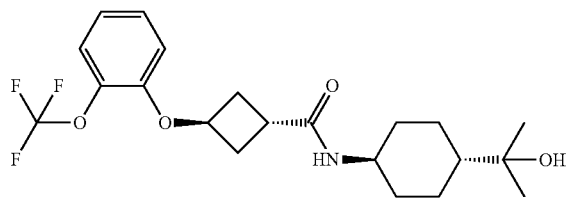 [SMILES: CC(C)(O)[C@H]1CC[C@H](NC(=O)[C@H]2C[C@H](Oc3ccccc3OC(F)(F)F)C2)CC1]

To a DMF (4 mL) solution of (trans)-3-(2-(trifluoromethoxy)phenoxy)cyclobutanecarboxylic acid (Intermediate 109) (50 mg, 0.18 mmol) was added HATU (83 mg, 0.22 mmol) and N,N-diisopropylethylamine (0.10 mL, 0.54 mmol). After 5 minutes, 2-((trans)-4-aminocyclohexyl)propan-2-ol (31 mg, 0.20 mmol) was added, and the mixture was stirred for 12 h, poured into water, extracted with EtOAc (3×), dried over $Na_2SO_4$, filtered and concentrated. The residue was purified on silica gel, eluting with a 5%-75% EtOAc:EtOH (3:1)-hexanes gradient, to give the title compound (53 mg, 71%). $^1$H NMR (400 MHz, $CD_3SOCD_3$) δ 0.92-1.18 (m, 5H), 1.00 (s, 6H), 1.78 (t, J=12 Hz, 4H), 2.09-2.20 (m, 2H), 2.53 (ddd, J=13, 7, 4 Hz, 2H), 2.90-3.02 (m, 1H), 3.42 (dd, J=8, 3 Hz, 1H), 3.99 (s, 1H), 4.88 (t, J=6 Hz, 1H), 6.89-7.02 (m, 2H), 7.25-7.34 (m, 2H), 7.69 (d, J=8 Hz, 1H); LC-MS (LC-ES) M+H=416.

Example 260

3-(Benzofuran-7-yloxy)-N-((trans)-4-(2-hydroxypropan-2-yl)cyclohexyl)azetidine-1-carboxamide

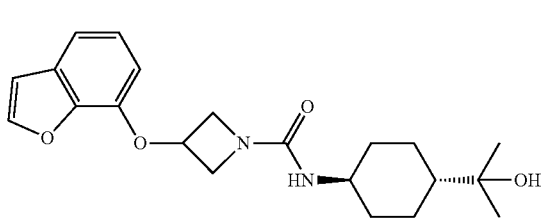 [SMILES: CC(C)(O)[C@H]1CC[C@H](NC(=O)N2CC(Oc3cccc4ccoc34)C2)CC1]

To 3-(benzofuran-7-yloxy)azetidine hydrochloride (Intermediate 110) (38 mg, 0.17 mmol) and 4-nitrophenyl ((trans)-4-(2-hydroxypropan-2-yl)cyclohexyl)carbamate (60 mg, 0.19 mmol) (Intermediate 3) in DCM (2 mL) was added N,N-diisopropylethylamine (0.10 mL, 0.57 mmol). After 5 h, the reaction was poured into 1 N aqueous NaOH solution and extracted twice with DCM. The combined organic layers were washed with brine, dried over $Na_2SO_4$, filtered and concentrated. The residue was purified on silica gel, eluting with a 5%-30% EtOAc:EtOH (3:1)-hexanes gradient, to give the title compound (54 mg, 86%) as a white solid. $^1$H NMR (400 MHz, $CD_3SOCD_3$) δ 0.94-1.13 (m, 5H), 1.00 (s, 6H), 1.70-1.80 (m, 4H), 3.21-3.28 (m, 1H), 3.74-3.80 (m, 2H), 3.97 (s, 1H), 4.21-4.26 (m, 2H), 5.08-5.13 (m, 1H), 6.14 (d, J=8 Hz, 1H), 6.78 (d, J=8 Hz, 1H), 6.92-6.94 (m, 1H), 7.12 (t, J=8 Hz, 1H), 7.24 (d, J=8 Hz, 1H), 7.94-7.97 (m, 1H); LC-MS (LC-ES) M+H=373.

Example 261

(trans)-3-(Benzofuran-7-yloxy)-N-(5-cyanothiazol-2-yl)cyclobutanecarboxamide

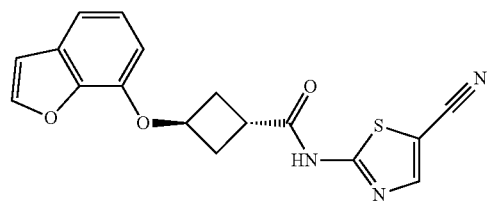 [SMILES: N#Cc1cnc(NC(=O)[C@H]2C[C@H](Oc3cccc4ccoc34)C2)s1]

To a DMF (4 mL) solution of (trans)-3-(benzofuran-7-yloxy)cyclobutanecarboxylic acid (Intermediate 111) (80 mg, 0.34 mmol) was added HATU (157 mg, 0.413 mmol) and N,N-diisopropylethylamine (0.18 mL, 1.0 mmol). After 5 minutes, 2-aminothiazole-5-carbonitrile (47 mg, 0.38 mmol) was added, and the mixture was stirred for 12 h, poured into water, extracted with EtOAc (3×), dried over $Na_2SO_4$, filtered and concentrated. The residue was purified on reverse phase silica gel, eluting with 0%-100% acetonitrile-water (0.1% TFA additive) to give the title compound (48 mg, 29%). $^1$H NMR (400 MHz, $CD_3SOCD_3$) δ 2.35-2.45 (m, 2H), 2.72-2.80 (m, 2H), 3.42-3.48 (m, 1H), 5.00-5.08 (m, 1H), 6.72 (d, J=8 Hz, 1H), 6.88-6.91 (m, 1H), 7.11 (t, J=8 Hz, 1H), 7.29 (d, J=4 Hz, 1H), 7.88-7.91 (m, 1H), 8.37 (s, 1H), 12.97 (s, 1H); LC-MS (LC-ES) M+H=340.

Example 262

Ethyl 2-(2-((trans)-3-(benzofuran-7-yloxy)cyclobutanecarboxamido)thiazol-4-yl)acetate

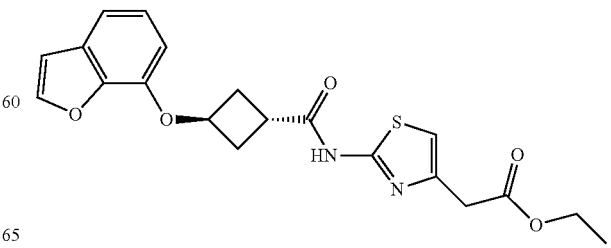

To a DMF (4 mL) solution of (trans)-3-(benzofuran-7-yloxy)cyclobutanecarboxylic acid (Intermediate 111) (80 mg, 0.34 mmol) was added HATU (157 mg, 0.413 mmol) and N,N-diisopropylethylamine (0.18 mL, 1.0 mmol). After 5 minutes, ethyl 2-(2-aminothiazol-4-yl)acetate (71 mg, 0.38 mmol) was added, and the mixture was stirred for 12 h, poured into water, and the resulting solid was collected by filtration. This residue was purified on reverse phase silica gel, eluting with 0%-100% acetonitrile-water (0.1% TFA additive) to give the title compound (61 mg, 29%). $^1$H NMR (400 MHz, CD$_3$SOCD$_3$) δ 1.16 (t, J=7 Hz, 3H), 2.29-2.46 (m, 4H), 2.73 (qd, J=7, 4 Hz, 2H), 3.39 (d, J=10 Hz, 1H), 4.05 (q, J=7 Hz, 2H), 4.95-5.05 (m, 1H), 6.71 (d, J=7 Hz, 1H), 6.86-6.90 (m, 1H), 6.95-6.98 (m, 1H), 7.10 (t, J=8 Hz, 1H), 7.15-7.20 (m, 1H), 7.90-7.95 (m, 1H), 12.19 (s, 1H); LC-MS (LC-ES) M+H=401.

Example 263

Ethyl 2-(5-((trans)-3-(benzofuran-7-yloxy)cyclobutanecarboxamido)-1,3,4-thiadiazol-2-yl)acetate

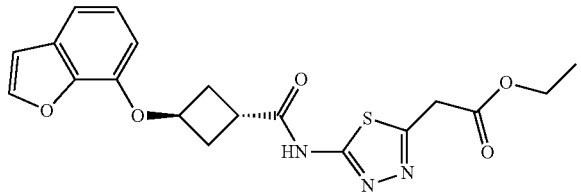 [SMILES: CCOC(=O)Cc1nnc(NC(=O)[C@H]2C[C@H](Oc3cccc4ccoc34)C2)s1]

To a DMF (4 mL) solution of (trans)-3-(benzofuran-7-yloxy)cyclobutanecarboxylic acid (Intermediate 111) (80 mg, 0.34 mmol) was added HATU (157 mg, 0.413 mmol) and N,N-diisopropylethylamine (0.18 mL, 1.0 mmol). After 5 minutes, 2-(5-amino-1,3,4-thiadiazol-2-yl)acetate (71 mg, 0.38 mmol) was added, and the mixture was stirred for 12 h, poured into water, and the resulting solid was collected by filtration. This solid was rinsed with hexanes to give the title compound (113 mg, 59%). $^1$H NMR (400 MHz, CD$_3$SOCD$_3$) δ 1.20 (t, J=7 Hz, 3H), 2.67 (s, 2H), 2.71-2.86 (m, 2H), 3.47 (s, 1H), 4.01-4.26 (m, 4H), 5.03 (t, J=6 Hz, 1H), 6.72 (d, J=8 Hz, 1H), 6.92 (d, J=2 Hz, 1H), 7.11 (t, J=8 Hz, 1H), 7.20 (dd, J=8, 1 Hz, 1H), 7.94 (d, J=2 Hz, 1H), 12.51 (s, 1H); LC-MS (LC-ES) M+H=402.

Example 264

(trans)-N-(5-Acetylthiazol-2-yl)-3-(benzofuran-7-yloxy)cyclobutanecarboxamide

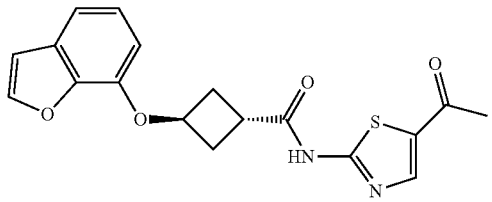 [SMILES: CC(=O)c1cnc(NC(=O)[C@H]2C[C@H](Oc3cccc4ccoc34)C2)s1]

To a DMF (5 mL) solution of (trans)-3-(benzofuran-7-yloxy)cyclobutanecarboxylic acid (Intermediate 111) (100 mg, 0.43 mmol) was added HATU (196 mg, 0.517 mmol) and N,N-diisopropylethylamine (0.23 mL, 1.3 mmol). After 5 minutes, 1-(2-aminothiazol-5-yl)ethanone (67 mg, 0.47 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc in hexanes to give the title compound (100 mg, 62%). $^1$H NMR (400 MHz, CD$_3$SOCD$_3$) δ 2.36-2.45 (m, 2H), 2.48 (s, 3H), 2.77 (ddd, J=14, 7, 5 Hz, 2H), 3.41-3.55 (m, 1H), 5.03 (t, J=6 Hz, 1H), 6.72 (d, J=8 Hz, 1H), 6.92 (d, J=2 Hz, 1H), 7.11 (t, J=8 Hz, 1H), 7.20 (dd, J=8, 1 Hz, 1H), 7.94 (d, J=2 Hz, 1H), 8.34 (s, 1H), 12.58 (s, 1H); LC-MS (LC-ES) M+H=357.

Example 265

(trans)-3-(Benzofuran-7-yloxy)-N-(5-(2-hydroxypropan-2-yl)thiazol-2-yl)cyclobutanecarboxamide

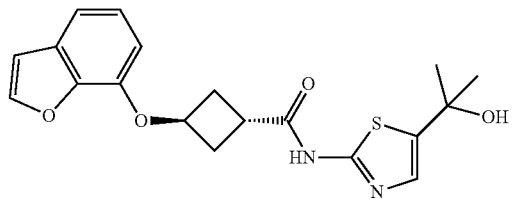 [SMILES: CC(C)(O)c1cnc(NC(=O)[C@H]2C[C@H](Oc3cccc4ccoc34)C2)s1]

(trans)-N-(5-Acetylthiazol-2-yl)-3-(benzofuran-7-yloxy)cyclobutanecarboxamide (Example 264) (23 mg, 0.065 mmol) was stirred in THF (5 mL) at 0° C., and a 3.0 M solution of methylmagnesium bromide (0.04 mL, 0.1 mmol) in diethyl ether was added. The reaction was stirred 1 h, quenched with saturated aqueous NH$_4$Cl, extracted with EtOAc (3×), and the organic extracts dried over Na$_2$SO$_4$, filtered, and concentrated under reduced pressure. The residue was purified on silica gel, eluting with a 0%-100% EtOAc:EtOH (3:1) in hexanes gradient to give the title compound (19 mg, 74%). $^1$H NMR (CD$_3$SOCD$_3$) δ 1.48 (s, 6H), 2.32-2.50 (m, 2H), 2.65-2.82 (m, 2H), 3.40 (dt, J=10, 5 Hz, 1H), 5.03 (t, J=6 Hz, 1H), 5.41 (s, 1H), 6.71 (d, J=8 Hz, 1H), 6.92 (d, J=2 Hz, 1H), 7.11 (t, J=8 Hz, 1H), 7.15-7.28 (m, 2H), 7.94 (d, J=2 Hz, 1H), 11.91 (s, 1H); LC-MS (LC-ES) M+H=373.

Example 266

(trans)-3-(Benzofuran-7-yloxy)-N-(5-methyl-1,3,4-thiadiazol-2-yl)cyclobutanecarboxamide

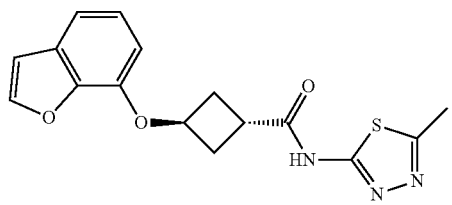 [SMILES: Cc1nnc(NC(=O)[C@H]2C[C@H](Oc3cccc4ccoc34)C2)s1]

To a DMF (4 mL) solution of (trans)-3-(benzofuran-7-yloxy)cyclobutanecarboxylic acid (Intermediate 111) (80 mg, 0.34 mmol) was added HATU (157 mg, 0.413 mmol) and N,N-diisopropylethylamine (0.18 mL, 1.0 mmol). After 5 minutes, 5-methyl-1,3,4-thiadiazol-2-amine (44 mg, 0.38 mmol) was added, and the mixture was stirred for 12 h, poured into water, and the resulting solid was collected by filtration. This solid was rinsed with hexanes to give the title compound (80 mg, 68%). $^1$H NMR (400 MHz, CD$_3$SOCD$_3$) δ 2.36-2.45 (m, 2H), 2.60 (s, 3H), 2.74 (ddd, J=13, 7, 5 Hz, 2H), 3.45 (dt, J=10, 5 Hz, 1H), 5.02 (t, J=6 Hz, 1H), 6.71 (d, J=7 Hz, 1H), 6.92 (d, J=2 Hz, 1H), 7.10 (t, J=8 Hz, 1H), 7.20 (dd, J=8, 1 Hz, 1H), 7.94 (d, J=2 Hz, 1H), 12.40 (s, 1H); LC-MS (LC-ES) M+H=330.

Example 267

(trans)-3-(Benzofuran-7-yloxy)-N-((trans)-4-(2-hydroxypropan-2-yl)cyclohexyl)cyclobutanecarboxamide

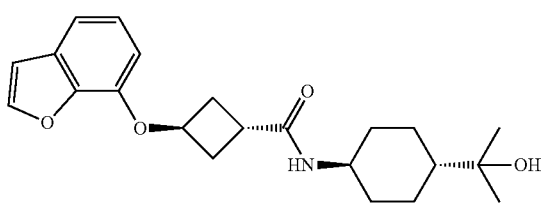 [SMILES: CC(C)(O)[C@H]1CC[C@H](NC(=O)[C@H]2C[C@H](Oc3cccc4ccoc34)C2)CC1]

To a DMF (4 mL) solution of (trans)-3-(benzofuran-7-yloxy)cyclobutanecarboxylic acid (Intermediate 111) (80 mg, 0.34 mmol) was added HATU (157 mg, 0.413 mmol) and N,N-diisopropylethylamine (0.18 mL, 1.0 mmol). After 5 minutes, 2-((trans)-4-aminocyclohexyl)propan-2-ol (60 mg, 0.38 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc:EtOH (3:1) in hexanes to give the title compound (112 mg, 83%). $^1$H NMR (400 MHz, CD$_3$SOCD$_3$) δ 0.92-1.16 (m, 5H), 1.00 (s, 6H), 1.64-1.82 (m, 4H), 2.21-2.31 (m, 2H), 2.51-2.61 (m, 2H), 2.89-3.02 (m, 1H), 3.36-3.51 (m, 1H), 3.99 (s, 1H), 4.98 (t, J=6 Hz, 1H), 6.66 (d, J=8 Hz, 1H), 6.84-6.98 (m, 1H), 7.10 (t, J=8 Hz, 1H), 7.18 (d, J=8 Hz, 1H), 7.68 (d, J=8 Hz, 1H), 7.93 (s, 1H); LC-MS (LC-ES) M+H=372.

Example 268

(trans)-3-((2,3-Dihydrobenzofuran-7-yl)oxy)-N-((trans)-4-(2-hydroxypropan-2-yl)cyclohexyl)cyclobutanecarboxamide

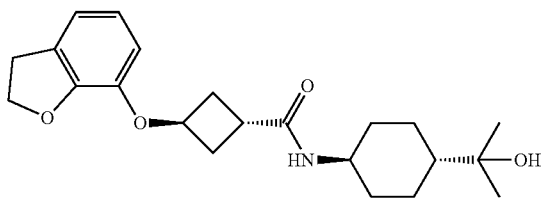 [SMILES: CC(C)(O)[C@H]1CC[C@H](NC(=O)[C@H]2C[C@H](Oc3cccc4c3OCC4)C2)CC1]

A nitrogen-purged mixture of (trans)-3-(benzofuran-7-yloxy)-N-((trans)-4-(2-hydroxypropan-2-yl)cyclohexyl)cyclobutanecarboxamide (Example 267) (25 mg, 0.067 mmol) and palladium on carbon (9 mg, 0.08 mmol) in EtOH (10 mL) was stirred under 50 psi of hydrogen for 3 days. The reaction mixture was filtered through a plug of Celite® and concentrated to give the title compound (18 mg, 65%). $^1$H NMR (400 MHz, CD$_3$SOCD$_3$) δ 0.89-1.14 (m, 5H), 1.00 (s, 6H), 1.77 (t, J=11 Hz, 4H), 2.07-2.28 (m, 2H), 2.38-2.46 (m, 2H), 2.93 (t, J=5 Hz, 1H), 3.13 (t, J=9 Hz, 2H), 3.41 (br s, 1H), 3.95-4.01 (m, 1H), 4.40-4.50 (m, 2H), 4.78 (t, J=6 Hz, 1H), 6.54 (d, J=8 Hz, 1H), 6.69 (t, J=8 Hz, 1H), 6.74-6.81 (m, 1H), 7.64 (d, J=8 Hz, 1H); LC-MS (LC-ES) M+H=374.

Example 269

(trans)-3-((3-Bromobenzofuran-7-yl)oxy)-N-((trans)-4-(2-hydroxypropan-2-yl)cyclohexyl)cyclobutanecarboxamide

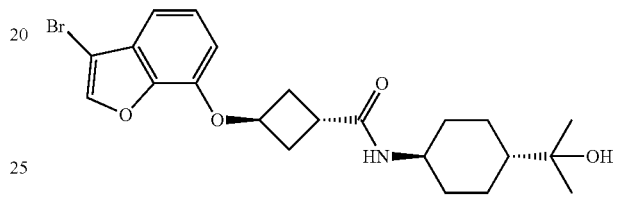

To a DMF (5 mL) solution of (trans)-3-((3-bromobenzofuran-7-yl)oxy)cyclobutanecarboxylic acid (Intermediate 112) (100 mg, 0.321 mmol) was added HATU (147 mg, 0.386 mmol) and N,N-diisopropylethylamine (0.17 mL, 0.96 mmol). After 5 minutes, 2-((trans)-4-aminocyclohexyl)propan-2-ol (51 mg, 0.32 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (132 mg, 79%). $^1$H NMR (400 MHz, CD$_3$SOCD$_3$) δ 0.89-1.18 (m, 5H), 1.00 (s, 6H), 1.68-1.91 (m, 4H), 2.23-2.37 (m, 2H), 2.56-2.64 (m, 2H), 2.90-3.07 (m, 1H), 3.43 (d, J=7 Hz, 1H), 4.01 (s, 1H), 4.98 (t, J=6 Hz, 1H), 6.66 (d, J=8 Hz, 1H), 6.87 (d, J=2 Hz, 1H), 7.32 (d, J=8 Hz, 1H), 7.71 (d, J=8 Hz, 1H), 8.07 (d, J=2 Hz, 1H); LC-MS (LC-ES) M+H=450, 452 (Br pattern).

Example 270

(trans)-N-((trans)-4-(2-Hydroxypropan-2-yl)cyclohexyl)-3-((3-methylbenzofuran-7-yl)oxy)cyclobutanecarboxamide

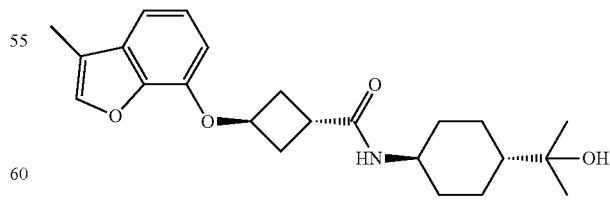

A suspension of cesium carbonate (109 mg, 0.333 mmol), (trans)-3-((3-bromobenzofuran-7-yl)oxy)-N-((trans)-4-(2-hydroxypropan-2-yl)cyclohexyl)cyclobutanecarboxamide (Example 269) (50 mg, 0.111 mmol), potassium trifluoro(methyl)borate (16 mg, 0.13 mmol) and PdCl$_2$(dppf)-

CH₂Cl₂ adduct (9 mg, 0.01 mmol) in THF (2 mL) was heated in a microwave at 120° C. for 45 min, at 140° C. for 2 h, then at 170° C. for 2 h. The reaction mixture was filtered through a pad of Celite, concentrated and purified on silica gel, eluting with 0%-100% EtOAc: EtOH (3:1) in hexane, to give the title compound (3 mg, 5%). LC-MS (LC-ES) Peak T=0.81; M+H=386.

Example 271

(trans)-N-(4-Acetylthiazol-2-yl)-3-((3-bromobenzofuran-7-yl)oxy)cyclobutanecarboxamide

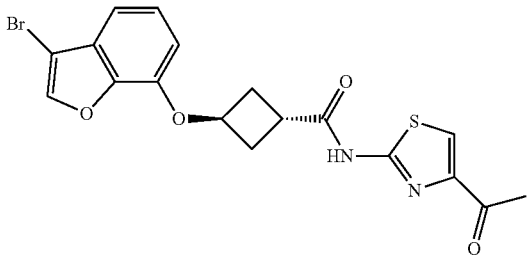 [SMILES: CC(=O)c1csc(NC(=O)[C@H]2C[C@H](Oc3cccc4c(Br)coc34)C2)n1]

To a DMF (5 mL) solution of (trans)-3-((3-bromobenzofuran-7-yl)oxy)cyclobutanecarboxylic acid (Intermediate 112) (100 mg, 0.321 mmol) was added HATU (147 mg, 0.386 mmol) and N,N-diisopropylethylamine (0.17 mL, 0.96 mmol). After 5 minutes, 1-(2-aminothiazol-4-yl)ethanone (50 mg, 0.35 mmol) was added, and the mixture was stirred for 12 h, poured into water, and extracted with EtOAc (3×). The combined organic layers were dried over Na₂SO₄, filtered and concentrated. This residue was purified on silica gel, eluting with 0%-100% EtOAc: EtOH (3:1) in hexanes to give the title compound (97 mg, 58%). ¹H NMR (400 MHz, CD₃SOCD₃) δ 2.37-2.44 (m, 2H), 2.66 (s, 3H), 2.67-2.75 (m, 2H), 3.42 (d, J=5 Hz, 1H), 5.03 (t, J=6 Hz, 1H), 6.72 (d, J=8.40 Hz, 1H), 6.82-6.94 (m, 1H), 7.32-7.41 (m, 1H), 8.03-8.15 (m, 2H), 12.50 (s, 1H); LC-MS (LC-ES) M+H=435, 437 (Br pattern).

Example 272

(trans)-N-(4-Acetylthiazol-2-yl)-3-(5-chloro-2-(difluoromethoxy)phenoxy)cyclobutanecarboxamide

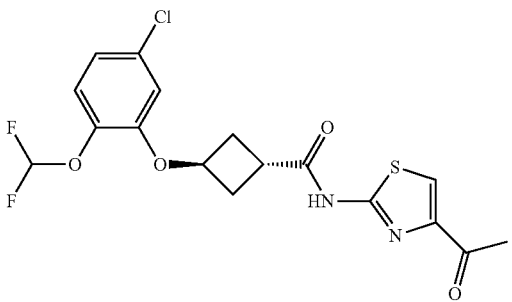 [SMILES: CC(=O)c1csc(NC(=O)[C@H]2C[C@H](Oc3cc(Cl)ccc3OC(F)F)C2)n1]

To a DMF (4 mL) solution of (trans)-3-(5-chloro-2-(difluoromethoxy)phenoxy)cyclobutanecarboxylic acid (Intermediate 113) (80 mg, 0.27 mmol) was added HATU (125 mg, 0.328 mmol) and N,N-diisopropylethylamine (0.14 mL, 0.82 mmol). After 5 minutes, 1-(2-aminothiazol-4-yl)ethanone (39 mg, 0.27 mmol) was added, and the mixture was stirred for 5 h, poured into water, and extracted with EtOAc (3×). The combined organic layers were dried over Na₂SO₄, filtered and concentrated. This residue was purified on silica gel, eluting with 0%-100% EtOAc: EtOH (3:1) in hexanes to give the title compound (28 mg, 20%). ¹H NMR (400 MHz, CD₃SOCD₃) δ 2.22-2.39 (m, 2H), 2.60-2.69 (m, 2H), 2.69 (s, 3H), 3.35-3.45 (m, 1H), 4.89-4.99 (m, 1H), 6.89-7.09 (m, 3H), 7.13-7.22 (m, 1H), 8.08 (s, 1H), 12.47 (br s, 1H); LC-MS (LC-ES) M+H=417, 419 (CI pattern).

Example 273

(trans)-3-(5-Chloro-2-(difluoromethoxy)phenoxy)-N-((trans)-4-(2-hydroxypropan-2-yl)cyclohexyl)cyclobutanecarboxamide

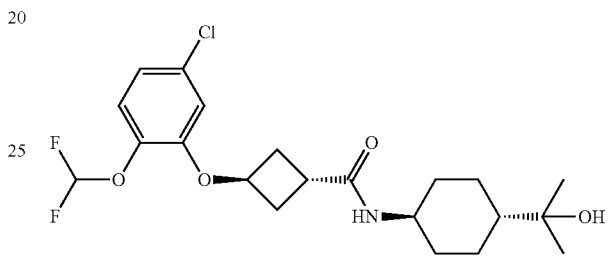

To a DMF (4 mL) solution of (trans)-3-(5-chloro-2-(difluoromethoxy)phenoxy)cyclobutanecarboxylic acid (Intermediate 113) (80 mg, 0.27 mmol) was added HATU (125 mg, 0.328 mmol) and N,N-diisopropylethylamine (0.14 mL, 0.82 mmol). After 5 minutes, 2-((trans)-4-aminocyclohexyl)propan-2-ol (43 mg, 0.27 mmol) was added, and the mixture was stirred for 5 h, poured into water, and extracted with EtOAc (3×). The combined organic layers were dried over Na₂SO₄, filtered and concentrated. This residue was purified on silica gel, eluting with 0%-100% EtOAc: EtOH (3:1) in hexanes to give the title compound (80 mg, 63%). ¹H NMR (400 MHz, CD₃SOCD₃) δ 0.96-1.22 (m, 5H), 1.02 (s, 6H), 1.80 (t, J=13 Hz, 4H), 2.13-2.36 (m, 2H), 2.54-2.63 (m, 2H), 2.99 (dq, J=10, 5 Hz, 1H), 3.45 (dd, J=8, 4 Hz, 1H), 4.01 (s, 1H), 4.91 (t, J=6.35 Hz, 1H), 6.90-7.27 (m, 4H), 7.70 (d, J=8 Hz, 1H); LC-MS (LC-ES) M+H=432, 434 (CI pattern).

Example 274

(trans)-N-(4-Acetylthiazol-2-yl)-3-(5-chloro-2-methoxyphenoxy)cyclobutanecarboxamide

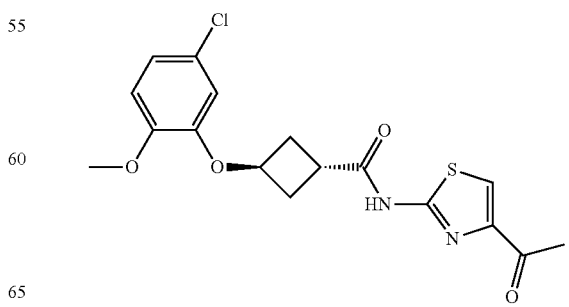

To a DMF (4 mL) solution of (trans)-3-(5-chloro-2-methoxyphenoxy)cyclobutanecarboxylic acid (Intermediate 114) (80 mg, 0.31 mmol) was added HATU (141 mg, 0.370 mmol) and N,N-diisopropylethylamine (0.16 mL, 0.93 mmol). After 5 minutes, 1-(2-aminothiazol-4-yl)ethanone (52 mg, 0.37 mmol) was added, and the mixture was stirred for 3 h, poured into water, and extracted with EtOAc (3×). The combined organic layers were dried over $Na_2SO_4$, filtered and concentrated. This residue was purified on silica gel, eluting with 0%-100% EtOAc: EtOH (3:1) in hexanes to give the title compound (33 mg, 23%) as a white solid. $^1$H NMR (400 MHz, $CD_3SOCD_3$) δ 2.19-2.35 (m, 2H), 2.50 (s, 3H), 2.59-2.70 (m 2H), 3.32-3.42 (m, 1H), 3.76 (d, J=6 Hz, 3H), 4.72-4.89 (m, 1H), 6.72-6.78 (m, 1H), 6.89-7.01 (m, 2H), 8.08 (s, 1H), 12.46 (br s, 1H); LC-MS (LC-ES) M+H=381, 383 (Cl pattern).

Example 275

(trans)-3-(5-Chloro-2-methoxyphenoxy)-N-((trans)-4-(2-hydroxypropan-2-yl)cyclohexyl)cyclobutanecarboxamide

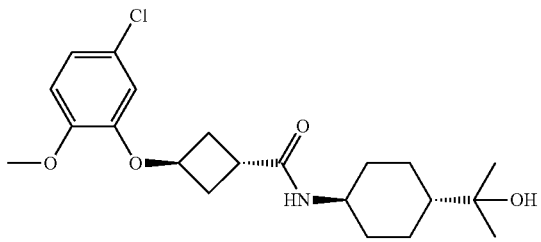

To a DMF (4 mL) solution of (trans)-3-(5-chloro-2-methoxyphenoxy)cyclobutanecarboxylic acid (Intermediate 114) (80 mg, 0.31 mmol) was added HATU (141 mg, 0.37 mmol) and N,N-diisopropylethylamine (0.16 mL, 0.93 mmol). After 5 minutes, 2-((trans)-4-aminocyclohexyl)propan-2-ol (59 mg, 0.37 mmol) was added, and the mixture was stirred for 3 h, poured into water, and extracted with EtOAc (3×). The combined organic layers were dried over $Na_2SO_4$, filtered and concentrated. This residue was purified on silica gel, eluting with 0%-100% EtOAc: EtOH (3:1) in hexanes to give an oil that was crystallized using 2:1 hexane:DCM that was slowly evaporated over 18 h to give the title compound (58 mg, 47%) as white crystals. $^1$H NMR (400 MHz, $CD_3SOCD_3$) δ 0.95-1.22 (m, 5H), 1.02 (s, 6H), 1.80 (t, J=13 Hz, 4H), 2.23 (ddd, J=13, 10, 6 Hz, 2H), 2.43-2.52 (m, 2H), 2.91-3.00 (m, 1H), 3.35-3.45 (m, 1H), 3.76 (s, 3H), 4.01 (s, 1H), 4.80 (t, J=6 Hz, 1H), 6.68 (d, J=2 Hz, 1H), 6.91-7.00 (m, 2H), 7.68 (d, J=8 Hz, 1H); LC-MS (LC-ES) M+H=396, 398 (Cl pattern).

Example 276

(trans)-N-(4-Acetylthiazol-2-yl)-3-(4-fluoro-2-methoxyphenoxy)cyclobutanecarboxamide

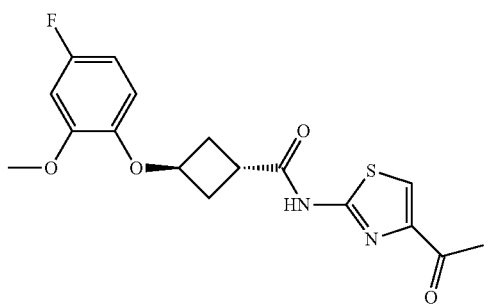 [SMILES: COc1cc(F)ccc1O[C@H]1C[C@H](C(=O)Nc2nc(C(C)=O)cs2)C1]

To a DMF (4 mL) solution of (trans)-3-(4-fluoro-2-methoxyphenoxy)cyclobutanecarboxylic acid (Intermediate 115) (80 mg, 0.33 mmol) was added HATU (152 mg, 0.400 mmol) and N,N-diisopropylethylamine (0.17 mL, 0.99 mmol). After 5 minutes, 1-(2-aminothiazol-4-yl)ethanone (57 mg, 0.40 mmol) was added, and the mixture was stirred for 3 h, poured into water, and extracted with EtOAc (3×). The combined organic layers were dried over $Na_2SO_4$, filtered and concentrated. This residue was purified on silica gel, eluting with 0%-100% EtOAc: EtOH (3:1) in hexanes to give the title compound (46 mg, 35%). $^1$H NMR (400 MHz, $CD_3SOCD_3$) δ 2.23-2.38 (m, 2H), 2.49 (s, 3H), 2.60-2.69 (m, 2H), 3.35-3.47 (m, 1H), 3.78 (s, 3H), 4.78 (t, J=6 Hz, 1H), 6.58-6.65 (m, 1H), 6.72-6.78 (m, 1H), 6.92 (d, J=3 Hz, 1H), 8.08 (s, 1H), 12.46 (s, 1H); LC-MS (LC-ES) M+H=365.

Example 277

(trans)-3-(4-Fluoro-2-methoxyphenoxy)-N-((trans)-4-(2-hydroxypropan-2-yl)cyclohexyl)cyclobutanecarboxamide

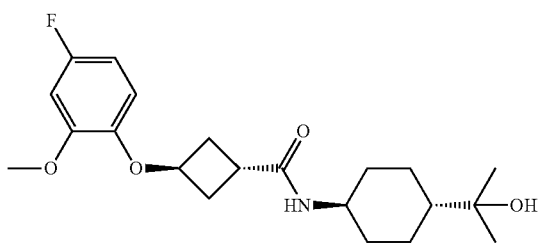 [SMILES: COc1cc(F)ccc1O[C@H]1C[C@H](C(=O)N[C@H]2CC[C@H](C(C)(C)O)CC2)C1]

To a DMF (4 mL) solution of (trans)-3-(4-fluoro-2-methoxyphenoxy)cyclobutanecarboxylic acid (Intermediate 115) (80 mg, 0.33 mmol) was added HATU (152 mg, 0.40 mmol) and N,N-diisopropylethylamine (0.17 mL, 0.99 mmol). After 5 minutes, 2-((trans)-4-aminocyclohexyl)propan-2-ol (63 mg, 0.40 mmol) was added, and the mixture was stirred for 3 h, poured into water, and extracted with EtOAc (3×). The combined organic layers were dried over $Na_2SO_4$, filtered and concentrated. This residue was purified on silica gel, eluting with 0%-100% EtOAc: EtOH (3:1) in hexanes to give an oil that was crystallized using 2:1 hexane:DCM that was slowly evaporated over 18 h to give the title compound (58 mg, 47%) as white crystals. ¹H NMR (400 MHz, CD₃SOCD₃) δ 0.92-1.11 (m, 5H), 1.02 (s, 6H), 1.72-1.83 (m, 4H), 2.12-2.21 (m, 2H), 2.46 (td, J=6, 4 Hz, 2H), 2.95 (dt, J=9, 5 Hz, 1H), 3.32 (s, 3H), 3.43 (dd, J=8, 3 Hz, 1H), 4.01 (s, 1H), 4.73 (t, J=7 Hz, 1H), 6.59-6.65 (m, 2H), 6.88 (d, J=3 Hz, 1H), 7.66 (d, J=8 Hz, 1H); LC-MS (LC-ES) M+H=380.

Example 278

(trans)-3-(2-(Difluoromethoxy)phenoxy)-N-((trans)-4-(2-hydroxypropan-2-yl)cyclohexyl)cyclobutanecarboxamide

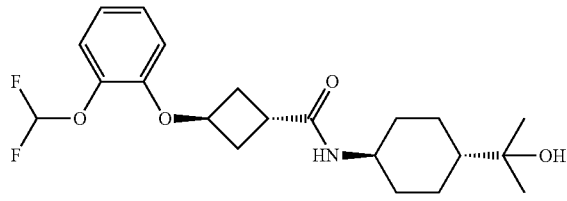 [SMILES: CC(C)(O)[C@H]1CC[C@H](NC(=O)[C@H]2C[C@H](Oc3ccccc3OC(F)F)C2)CC1]

To a DMF (5 mL) solution of (trans)-3-(2-(difluoromethoxy)phenoxy)cyclobutanecarboxylic acid (Intermediate 116) (100 mg, 0.321 mmol) was added HATU (147 mg, 0.386 mmol) and N,N-diisopropylethylamine (0.17 mL, 0.97 mmol). After 5 minutes, 2-((trans)-4-aminocyclohexyl)propan-2-ol (54 mg, 0.34 mmol) was added, and the mixture was stirred for 12 h, poured into water, and extracted with EtOAc (3×). The combined organic layers were dried over Na₂SO₄, filtered and concentrated. This residue was purified on silica gel, eluting with 0%-100% EtOAc: EtOH (3:1) in hexanes to give the title compound (49 mg, 39%). ¹H NMR (400 MHz, CD₃SOCD₃) δ 0.95-1.16 (m, 5H), 1.00 (s, 6H), 1.77 (t, J=12 Hz, 4H), 2.17-2.23 (m, 2H), 2.49-2.59 (m, 2H), 2.88-3.00 (m, 1H), 3.39-3.47 (m, 1H), 4.01 (s, 1H), 4.84 (t, J=6 Hz, 1H), 6.83-6.88 (m, 1H), 6.88-6.95 (m, 1H), 7.04 (t, J=76 Hz, 1H), 7.11-7.19 (m, 2H), 7.70 (d, J=8 Hz, 1H); LC-MS (LC-ES) M+H=398.

Example 279

(trans)-N-(4-Acetylthiazol-2-yl)-3-(4-fluoro-2-methoxyphenoxy)cyclobutanecarboxamide

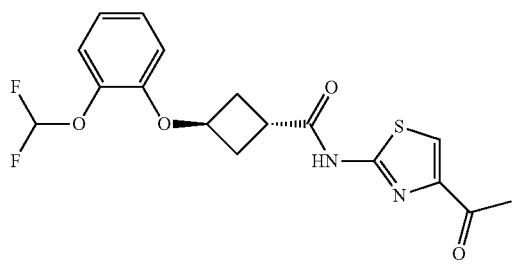 [SMILES: CC(=O)c1csc(NC(=O)[C@H]2C[C@H](Oc3ccccc3OC(F)F)C2)n1]

To a DMF (5 mL) solution of (trans)-3-(2-(difluoromethoxy)phenoxy)cyclobutanecarboxylic acid (Intermediate 116) (80 mg, 0.310 mmol) was added HATU (141 mg, 0.372 mmol) and N,N-diisopropylethylamine (0.16 mL, 0.93 mmol). After 5 minutes, 1-(2-aminothiazol-4-yl)ethanone (49 mg, 0.34 mmol) was added, and the mixture was stirred for 12 h, poured into water, and extracted with EtOAc (3×). The combined organic layers were dried over Na₂SO₄, filtered and concentrated. This residue was purified on silica gel, eluting with 0%-100% EtOAc: EtOH (3:1) in hexanes to give the title compound (35 mg, 25%). ¹H NMR (400 MHz, CD₃SOCD₃) δ 2.28-2.38 (m, 2H), 2.48 (s, 3H), 2.61-2.65 (m, 2H), 3.32-3.49 (m, 1H), 4.82-4.92 (m, 1H), 6.89-6.95 (m, 2H), 7.04 (t, J=76 Hz, 1H), 7.12-7.20 (m, 2H), 8.07 (s, 1H), 12.47 (br s, 1H); LC-MS (LC-ES) M+H=383.

Example 280

(trans)-3-((3-Fluoroquinolin-8-yl)oxy)-N-((trans)-4-(2-hydroxypropan-2-yl)cyclohexyl)cyclobutanecarboxamide

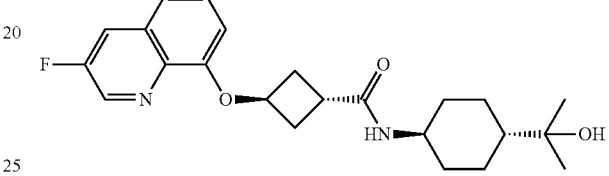

To a DMF (4 mL) solution of (trans)-3-((3-fluoroquinolin-8-yl)oxy)cyclobutanecarboxylic acid (Intermediate 117) (80 mg, 0.31 mmol) was added HATU (140 mg, 0.367 mmol) and N,N-diisopropylethylamine (0.16 mL, 0.92 mmol). After 5 minutes, 2-((trans)-4-aminocyclohexyl)propan-2-ol (53 mg, 0.34 mmol) was added, and the mixture was stirred for 12 h, poured into water, and extracted with EtOAc (3×). The combined organic layers were dried over Na₂SO₄, filtered and concentrated. This residue was purified on silica gel, eluting with 0%-100% EtOAc: EtOH (3:1) in hexanes to give the title compound (42 mg, 34%). ¹H NMR (400 MHz, CD₃SOCD₃) δ 0.97-1.09 (m, 5H), 1.00 (s, 6H), 1.69-1.80 (m, 4H), 2.26-2.35 (m, 2H), 2.56-2.62 (m, 2H), 3.03 (dt, J=9, 5 Hz, 1H), 3.44 (dd, J=7, 4 Hz, 1H), 3.99 (s, 1H), 5.00 (t, J=6 Hz, 1H), 6.90 (dd, J=7, 1 Hz, 1H), 7.42-7.55 (m, 2H), 7.70 (d, J=8 Hz, 1H), 8.17 (dd, J=10, 3 Hz, 1H), 8.84 (d, J=3 Hz, 1H); LC-MS (LC-ES) M+H=401.

Example 281

(trans)-3-((3-Fluoroquinolin-8-yl)oxy)-N-(thiazol-2-yl)cyclobutanecarboxamide

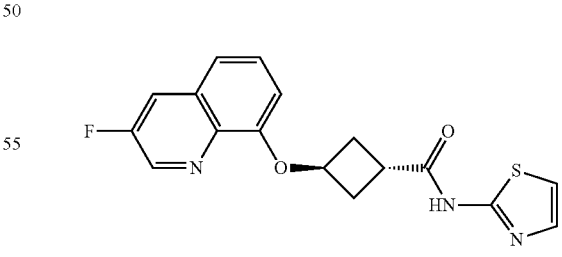

To a DMF (4 mL) solution of (trans)-3-((3-fluoroquinolin-8-yl)oxy)cyclobutanecarboxylic acid (Intermediate 117) (80 mg, 0.31 mmol) was added HATU (140 mg, 0.367 mmol) and N,N-diisopropylethylamine (0.16 mL, 0.92 mmol). After 5 minutes, thiazol-2-amine (37 mg, 0.37 mmol) was added, and the mixture was stirred for 3 h and poured into water. The resulting solid was collected by filtration to give the title compound (45 mg, 41%). $^1$H NMR (400 MHz, CD$_3$SOCD$_3$) δ 2.45-2.55 (m, 2H), 2.75-2.82 (m, 2H), 3.39-3.49 (m, 1H), 5.06 (t, J=6 Hz, 1H), 6.96 (dd, J=7, 2 Hz, 1H), 7.21 (d, J=4 Hz, 1H), 7.41-7.54 (m, 3H), 8.19 (dd, J=10, 3 Hz, 1H), 8.86 (d, J=3 Hz, 1H), 12.14 (s, 1H); LC-MS (LC-ES) M+H=344.

Example 282

(trans)-3-(2-Chlorophenoxy)-N-((trans)-4-(2-hydroxypropan-2-yl)cyclohexyl)cyclobutanecarboxamide

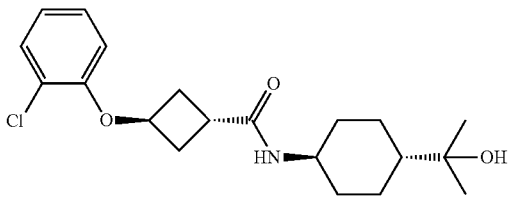 [SMILES: CC(C)(O)[C@H]1CC[C@H](NC(=O)[C@H]2C[C@H](Oc3ccccc3Cl)C2)CC1]

To a DMF (4 mL) solution of (trans)-3-(2-chlorophenoxy)cyclobutanecarboxylic acid (Intermediate 118) (80 mg, 0.35 mmol) was added HATU (161 mg, 0.424 mmol) and N,N-diisopropylethylamine (0.19 mL, 1.1 mmol). After 5 minutes, 2-((trans)-4-aminocyclohexyl)propan-2-ol (61 mg, 0.39 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (105 mg, 72%). $^1$H NMR (400 MHz, CD$_3$SOCD$_3$) δ 0.97-1.15 (m, 5H), 1.00 (s, 6H), 1.72-1.81 (m, 4H), 2.19-2.30 (m, 2H), 2.54 (ddd, J=13, 7, 4 Hz, 2H), 2.91-3.01 (m, 1H), 3.38-3.45 (m, 1H), 3.99 (s, 1H), 4.87 (t, J=6 Hz, 1H), 6.81-6.88 (m, 1H), 6.88-6.93 (m, 1H), 7.21-7.26 (m, 1H), 7.39 (dd, J=8, 1 Hz, 1H), 7.69 (d, J=8 Hz, 1H); LC-MS (LC-ES) M+H=366, 368 (Cl pattern).

Example 283

(trans)-3-(3,5-Difluorophenoxy)-N-((trans)-4-(2-hydroxypropan-2-yl)cyclohexyl)cyclobutanecarboxamide

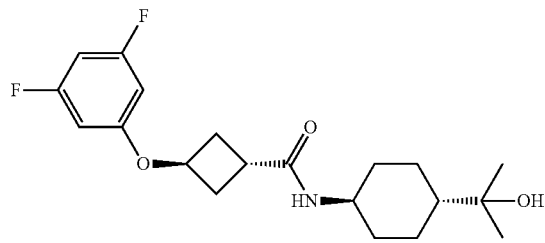 [SMILES: CC(C)(O)[C@H]1CC[C@H](NC(=O)[C@H]2C[C@H](Oc3cc(F)cc(F)c3)C2)CC1]

To a DMF (4 mL) solution of (trans)-3-(3,5-difluorophenoxy)cyclobutanecarboxylic acid (Intermediate 119) (80 mg, 0.35 mmol) was added HATU (160 mg, 0.421 mmol) and N,N-diisopropylethylamine (0.18 mL, 1.1 mmol). After 5 minutes, 2-((trans)-4-aminocyclohexyl)propan-2-ol (61 mg, 0.39 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (78 mg, 59%). $^1$H NMR (400 MHz, CD$_3$SOCD$_3$) δ 0.96-1.11 (m, 5H), 1.00 (s, 6H), 1.78 (t, J=12 Hz, 4H), 2.13-2.20 (m, 2H), 2.53 (ddd, J=13, 7, 4 Hz, 2H), 2.96 (dt, J=10, 5 Hz, 1H), 3.42 (dd, J=8, 4 Hz, 1H), 3.99 (s, 1H), 4.81 (t, J=6 Hz, 1H), 6.46-6.55 (m, 2H), 6.75 (tt, J=9, 2 Hz, 1H), 7.66 (d, J=8 Hz, 1H); LC-MS (LC-ES) M+H=368.

Example 284

(trans)-N-((trans)-4-(2-hydroxypropan-2-yl)cyclohexyl)-3-(2-methoxyphenoxy)cyclobutanecarboxamide

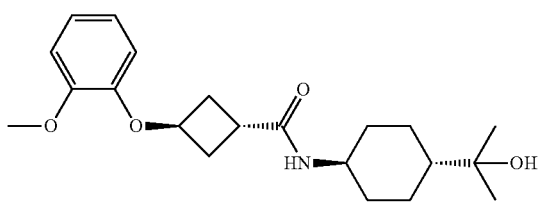 [SMILES: COc1ccccc1O[C@H]1C[C@H](C(=O)N[C@H]2CC[C@H](C(C)(C)O)CC2)C1]

To a DMF (4 mL) solution of (trans)-3-(2-methoxyphenoxy)cyclobutanecarboxylic acid (Intermediate 120) (80 mg, 0.36 mmol) was added HATU (164 mg, 0.432 mmol) and N,N-diisopropylethylamine (0.19 mL, 1.1 mmol). After 5 minutes, 2-((trans)-4-aminocyclohexyl)propan-2-ol (62 mg, 0.40 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (57 mg, 43%). $^1$H NMR (400 MHz, CD$_3$SOCD$_3$) δ 0.95-1.10 (m, 5H), 1.00 (s, 6H), 1.77 (t, J=12 Hz, 4H), 2.12-2.20 (m, 2H), 2.45-2.52 (m, 2H), 2.94 (dt, J=9, 5 Hz, 1H), 3.30 (s, 3H), 3.42 (dd, J=8, 4 Hz, 1H), 3.99 (s, 1H), 4.75 (t, J=7 Hz, 1H), 6.67 (dd, J=8, 2 Hz, 1H), 6.82-6.89 (m, 2H), 6.93 (dd, J=8, 2 Hz, 1H), 7.65 (d, J=8 Hz, 1H); LC-MS (LC-ES) M+H=362.

Example 285

(trans)-3-(3-Ethylphenoxy)-N-((trans)-4-(2-hydroxypropan-2-yl)cyclohexyl)cyclobutanecarboxamide

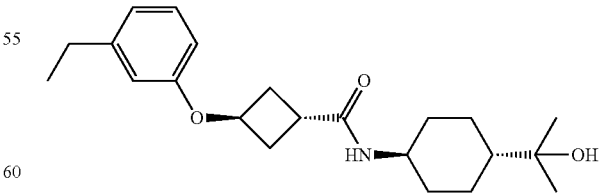

To a DMF (4 mL) solution of (trans)-3-(3-ethylphenoxy)cyclobutanecarboxylic acid (Intermediate 121) (80 mg, 0.36 mmol) was added HATU (166 mg, 0.436 mmol) and N,N-diisopropylethylamine (0.19 mL, 1.1 mmol). After 5 minutes, 2-((trans)-4-aminocyclohexyl)propan-2-ol (63 mg, 0.40 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (58 mg, 31%). $^1$H NMR (400 MHz, CD$_3$SOCD$_3$) δ 0.95-1.15 (m, 8H), 1.00 (s, 6H), 1.71-1.82 (m, 4H), 2.12-2.22 (m, 2H), 2.46-2.60 (m, 4H), 2.94 (t, J=4 Hz, 1H), 3.36-3.48 (m, 1H), 3.99 (s, 1H), 4.77 (t, J=6 Hz, 1H), 6.54-6.62 (m, 2H), 6.74 (d, J=7 Hz, 1H), 7.11-7.18 (m, 1H), 7.65 (d, J=8 Hz, 1H); LC-MS (LC-ES) M+H=360.

Example 286

Racemic (trans)-3-(3-Chlorophenoxy)-N-(2,3-dihydro-1H-inden-1-yl)cyclobutanecarboxamide

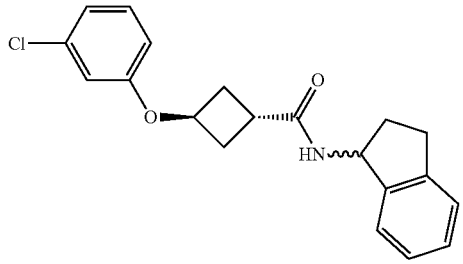 [SMILES: O=C(NC1CCc2ccccc21)[C@H]1C[C@H](Oc2cccc(Cl)c2)C1]

To a DMF (4 mL) solution of (trans)-3-(3-chlorophenoxy) cyclobutanecarboxylic acid (Intermediate 122) (80 mg, 0.35 mmol) was added HATU (161 mg, 0.424 mmol) and N,N-diisopropylethylamine (0.19 mL, 1.1 mmol). After 5 minutes, 1-aminoindane (0.05 mL, 0.4 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (70 mg, 57%). $^1$H NMR (400 MHz, CD$_3$SOCD$_3$) δ 1.74 (dd, J=13, 8 Hz, 1H), 2.14-2.24 (m, 2H), 2.24-2.36 (m, 1H), 2.61 (tt, J=8, 4 Hz, 2H), 2.76-2.82 (m, 1H), 2.83-2.92 (m, 1H), 3.05 (t, J=5 Hz, 1H), 4.88-4.91 (m, 1H), 5.21-5.30 (m, 1H), 6.75-6.85 (m, 2H), 6.95-6.98 (m, 1H), 7.11-7.19 (m, 3H), 7.20-7.30 (m, 2H), 8.22 (d, J=8 Hz, 1H); LC-MS (LC-ES) M+H=342, 344 (Cl pattern).

Example 287

(trans)-3-(3-Chlorophenoxy)-N-(thiazol-2-yl)cyclobutanecarboxamide

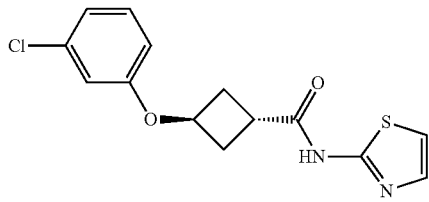 [SMILES: O=C(Nc1nccs1)[C@H]1C[C@H](Oc2cccc(Cl)c2)C1]

To a DMF (4 mL) solution of (trans)-3-(3-chlorophenoxy) cyclobutanecarboxylic acid (Intermediate 122) (80 mg, 0.35 mmol) was added HATU (161 mg, 0.424 mmol) and N,N-diisopropylethylamine (0.19 mL, 1.1 mmol). After 5 minutes, thiazol-2-amine (35 mg, 0.35 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (70 mg, 57%). $^1$H NMR (400 MHz, CD$_3$SOCD$_3$) δ 2.22-2.35 (m, 2H), 2.66-2.81 (m, 2H), 3.32-3.44 (m, 1H), 4.75-4.85 (m, 1H), 6.72-6.82 (m, 2H), 6.94-7.00 (m, 1H), 7.16-7.20 (m, 1H), 7.21-7.30 (m, 1H), 7.41-7.45 (m, 1H), 12.11 (br s, 1H); LC-MS (LC-ES) M+H=309, 311 (Cl pattern).

Example 288

(trans)-3-(3-Chlorophenoxy)-N-((trans)-4-(2-hydroxypropan-2-yl)cyclohexyl)cyclobutanecarboxamide

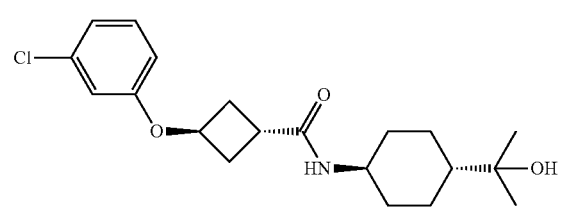 [SMILES: CC(C)(O)[C@H]1CC[C@H](NC(=O)[C@H]2C[C@H](Oc3cccc(Cl)c3)C2)CC1]

To a DMF (4 mL) solution of (trans)-3-(3-chlorophenoxy) cyclobutanecarboxylic acid (Intermediate 122) (80 mg, 0.35 mmol) was added HATU (161 mg, 0.424 mmol) and N,N-diisopropylethylamine (0.19 mL, 1.1 mmol). After 5 minutes, 2-((trans)-4-aminocyclohexyl)propan-2-ol (61 mg, 0.39 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (40 mg, 29%). $^1$H NMR (400 MHz, CD$_3$SOCD$_3$) δ 0.95-1.10 (m, 5H), 0.99 (s, 6H), 1.71-1.81 (m, 4H), 2.14-2.22 (m, 2H), 2.47-2.54 (m, 2H), 2.90-2.98 (m, 1H), 3.38-3.47 (m, 1H), 3.99 (s, 1H), 4.76-4.84 (m, 1H), 6.72-6.77 (m, 1H), 6.79-6.83 (m, 1H), 6.94-6.97 (m, 1H), 7.24-7.29 (m, 1H), 7.63-7.68 (m, 1H); LC-MS (LC-ES) M+H=366, 368 (Cl pattern).

Example 289

(trans)-3-(3-Fluorophenoxy)-N-((trans)-4-(2-hydroxypropan-2-yl)cyclohexyl)cyclobutanecarboxamide

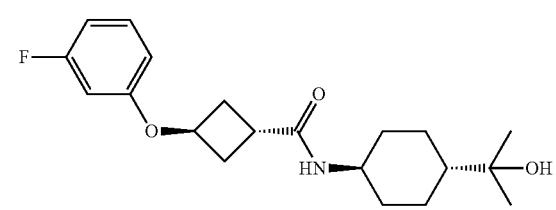 [SMILES: CC(C)(O)[C@H]1CC[C@H](NC(=O)[C@H]2C[C@H](Oc3cccc(F)c3)C2)CC1]

To a DMF (4 mL) solution of (trans)-3-(3-fluorophenoxy) cyclobutanecarboxylic acid (Intermediate 123) (80 mg, 0.38 mmol) was added HATU (174 mg, 0.457 mmol) and N,N-diisopropylethylamine (0.20 mL, 1.1 mmol). After 5 minutes, 2-((trans)-4-aminocyclohexyl)propan-2-ol (66 mg, 0.42 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (105 mg, 70%). $^1$H NMR (400 MHz, CD$_3$SOCD$_3$) δ 0.96-1.10 (m, 5H), 0.99 (s, 6H), 1.71-1.80 (m, 4H), 2.18 (ddd, J=13, 10, 6 Hz, 2H), 2.42-2.55 (m., 2H), 2.95 (t, J=5 Hz, 1H), 3.36-3.43 (m, 1H), 3.99 (s, 1H), 4.79 (t, J=6 Hz, 1H), 6.54-6.61 (m, 2H), 6.68-6.73 (m, 1H), 7.21-7.29 (m, 1H), 7.65 (d, J=8 Hz, 1H); LC-MS (LC-ES) M−H=348.

Example 290

(trans)-3-(3-Chloro-5-fluorophenoxy)-N-((trans)-4-(2-hydroxypropan-2-yl)cyclohexyl)cyclobutanecarboxamide

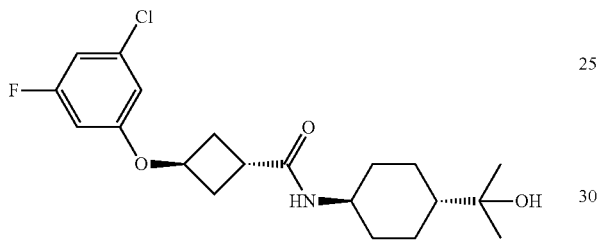

To a DMF (4 mL) solution of (trans)-3-(3-fluorophenoxy)cyclobutanecarboxylic acid (Intermediate 124) (80 mg, 0.33 mmol) was added HATU (145 mg, 0.392 mmol) and N,N-diisopropylethylamine (0.17 mL, 0.98 mmol). After 5 minutes, 2-((trans)-4-aminocyclohexyl)propan-2-ol (57 mg, 0.36 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (63 mg, 41%). $^1$H NMR (400 MHz, CD$_3$SOCD$_3$) δ 0.93-1.10 (m, 5H), 0.99 (s, 6H), 1.69-1.80 (m, 4H), 2.18 (ddd, J=13, 10, 6 Hz, 2H), 2.47-2.54 (m., 2H), 2.95-2.99 (m, 1H), 3.34-3.43 (m, 1H), 3.99 (s, 1H), 4.82 (t, J=6 Hz, 1H), 6.61-6.70 (m, 2H), 6.94 (dt, J=9, 2 Hz, 1H), 7.66 (d, J=8 Hz, 1H); LC-MS (LC-ES) M−OH=366, 368 (Cl pattern).

Example 291

(trans)-3-((5-Fluoroquinolin-8-yl)oxy)-N-(thiazol-2-yl)cyclobutanecarboxamide, trifluoroacetic acid salt

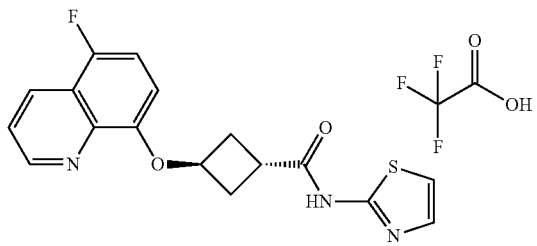

To a DMF (4 mL) solution of (trans)-3-((5-fluoroquinolin-8-yl)oxy)cyclobutanecarboxylic acid (Intermediate 125) (80 mg, 0.31 mmol) was added HATU (140 mg, 0.367 mmol) and N,N-diisopropylethylamine (0.16 mL, 0.92 mmol). After 5 minutes, thiazol-2-amine (34 mg, 0.34 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% water in AcCN (with 0.1% TFA additive) to give the title compound (50 mg, 35%). $^1$H NMR (400 MHz, CD$_3$SOCD$_3$) δ 2.42-2.49 (m, 2H), 2.72-2.81 (m, 2H), 3.40-3.48 (m, 1H), 5.01-5.09 (m, 1H), 6.96-7.00 (m, 1H), 7.19-7.22 (m, 1H), 7.29-7.35 (m, 1H), 7.44-7.47 (m, 1H), 7.67-7.70 (m, 1H), 8.46-8.49 (m, 1H), 8.96-8.99 (m, 1H), 12.15 (br s, 1H); LC-MS (LC-ES) M+H=344.

Example 292

(trans)-3-((5-Fluoroquinolin-8-yl)oxy)-N-((trans)-4-(2-hydroxypropan-2-yl)cyclohexyl)cyclobutanecarboxamide

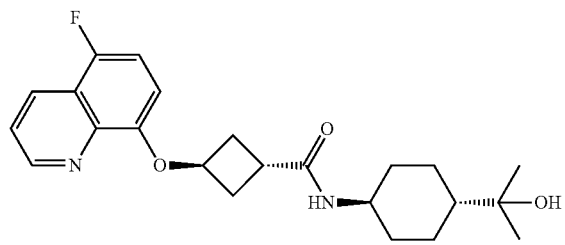 [SMILES: CC(C)(O)[C@H]1CC[C@H](NC(=O)[C@H]2C[C@H](Oc3ccc(F)c4cccnc34)C2)CC1]

To a DMF (4 mL) solution of (trans)-3-((5-fluoroquinolin-8-yl)oxy)cyclobutanecarboxylic acid (Intermediate 125) (80 mg, 0.31 mmol) was added HATU (140 mg, 0.367 mmol) and N,N-diisopropylethylamine (0.16 mL, 0.92 mmol). After 5 minutes, 2-((trans)-4-aminocyclohexyl)propan-2-ol (53 mg, 0.34 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (65 mg, 53%). $^1$H NMR (400 MHz, CD$_3$SOCD$_3$) δ 0.95-1.11 (m, 5H), 0.99 (s, 6H), 1.71-1.83 (m, 4H), 2.28-2.37 (m, 2H), 2.55-2.62 (m., 2H), 2.98-3.03 (m, 1H), 3.38-3.45 (m, 1H), 3.99 (s, 1H), 4.94-5.00 (m, 1H), 6.84-6.90 (m, 1H), 7.25-7.32 (m, 1H), 7.61-7.66 (m, 1H), 7.66-7.71 (m, 1H), 8.38-8.42 (m, 1H), 8.92-8.95 (m, 1H); LC-MS (LC-ES) M+H=401.

Example 293

(trans)-3-((6-Fluoroquinolin-8-yl)oxy)-N-((trans)-3-(2-hydroxypropan-2-yl)cyclobutyl)cyclobutanecarboxamide

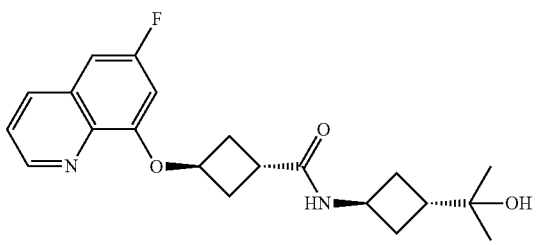 [SMILES: CC(C)(O)[C@H]1C[C@H](NC(=O)[C@H]2C[C@H](Oc3cc(F)cc4cccnc34)C2)C1]

To a DMF (4 mL) solution of (trans)-3-((6-fluoroquinolin-8-yl)oxy)cyclobutanecarboxylic acid (Intermediate 126) (60 mg, 0.23 mmol) was added HATU (105 mg, 0.276 mmol) and N,N-diisopropylethylamine (0.12 mL, 0.69 mmol). After 5 minutes, 2-(3-aminocyclobutyl)propan-2-ol (Intermediate 127) (33 mg, 0.25 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give a mixture of cis and trans isomers, then furthered purified on a Whelk 0 column, eluting with 40% EtOH in hexanes to give the title compound (13 mg, 15%). $^1$H NMR (400 MHz, CD$_3$SOCD$_3$) δ 1.03 (s, 6H), 1.77-1.92 (m, 2H), 2.13-2.28 (m, 3H), 2.33-2.42 (m, 2H), 2.69 (ddd, J=13, 7, 5 Hz, 2H), 3.03-3.17 (m, 1H), 4.12 (d, J=7 Hz, 1H), 4.17 (s, 1H), 5.05 (t, J=6 Hz, 1H), 6.84 (dd, J=11, 3 Hz, 1H), 7.30 (dd, J=9, 3 Hz, 1H), 7.59 (dd, J=8, 4 Hz, 1H), 8.12 (d, J=7 Hz, 1H), 8.30 (dd, J=8, 2 Hz, 1H), 8.84 (dd, J=4, 2 Hz, 1H); LC-MS (LC-ES) M+H=373.

Example 294

(trans)-3-((6-Fluoroquinolin-8-yl)oxy)-N-(thiazol-2-yl)cyclobutanecarboxamide

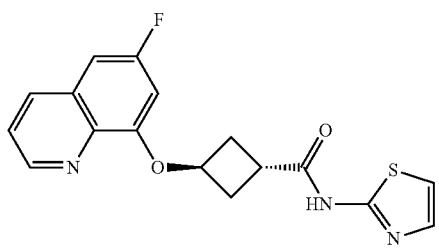 [SMILES: O=C(Nc1nccs1)[C@H]1C[C@H](Oc2cc(F)cc3cccnc23)C1]

To a DMF (4 mL) solution of (trans)-3-((6-fluoroquinolin-8-yl)oxy)cyclobutanecarboxylic acid (Intermediate 126) (26 mg, 0.10 mmol) was added HATU (46 mg, 0.12 mmol) and N,N-diisopropylethylamine (0.05 mL, 0.3 mmol). After 5 minutes, thiazol-2-amine (11 mg, 0.11 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (16 mg, 47%). $^1$H NMR (400 MHz, CD$_3$SOCD$_3$) δ 2.44-2.51 (m, 2H), 2.78-2.86 (m, 2H), 3.41-3.50 (m, 1H), 5.04-5.11 (m, 1H), 6.86-6.92 (m, 1H), 7.20-7.22 (m, 1H), 7.26-7.31 (m, 1H), 7.44-7.47 (m, 1H), 7.53-7.59 (m, 1H), 8.26-8.29 (m, 1H), 8.80-8.83 (m, 1H), 12.11 (br s, 1H); LC-MS (LC-ES) M+H=344.

Example 295

(trans)-3-((6-Fluoroquinolin-8-yl)oxy)-N-((trans)-4-(2-hydroxypropan-2-yl)cyclohexyl)cyclobutanecarboxamide

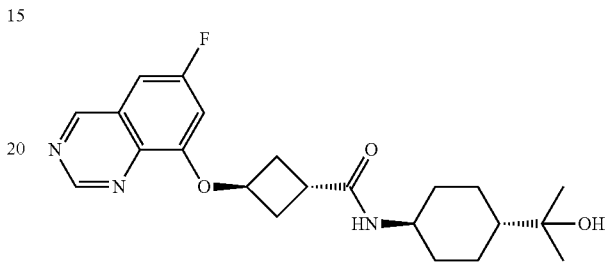

To a DMF (4 mL) solution of (trans)-3-((6-fluoroquinolin-8-yl)oxy)cyclobutanecarboxylic acid (Intermediate 126) (60 mg, 0.23 mmol) was added HATU (105 mg, 0.276 mmol) and N,N-diisopropylethylamine (0.12 mL, 0.69 mmol). After 5 minutes, 2-((trans)-4-aminocyclohexyl)propan-2-ol (40 mg, 0.25 mmol) was added, and the mixture was stirred for 12 h, poured into water, and extracted with EtOAc (3×). The combined organic layers were dried over Na$_2$SO$_4$, filtered and concentrated. This residue was purified on silica gel, eluting with 0%-100% EtOAc: EtOH (3:1) in hexanes to give the title compound (72 mg, 79%). $^1$H NMR (400 MHz, CD$_3$SOCD$_3$) δ 0.92-1.12 (m, 5H), 0.99 (s, 6H), 1.71-1.83 (m, 4H), 2.30-2.40 (m, 2H), 2.60-2.69 (m., 2H), 3.00-3.09 (m, 1H), 3.41-3.49 (m, 1H), 3.99 (s, 1H), 4.98-5.03 (m, 1H), 6.76-6.81 (m, 1H), 7.21-7.26 (m, 1H), 7.51-7.56 (m, 1H), 7.66-7.72 (m, 1H), 8.21-8.23 (m, 1H), 8.75-8.80 (m, 1H); LC-MS (LC-ES) M+H=401.

Example 296

(trans)-N-((trans)-4-(2-Hydroxypropan-2-yl)cyclohexyl)-3-(quinazolin-8-yloxy)cyclobutanecarboxamide

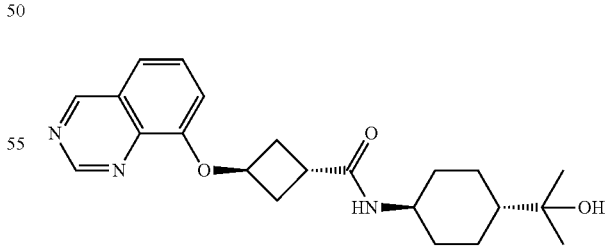

To a DMF (4 mL) solution of (trans)-3-(quinazolin-8-yloxy)cyclobutanecarboxylic acid (Intermediate 128) (100 mg, 0.409 mmol) was added HATU (195 mg, 0.512 mmol) and N,N-diisopropylethylamine (0.22 mL, 1.2 mmol). After 5 minutes, 2-((trans)-4-aminocyclohexyl)propan-2-ol (80 mg, 0.51 mmol) was added, and the mixture was stirred for 18 h, poured into water, and extracted with EtOAc (3×). The combined organic layers were dried over Na₂SO₄, filtered and concentrated. This residue was purified on silica gel, eluting with 0%-75% EtOAc: EtOH (3:1) in hexanes to give the title compound (72 mg, 46%) as a white solid. ¹H NMR (400 MHz, CD₃SOCD₃) δ 0.96-1.12 (m, 5H), 0.99 (s, 6H), 1.73-1.83 (m, 4H), 2.29-2.38 (m, 2H), 2.59-2.67 (m., 2H), 2.99-3.07 (m, 1H), 3.39-3.49 (m, 1H), 4.01 (s, 1H), 4.99-5.05 (m, 1H), 7.16-7.19 (m, 1H), 7.61-7.66 (m, 2H), 7.70-7.75 (m, 1H), 9.23-9.25 (m, 1H), 9.53 (s, 1H); LC-MS (LC-ES) M+H=384.

Example 297

(trans)-3-((1H-Benzo[d]imidazol-4-yl)oxy)-N-(thiazol-2-yl)cyclobutanecarboxamide, di-trifluoroacetic acid salt

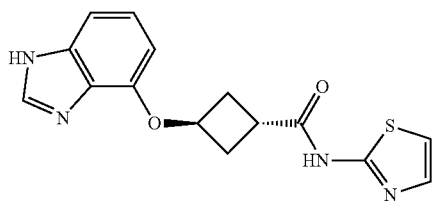 [SMILES: O=C(Nc1nccs1)[C@H]1C[C@H](Oc2cccc3[nH]cnc23)C1]

To (trans)-3-(2,3-diaminophenoxy)-N-(thiazol-2-yl)cyclobutanecarboxamide (Intermediate 130) (26 mg, 0.10 mmol) was added triethyl orthoformate (5.00 mL, 30.0 mmol). The mixture was heated to reflux for 1.5 h and concentrated. The residue was purified on silica gel, eluting with 0%-60% AcCN in water (with 0.1% TFA additive) to give the title compound (11 mg, 23%) as a white solid. ¹H NMR (400 MHz, CD₃SOCD₃) δ 2.47-2.56 (m, 2H), 2.78-2.88 (m, 2H), 3.42-3.50 (m, 1H), 5.09-5.18 (m, 1H), 6.89-6.94 (m, 1H), 7.23-7.26 (m, 1H), 7.35-7.45 (m, 3H), 7.48-7.50 (M, 1H), 9.39 (br s, 1H), 12.10 (br s, 1H); LC-MS (LC-ES) M+H=315.

Example 298

(trans)-N-((trans)-4-(2-Hydroxypropan-2-yl)cyclohexyl)-3-(imidazo[1,2-a]pyridin-8-yloxy)cyclobutanecarboxamide

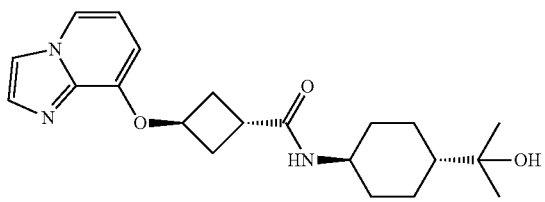 [SMILES: CC(C)(O)[C@H]1CC[C@H](NC(=O)[C@H]2C[C@H](Oc3cccn4ccnc34)C2)CC1]

To a DMF (4 mL) solution of (trans)-3-(imidazo[1,2-a]pyridin-8-yloxy)cyclobutanecarboxylic acid (Intermediate 131) (75 mg, 0.32 mmol) was added HATU (160 mg, 0.420 mmol) and N,N-diisopropylethylamine (0.17 mL, 0.97 mmol). After 5 minutes, 2-((trans-4-aminocyclohexyl)propan-2-ol (66 mg, 0.42 mmol) was added, and the mixture was stirred for 6 h, poured into water, and extracted with EtOAc (3×). The combined organic layers were dried over Na₂SO₄, filtered and concentrated. This residue was purified twice on silica gel, eluting with 0%-100% EtOAc in hexanes to give the title compound (12 mg, 10%) as a white solid. ¹H NMR (400 MHz, CD₃SOCD₃) δ 0.97-1.12 (m, 5H), 1.00 (s, 6H), 1.72-1.82 (m, 4H), 2.34-2.42 (m, 2H), 2.60-2.69 (m., 2H), 2.98-3.07 (m, 1H), 3.39-3.49 (m, 1H), 5.07-5.16 (m, 1H), 7.12-7.16 (m, 1H), 7.27-7.34 (m, 1H), 7.71-7.76 (m, 1H), 8.12-8.16 (m, 1H), 8.32-8.35 (m, 1H), 8.42-8.47 (m, 1H); LC-MS (LC-ES) M+H=372.

Example 299

3-(Benzo[d]isothiazol-4-yloxy)-N-((trans)-4-(2-hydroxypropan-2-yl)cyclohexyl)azetidine-1-carboxamide

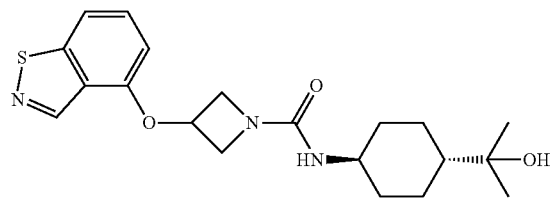 [SMILES: CC(C)(O)[C@H]1CC[C@H](NC(=O)N2CC(Oc3cccc4sncc34)C2)CC1]

To 4-(azetidin-3-yloxy)benzo[d]isothiazole hydrochloride (Intermediate 132) (60 mg, 0.25 mmol) and 4-nitrophenyl ((trans)-4-(2-hydroxypropan-2-yl)cyclohexyl)carbamate (80 mg, 0.25 mmol) (Intermediate 3) in DCM (2 mL) was added N,N-diisopropylethylamine (0.13 mL, 0.74 mmol). After 18 h, the reaction was poured into 1 N aqueous NaOH solution and extracted twice with DCM. The combined organic layers were washed with brine, dried over Na₂SO₄, filtered and concentrated. The residue was purified on silica gel, eluting with a 5%-75% EtOAc:EtOH (3:1)-hexanes gradient, to give the title compound (79 mg, 82%) as a white solid. ¹H NMR (400 MHz, CD₃SOCD₃) δ 0.95-1.20 (m, 5H), 1.02 (s, 6H), 1.70-1.88 (m, 4H), 3.27 (dd, J=8, 4 Hz, 1H), 3.86 (dd, J=9, 4 Hz, 2H), 4.02 (s, 1H), 4.25-4.36 (m, 2H), 5.14-5.27 (m, 1H), 6.22 (d, J=8 Hz, 1H), 6.73 (d, J=8 Hz, 1H), 7.53 (t, J=8 Hz, 1H), 7.80 (d, J=8 Hz, 1H), 9.14 (d, J=1 Hz, 1H); LC-MS (LC-ES) M+H=390.

Example 300

N-((trans)-4-(2-Hydroxypropan-2-yl)cyclohexyl)-3-((2-methylbenzo[d]thiazol-4-yl)oxy)azetidine-1-carboxamide To 7-(azetidin-3-yloxy)-2-methylbenzo[d]thiazole hydrochloride (Intermediate 133) (26 mg, 0.10 mmol) and 4-nitrophenyl ((trans)-4-(2-hydroxypropan-2-yl)cyclohexyl)carbamate (33 mg, 0.10 mmol) (Intermediate 3) in DMF (2 mL) was added N,N-diisopropylethylamine (0.02 mL, 0.1 mmol). After 30 min, the reaction was diluted with MeOH and loaded onto a semi-prep HPLC (NH₄OH as modifier) to afford the title compound (37 mg, 91%) as a white solid. ¹H NMR (400 MHz, CD₃SOCD₃) δ 1.15 (s, 6H), 1.17-1.35 (m, 5H), 1.81-2.06 (m, 4H), 2.85 (s, 3H), 3.38-3.46 (m, 1H), 4.09 (dd, J=10, 4 Hz, 2H), 4.41 (dd, J=9, 6 Hz, 2H), 5.16-5.32 (m, 1H), 6.79 (d, J=8 Hz, 1H), 7.34 (t, J=8 Hz, 1H), 7.54 (d, J=8 Hz, 1H); LC-MS (LC-ES) M+H=404.

Example 301

(trans)-3-(Benzo[d]thiazol-4-yloxy)-N-1H-pyrazol-5-yl)cyclobutanecarboxamide

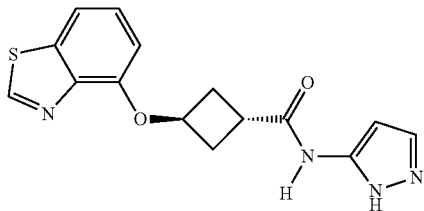 [SMILES: O=C(Nc1ccn[nH]1)[C@H]1C[C@H](Oc2cccc3scnc23)C1]

To a stirred, cooled (0° C.) solution of (trans)-3-(benzo[d]thiazol-4-yloxy)-N-(1-((2-(trimethylsilyl)ethoxy)methyl)-1H-pyrazol-5-yl)cyclobutanecarboxamide (250 mg, 0.562 mmol, Intermediate 134) in tetrahydrofuran (10 mL) was slowly added triethylamine (0.094 mL, 0.675 mmol) dropwise, followed by 1M tetrabutylammonium fluoride in tetrahydrofuran (5.62 mL, 5.62 mmol). The mixture was heated to 70° C. and stirred for 12 hours. The mixture was cooled to room temperature, diluted with ice cold water (20 mL) and extracted with ethyl acetate (3×). The combined organic layers were washed with brine, dried over sodium sulfate, and filtered. Solvent was removed under reduced pressure and the remaining material was dissolved in dichloromethane, pre-adsorbed onto silica gel and chromatographed on silica gel, eluting with a 4:1 ethyl acetate in hexanes gradient followed by a 4:96 methanol in dichloromethane gradient. The appropriate fractions were combined and evaporated under reduced pressure. The remaining solid was washed with diethyl ether and dried to give the title compound (43 mg, 22%) as an off white solid. ¹H NMR (400 MHz CD₃SOCD₃) δ 2.38-2.45 (m, 2H) 2.71-2.79 (m, 2H), 3.29-3.40 (m, 1H), 5.05-5.17 (m, 1H), 6.55 (br s, 1H), 6.86 (d, J=8 Hz, 1H), 7.39 (t, J=8 Hz, 1H), 7.59 (br s, 1H), 7.69 (dd, J=8, 1 Hz, 1H), 9.25 (s, 1H), 10.39 (br s, 1H), 12.35 (br s, 1H); LC-MS (LC-ES) M+H=315.

Example 302

(trans)-3-(Benzo[d]thiazol-4-yloxy)-N-(3-cyclopropyl-1H-pyrazol-5-yl)cyclobutanecarboxamide

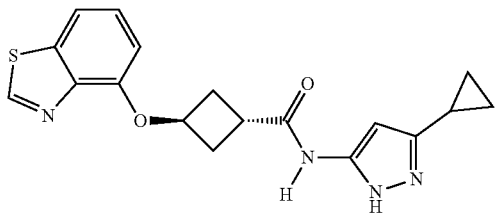 [SMILES: O=C(Nc1cc(C2CC2)n[nH]1)[C@H]1C[C@H](Oc2cccc3scnc23)C1]

To a stirred, cooled (0° C.) solution of (trans)-3-(benzo[d]thiazol-4-yloxy)-N-(3-cyclopropyl-1-((2-(trimethylsilyl)ethoxy)methyl)-1H-pyrazol-5-yl)cyclobutanecarboxamide (220 mg, 0.379 mmol, Intermediate 135) in tetrahydrofuran (10 mL) was added triethylamine (1.59 mL, 11.4 mmol), followed by 1M tetrabutylammonium fluoride in tetrahydrofuran (3.79 mL, 3.79 mmol). The mixture was heated to 70° C. and stirred for 18 hours. The mixture was cooled to room temperature, diluted with ice cold water (20 mL) and extracted with ethyl acetate (4×). The combined organic layers were washed with cold water, brine, dried over sodium sulfate, and filtered. Solvent was removed under reduced pressure and the remaining material was chromatographed on silica gel, eluting with a 40%-45% ethyl acetate in hexanes gradient to give the title compound (50 mg, 35%) as an off white solid. ¹H NMR (400 MHz, CD₃SOCD₃) δ 0.59-0.70 (m, 2H), 0.85-0.97 (m, 2H), 1.74-1.91 (m, 1H), 2.32-2.46 (m, 2H), 2.60-2.76 (m, 2H), 3.28-3.35 (m, 1H) 5.05-5.14 (m, 1H), 6.23 (d, J=1 Hz, 1H), 6.84 (d, J=8 Hz, 1H), 7.39 (t, J=8 Hz, 1H), 7.69 (d, J=8 Hz, 1H), 9.26 (s, 1H), 10.30 (br s, 1H) 12.05 (br s, 1H); LC-MS (LC-ES) M+H=355.

Example 303

(trans)-3-((6-Fluorobenzo[d]thiazol-4-yl)oxy)-N-(1-(2-hydroxy-2-methylpropanoyl)piperidin-4-yl)cyclobutanecarboxamide

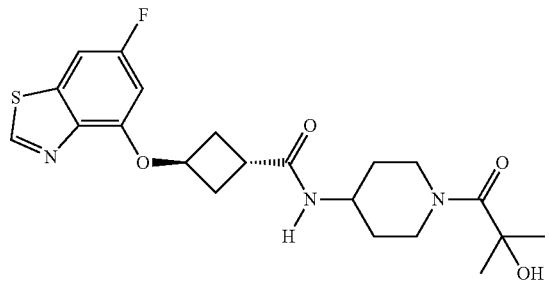 [SMILES: CC(C)(O)C(=O)N1CCC(NC(=O)[C@H]2C[C@H](Oc3cc(F)cc4scnc34)C2)CC1]

To a stirred solution of (trans)-3-((6-fluorobenzo[d]thiazol-4-yl)oxy)cyclobutanecarboxylic acid (20 mg, 0.075 mmol, Intermediate 59) in N,N-dimethylformamide (1.5 mL) was added N,N-diisopropylethylamine (0.033 mL, 0.187 mmol), followed by 1-[bis(dimethylamino)methylene]-1H-1,2,3-triazolo[4,5-b]pyridinium 3-oxide hexafluorophosphate (28.5 mg, 0.075 mmol). The mixture was stirred for 5 minutes and then 1-(4-aminopiperidin-1-yl)-2-hydroxy-2-methylpropan-1-one (13.94 mg, 0.075 mmol, Intermediate 136) was added. The resulting mixture was stirred for 30 minutes, diluted with water (0.5 mL) and stirred an additional 5 minutes. The mixture was diluted with methanol (0.5 mL) and loaded onto a semi-prep reverse phase HPLC (ammonium hydroxide as modifier) to afford the title compound (32 mg, 98%) as a white solid. ¹H NMR (??? MHz, CDCl₃) δ 1.37 (qd, J=12, 4 Hz, 2H), 1.51 (d, J=1 Hz, 6H), 1.98-2.14 (m, 2H), 2.53-2.71 (m, 2H), 2.77-2.90 (m, 2H), 2.94-3.19 (m, 3H), 4.09 (d, J=7 Hz, 1H), 4.45 (br s, 3H), 5.17 (t, J=6 Hz, 1H), 5.44-5.71 (m, 1H), 6.57 (d, J=11 Hz, 1H), 7.22 (d, J=8 Hz, 1H), 8.87 (d, J=1 Hz, 1H); LC-MS (LC-ES) M+H=436.

Example 304

(2S,3S)-3-(Benzo[d]thiazol-4-yloxy)-N-((trans)-4-(2-hydroxypropan-2-yl)cyclohexyl)-2-methylazetidine-1-carboxamide

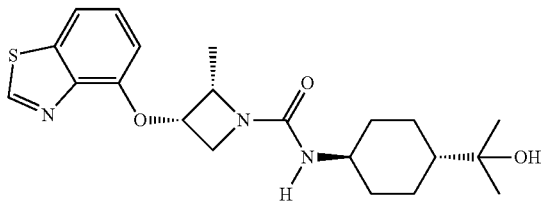 [SMILES: C[C@H]1[C@@H](Oc2cccc3scnc23)CN1C(=O)N[C@H]1CC[C@H](C(C)(C)O)CC1]

To a stirred mixture of 4-(((2S,3S)-2-methylazetidin-3-yl)oxy)benzo[d]thiazole hydrochloride (23 mg, 0.090 mmol, Intermediate 139) in dichloromethane (2 mL) was added N,N-diisopropylethylamine (0.05 mL, 0.286 mmol) followed by 4-nitrophenyl ((trans)-4-(2-hydroxypropan-2-yl)cyclohexyl)carbamate (30 mg, 0.093 mmol, Intermediate 5). The resulting yellow mixture was stirred overnight. Solvent was removed under reduced pressure. The remaining material was dissolved in a minimal amount of dichloromethane and chromatographed on silica gel, eluting with a 5%-75% ethyl acetate:ethanol (3:1 v/v) in hexanes gradient. The appropriate fractions were combined and evaporated under reduced pressure. The remaining material was triturated with hexanes and placed in vacuo to give the title compound (32 mg, 89%) as a white solid. $^1$H NMR (400 MHz, CD$_3$SOCD$_3$) δ 1.03 (s, 9H), 1.08-1.21 (m, 3H), 1.27 (d, J=6 Hz, 3H), 1.79 (d, J=9 Hz, 4H), 3.87 (dd, J=9, 4 Hz, 1H), 4.00-4.07 (m, 2H), 4.19 (dd, J=9, 7 Hz, 1H), 4.64 (t, J=6 Hz, 1H), 5.25 (td, J=7, 4 Hz, 1H), 6.02 (d, J=8 Hz, 1H), 6.90 (d, J=8 Hz, 1H), 7.40 (t, J=8 Hz, 1H), 7.74 (d, J=8 Hz, 1H), 9.30 (s, 1H); LC-MS (LC-ES) M+H=404.

Example 305

(2R,3R)-3-(Benzo[d]thiazol-4-yloxy)-N-((trans)-4-(2-hydroxypropan-2-yl)cyclohexyl)-2-methylazetidine-1-carboxamide

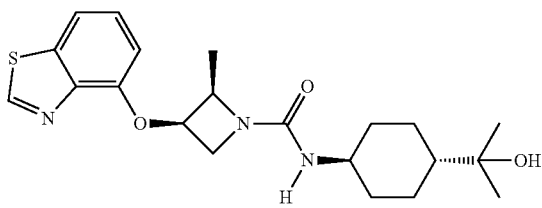 [SMILES: C[C@@H]1[C@H](Oc2cccc3scnc23)CN1C(=O)N[C@H]1CC[C@H](C(C)(C)O)CC1]

To a stirred mixture of 4-(((2R,3R)-2-methylazetidin-3-yl)oxy)benzo[d]thiazole hydrochloride (14.4 mg, 0.056 mmol, Intermediate 140) in dichloromethane (2 mL) was added N,N-diisopropylethylamine (0.03 mL, 0.172 mmol), followed by 4-nitrophenyl ((trans)-4-(2-hydroxypropan-2-yl)cyclohexyl)carbamate (20 mg, 0.062 mmol, Intermediate 5). The resulting yellow mixture was stirred overnight. Solvent was removed under reduced pressure. The remaining material was dissolved in a minimal amount of dichloromethane and chromatographed on silica gel, eluting with a 5%-75% ethyl acetate:ethanol (3:1 v/v) in hexanes gradient. The appropriate fractions were combined and evaporated under reduced pressure. The remaining material was triturated with hexanes and placed in vacuo to give the title compound (13 mg, 57%) as a white solid. $^1$H NMR (400 MHz, CD$_3$SOCD$_3$) δ 1.01 (s, 6H), 0.96-1.18 (s, 5H), 1.27 (d, J=6 Hz, 3H), 1.79 (d, J=9 Hz, 4H), 3.22-3.32 (m, 1H), 3.87 (dd, J=9, 4.02 Hz, 1H), 4.02 (s, 1H), 4.19 (dd, J=9, 7 Hz, 1H), 4.64 (t, J=6 Hz, 1H), 5.25 (td, J=7, 4 Hz, 1H), 6.02 (d, J=8 Hz, 1H), 6.90 (d, J=8 Hz, 1H), 7.40 (t, J=8 Hz, 1H), 7.74 (d, J=8 Hz, 1H), 9.30 (s, 1H); LC-MS (LC-ES) M+H=404.

Example 306

3-(Benzo[d]thiazol-4-yloxy)-N-(4-(methylsulfonyl)phenyl)azetidine-1-carboxamide

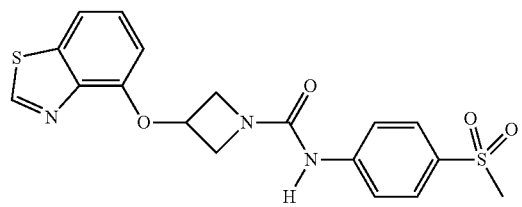 [SMILES: CS(=O)(=O)c1ccc(NC(=O)N2CC(Oc3cccc4scnc34)C2)cc1]

To a stirred, cooled (0° C.) solution of 4-nitrophenyl chloroformate (90 mg, 0.447 mmol) in dichloromethane (1 mL) was added a solution of 4-(methylsulfonyl)aniline (70 mg, 0.409 mmol) and N,N-diisopropylethylamine (0.07 mL, 0.401 mmol) in dichloromethane (2 mL) dropwise. The mixture was stirred for 2.5 hours and then a mixture of 4-(azetidin-3-yloxy)benzo[d]thiazole hydrochloride (100 mg, 0.412 mmol, Intermediate 28) and N,N-diisopropylethylamine (0.20 mL, 1.145 mmol) in dichloromethane (2 mL) was added dropwise. The mixture was warmed to room temperature and stirred overnight. The mixture was poured into 1N aqueous sodium hydroxide and extracted with dichloromethane (2×). The combined organic layers were washed with brine, dried over sodium sulfate, and filtered. Solvent was removed under reduced pressure. The remaining material was dissolved in a minimal amount of dichloromethane, and chromatographed on silica gel, eluting with a 5%-70% ethyl acetate:ethanol (3:1 v/v) in hexanes gradient. The appropriate fractions were combined and evaporated under reduced pressure. The remaining material was triturated with hexanes and the solid was collected via vacuum filtration and dried in vacuo to give the title compound (68 mg). This material was dissolved in 3:1 acetonitrile-methanol (4 mL) and further purified by reverse phase HPLC (4×1 mL injections), eluting with a 20%-90% acetonitrile:water gradient containing 1% ammonium hydroxide to give the title compound (51 mg, 31%) as a white solid. $^1$H NMR (400 MHz, CD$_3$SOCD$_3$) δ 3.15 (s, 3H), 4.08 (dd, J=10, 4 Hz, 2H), 4.55 (dd, J=10, 7 Hz, 2H), 5.28-5.35 (m, 1H), 6.91 (d, J=8 Hz, 1H), 7.43 (t, J=8 Hz, 1H), 7.75-7.82 (m, 5H), 9.10 (s, 1H), 9.32 (s, 1H); LC-MS (LC-ES) M+H=404.

Example 307

(trans)-3-(Benzo[d]thiazol-4-yloxy)-N-(6-methylpyrimidin-4-yl)cyclobutanecarboxamide

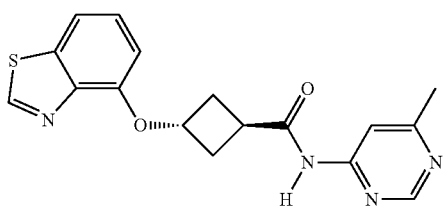 [SMILES: Cc1cc(NC(=O)[C@H]2C[C@H](Oc3cccc4scnc34)C2)ncn1]

To a stirred, cooled (0° C.) solution of (trans)-3-(benzo[d]thiazol-4-yloxy)cyclobutanecarboxylic acid (150 mg, 0.602 mmol, Intermediate 25) and 6-methylpyrimidin-4-amine (65.7 mg, 0.602 mmol) in pyridine (6 mL) was added phosphorous(V) oxychloride (0.168 mL, 1.81 mmol). The mixture was warmed to room temperature and stirred for 16 hours. The mixture was diluted with ice cold water (25 mL) and extracted with dichloromethane (2×). The combined organic layers were dried over sodium sulfate, filtered, and evaporated to dryness. The crude product was purified by preparative TLC, eluting with 1:9 methanol:dichloromethane to provide impure material (55 mg). This material was repurified by reverse phase HPLC, eluting with acetonitrile in water (ammonium bicarbonate modifier) to give the title compound (10 mg, 4.8%) as an off-white solid. $^1$H NMR (400 MHz, CD$_3$SOCD$_3$) δ 2.41 (s, 3H), 2.42-2.52 (m, 2H), 2.71-2.89 (m, 2H), 3.45-3.52 (m, 1H), 5.05-5.13 (m, 1H), 6.86 (dd, J=8, 1 Hz, 1H), 7.39 (t, J=8 Hz, 1H), 7.70 (dd, J=8, 1 Hz, 1H), 8.04 (s, 1H), 8.73 (d, J=1 Hz, 1H), 9.26 (s, 1H), 10.83 (s, 1H); LC-MS (LC-ES) M+H=341.

Example 308

3-(Benzo[d]thiazol-4-yloxy)-N-(2-fluoro-4-(methylsulfonyl)phenyl)azetidine-1-carboxamide

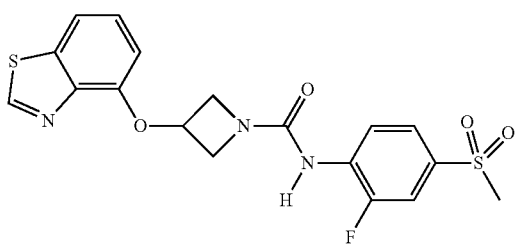 [SMILES: CS(=O)(=O)c1ccc(NC(=O)N2CC(Oc3cccc4scnc34)C2)c(F)c1]

To a stirred solution of triphosgene (30 mg, 0.101 mmol) in dichloromethane (1 mL) was added a mixture of 2-fluoro-4-(methylsulfonyl)aniline (60 mg, 0.317 mmol) and N,N-diisopropylethylamine (0.07 mL, 0.401 mmol) in dichloromethane (1 mL) dropwise over 5 minutes. The mixture was stirred an additional 10 minutes and then a mixture of 4-(azetidin-3-yloxy)benzo[d]thiazole hydrochloride (75 mg, 0.309 mmol, Intermediate 28) and N,N-diisopropylethylamine (0.12 mL, 0.687 mmol) in dichloromethane (1 mL) was added in one portion. After stirring overnight, the mixture was diluted with dichloromethane, washed with 1N aqueous hydrochloric acid, brine, dried over sodium sulfate, and filtered. Solvent was removed under reduced pressure. The remaining material was dissolved in a minimal amount of dichloromethane, and chromatographed on silica gel, eluting with a 5%-75% ethyl acetate:ethanol (3:1 v/v) in hexanes gradient to give the title compound (81 mg, 62%) as a yellow solid. $^1$H NMR (400 MHz, CD$_3$SOCD$_3$) δ 3.23 (s, 3H), 4.12 (dd, J=10, 3 Hz, 2H), 4.57 (dd, J=10, 7 Hz, 2H), 5.28-5.35 (m, 1H), 6.90 (d, J=8 Hz, 1H), 7.43 (t, J=8 Hz, 1H), 7.69 (dd, J=9, 2 Hz, 1H), 7.75-7.80 (m, 2H), 8.09 (t, J=8 Hz, 1H), 8.78 (s, 1H), 9.32 (s, 1H); LC-MS (LC-ES) M+H=422.

Example 309

3-(Benzo[d]thiazol-4-yloxy)-N-(3-morpholinophenyl)azetidine-1-carboxamide

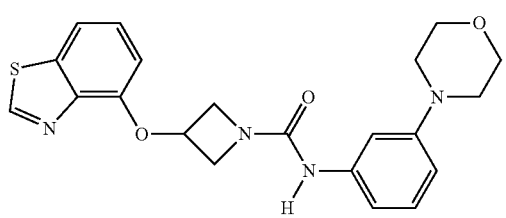 [SMILES: O=C(Nc1cccc(N2CCOCC2)c1)N1CC(Oc2cccc3scnc23)C1]

To a stirred solution of triphosgene (30 mg, 0.101 mmol) in dichloromethane (1 mL) was added a mixture of 3-morpholinoaniline (60 mg, 0.337 mmol) and N,N-diisopropylethylamine (0.07 mL, 0.401 mmol) in dichloromethane (1 mL) dropwise over 5 minutes. The mixture was stirred an additional 10 minutes and then a mixture of 4-(azetidin-3-yloxy)benzo[d]thiazole hydrochloride (75 mg, 0.309 mmol, Intermediate 28) and N,N-diisopropylethylamine (0.12 mL, 0.687 mmol) in dichloromethane (1 mL) was added in one portion. The mixture became a suspension and was stirred overnight. The suspension was filtered and the collected solid was washed with dichloromethane and dried in vacuo to give the title compound (34 mg, 27%) as a white solid. The filtrate was evaporated to dryness under reduced pressure and the remaining material was dissolved in a minimal amount of dichloromethane, and chromatographed on silica gel, eluting with a 5%-70% ethyl acetate:ethanol (3:1 v/v) in hexanes gradient to give additional title compound (43 mg, 34%) as a beige solid. $^1$H NMR (400 MHz, CD$_3$SOCD$_3$) δ 3.07-3.12 (m, 4H), 3.74-3.78 (m, 4H), 4.02 (dd, J=9, 4 Hz, 2H), 4.49 (dd, J=9, 6 Hz, 2H), 5.26-5.32 (m, 1H), 6.63 (d, J=8 Hz, 1H), 6.90 (d, J=8 Hz, 1H), 7.03-7.08 (m, 1H), 7.09-7.15 (m, 1H), 7.23 (br s, 1H), 7.43 (t, J=8 Hz, 1H), 7.78 (d, J=8 Hz, 1H), 8.52 (s, 1H), 9.31 (s, 1H); LC-MS (LC-ES) M+H=411.

Example 310

3-(Benzo[d]thiazol-4-yloxy)-N-(4-morpholinophenyl)azetidine-1-carboxamide

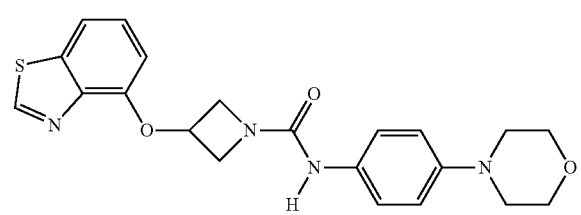 [SMILES: O=C(Nc1ccc(N2CCOCC2)cc1)N1CC(Oc2cccc3scnc23)C1]

To a stirred solution of triphosgene (30 mg, 0.101 mmol) in dichloromethane (1 mL) was added a mixture of 4-morpholinoaniline (60 mg, 0.337 mmol) and N,N-diisopropylethylamine (0.07 mL, 0.401 mmol) in dichloromethane (1 mL) dropwise over 5 minutes. The mixture was stirred an additional 30 minutes and then a mixture of 4-(azetidin-3-yloxy)benzo[d]thiazole hydrochloride (75 mg, 0.309 mmol, Intermediate 28) and N,N-diisopropylethylamine (0.12 mL, 0.687 mmol) in dichloromethane (1 mL) was added in one portion. The mixture became a suspension and was stirred overnight. The suspension was filtered and the collected solid was washed with dichloromethane and dried in vacuo to give the title compound (47 mg, 37%) as a white solid. $^1$H NMR (400 MHz, CD$_3$SOCD$_3$) δ 2.99-3.03 (m, 4H), 3.70-3.75 (m, 4H), 3.99 (dd, J=9, 4 Hz, 2H), 4.5 (dd, J=9, 6 Hz, 2H), 5.25-5.31 (m, 1H), 6.83-6.91 (m, 4H), 7.35 (d, J=9 Hz, 1H), 7.43 (t, J=8 Hz, 1H), 7.78 (d, J=8 Hz, 1H), 8.39 (s, 1H), 9.31 (s, 1H); LC-MS (LC-ES) M+H=411.

Example 311

3-(Benzo[d]thiazol-4-yloxy)-N-(5-(methylsulfonyl)pyridin-2-yl)azetidine-1-carboxamide

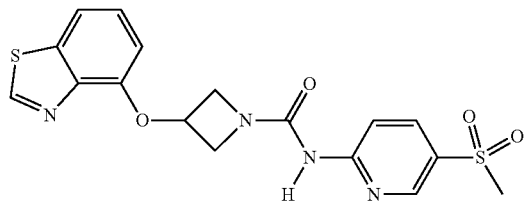 [SMILES: CS(=O)(=O)c1ccc(NC(=O)N2CC(Oc3cccc4scnc34)C2)nc1]

To a stirred solution of triphosgene (30 mg, 0.101 mmol) in dichloromethane (1 mL) was added a mixture of 5-(methylsulfonyl)pyridin-2-amine (55 mg, 0.319 mmol) and N,N-diisopropylethylamine (0.07 mL, 0.401 mmol) in dichloromethane (1 mL) dropwise over 5 minutes. The mixture was stirred an additional 30 minutes and then a mixture of 4-(azetidin-3-yloxy)benzo[d]thiazole hydrochloride (75 mg, 0.309 mmol, Intermediate 28) and N,N-diisopropylethylamine (0.12 mL, 0.687 mmol) in dichloromethane (1 mL) was added in one portion. The mixture was stirred overnight and then evaporated under reduced pressure. The remaining material was dissolved in a minimal amount of dichloromethane and chromatographed on silica gel, eluting with a 5%-70% ethyl acetate:ethanol (3:1 v/v) in hexanes gradient to give the title compound (44 mg, 35%) as a white solid. $^1$H NMR (400 MHz, CD$_3$SOCD$_3$) δ 3.24 (s, 3H), 4.08 (br d, J=8 Hz, 2H), 4.56 (dd, J=9, 7 Hz, 2H), 5.24-5.30 (m, 1H), 6.86 (d, J=8 Hz, 1H), 7.41 (t, J=8 Hz, 1H), 7.74 (dd, J=9, 2 Hz, 1H), 8.11 (d, J=9 Hz, 1H), 8.18 (dd, J=9, 2 Hz, 1H), 8.69 (d, J=3 Hz, 1H), 9.30 (s, 1H), 10.04 (br s, 1H); LC-MS (LC-ES) M+H=405.

Example 312

3-(Benzo[d]thiazol-4-yloxy)-N-(2-cyclopropylpyrimidin-4-yl)azetidine-1-carboxamide

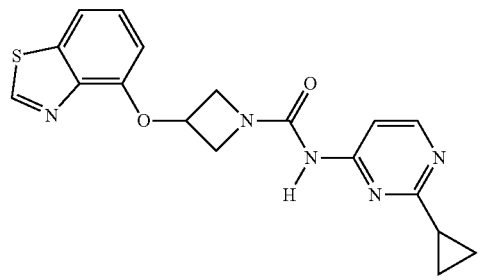 [SMILES: O=C(Nc1ccnc(C2CC2)n1)N1CC(Oc2cccc3scnc23)C1]

To a stirred, cooled (0° C.) solution of 4-nitrophenyl chloroformate (112 mg, 0.555 mmol) in dichloromethane (2 mL) was added 2-cyclopropylpyrimidin-4-amine (50 mg, 0.370 mmol), followed by pyridine (1 mL, 12.36 mmol). The mixture was allowed to warm slowly to room temperature over 3 hours. Solvent was removed under reduced pressure. The remaining material was dissolved in N,N-dimethylformamide (1 mL) and 4-(azetidin-3-yloxy)benzo[d]thiazole trifluoroacetic acid salt (118 mg, 0.370 mmol, Intermediate 28C) was added. The mixture was stirred for 1 hour, quenched with water, diluted with methanol, and purified by reverse phase HPLC, eluting with a acetonitrile:water (ammonium hydroxide as modifier) gradient to give the title compound (74 mg, 54%) as a white solid. $^1$H NMR (400 MHz, CDCl$_3$) δ 0.96-1.15 (m, 4H), 2.04-2.23 (m, 1H), 4.42 (dd, J=10, 4 Hz, 2H), 4.62 (dd, J=9, 7 Hz, 2H), 5.38 (tt, J=7, 4 Hz, 1H), 6.74 (d, J=8 Hz, 1H), 7.41 (t, J=8 Hz, 1H), 6.96 (br s, 1H), 7.66 (dd, J=8, 1 Hz, 1H), 7.83 (d, J=6 Hz, 1H), 8.41 (d, J=6 Hz, 1H), 8.98 (s, 1H); LC-MS (LC-ES) M+H=368.

Example 313

N-(2-Cyclopropylpyrimidin-4-yl)-3-((6-fluorobenzo[d]thiazol-4-yl)oxy)azetidine-1-carboxamide

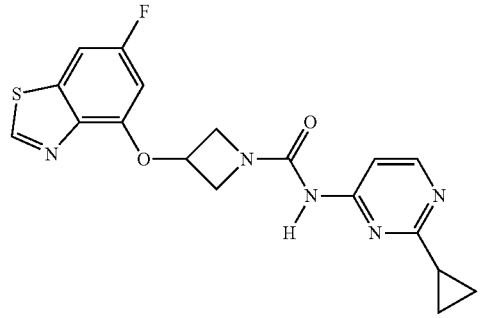 [SMILES: O=C(Nc1ccnc(C2CC2)n1)N1CC(Oc2cc(F)cc3scnc23)C1]

To a stirred, cooled (0° C.) solution of 4-nitrophenyl chloroformate (112 mg, 0.555 mmol) in dichloromethane (2 mL) was added 2-cyclopropylpyrimidin-4-amine (50 mg, 0.370 mmol), followed by pyridine (1 mL, 12.36 mmol). The mixture was allowed to warm slowly to room temperature over 3 hours. Solvent was removed under reduced pressure. The remaining material was dissolved in N,N-dimethylformamide (1 mL) and 4-(azetidin-3-yloxy)benzo[d]thiazole trifluoroacetic acid salt (118 mg, 0.370 mmol, Intermediate 28C) was added. The mixture was stirred for 1 hour, quenched with water, diluted with methanol, and purified by reverse phase HPLC, eluting with a acetonitrile:water (ammonium hydroxide as modifier) gradient to give the title compound (95 mg, 66%) as a light yellow solid. $^1$H NMR (400 MHz, CDCl$_3$) δ 0.93-1.14 (m, 4H), 1.99-2.20 (m, 1H), 4.40 (dd, J=10, 4 Hz, 2H), 4.54-4.74 (m, 2H), 5.36 (ddd, J=6, 4, 2 Hz, 1H), 6.54 (dd, J=10, 2 Hz, 1H), 6.86 (br s, 1H), 7.34 (dd, J=8, 2 Hz, 1H), 7.80 (d, J=6 Hz, 1H), 8.41 (d, J=6 Hz, 1H), 8.92 (s, 1H); LC-MS (LC-ES) M+H=386.

Example 314

3-(Benzo[d]thiazol-4-yloxy)-N-(3-cyclopropyl-1-methyl-1H-pyrazol-5-yl)azetidine-1-carboxamide

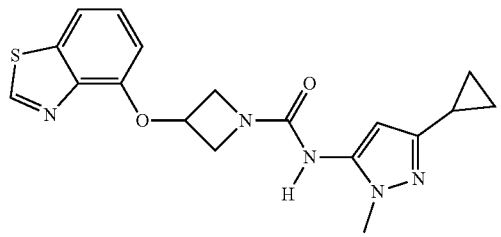 [SMILES: Cn1nc(C2CC2)cc1NC(=O)N1CC(Oc2cccc3scnc23)C1]

To a stirred solution of 4-(azetidin-3-yloxy)benzo[d]thiazole hydrochloride (75 mg, 0.309 mmol, Intermediate 28) in dichloromethane (3 mL) was added N,N-diisopropylethylamine (0.16 mL, 0.916 mmol), followed by 4-nitrophenyl (3-cyclopropyl-1-methyl-1 H-pyrazol-5-yl)carbamate (115 mg, 0.301 mmol, Intermediate 141). The resulting yellow mixture was stirred overnight. The mixture was poured into 1N aqueous sodium hydroxide and extracted with dichloromethane (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 5%-100% ethyl acetate:ethanol (3:1 v/v) in hexanes gradient to give the title compound (34 mg) in 71% purity. This material was repurified by reverse phase HPLC, eluting with a 20%-95% acetonitrile:water (0.1% ammonium hydroxide modifier) gradient to give the title compound (21 mg, 18%) as a white solid. $^1$H NMR (400 MHz, CD$_3$SOCD$_3$) δ 0.55-0.60 (m, 2H), 0.77-0.82 (m, 2H), 1.72-1.80 (m, 1H), 3.52 (s, 3H), 4.00 (dd, J=10, 4 Hz, 2H), 4.47 (dd, J=10, 6 Hz, 2H), 5.27-5.33 (m, 1H), 5.74 (s, 1H), 6.89 (d, J=8 Hz, 1H), 7.42 (t, J=8 Hz, 1H), 7.78 (d, J=8 Hz, 1H), 8.49 (s, 1H), 9.32 (s, 1H); LC-MS (LC-ES) M+H=370.

Example 315

(trans)-3-(Benzo[d]thiazol-4-yloxy)-N-(3-(pyrimidin-2-ylamino)bicyclo[1.1.1]pentan-1-yl)cyclobutane-1-carboxamide

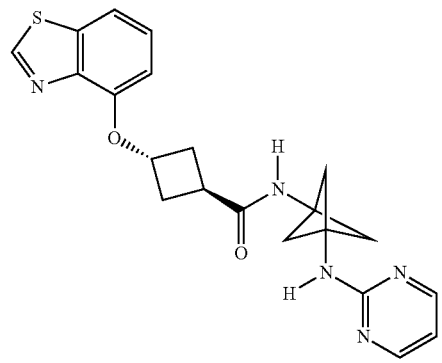 [SMILES: O=C(NC12CC(Nc3ncccn3)(C1)C2)[C@H]1C[C@H](Oc2cccc3scnc23)C1]

To a stirred solution of (trans)-3-(benzo[d]thiazol-4-yloxy)cyclobutanecarboxylic acid (21 mg, 0.084 mmol, Intermediate 25) and N1-(pyrimidin-2-yl)bicyclo[1.1.1]pentane-1,3-diamine hydrochloride (17.9 mg, 0.084 mmol, Intermediate 142) in N,N-dimethylformamide (2 mL) was added N,N-diisopropylethylamine (0.044 mL, 0.253 mmol), followed by a 50% by weight solution of 2,4,6-tripropyl-1,3,5,2,4,6-trioxatriphosphinane 2,4,6-trioxide (T3P) in ethyl acetate (0.054 mL, 0.084 mmol). The mixture was stirred for 20 minutes, quenched with water, loaded onto a semi-prep HPLC and purified, eluting with an acetonitrile:water gradient (ammonium hydroxide modifier) to give the title compound (16.8 mg, 49% yield) as a pale yellow solid. $^1$H NMR (400 MHz, CDCl$_3$) δ 2.52 (s, 6H), 2.58-2.73 (m, 2H), 2.87 (ddd, J=13, 7, 4 Hz, 2H), 5.24 (t, J=7 Hz, 1H), 3.04 (s, 1H), 5.79 (br s, 1H), 5.92 (s, 1H), 6.63 (t, J=5 Hz, 1H), 6.81 (d, J=8 Hz, 1H), 7.36 (t, J=8 Hz, 1H), 7.55 (d, J=8 Hz, 1H), 8.32 (d, J=5 Hz, 2H), 8.94 (s, 1H); LC-MS (LC-ES) M+H=408.

Example 316

3-(Benzo[d]thiazol-4-yloxy)-N-(3-(2-hydroxypropan-2-yl)bicyclo[1.1.1]pentan-1-yl)azetidine-1-carboxamide

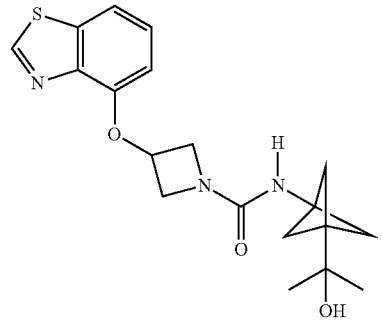 [SMILES: CC(C)(O)C12CC(NC(=O)N3CC(Oc4cccc5scnc45)C3)(C1)C2]

To a stirred, cooled (0° C.) solution of 4-nitrophenyl chloroformate (35 mg, 0.174 mmol) and 2-(3-aminobicyclo

[1.1.1]pentan-1-yl)propan-2-ol hydrochloride (25 mg, 0.177 mmol, Intermediate 143) in dichloromethane (1 mL) was added pyridine (0.50 mL, 6.18 mmol). The mixture was allowed to warm slowly to room temperature, while stirring overnight. Solvent was removed under reduced pressure and the remaining material was dissolved in N,N-dimethylformamide (1 mL). To this stirring mixture was added 4-(azetidin-3-yloxy)benzo[d]thiazole hydrochloride (40 mg, 0.165 mmol, Intermediate 28). The mixture was stirred for 30 minutes and then N,N-diisopropylethylamine (0.10 mL, 0.573 mmol) was added. After stirring for 1 hour, the mixture was poured into 1N aqueous sodium hydroxide and extracted with dichloromethane (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 0%-75% ethyl acetate:ethanol (3:1 v/v) in hexanes gradient to give the title compound (22 mg, 36%) as a white solid. $^1$H NMR (400, MHz, CD$_3$SOCD$_3$) δ 1.04 (s, 6H), 1.75 (s, 6H), 3.82 (dd, J=9, 4 Hz, 2H), 4.11 (s, 1H), 4.30 (dd, J=9, 6 Hz, 2H), 5.21 (t, J=4 Hz, 1H), 6.84 (d, J=8 Hz, 1H), 7.02 (s, 1H), 7.41 (t, J=8 Hz, 1H), 7.76 (d, J=8 Hz, 1H), 9.30 (s, 1H); LC-MS (LC-ES) M+H=374.

Example 317

3-(Benzo[d]thiazol-4-yloxy)-N-(4-(2-hydroxypropan-2-yl)cuban-1-yl)azetidine-1-carboxamide

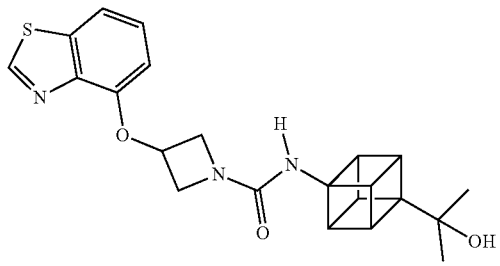 [SMILES: CC(C)(O)C12C3C4C1C1C2C3C41NC(=O)N1CC(Oc2cccc3scnc23)C1]

To a stirred, cooled (0° C.) solution of 4-nitrophenyl chloroformate (40 mg, 0.198 mmol) and (4-aminocuban-1-yl)propan-2-ol hydrochloride (43 mg, 0.201 mmol, Intermediate 144) in dichloromethane (1 mL) was added pyridine (0.50 mL, 6.18 mmol). The mixture was allowed to warm slowly to room temperature, while stirring for 5 hours. To this mixture was added 4-(azetidin-3-yloxy)benzo[d]thiazole hydrochloride (42 mg, 0.173 mmol, Intermediate 28), followed by N,N-diisopropylethylamine (0.10 mL, 0.573 mmol). After stirring overnight, the mixture was poured into 1N aqueous sodium hydroxide and extracted with dichloromethane (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 5%-75% ethyl acetate:ethanol (3:1 v/v) in hexanes gradient to give the title compound (12.3 mg, 17%) as a white solid. $^1$H NMR (400 MHz, CD$_3$SOCD$_3$) δ 0.63 (s, 6H), 2.90 (t, J=6 Hz, 3H), 3.22-3.27 (m, 3H), 3.84 (dd, J=9, 4 Hz, 2H), 4.31 (dd, J=9, 6 Hz, 2H), 5.07 (s, 1H), 5.19-5.25 (m, 1H), 6.85 (d, J=8 Hz, 1H), 6.97 (s, 1H), 7.41 (t, J=8 Hz, 1H), 7.76 (d, J=8 Hz, 1H), 9.30 (s, 1H); LC-MS (LC-ES) M+H=410.

Example 318

(trans)-3-(Benzo[d]thiazol-4-yloxy)-N-(3-(2-hydroxypropan-2-yl)bicyclo[1.1.1]pentan-1-yl)cyclobutane-1-carboxamide

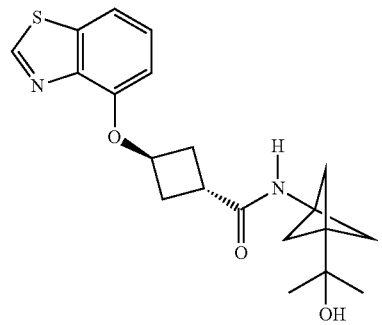 [SMILES: CC(C)(O)C12CC(NC(=O)[C@H]3C[C@H](Oc4cccc5scnc45)C3)(C1)C2]

To a stirred, cooled (0° C.) solution of (trans)-3-(benzo[d]thiazol-4-yloxy)cyclobutane-1-carboxylic acid (60 mg, 0.241 mmol, Intermediate 25) and 2-(3-aminobicyclo[1.1.1]pentan-1-yl)propan-2-ol hydrochloride (30 mg, 0.169 mmol, Intermediate 143) in N,N-dimethylformamide (2 mL) was added N,N-diisopropylethylamine (0.075 mL, 0.429 mmol), followed by a 50% by weight solution of 2,4,6-tripropyl-1,3,5,2,4,6-trioxatriphosphinane 2,4,6-trioxide (T3P) in ethyl acetate (0.25 mL, 0.420 mmol). The mixture was allowed to warm slowly to room temperature over 3 hours. LCMS analysis of the mixture showed the reaction was incomplete. Additional T3P solution (0.125 mL, 0.21 mmol) was added to the mixture and stirring was continued overnight. The mixture was poured into 1N aqueous sodium hydroxide and extracted with ethyl acetate (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 5%-75% ethyl acetate:ethanol (3:1 v/v) in hexanes gradient to give the title compound (36 mg, 57%) as a white solid. $^1$H NMR (400 MHz, CD$_3$SOCD$_3$) δ 1.05 (s, 6H), 1.81 (s, 6H), 2.28-2.37 (m, 2H), 2.62 (qd, J=7, 4 Hz, 2H), 3.02 (dt, J=9, 5 Hz, 1H), 4.16 (s, 1H), 5.04 (t, J=6 Hz, 1H), 6.83 (d, J=8 Hz, 1H), 7.38 (t, J=8 Hz, 1H), 7.69 (d, J=8 Hz, 1H), 8.37 (s, 1H), 9.26 (s, 1H); LC-MS (LC-ES) M+H=373.

Example 319

Ethyl (3-((trans)-3-(benzo[d]thiazol-4-yloxy)cyclobutane-1-carboxamido)bicyclo[1.1.1]pentan-1-yl)carbamate

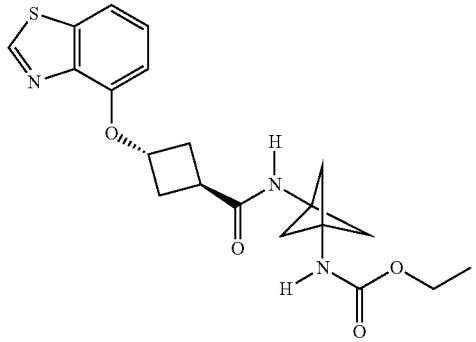 [SMILES: CCOC(=O)NC12CC(NC(=O)[C@H]3C[C@H](Oc4cccc5scnc45)C3)(C1)C2]

To a stirred, cooled (0° C.) solution of (trans)-3-(benzo[d]thiazol-4-yloxy)cyclobutane-1-carboxylic acid (42 mg, 0.168 mmol, Intermediate 25) and ethyl (3-aminobicyclo[1.1.1]pentan-1-yl)carbamate hydrochloride (30 mg, 0.145 mmol, Intermediate 145) in N,N-dimethylformamide (2 mL) was added N,N-diisopropylethylamine (0.075 mL, 0.429 mmol), followed by a 50% by weight solution of 2,4,6-tripropyl-1,3,5,2,4,6-trioxatriphosphinane 2,4,6-trioxide (T3P) in ethyl acetate (0.25 mL, 0.420 mmol). The mixture was allowed to warm to room temperature and stir overnight. LCMS analysis of the mixture showed the reaction was incomplete. Additional T3P solution (0.125 mL, 0.21 mmol) was added to the mixture and stirring was continued for 1 hour. The mixture was poured into 1N aqueous sodium hydroxide and extracted with ethyl acetate (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 5%-75% ethyl acetate:ethanol (3:1 v/v) in hexanes gradient to give the title compound (46 mg, 79%) as a white solid. $^1$H NMR (400 MHz, CD$_3$SOCD$_3$) δ 1.15 (t, J=7 Hz, 3H), 2.15 (s, 6H), 2.29-2.38 (m, 2H), 2.58-2.66 (m, 2H), 3.03 (dt, J=9, 5 Hz, 1H), 3.97 (q, J=7 Hz, 2H), 5.04 (t, J=6 Hz, 1H), 6.83 (d, J=8 Hz, 1H), 7.38 (t, J=8 Hz, 1H), 7.69 (d, J=8 Hz, 1H), 7.83 (br s, 1H), 8.49 (s, 1H), 9.26 (s, 1H); LC-MS (LC-ES) M+H=402.

Example 320

(trans)-3-(Benzo[d]thiazol-4-yloxy)-N-(4-(2-hydroxypropan-2-yl)cuban-1-yl)cyclobutane-1-carboxamide

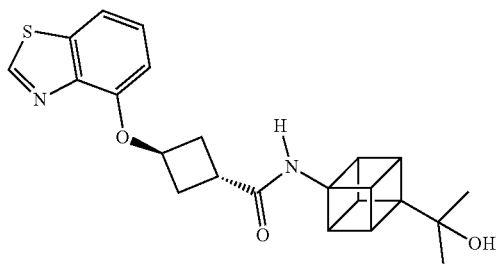 [SMILES: CC(C)(O)C12C3C4C1C1C2C3C41NC(=O)[C@H]1C[C@H](Oc2cccc3scnc23)C1]

To a stirred, cooled (0° C.) solution of (trans)-3-(benzo[d]thiazol-4-yloxy)cyclobutane-1-carboxylic acid (35 mg, 0.140 mmol, Intermediate 25) and (4-aminocuban-1-yl)propan-2-ol hydrochloride (30 mg, 0.140 mmol, Intermediate 144) in N,N-dimethylformamide (1 mL) was added N,N-diisopropylethylamine (0.07 mL, 0.401 mmol), followed by a 50% by weight solution of 2,4,6-tripropyl-1,3,5,2,4,6-trioxatriphosphinane 2,4,6-trioxide (T3P) in ethyl acetate (0.20 mL, 0.336 mmol). The mixture was allowed to warm slowly to room temperature, while stirring overnight. The mixture was poured into 1N aqueous sodium hydroxide and extracted with ethyl acetate (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 5%-75% ethyl acetate:ethanol (3:1 v/v) in hexanes gradient to give the title compound (35 mg, 61%) as a white solid. $^1$H NMR (400 MHz, CD$_3$SOCD$_3$) δ 0.65 (s, 6H), 2.31-2.39 (m, 2H), 2.56-2.66 (m, 4H), 2.93-2.98 (m, 2H), 3.06 (td, J=9, 5 Hz, 1H), 3.27-3.31 (m, 2H), 5.05 (quin, J=6 Hz, 1H), 5.13 (s, 1H), 6.83 (d, J=8 Hz, 1H), 7.39 (t, J=8 Hz, 1H), 7.69 (d, J=8 Hz, 1H), 8.38 (s, 1H), 9.26 (s, 1H); LC-MS (LC-ES) M+H=409.

Example 321

3-(Benzo[d]thiazol-4-yloxy)-N-(5-methyl-1,3,4-thiadiazol-2-yl)azetidine-1-carboxamide

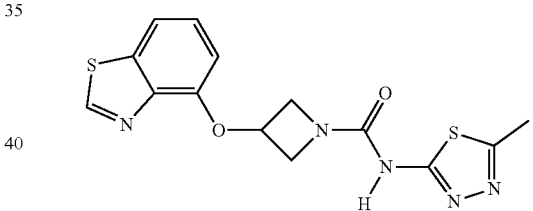

To a stirred, cooled (0° C.) solution of 4-(azetidin-3-yloxy)benzo[d]thiazole trifluoroacetic acid salt (50 mg, 0.150 mmol, Intermediate 28C) in acetonitrile (4 mL) was added N,N-diisopropylethylamine (0.105 mL, 0.599 mmol). The mixture was stirred for 10 minutes and then phenyl (5-methyl-1,3,4-thiadiazol-2-yl)carbamate (42.3 mg, 0.180 mmol, Intermediate 146) was added. The mixture was allowed to warm to room temperature and stirred for 16 hours. Solvent was removed under reduced pressure to give 55 mg of crude material. This reaction was repeated (Intermediate 28C (150 mg) and Intermediate 146 (127 mg)) to give 175 mg of crude material. Both batches of crude material (230 mg) were combined, dissolved in 1:9 methanol:dichloromethane, pre-adsorbed onto neutral alumina and purified by silica gel chromatography, eluting with 1:1 ethyl acetate in hexanes gradient, followed by a 5:95 methanol in dichloromethane gradient to give the title compound (121 mg, 61%) as an off-white solid. $^1$H NMR (400 MHz, CD$_3$SOCD$_3$) δ 2.55 (s, 3H), 3.98-4.19 (m, 2H), 4.56 (dd, J=9, 7 Hz, 2H), 5.21-5.38 (m, 1H), 6.88 (d, J=8 Hz, 1H), 7.42 (t, J=8 Hz, 1H), 7.71-7.84 (m, 1H), 9.30 (s, 1H), 11.29 (br s, 1H); LC-MS (LC-ES) M+H=348.

Example 322

3-(Benzo[d]thiazol-4-yloxy)-N-(1-methyl-1H-pyrazol-3-yl)azetidine-1-carboxamide

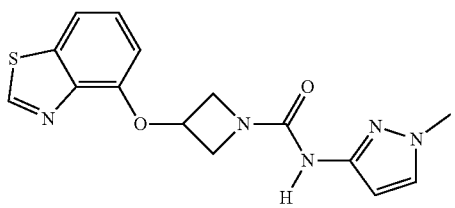 [SMILES: Cn1ccc(NC(=O)N2CC(Oc3cccc4scnc34)C2)n1]

To a stirred, cooled (0° C.) solution of 4-(azetidin-3-yloxy)benzo[d]thiazole trifluoroacetic acid salt (700 mg, 3.30 mmol, Intermediate 28C) in tetrahydrofuran (50 mL) was added triethylamine (1.84 mL, 13.2 mmol). The mixture was stirred for 5 minutes and then phenyl (1-methyl-1H-pyrazol-3-yl)carbamate (500 mg, 0.920 mmol, Intermediate 147) was added. The mixture was allowed to warm to room temperature and then heated at 75° C. for 18 hours. The mixture was quenched with ice cold water and extracted with ethyl acetate (3×). The combined organic layers were dried over sodium sulfate and filtered. Solvent was removed under reduced pressure and the remaining material was chromatographed on silica gel, eluting with a 5:95 methanol:dichloromethane gradient to give the title compound (80 mg, 7%) as a white solid. $^1$H NMR (400 MHz, CD$_3$SOCD$_3$) δ 3.70 (s, 3H), 3.97 (dd, J=9, 3 Hz, 2H), 4.32-4.48 (m, 2H), 5.16-5.34 (m, 1H), 6.27 (d, J=2 Hz, 1H), 6.87 (d, J=8 Hz, 1H), 7.32-7.52 (m, 2H), 7.76 (d, J=8 Hz, 1H), 9.10 (s, 1H), 9.29 (s, 1H); LC-MS (LC-ES) M+H=330.

Example 323

3-(Benzo[d]thiazol-4-yloxy)-N-(5-methoxypyridin-3-yl)azetidine-1-carboxamide

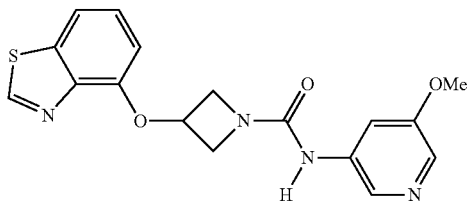 [SMILES: COc1cncc(NC(=O)N2CC(Oc3cccc4scnc34)C2)c1]

To a stirred, cooled (0° C.) solution of phenyl (5-methoxypyridin-3-yl)carbamate (100 mg, 0.300 mmol, Intermediate 148) in tetrahydrofuran (6 mL) was added triethylamine (0.167 mL, 1.20 mmol). The mixture was stirred for 5 minutes and then 4-(azetidin-3-yloxy)benzo[d]thiazole trifluoroacetic acid salt (91 mg, 0.270 mmol, Intermediate 28C) was added. The mixture was allowed to warm to room temperature and then heated at 80° C. for 16 hours. The mixture was quenched with water and extracted with ethyl acetate (2×). The combined organic layers were dried over sodium sulfate and filtered. Solvent was removed under reduced pressure and the remaining material was dissolved in dichloromethane, pre-adsorbed onto silica gel and chromatographed on silica gel, eluting with a 1:9 methanol-dichloromethane gradient and then by reverse phase HPLC eluting with acetonitrile in water (ammonium bicarbonate modifier) to give the title compound (60 mg, 56%) as a white solid. $^1$H NMR (400 MHz, CD$_3$SOCD$_3$) δ 3.78 (s, 3H), 4.06 (dd, J=10, 4 Hz, 2H), 4.52 (dd, J=10, 6 Hz, 2H), 5.28-5.37 (m, 1H), 6.91 (d, J=8 Hz, 1H), 7.42 (t, J=8 Hz, 1H), 7.63 (t, J=2 Hz, 1H), 7.77 (dd, J=8, 1 Hz, 1H), 7.9 (d, J=3 Hz, 1H), 8.3 (d, J=2 Hz, 1H), 8.8 (s, 1H), 9.30 (s, 1H); LC-MS (LC-ES) M+H=357.

Example 324

3-(Benzo[d]thiazol-4-yloxy)-N-(1-methyl-1H-pyrazol-4-yl)azetidine-1-carboxamide

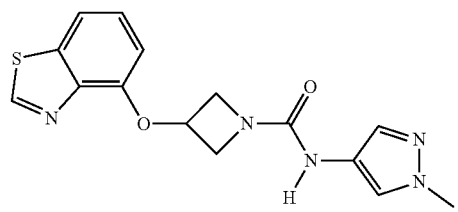 [SMILES: Cn1cc(NC(=O)N2CC(Oc3cccc4scnc34)C2)cn1]

To a stirred, cooled (0° C.) solution of 4-(azetidin-3-yloxy)benzo[d]thiazole trifluoroacetic acid salt (300 mg, 0.85 mmol, Intermediate 28C) in acetonitrile (10 mL) was added N,N-diisopropylethylamine (0.149 mL, 0.85 mmol). The mixture was stirred for 10 minutes and then phenyl (1-methyl-1H-pyrazol-4-yl)carbamate (200 mg, 0.57 mmol, Intermediate 149) was added. The mixture was allowed to warm to room temperature and stirred for 16 hours. The mixture was diluted with water and extracted with ethyl acetate (2×). The combined organic layers were washed with brine, dried over sodium sulfate, and filtered. Solvent was removed under reduced pressure and the remaining material was dissolved in dichloromethane, pre-adsorbed onto silica gel and chromatographed on silica gel, eluting with a 1:9 methanol:dichloromethane gradient to give the title compound (80 mg, 28%) as a brown solid. $^1$H NMR (400 MHz, CD$_3$SOCD$_3$) δ 3.75 (s, 3H), 3.96 (dd, J=9, 4 Hz, 2H), 4.42 (dd, J=9, 7 Hz, 2H) 5.24-5.32 (m, 1H), 6.88 (d, J=8 Hz, 1H), 7.30 (s, 1H), 7.41 (t, J=8 Hz, 1H), 7.64 (s, 1H), 7.76 (d, J=8 Hz, 1H), 8.53 (s, 1H), 9.29 (s, 1H); LC-MS (LC-ES) M+H=330.

Example 325

3-(Benzo[d]thiazol-4-yloxy)-N-(1-ethyl-1H-tetrazol-5-yl)azetidine-1-carboxamide

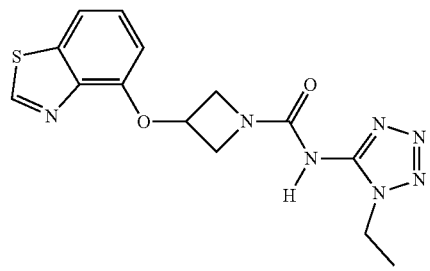 [SMILES: CCn1nnnc1NC(=O)N1CC(Oc2cccc3scnc23)C1]

To a stirred ambient solution of 4-(azetidin-3-yloxy)benzo[d]thiazole trifluoroacetic acid salt (200 mg, 0.618 mmol, Intermediate 28C) in dichloromethane (20 mL) was added N,N-diisopropylethylamine (0.216 mL, 1.24 mmol), followed by phenyl (1-ethyl-1H-tetrazol-5-yl)carbamate (224 mg, 0.742 mmol, Intermediate 150). The mixture was stirred for 16 hours. The solvent was removed under reduced pressure and the remaining material was purified by reverse phase HPLC, eluting with acetonitrile in water (ammonium bicarbonate modifier) to give the title compound (90 mg, 42%) as an off-white solid. ¹H NMR (400 MHz, CD₃SOCD₃) δ 1.49 (t, J=7 Hz, 3H), 4.04 (dd, J=10, 4 Hz, 2H), 4.50 (dd, J=10, 7 Hz, 2H), 4.59 (q, J=7 Hz, 2H), 5.21-5.36 (m, 1H), 6.88 (d, J=8 Hz, 1H), 7.42 (t, J=8 Hz, 1H), 7.77 (d, J=8 Hz, 1H), 9.30 (s, 1H), 9.77 (s, 1H); LC-MS (LC-ES) M+H=346.

Example 326

Methyl 4-((trans)-3-(benzo[d]thiazol-4-yloxy)cyclobutane-1-carboxamido)bicyclo[2.2.2]octane-1-carboxylate

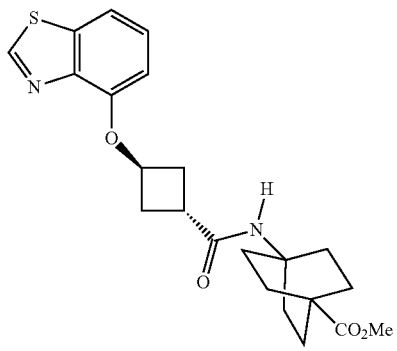 [SMILES: COC(=O)C12CCC(NC(=O)[C@H]3C[C@H](Oc4cccc5scnc45)C3)(CC1)CC2]

To a stirred, cooled (0° C.) solution of (trans)-3-(benzo[d]thiazol-4-yloxy)cyclobutane-1-carboxylic acid (100 mg, 0.401 mmol, Intermediate 25) and methyl 4-aminobicyclo[2.2.2]octane-1-carboxylate (75 mg, 0.409 mmol) in N,N-dimethylformamide (2 mL) was added N,N-diisopropylethylamine (0.25 mL, 1.431 mmol), followed by a 50% solution of 2,4,6-tripropyl-1,3,5,2,4,6-trioxatriphosphinane 2,4,6-trioxide (T3P) in ethyl acetate (0.75 mL, 1.260 mmol). The mixture was allowed to warm slowly to room temperature, while stirring for 2 hours, quenched with saturated aqueous sodium bicarbonate, and extracted with dichloromethane (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 5%-70% ethyl acetate:ethanol (3:1 v/v) in hexanes gradient to give the title compound (120 mg, 72%) as a white solid. ¹H NMR (400 MHz, CD₃SOCD₃) δ 1.73-1.89 (m, 12H), 2.27-2.35 (m, 2H), 2.54-2.61 (m, 2H), 3.07 (tt, J=9., 5 Hz, 1H), 3.57 (s, 3H), 5.03 (quin, J=6 Hz, 1H), 6.81 (d, J=8 Hz, 1H), 7.38 (t, J=8 Hz, 1H), 7.43 (s, 1H), 7.69 (d, J=8 Hz, 1H), 9.25 (s, 1H); LC-MS (LC-ES) M+H=415.

Example 327

Methyl 4-(3-(benzo[d]thiazol-4-yloxy)azetidine-1-carboxamido)bicyclo[2.2.2]octane-1-carboxylate

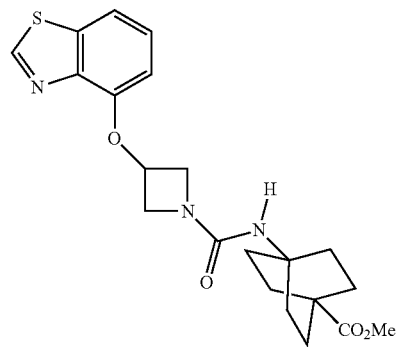 [SMILES: COC(=O)C12CCC(NC(=O)N3CC(Oc4cccc5scnc45)C3)(CC1)CC2]

To a stirred, cooled (0° C.) solution of 4-nitrophenyl chloroformate (115 mg, 0.571 mmol) and methyl 4-aminobicyclo[2.2.2]octane-1-carboxylate (100 mg, 0.546 mmol) in dichloromethane (3 mL) was added pyridine (1.20 mL, 14.8 mmol). The mixture was stirred for 2 hours and then 4-(azetidin-3-yloxy)benzo[d]thiazole hydrochloride (120 mg, 0.494 mmol, Intermediate 28) was added, followed by N,N-diisopropylethylamine (0.30 mL, 1.72 mmol). After stirring overnight, the mixture was poured into 1N aqueous sodium hydroxide and extracted with dichloromethane (2×). The combined organic layers were washed with brine, dried over sodium sulfate, and filtered. Solvent was removed under reduced pressure. The remaining material was dissolved in a minimal amount of dichloromethane and chromatographed on silica gel, eluting with a 5%-50% ethyl acetate:ethanol (3:1 v/v) in hexanes gradient to give the title compound (95 mg, 46%) as a white solid. ¹H NMR (400 MHz, CD₃SOCD₃) δ 1.78 (q, J=9 Hz, 12H), 3.56 (s, 3H), 3.82 (dd, J=9, 4 Hz, 2H), 4.27 (dd, J=9, 6 Hz, 2H), 5.18 (td, J=7, 3 Hz, 1H), 5.80 (s, 1H), 6.84 (d, J=8 Hz, 1H), 7.40 (t, J=8 Hz, 1H), 7.73-7.77 (m, 1H), 9.30 (s, 1H); LC-MS (LC-ES) M+H=416.

Example 328

3-(Benzo[d]thiazol-4-yloxy)-N-(5-isopropyl-1,3,4-oxadiazol-2-yl)azetidine-1-carboxamide

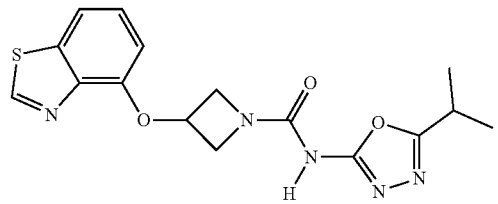 [SMILES: CC(C)c1nnc(NC(=O)N2CC(Oc3cccc4scnc34)C2)o1]

To a stirred solution of 4-(azetidin-3-yloxy)benzo[d]thiazole trifluoroacetic acid salt (170 mg, 0.488 mmol, Intermediate 28C) in tetrahydrofuran (8 mL) was added triethylamine (0.272 mL, 1.95 mmol) and phenyl (5-isopropyl-1,3,4-oxadiazol-2-yl)carbamate (180 mg, 0.248 mmol, Intermediate 151). The mixture was heated at 70° C. and stirred for 16 hours. The mixture was quenched with water and extracted with ethyl acetate (2×). The combined organic layers were dried over sodium sulfate and filtered. Solvent was removed under reduced pressure and the crude material was purified by reverse phase HPLC, eluting with acetonitrile in water (ammonium bicarbonate modifier) to give the title compound (15 mg, 8%) as an off-white solid. $^1$H NMR (400 MHz, CD$_3$SOCD$_3$) δ 1.26 (d, J=7 Hz, 6H), 3.05-3.17 (m, 1H), 4.05 (dd, J=9, 2 Hz, 2H), 4.47-4.61 (m, 2H), 5.26-5.35 (m, 1H), 6.88 (d, J=8 Hz, 1H), 7.41 (t, J=8 Hz, 1H), 7.77 (d, J=8 Hz, 1H), 9.30 (s, 1H), 10.36 (br s, 1H); LC-MS (LC-ES) M+H=360.

Example 329

3-(Benzo[d]thiazol-4-yloxy)-N-(4-cyano-3-methyl-1H-pyrazol-5-yl)azetidine-1-carboxamide

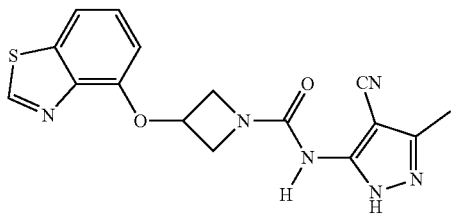 [SMILES: Cc1n[nH]c(NC(=O)N2CC(Oc3cccc4scnc34)C2)c1C#N]

To a stirred solution of 4-(azetidin-3-yloxy)benzo[d]thiazole trifluoroacetic acid salt (178 mg, 0.534 mmol, Intermediate 28C) in tetrahydrofuran (8 mL) was added triethylamine (0.149 mL, 1.07 mmol) and phenyl (4-cyano-3-methyl-1H-pyrazol-5-yl)carbamate (245 mg, 0.267 mmol, Intermediate 152). The mixture was heated at 70° C. and stirred for 16 hours. The mixture was diluted with water and extracted with ethyl acetate (2×). The combined organic layers were dried over sodium sulfate and filtered. Solvent was removed under reduced pressure. The crude material was dissolved in dichloromethane, pre-adsorbed onto silica gel and chromatographed on silica gel, eluting with a 1:9 methanol:dichloromethane gradient and then further purified by reverse phase HPLC, eluting with acetonitrile in water (ammonium bicarbonate modifier) to give the title compound (22 mg, 23%) as an off-white solid. $^1$H NMR (400 MHz, CD$_3$SOCD$_3$) δ 2.26 (s, 3H), 3.99 (dd, J=10, 4 Hz, 2H), 4.45 (dd, J=10, 7 Hz, 2H), 5.20-5.34 (m, 1H), 6.88 (d, J=8 Hz, 1H), 7.41 (t, J=8 Hz, 1H), 7.76 (dd, J=8, 1 Hz, 1H), 9.29 (s, 1H), 11.45 (br s, 2H); LC-MS (LC-ES) M+H=355.

Example 330

4-((1-(((trans)-4-(2-Hydroxypropan-2-yl)cyclohexyl)carbamoyl)azetidin-3-yl)oxy)benzo[d]thiazole-6-carboxamide

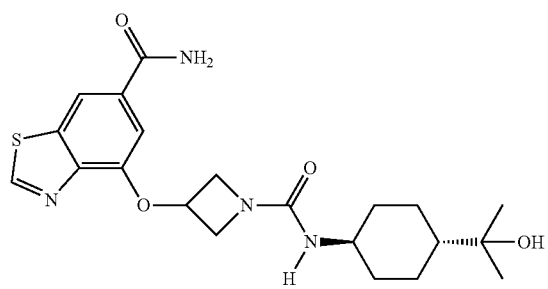

To a stirred solution of 4-((1-(((trans)-4-(2-hydroxypropan-2-yl)cyclohexyl)carbamoyl)azetidin-3-yl)oxy)benzo[d]thiazole-6-carboxylic acid (45 mg, 0.104 mmol, Intermediate 153) in N,N-dimethylformamide (2 mL) was added 1-hydroxybenzotriazole hydrate (22 mg, 0.144 mmol), ammonium chloride (20 mg, 0.374 mmol), and 1-(3-dimethylaminopropyl)-3-ethylcarbodiimide hydrochloride (28 mg, 0.146 mmol), followed by N,N-diisopropylethylamine (0.10 mL, 0.573 mmol). The mixture was stirred overnight, poured into 1N aqueous hydrochloric acid and extracted with ethyl acetate (2×). The combined organic layers were washed with 1N aqueous sodium hydroxide, brine, dried over sodium sulfate, and filtered. Solvent was removed under reduced pressure. The crude material was purified by reverse phase HPLC, eluting with 10%-50% acetonitrile in water (ammonium hydroxide modifier) to give the title compound (2.5 mg, 5.5%). $^1$H NMR (400 MHz, CD$_3$OD) δ 1.12-1.33 (m, 10H), 1.85-2.02 (m, 5H), 3.46 (br s, 1H), 3.62 (s, 1H), 4.11 (dd, J=10, 4 Hz, 2H), 4.47 (dd, J=9, 6 Hz, 2H), 5.32-5.38 (m, 1H), 6.30 (d, J=8 Hz, 1H), 7.32 (d, J=1 Hz, 1H), 8.26 (d, J=1 Hz, 1H), 9.36 (s, 1H); LC-MS (LC-ES) M+H=433.

Example 331

(trans)-3-(Benzo[d]thiazol-4-yloxy)-N-(5-methyl-1,3,4-thiadiazol-2-yl)cyclobutane-1-carboxamide

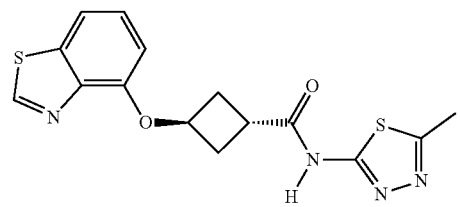 [SMILES: Cc1nnc(NC(=O)[C@H]2C[C@H](Oc3cccc4scnc34)C2)s1]

To a stirred solution of (trans)-3-(benzo[d]thiazol-4-yloxy)cyclobutane-1-carboxylic acid (50 mg, 0.201 mmol, Intermediate 25) and 5-methyl-1,3,4-thiadiazol-2-amine (25 mg, 0.217 mmol) in N,N-dimethylformamide (1 mL) was added N,N-diisopropylethylamine (0.125 mL, 0.716 mmol), followed by a 50% solution of 2,4,6-tripropyl-1,3,5,2,4,6-trioxatriphosphinane 2,4,6-trioxide (T3P) in ethyl acetate (0.25 mL, 0.424 mmol). The mixture was stirred for 2 hours, quenched with saturated aqueous sodium bicarbonate and extracted with dichloromethane (2×). The combined organic layers were washed with brine, dried over sodium sulfate, and filtered. Solvent was removed under reduced pressure. The remaining material was triturated with hexanes, containing a small amount of ethyl acetate, collected via vacuum filtration, and placed in vacuo to give the title compound (41 mg, 59%) as a white solid. $^1$H NMR (400 MHz, CD$_3$SOCD$_3$) δ 2.40-2.54 (m, 2H), 2.63 (s, 3H), 2.80 (qd, J=7, 5 Hz, 2H), 3.50 (dt, J=10, 5 Hz, 1H), 5.10 (t, J=6 Hz, 1H), 6.88 (d, J=7 Hz, 1H), 7.39 (t, J=8 Hz, 1H), 7.71 (dd, J=8, 1 Hz, 1H), 9.28 (s, 1H), 12.46 (s, 1H); LC-MS (LC-ES) M+H=347.

Example 332

3-(Benzo[d]thiazol-4-yloxy)-N-(5-(tert-butyl-1,3,4-thiadiazol-2-yl)azetidine-1-carboxamide

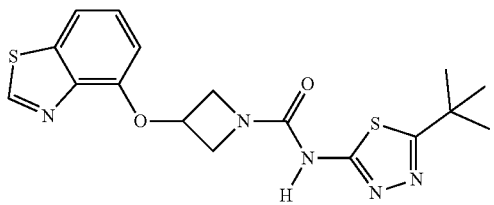 [SMILES: CC(C)(C)c1nnc(NC(=O)N2CC(Oc3cccc4scnc34)C2)s1]

To a stirred, cooled (0° C.) solution of 4-nitrophenyl chloroformate (50 mg, 0.248 mmol) in dichloromethane (2 mL) was added 5-(tert-butyl)-1,3,4-thiadiazol-2-amine (40 mg, 0.254 mmol) followed by pyridine (0.50 mL, 6.18 mmol). The mixture was allowed to warm slowly to room temperature, while stirring for 4 hours. 4-(Azetidin-3-yloxy) benzo[d]thiazole hydrochloride (50 mg, 0.206 mmol, Intermediate 28) was added to the mixture, followed by N,N-diisopropylethylamine (0.12 mL, 0.687 mmol). The mixture immediately turned bright yellow and was stirred for 2.5 hours. Solvent was removed under reduced pressure. The remaining material was dissolved in acetonitrile, containing a small amount of methanol and chromatographed by reverse phase chromatography using a C18 silica column, eluting with a 5%:90% acetonitrile:water (0.1% ammonium hydroxide) gradient to give the title compound (47 mg, 59%) as a white solid. $^1$H NMR (400 MHz, CD$_3$SOCD$_3$) δ 1.38 (s, 9H), 4.09 (d, J=8 Hz, 2H), 4.53-4.60 (m, 2H), 5.28-5.34 (m, 1H), 6.89 (d, J=85 Hz, 1H), 7.43 (t, J=8 Hz, 1H), 7.78 (d, J=8 Hz, 1H), 9.31 (s, 1H), 11.39 (br s, 1H); LC-MS (LC-ES) M+H=390.

Example 333

3-(Benzo[d]thiazol-4-yloxy)-N-(5-cyclopropyl-1,3,4-thiadiazol-2-yl)azetidine-1-carboxamide

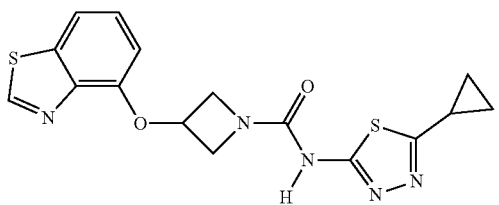 [SMILES: O=C(Nc1nnc(C2CC2)s1)N1CC(Oc2cccc3scnc23)C1]

To a stirred, cooled (0° C.) solution of 4-nitrophenyl chloroformate (55 mg, 0.273 mmol) in dichloromethane (2 mL) was added 5-cyclopropyl-1,3,4-thiadiazol-2-amine (40 mg, 0.283 mmol), followed by pyridine (0.50 mL, 6.18 mmol). The mixture was allowed to warm slowly to room temperature while stirring for 1.5 hours. 4-(Azetidin-3-yloxy)benzo[d]thiazole hydrochloride (50 mg, 0.206 mmol, Intermediate 28) was added to the mixture, followed by N,N-diisopropylethylamine (0.12 mL, 0.687 mmol). The mixture immediately turned bright yellow and was stirred for 1 hour. Solvent was removed under reduced pressure. The remaining material was dissolved in acetonitrile, containing a small amount of methanol and chromatographed by reverse phase chromatography using a C18 silica column, eluting with a 5%-70% acetonitrile:water (0.1% ammonium hydroxide) gradient to give the title compound (35 mg, 45%) as a white solid. $^1$H NMR (400 MHz, CD$_3$SOCD$_3$) δ 0.91-0.97 (m, 2H), 1.06-1.13 (m, 2H), 2.28-2.37 (m, 1H), 4.09 (d, J=8 Hz, 2H), 4.53-4.60 (m, 2H), 5.27-5.33 (m, 1H), 6.88 (d, J=8 Hz, 1H), 7.43 (t, J=8 Hz, 1H), 7.78 (d, J=8 Hz, 1H), 9.31 (s, 1H), 11.35 (br s, 1H); LC-MS (LC-ES) M+H=374.

Example 334

3-(Benzo[d]thiazol-4-yloxy)-N-(5-isopropyl-1,3,4-thiadiazol-2-yl)azetidine-1-carboxamide

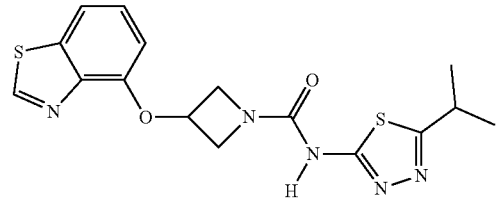

To a stirred, cooled (0° C.) solution of 4-nitrophenyl chloroformate (55 mg, 0.273 mmol) in dichloromethane (2 mL) was added 5-isopropyl-1,3,4-thiadiazol-2-amine (40 mg, 0.279 mmol), followed by pyridine (0.50 mL, 6.18 mmol). The mixture was allowed to warm slowly to room temperature, while stirring for 1.5 hours. 4-(Azetidin-3-yloxy)benzo[d]thiazole hydrochloride (50 mg, 0.206 mmol, Intermediate 28) was added to the mixture, followed by N,N-diisopropylethylamine (0.12 mL, 0.687 mmol). The mixture immediately turned bright yellow and was stirred for 1 hour. Solvent was removed under reduced pressure. The remaining material was dissolved in acetonitrile, containing a small amount of methanol and chromatographed by reverse phase chromatography using a C18 silica column, eluting with a 5%-70% acetonitrile:water (0.1% ammonium hydroxide) gradient to give a pinkish colored solid. This material was dissolved in dichloromethane, containing a small amount of methanol and chromatographed on silica gel, eluting with a 10%-75% ethyl acetate:ethanol (3:1 v/v) in hexanes gradient to give the title compound (37 mg, 48%) as a white solid. $^1$H NMR (400 MHz, CD$_3$SOCD$_3$) δ 1.32 (d, J=7 Hz, 6H), 3.27 (dt, J=13, 7 Hz, 1H), 4.09 (d, J=7 Hz, 2H), 4.53-4.61 (m, 2H), 5.27-5.34 (m, 1H), 6.88 (d, J=8 Hz, 1H), 7.43 (t, J=8 Hz, 1H), 7.78 (d, J=8 Hz, 1H), 9.31 (s, 1H), 11.36 (br s, 1H); LC-MS (LC-ES) M+H=376.

Example 335

(trans)-N-(5-(Ethoxymethyl)-1H-1,2,4-triazol-3-yl-3-((6-fluorobenzo[d]thiazol-4-yl)oxy)cyclobutanecarboxamide

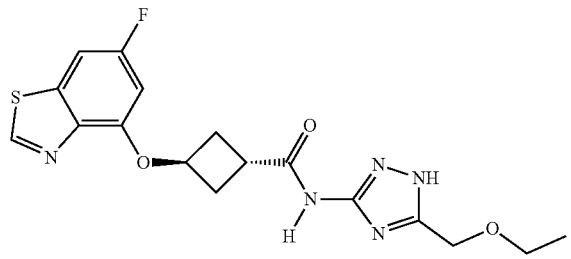 [SMILES: CCOCc1nc(NC(=O)[C@H]2C[C@H](Oc3cc(F)cc4scnc34)C2)n[nH]1]

To a stirred, cooled (0° C.) solution of (trans)-3-((6-fluorobenzo[d]thiazol-4-yl)oxy)cyclobutanecarboxylic acid (100 mg, 0.355 mmol, Intermediate 59) in dichloromethane (5 mL) was added N,N-dimethylformamide (0.05 mL), followed by oxalyl chloride (0.03 mL, 0.343 mmol). The mixture was warmed to room temperature and stirred for 2 hours. Solvent was removed under reduced pressure to give (trans)-3-((6-fluorobenzo[d]thiazol-4-yl)oxy)cyclobutanecarbonyl chloride (120 mg). To a stirred, cooled (10° C.) solution of 5-(ethoxymethyl)-1H-1,2,4-triazol-3-amine (10 mg, 0.070 mmol) in toluene (5 mL) was added 4-dimethylaminopyridine (8.6 mg, 0.070 mmol), followed by a solution of the above prepared (trans)-3-((6-fluorobenzo[d]thiazol-4-yl)oxy)cyclobutanecarbonyl chloride (60 mg, 0.211 mmol) dissolved in toluene (2 mL) and tetrahydrofuran (3 mL). The mixture heated to 100° C. for 16 hours, cooled to room temperature, and evaporated to dryness under reduced pressure. The remaining material was diluted with water and extracted with ethyl acetate (5×). The combined organic layers were combined, dried over sodium sulfate, and filtered. Solvent was removed under reduced pressure to give crude product (32 mg). This procedure was repeated two additional times to give additional crude product (70 mg). The combined crude material (102 mg) was purified by reverse phase HPLC, eluting with acetonitrile in water (ammonium bicarbonate modifier) and then repurified by reverse phase HPLC, eluting with acetonitrile in water (formic acid modifier) to give the title compound (3.4 mg, 10%) as an off-white solid. $^1$H NMR (400 MHz, CD$_3$SOCD$_3$) δ 1.11 (t, J=7 Hz, 3H), 2.45-2.49 (m, 2H), 2.71-2.89 (m, 2H), 3.35-3.42 (m, 1H), 3.49 (q, J=7 Hz, 2H), 4.36 (s, 2H), 5.04-5.16 (m, 1H), 6.77 (dd, J=11, 2 Hz, 1H), 7.60 (dd, J=8, 2 Hz, 1H), 9.23 (s, 1H), 11.45 (br s, 1H) 13.3 (br s, 1H); LC-MS (LC-ES) M+H=392.

Example 336

3-(Benzo[d]thiazol-4-yloxy)-N-(5-methyl-1,2,4-thiadiazol-3-yl)azetidine-1-carboxamide

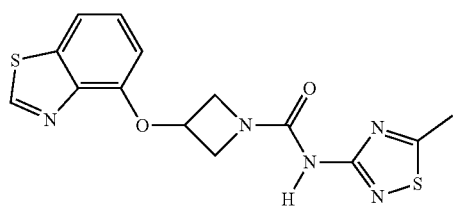 [SMILES: Cc1nc(NC(=O)N2CC(Oc3cccc4scnc34)C2)ns1]

To a stirred, cooled (0° C.) solution of 4-nitrophenyl chloroformate (55 mg, 0.273 mmol) in dichloromethane (2 mL) was added 5-methyl-1,2,4-thiadiazol-3-amine (33 mg, 0.287 mmol) followed by pyridine (0.50 mL, 6.18 mmol). The mixture was allowed to stir for 1 h. 4-(Azetidin-3-yloxy)benzo[d]thiazole hydrochloride (Intermediate 28) (50 mg, 0.206 mmol) was added to the mixture followed by N,N-diisopropylethylamine (0.12 mL, 0.687 mmol). The mixture immediately turned bright yellow and was stirred overnight. The mixture was poured into 1N aqueous sodium hydroxide and extracted twice with dichloromethane. The combined organic layers were washed with brine, dried over sodium sulfate and filtered. Solvent was removed under reduced pressure. The remaining material was dissolved in acetonitrile containing a small amount of methanol and chromatographed by reverse phase chromatography using a C18 silica column, eluting with a 5%-70% acetonitrile:water (0.1% ammonium hydroxide) gradient to give the title compound (15 mg, 21%) as a yellow solid. $^1$H NMR (400 MHz, CD$_3$SOCD$_3$) δ 2.73 (s, 3H), 4.04 (dd, J=9.8, 3.0 Hz, 2H), 4.50 (dd, J=9.7, 6.7 Hz, 2H), 5.25-5.31 (m, 1H), 6.87 (d, J=7.8 Hz, 1H), 7.42 (t, J=8.0 Hz, 1H), 7.77 (d, J=8.0 Hz, 1H), 9.31 (s, 1H), 10.14 (s, 1H); LC-MS (LC-ES) M+H=348.

Example 337

3-(Benzo[d]thiazol-4-yloxy)-N-(3-isopropyl-1,2,4-thiadiazol-5-yl)azetidine-1-carboxamide

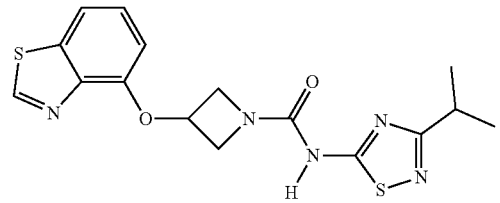 [SMILES: CC(C)c1nsc(NC(=O)N2CC(Oc3cccc4scnc34)C2)n1]

To a stirred, cooled (0° C.) solution of 4-nitrophenyl chloroformate (55 mg, 0.273 mmol) in dichloromethane (2 mL) was added 3-isopropyl-1,2,4-thiadiazol-5-amine (40 mg, 0.279 mmol), followed by pyridine (0.50 mL, 6.18 mmol). The mixture was allowed to warm slowly to room temperature, while stirring for 2 hours. 4-(Azetidin-3-yloxy)benzo[d]thiazole hydrochloride (50 mg, 0.206 mmol, Intermediate 28) was added to the mixture, followed by N,N-diisopropylethylamine (0.12 mL, 0.687 mmol). The mixture immediately turned bright yellow and was stirred overnight. Solvent was removed under reduced pressure. The remaining material was dissolved in acetonitrile and chromatographed by reverse phase chromatography using a C18 silica column, eluting with a 5%-70% acetonitrile:water (0.1% ammonium hydroxide) gradient to give the title compound (34.5 mg, 45%) as a pale yellow solid. $^1$H NMR (400 MHz, CD$_3$SOCD$_3$) δ 1.26 (d, J=7.0 Hz, 6H), 3.04 (quin, J=6.9 Hz, 1H), 4.07-4.18 (m, 2H), 4.60 (br. s., 2H), 5.29-5.35 (m, 1H), 6.89 (d, J=7.8 Hz, 1H), 7.43 (t, J=8.0 Hz, 1H), 7.79 (d, J=7.8 Hz, 1H), 9.32 (s, 1H), 11.89 (br. s., 1H); LC-MS (LC-ES) M+H=376.

Example 338

3-(Benzo[d]thiazol-4-yloxy)-N-(3-cyclopropyl-1,2,4-thiadiazol-5-yl)azetidine-1-carboxamide

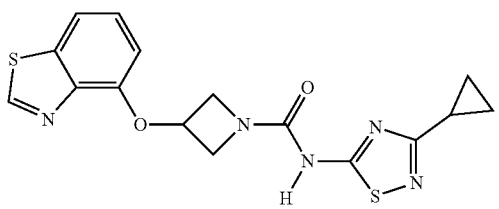 [SMILES: O=C(Nc1nc(C2CC2)ns1)N1CC(Oc2cccc3scnc23)C1]

To a stirred, cooled (0° C.) solution of 4-nitrophenyl chloroformate (55 mg, 0.273 mmol) in dichloromethane (2 mL) was added 3-cyclopropyl-1,2,4-thiadiazol-5-amine (40 mg, 0.283 mmol), followed by pyridine (0.50 mL, 6.18 mmol). The mixture was allowed to warm slowly to room temperature, while stirring for 2 hours. 4-(Azetidin-3-yloxy)benzo[d]thiazole hydrochloride (50 mg, 0.206 mmol, Intermediate 28) was added to the mixture, followed by N,N-diisopropylethylamine (0.12 mL, 0.687 mmol). The mixture immediately turned bright yellow and was stirred overnight. Solvent was removed under reduced pressure. The remaining material was dissolved in acetonitrile and chromatographed by reverse phase chromatography using a C18 silica column, eluting with a 5%-70% acetonitrile:water (0.1% ammonium hydroxide) gradient to give the title compound (27 mg, 35%) as a white solid. $^1$H NMR (400 MHz, CD$_3$SOCD$_3$) δ 0.89-1.01 (m, 4H), 2.11 (d, J=4.8 Hz, 1H), 4.12 (br. s., 2H), 4.59 (br. s., 2H), 5.32 (br. s., 1H), 6.88 (d, J=8.0 Hz, 1H), 7.43 (t, J=8.0 Hz, 1H), 7.79 (d, J=8.0 Hz, 1H), 9.31 (s, 1H), 11.85 (br. s., 1H); LC-MS (LC-ES) M+H=374.

Example 339

3-(Benzo[d]thiazol-4-yloxy)-N-(3-(tert-butyl-1,2,4-thiadiazol-5-yl)azetidine-1-carboxamide

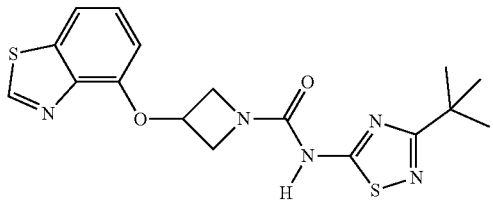 [SMILES: CC(C)(C)c1nsc(NC(=O)N2CC(Oc3cccc4scnc34)C2)n1]

To a stirred, cooled (0° C.) solution of 4-nitrophenyl chloroformate (55 mg, 0.273 mmol) in dichloromethane (2 mL) was added 3-(tert-butyl)-1,2,4-thiadiazol-5-amine (45 mg, 0.286 mmol), followed by pyridine (0.50 mL, 6.18 mmol). The mixture was allowed to warm slowly to room temperature, while stirring for 2 hours. 4-(Azetidin-3-yloxy)benzo[d]thiazole hydrochloride (50 mg, 0.206 mmol, Intermediate 28) was added to the mixture, followed by N,N-diisopropylethylamine (0.12 mL, 0.687 mmol). The mixture immediately turned bright yellow and was stirred overnight. Solvent was removed under reduced pressure. The remaining material was dissolved in acetonitrile and chromatographed by reverse phase chromatography using a C18 silica column, eluting with a 5%-70% acetonitrile:water (0.1% ammonium hydroxide) gradient to give the title compound (28 mg, 35%) as a white solid. $^1$H NMR (400 MHz, CD$_3$SOCD$_3$) δ 1.32 (s, 9H), 4.12 (d, J=5.3 Hz, 2H), 4.60 (br. s., 2H), 5.32 (td, J=6.6, 3.4 Hz, 1H), 6.89 (d, J=7.5 Hz, 1H), 7.43 (t, J=8.0 Hz, 1H), 7.77-7.81 (m, 1H), 9.32 (s, 1H), 11.88 (br. s., 1H); LC-MS (LC-ES) M+H=390.

Example 340

Capsule Composition

An oral dosage form for administering the present invention is produced by filing a standard two piece hard gelatin capsule with the ingredients in the proportions shown in Table 1, below.

TABLE 1

| INGREDIENTS | AMOUNTS |
| --- | --- |
| 3-(2-(Difluoromethoxy)-5-fluorophenoxy)-N-((trans)-4-(2-hydroxypropan-2-yl)cyclohexyl)azetidine-1-carboxamide (Compound of Example 1) | 7 mg |
| Lactose | 53 mg |
| Talc | 16 mg |
| Magnesium Stearate | 4 mg |

Example 341

Injectable Parenteral Composition

An injectable form for administering the present invention is produced by stirring 1.7% by weight of (trans)-N-(1-Butyl-1H-tetrazol-5-yl)-3-(2-(difluoromethoxy)-5-fluorophenoxy)cyclobutanecarboxamide (Compound of Example 2) in 10% by volume propylene glycol in water.

Example 342

Tablet Composition

The sucrose, calcium sulfate dihydrate and a PERK inhibitor as shown in Table 2 below, are mixed and granulated in the proportions shown with a 10% gelatin solution. The wet granules are screened, dried, mixed with the starch, talc and stearic acid, screened and compressed into a tablet.

TABLE 2

| INGREDIENTS | AMOUNTS |
| --- | --- |
| (trans)-3-(2-(Difluoromethoxy)-5-fluorophenoxy)-N-(1-methyl-1H-tetrazol-5-yl)cyclobutanecarboxamide (Compound of Example 3) | 12 mg |
| calcium sulfate dihydrate | 30 mg |
| sucrose | 4 mg |
| starch | 2 mg |
| talc | 1 mg |
| stearic acid | 0.5 mg |

BIOLOGICAL ASSAYS

H-PGDS RapidFire™ High Throughput Mass Spectrometry Assay

The H-PGDS RapidFire™ mass spectrometric assay monitors conversion of prostaglandin H2 (PGH$_2$) to prostaglandin D2 (PGD$_2$) by haematopoietic prostaglandin D synthase (H-PGDS). In the assay format described here, the substrate ($PGH_2$) is formed in situ by the action of cyclooxygenase-2 on arachidonic acid. This first step is set up to be fast, and generates a burst of $PGH_2$ at ~10 µM. The $PGH_2$ is then further converted to $PGD_2$ by the H-PGDS enzyme. The reaction is quenched with tin (II) chloride in citric acid, which converts any remaining $PGH_2$ to the more stable $PGF_2\alpha$. Plates are then read on the RapidFire™ high throughput solid phase extraction system (Agilent) which incorporates a solid phase extraction step coupled to a triple quadrupole mass spectrometer (AB SCIEX). Relative levels of $PGD_2$ and $PGF_2\alpha$, which acts as a surrogate for substrate, are measured and a percent conversion calculated. Inhibitors are characterised as compounds which lower the conversion of $PGH_2$ to $PGD_2$.

Expression and Purification of H-PGDS Protein

Full length human H-PGDS cDNA (Invitrogen Ultimate ORF 10H13026) was amplified by PCR with the addition of a 5' 6-His tag and TEV protease cleavage site. The PCR product was digested with NdeI and XhoI and ligated into pET22b+ (Merck Novagen®). Expression was carried out in *E. coli* strain BL21 (DE3*) using auto-induction Overnight Express™ Instant TB medium (Merck Novagen®) supplemented with 1% glycerol. The culture was first grown at 37° C. and the temperature was reduced to 25° C. when $OD_{600}$ reached 2.0. Cells were harvested by centrifugation after a further 18 hr. 10 g of *E. coli* cell pellet was suspended to a total volume of 80 mL in lysis buffer (20 mM Tris-Cl pH 7.5, 300 mM NaCl, 20 mM imidazole, 5 mM β-mercaptoethanol, 10% glycerol). 1 mg/mL protease inhibitors (Protease Inhibitor Cocktail Set III, Merck Calbiochem®) and 1 mg/mL lysozyme were added to the cell suspension. The suspension was then sonicated for 5 min (UltraSonic Processor VCX 750, Cole-Parmer Instrument Co.) with a micro probe (50% amplitude, 10 sec on/off) and then centrifuged at 100,000 g for 90 min (at 4° C.). The supernatant was loaded onto a Ni-NTA HiTrap column (5 mL, GE Healthcare, pre-equilibrated in lysis buffer). The column was washed with 10 column volumes of lysis buffer and eluted with lysis buffer containing 500 mM imidazole. The pooled protein peak fractions were concentrated using a 10 kDa centrifugal filter at 3500 g and 4° C. (Amicon Ultra-15 centrifugal filter unit with Ultracel-10 membrane from Millipore). Further purification of the concentrated protein was carried out using gel filtration chromatography on a HiLoad 26/600 Superdex 75 preparative grade column (GE Healthcare Life Sciences) using 50 mM Tris pH 7.5, 50 mM NaCl, 1 mM dithiothreitol, 1 mM $MgCl_2$. Fractions containing the protein were pooled, concentrated as described above, and stored at −80° C.

Expression and Purification of Cyclooxygenase-2 (COX-2) Protein

The full length human COX-2 gene (accession number L15326) was amplified by PCR to generate an EcoRI-HindIII fragment containing an in-frame FLAG tag. This was subcloned into pFastBac 1 (Invitrogen). The COX2 FLAG plasmid was recombined into the baculovirus genome according to the BAC-to-BAC protocol described by Invitrogen. Transfection into Spodoptera frugiperda (Sf9) insect cells was performed using Cellfectin (Invitrogen), according to the manufacturer's protocol. Super Sf9 cells were cultured in EX420 media (SAFC Biosciences) to a density of approximately $1.5\times10^6$ cells/mL within a wave bioreactor. Recombinant virus was added at a Multiplicity of Infection (MOI) of 5 and the culture was allowed to continue for 3 days. Cells were harvested using a continuous feed centrifuge run at 2500 g at a rate of approximately 2 L/min with cooling. The resultant cell slurry was re-centrifuged in pots (2500 g, 20 min, 4° C.) and the cell paste was stored at −80° C. 342 g of cell paste was re-suspended to a final volume of 1600 mL in a buffer of 20 mM Tris-Cl pH 7.4, 150 mM NaCl, 0.1 mM EDTA, 1.3% w/v n-octyl-3-D-glucopyranoside containing 20 Complete EDTA-free Protease Inhibitor Cocktail tablets (Roche Applied Science). The suspension was sonicated in 500 mL batches for 8×5 seconds at 10 u amplitude with the medium tip of an MSE probe sonicator and subsequently incubated at 4° C. for 90 min with gentle stirring. The lysate was centrifuged at 12000 rpm for 45 min at 4° C. in a Sorvall SLA1500 rotor. The supernatant (1400 mL) was added to 420 mL of 20 mM Tris-Cl pH 7.4, 150 mM NaCl, 0.1 mM EDTA to reduce the concentration of n-octyl-6-D-glucopyranoside to 1% w/v. The diluted supernatant was incubated overnight at 4° C. on a roller with 150 mL of anti-FLAG M2 agarose affinity gel (Aldrich-Sigma) which had been pre-equilibrated with 20 mM Tris-Cl pH 7.4, 150 mM NaCl, 0.1 mM EDTA, 1% w/v n-octyl-β-D-glucopyranoside (purification buffer). The anti-Flag M2 agarose beads were pelleted by centrifugation in 500 mL conical Corning centrifuge pots at 2000 rpm for 10 min at 4° C. in a Sorvall RC3 swing-out rotor. The supernatant (unbound fraction) was discarded and the beads were re-suspended to half the original volume in purification buffer and re-centrifuged as above. The beads were then packed into a BioRad Econo Column (5 cm diameter) and washed with 1500 mL of purification buffer at 4° C. Bound proteins were eluted with 100 µg/mL triple FLAG peptide (Aldrich-Sigma) in purification buffer. Six fractions each of 0.5 column volume were collected. After each 0.5 column volume of purification buffer was added into the column the flow was held for 10 min before elution. Fractions containing COX-2 were pooled resulting in a protein concentration of ~1 mg/mL. The protein was further concentrated on Vivaspin 20 centrifugal concentrators (10 kDa cut-off) to 2.4 mg/mL and then stored at −80° C.

Test Compound Plate Preparation

Test compounds were diluted to 1 mM in DMSO and a 1:3, 11 point serial dilution was performed across a 384 well HiBase plate (Greiner Bio-one). 100 nL of this dilution series was then transferred into a 384 well v-base plate (Greiner Bio-one) using an Echo™ acoustic dispenser (Labcyte Inc) to create the assay plate. 100 nL of DMSO was added to each well in columns 6 and 18 for use as control columns.

Assay Method

5 µL of an enzyme solution containing 10 nM H-PGDS enzyme, 1.1 µM COX-2 enzyme and 2 mM reduced glutathione (Sigma-Aldrich), diluted in a buffer of 50 mM Tris-Cl pH 7.4, 10 mM $MgCl_2$ and 0.1% Pluronic F-127 (all Sigma-Aldrich) was added to each well of the plate except column 18 using a Multidrop Combi® dispenser (Thermo Fisher Scientific). 5 µL of enzyme solution without H-PGDS was added to each well in column 18 of the assay plate to generate 100% inhibition control wells.

Immediately after the addition of enzyme solution, 2.5 µL of a co-factor solution containing 4 µM Hemin (Sigma-Aldrich) diluted in buffer of 50 mM Tris-Cl pH 7.4 and 10 mM $MgCl_2$ (all Sigma-Aldrich), was added to each well using a Multidrop Combi® dispenser. 2.5 µL of substrate solution containing 80 µM arachidonic acid (Sigma-Aldrich) and 1 mM sodium hydroxide (Sigma-Aldrich) diluted in HPLC grade water (Sigma-Aldrich) was then added to each well using a Multidrop Combi® dispenser, to initiate the reaction.

The assay plates were incubated at room temperature for the duration of the linear phase of the reaction (usually 1 min 30 s-2 min, this timing should be checked on a regular basis). Precisely after this time, the reaction was quenched by the addition of 30 μL of quench solution containing 32.5 mM SnCl$_2$ (Sigma-Aldrich) in 200 mM citric acid (adjusted to pH 3.0 with 0.1 mM NaOH solution) to all wells using a Multidrop Combi® dispenser (Thermo Fisher Scientific). The SnCl$_2$ was initially prepared as a suspension at an equivalent of 600 mM in HPLC water (Sigma-Aldrich) and sufficient concentrated hydrochloric acid (Sigma-Aldrich) was added in small volumes until dissolved. The assay plates were centrifuged at 1000 rpm for 5 min prior to analysis.

The assay plates were analysed using a RapidFire® high throughput solid phase extraction system (Agilent) coupled to a triple quadrupole mass spectrometer (AB SCIEX) to measure relative peak areas of PGF$_{2\alpha}$, and PGD$_2$ product. Peaks were integrated using the RapidFire™ integrator software before percentage conversion of substrate to PGD$_2$ product was calculated as shown below:

Conversion=((PGD$_2$ peak area)/(PGD$_2$ peak area+ PGF$_{2\alpha}$peak area))×100.

Data were further analysed within Activitybase software (IDBS) using a four parameter curve fit of the following form:

$$y = \frac{a-d}{1+(x/c)^b} + d$$

where a is the minimum, b is the Hill slope, c is the IC$_{50}$ and d is the maximum. Data are presented as the mean pIC$_{50}$ in Table 3 below.

TABLE 3

| Ex # | Potency Range |
|---|---|
| 1 | ** |
| 2 | *** |
| 3 | ** |
| 4 | *** |
| 4 | *** |
| 4 | *** |
| 5 | *** |
| 5 | *** |
| 6 | *** |
| 7 | **** |
| 8 | *** |
| 9 | *** |
| 10 | *** |
| 11 | *** |
| 12 | *** |
| 13 | ** |
| 14 | *** |
| 14 | ** |
| 15 | ** |
| 16 | *** |
| 17 | *** |
| 18 | *** |
| 19 | *** |
| 20 | *** |
| 21 | *** |
| 22 | ** |
| 23 | *** |
| 24 | *** |
| 25 | *** |
| 26 | *** |
| 27 | *** |
| 28 | *** |
| 29 | *** |
| 30 | ** |
| 30 | ** |
| 30 | ** |
| 31 | **** |
| 32 | **** |
| 33 | *** |
| 34 | *** |
| 35 | **** |
| 36 | *** |
| 37 | *** |
| 38 | *** |
| 39 | *** |
| 40 | *** |
| 41 | *** |
| 42 | *** |
| 43 | *** |
| 44 | *** |
| 45 | ** |
| 46 | *** |
| 47 | ** |
| 48 | ** |
| 49 | *** |
| 50 | *** |
| 51 | *** |
| 52 | *** |
| 53 | *** |
| 54 | *** |
| 55 | *** |
| 56 | ** |
| 57 | ** |
| 58 | ** |
| 59 | *** |
| 60 | *** |
| 61 | *** |
| 62 | *** |
| 63 | ** |
| 64 | ** |
| 65 | ** |
| 66 | ** |
| 67 | ** |
| 68 | *** |
| 69 | *** |
| 70 | ** |
| 71 | *** |
| 71 | *** |
| 72 | ** |
| 73 | ** |
| 74 | *** |
| 75 | *** |
| 76 | ** |
| 77 | *** |
| 77 | *** |
| 78 | *** |
| 79 | ** |
| 80 | *** |
| 81 | *** |
| 82 | *** |
| 83 | *** |
| 84 | *** |
| 85 | *** |
| 86 | *** |
| 87 | ** |
| 88 | *** |
| 89 | *** |
| 90 | ** |
| 91 | *** |
| 92 | ** |
| 93 | ** |
| 94 | ** |
| 95 | *** |
| 96 | ** |
| 97 | ** |
| 98 | ** |
| 99 | ** |
| 100 | *** |
| 101 | *** |
| 102 | ** |

TABLE 3-continued

| Ex # | Potency Range |
|---|---|
| 103 | ** |
| 104 | *** |
| 105 | ** |
| 106 | *** |
| 107 | *** |
| 108 | *** |
| 109 | *** |
| 110 | *** |
| 111 | ** |
| 112 | *** |
| 113 | *** |
| 114 | *** |
| 115 | ** |
| 116 | *** |
| 117 | *** |
| 118 | *** |
| 119 | *** |
| 120 | *** |
| 121 | *** |
| 122 | *** |
| 123 | *** |
| 124 | *** |
| 125 | *** |
| 126 | *** |
| 127 | *** |
| 128 | *** |
| 129 | *** |
| 130 | *** |
| 131 | ** |
| 132 | *** |
| 133 | *** |
| 134 | *** |
| 135 | *** |
| 136 | *** |
| 137 | *** |
| 138 | **** |
| 139 | *** |
| 140 | *** |
| 141 | *** |
| 142 | *** |
| 143 | *** |
| 144 | *** |
| 145 | *** |
| 146 | *** |
| 147 | *** |
| 148 | *** |
| 149 | **** |
| 150 | *** |
| 151 | ** |
| 152 | *** |
| 153 | *** |
| 154 | *** |
| 155 | *** |
| 156 | *** |
| 157 | *** |
| 158 | *** |
| 159 | *** |
| 160 | **** |
| 161 | *** |
| 162 | ** |
| 163 | *** |
| 164 | **** |
| 165 | *** |
| 166 | *** |
| 167 | **** |
| 168 | *** |
| 169 | *** |
| 170 | *** |
| 171 | *** |
| 172 | *** |
| 173 | *** |
| 174 | *** |
| 175 | *** |
| 176 | ** |
| 177 | *** |
| 178 | *** |
| 179 | *** |
| 180 | ** |
| 181 | *** |
| 182 | ** |
| 183 | ** |
| 184 | **** |
| 185 | *** |
| 186 | *** |
| 187 | *** |
| 188 | **** |
| 189 | *** |
| 190 | *** |
| 191 | *** |
| 192 | **** |
| 193 | *** |
| 194 | *** |
| 195 | ** |
| 196 | *** |
| 197 | **** |
| 198 | *** |
| 199 | *** |
| 200 | *** |
| 201 | *** |
| 202 | *** |
| 203 | *** |
| 204 | *** |
| 205 | **** |
| 206 | **** |
| 207 | **** |
| 208 | ** |
| 209 | *** |
| 210 | *** |
| 211 | *** |
| 212 | *** |
| 213 | *** |
| 214 | ** |
| 215 | *** |
| 216 | *** |
| 217 | *** |
| 218 | *** |
| 219 | ** |
| 220 | ** |
| 221 | ** |
| 222 | ** |
| 223 | ** |
| 224 | *** |
| 225 | *** |
| 226 | *** |
| 227 | *** |
| 228 | ** |
| 229 | ** |
| 230 | ** |
| 231 | *** |
| 232 | *** |
| 233 | *** |
| 234 | *** |
| 235 | *** |
| 236 | *** |
| 237 | ** |
| 238 | ** |
| 239 | *** |
| 240 | *** |
| 241 | *** |
| 242 | *** |
| 243 | *** |
| 244 | *** |
| 245 | *** |
| 246 | *** |
| 247 | *** |
| 248 | *** |
| 249 | ** |
| 250 | ** |
| 251 | ** |
| 252 | ** |
| 253 | ** |
| 254 | ** |
| 255 | ** |
| 256 | ** |

TABLE 3-continued

| Ex # | Potency Range |
|---|---|
| 257 | ** |
| 258 | ** |
| 259 | ** |
| 260 | *** |
| 261 | *** |
| 262 | *** |
| 263 | *** |
| 264 | *** |
| 265 | *** |
| 266 | *** |
| 267 | *** |
| 268 | *** |
| 269 | *** |
| 270 | ** |
| 271 | *** |
| 272 | *** |
| 273 | *** |
| 274 | **** |
| 275 | *** |
| 276 | *** |
| 277 | ** |
| 278 | *** |
| 279 | *** |
| 280 | ** |
| 281 | *** |
| 282 | ** |
| 283 | ** |
| 284 | *** |
| 285 | ** |
| 286 | *** |
| 287 | *** |
| 288 | ** |
| 289 | ** |
| 290 | ** |
| 291 | ** |
| 292 | ** |
| 293 | ** |
| 294 | *** |
| 295 | *** |
| 296 | ** |
| 297 | ** |
| 298 | ** |
| 299 | ** |
| 300 | * |
| 301 | ** |
| 302 | *** |
| 303 | ** |
| 304 | *** |
| 305 | *** |
| 306 | *** |
| 307 | *** |
| 308 | *** |
| 309 | ** |
| 310 | *** |
| 311 | *** |
| 312 | *** |
| 313 | *** |
| 314 | *** |
| 315 | *** |
| 316 | ** |
| 317 | *** |
| 318 | *** |
| 319 | *** |
| 320 | *** |
| 321 | *** |
| 322 | ** |
| 323 | *** |
| 324 | ** |
| 325 | ** |
| 326 | *** |
| 327 | *** |
| 328 | ** |
| 329 | ** |
| 330 | *** |
| 331 | *** |
| 332 | **** |
| 333 | **** |

TABLE 3-continued

| Ex # | Potency Range |
|---|---|
| 334 | *** |
| 335 | *** |
| 336 | *** |
| 337 | **** |
| 338 | **** |
| 339 | *** |

**** $pIC_{50} > 8.0$
*** $pIC_{50} = 7.1\text{-}8.0$
** $pIC_{50} = 6.0\text{-}7.0$
* $pIC_{50} = 5.7\text{-}5.9$ In Vivo Assays for Functional Response to Muscle Injury Under anesthesia, the right hind limb of a mouse is restrained at the knee and the foot attached to a motorized footplate/force transducer. Needle electrodes are inserted into the upper limb, either side of the sciatic nerve and a current sufficient to elicit a maximal muscle contraction is applied. Muscle tension is produced by moving the footplate to lengthen the plantarflexor muscles while the limb is under maximal stimulation. This is repeated 60 times to fatigue the muscles of the lower limb. Anesthesia, limb immobilization and limb stimulation are then repeated at regular intervals to measure maximal isometric force in the recovering limb. 7 to 9 animals are tested for each test condition.

Eccentric contraction-induced muscle fatigue in vehicle-treated male C57Bl/6N mice, 10-12 weeks of age, significantly reduced (~35%) maximal isometric torque 24-hours after injury and took ~5 weeks for full functional restoration. In contrast, animals (PO) dosed with 3, 10, and 30 mg/kg BID of the compound of Example 141 beginning 10 min prior to eccentric contraction challenge exhibited an acceleration in the kinetics of recovery. And 3, 10 and 30 mg/kg BID of the compound of Example 141 also reduced the initial magnitude of the injury, as determined by isometric limb force 24-hours following protocol initiation. See FIG. 1.

While the preferred embodiments of the invention are illustrated by the above, it is to be understood that the invention is not limited to the precise instructions herein disclosed and that the right to all modifications coming within the scope of the following claims is reserved.

The invention claimed is:
1. A compound which is:

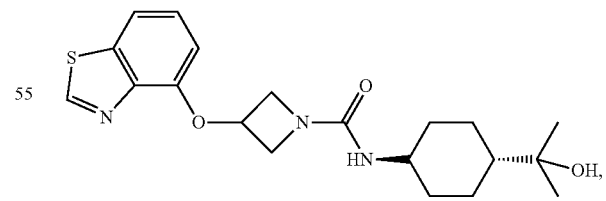

or a pharmaceutically acceptable salt thereof.

2. A pharmaceutical composition comprising the compound or a pharmaceutically acceptable salt thereof, of claim 1 and one or more pharmaceutically acceptable carriers or excipients.

3. A method for the treatment of a disorder in a human in which inhibition of H-PGDS is beneficial, comprising administering to the human in need thereof, a therapeutically effective amount of the compound, or a pharmaceutically acceptable salt thereof, of claim 1.

4. A method for the treatment of an allergic disease or an inflammatory condition selected from asthma, aspirin-exacerbated respiratory disease (AERD), cough, chronic obstructive pulmonary disease, chronic bronchitis, emphysema, bronchoconstriction, seasonal allergic rhinitis, perennial allergic rhinitis, vasomotor rhinitis, rhinoconjuctivitis, allergic conjunctivitis, food allergy, hypersensitivity lung diseases, eosinophilic syndromes, eosinophilic asthma, eosinophilic pneumonitis, eosinophilic oesophagitis, eosinophilic granuloma, delayed-type hypersensitivity disorders, atherosclerosis, rheumatoid arthritis, pancreatitis, gastritis, inflammatory bowel disease, osteoarthritis, psoriasis, sarcoidosis, pulmonary fibrosis, respiratory distress syndrome, bronchiolitis, sinusitis, cystic fibrosis, actinic keratosis, skin dysplasia, chronic urticaria, eczema dermatitis, atopic dermatitis and contact dermatitis in a human comprising administering to the human in need thereof, a therapeutically effective amount of the compound, or a pharmaceutically acceptable salt thereof, of claim 1.

5. A method for the treatment of a neuromuscular-related condition selected from: Duchenne muscular dystrophy (MD), Becker MD, Congenital MD (Fukuyama), Dreifuss MD, Limb girdle MD, Fascioscapulohumeral MD, DM1 Myotonic dystrophy type I, Steinert's Myotonic dystrophy type I, DM2 myotonic dystrophy type IL proximal myotonic myopathy Myotonic dystrophy type II, congenital myotonia, polymyositis, dermatomyositis, amyotrophic Lateral Sclerosis (ALS), muscle injury, surgery-related muscle injury, traumatic muscle injury, work-related skeletal muscle injury, overtraining-related muscle injury, muscle damage due to knee replacement, muscle damage due to anterior cruciate ligament (ACL) repair, muscle damage due to plastic surgery, muscle damage due to hip replacement surgery, muscle damage due to joint replacement surgery, muscle damage due to tendon repair surgery, muscle damage due to surgical repair of rotator cuff disease, muscle damage due to surgical repair of rotator cuff injury, muscle damage due to amputation, battlefield muscle injuries, auto accident-related muscle injuries, sports-related muscle injuries, muscle lacerations, traumatic injury due to blunt force contusions, traumatic injury due to shrapnel wounds, muscle pulls or tears, traumatic injury due to burns, acute muscle strains, chronic muscle strains, weight or force stress muscle injuries, repetitive stress muscle injuries, avulsion muscle injury, compartment syndrome, muscle injuries caused by highly repetitive motions, muscle injuries caused by forceful motions, muscle injuries caused by awkward postures, muscle injuries caused by prolonged and forceful mechanical coupling between the body and an object, muscle injuries caused by vibration, muscle injuries due to unrepaired or under-repaired muscle damage coincident with a lack of recovery or lack of an increase of physical work capacity, exercise-induced delayed onset muscle soreness (DOMS), wound healing and disuse atrophy in a human comprising administering to the human in need thereof, a therapeutically effective amount of the compound, or a pharmaceutically acceptable salt thereof, of claim 1.

6. A method for the treatment of Duchenne muscular dystrophy (MD) in a human in need thereof, comprising administering to the human a therapeutically effective amount of the compound, or a pharmaceutically acceptable salt thereof, of claim 1.

7. A compound which is:

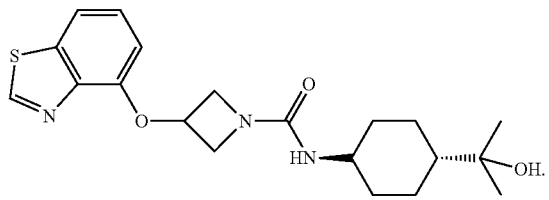

8. A pharmaceutical composition comprising the compound of claim 7 and one or more pharmaceutically acceptable carriers or excipients.

9. A method for the treatment of a disorder in a human in which inhibition of H-PGDS is beneficial, comprising administering to the human in need thereof a therapeutically effective amount of the compound of claim 7.

10. A method for the treatment of an allergic disease or an inflammatory condition selected from asthma, aspirin-exacerbated respiratory disease (AERD), cough, chronic obstructive pulmonary disease, chronic bronchitis, emphysema, bronchoconstriction, seasonal allergic rhinitis, perennial allergic rhinitis, vasomotor rhinitis, rhinoconjuctivitis, allergic conjunctivitis, food allergy, hypersensitivity lung diseases, eosinophilic syndromes, eosinophilic asthma, eosinophilic pneumonitis, eosinophilic oesophagitis, eosinophilic granuloma, delayed-type hypersensitivity disorders, atherosclerosis, rheumatoid arthritis, pancreatitis, gastritis, inflammatory bowel disease, osteoarthritis, psoriasis, sarcoidosis, pulmonary fibrosis, respiratory distress syndrome, bronchiolitis, sinusitis, cystic fibrosis, actinic keratosis, skin dysplasia, chronic urticaria, eczema dermatitis, atopic dermatitis and contact dermatitis in a human comprising administering to the human in need thereof a therapeutically effective amount of the compound of claim 7.

11. A method for the treatment of a neuromuscular-related condition selected from: Duchenne muscular dystrophy (MD), Becker MD, Congenital MD (Fukuyama), Dreifuss MD, Limb girdle MD, Fascioscapulohumeral MD, DM1 Myotonic dystrophy type I, Steinert's Myotonic dystrophy type I, DM2 myotonic dystrophy type II, proximal myotonic myopathy myotonic dystrophy type II, congenital myotonia, polymyositis, dermatomyositis, amyotrophic Lateral Sclerosis (ALS), muscle injury, surgery-related muscle injury, traumatic muscle injury, work-related skeletal muscle injury, overtraining-related muscle injury, muscle damage due to knee replacement, muscle damage due to anterior cruciate ligament (ACL) repair, muscle damage due to plastic surgery, muscle damage due to hip replacement surgery, muscle damage due to joint replacement surgery, muscle damage due to tendon repair surgery, muscle damage due to surgical repair of rotator cuff disease, muscle damage due to surgical repair of rotator cuff injury, muscle damage due to amputation, battlefield muscle injuries, auto accident-related muscle injuries, sports-related muscle injuries, muscle lacerations, traumatic injury due to blunt force contusions, traumatic injury due to shrapnel wounds, muscle pulls or tears, traumatic injury due to burns, acute muscle strains, chronic muscle strains, weight or force stress muscle injuries, repetitive stress muscle injuries, avulsion muscle injury, compartment syndrome, muscle injuries caused by highly repetitive motions, muscle injuries caused by forceful motions, muscle injuries caused by awkward postures, muscle injuries caused by prolonged and forceful mechanical coupling between the body and an object, muscle injuries caused by vibration, muscle injuries due to unrepaired or under-repaired muscle damage coincident with a lack of recovery or lack of an increase of physical work capacity, exercise-induced delayed onset muscle soreness (DOMS), wound healing and disuse atrophy in a human comprising administering to the human in need thereof, a therapeutically effective amount of the compound of claim 7.

12. A method for the treatment of Duchenne muscular dystrophy (MD) in a human in need thereof, comprising administering to the human a therapeutically effective amount of the compound of claim 7.

* * * * *